(12) United States Patent
Chessari et al.

(10) Patent No.: US 11,236,047 B2
(45) Date of Patent: Feb. 1, 2022

(54) COMBINATION OF ISOINDOLINONE DERIVATIVES WITH SGI-110

(71) Applicants: ASTEX THERAPEUTICS LIMITED, Cambridge (GB); CANCER RESEARCH TECHNOLOGY LIMITED, London (GB)

(72) Inventors: Gianni Chessari, Cambridge (GB); John Francis Lyons, London (GB)

(73) Assignees: ASTEX THERAPEUTICS LIMITED, Cambridge (GB); CANCER RESEARCH TECHNOLOGY LIMITED, London (GB)

( * ) Notice: Subject to any disclaimer, the term of this patent is extended or adjusted under 35 U.S.C. 154(b) by 0 days.

(21) Appl. No.: 16/497,135

(22) PCT Filed: Mar. 28, 2018

(86) PCT No.: PCT/GB2018/050832
§ 371 (c)(1),
(2) Date: Sep. 24, 2019

(87) PCT Pub. No.: WO2018/178679
PCT Pub. Date: Oct. 4, 2018

(65) Prior Publication Data
US 2020/0207711 A1 Jul. 2, 2020

(30) Foreign Application Priority Data

Mar. 28, 2017 (GB) .................. 1704966

(51) Int. Cl.
*C07D 209/48* (2006.01)
*C07H 21/04* (2006.01)
(Continued)

(52) U.S. Cl.
CPC .......... *C07D 209/48* (2013.01); *A61P 35/00* (2018.01); *C07D 401/10* (2013.01);
(Continued)

(58) Field of Classification Search
CPC .. C07D 209/48; C07D 403/06; C07D 401/10; C07D 403/12; C07D 405/12;
(Continued)

(56) References Cited

U.S. PATENT DOCUMENTS 3,466,298 A 9/1969 Sulkowski et al.
3,763,178 A 10/1973 Sulkowski et al.
(Continued)

FOREIGN PATENT DOCUMENTS

CH 374071 12/1963
DE 2313227 9/1973
(Continued)

OTHER PUBLICATIONS

Great Britain Search Report for GB1704966.9, dated Dec. 21, 2017, 4 pp.
(Continued)

*Primary Examiner* — Kristin A Vajda
(74) *Attorney, Agent, or Firm* — Heslin Rothenberg Farley & Mesiti P.C.

(57) ABSTRACT

The invention provides a combination comprising:
(i) a compound of formula (I°):

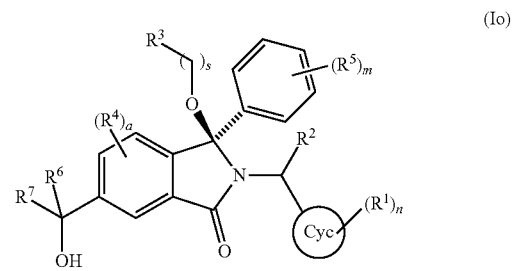

or a tautomer or a solvate or a pharmaceutically acceptable salt thereof, wherein the various substituents are as defined in the claims; and
(ii) a compound which is SGI-110

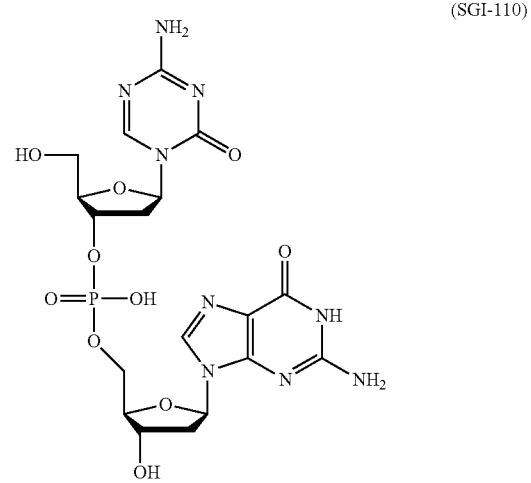

or a tautomer or a solvate or a pharmaceutically acceptable salt thereof.

Also provided are pharmaceutical compositions containing the combinations and medical uses of the combinations.

21 Claims, 3 Drawing Sheets

(51) Int. Cl.
    *C07D 403/12* (2006.01)
    *C07D 405/12* (2006.01)
    *C07D 405/14* (2006.01)
    *C07D 401/10* (2006.01)
    *A61P 35/00* (2006.01)
    *C07D 403/06* (2006.01)
    *A61K 45/06* (2006.01)

(52) U.S. Cl.
    CPC ......... *C07D 403/06* (2013.01); *C07D 403/12* (2013.01); *C07D 405/12* (2013.01); *C07D 405/14* (2013.01); *C07H 21/04* (2013.01); *A61K 45/06* (2013.01)

(58) Field of Classification Search
    CPC ....... C07D 405/14; A61P 35/00; C07H 21/04; A61K 45/06
    USPC .................................................. 514/254.01
    See application file for complete search history.

(56) References Cited

U.S. PATENT DOCUMENTS

| | | |
|---|---|---|
| 3,898,232 A | 8/1975 | Cotrel et al. |
| 4,001,271 A | 1/1977 | Cotrel et al. |
| 4,200,759 A | 4/1980 | Dickinson |
| 4,244,966 A | 1/1981 | Lippman et al. |
| 4,312,809 A | 1/1982 | Haugwitz |
| 4,331,600 A | 5/1982 | Golec, Jr. et al. |
| 4,505,921 A | 3/1985 | Beregi et al. |
| 6,344,468 B1 | 2/2002 | Schindler et al. |
| 8,258,175 B2 | 9/2012 | Willems et al. |
| 8,618,158 B2 | 12/2013 | Golding et al. |
| 9,358,222 B2 | 6/2016 | Golding et al. |
| 10,414,726 B2 | 9/2019 | Golding et al. |
| 10,526,311 B2 | 1/2020 | Chessari et al. |
| 10,544,132 B2 | 1/2020 | Chessari et al. |
| 10,981,898 B2 | 4/2021 | Chessari et al. |
| 2005/0004207 A1 | 1/2005 | Straub et al. |
| 2006/0264473 A1 | 11/2006 | Khazak et al. |
| 2012/0264738 A1 | 10/2012 | Sugimoto et al. |
| 2014/0194486 A1 | 7/2014 | Golding et al. |
| 2016/0355478 A1 | 12/2016 | Golding et al. |
| 2018/0118684 A1 | 5/2018 | Golding et al. |
| 2019/0016708 A1 | 1/2019 | Chessari et al. |
| 2019/0055215 A1 | 2/2019 | Chessari et al. |
| 2020/0040403 A1 | 2/2020 | Stanford et al. |
| 2020/0079761 A1 | 3/2020 | Chessari et al. |
| 2021/0101887 A1 | 4/2021 | Howard et al. |

FOREIGN PATENT DOCUMENTS

| | | |
|---|---|---|
| EP | 0461079 A2 | 12/1991 |
| EP | 1199306 A1 | 4/2002 |
| EP | 1566378 A1 | 8/2005 |
| EP | 2108642 A1 | 10/2009 |
| GB | 1325065 | 8/1973 |
| GB | 1601701 | 11/1981 |
| JP | 2000506163 A | 5/2000 |
| JP | 2004217591 | 8/2004 |
| JP | 2005255660 A | 9/2005 |
| KR | 2013/0088577 A | 8/2013 |
| WO | 97/32846 A1 | 9/1997 |
| WO | 99/42444 A1 | 8/1999 |
| WO | 01/32928 A2 | 5/2001 |
| WO | 03/051359 A1 | 6/2003 |
| WO | 03/101450 A1 | 12/2003 |
| WO | 2005/021532 A1 | 3/2005 |
| WO | 2005/095341 A1 | 10/2005 |
| WO | 2006/020879 A1 | 2/2006 |
| WO | 2006/024837 A1 | 3/2006 |
| WO | 2006/091646 A2 | 8/2006 |
| WO | 2007/021309 A1 | 2/2007 |
| WO | 2008/024892 A2 | 2/2008 |
| WO | 2008/117061 A2 | 10/2008 |
| WO | 2008/151184 A1 | 12/2008 |
| WO | 2009/156735 A2 | 12/2009 |
| WO | 2010/031713 A1 | 3/2010 |
| WO | 2011/060049 A2 | 5/2011 |
| WO | 2011/076786 A1 | 6/2011 |
| WO | 2011/098398 A1 | 8/2011 |
| WO | 2011/153509 A1 | 12/2011 |
| WO | 2012/175487 A1 | 12/2012 |
| WO | 2012/175520 A1 | 12/2012 |
| WO | 2013/033176 A1 | 3/2013 |
| WO | 2013/111105 A1 | 8/2013 |
| WO | 2013/120835 A1 | 8/2013 |
| WO | 2014/070948 A1 | 5/2014 |
| WO | 2014/134355 A1 | 9/2014 |
| WO | 2015/000945 A1 | 1/2015 |
| WO | 2015/108175 A1 | 7/2015 |
| WO | 2015/161032 A1 | 10/2015 |
| WO | 2016/056673 A1 | 4/2016 |
| WO | 2017/004538 A1 | 1/2017 |
| WO | 2017/055859 A1 | 4/2017 |
| WO | 2017/055860 A1 | 4/2017 |
| WO | 2017/068412 A1 | 4/2017 |
| WO | 2017/087607 A1 | 5/2017 |
| WO | 2018/178691 A1 | 10/2018 |
| WO | 2020/0169073 A1 | 8/2020 |

OTHER PUBLICATIONS

International Search Report for PCT/GB2018/050832, dated Jun. 6, 2018, 4 pp.
Prodrug [online, wikipedia], [retrieved on Mar. 11, 2007], Retrieved from the URL http://en.wikipedia.org/wiki/Prodrugs.
Lala, P.K., et al., Role of nitric oxide in tumor progression: Lessons from experimental tumors, Cancer and Metastasis Reviews, vol. 17, No. 1, pp. 91-106 (1998).
Golub, T.R., et al., Molecular Classification of Cancer: Class Discovery and Class Prediction by Gene Expression Monitoring, Science, vol. 286, pp. 531-537 (1999).
Cancer [online, medline], [retrieved on Jul. 6, 2007], Retrieved from the internet, URL http://www.nlm.nih.gov/medlineplus/cancer.html.
Cancer [online, wikipedia], [retrieved on Jul. 6, 2007], Retrieved from the internet, URL http://en.wikipedia.org/wiki/Cancer.
Bartfeld, H.D., et al., 3-Oxo-Isoindole, Tetrahedron Letters, No. 10, pp. 757-760 (1970).
CAPLUS 95:150329 record for Lencbergs, I., et al., 3-Hydroxy-3-(α-aminobenzyl)-2-substituted 1-isoindolinones, Latvijas PSR Zinatnu Akademijas Vestis, Kimijas Serija (1981), (3), 335-40.
Rebek, Jr., J., et al., Olefin Epoxidation with α-Substituted Hydroperoxides, J. Am. Chem. Soc., vol. 102, pp. 5602-5605 (1980).
Griffiths, J., et al., Model Studies for Damage to Nucleic Acids Mediated by Thiyl Radicals, Tetrahedron, vol. 48, No. 26, pp. 5543-5556 (1992).
Park, J.S., Noble 2-[3(Cyclopentyloxy)-4-Methoxyphenyl]-1-Isoindolinone Derivatives. Part I; Synthesis and SAR Studies for the Inhibition of TNF-α Production, Arch. Pharma. Res., vol. 24, No. 5, pp. 367-370 (2001).
Ito, Y., et al., Solid-State and Solution Photolyses of Tetracyanobenzene with Benzyl Cyanides or Benzyl Alcohols, Tetrahedron, vol. 56, pp. 7139-7152 (2000).
Vivekananda Bhatt, M., et al., Aspects of Tautomerism. Part V. † Solvent, Substituent, and Steric Effects on the Ring-Chain Tautomerism of o-Benzoylbenzamides, Journal of the Chemical Society, Perkin Transactions II, pp. 1160-1166 (1973).
Topliss, J.G., et al., Antihypertensive Agents. III. 3-Hydroxy-3-phenylphthalimidines, Journal of Medicinal Chemistry, vol. 7, pp. 453-456 (1964).
Charlesworth, E.H., et al., Fluoranthene studies. III. A synthesis of 3-bromo-6-nitrofluorenone, Canadian Journal of Chemistry, vol. 46, No. 3, pp. 463-465 (1968).
STN 1972:419475 (CAPLUS) record for Valters, R., et al., Ring-chain transformations involving the carbonyl group. XI. Acid chlorides and amides of 2-benzoyl-3-,4-, 5-, and 6-nitrobenzoic acids,

(56) References Cited

OTHER PUBLICATIONS

Rizh. Politekh. Inst., Riga, USSR, Latvijas PSR Zinatnu Akademijas Vestis, Kimijas Serija, vol. 1, pp. 61-65 (1972).
Yang et al., "Practical Proline-Catalyzed Asymmetric Mannich Reaction of Aldehydes with N-Boc-Imines," Nature Protocols, vol. 2, No. 8, 2007, pp. 1937-1942.
Körmendy, K., Über Reaktionen In Polyaminsynthesen Mit Phthaliminoakjylhaloiden, I., Acta Chimica Academiae Scientiarum Hungaricae, pp. 255-264 (1958).
Inaba, M., et al., Reversal of Resistance to Vincristine in P388 Leukemia by Various Polycyclic Clinical Drugs, with a Special Emphasis on Quinacrine, Cancer Research, vol. 48, No. 8, pp. 2064-2067 (1988).
Croisy-Delcey, M., et al., Dipheyl Quinolines and Isoquinolines: Synthesis and Primary Biological Evaluation, Bioorganic and Medicinal Chemistry, vol. 8, pp. 2629-2641 (2000).
Kitching, M.S., et al., Synthesis of 3-Alkoxy- and 3-Alkylamino-2-alkyl-3-arylisoindolinones, Synlett, vol. 81, pp. 997-999 (1999).
Nikitin, K.V., et al., Synthesis of 5-alkyl- and 5-aryl-1,5-dihydro-2H-pyrrol-2-ones via coupling of 5-chloro-1,5-dihydro-2H-pyrrol-2-ones with organometallic compounds, Can. J. Chem., vol. 78, pp. 1285-1288 (2000).
Truitt, P., et al., 3-Phenylphthalimidines, New Compounds, J. Med. Chem., vol. 8, pp. 731-732 (1965).
Liebl, R., et al., Notiz zur Synthese von 3-[Aklyl(aryl)thio]isoindolinonen aus 2-Formylbenzoesäure-methylester, Liebigs Ann. Chem., pp. 1093-1094 (1985).
Usov, V.A., et al., Formation of Isoquinolones and Isoindolones in the Oxidation of 2-Aryl-1-phenylamino-3-phenyliminoindenes, Chemistry of Heterocyclic Compounds (Khimiya Geterotsiklicheskikh Soedinenil), vol. 5, No. 4, pp. 474-477 (1969).
Ahmed, M., et al., Preparation of Some Isoindolo[2,1-ƒ]phenanthridine Derivatives, J. Chem. Soc., Perkins Trans. 1, pp. 601-605 (1977).
Beanlands, D.S., et al., Therapeutic Trial Of A New Oral Diuretic, Canadian Medical Association Journal, vol. 84, pp. 91-95 (1961).
Chene, P., et al., A Small Synthetic Peptide, which Inhibits the p53-hdm2 Interaction, Stimulates the p53 Pathway in Tumour Cell Lines, J. Molecular Biology, vol. 299, pp. 245-253 (2000).
Donehower, L.A., et al., Mice deficient for p53 are developmentally normal but susceptible to spontaneous tumours, Nature, vol. 356, pp. 215-221 (1992).
Epsztajn, J., et al., Application of Organolithium and Related Reagents in Synthesis. Part 23: Synthetic Strategies Based on ortho-Aromatic Metallation. Synthesis of 4b-Arylisoindolo[2,1-α]quinolone derivatives, Tetrahedron, vol. 56 pp. 4837-4844 (2000).
Ghosh, M., et al., Overexpression of Mdm2 and MdmX Fusion Proteins Alters p53 Mediated Transactivation, Ubiquitination, and Degradation, American Chemical Society, Biochemistry, vol. 42, pp. 2291-2299 (2003).
Lane, D.P., p53, guardian of the genome, Nature, vol. 358, pp. 15-16 (1992).
Levine, A.J., p53, the Cellular Gatekeeper for Growth and Division, Cell, vol. 88, pp. 323-331 (1997).
Oliner, J.D., et al., Amplification of a gene encoding a p53-associated protein in human sarcomas, Nature, vol. 358, pp. 80-83 (1992).
Schon, O., et al., Molecular Mechanism of the Interaction between MDM2 and p53, Journal of Molecular Biology, vol. 323, pp. 491-501 (2002).
Toledo, F., et al., Regulating the p53 pathway: in vitro hypotheses, in vivo veritas, Nature Reviews Cancer, vol. 6, pp. 909-923 (2006).
Vassilev, L.T., et al., In Vivo Activation of the p53 Pathway by Small-Molecule Antagonists of MDM2, Science, vol. 303, pp. 844-848 (2004).
Golik, U., The Synthesis of some 2,4-Benzodiazepin-1-ones, Potent C.N.S. Agents (I), Journal of Heterocyclic Chemistry, vol. 12, No. 5, pp. 903-908 (1975).

Hardcastle, I.R., et al., Small-Molecule Inhibitors of the MDM2-p53 Protein-Protein Interaction Based on an Isoindolinone Scaffold, Journal of Medicinal Chemistry (2006), 49(21), 6209-6221.
Suzuki, T., et al., Novel Chemoselective Desulfurization of γ-Phenylthio-Substituted Aromatic Lactams: Application to the Synthesis of Isoindolobenzazepine Alkaloid, Lennoxamine, *Synlett*, No. 20, pp. 3407-3410 (2006).
Ying, H., et al., The Docking Based 3D-Qsar Studies on Isoindolinone Derived Inhibitors of p53-MDM2 Binding, Letters in Drug Design & Discovery, vol. 11, pp. 50-58 (2014).
Mondal, C., et al., Comparative validated molecular modeling of p53-HDM2 inhibitors as antiproliferative agents, European Journal of Medicinal Chemistry, vol. 90, pp. 860-875 (2015).
Dong, X., et al., QSAR Models for isoindolinone-based p53-MDM2 Interaction Inhibitors Using Linear and Non-linear Statistical Methods, Chem Biol Drug Des, vol. 79, pp. 691-702 (2012).
Watson, A.F., et al., MDM2-p53 protein-protein interactions inhibitors: A-ring substituted isoindolinones, Bioorganic & Medicinal Chemistry Letters, vol. 21, pp. 5916-5919 (2011).
Riedinger, C., et al., Understanding Small-Molecule Binding to MDM2: Insights into Structural Effects of Isoindolinone Inhibitors from NMR Spectroscopy, Chem Biol Drug Des, vol. 77, pp. 301-308 (2011).
Hardcastle, I.R., et al., "Isoindolinone Inhibitors of the Murine Double Minute 2 (MDM2)-p53 Protein-Protein Interaction: Structure-Activity Studies Leading to Improved Potency", Journal of Medicinal Chemistry, vol. 54, pp. 1233-1243 (2011).
Grigoreva, T.A., et al., "Proapoptotic modification of substituted isoindolinones as MDM2-p53 inhibitors", *Bioorganic & Medicinal Chemistry Letters*, vol. 27, pp. 5197-5202 (2017).
Riedinger, C., et al., "Analysis of Chemical Shift Changes Reveals the Binding Modes of Isoindolinone Inhibitors of the MDM2-p53 Interaction", *Journal of the American Chemical Society*, vol. 130, No. 47, pp. 16038-16044 (2008).
Esfandiari, Armen et al., "Chemical Inhibition of Wild-Type p53-Induced Phosphatase 1 (WIP1/PPM1D) by GSK2830371 Potentiates the Sensitivity to MDM2 Inhibitors in a p53-Dependent Manner," Molecular Cancer Therapeutics, Feb. 1, 2016, pp. 379-391.
Zhang, Xiaoling et al., "Degradation of MDM2 by the Interaction Between Berberine and DAXX Leads to Potent Apoptosis in MDM2-Overexpressing Cancer Cells," Cancer Research, Therapeutics, Targets and Chemical Biology, Oct. 8, 2010, pp. 9895-9904.
Howard, Steven et al., "Isoindolinone Inhibitors of the MDM2-P53 Interaction and Process for Making Them," U.S. Appl. No. 16/498,207, filed Sep. 26, 2019, 289 pp.
Encyclopedic Dictionary of Chemistry, Moscow, Soviet Encyclopedia, 1983, pp. 130-131.
Khimicheskaya entsiklopediya (Chemical Encyclopedia), vol. 1, Bol' shaya Rossiyskaya Entsiklopediya, Moscow, 1998.
Nag., S. et al., "Targeting MDM2-p53 Interaction for Cancer Therapy: Are We There Yet?," *Curr Med Chem*. 2014, 21(5), pp. 553-574.
Chessari, Gianni et al., "Isoindolinone Inhibitors of The MDM2-P53 Interaction Having Anticancer Activity," U.S. Appl. No. 16/680,969, filed Nov. 12, 2019, 551 pp.
Chessari, Gianni et al., "Isoindolinone Inhibitors of The MDM2-P53 Interaction Having Anticancer Activity," U.S. Appl. No. 17/164,045, filed Feb. 1, 2021, 286 pp.
Chessari, Gianni et al., "Isoindolinone inhibitors of the MDM2-P53 Interaction Having Anticancer Activity," U.S. Appl. No. 17/228,151, filed Apr. 12, 2021, 525 pp.
Dyson, G., May P. "Chemistry of Synthetic Drugs", Moscow, Publishing house "Mir", 1964, pp. 12-19.
Belikov, V.G. "Farmatsevticheskaya khimiya" (English: "Pharmaceutical Chemistry"),Chapter 2.2., Moscow, Publishing house "Vysshaya shkola", 1993, pp. 43-47.
Zhao et al., Implications of Genetic and Epigenetic Alterations of CDKN2A (p16$^{INK4a}$) in Cancer, EBioMedicine 8 (2016) 30-39.
Belikov V. G., "Farmacevtičeskaâ himiâ (Pharmaceutical chemistry)", Chapter 2.6, M.: MEDpress-inform, 2007, pp. 27-29.
Petrovskij, B. V., "Bol'šaâ medicinskaâènciklopediâ (Big encyclopedia of medicine)", 1981, vol. 16, pp. 452-463.

(56) References Cited

OTHER PUBLICATIONS

Durnov, L. A., Goldobenko, G. V., Detskaâ onkologiâ (Pediatric oncology), Moscow: "Medicina", 2002, p. 139.

"Malaâ medicinskaâênciklopediâ (Small encyclopedia of medicine)", vol. 5, Moscow: "Medicina", 1996, pp. 90-96.

Maŝkovskij M. D., "Lekarstvennye sredstva (Medicaments)", 14th edition, vol. 1, 2011, p. 11.

Žulenko, V. N., Gorškov, G. I. "Farmakologiâ (English: "Pharmacolog")", 2008, pp. 34-35.

Harkevič, D. A., "Farmakologiâ (English: "Pharmacology")", 10th edition, 2010, pp. 72-74.

Uy et al., Phase 1 study of the MDM2 antagonist RO6839921 in patients with acute myeloid leukemia, Investigational New Drugs, 2020, vol. 38, pp. 1430-1441.

Kojima et al., MDM2 antagonists induce p53-dependent apoptosis in AML: implications for leukemia therapy, Blood, 2005, vol. 106(9), pp. 3150-3159.

Iorio et al., A Landscape of Pharmacogenomic Interactions in Cancer, 2016, Cell 166, 740-754.

Ji et al., p53 Rescue through HDM2 Antagonism Suppresses Melanoma Growth and Potentiates MEK Inhibition, Journal of Investigative Dermatology (2012) vol. 132, 356-364.

Crane et al., Nutlin-3a: A Potential Therapeutic Opportunity for TP53 Wild-Type Ovarian Carcinomas, Plos One 10(8): e0135101 2015.

Tagawa et al., Molecular Therapy, vol. 24, Supplement 1, Abstract 211., 2016, Combination of Forced Transduction of P53 and an Agent That Blocks MDM2-p53 Interactions Produces Synergistic Cytotoxicity on Mesothelioma Defective of the INK4A/ARF Region.

Tagawa et al., Human Gene Therapy, vol. 26 (10), Abstracts supplement, abstract: P014, 2016, Inhibited interaction between p53 and Mdm2 enhances p53-mediated cytotoxic activities on INK4A/ARF defective mesothelioma.

Kitagawa et al., Skp2 Suppresses p53-Dependent Apoptosis by Inhibiting p300, Molecular Cell 29, 217-231, 2008.

Knijnenburg et al., 2018, Cell Reports 23, 239-254.

Chander, et al., Skp2B attenuates p53 function by inhibiting prohibitin, EMBO reports vol. 11, No. 3, 2010.

Molm-13:

| SGI-110 (μM) | (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (μM) | | | | | | | | | |
|---|---|---|---|---|---|---|---|---|---|---|
| | 0 | 0.001 | 0.003 | 0.01 | 0.03 | 0.1 | 0.3 | 1 | 3 | 10 |
| 0 | 100 | 98 | 99 | 84 | 52 | 37 | 27 | 24 | 22 | 15 |
| 0.003 | 96 | 96 | 89 | 68 | 33 | 25 | 18 | 16 | 16 | 14 |
| 0.01 | 84 | 76 | 68 | 41 | 27 | 18 | 14 | 12 | 12 | 10 |
| 0.03 | 72 | 66 | 55 | 35 | 23 | 17 | 13 | 12 | 12 | 10 |
| 0.1 | 53 | 41 | 35 | 27 | 18 | 13 | 11 | 10 | 11 | 9 |
| 0.3 | 39 | 31 | 29 | 23 | 16 | 13 | 10 | 10 | 10 | 9 |
| 1 | 31 | 25 | 24 | 19 | 14 | 11 | 10 | 9 | 10 | 8 |
| 3 | 22 | 23 | 22 | 18 | 13 | 11 | 10 | 10 | 9 | 8 |

| | (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (μM) | | | | | | | | | |
|---|---|---|---|---|---|---|---|---|---|---|
| SGI-110 (μM) | 0 | 0.001 | 0.003 | 0.01 | 0.03 | 0.1 | 0.3 | 1 | 3 | 10 |
| 0 | 100 | 92 | 82 | 70 | 54 | 29 | 16 | 13 | 13 | 12 |
| 0.003 | 92 | 80 | 71 | 56 | 43 | 27 | 16 | 13 | 13 | 13 |
| 0.01 | 89 | 68 | 62 | 50 | 37 | 23 | 15 | 13 | 13 | 13 |
| 0.03 | 89 | 64 | 58 | 47 | 35 | 22 | 14 | 13 | 13 | 12 |
| 0.1 | 83 | 65 | 58 | 47 | 37 | 22 | 14 | 13 | 13 | 12 |
| 0.3 | 76 | 57 | 53 | 45 | 36 | 22 | 14 | 13 | 13 | 12 |
| 1 | 60 | 51 | 47 | 41 | 33 | 21 | 14 | 13 | 13 | 12 |
| 3 | 50 | 49 | 46 | 38 | 32 | 22 | 14 | 12 | 12 | 12 |

| SGI-110 (μM) | (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (μM) | | | | | | | | | |
| --- | --- | --- | --- | --- | --- | --- | --- | --- | --- | --- |
| | 0 | 0.001 | 0.003 | 0.01 | 0.03 | 0.1 | 0.3 | 1 | 3 | 10 |
| 0 | 100 | 100 | 94 | 78 | 59 | 47 | 30 | 16 | 15 | 9 |
| 0.003 | 94 | 96 | 85 | 69 | 52 | 38 | 23 | 14 | 13 | 10 |
| 0.01 | 92 | 91 | 77 | 59 | 47 | 31 | 19 | 13 | 12 | 9 |
| 0.03 | 87 | 82 | 68 | 53 | 45 | 30 | 19 | 13 | 12 | 9 |
| 0.1 | 78 | 78 | 65 | 51 | 43 | 29 | 20 | 14 | 13 | 8 |
| 0.3 | 74 | 72 | 62 | 51 | 43 | 29 | 19 | 14 | 13 | 8 |
| 1 | 61 | 58 | 55 | 48 | 44 | 29 | 21 | 15 | 14 | 8 |
| 3 | 45 | 45 | 45 | 41 | 36 | 26 | 19 | 15 | 14 | 8 |

FIG. 1C

COMBINATION OF ISOINDOLINONE DERIVATIVES WITH SGI-110

CROSS REFERENCE TO RELATED APPLICATIONS

This application is a national stage filing under section 371 of International Application No. PCT/GB2018/050832, filed on Mar. 28, 2018, and published on Oct. 4, 2018 as WO 2018/178679, which claims priority to Great Britain Application No. 1704966.9, filed on Mar. 28, 2017. The entire contents of WO 2018/178679 are hereby incorporated herein by reference.

FIELD OF THE INVENTION

This invention relates to combinations of isoindolin-1-one derivatives that inhibit or modulate the activity of MDM2-p53 and a dinucleotide compound that is a hypomethylating agent (HMA), and to the therapeutic uses of such combinations.

BACKGROUND OF THE INVENTION

Isoindoline Compounds

Isoindoline compounds are disclosed in our earlier international patent applications PCT/GB2016/053042 and PCT/GB2016/053041 filed 29 Sep. 2016 claiming priority from United Kingdom patent application numbers 1517216.6 and 1517217.4 filed 29 Sep. 2015, the contents of all of which are incorporated herein by reference in their entirety. In particular, the compound (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid is disclosed in our earlier international patent application PCT/GB2016/053042.

The transformation-related protein 53 (TP53) gene encodes a 53 KDa protein p53. The tumour suppressor protein p53 reacts to cellular stresses, such as hypoxia, DNA damage and oncogenic activation, via a number of post-translational modifications including phosphorylation, acetylation and methylation, and acts as a signalling node in the diverse pathways that become activated. p53 has additional roles in other physiological processes, including autophagy, cell adhesion, cell metabolism, fertility, and stem cell aging and development. Phosphorylation of p53, resulting from activation of kinases including ATM, CHK1 and 2, and DNA-PK, results in a stabilised and transcriptionally active form of the protein, thus producing a range of gene products. The responses to p53 activation include apoptosis, survival, cell-cycle arrest, DNA-repair, angiogenesis, invasion and autoregulation. The specific combination of which, in concert with the cell's genetic background, gives rise to the observed cellular effect i.e. apoptosis, cell-cycle arrest or senescence. For tumour cells, the apoptotic pathway may be favoured due to the loss of tumour suppressor proteins and associated cell cycle checkpoint controls, coupled with oncogenic stress.

Under conditions of stress such as hypoxia and DNA damage it is known that the cellular level of the protein p53 increases. p53 is known to initiate transcription of a number of genes which govern progression through the cell cycle, the initiation of DNA repair and programmed cell death. This provides a mechanism for the tumour suppressor role of p53 evidenced through genetic studies.

The activity of p53 is negatively and tightly regulated by a binding interaction with the MDM2 protein, the transcription of which is itself directly regulated by p53. p53 is inactivated when its transactivation domain is bound by the MDM2 protein. Once inactivated the functions of p53 are repressed and the p53-MDM2 complex becomes a target for ubiquitinylation.

In normal cells the balance between active p53 and inactive MDM2-bound p53 is maintained in an autoregulatory negative feedback loop. That is to say that p53 can activate MDM2 expression, which in turn leads to the repression of p53.

It has been found that inactivation of p53 by mutation is common in around half of all common adult sporadic cancers. Furthermore, in around 10% of tumours, gene amplification and over-expression of MDM2 results in the loss of functional p53, thereby allowing malignant transformation and uncontrolled tumour growth.

Inactivation of p53 by a range of mechanisms is a frequent causal event in the development and progression of cancer. These include inactivation by mutation, targeting by oncogenic viruses and, in a significant proportion of cases, amplification and/or an elevated rate of transcription of the MDM2 gene resulting in overexpression or increased activation of the MDM2 protein. Gene amplification of MDM2 giving rise to overexpression of MDM2 protein has been observed in tumour samples taken from common sporadic cancers. Overall, around 10% of tumours had MDM2 amplification, with the highest incidence found in hepatocellular carcinoma (44%), lung (15%), sarcomas and osteosarcomas (28%), and Hodgkin disease (67%) (Danovi et al., Mol. Cell. Biol. 2004, 24, 5835-5843, Toledo et al., Nat Rev Cancer 2006, 6, 909-923, Gembarska et al., Nat Med 2012, 18, 1239-1247). Normally, transcriptional activation of MDM2 by activated p53 results in increased MDM2 protein levels, forming a negative feedback loop. The essential nature of p53 regulation by MDM2 and MDMX is demonstrated by gene knockout mouse models. MDM2−/− knockout mice are embryonically lethal around the time of implantation. Lethality is rescued in the double knockout for Mdm2 and Trp53. MDM2 inhibits the activity of p53 directly, by binding to and occluding the p53 transactivation domain, and by promoting the proteosomal destruction of the complex, through its E3-ubiquitin ligase activity. In addition, MDM2 is a transcriptional target of p53, and so the two proteins are linked in an autoregulatory feedback loop, ensuring that p53 activation is transient.

The induction of the p14ARF protein, the alternate reading frame (ARF) product of the p16INK4a locus, is also a mechanism of negatively regulating the p53-MDM2 interaction. p14ARF directly interacts with MDM2 and leads to up-regulation of p53 transcriptional response. Loss of p14ARF by a homozygous mutation in the CDKN2A (INK4A) gene will lead to elevated levels in MDM2 and, therefore, loss of p53 function and cell cycle control.

Although MDMX shows strong amino acid sequence and structural homology to MDM2, neither protein can substitute for loss of the other; MDMX null mice die in utero, whereas MDM2 knockout is lethal during early embryogenesis, however both can be rescued by p53 knockout, demonstrating p53-dependence of the lethality. MDMX also binds p53 and inhibits p53-dependent transcription, but unlike MDM2 it is not transcriptionally activated by p53 and so does not form the same autoregulatory loop. Furthermore, MDMX has neither E3 ubiquitin ligase activity nor a nuclear localisation signal, however it is believed to contribute to p53 degradation by forming heterodimers with MDM2 and contributing to MDM2 stabilisation.

The therapeutic rationale for MDM2-p53 inhibition is that a potent inhibitor of the protein-protein interaction will liberate p53 from the repressive control of MDM2, and activate p53 mediated cell death in the tumour. In tumours, selectivity is envisioned to result from p53 sensing preexisting DNA-damage or oncogenic activation signals that had previously been blocked by the action of MDM2 at normal or overexpressed levels. In normal cells, p53 activation is anticipated to result in activation of non-apoptotic pathways and if anything a protective growth inhibition response. In addition due to the non-genotoxic mechanism of action for MDM2-p53 inhibitors they are suitable for the treatment of cancer in particular in the pediatric population.

About 50% of cancers harbour cells in which TP53, the gene that encodes for p53, is mutated resulting in a loss of the protein's tumour suppressor function and sometimes even in p53 protein versions that gain novel oncogenic functions.

Cancers where there is a high level of MDM2 amplification include liposarcoma (88%), soft tissue sarcoma (20%), osteosarcoma (16%) oesophageal cancer (13%), and certain paediatric malignancies including B-cell malignancies.

Dinucleotide Compound

The dinucleotide compound SGI-110 (or 2'-deoxy-5-azacytidylyl-(3'→5')-2'-deoxy-guanosine or guadecitabine) was disclosed in WO2007/041071:

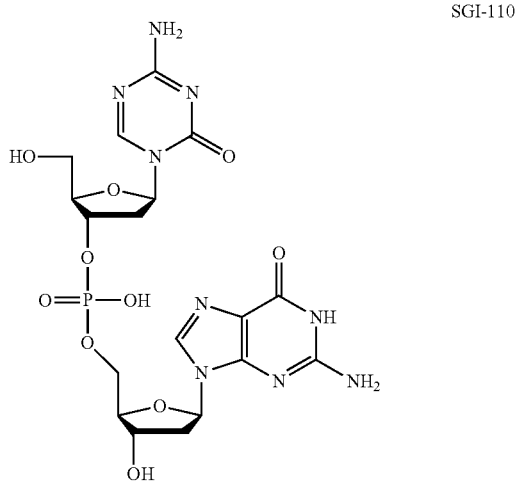

SGI-110

SGI-110 is a next generation hypomethylating agent, which inhibits DNA methyltransferases.

Drug formulations containing SGI-110 are disclosed in WO2013/033176 and WO2017/004538, and combinations containing SGI-110 are disclosed in WO2014/134355. The contents of WO2007/041071, WO2013/033176, WO2014/134355 and WO2017/004538 are incorporated herein by reference in their entirety.

Epigenetic modification of the genome, and in particular DNA methylation, plays a major role in human malignancies by influencing crucial cellular pathways in cancer initiation and progression (including cell cycle control, apoptosis, invasive and metastatic potential and angiogenesis). DNA methylation is mediated by the enzyme DNA methyltransferase, and results in the addition of a methyl group to a cytosine when the cytosine occurs in the context of a CpG dinucleotide.

DNA methylation of promoter-associated CpG islands results in silencing of the corresponding gene—in general, promoter-associated CpG islands are unmethylated in non-malignant cells. Aberrant DNA hypermethylation in tumour cells is therefore a functional equivalent to inactivation of tumour suppressor genes by mutation, and so promotes tumour escape from host immune recognition via the down-regulation of various components of the tumour recognition complex in neoplastic cells (including HLA class I antigens, CTA antigens and accessory/co-stimulatory molecules). This results in a reduction in clinical efficacy of immunotherapeutic approaches for cancer treatment.

DNA hypomethylating agents (HMAs) induce global and gene-specific DNA hypomethylation. This promotes re-expression of tumour-associated antigens and thereby boosts immune recognition. Examples include 5-azacytidine, 5-aza-2'-deoxycytidine (decitabine) and Zebularine: 5-azacytidine and 5-aza-2'-deoxycytidine are currently approved by the US Food and Drug Administration for the treatment of patients with myelodysplastic syndromes, and decitabine is currently being developed as a pharmaceutical for the treatment of chronic myelogenous leukemia (CML), myelodysplastic syndrome (MDS), non-small cell lung cancer (NSCLC), sickle-cell anaemia and acute myelogenous leukemia (AML).

SUMMARY OF THE INVENTION

The invention provides combinations of isoindolin-1-one derivatives that inhibit or modulate the activity of MDM2-p53 and a dinucleotide compound that is a hypomethylating agent (HMA), wherein the combinations have efficacy against abnormal cell growth.

In one aspect, the invention provides a combination of
(i) a compound of formula (I°):

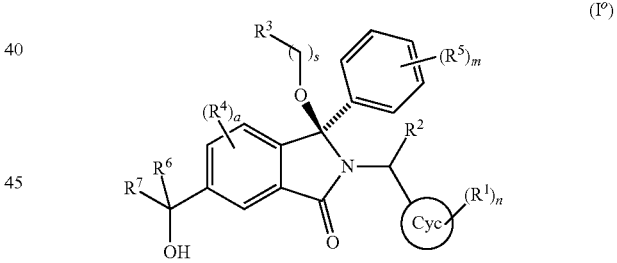

(I°)

or a tautomer or a solvate or a pharmaceutically acceptable salt thereof, wherein:

wherein cyc is phenyl or a heterocyclic group Het which is pyridinyl, pyrimidinyl, pyrazinyl or pyridazinyl, or an N-oxide thereof;

$R^1$ is independently selected from hydroxy, halogen, nitro, nitrile, $C_{1-4}$ alkyl, halo$C_{1-4}$alkyl, hydroxy$C_{1-4}$alkyl, $C_{2-6}$ alkenyl, $C_{1-4}$ alkoxy, halo$C_{1-4}$alkoxy, $C_{2-4}$ alkynyl, $-O_{0-1}-(CR^xR^y)_v-CO_2H$, $-(CR^xR^y)_v-CO_2C_{1-4}$alkyl, $-(CR^xR^y)_v-CON(C_{1-4}$alkyl$)_2$, $-P(=O)(R^x)_2$, $-S(O)_d-R^x$, $-S(O)_d$-heterocyclic group with 3 to 6 ring members and $-S(O)_d-N(R^8)_2$, wherein when cyc is Het then $R^1$ is attached to a carbon atom;

$R^2$ is selected from hydrogen, $C_{1-4}$ alkyl, $C_{2-6}$ alkenyl, hydroxy$C_{1-4}$alkyl, $-(CR^xR^y)_u-CO_2H$, $-(CR^xR^y)_u-CO_2C_{1-4}$alkyl, and $-(CR^xR^y)_u-CONR^xR^y$;

s is selected from 0 and 1;

$R^3$ is hydrogen or $-(A)_t-(CR^xR^y)_q-X$;

t is selected from 0 and 1;

q is selected from 0, 1 and 2;

wherein when $R^3$ is $-(A)_r-(CR^xR^y)_q-X$ then (i) at least one of s, t and q is other than 0 and (ii) when t is 0 then s is 1 and q is other than 0;

A is a $C_{3-6}$ cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$ alkyl, —S(O)$_d$—R$^x$, —C(=O)—C$_{1-4}$alkyl, —S(O)$_d$—N(H)$_e$(C$_{1-4}$alkyl)$_{2-e}$, —NR$^x$R$^y$, —NHSO$_2$R$^x$, —NR$^x$COR$^y$, and —C(=O)NR$^x$R$^y$;

$R^4$ and $R^5$ are independently selected from halogen, nitrile, $C_{1-4}$ alkyl, haloC$_{1-4}$alkyl, $C_{1-4}$alkoxy and haloC$_{1-4}$alkoxy;

$R^6$ and $R^7$ are independently selected from hydrogen, $C_{1-6}$alkyl, $C_{2-6}$ alkenyl, $C_{2-6}$alkynyl, hydroxy, hydroxyC$_{1-6}$alkyl, —COOC$_{1-6}$alkyl, —(CH$_2$)$_j$—O—C$_{1-6}$alkyl, —(CH$_2$)$_j$—O-(hydroxyC$_{1-6}$ alkyl), —C$_{1-6}$ alkyl-NR$^x$R$^y$, —(CR$^x$R$^y$)$_p$—CONR$^x$R$^y$, —(CR$^x$R$^y$)$_p$—NR$^x$COR$^y$, —(CR$^x$R$^y$)$_p$—O—CH$_2$—CONR$^x$R$^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-8}$alkyl)-heterocyclic group with 3 to 7 ring members, —C(=O)NH-heterocyclic group with 3 to 7 ring members, $C_{3-8}$cycloalkyl, —CH$_2$—C$_{3-8}$ cycloalkyl, —CH$_2$—O—C$_{3-8}$cycloalkyl, and $C_{3-6}$ cycloalkenyl, wherein said cycloalkyl, cycloalkenyl or heterocyclic groups may be optionally substituted by one or more Rz groups, and wherein in each instance the heterocyclic group comprises one or more (e.g. 1, 2, or 3) heteroatoms selected from N, O, S and oxidised forms thereof;

or the $R^6$ and $R^7$ groups, together with the carbon atom to which they are attached, can join to form a $C_{3-6}$ cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-6}$cycloalkyl and heterocyclyl groups may be optionally substituted by one or more RZ groups;

$R^8$ and $R^9$ are independently selected from hydrogen, $C_{1-6}$alkyl, hydroxyC$_{1-6}$alkyl, —(CH$_2$)$_k$—O—C$_{1-6}$ alkyl, —(CH$_2$)$_k$—O-(hydroxyC$_{1-6}$alkyl), hydroxyC$_{1-6}$ alkoxy, —(CH$_2$)$_k$—CO$_2$C$_{1-6}$ alkyl, —(CH$_2$)$_k$—CO$_2$H, —C$_{1-6}$ alkyl-N(H)$_e$(C$_{1-4}$ alkyl)$_{2-e}$, —(CH$_2$)$_j$—C$_{3-8}$cycloalkyl and —(CH$_2$)$_j$—C$_{3-8}$cycloalkenyl;

$R^x$ and $R^y$ are independently selected from hydrogen, halogen, nitro, nitrile, $C_{1-6}$alkyl, haloC$_{1-6}$alkyl, $C_{2-6}$alkenyl, $C_{2-6}$ alkynyl, hydroxy, hydroxyC$_{1-6}$ alkyl, $C_{1-6}$alkoxy, —(CH$_2$)$_k$—O—C$_{1-6}$alkyl, hydroxyC$_{1-6}$ alkoxy, —N(H)$_e$(C$_{1-4}$alkyl)$_{2-e}$, —C$_{1-6}$alkyl-N(H)$_e$ (C$_{1-4}$ alkyl)$_{2-e}$, —(CH$_2$)$_k$—C(=O)N(H)$_e$(C$_{1-4}$ alkyl)$_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =CH$_2$ group;

$R^z$ is independently selected from halogen, nitro, nitrile, $C_{1-6}$alkyl, haloC$_{1-6}$alkyl, $C_{2-6}$ alkenyl, $C_{2-6}$alkynyl, =O, hydroxy, hydroxyC$_{1-6}$alkyl, $C_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$ alkyl-OH, —C(=O)C$_{1-6}$ alkyl-N(H)$_e$(C$_{1-4}$alkyl)$_{2-e}$, —C(=O)N(H)$_e$(C$_{1-4}$alkyl)$_{2-e}$, —(CH$_2$)$_r$—CO$_2$C$_{1-6}$alkyl, —(CH$_2$)$_r$—CO$_2$H, —N(H)$_e$ (C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, $C_{3-8}$ cycloalkyl and $C_{3-8}$cycloalkenyl, wherein if $R^7$ is pyridine then $R^z$ is other then —NH$_2$;

a, j, d, e, n, r and p are independently selected from 0, 1 and 2;

k and m are independently selected from 1 and 2;

u is selected from 0, 1, 2 and 3; and v and w are independently selected from 0 and 1; and (ii) a compound which is SGI-110

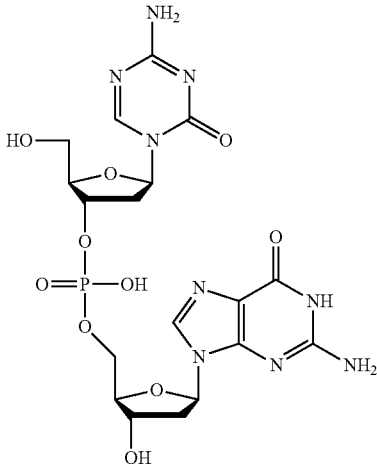

(SGI-110)

or a tautomer or a solvate or a pharmaceutically acceptable salt thereof.

In further aspects of the invention there is provided the combination for use in the prophylaxis or treatment of a disease or condition as described herein, methods for the prophylaxis or treatment of a disease or condition as described herein comprising administering to a patient the combination, and pharmaceutical compositions comprising the combination.

In particular, the invention provides:

A combination comprising a combination as disclosed herein and one or more (e.g. 1 or 2) other therapeutic agents (e.g. anticancer agents).

A combination as disclosed herein wherein the compound of formula (I°) and SGI-110 are physically associated.

A combination as disclosed herein wherein the compound of formula (I°) and SGI-110 are: (a) in admixture; (b) chemically/physicochemically linked; (c) chemically/physicochemically co-packaged; or (d) unmixed but co-packaged or co-presented.

A combination as disclosed herein wherein the compound of formula (I°) and SGI-110 are non-physically associated.

A combination as disclosed herein wherein the combination comprises: (a) at least one of the two or more compounds together with instructions for the extemporaneous association of the at least one compound to form a physical association of the two or more compounds; or (b) at least one of the two or more compounds together with instructions for combination therapy with the two or more compounds; or (c) at least one of the two or more compounds together with instructions for administration to a patient population in which the other(s) of the two or more compounds have been (or are being) administered; or (d) at least one of the two or more compounds in an amount or in a form which is specifically adapted for use in combination with the other(s) of the two or more compounds.

A combination as disclosed herein in the form of a pharmaceutical kit or patient pack.

A pharmaceutical composition comprising a combination as disclosed herein.

A combination or a pharmaceutical composition as disclosed herein for use in therapy.

A combination or a pharmaceutical composition as disclosed herein for use in the prophylaxis or treatment of a disease state or condition as described herein.

A use of a combination or a pharmaceutical composition as disclosed herein for the manufacture of a medicament for use in the prophylaxis or treatment of a disease state or condition as described herein.

A method for the prophylaxis or treatment of a disease or condition as described herein comprising administering to a patient a combination or a pharmaceutical composition as disclosed herein.

A method for the prophylaxis or treatment of a disease or condition as described herein, comprising administering to patient in need thereof (i) SGI-110, or a tautomer, N-oxide, pharmaceutically acceptable salt or solvate thereof and (ii) a compound of formula (I°) as defined herein, or a tautomer, N-oxide, pharmaceutically acceptable salt or solvate thereof.

A combination or a pharmaceutical composition for use as disclosed herein, or a method for the prophylaxis or treatment as disclosed herein, wherein the disease state or condition is mediated by MDM2-p53.

A combination or a pharmaceutical composition for use as disclosed herein, or a method for the prophylaxis or treatment as disclosed herein, wherein the disease state or condition is cancer.

A combination or a pharmaceutical composition for use as disclosed herein, or a method for the prophylaxis or treatment as disclosed herein, wherein the disease state or condition is a cancer which is acute myeloid leukaemia.

A combination of (i) (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, or a tautomer, N-oxide, pharmaceutically acceptable salt or solvate thereof; and (ii) and SGI-110, or a tautomer, N-oxide, pharmaceutically acceptable salt or solvate thereof, for the prophylaxis or treatment of a disease state or condition which is cancer.

A combination for use as disclosed herein forr the prophylaxis or treatment of acute myeloid leukaemia.

A compound of formula (I°) as disclosed herein, or a tautomer, N-oxide, pharmaceutically acceptable salt or solvate thereof, for use in the prophylaxis or treatment of a disease state or condition as described herein, wherein the compound of formula (I°) is used in combination with SGI-110, or a tautomer, N-oxide, pharmaceutically acceptable salt or solvate thereof.

(2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid or a tautomer, N-oxide, pharmaceutically acceptable salt or solvate thereof, for use in the prophylaxis or treatment of a disease state or condition as described herein, wherein the compound of formula (I°) is used in combination with SGI-110, or a tautomer, N-oxide, pharmaceutically acceptable salt or solvate thereof.

SGI-110, or a tautomer, N-oxide, pharmaceutically acceptable salt or solvate thereof, for use in the prophylaxis or treatment of a disease state or condition as described herein, wherein SGI-110 is used in combination with a compound of formula (I°) as disclosed herein, or a tautomer, N-oxide, pharmaceutically acceptable salt or solvate thereof, for example wherein the compound of formula (I°) is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid.

A compound of formula (I°) as disclosed herein, or a tautomer, N-oxide, pharmaceutically acceptable salt or solvate thereof, for use in combination therapy with SG1-110, and optionally with one or more other therapeutic agent to prevent, treat or manage cancer in a patient in need thereof.

The use of a compound of Formula (I°) as disclosed herein, or a tautomer, N-oxide, pharmaceutically acceptable salt or solvate thereof, for treatment of a patient suffering from a cancer where the patient is being treated with SGI-110, or a tautomer, N-oxide, pharmaceutically acceptable salt or solvate thereof.

The use of SGI-110, or a tautomer, N-oxide, pharmaceutically acceptable salt or solvate thereof, for treatment of a patient suffering from a cancer where the patient is being treated with a compound of Formula (I°) as disclosed herein, or a tautomer, N-oxide, pharmaceutically acceptable salt or solvate thereof, as disclosed herein.

The use of a compound of Formula (I°) as disclosed herein, or a tautomer, N-oxide, pharmaceutically acceptable salt or solvate thereof, for the manufacture of a medicament for use in enhancing or potentiating the response rate in a patient suffering from a cancer where the patient is being treated with SGI-110, or a tautomer, N-oxide, pharmaceutically acceptable salt or solvate thereof.

A compound of formula (I°) as disclosed herein, or a tautomer, N-oxide, pharmaceutically acceptable salt or solvate thereof, for use in treating a disease or condition comprising or arising from abnormal cell growth in a mammal, wherein the mammal is undergoing treatment with SGI-110, or a tautomer, N-oxide, pharmaceutically acceptable salt or solvate thereof.

A compound of formula (I°) as disclosed herein, or a tautomer, N-oxide, pharmaceutically acceptable salt or solvate thereof, for use in alleviating or reducing the incidence of a disease or condition comprising or arising from abnormal cell growth in a mammal, wherein the mammal is undergoing treatment with SGI-110, or a tautomer, N-oxide, pharmaceutically acceptable salt or solvate thereof, The use of a combination as disclosed herein in the manufacture of a pharmaceutical composition for inhibiting the growth of tumour cells.

A product containing as a first active ingredient a compound of formula (I°) as disclosed herein, or a tautomer, N-oxide, pharmaceutically acceptable salt or solvate thereof, and as a further active ingredient SGI-110, or a tautomer, N-oxide, pharmaceutically acceptable salt or solvate thereof, as a combined preparation for simultaneous, separate or sequential use in the treatment of patients suffering from cancer.

BRIEF DESCRIPTION OF THE DRAWINGS

FIGS. 1A-C show percentage viability relative to the DMSO control at various dose combinations of SGI-110 and (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid. Dose combinations with synergistic effects are highlighted in grey.

DEFINITIONS

Unless the context indicates otherwise, references to formula (I°) in all sections of this document (including the uses, methods and other aspects of the invention) include references to all other sub-formula, sub-groups, embodiments and examples as defined herein.

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to a receptor. Efficacy is the relationship between receptor occupancy and the ability to initiate a response at the molecular, cellular, tissue or system level.

The term "antagonist" refers to a type of receptor ligand or drug that blocks or dampens agonist-mediated biological responses. Antagonists have affinity but no agonistic efficacy for their cognate receptors, and binding will disrupt the interaction and inhibit the function of any ligand (e.g. endogenous ligands or substrates, an agonist or inverse agonist) at receptors. The antagonism may arise directly or indirectly, and may be mediated by any mechanism and at any physiological level. As a result, antagonism of ligands may under different circumstances manifest itself in functionally different ways. Antagonists mediate their effects by binding to the active site or to allosteric sites on receptors, or they may interact at unique binding sites not normally involved in the biological regulation of the receptors activity. Antagonist activity may be reversible or irreversible depending on the longevity of the antagonist-receptor complex, which, in turn, depends on the nature of antagonist receptor binding.

As used herein, the term "mediated", as used e.g. in conjunction with MDM2/p53 as described herein (and applied for example to various physiological processes, diseases, states, conditions, therapies, treatments or interventions) is intended to operate limitatively so that the various processes, diseases, states, conditions, treatments and interventions to which the term is applied are those in which the protein plays a biological role. In cases where the term is applied to a disease, state or condition, the biological role played by the protein may be direct or indirect and may be necessary and/or sufficient for the manifestation of the symptoms of the disease, state or condition (or its aetiology or progression). Thus, the protein function (and in particular aberrant levels of function, e.g. over- or under-expression) need not necessarily be the proximal cause of the disease, state or condition: rather, it is contemplated that the mediated diseases, states, or conditions include those having multifactorial aetiologies and complex progressions in which the protein in question is only partially involved. In cases where the term is applied to treatment, prophylaxis or intervention, the role played by the protein may be direct or indirect and may be necessary and/or sufficient for the operation of the treatment, prophylaxis or outcome of the intervention. Thus, a disease state or condition mediated by a protein includes the development of resistance to any particular cancer drug or treatment.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurance of a disease or guarding from a disease.

Prophylaxis includes complete and total blocking of all symptoms of a disorder for an indefinite period of time, the mere slowing of the onset of one or several symptoms of the disease, or making the disease less likely to occur.

References to the prophylaxis or treatment of a disease state or condition such as cancer include within their scope alleviating or reducing the incidence e.g. of cancer.

The term "combination" and "combinations of the invention" refer to combinations of the compounds of formula (I°) and SGI-110.

The term "compound", "compounds" "compound of the invention" and "compounds of the invention" refers to the compounds which are present in the combination, that is the SG1-110 and compounds of formula (I°) and all sub-groups and specific examples thereof.

The combinations may produce a therapeutically efficacious effect relative to the therapeutic effect of the individual compounds/agents when administered separately.

The term 'efficacious' includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect. A "synergistic" effect in the present context refers to a therapeutic effect produced by the combination which is larger than the sum of the therapeutic effects of the agents of the combination when presented individually. An "additive" effect in the present context refers to a therapeutic effect produced by the combination which is larger than the therapeutic effect of any of the agents of the combination when presented individually. The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50%.

As used herein, the term combination, as applied to two or more compounds and/or agents, is intended to define material in which the two or more agents are associated. The terms "combined" and "combining" in this context are to be interpreted accordingly.

The association of the two or more compounds/agents in a combination may be physical or non-physical. Examples of physically associated combined compounds/agents include:
- compositions (e.g. unitary formulations) comprising the two or more compounds/agents in admixture (for example within the same unit dose);
- compositions comprising material in which the two or more compounds/agents are chemically/physicochemically linked (for example by crosslinking, molecular agglomeration or binding to a common vehicle moiety);
- compositions comprising material in which the two or more compounds/agents are chemically/physicochemically co-packaged (for example, disposed on or within lipid vesicles, particles (e.g. micro- or nanoparticles) or emulsion droplets);
- pharmaceutical kits, pharmaceutical packs or patient packs in which the two or more compounds/agents are co-packaged or co-presented (e.g. as part of an array of unit doses);

Examples of non-physically associated combined compounds/agents include:
- material (e.g. a non-unitary formulation) comprising at least one of the two or more compounds/agents together with instructions for the extemporaneous association of the at least one compound to form a physical association of the two or more compounds/agents;
- material (e.g. a non-unitary formulation) comprising at least one of the two or more compounds/agents together with instructions for combination therapy with the two or more compounds/agents;
- material comprising at least one of the two or more compounds/agents together with instructions for administration to a patient population in which the other(s) of the two or more compounds/agents have been (or are being) administered;
- material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: Each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

The term 'optionally substituted' as used herein refers to a group which may be unsubstituted or substituted by a substituent as herein defined.

The prefix "$C_{x-y}$" (where x and y are integers) as used herein refers to the number of carbon atoms in a given group. Thus, a $C_{1-6}$ alkyl group contains from 1 to 6 carbon atoms, a $C_{3-6}$ cycloalkyl group contains from 3 to 6 carbon atoms, a $C_{1-4}$ alkoxy group contains from 1 to 4 carbon atoms, and so on.

The term 'halo' or 'halogen' as used herein refers to fluorine, chlorine, bromine or iodine, in particular fluorine or chlorine.

Each and every hydrogen in the compound (such as in an alkyl group or where referred to as hydrogen) includes all isotopes of hydrogen, in particular $^1H$ and $^2H$ (deuterium).

The term 'oxo' as used herein refers to the group =O.

The term '$C_{1-4}$alkyl' as used herein as a group or part of a group refers to a linear or branched saturated hydrocarbon group containing from 1 to 4 carbon atoms respectively. Examples of such groups include methyl, ethyl, n-propyl, isopropyl, n-butyl, isobutyl, sec-butyl, tert butyl and the like.

The term '$C_{2-4}$ alkenyl' or '$C_{2-6}$alkenyl' as used herein as a group or part of a group refers to a linear or branched hydrocarbon group containing from 2 to 4, or 2 to 6 carbon atoms, respectively, and containing a carbon carbon double bond. Examples of such groups include $C_{3-4}$alkenyl or $C_{3-8}$alkenyl groups, such as ethenyl (vinyl), 1-propenyl, 2-propenyl (allyl), isopropenyl, butenyl, buta-1,4-dienyl, pentenyl, and hexenyl.

The term '$C_{2-4}$ alkynyl' or '$C_{2-6}$ alkynyl' as used herein as a group or part of a group refers to a linear or branched hydrocarbon group having from 2 to 4 or 2 to 6 carbon atoms, respectively, and containing a carbon carbon triple bond. Examples of such groups include $C_{3-4}$ alkynyl or $C_{3-6}$alkynyl groups such as ethynyl and 2 propynyl (propargyl) groups.

The term '$C_{1-4}$alkoxy' as used herein as a group or part of a group refers to an —O—$C_{1-4}$alkyl group wherein $C_{1-4}$alkyl is as defined herein. Examples of such groups include methoxy, ethoxy, propoxy, butoxy, and the like.

The term '$C_{3-8}$ cycloalkyl' as used herein refers to a saturated monocyclic hydrocarbon ring of 3 to 6 carbon atoms. Examples of such groups include cyclopropyl, cyclobutyl, cyclopentyl or cyclohexyl and the like.

The term 'C$_{3-6}$ cycloalkenyl' as used herein refers to a partially saturated monocyclic hydrocarbon ring of 3 to 6 carbon atoms having one or more (usually one) carbon carbon double bond(s). Examples of such groups include cyclopentenyl, cyclohexenyl, and cyclohexadienyl.

The term 'hydroxyC$_{1-4}$alkyl' as used herein as a group or part of a group refers to a C$_{1-4}$ alkyl group as defined herein wherein one or more (e.g. 1, 2 or 3) than one hydrogen atom is replaced with a hydroxyl group. The term 'hydroxyC$_{1-4}$alkyl' therefore includes monohydroxyC$_{1-4}$alkyl, and also polyhydroxyC$_{1-4}$alkyl. There may be one, two, three or more hydrogen atoms replaced with a hydroxyl group, so the hydroxyC$_{1-4}$alkyl may have one, two, three or more hydroxyl groups. Examples of such groups include hydroxymethyl, hydroxyethyl, hydroxypropyl and the like.

The term 'haloC$_{1-4}$alkyl' as used herein as a group or part of a group refers to a C$_{1-4}$alkyl group as defined herein wherein one or more (e.g. 1, 2 or 3) than one hydrogen atom is replaced with a halogen. The term 'haloC$_{1-4}$alkyl' therefore includes monohaloC$_{1-4}$alkyl and also polyhaloC$_{1-4}$alkyl. There may be one, two, three or more hydrogen atoms replaced with a halogen, so the haloC$_{1-4}$alkyl may have one, two, three or more halogens. Examples of such groups include fluoroethyl, fluoromethyl, difluoromethyl, trifluoromethyl or trifluoroethyl and the like.

The term 'haloC$_{1-4}$alkoxy' as used herein as a group or part of a group refers to a —O—C$_{1-4}$ alkyl group as defined herein wherein one or more (e.g. 1, 2 or 3) than one hydrogen atom is replaced with a halogen. The terms 'haloC$_{1-4}$alkoxy' therefore include monohaloC$_{1-4}$alkoxy, and also polyhaloC$_{1-4}$alkoxy. There may be one, two, three or more hydrogen atoms replaced with a halogen, so the haloC$_{1-4}$alkoxy may have one, two, three or more halogens. Examples of such groups include fluoroethyloxy, difluoromethoxy or trifluoromethoxy and the like.

The term "heterocyclyl group" as used herein shall, unless the context indicates otherwise, include both aromatic and non-aromatic ring systems. Thus, for example, the term "heterocyclyl group" include within their scope aromatic, non-aromatic, unsaturated, partially saturated and saturated heterocyclyl ring systems. In general, unless the context indicates otherwise, such groups may be monocyclic or bicyclic (including fused, spiro and bridged bicyclic groups) and may contain, for example, 3 to 12 ring members, more usually 5 to 10 ring members. Reference to 4 to 7 ring members includes 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, or 4 to 7 and preferably 5, 6 or 7 ring members, more preferably 5 or 6 ring members. Examples of bicyclic groups are those containing 8, 9, 10, 11 and 12 ring members, and more usually 9 or 10 ring members. The heterocyclyl groups can be heteroaryl groups having from 5 to 12 ring members, more usually from 5 to 10 ring members. Where reference is made herein to a heterocyclyl group, the heterocyclyl ring can, unless the context indicates otherwise, be optionally substituted i.e. unsubstituted or substituted, by one or more (e.g. 1, 2, 3, or 4 in particular one or two) substituents as defined herein.

The heterocyclyl group can be, for example, a five membered or six membered monocyclic ring or a bicyclic structure formed from fused five and six membered rings or two fused six membered rings, or two fused five membered rings. Each ring may contain up to five heteroatoms particularly selected from nitrogen, sulfur and oxygen and oxidised forms of nitorgen or sulfur. Particularly the heterocyclyl ring will contain up to 4 heteroatoms, more particularly up to 3 heteroatoms, more usually up to 2, for example a single heteroatom. In one embodiment, the heterocyclyl ring will contain one or two heteroatoms selected from N, O, S and oxidised forms of N or S. In one embodiment, the heterocyclyl ring contains at least one ring nitrogen atom. The nitrogen atoms in the heterocyclyl rings can be basic, as in the case of an imidazole or pyridine, or essentially non-basic as in the case of an indole or pyrrole nitrogen. In general the number of basic nitrogen atoms present in the heterocyclyl group, including any amino group substituents of the ring, will be less than five.

The heterocyclyl groups can be attached via a carbon atom or a heteroatom (e.g. nitrogen). Equally the heterocyclyl groups can be substituted on a carbon atom or on a heteroatom (e.g. nitrogen).

Examples of five membered aromatic heterocyclyl groups include but are not limited to pyrrolyl, furanyl, thienyl, imidazolyl, furazanyl, oxazolyl, oxadiazolyl, oxatriazolyl, isoxazolyl, thiazolyl, thiadiazolyl, isothiazolyl, pyrazolyl, triazolyl and tetrazolyl groups.

Examples of six membered aromatic heterocyclic groups include but are not limited to pyridinyl, pyrazinyl, pyridazinyl, pyrimidinyl and triazinyl.

The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;
c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;

l) a furan ring fused to a 5- or 6-membered ring containing 0, 1, 2 or 3 ring heteroatoms;

m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, isochroman, chromene, isochromene, benzodioxan, quinolizine, benzoxazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiophene, dihydrobenzofuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), chroman, thiochroman, isochroman, chromene, isochromene, benzodioxan, benzoxazine, benzodiazepine, and indoline groups.

A nitrogen-containing heteroaryl ring must contain at least one ring nitrogen atom. The nitrogen-containing heteroaryl ring can be N-linked or C-linked. Each ring may, in addition, contain up to about four other heteroatoms particularly selected from nitrogen, sulfur and oxygen. Particularly the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, monocyclic groups such as pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, and bicyclic groups such as quinolinyl, isoquinolinyl, benzimidazolyl, benzoxazolyl, benzisoxazole, benzothiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazepinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic" embraces, unless the context indicates otherwise, unsaturated ring systems without aromatic character, partially saturated and saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "saturated" refers to rings where there are no multiple bonds between ring atoms. Saturated heterocyclyl groups include piperidinyl, morpholinyl, and thiomorpholinyl. Partially saturated heterocyclyl groups include pyrazolinyl, for example pyrazolin-2-yl and pyrazolin-3-yl.

Examples of non-aromatic heterocyclyl groups are groups having from 3 to 12 ring members, more usually 5 to 10 ring members. Such groups can be monocyclic or bicyclic, for example, have 3 to 7 ring members in particular 4 to 6 ring members. Such groups particularly have from 1 to 5 or 1 to 4 heteroatom ring members (more usually 1, 2, or 3 heteroatom ring members), usually selected from nitrogen, oxygen and sulfur and oxidised forms thereof. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulfones (e.g. as in sulfolane and sulfolene), cyclic sulfoxides, cyclic sulfonamides and combinations thereof (e.g. thiomorpholine).

Particular examples include morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, pyranyl (2H-pyran or 4H-pyran), dihydrothienyl, dihydropyranyl, dihydrofuranyl, dihydrothiazolyl, tetrahydrofuranyl, tetrahydrothienyl, dioxanyl, oxanyl (also known as tetrahydropyranyl) (e.g. oxan-4-yl), imidazolinyl, imidazolidinonyl, oxazolinyl, thiazolinyl, pyrazolin-2-yl, pyrazolidinyl, piperazinonyl, piperazinyl, and N-alkyl piperazines such as N-methyl piperazinyl. In general, typical non-aromatic heterocyclyl groups include saturated groups such as piperidinyl, pyrrolidinyl, azetidinyl, morpholinyl, piperazinyl and N-alkyl piperazines such as N-methyl piperazinyl.

The terms "oxan" and "oxanyl" as used herein refer to the group:

which may also be referred to as "tetrahydropyran" or tetrahydropyranyl".

In a nitrogen-containing non-aromatic heterocyclyl ring the ring must contain at least one ring nitrogen atom. The nitrogen-containing heterocyclyl ring can be N-linked or C-linked. The heterocylic groups can contain, for example, cyclic amine moieties (e.g. as in pyrrolidinyl), cyclic amides (such as a pyrrolidinonyl, piperidinonyl or caprolactamyl), cyclic sulfonamides (such as an isothiazolidinyl 1,1-dioxide, [1,2]thiazinanyl 1,1-dioxide or [1,2]thiazepanyl 1,1-dioxide) and combinations thereof.

Particular examples of nitrogen-containing non-aromatic heterocyclyl groups include aziridinyl, morpholinyl, thiomorpholinyl, piperidinyl (e.g. piperidin-1-yl, piperidin-2yl, piperidin-3-yl and piperidin-4-yl), pyrrolidinyl; (e.g. pyrrolidin-1-yl, pyrrolidin-2-yl and pyrrolidin-3-yl), pyrrolidonyl, dihydrothiazolyl, imidazolinyl, imidazolidinonyl, oxazolinyl, thiazolinyl, 6H-1,2,5-thiadiazinyl, pyrazolin-2-yl, pyrazolin-3-yl, pyrazolidinyl, piperazinyl, and N-alkyl piperazines such as N-methyl piperazinyl.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see Advanced Organic Chemistry, by Jerry March, 4th Edition, Wiley Interscience, pages 131-133, 1992.

Where, in a definition of a cyclic group or ring, it is stated that the cyclic group contains a certain number of heteroatom ring members, e.g. as in the phrase "a 5 or 6 membered ring containing 0, 1 or 2 nitrogen ring members", this is to be taken as meaning that apart from the certain number of heteroatom ring members specified, the remaining ring members are carbon atoms.

The compound of formula (I°) may contain saturated cyclic groups that can be joined to the rest of the molecule by one or more bonds. When the cyclic group is joined to the rest of the molecule by two or more bonds, these bonds (or two of these bonds) can be made to the same atom (usually a carbon atom) of the ring or different atoms of the ring. Where the bonds are made to the same atom of the ring, this results in a cyclic group with a single atom (usually a quaternary carbon) bound to two groups. In other words, when the compound of formula (I°) includes a cyclic group that group may either be linked to the rest of the molecule by a bond or the cyclic group and the rest of the molecule can have an atom in common e.g. a Spiro compound.

The heterocyclyl group can each be unsubstituted or substituted by one or more (e.g. 1, 2 or 3) substituent groups. For example, heterocyclyl or carbocyclyl groups can be unsubstituted or substituted by 1, 2, 3 or 4 substituents and particularly it is unsubstituted or has 1, 2 or 3 substituents as defined herein. Where the cyclic group is saturated there may be 2 substituents joined to the same carbon (where the substituents are the same so called geminal or 'gem' disubstitution).

A combination of substituents is permissible only if such as combination results in a stable or chemically feasible compound (i.e. one that is not substantially altered when kept at 40° C. or less for at least a week).

The various functional groups and substituents making up the compounds of the invention are particularly chosen such that the molecular weight of the compound of the invention does not exceed 1000. More usually, the molecular weight of the compound will be less than 750, for example less than 700, or less than 650, or less than 600, or less than 550. More particularly, the molecular weight is less than 525 and, for example, is 500 or less.

DETAILED DESCRIPTION OF THE INVENTION

Compounds of Formula (I°)

The combinations include a compound of formula (I°):

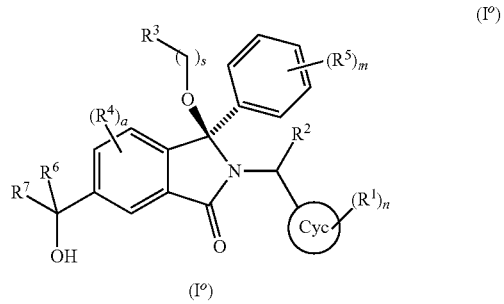

or a tautomer or a solvate or a pharmaceutically acceptable salt thereof, wherein cyc, $R^1$, $R^2$, $R^3$, $R^4$, $R^5$, $R^6$, $R^7$, a, m, n and s are as defined herein.

The compounds of the formula (I°): have a chiral centre, marked below with a "*":

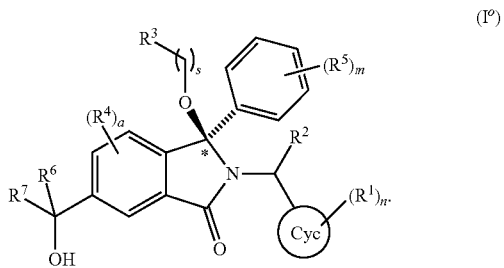

The compounds of formula (I°) include a stereocentre at the position indicated (referred to herein as (3)) and are chiral non-racemic. Compounds of formula (I°) have the stereochemistry shown by the hashed and solid wedged bonds and this stereoisomer predominates.

Typically, at least 55% (e.g. at least 60%, 65%, 70%, 75%, 80%, 85%, 90% or 95%) of the compound of the formula (I°) is present as the shown stereoisomer. In one general embodiment, 97% (e.g. 99%) or more (e.g. substantially all) of the total amount of the compound of the formula (I°) may be present as a single stereoisomer.

The compounds may also include one or more further chiral centres (e.g. in the —$CR^8R^7OH$ group and/or in the $R^3$ group and/or in the —$CHR^2$ group).

Typically, the compound of formula (I°) has an enantiomeric excess of at least 10% (e.g. at least 20%, 40%, 60%, 80%, 85%, 90% or 95%). In one general embodiment, the compound of formula (I°) has an enantiomeric excess of 97% (e.g. 99%) or more.

For the purposes of this section the isoindolin-1-one ring is numbered as followed:

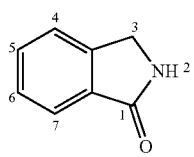

Compounds are named in accordance with protocols utilized by chemical naming software packages.

Compounds of Formula (I°) Wherein Cyc is Phenyl $R^1$ and n $R^1$ is the substituent(s) on the phenyl group bonded to —$CHR^2$—.

n is 0, 1, 2 or 3. In other words, the phenyl group bonded to —$CHR^2$— group may have 0, 1, 2 or 3 substituents $R^1$.

In one embodiment n is 1, 2 or 3. In one embodiment n is 1 or 2. In another embodiment n is 1.

When n is 2 or 3 (i.e. the phenyl group bonded to —$CHR^2$— group is substituted with more than one $R^1$) the substituents $R^1$ may be the same or different (i.e. are independently selected from the definitions of $R^1$).

$R^1$ may be attached at the ortho (or o-), meta (or m-) or para (or p-) position of the phenyl group, wherein the position is defined relative to the point of attachment of the phenyl group to the group —$CHR^2$—.

$R^1$ is independently selected from hydroxy, halogen, nitro, nitrile, $C_{1-4}$alkyl, halo$C_{1-4}$alkyl, hydroxy$C_{1-4}$alkyl, $C_{2-6}$ alkenyl, $C_{1-4}$alkoxy, halo$C_{1-4}$alkoxy, $C_{2-4}$ alkynyl, —$O_{0-1}$—$(CR^xR^y)_v$—$CO_2H$, —$(CR^xR^y)_v$—$CO_2C_{1-4}$alkyl, —$(CH_2)_v$—$CON(C_{1-4}$alkyl$)_2$, —$P(=O)(R^x)_2$, —$S(O)_d$—$R^x$, —$S(O)_d$-heterocyclic group with 3 to 6 ring members and —$S(O)_d$—$N(R^8)_2$.

$R^1$ is independently selected from hydroxy, halogen, nitro, nitrile, $C_{1-4}$ alkyl, hydroxy$C_{1-4}$alkyl, $C_{2-6}$ alkenyl, $C_{1-4}$alkoxy, halo$C_{1-4}$alkoxy, $C_{2-4}$ alkynyl, —$O_{0-1}$—$(CH_2)_v$—$CO_2H$, —$(CH_2)_v$—$CO_2C_{1-4}$alkyl, —$(CH_2)_v$—$CON(C_{1-4}$alkyl$)_2$, —$P(=O)(R^x)_2$, —$S(O)_d$—$R^x$, —$S(O)_d$-heterocyclic group with 3 to 6 ring members and —$S(O)_d$—$N(R^8)_2$.

$R^1$ is independently selected from hydroxy, halogen, nitro, nitrile, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$ alkynyl, —$(CH_2)_v$—$CO_2H$, —$(CH_2)_v$—$CO_2C_{1-4}$ alkyl, —$(CH_2)_v$—$CON(C_{1-4}$alkyl$)_2$, —$P(=O)(R^x)_2$, —$S(O)_d$—$R^x$, —$S(O)_d$-heterocyclic group with 3 to 6 ring members and —$S(O)_d$—$N(R^8)_2$.

In one embodiment, $R^1$ is independently selected from halogen, hydroxy, nitrile, $C_{1-4}$alkyl, $C_{2-4}$ alkynyl, or $C_{1-4}$ alkoxy, for example $R^1$ is independently selected from chloro, hydroxy, nitrile, methyl or methoxy.

In one embodiment $R^1$ is independently selected from halogen (e.g. chloro), $C_{1-4}$alkyl (e.g. methyl), $C_{1-4}$alkoxy (e.g. methoxy), —$O_{0-1}$—$(CR^xR^y)_v$—$CO_2H$ (e.g. —$CO_2H$, —$(CH_2)$—$CO_2H$, —$(C(CH_3)_2)$—$CO_2H$, or —$O(CH_2)$—$CO_2H$) or —$S(O)_d$—$R^x$ (e.g. $SO_2CH_3$).

In one embodiment $R^1$ is $O_{0-1}$—$(CR^xR^y)_v$—$CO_2H$ in particular —$CO_2H$, —$(CH_2)$—$CO_2H$, —$(C(CH_3)_2)$—$CO_2H$, or —$O(CH_2)$—$CO_2H$), such as —$(C(CH_3)_2)$—$CO_2H$.

In one embodiment, $R^1$ is chloro or nitrile, in particular chloro.

In one embodiment, $R^1$ is nitro (e.g. p-$NO_2$).

In one embodiment, $R^1$ is nitro at the ortho or meta position.

In one embodiment, $R^1$ is independently selected from hydroxy, halogen, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, —$(CH_2)_v$—$CO_2H$, —$(CH_2)_v$—$CO_2C_{1-4}$alkyl, —$(C_{1-42})_v$—$CON(C_{1-4}$alkyl$)_2$, —$P(=O)(R^x)_2$, —$S(O)_d$—$C_{1-4}$alkyl, —$S(O)_d$-heterocyclic group with 3 to 6 ring members and —$S(O)_d$—$N(R^8)_2$.

In another embodiment, n is 1 and $R^1$ is chloro or nitrile.

In another embodiment, n is 1 and $R^1$ is chloro.

In another embodiment, n is 1 and $R^1$ is nitrile.

In one embodiment, one of the $R^1$ groups or the $R^1$ group (where n=1) is at the para-position (i.e. para to the point of attachment of the phenyl ring). In one embodiment n is 1 and $R^1$ is p-chloro or p-nitrile.

In one embodiment, n is 1 and $R^1$ is halogen (e.g. Cl or F), nitrile, $C_{1-4}$alkoxy (e.g. —$OCH_3$) or $C_{1-4}$alkyl (e.g. —$CH_3$).

In one embodiment, $R^1$ is —$S(O)_d$—$C_{1-6}$alkyl, or —$S(O)_d$-heterocyclic group with 3 to 6 ring members and —$S(O)_d$—$N(R^8)_2$. In one embodiment, $R^1$ is —$S$—$C_{1-6}$ alkyl, —$S(O)$—$C_{1-6}$alkyl, —$S(O)_2$—$C_{1-6}$alkyl, —$S(O)_d$-heterocyclic group with 3 to 6 ring members or —$S(O)_d$—$N(C_{1-6}$ alkyl$)_2$.

In another embodiment, $R^1$ is —$S$—$CH_3$, —$S(O)$—$CH_3$, —$S(O)_2$—$CH_3$, or —$S(O)_2$-morpholinyl. In another embodiment, one or more $R^1$ is —$SO_2CH_3$, or —$SO_2$-heterocyclic group with 6 ring members e.g. —$SO_2$-(morpholinyl), in particular —$SO_2$-(1-morpholinyl).

In one embodiment, $R^1$ is o-(-$S(O)_d$—$C_{1-4}$alkyl) or o-(-$S(O)_d$-heterocyclic group with 3 to 6 ring members). In one embodiment, $R^1$ is o-$S$—$C_{1-4}$alkyl, o-(-$S(O)_d$—$C_{1-4}$alkyl) or o-(-$S(O)_d$-heterocyclic group with 3 to 6 ring members). In one embodiment, $R^1$ is o-(-$S(O)_2$—$CH_3$)

In one embodiment, $R^1$ is —$(CH_2)_u$—$CO_2H$. In one embodiment, $R^1$ is —$CO_2H$. In one embodiment, $R^1$ is —$(CH_2)_u$—$CO_2H$ at the meta or para position. In one embodiment, $R^1$ is —$(CH_2)_u$—$CO_2H$ at the ortho position.

In one embodiment, $R^1$ is independently selected from hydroxy, halogen, nitrile, $C_{1-4}$alkyl, hydroxy$C_{1-4}$alkyl, $C_{2-6}$alkenyl, $C_{1-4}$alkoxy, halo$C_{1-4}$alkoxy, $C_{2-4}$ alkynyl, —$(CH_2)_v$—$CO_2C_{1-4}$alkyl, —$(CH_2)_v$—$CON(C_{1-4}$alkyl$)_2$, —$P(=O)(R^x)_2$, —$S(O)_d$—$C_{1-8}$alkyl, —$S(O)_d$-heterocyclic group with 3 to 6 ring members and —$S(O)_d$—$N(R^8)_2$.

In one embodiment, n is 2. In one embodiment when n is 2, the phenyl group is substituted with (i) o-(-$S(O)_d$—$C_{1-4}$ alkyl) or o-(-$S(O)_d$-heterocyclic group with 3 to 6 ring members) and (ii) halogen (e.g. Cl or F), nitrile, or $C_{1-4}$ alkyl, in particular chloro, nitrile or methyl.

In one embodiment, n is 2 and $R^1$ is (i) —$SO_2CH_3$ and (ii) chloro.

In one embodiment n is 2 and $R^1$ is (i) —$SO_2CH_3$ and (ii) chloro, nitrile or methyl.

In one embodiment, n is 2 and $R^1$ is (i) —$CO_2H$ and (ii) chloro.

In one embodiment n is 2 and $R^1$ is (i) —$CO_2H$ and (ii) chloro, or nitrile.

In one embodiment, when n is 2, the phenyl group bonded to —$CHR^2$— is substituted with (i) hydroxyl and (ii) halogen (e.g. Cl or F), or nitrile, in particular chloro, or nitrile.

In one embodiment, the phenyl group bonded to —$CHR^2$— and $R^1$ form a group:

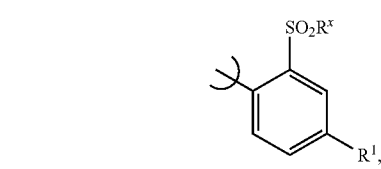

wherein in particular, $R^1$ is halogen (for example chloro), nitrile or $C_{1-4}$alkyl (for example —$CH_3$) and $R^x$ is $C_{1-4}$alkyl (for example —$CH_3$).

In one embodiment, the phenyl group bonded to —$CHR^2$— and $R^1$ form a group:

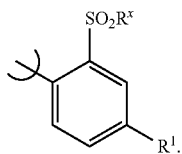

wherein in particular, $R^1$ is $C_{1-4}$alkyl (for example —$CH_3$) and $R^x$ is $C_{1-4}$alkyl (for example —$CH_3$).

In one embodiment when n is 2, the phenyl group is substituted with (i) o-OH or o-$CH_2OH$ and (ii) halogen (e.g. Cl or F), nitrile, or $C_{1-4}$ alkyl, in particular chloro, or nitrile. In one embodiment, when n is 2, the phenyl group is substituted with (i) hydroxy and (ii) halogen (e.g. Cl or F) or nitrile, in particular chloro or nitrile. In one embodiment, when n is 2, the phenyl group is substituted with (i) o-hydroxy and (ii) p-Cl or p-CN (e.g. p-Cl).

In one embodiment, n is 2 and $R^1$ is fluorine (e.g. at the ortho and para positions of the phenyl group).

In one embodiment, $R^1$ is halogen (e.g. Cl or F), $C_{1-4}$alkynyl (e.g. —C≡CH), nitrile, —$(CH_2)_v$COOH (e.g. —COOH) or $SO_2C_{1-4}$ alkyl (e.g. $SO_2CH_3$) and n is 1 or 2.

In one embodiment, $R^1$ is halogen (e.g. Cl), $C_{1-4}$alkynyl (e.g. —C≡CH), nitrile, hydroxy$C_{1-4}$alkyl (e.g. $CH_2OH$), —$(CH_2)_v$COOH (e.g. —COOH), —$S(O)_d$—$C_{1-4}$alkyl (e.g. $SCH_3$, $SOCH_3$, or $SO_2CH_3$), —$SO_2$-(1-morpholinyl) or —P(=O)($R^x$)$_2$, (e.g. —P(=O)($CH_3$)$_2$).

In one embodiment, n is 1 and $R^1$ is Cl (e.g. p-Cl), CN (e.g. p-CN), or $C_{2-4}$ alkynyl (e.g. p-$C_1$alkynyl), or n is 2 and (i) $R^1$ is p-Cl, o-$CH_2OH$; (ii) p-CN, o-$CH_2OH$; or (iii) p-Cl, o-COOH, (iv) p-Cl, o-$SCH_3$, (v) p-Cl, o-$S(O)CH_3$, (vi) p-Cl, o-$SO_2CH_3$, (vii) p-Cl, o-$SO_2$-(1-morpholinyl), or (viii) p-Cl, o-P(O)($CH_3$)$_2$.

In one embodiment, n is 1 and $R^1$ is Cl (e.g. p-Cl), CN (e.g. p-CN), or $C_{2-4}$alkynyl (e.g. p-$C_1$alkynyl).

In one embodiment, n is 2 and (i) $R^1$ is p-Cl, o-$CH_2OH$; (ii) p-CN, o-$CH_2OH$; or (iii) p-Cl, o-COOH, (iv) p-Cl, o-$SCH_3$, (v) p-Cl, o-$S(O)CH_3$, (vi) p-Cl, o-$SO_2CH_3$, (vii) p-Cl, o-$SO_2$-(1-morpholinyl), or (viii) p-Cl, o-P(O)($CH_3$)$_2$.

In one embodiment n is 1 and $R^1$ is —Cl, —CN or —OMe (e.g. p-Cl, p-CN or p-OMe). In one embodiment n is 1 and $R^1$ is —Cl or —CN (e.g. p-Cl or p-CN).

In one embodiment, n is 2. When n is 2, typically the phenyl group is substituted at the o- and p-positions. In particular, n is 2 and $R^1$ is substituted by a p-chloro and either o-(-S(O)$_d$—$C_{1-4}$alkyl) or o-(-S(O)$_d$-heterocyclic group with 3 to 6 ring members).

In one embodiment, n is 2 and $R^1$ is o-$CO_2H$ and p-chloro.
In one embodiment, n is 2 and $R^1$ is o-$CO_2H$ and p-nitrile.
In one embodiment, n is 2 and $R^1$ is o-$CH_2OH$ and p-chloro.
In one embodiment, n is 2 and $R^1$ is o-$CH_2OH$ and p-nitrile.
In one embodiment, n is 2 and $R^1$ is o-OH and p-chloro.
In one embodiment, n is 2 and $R^1$ is o-OH and p-nitrile.
In one embodiment, n is 2 and $R^1$ is o-$SO_2CH_3$ and p-chloro.
In one embodiment n is 2 and $R^1$ is —$SO_2$-(1-morpholinyl) and p-chloro.

In one embodiment, $R^1$ is —$O_{0,1}(CR^xR^y)_v$COOH (e.g. —COOH, —$CH_2$COOH, —$OCH_2$COOH or —$C(CH_3)_2$COOH In one embodiment, n is 2 and $R^1$ is p-Cl and o-$O_{0,1}$($CR^xR^y$)$_v$COOH (e.g. —COOH, —$CH_2$COOH, —$OCH_2$COOH or —$C(CH_3)_2$COOH).

In one embodiment, $R^1$ is halogen (e.g. Cl), hydroxyalkyl (e.g. —$CH_2OH$), $C_{1-4}$ alkynyl (e.g. —C≡CH), nitrile, —$O_{0,1}$($CR^xR^y$)$_v$COOH (e.g. —COOH, —$CH_2$COOH, —$OCH_2$COOH or —$C(CH_3)_2$COOH) or —$SO_2C_{1-4}$alkyl (e.g. —$SO_2CH_3$) and n is 1 or 2.

In one embodiment, $R^1$ is halogen (e.g. Cl), hydroxyalkyl (e.g. —$CH_2OH$), $C_{1-4}$ alkynyl (e.g. —C≡CH), nitrile, —$(CH_2)_v$COOH (e.g. —COOH) or —$SO_2C_{1-4}$ alkyl (e.g. —$SO_2CH_3$) and n is 1 or 2.

In one embodiment, $R^1$ is independently selected from hydroxy, halogen, nitrile, $C_{1-4}$ alkyl, halo$C_{1-4}$alkyl, hydroxy$C_{1-4}$alkyl, $C_{2-6}$ alkenyl, $C_{1-4}$alkoxy, halo$C_{1-4}$alkoxy, $C_{2-4}$ alkynyl, —$(CH_2)_v$CO$_2$H, —$O_{0,1}$—($CR^xR^y$)$_v$—$CO_2C_{1-4}$ alkyl (e.g. —$(CH_2)_v$—$CO_2C_{1-4}$ alkyl), —$(CH_2)_v$CON($C_{1-6}$ alkyl)$_2$, —P(=O)($R^x$)$_2$, —$S(O)_d$—$C_{1-6}$alkyl, —$S(O)_d$-heterocyclic group with 3 to 6 ring members and —$S(O)_d$—N($R^8$)$_2$.

In one embodiment wherein n is 2, and one $R^1$ is —$O_{0,1}$—($CR^xR^y$)$_v$—$CO_2C_{1-4}$alkyl, o-(-S(O)$_d$—$C_{1-4}$alkyl) or o-(-S(O)$_d$-heterocyclic group with 3 to 6 ring members) and one $R^1$ is halogen (e.g. Cl or F), nitrile, or $C_{1-4}$ alkyl, in particular chloro, nitrile or methyl.

In one embodiment wherein n is 2, and one $R^1$ is o-(-S(O)$_d$—$C_{1-4}$alkyl) or o-(-S(O)$_d$-heterocyclic group with 3 to 6 ring members) and one $R^1$ is halogen (e.g. Cl or F), nitrile, or $C_{1-4}$ alkyl, in particular chloro, nitrile or methyl.

In one embodiment wherein n is 2, and one $R^1$ is —$O_{0,1}$—($CR^xR^y$)$_v$—$CO_2C_{1-4}$ alkyl, and one $R^1$ is halogen (e.g. Cl or F), nitrile, or $C_{1-4}$ alkyl, in particular chloro, nitrile or methyl, such as chloro.

$R^2$ $R^2$ is selected from hydrogen, $C_{1-4}$ alkyl, $C_{2-6}$ alkenyl, hydroxy$C_{1-4}$alkyl, —$(CR^xR^y)_u$—$CO_2H$, —$(CR^xR^y)_u$—$CO_2C_{1-4}$alkyl, and —$(CR^xR^y)_u$—$CONR^xR^y$.

In one embodiment u is selected from 0, 1, or 2. In one embodiment u is selected from 0 or 1.

In one embodiment, $R^2$ is selected from hydrogen, $C_{1-4}$ alkyl, $C_{2-6}$ alkenyl, hydroxy$C_{1-4}$alkyl and —$(CR^xR^y)_u$—$CO_2H$. In one embodiment, $R^2$ is selected from hydrogen, $C_{1-4}$ alkyl, hydroxy$C_{1-4}$alkyl and —$(CR^xR^y)_u$—$CO_2H$. In one embodiment, $R^2$ is selected from hydrogen, $C_{1-4}$ alkyl, $C_{2-6}$ alkenyl, and hydroxy$C_{1-4}$alkyl. In another embodiment $R^2$ is selected from hydrogen and —$(CH_2)_u$—$CO_2H$ (e.g. —$CH_2$—$CO_2H$).

In one embodiment, $R^2$ is hydrogen, $C_{1-4}$ alkyl (e.g. —$CH_3$), hydroxy$C_{1-4}$alkyl (e.g. $CH_2OH$) or —$(CH_2)_v$COOH (e.g. —COOH, —$CH_2$COOH, —$CH_2CH_2$—$CO_2H$, —$(CH(CH_3))$—$CO_2H$ or —$(C(CH_3)_2$—$CO_2H$, such as —COOH, —$CH_2$COOH, —$CH_2CH_2$—$CO_2H$, or —$(CH(CH_3))$—$CO_2H$).

In one embodiment, $R^2$ is selected from hydrogen, $C_{1-4}$ alkyl, $C_{2-6}$ alkenyl, and hydroxy$C_{1-4}$alkyl.

In one embodiment, $R^2$ is hydrogen, $C_{1-4}$ alkyl (e.g. —$CH_3$), hydroxy$C_{1-4}$alkyl (e.g. $CH_2OH$) or —$(CH_2)_u$COOH (e.g. —$CH_2$COOH). In one embodiment, $R^2$ is selected from hydrogen, —$CH_3$, —$CH_2OH$, and —$CH_2CO_2H$.

In one embodiment, $R^2$ is selected from hydrogen, —$CH_3$, —$CH_2OH$, —CH=$CH_2$ and —CH(OH)$CH_2OH$.

In one embodiment, $R^2$ is selected from hydrogen, —$CH_3$, —$CH_2OH$, and —$CH_2CO_2H$.

In one embodiment, $R^2$ is hydrogen or $C_{1-4}$ alkyl (e.g. —$CH_3$ or —$CH_2CH_3$).

In one embodiment, $R^2$ is selected from hydrogen, —$CH_3$ and —$CH_2CH_3$. In one embodiment, $R^2$ is selected from hydrogen and methyl.

In one embodiment, $R^2$ is selected from hydrogen and —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$.

In one embodiment, $R^2$ is —$(R^xR^y)_u$COOH (e.g. —$CH_2COOH$, —$CH_2CH_2$—$CO_2H$, —$(CH(CH_3))$—$CO_2H$

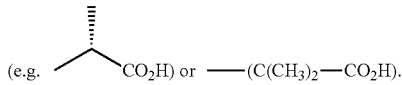

In one embodiment, $R^2$ is hydrogen, $C_{1-4}$ alkyl (e.g. —$CH_3$) or —$(CH_2)_u$COOH (e.g. —$CH_2COOH$, —$CH_2CH_2$—$CO_2H$ or —$(CH(CH_3))$—$CO_2H$).

In one embodiment, $R^2$ is hydrogen, $C_{1-4}$ alkyl (e.g. —$CH_3$) or —$(CH_2)_u$COOH (e.g. —$CH_2COOH$).

In one embodiment, $R^2$ is —$(CR^xR^y)_u$—$CO_2H$ (e.g. —$CH_2$—$CO_2H$).

In another embodiment, $R^2$ is selected from —$(CH(CH_3))$—$CO_2H$ and —$(C(CH_3)_2$—$CO_2H)$

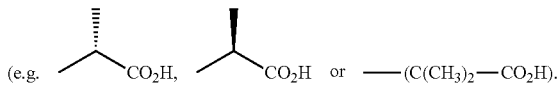

In another embodiment, $R^2$ is hydrogen and the compound of formula (I°) is a compound of formula (Ie) or a tautomer or a solvate or a pharmaceutically acceptable salt thereof:

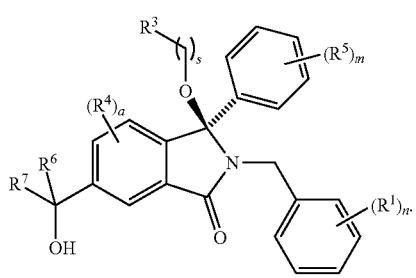

(Ie)

When $R^2$ is other than hydrogen, the compound of formula (I°) can exist as at least two diastereoisomers:

Diastereomer 1A

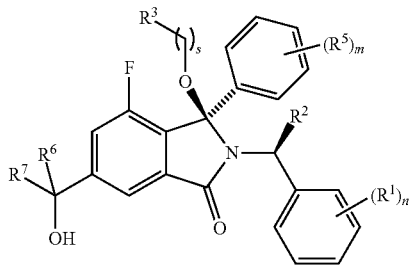

Diastereomer 1B

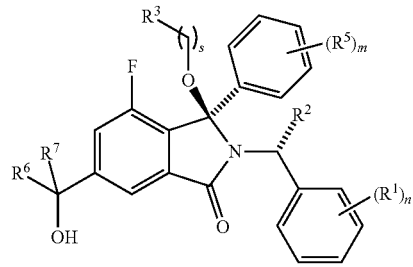

For the avoidance of doubt, the general formula (I°) and all subformulae cover both individual diastereoisomers and mixtures of the diastereoisomers which are related as epimers at the —$CHR^2$— group. In one embodiment the compound of formula I is diastereoisomer 1A or a tautomer or a solvate or a pharmaceutically acceptable salt thereof. In one embodiment the compound of formula I is diastereoisomer 1B or a tautomer or a solvate or a pharmaceutically acceptable salt thereof.

In one embodiment, the compound is diastereoisomer 1A and $R^2$ is selected from:
  i. $C_{1-4}$ alkyl, $C_{2-6}$alkenyl, hydroxy$C_{1-4}$alkyl, —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$, —$(CH_2)_u$—$CO_2C_{1-4}$alkyl, and —$(CH_2)_u$—$CONR^xR^y$; or
  ii. $C_{1-4}$ alkyl, $C_{2-8}$alkenyl, and hydroxy$C_{1-4}$alkyl.

In one embodiment, the compound is diastereoisomer 1A and $R^2$ is selected from:
  i. $C_{1-4}$ alkyl, $C_{2-6}$alkenyl, hydroxy$C_{1-4}$alkyl, —$(CH_2)_u$—$CO_2H$, —$(CH_2)_u$—$CO_2C_{1-4}$alkyl, and —$(CH_2)_u$—$CONR^xR^y$; or
  ii. $C_{1-4}$ alkyl, $C_{2-6}$alkenyl, and hydroxy$C_{1-4}$alkyl.

In another embodiment $R^2$ is selected from hydrogen and —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$, In another embodiment $R^2$ is selected from hydrogen and —$(CH_2)_u$—$CO_2H$ (e.g. —$CH_2$—$CO_2H$).

In one embodiment, the compound is diastereoisomer 1A and $R^2$ is selected from:
  i. —$CH_3$, —$CH_2OH$, —CH=$CH_2$ and —CH(OH)$CH_2OH$; or
  ii. $C_{1-4}$ alkyl (e.g. —$CH_3$ or —$CH_2CH_3$); or
  iii. —$CH_3$ and —$CH_2CH_3$.

In one embodiment, the compound is diastereoisomer 1B and $R^2$ is selected from:
  i. $C_{1-4}$ alkyl, $C_{2-6}$ alkenyl, hydroxy$C_{1-4}$alkyl, —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$, —$(CH_2)_u$—$CO_2C_{1-4}$ alkyl, and —$(CH_2)_u$—$CONR^xR^y$; or
  ii. $C_{1-4}$ alkyl, $C_{2-6}$alkenyl, and hydroxy$C_{1-4}$alkyl.

In one embodiment, the compound is diastereoisomer 1B and $R^2$ is selected from:
  i. $C_{1-4}$ alkyl, $C_{2-6}$alkenyl, hydroxy$C_{1-4}$alkyl, —$(CH_2)_u$—$CO_2H$, —$(CH_2)_u$—$CO_2C_{1-4}$alkyl, and —$(CH_2)_u$—$CONR^xR^y$; or
  ii. $C_{1-4}$ alkyl, $C_{2-6}$ alkenyl, and hydroxy$C_{1-4}$ alkyl.

In another embodiment $R^2$ is selected from hydrogen and —$(CH_2)_u$—$CO_2H$ (e.g. —$CH_2$—$CO_2H$).

In one embodiment, the compound is diastereoisomer 1B and $R^2$ is selected from:

i. —CH$_3$, —CH$_2$OH, —CH=CH$_2$ and —CH(OH)CH$_2$OH; or
ii. C$_{1-4}$ alkyl (e.g. —CH$_3$ or —CH$_2$CH$_3$); or
iii. —CH$_3$ and —CH$_2$CH$_3$.

In another embodiment R$^2$ is selected from hydrogen and —(R$^x$R$^y$)$_u$—OO$_2$H (e.g. —COOH, —CH$_2$COOH, —CH$_2$CH$_2$—CO$_2$H, —(CH(CH$_3$))—CO$_2$H and —C(CH$_3$)$_2$—CO$_2$H), In one embodiment R$^2$ is selected from C$_{1-4}$ alkyl, hydroxyC$_{1-4}$alkyl, —(CH$_2$)$_u$—CO$_2$H, —(CH$_2$)$_u$—CO$_2$C$_{1-4}$ alkyl, and —(CH$_2$)$_w$—CONR$^x$R$^y$ (in particular —CH$_2$—CO$_2$H) and the compound is diastereoisomer 1A.

In one embodiment R$^2$ is selected from C$_{1-4}$ alkyl, hydroxyC$_{1-4}$alkyl, —(CH$_2$)$_u$—CO$_2$H, —(CH$_2$)$_u$—CO$_2$C$_{1-4}$ alkyl, and —(CH$_2$)$_u$—CONR$^x$R$^y$ (in particular —CH$_2$—CO$_2$H) and the compound is diastereoisomer 1B.

In one embodiment R$^2$ is hydroxyC$_{1-4}$alkyl (e.g. —CH$_2$OH) and the compound is diastereoisomer 1A.

In one embodiment R$^2$ is —(CH$_2$)$_u$—CO$_2$H (e.g. —CH$_2$—CO$_2$H) and the compound is diastereoisomer 1A.

In one embodiment R$^2$ and the hydrogen on the carbon to which it is attached are $^2$H (i.e. deuterium).

R$^3$ and s

R$^3$ is hydrogen or -(A)$_t$-(CR$^x$R$^y$)$_q$—X;
s is selected from 0 and 1;
t is selected from 0 and 1;
q is selected from 0, 1 and 2;
wherein when R$^3$ is -(A)$_t$-(CR$^x$R$^y$)$_u$—X then (i) at least one of s, t and q is other than 0 and (ii) when t is 0 then s is 1 and q is other than 0;
A is a C$_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;
X is selected from hydrogen, halogen, —CN, —OR$^9$, —(CH$_2$)$_v$—CO$_2$H, —(CH$_2$)$_v$—CO$_2$C$_{1-4}$alkyl, —S(O)$_d$—R$^x$, —C(=O)—C$_{1-4}$alkyl, —S(O)$_d$—N(H)$_e$(C$_{1-4}$alkyl)$_{2-e}$, —NR$^x$R$^y$, —NHSO$_2$R$^x$, —NR$^x$COR$^y$, and —C(=O)NR$^x$R$^y$;
R$^9$ is independently selected from hydrogen, C$_{1-6}$alkyl, haloC$_{1-6}$alkyl, hydroxyC$_{1-6}$alkyl, —(CH$_2$)$_k$—O—C$_{1-6}$alkyl, —(CH$_2$)$_k$—O-(hydroxyC$_{1-6}$alkyl), hydroxyC$_{1-6}$alkoxy, —(CH$_2$)$_k$—CO$_2$C$_{1-6}$ alkyl, —(CH$_2$)$_k$—CO$_2$H, —C$_{1-6}$ alkyl-N(H)$_e$(C$_{1-4}$alkyl)$_{2-e}$, —(CH$_2$)$_j$—C$_{3-6}$ cycloalkyl and —(CH$_2$)$_j$—C$_{3-8}$ cycloalkenyl;
R$^x$ and R$^y$ are independently selected from hydrogen, halogen, nitro, nitrile, C$_{1-6}$alkyl, haloC$_{1-6}$ alkyl, C$_{2-6}$alkenyl, C$_{2-6}$ alkynyl, hydroxy, hydroxyC$_{1-6}$alkyl, C$_{1-6}$alkoxy, —(CH$_2$)$_k$—O—C$_{1-6}$ alkyl, hydroxyC$_{1-6}$alkoxy, —COOC$_{1-6}$ alkyl, —N(H)$_e$(C$_{1-4}$alkyl)$_{2-e}$, —C$_{1-6}$alkyl-N(H)$_e$(C$_{1-4}$alkyl)$_{2-e}$, —(CH$_2$)$_k$—C(=O)N(H)$_e$(C$_{1-4}$alkyl)$_{2-e}$, C$_{3-8}$cycloalkyl and C$_{3-8}$ cycloalkenyl;
or the R$^x$ and R$^y$ groups, together with the carbon or nitrogen atom to which they are attached, can join to form a C$_{3-6}$cycloalkyl or saturated heterocyclyl group with 3 to 6 ring members which may be optionally fused to an aromatic heterocyclyl group of 3 to 5 ring members or can join to form a =CH group;
j, d, and e are independently selected from 0, 1 and 2;
k is selected from 1 and 2; and
v is independently selected from 0 and 1.

In one embodiment when t is 1 the group —(CR$^x$R$^y$)$_d$—X and the rest of the molecule are attached to the same carbon atom in the group A. In one embodiment when t is 1 the group (CR$^x$R$^y$)$_d$—X and the rest of the molecule are attached to different carbon atoms in the group A.

In one embodiment, R$^3$ is hydrogen or -(A)$_t$-(CR$^x$R$^y$)$_d$—X;
s is selected from 0 and 1;
t is selected from 0 and 1;
q is selected from 0, 1 and 2;
wherein when R$^3$ is -(A)$_t$-(CR$^x$R$^y$)$_d$—X then (i) at least one of s, t and q is other than 0 and (ii) when t is 0 then s is 1 and q is other than 0;
A is a C$_{3-6}$ cycloalkyl group or a heterocyclic group with 3 to 6 ring members, wherein the heterocyclic group comprises one or more (e.g. 1, 2, or 3) heteroatoms selected from N, O, S and oxidised forms thereof;
X is selected from hydrogen, halogen, —CN, —OR$^9$, —(CH$_2$)$_v$—CO$_2$H, —(CH$_2$)$_v$—CO$_2$C$_{1-4}$alkyl, —S(O)$_d$—R$^x$, —C(=O)—C$_{1-4}$alkyl, —S(O)$_d$—N(H)$_e$(C$_{1-4}$alkyl)$_{2-e}$, —NR$^x$R$^y$, —NHSO$_2$R$^x$, —NR$^x$COR$^y$, and —C(=O)NR$^x$R$^y$;
R$^9$ is independently selected from hydrogen and C$_{1-6}$alkyl;
R$^x$ and R$^y$ are independently selected from hydrogen and C$_{1-6}$alkyl;
d and e are independently selected from 0, 1 and 2;
v is independently selected from 0 and 1.

In one embodiment, R$^3$ is hydrogen or -(A)$_t$-(CR$^x$R$^y$)$_d$—X;
s is selected from 0 and 1;
t is selected from 0 and 1;
q is selected from 0, 1 and 2;
wherein when R$^3$ is -(A)$_t$-(CR$^x$R$^y$)$_d$—X then (i) at least one of s, t and q is other than 0 and (ii) when t is 0 then s is 1 and q is other than 0;
A is a C$_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;
X is selected from hydrogen, halogen, —CN, —(CH$_2$)$_v$—CO$_2$H, —(CH$_2$)$_v$—CO$_2$C$_{1-4}$alkyl, —C(=O)—C$_{1-4}$alkyl, —NR$^x$R$^y$, —NR$^x$COR$^y$, and —C(=O)NR$^x$R$^y$;
R$^9$ is independently selected from hydrogen and C$_{1-6}$ alkyl;
R$^x$ and R$^y$ are independently selected from hydrogen and C$_{1-6}$alkyl;
v is independently selected from 0 and 1.

In one embodiment, R$^3$ is hydrogen or -(A)$_t$-(CR$^x$R$^y$)$_q$—X;
s is selected from 0 and 1;
t is selected from 0 and 1;
q is selected from 0, 1 and 2;
wherein when R$^3$ is -(A)$_t$-(CR$^x$R$^y$)$_q$—X then (i) at least one of s, t and q is other than 0 and (ii) when t is 0 then s is 1 and q is other than 0;
A is a C$_{3-6}$ cycloalkyl group or a heterocyclic group with 3 to 6 ring members, wherein the heterocyclic group comprises one or more (e.g. 1, 2, or 3) heteroatoms selected from N, O, S and oxidised forms thereof;
X is selected from hydrogen, halogen, —CN, —OR$^9$, —NR$^x$COR$^y$, and —C(=O)NR$^x$R$^y$;
R$^9$ is independently selected from hydrogen and C$_{1-6}$alkyl;
R$^x$ and R$^y$ are independently selected from hydrogen and C$_{1-6}$alkyl;
v is independently selected from 0 and 1.

In one embodiment, R$^3$ is hydrogen or -(A)$_t$-(CR$^x$R$^y$)$_q$—X;
s is selected from 0 and 1;
t is selected from 0 and 1;
q is selected from 0, 1 and 2;
wherein when R$^3$ is -(A)$_t$-(CR$^x$R$^y$)$_q$—X then (i) at least one of s, t and q is other than 0 and (ii) when t is 0 then s is 1 and q is other than 0;

A is a $C_{3-6}$ cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen (e.g. fluoro), —OR$^9$, —NR$^x$COR$^y$; and —C(=O)NR$^x$R$^y$;

R$^9$ is independently selected from hydrogen and $C_{1-6}$alkyl;

R$^x$ and R$^y$ are independently selected from hydrogen and $C_{1-6}$alkyl;

v is independently selected from 0 and 1.

In one embodiment, R$^3$ is hydrogen and s is 1 i.e. the moiety —(CH$_2$)$_s$R$^3$ is —CH$_3$.

In one embodiment, R$^3$ is hydrogen and s is 0 i.e. the moiety —(CH$_2$)$_s$R$^3$ is —H.

In one embodiment, t is 1 and A is a $C_{3-6}$cycloalkyl group or a heterocyclic group with 3 to 6 ring members, wherein the heterocyclic group comprises one or more (e.g. 1 or 2) heteroatoms selected from N, O, S and oxidised forms thereof.

In one embodiment, t is 1 and A is a $C_{3-6}$cycloalkyl group. In one embodiment, A is a $C_{3-5}$cycloalkyl group. For example, A is selected from a cyclopropyl group, a cyclobutyl group and a cyclopentyl group.

In one embodiment, A is a cyclopropyl group. In one embodiment, A is a cyclobutyl group.

In particular, t is 1 and A is cyclopropyl.

In one embodiment, t is 1 and A is a heterocyclic group with 3 to 6 ring members, wherein the heterocyclic group comprises one or more (e.g. 1, 2, or 3) heteroatoms selected from N, O, S and oxidised forms thereof.

In one embodiment, t is 1 and A is a heterocyclic group with 3 to 5 ring members, wherein the heterocyclic group comprises one or more (e.g. 1, 2, or 3) heteroatoms selected from N, O, S and oxidised forms thereof.

In one embodiment, t is 1 and A is an unsaturated heterocyclic group with 3 to 5 ring members, wherein the heterocyclic group comprises one or more (e.g. 1, 2, or 3) heteroatoms selected from N, O, S and oxidised forms thereof, in particular O.

In one embodiment, t is 1 and A is a saturated heterocyclic group with 3 to 5 ring members, wherein the heterocyclic group comprises one or more (e.g. 1, 2, or 3) heteroatoms selected from N, O, S and oxidised forms thereof, in particular O.

In one embodiment, t is 1 and A is a heterocyclic group which is selected from morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, oxetanyl, pyranyl (2H-pyran or 4H-pyran), dihydrothienyl, dihydropyranyl, dihydrofuranyl, dihydrothiazolyl, tetrahydrofuranyl (e.g. tetrahydrofuran-3-yl), tetrahydrothienyl, dioxanyl, oxanyl (e.g. oxan-4-yl), imidazolinyl, imidazolidinonyl, oxazolinyl, thiazolinyl, pyrazolin-2-yl, pyrazolidinyl, piperazinonyl, piperazinyl, and N-alkyl piperazines such as N-methyl piperazinyl.

In one embodiment, t is 1 and A is a heterocyclic group which is selected from morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, oxetanyl, pyranyl (2H-pyran or 4H-pyran), dihydropyranyl, dihydrofuranyl, dihydrothiazolyl, tetrahydrofuranyl (e.g. tetrahydrofuran-3-yl), dioxanyl, oxanyl (e.g. oxan-4-yl), imidazolinyl, imidazolidinonyl, oxazolinyl, pyrazolin-2-yl, pyrazolidinyl, piperazinonyl, piperazinyl, and N-alkyl piperazines such as N-methyl piperazinyl.

In particular, t is 1 and A is a heterocyclic group which is oxetanyl (e.g. oxetan-3-yl).

In particular, t is 1 and A is a heterocyclic group which is tetrahydrofuranyl (e.g. tetrahydrofuran-3-yl).

In one embodiment, X is hydrogen, s is 0 and q is 0, and R$^3$ is a heterocyclic group with 3 to 6 ring members, wherein the heterocyclic group comprises one or more (e.g. 1, 2, or 3) heteroatoms selected from N, O, S and oxidised forms thereof. In particular, R$^3$ is tetrahydrofuranyl (e.g. tetrahydrofuran-3-yl).

In one embodiment, s is 0 and t is 1 and A is attached directly to the oxygen atom bound to the isoindolinone. In one embodiment s is 1 and the cycloalkyl group is attached via a methylene group (i.e. —CH$_2$—) to the oxygen atom bound to the isoindolinone.

In one embodiment, A is tetrahydrofuranyl and X is hydrogen.

In one embodiment A is selected from cyclopropyl, oxetanyl and tetrahydrofuranyl.

In one embodiment, q is 0. In one embodiment, q is 1. In one embodiment, q is 2.

In one embodiment, A is oxetanyl and X is fluorine.

When q is not 0, R$^x$ and R$^y$ are selected from hydrogen, halogen (e.g. fluorine), hydroxy and methyl e.g. hydrogen and methyl, in particular hydrogen.

In one embodiment, q is 1 and at least one R$^x$ and R$^y$ is hydrogen. In one embodiment, q is 2 and at least two R$^x$ and R$^y$ are hydrogen e.g. three R$^x$ and R$^y$ are hydrogen.

In one embodiment, —(CR$^x$R$^y$)$_q$— is selected from —CH$_2$— and —CH$_2$CH$_2$—.

In one embodiment, R$^x$ and R$^y$ together form a saturated heterocyclyl group with 3 to 6 ring members.

In one embodiment t is 0 and —(CR$^x$R$^y$)$_q$— is —CH$_2$—.

In one embodiment t is 0, s is 0, —(CR$^x$R$^y$)$_q$— is —CH$_2$— and X is hydroxy.

In one embodiment, X is selected from —CN, —OH, —O—$C_{1-4}$alkyl, —O-hydroxy$C_{1-4}$alkyl, —S(O)$_d$—$C_{1-4}$alkyl, —C(=O)—$C_{1-4}$alkyl, —NR$^x$R$^y$, —NRxCOR$^9$ and —C(=O)NR$^x$R$^y$.

In one embodiment, X is selected from —CN, —OH, —O—CH$_2$CH$_2$OH, —S(O)$_d$—$C_{1-4}$ alkyl and —C(=O)NR$^x$R$^y$ (e.g. —C(=O)NH$_2$ or —C(=O)NH(CH$_3$)). In one embodiment X is selected from —CN, —OH, —C(=O)NH$_2$ or —C(=O)NH(CH$_3$).

In one embodiment, X is selected from hydrogen, halogen, —CN, —OR$^9$, and —C(=O)NR$^x$R$^y$. In another embodiment, X is selected from hydrogen, halogen, —CN, —OH, —OCH$_3$, and —C(=O)NH$_2$. In another embodiment, X is selected from hydrogen, fluorine, —CN, —OH, and —C(=O)NH$_2$.

In one embodiment, X is selected from hydrogen, fluorine, —CN, —OH and —C(=O)NH$_2$. In one embodiment, X is selected from hydrogen, —CN, —OH and —C(=O)NH$_2$. In one embodiment, X is selected from —CN, —OH and —C(=O)NH$_2$.

In one embodiment X is selected from —OH and —C(=O)NH$_2$ e.g. —OH.

In one embodiment, X is —C(=O)NR$^x$R$^y$ (e.g. —C(=O)NH$_2$ or —C(=O)NH(CH$_3$).

In one embodiment, R$^x$ and R$^y$ are hydrogen, halogen (e.g. fluorine), hydroxy and methyl. In one embodiment, R$^x$ and R$^y$ are hydrogen and methyl. In one embodiment, R$^x$ and R$^y$ together form a saturated heterocyclyl group with 3 to 6 ring members.

In one embodiment, A is a $C_{3-6}$ cycloalkyl group (i.e. g is 1, 2 or 3) and t is 1 and s is 0 or 1, and the compound of formula (I°) is a compound of formula (If) or a tautomer or a solvate or a pharmaceutically acceptable salt thereof:

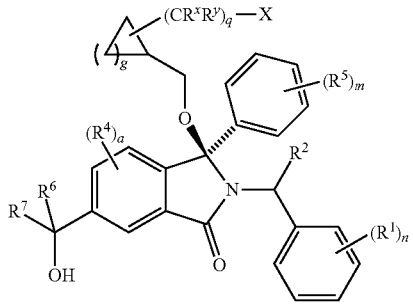
(If)

In one embodiment, A is a $C_{3-6}$ cycloalkyl group (i.e. g is 1, 2 or 3) and t is 1 and s is 1, and the compound of formula (I°) is a compound of formula (Ig) or a tautomer or a solvate or a pharmaceutically acceptable salt thereof:

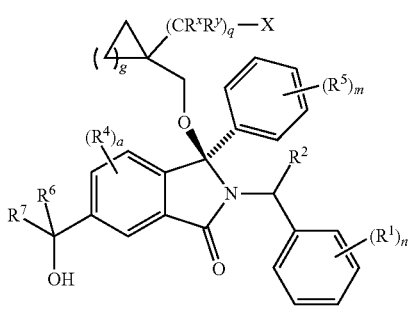
(Ig)

In one embodiment, A is a $C_{3-8}$ cycloalkyl group (i.e. g is 1, 2 or 3) and t is 1 and s is 0, and the compound of formula (I°) is a compound of formula (Ig') or a tautomer or a solvate or a pharmaceutically acceptable salt thereof:

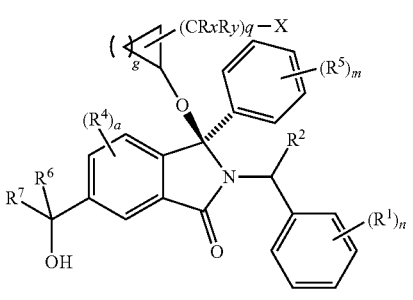
(Ig')

In one embodiment, the compound of formula (I°) is a compound of formula (Ig') and g is 2.

In one embodiment, A is a $C_{3-6}$ cycloalkyl group (i.e. g is 1, 2 or 3) and t is 1 and s is 1, and the cycloalkyl group is geminally disubstituted (i.e. the group —$(CR^xR^y)_q$—X and the —$CH_2$—O-isoindolinone group are both attached to the same atom of the cycloalkyl group), and the compound of formula (I°) is a compound of formula (Ih) or a tautomer or a solvate or a pharmaceutically acceptable salt thereof:

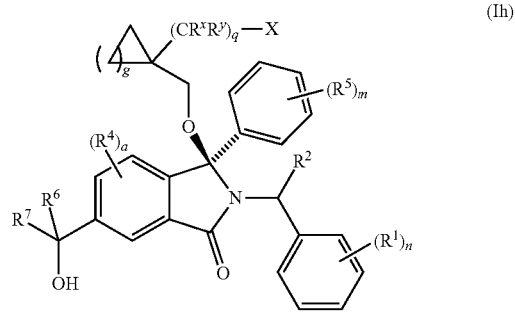
(Ih)

In one embodiment, A is a cyclopropyl group (i.e. g is 1), t is 1 and s is 1. Therefore the cycloalkyl group is a cyclopropyl group and the compound of formula (I°) is a compound of formula (Ii) or a tautomer or a solvate or a pharmaceutically acceptable salt thereof:

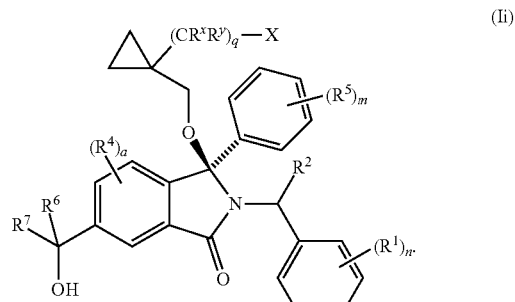
(Ii)

In one embodiment, A is a $C_{3-6}$ cycloalkyl group (i.e. g is 1, 2 or 3), t is 1, s is 1 and X is hydroxy, and the compound of formula (I°) is a compound of the formula (IJ or a tautomer or a solvate or a pharmaceutically acceptable salt thereof:

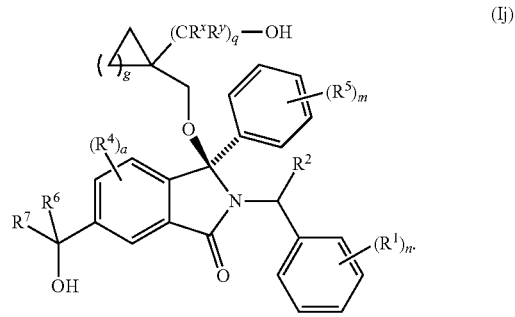
(Ij)

In one embodiment, A is a $C_{3-6}$ cycloalkyl group (i.e. g is 1, 2 or 3), t is 1, s is 1 and X is —C(=O)NH$_2$ and the compound of formula (I°) is a compound of the formula (Ik) or a tautomer or a solvate or a pharmaceutically acceptable salt thereof:

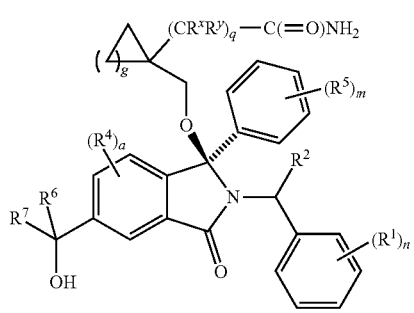

In one embodiment, A is a $C_{3-6}$cycloalkyl group (i.e. g is 1, 2 or 3), t is 1, s is 1 and X is CN and the compound of formula (I°) is a compound of the formula (Ik') or a tautomer or a solvate or a pharmaceutically acceptable salt thereof:

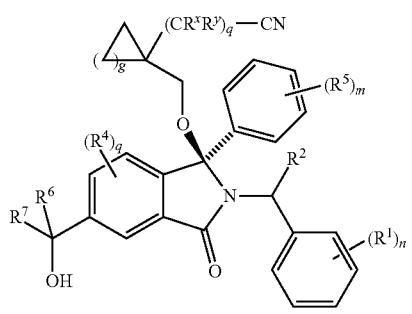

In another embodiment, A is a $C_{3-6}$ cycloalkyl group (i.e. g is 1, 2 or 3), t is 1, s is 1 and $R^x$ and $R^y$ are hydrogen (including $^1H$ and $^2H$) and the compound of formula (I°) is a compound of formula (IL) or a tautomer or a solvate or a pharmaceutically acceptable salt thereof:

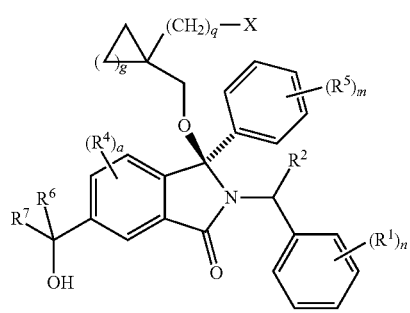

In one embodiment, A is a cyclopropyl or cyclobutyl group (i.e. g is 1 or 2), t is 1, s is 1 and X is hydroxy and the compound of formula (IL) is a compound of formula (Im) or a tautomer or a solvate or a pharmaceutically acceptable salt thereof:

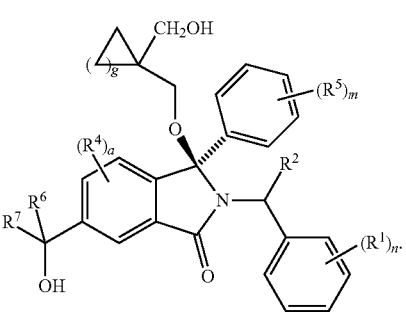

In one embodiment, g is 1 and the compound of formula (Im) is a compound of the formula (Im') or a tautomer or a solvate or a pharmaceutically acceptable salt thereof:

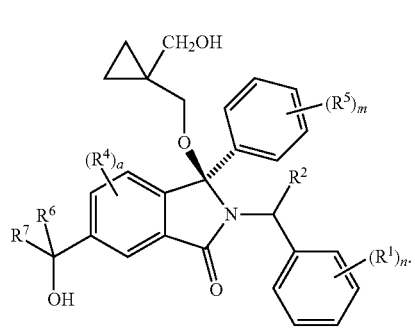

In one embodiment, A is a $C_3$-cycloalkyl group (i.e. g is 1), t is 1, s is 1 and X is $-C(=O)NH_2$ and the compound of formula (I°) is a compound of formula (In) or a tautomer or a solvate or a pharmaceutically acceptable salt thereof:

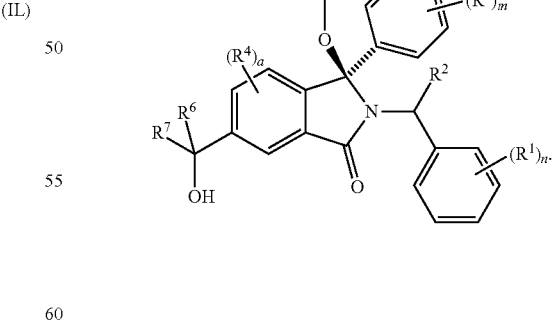

wherein q is 0 or 1. In one embodiment of the compound (In), q is 0.

In one embodiment, A is a $C_3$-cycloalkyl group (i.e. g is 1), t is 1, s is 1 and X is —CN and the compound of formula (I°) is a compound of formula (In') or a tautomer or a solvate or a pharmaceutically acceptable salt thereof:

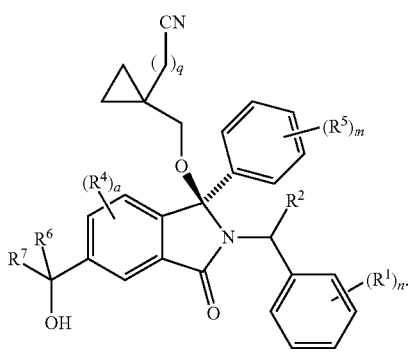

(In')

wherein q is 0 or 1. In one embodiment of the compound (In), q is 0.

In one embodiment of formula (I°) and subformulae thereof, the hydrogens in the —(CR$^x$R$^y$)— group of R$^3$ are $^2$H (i.e. deuterium, D). In one embodiment, the hydrogens in the group —CH$_2$—O group are $^2$H (i.e. deuterium, D). In one embodiment, the hydrogens in the —(CR$^x$R$^y$)— and —CH$_2$—O groups are $^2$H (i.e. deuterium, D).

In one embodiment q is 0 or 1 and R$^x$ and R$^y$ are hydrogen or deuterium.

In one embodiment, A is cyclopropyl (i.e. g is 1), t is 1, s is 1, X is hydroxy and the hydrogens in the —(CR$^x$R$^y$)— and —CH$_2$—O groups are $^2$H (or D), and the compound of formula (I°) is a compound of formula (Io) or a tautomer or a solvate or a pharmaceutically acceptable salt thereof:

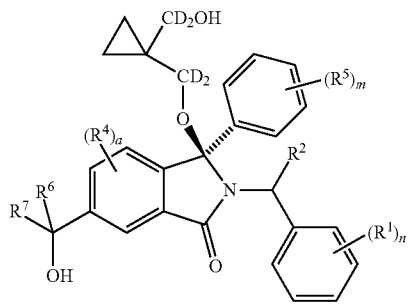

(Io)

In one embodiment the compound of formula (I°) is a compound of formula (Io') or (Io") or a tautomer or a solvate or a pharmaceutically acceptable salt thereof:

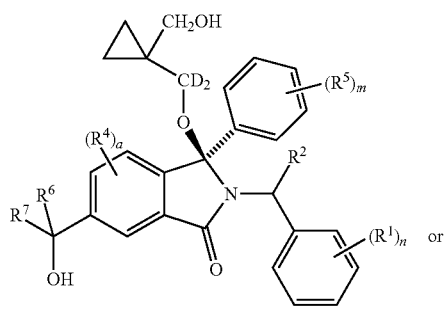

(Io')

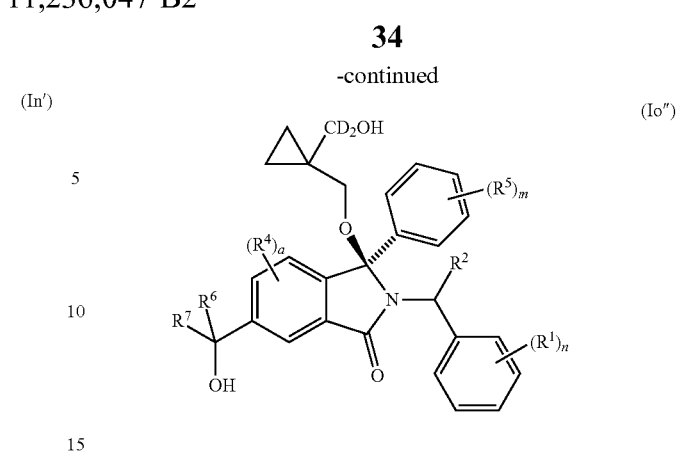

(Io")

In one embodiment, R$^3$ is —(CR$^x$R$^y$)$_q$—X and s is 1, t is 0 and q is 1 or 2, and the compound of formula (I°) is a compound of the formula (Ip):

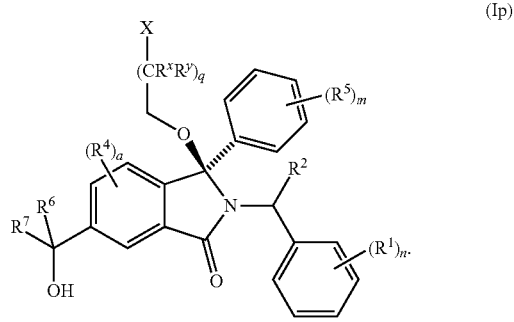

(Ip)

In one embodiment, R$^x$ and R$^y$ are H, and the compound of formula (Ip) is a compound of the formula (Ip') or a tautomer or a solvate or a pharmaceutically acceptable salt thereof:

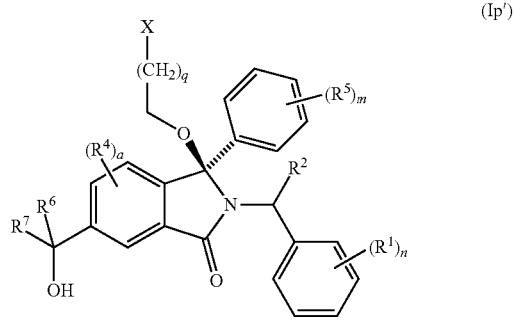

(Ip')

In one embodiment, A is a C$_{3-6}$ cycloalkyl group or saturated heterocyclic group with 3 to 6 ring members, wherein t is 1, and s is 1, Y is independently selected from —CH$_2$—, O, or SO$_2$, i is 0 or 1, g is 1, 2, 3 or 4 and i+g is 1, 2, 3 or 4 and the compound of formula (I°) is a compound of the formula (Iq) or a tautomer or a solvate or a pharmaceutically acceptable salt thereof:

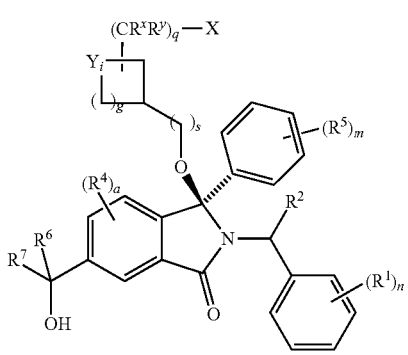

(Iq)

In one embodiment the compound of formula (I°) is a compound of the formula (Iq') or a tautomer or a solvate or a pharmaceutically acceptable salt thereof:

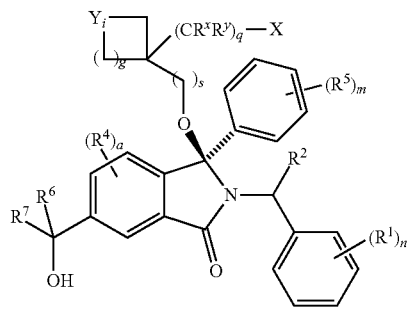

(Iq')

In one embodiment of the compound of formula (Iq'), q is 1 and $R^x$, $R^y$ and X are hydrogen.

In one embodiment of the compound of formula (Iq'), q is 1, Fix and $R^y$ are hydrogen, and X is hydroxy.

In one embodiment of the compound of formula (Iq'), q is 1, $R^x$ and $R^y$ are hydrogen, and X is fluorine.

In one embodiment of the compound of formula (Iq'), q is 0. In one embodiment of the compound of formula (Iq), q is 0 and X is fluorine.

In one embodiment q is 0 and X is fluorine and the compound of formula (Iq') is a compound of the formula (Iq") or a tautomer or a solvate or a pharmaceutically acceptable salt thereof:

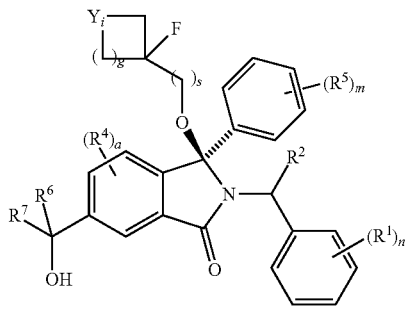

(Iq")

In one embodiment of the compound of (Iq') or the compound of (Iq"), g is 1, i is 1 and Y is 0.

In one embodiment g is 1, i is 1, Y is 0, q is 0 and X is F and the compound of formula (Iq') is a compound of the formula (Iq''') or a tautomer or a solvate or a pharmaceutically acceptable salt thereof:

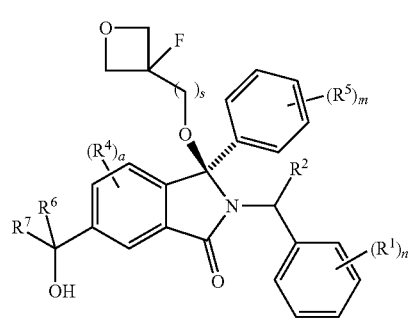

(Iq''')

In one embodiment, i is 1 and Y is 0 or $SO_2$, in particular O. In one embodiment, the compound of formula (Iq) is a compound of formula (Iq'''') or a tautomer or a solvate or a pharmaceutically acceptable salt thereof:

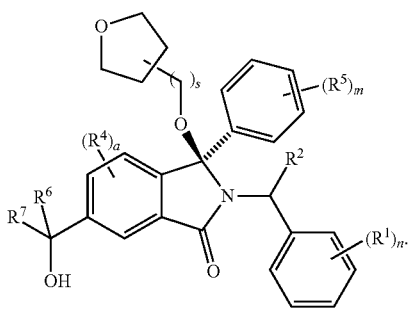

(Iq'''')

In one embodiment, s is 0, t is 1, A is tetrahydofuranyl, q is 0 and X is hydrogen. In one embodiment, $R^3$ is tetrahydrofuranyl and s is 0.

In one embodiment, $-(CH_2)_sR^3$ is selected from the following table (point of attachment to the oxygen represented by dashed bond or bond terminus marked "*"):

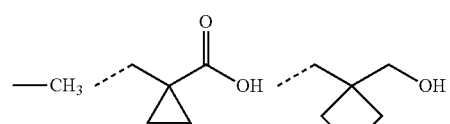

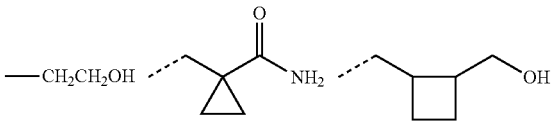

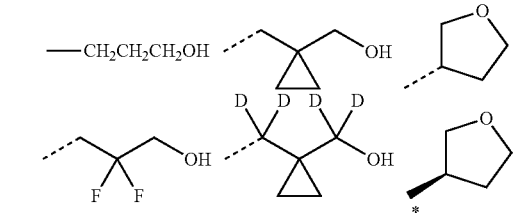

-continued

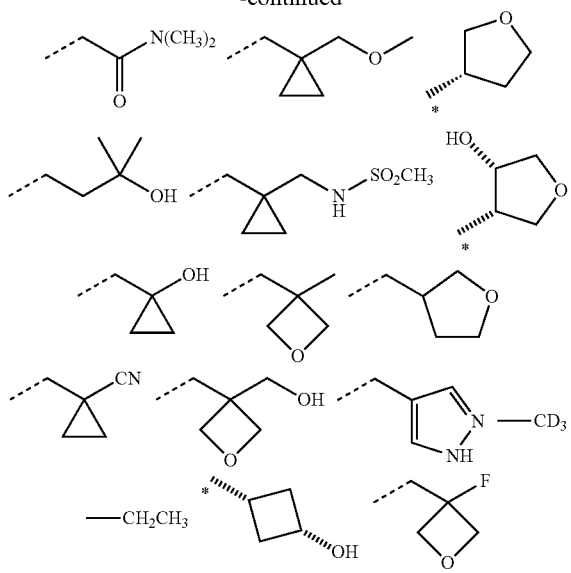

In one embodiment, —(CH$_2$)$_s$R$^3$ is selected from the following table (point of attachment to the oxygen represented by dashed bond or bond terminus marked "*"):

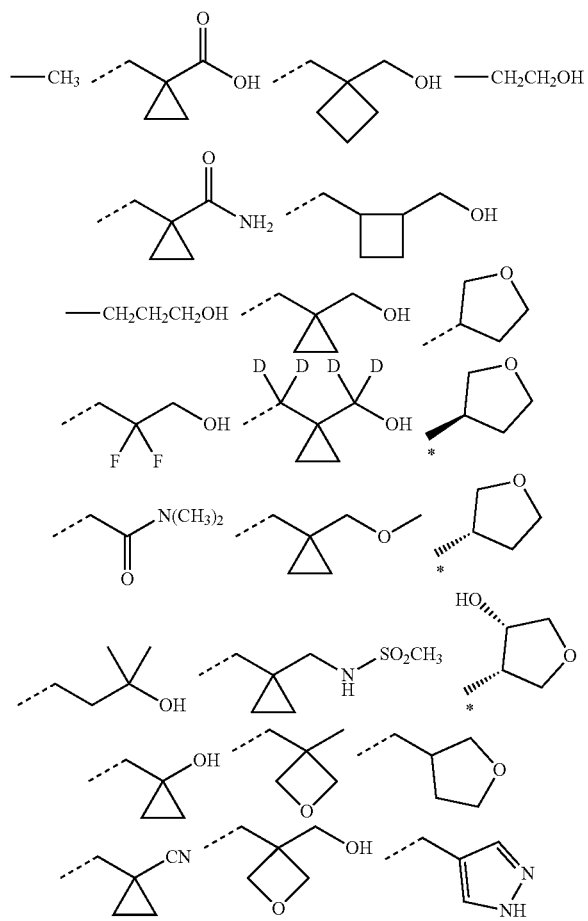

In one embodiment A is cyclopropyl, t is 1, s is 1, R$^x$ and R$^y$ are hydrogen and X is —OH.

In one embodiment A is cyclopropyl, t is 1, s is 1, R$^x$ and R$^y$ are hydrogen and X is —CN.

In one embodiment R$^3$ is hydrogen and s is 1. In one embodiment, X is hydrogen and s, t, and q are 0.

R$^4$ and a a is 0, 1, 2 or 3. In other words, the phenyl group of the isoindolin-1-one may have 0, 1, 2 or 3 substituents R$^4$.

In one embodiment a is 0 or 1. In another embodiment a is 0. In another embodiment a is 1.

When a is 2 or 3 (i.e. the phenyl group of the isoindolin-1-one is substituted with more than one R$^4$) the substituents R$^4$ may be the same or different (i.e. are independently selected from the definitions of R$^4$).

In one embodiment, a is 1 and the substituent R$^4$ is at the 4-position of the isoindolin-1-one, and the compound of formula (I°) is a compound of formula (Ir) or a tautomer or a solvate or a pharmaceutically acceptable salt thereof:

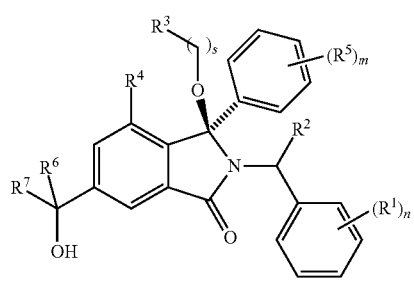

R$^4$ is independently selected from halogen, nitrile, C$_{1-4}$ alkyl, haloC$_{1-4}$alkyl, C$_{1-4}$alkoxy and haloC$_{1-4}$alkoxy.

In one embodiment, R$^4$ is halogen. In one embodiment, R$^4$ is fluoro or chloro. In another embodiment, R$^4$ is fluoro.

In one embodiment, a is 1, the substituent R$^4$ is at the 4-position of the isoindolin-1-one, and R$^4$ is F and the compound of formula (I°) is a compound of formula (Is) or a tautomer or a solvate or a pharmaceutically acceptable salt thereof:

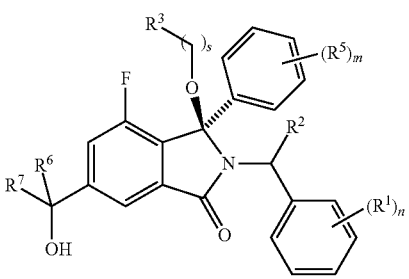

In one embodiment, a is 0, and the compound of formula (I°) is a compound of formula (If) or a tautomer or a solvate or a pharmaceutically acceptable salt thereof:

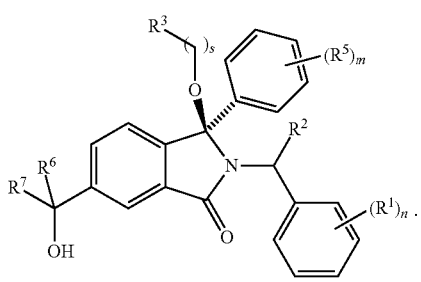

(It)

In one embodiment, $R^4$ is $C_{1-4}$ alkyl (e.g. —$CH_3$), or halogen (e.g. F or Cl) and a is 1.

In one embodiment, a is 0 and $R^4$ is absent (i.e. hydrogen).

In one embodiment a is 0 or 1 and $R^4$ is halogen (e.g. fluorine).

$R^5$ and m m is 1 or 2. In other words, the phenyl group may have 1 or 2 substituents $R^5$.

In one embodiment, m is 1 and the phenyl group has one substituent.

$R^5$ may be attached at the ortho (or o-), meta (or m-) or para (or p-) position of the phenyl group, wherein the position is defined relative to the point of attachment of the phenyl group to the 3-position of the isoindolin-1-one ring.

When m is 2 (i.e. the phenyl group is substituted with more than one $R^5$) the substituents $R^5$ may be the same or different (i.e. are independently selected from the definitions of $R^5$).

In one embodiment, m is 1 and the substituent $R^4$ is at the p-position of the phenyl group, and the compound of formula (I°) is a compound of formula (Iu) or a tautomer or a solvate or a pharmaceutically acceptable salt thereof:

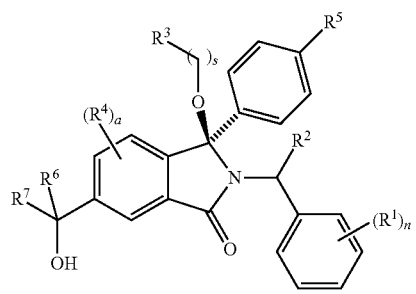

(Iu)

$R^5$ is independently selected from halogen, nitrile, $C_{1-4}$ alkyl, halo$C_{1-4}$alkyl, $C_{1-4}$ alkoxy and halo$C_{1-4}$alkoxy.

In one embodiment, $R^5$ is halogen, $C_{1-4}$ alkyl, halo$C_{1-4}$ alkyl or $C_{1-4}$ alkoxy. In another embodiment $R^5$ is halogen (e.g. chloro).

In one embodiment, $R^5$ is halogen (e.g. Cl or F), $C_{1-4}$ alkyl (e.g. —$CH_2CH_3$), nitrile, halo$C_{1-4}$alkyl (e.g. —$CF_3$, or —$CF_2CH_3$), or halo$C_{1-4}$alkoxy (e.g. —$OCF_3$), and m is 1 or 2.

In one embodiment, m is 1 and $R^5$ is selected from halogen, nitrile, $C_{1-4}$ alkyl, halo$C_{1-4}$alkyl, $C_{1-4}$alkoxy and halo$C_{1-4}$alkoxy.

In one embodiment, m=1 and $R^5$ is —Cl (e.g. p-Cl), —F (e.g. 4-F), —CN (e.g. p-CN), —$CF_3$ (e.g. p-$CF_3$), —$OCF_3$ (e.g. p-$OCF_3$), $CF_2CH_3$ (e.g. p-$CF_2CH_3$) or —$CH_2CH_3$ (e.g. p-$CH_2CH_3$), or m=2 and $R^5$ is p-F or m-F.

In one embodiment, m=1 and $R^5$ is —Cl (e.g. p-Cl)

$R^6$ and $R^7$ $R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, —$(CH_2)_j$—O—$C_{1-6}$alkyl, —$(CH_2)_j$—O—(hydroxy$C_{1-6}$alkyl), —$C_{1-6}$alkyl-N$R^xR^y$, —$(CR^xR^y)_p$—CONR$^x$R$^y$, —$(CR^xR^y)_p$—NR$^x$COR$^y$, —$(CR^xR^y)_p$—O—$CH_2$—CONR$^x$R$^y$, heterocyclic group with 3 to 7 ring members, —$CH_2$-heterocyclic group with 3 to 7 ring members, —CHz-O-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$cycloalkyl, —$CH_2$—$C_{3-8}$cycloalkyl, —$CH_2$—O—$C_{3-8}$cycloalkyl, and $C_{3-8}$ cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

or the $R^6$ and $R^7$ groups, together with the carbon atom to which they are attached, can join to form a $C_{3-6}$ cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-6}$ cycloalkyl and heterocyclyl groups may be optionally substituted by one or more $R^z$ groups;

$R^x$ and $R^y$ are independently selected from hydrogen, halogen, nitro, nitrile, halo$C_{1-6}$alkyl, $C_{2-6}$alkenyl, $C_{2-6}$ alkynyl, hydroxy, hydroxy$C_{1-6}$alkyl, $C_{1-6}$alkoxy, —$(CH_2)_k$—O—$C_{1-6}$ alkyl, hydroxy$C_{1-6}$alkoxy, —N(H)$_e$($C_{1-4}$alkyl)$_{2-e}$, —$C_{1-8}$ alkyl-N(H)$_e$($C_{1-4}$alkyl)$_{2-e}$, —$(CH_2)_k$—C(=O)N(H)$_e$ ($C_{1-4}$ alkyl)$_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$ cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =$CH_2$ group;

$R^z$ is independently selected from halogen, nitro, nitrile, $C_{1-6}$alkyl, halo$C_{1-6}$alkyl, $C_{2-6}$alkenyl, $C_{2-6}$ alkynyl, =O, hydroxy, hydroxy$C_{1-6}$alkyl, $C_{1-6}$ alkoxy, —$(CH_2)_k$—O—$C_{1-6}$ alkyl, hydroxy$C_{1-6}$alkoxy, —C(=O)$C_{1-6}$alkyl, —C(=O)$C_{1-6}$alkyl-OH, —C(=O)$C_{1-6}$ alkyl-N(H)$_e$($C_{1-4}$alkyl)$_{2-e}$, —C(=O)N(H)$_e$($C_{1-4}$alkyl)$_{2-e}$, —$(CH_2)_r$—CO$_2$$C_{1-6}$ alkyl, —$(CH_2)_r$—CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$ cycloalkyl and $C_{3-8}$ cycloalkenyl, wherein if $R^7$ is pyridine then $R^z$ is other then —$NH_2$;

j, e, r and p are independently selected from 0, 1 and 2; and k is selected from 1 and 2.

In one embodiment, $R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, —$(CH_2)_j$—O—$C_{1-6}$alkyl, —$(CH_2)_j$—O-(hydroxy$C_{1-6}$alkyl), —$C_{1-6}$alkyl-N$R^xR^y$, —$(CR^xR^y)_p$—CONR$^x$R$^y$, —$(CR^xR^y)_p$—NR$^x$COR$^y$, —$(CR^xR^y)_p$—O—$CH_2$—CONR$^x$R$^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, C$_{3-8}$ cycloalkyl, —CH$_2$—C$_{3-8}$cycloalkyl, —CH$_2$—O—C$_{3-8}$ cycloalkyl, and C$_{3-8}$cycloalkenyl, wherein said cycloalkyl, cycloalkenyl or heterocyclic groups may be optionally substituted by one or more Rz groups, and wherein in each instance the heterocyclic group comprises one or more (e.g. 1, 2, or 3) heteroatoms selected from N, O, S and oxidised forms thereof;

In one embodiment R$^7$ is a cycloalkyl, cycloalkenyl or heterocyclic group optionally substituted by one or more R$^z$ selected from C$_{1-6}$alkyl (e.g. methyl), C$_{1-6}$alkoxy (e.g. methoxy) and —C(=O)C$_{1-6}$alkyl (e.g. —C(=O)CH$_3$).

In one embodiment R$^7$ is a cycloalkyl or cycloalkenyl group optionally substituted by one or more R$^z$ groups wherein R$^z$ is hydroxy.

R$^6$ and R$^7$ may be the same or different.

When R$^6$ and R$^7$ are different, the compound of formula (I°) can exist as at least two diastereoisomers:

Diastereoisomer 2A

Diastereoisomer 2B

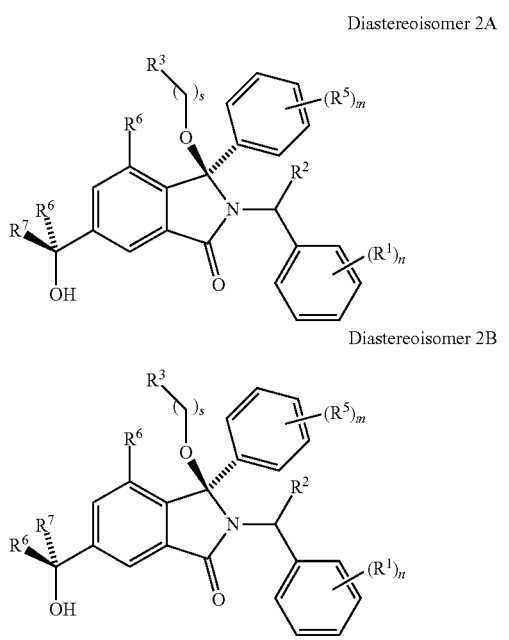

For the avoidance of doubt, the general formula (I°) and all subformulae cover both individual diastereoisomers and mixtures of the diastereoisomers which are related as epimers at the —CR$^6$R$^7$OH group.

In one embodiment of the compound of formula (I°) R$^6$ and R$^7$ are different and the compound is diastereoisomer 2A or a tautomer or a solvate or a pharmaceutically acceptable salt thereof.

In one embodiment of the compound of formula (I°) R$^6$ and R$^7$ are different and the compound is diastereoisomer 2B or a tautomer or a solvate or a pharmaceutically acceptable salt thereof.

In one embodiment, R$^6$ is methyl and the compound of formula (I°) is a compound of formula (Iv) or a tautomer or a solvate or a pharmaceutically acceptable salt thereof:

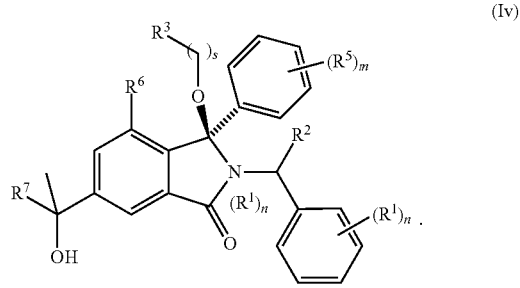

In one embodiment, R$^5$ is ethyl and the compound of formula (I°) is a compound of formula (Iv') or a tautomer or a solvate or a pharmaceutically acceptable salt thereof:

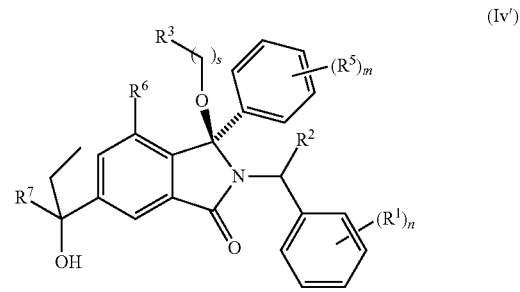

In one embodiment, R$^7$ is selected from C$_{1-6}$alkyl or haloC$_{1-6}$alkyl. In one embodiment R$^7$ is a C$_{3-6}$cycloalkyl (e.g. cyclopropyl, cyclobutyl or cyclohexyl) optionally substituted by one or more R$^z$ groups (e.g. —OH).

In one embodiment, R$^7$ is selected from C$_{1-4}$alkyl, hydroxyC$_{1-6}$alkyl, —(CH$_2$)$_j$—O—C$_{1-6}$alkyl, —(CH$_2$)$_j$—O-(hydroxyC$_{1-6}$alkyl), —C$_{1-6}$alkyl-NR$^x$R$^y$ (e.g. —C$_{1-8}$alkyl-N(H)$_e$(C$_{1-4}$alkyl)$_{2-e}$), —(CR$^x$R$^y$)$_p$—NR$^x$COR$^y$, heterocyclic group with 3 to 7 ring members, —CH$_2$-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, C$_{3-8}$ cycloalkyl, and —CH$_2$—C$_{3-6}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof.

In one embodiment, R$^7$ is selected from C$_{1-6}$alkyl, hydroxyC$_{1-6}$alkyl, —(CH$_2$)$_j$—O—C$_{1-4}$alkyl, —(CH$_2$)$_j$—O-(hydroxyC$_{1-6}$alkyl), —C$_{1-6}$alkyl-N(H)$_e$(C$_{1-4}$alkyl)$_{2-e}$, heterocyclic group with 3 to 7 ring members, —CH$_2$-heterocyclic group with 3 to 7 ring members, —C(=O)NH-heterocyclic group with 3 to 7 ring members, C$_{3-8}$cycloalkyl, and —CH$_2$—C$_{3-8}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof.

In one embodiment, R$^7$ is selected from heterocyclic group with 3 to 7 ring members, —CH$_2$-heterocyclic group with 3 to 7 ring members, —C(=O)NH-heterocyclic group with 3 to 7 ring members, C$_{3-8}$ cycloalkyl, and —CH$_2$—C$_{3-8}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof.

In one embodiment, $R^7$ is selected from heterocyclic group with 3 to 7 ring members and —$CH_2$-heterocyclic group with 3 to 7 ring members, wherein said heterocyclic groups may be optionally substituted by one or more $R^z$ groups, and wherein in each instance the heterocyclic group comprises one or more (e.g. 1, or 2) heteroatoms selected from N, O, S and oxidised forms thereof.

In embodiment, the heterocyclic group is saturated. In one embodiment, $R^7$ is saturated heterocyclic group with 3 to 6 ring members or —$CH_2$-(saturated heterocyclic group with 3 to 6 ring members) such as wherein the heterocyclic group is selected from oxetanyl, oxanyl, piperidinyl, piperazinyl, morpholinyl, pyrrolidinyl, imidazolinyl, azetidinyl, thiomorpolinyl, such as oxanyl, piperdinyl or piperazinyl.

In one embodiment, $R^7$ is selected from saturated heterocyclic group with 3 to 6 ring members and —$CH_2$-saturated heterocyclic group with 3 to 6 ring members, wherein said heterocyclic groups may be optionally substituted by one or more $R^z$ groups, and wherein in each instance the heterocyclic group comprises one or more (e.g. 1, 2, or 3) heteroatoms selected from N, O, S. In one embodiment, $R^7$ is selected from a nitrogen containing saturated heterocyclic group with 3 to 6 ring member and —$CH_2$-(nitrogen containing saturated heterocyclic group with 3 to 6 ring members), wherein said heterocyclic groups may be optionally substituted by one or more $R^z$ groups, and wherein the heterocyclic group may optionally contain one or more (e.g. 1, 2, or 3) additional heteroatoms selected from N, O, S.

In one embodiment, $R^7$ is nitrogen containing saturated heterocyclic group with 3 to 7 ring members or —$CH_2$-(nitrogen containing saturated heterocyclic group with 3 to 7 ring members), wherein said nitrogen containing saturated heterocyclic groups may be optionally substituted by one or more $R^z$ groups and wherein the nitrogen containing saturated heterocyclic group may optionally contain one or more (e.g. 1, 2, or 3) additional heteroatoms selected from N, O, S. In one embodiment the nitrogen containing saturated heterocyclic group with 3 to 7 ring members (such as 3 to 6 ring members) is selected from piperidinyl, piperazinyl, morpholinyl, pyrrolidinyl, imidazolinyl, azetidinyl, thiomorpolinyl, such as piperdinyl or piperazinyl.

In one embodiment, $R^7$ is nitrogen containing aromatic heterocyclic group with 3 to 6 ring members or —$CH_2$-(nitrogen containing aromatic heterocyclic group with 3 to 6 ring members), wherein said heterocyclic groups may be optionally substituted by one or more $R^z$ groups and wherein the heterocyclic group may optionally contain one or more (e.g. 1, 2, or 3) additional heteroatoms selected from N, O, S.

In another embodiment, $R^7$ is nitrogen containing aromatic heterocyclic group with 3 to 6 ring members, wherein said heterocyclic group may be unsubsituted or substituted by one or more $R^z$ groups, for example selected from halogen (e.g. fluorine), $C_{1-6}$alkyl (e.g. methyl), $C_{1-6}$alkoxy (e.g. methoxy), and —$C(=O)C_{1-6}$alkyl (e.g. —$C(=O)$ $CH_3$).

In one embodiment, $R^7$ is oxygen containing aromatic heterocyclic group with 3 to 6 ring members or —$CH_2$-(oxygen containing aromatic heterocyclic group with 3 to 6 ring members), wherein said heterocyclic groups may be optionally substituted by one or more $R^z$ groups and wherein the heterocyclic group may optionally contain one or more (e.g. 1, 2, or 3) additional heteroatoms selected from N, O, S.

In another embodiment, $R^7$ is oxygen containing aromatic heterocyclic group with 3 to 6 ring members, wherein said heterocyclic group may be unsubsituted or substituted by one or more $R^z$ groups, for example $R^z$ groups selected from halogen (e.g. fluorine), $C_{1-6}$alkyl (e.g. methyl), $C_{1-6}$alkoxy (e.g. methoxy), and —$C(=O)C_{1-6}$alkyl (e.g. —$C(=O)$ $CH_3$).

In one embodiment $R^7$ is selected from heterocyclyl groups containing 5 or 6 ring members optionally substituted by one or more $R^z$.

In one embodiment $R^7$ is selected from aromatic heterocyclyl groups containing 5 ring members optionally substituted by one or more $R^z$. In one embodiment $R^7$ is selected from an aromatic nitrogen containing (e.g. diaza) heterocyclyl group containing 5 ring members optionally substituted by one or more $R^z$. In one embodiment $R^7$ is pyrazolyl (e.g. pyrazol-4-yl or pyrazol-3-yl).

In one embodiment $R^7$ is selected from a saturated heterocyclyl group containing 6 ring members optionally substituted by one or more $R^z$. In one embodiment $R^7$ is selected from a saturated oxygen or nitrogen containing heteterocyclyl group containing 6 ring members optionally substituted by one or more $R^z$.

In one embodiment $R^7$ is selected from oxanyl, piperidinyl, pyrazolyl or imidazolyl optionally substituted by one or more $R^z$. In one embodiment $R^7$ is selected from oxanyl, piperidinyl, pyrazolyl or imidazolyl optionally substituted by one or more $R^z$, where $R^z$ is selected from halo (e.g. —F) or $C_{1-4}$alkyl (e.g. methyl).

In one embodiment $R^7$ is selected from oxanyl (also known as tetrahydropyranyl) or piperidinyl optionally substituted by one or more $R^z$. In one embodiment $R^7$ is selected from oxanyl or piperidinyl unsubstituted or substituted by one or more $R^z$, where $R^z$ is selected from halo (e.g. —F) or $C_{1-4}$alkyl (e.g. methyl), in particular halo (e.g. —F).

In one embodiment, $R^7$ is $C_{3-8}$ cycloalkyl such as $C_{3-6}$cycloalkyl (e.g. cyclobutyl or cyclohexyl) optionally substituted by one or more Ra, for example where $R^z$ is hydroxy. In one embodiment, $R^7$ is cyclohexyl optionally substituted by one or more hydroxy. In one embodiment $R^7$ is cyclohexyl optionally substituted by one or more hydroxyl, in the trans stereochemistry (e.g. trans-4-hydroxycyclohexane).

In one embodiment $R^7$ is selected from —$CH_2$—NH-heterocyclic group with 3 to 7 ring members (e.g. —$CH_2$—NH-oxanyl and —$CH_2$—N($C_{1-6}$ alkyl)-heterocyclic group with 3 to 7 ring members (e.g. —$CH_2NCH_3$-(piperidinyl) optionally substituted by one or more $R^z$ groups (e.g. methyl, —$COCH_3$).

In one embodiment, $R^7$ is —$(CR^xR^y)_p$—$CONR^xR^y$ or —$C(=O)NH$-heterocyclic group with 3 to 7 ring members. In one embodiment, $R^7$ is —$C(=O)NH$-heterocyclic group with 4 to 6 ring members (e.g. piperidinyl, pyrazolyl, or azetidinyl).

In one embodiment, $R^7$ is —$(CR^xR^y)_p$—$CONR^xR^y$. In one embodiment $R^7$ is —$(CR^xR^y)_p$—$CONH(C_{1-4}$alkyl), in particular —$(CO)NHCH_3$, —$(CO)NHCH_2CH_3$ or —$(CO)$ $NH(CH(CH_3)_2)$.

In one embodiment $R^7$ is —$C(=O)NH$-heterocyclic group with 3 to 7 ring members (e.g. —$C(=O)NH$-piperidinyl, —$C(=O)NH$-azetidinyl or —$C(=O)NH$-pyrazolyl) optionally substituted by one or more $R^z$ groups (e.g. methyl, —$COCH_3$).

In one embodiment, $R^7$ is —$C_{1-6}$alkyl-$NR^xR^y$ (e.g. —$C_{1-4}$ alkyl-$N(H)_e(C_{1-4}$alkyl)$_{2-e}$). In one embodiment $R^7$ is —$CH_2NH_2$, —$CH_2NHCH_3$, or —$CH_2N(CH_3)_2$. In one embodiment $R^7$ is —$C_{1-6}$alkyl-$NR^xR^y$ wherein $R^x$ is $C_3$-acycloalkyl. In one embodiment $R^7$ is —$C_{1-2}$ alkyl-NH—$C_{3-8}$ cycloalkyl (e.g. —$CH_2$—NH-cyclopropyl).

In one embodiment, $R^7$ is —$C_{1-6}$alkyl-$NR^xR^y$ wherein the $R^x$ and $R^y$ groups, together with the nitrogen atom to which they are attached, can join to form a $C_{3-8}$cycloalkyl or heterocyclyl group with 3 to 6 ring members. In one embodiment, $R^x$ and $R^y$ together form a saturated heterocyclyl group with 3 to 6 ring members e.g. piperazinyl.

In one embodiment $R^7$ is —$C_{1-6}$alkyl-$NR^xR^y$, wherein the $R^x$ and $R^y$ groups, together with the nitrogen atom to which they are attached, join to form a $C_{3-8}$cycloalkyl or saturated heterocyclyl group with 3 to 6 ring members which may be optionally fused to an aromatic heterocyclyl group of 3 to 5 ring members. In one embodiment $R^7$ is —$C_{1-6}$alkyl-$NR^xR^y$, wherein the $R^x$ and $R^y$ groups, together with the nitrogen atom to which they are attached, join to form a saturated heterocyclyl group with 3 to 6 ring members which is fused to an aromatic heterocyclyl group of 3 to 5 ring members. $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_r$—$CO_2C_{1-6}$alkyl, —$(CH_2)_r$—$CO_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl.

In one embodiment $R^z$ is independently selected from halogen (e.g. fluorine), $C_{1-6}$alkyl (e.g. methyl), $C_{1-6}$alkoxy (e.g. methoxy), and —C(=O)$C_{1-6}$alkyl (e.g. —C(=O)$CH_3$).

In one embodiment $R^z$ is independently selected from $C_{1-6}$alkyl (e.g. methyl), $C_{1-6}$alkoxy (e.g. methoxy), and —C(=O)$C_{1-6}$alkyl (e.g. —C(=O)$CH_3$).

In one embodiment, $R^7$ is $C_{1-6}$alkyl (e.g. methyl or ethyl), halo$C_{1-6}$alkyl (e.g. trifluoromethyl), $C_{2-6}$alkenyl (e.g. $C_2$alkenyl), hydroxy$C_{1-6}$alkyl (e.g. —$CH_2$OH, —$CH_2CH_2$OH), —$C_{1-6}$alkyl-$NR^xR^y$ (e.g. —$CH_2NH_2$, —$CH_2NHCH_3$, —$CH_2N(CH_3)_2$, or —$CH_2$—NH-cyclopropyl), —$(CR^xR^y)_p$—$CONR^xR^y$ (e.g. —(CO)$NHCH_3$, —(CO)$NHCH_2CH_3$, —(CO)$NHCH_2CH_2NH_2$ or —(CO)NH(CH($CH_3)_2$), —$(CH_2)_j$—O—$C_{1-6}$alkyl (e.g. —$CH_2OCH_3$, —$CH_2OCH_2CH_3$ or —$CH_2OCD_3$), —$(CR^xR^y)_p$—$NR^xCOR^y$ (e.g. —$CH_2NHCOCH_3$), —$(CR^xR^y)_p$—O—$CH_2$—$CONR^xR^y$ (e.g. —$CH_2$—O—$CH_2CON(CH_3)_2$), —$(CH_2)_j$—O-(hydroxy$C_{1-6}$alkyl) (e.g. —$CH_2$—O—$CH_2CH_2OH$,), —C(=O)NH-heterocyclic group with 3 to 7 ring members, $C_{3-6}$cycloalkyl, heterocyclic group with 3 to 7 ring members (e.g. oxanyl), or —$CH_2$-heterocyclic group with 3 to 7 ring members wherein the cycloalkyl or heterocyclic group comprises one or more (e.g. 1, 2, or 3) heteroatoms selected from N, O, S and oxidised forms and may be optionally substituted by one or more $R^z$ groups (for example selected from $C_{1-6}$ alkyl (e.g. methyl), $C_{1-6}$alkoxy (e.g. methoxy) and —C(=O)$C_{1-6}$ alkyl (e.g. —C(=O)$CH_3$)). In one embodiment, $R^6$ is methyl or ethyl and $R^7$ is $C_{1-6}$alkyl (e.g. methyl), hydroxy$C_{1-6}$alkyl, —$C_{1-6}$ alkyl-$NR^xR^y$, —$(CR^xR^y)_p$—$CONR^xR^y$, —$(CH_2)_j$—O—$C_{1-6}$ alkyl, —$(CR^xR^y)_p$—$NR^xCOR^y$, —$(CR^xR^y)_p$—O—$CH_2$—$CONR^xR^y$, —$(CH_2)_j$—O- (hydroxy$C_{1-6}$alkyl), heterocyclic group with 3 to 7 ring members (e.g. oxanyl), or —$CH_2$- heterocyclic group with 3 to 7 ring members wherein the heterocyclic group comprises one or more (e.g. 1, 2, or 3) heteroatoms selected from N, O, S and oxidised forms and may be optionally substituted by one or more $R^z$ groups selected from $C_{1-6}$alkyl (e.g. methyl), $C_{1-6}$alkoxy (e.g. methoxy) and —C(=O)$C_{1-6}$alkyl (e.g. —C(=O)$CH_3$).

In one embodiment, $R^8$ is selected from hydrogen, $C_{1-6}$ alkyl (e.g. —$CH_3$, —$CH_2CH_3$ or —$CH_2CH_2CH_3$), $C_{2-6}$alkenyl (e.g. —CH=$CH_2$) and halo$C_{1-6}$alkyl (e.g. —$CF_3$).

In one embodiment, $R^6$ is selected from hydrogen or $C_{1-6}$alkyl (e.g. —$CH_3$ or —$CH_2CH_3$).

In one embodiment, $R^7$ is $C_{1-6}$alkyl (e.g. —$CH_3$ or —$CH_2CH_3$), hydroxy$C_{1-6}$alkyl (e.g. —$CH_2$OH), —$C_{1-6}$alkyl-$NR^xR^y$ (e.g. —$CH_2N(CH_3)_2$), —$(CR^xR^y)_p$—$CONR^xR^y$ (e.g. —C(=O)N($CH_3)_2$ or —C(=O)$NHCH_3$ or

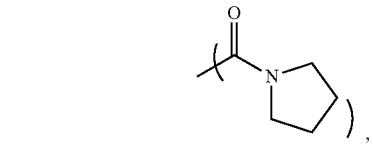

—$(CH_2)_j$—O—$C_{1-6}$alkyl (e.g. —$CH_2OCH_3$), $C_{3-8}$cycloalkyl (e.g. cyclobutyl or cyclohexyl), heterocyclic group with 3 to 7 ring members e.g.
(point of attachment represented by dashed bond):

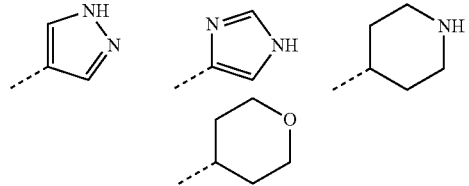

or —$CH_2$-heterocyclic group with 3 to 7 ring members e.g. (point of attachment represented by dashed bond)

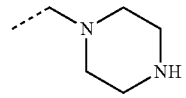

wherein when the moiety $R^7$ comprises a heterocyclic or cycloalkyl group, the heterocyclic group may be optionally substituted by one or more $R^z$ groups selected from $C_{1-6}$alkyl (e.g. methyl), hydroxy, halogen (e.g. fluoro), —C(=O)$C_{1-6}$ alkyl (e.g. —C(=O)C($CH_3)_3$), —$(CH_2)_r$—$CO_2$H (e.g. —$CH_2$COOH or $CH_2CH_2$COOH or —$(CH_2)_r$—$CO_2C_{1-6}$ alkyl (e.g. $CH_2CH_2$COO$CH_3$).

In one embodiment, $R^7$ is $C_{1-6}$alkyl (e.g. methyl or ethyl), halo$C_{1-6}$ alkyl (e.g. trifluoromethyl), $C_{2-6}$ alkenyl (e.g. $C_2$alkenyl), hydroxy$C_{1-6}$alkyl (e.g. —$CH_2$OH, —$CH_2CH_2$OH), —$C_{1-6}$alkyl-$NR^xR^y$ (e.g. —$CH_2NH_2$, —$CH_2NHCH_3$, —$CH_2N(CH_3)_2$, or —$CH_2$—NH-cyclopropyl), —$(CR^xR^y)_p$—$CONR^xR^y$ (e.g. —(CO)$NHCH_3$, —(CO)$NHCH_2CH_3$, —(CO)$NHCH_2CH_2NH_2$ or —(CO)NH(CH($CH_3)_2$), —$(CH_2)_j$—O—$C_{1-6}$alkyl (e.g. —$CH_2OCH_3$, —$CH_2OCH_2CH_3$ or —$CH_2OCD_3$), —$(CR^xR^y)_p$—$NR^xCOR^y$ (e.g. —$CH_2NHCOCH_3$), —$(CR^xR^y)_p$—O—$CH_2$—$CONR^xR^y$ (e.g. —$CH_2$—O—$CH_2CON(CH_3)_2$), —$(CH_2)_j$—O-(hydroxy$C_{1-6}$ alkyl) (e.g. —$CH_2$—O—

CH$_2$CH$_2$OH,), —C(=O)NH-heterocyclic group with 3 to 7 ring members, C$_{3-6}$cycloalkyl, heterocyclic group with 3 to 7 ring members (e.g. oxanyl), or —CH$_2$-heterocyclic group with 3 to 7 ring members wherein the cycloalkyl or heterocyclic group comprises one or more (e.g. 1, 2, or 3) heteroatoms selected from N, O, S and oxidised forms and may be optionally substituted by one or more R$^z$ groups (for example selected from C$_{1-4}$alkyl (e.g. methyl), C$_{1-6}$alkoxy (e.g. methoxy) and —C(=O)C$_{1-6}$alkyl (e.g. —C(=O)CH$_3$)). In one embodiment, R$^6$ is methyl or ethyl and R$^7$ is C$_{1-4}$alkyl (e.g. methyl), hydroxyC$_{1-6}$alkyl, —(CR$^x$R$^y$)$_p$—CONR$^x$R$^y$, —(CH$_2$)$_j$—O—C$_{1-6}$alkyl, —(CR$^x$R$^y$)$_p$—NR$^x$COR$^y$, —(CR$^x$R$^y$)$_p$—O—CH$_2$—CONR$^x$R$^y$, —(CH$_2$)$_j$—O-(hydroxyC$_{1-6}$alkyl), heterocyclic group with 3 to 7 ring members (e.g. oxanyl), or —CH$_2$-heterocyclic group with 3 to 7 ring members wherein the heterocyclic group comprises one or more (e.g. 1, 2, or 3) heteroatoms selected from N, O, S and oxidised forms and may be optionally substituted by one or more R$^z$ groups selected from C$_{1-6}$alkyl (e.g. methyl), C$_{1-6}$alkoxy (e.g. methoxy) and —C(=O)C$_{1-6}$alkyl (e.g. —C(=O)CH$_3$).

In one embodiment, R$^6$ is selected from hydrogen or C$_{1-6}$alkyl (e.g. —CH$_3$ or —CH$_2$CH$_3$).

In one embodiment, R$^7$ is C$_{1-6}$alkyl (e.g. —CH$_3$ or —CH$_2$CH$_3$), hydroxyC$_{1-6}$alkyl (e.g. —CH$_2$OH o), —c$_{1-6}$alkyl-NR$^x$R$^y$ (e.g. —CH$_2$N(CH$_3$)$_2$), —(CR$^x$R$^y$)$_p$—CONR$^x$R$^y$ (e.g. —C(=O)N(CH$_3$)$_2$ or

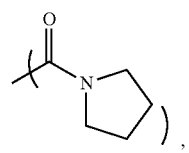

—(CH$_2$)$_j$—O—C$_{1-6}$alkyl (e.g. —CH$_2$OCH$_3$), heterocyclic group with 3 to 7 ring members e.g.
(point of attachment represented by dashed bond):

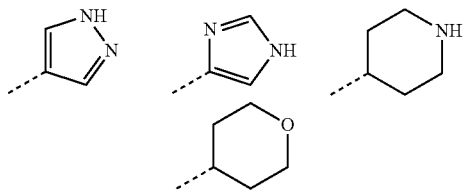

or —CH$_2$-heterocyclic group with 3 to 7 ring members e.g.
(point of attachment represented by dashed bond)

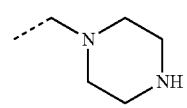

wherein when the moiety R$^7$ comprises a heterocyclic group, the heterocyclic group may be optionally substituted by one or more R$^z$ groups selected from C$_{1-6}$alkyl (e.g. methyl).

In one embodiment of formula (I°) R$^7$ is a heterocyclic group with 3 to 7 ring members optionally substituted by one or more R$^z$ groups e.g.
(point of attachment represented by dashed bond)

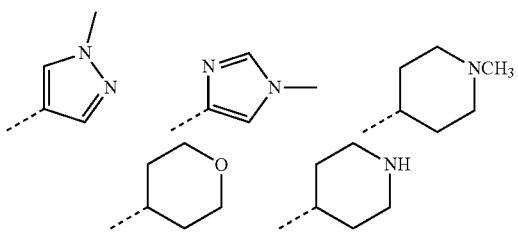

In one embodiment of formula (I°) R$^7$ is a heterocyclic group with 3 to 7 ring members optionally substituted by one or more R$^z$ groups e.g.
(point of attachment represented by dashed bond)

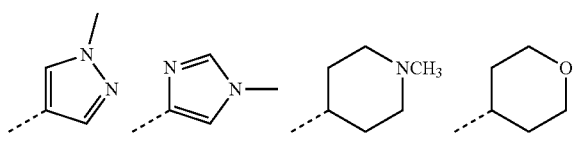

In one embodiment, R$^7$ is a —CH$_2$-heterocyclic group with 3 to 7 ring members optionally substituted by by one or more R$^z$ groups e.g.
(point of attachment represented by dashed bond)

In one embodiment, R$^7$ is selected from:
(point of attachment represented by dashed bond):

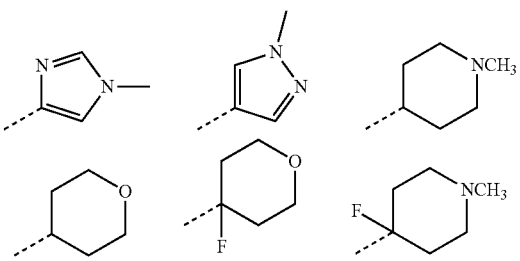

In one embodiment, R$^7$ is selected from:
(point of attachment represented by dashed bond):

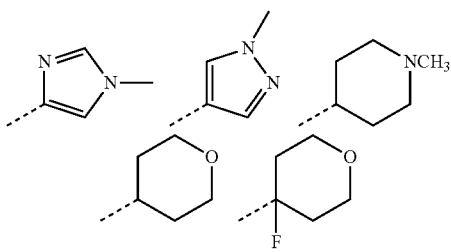

In one embodiment, R$^6$ is hydrogen or C$_{1-8}$ alkyl. In one embodiment, R$^6$ is C$_{1-6}$alkyl. In one embodiment, R$^6$ is methyl or ethyl. In one embodiment, R$^6$ is ethyl.

In one embodiment, $R^8$ is $C_{1-6}$alkyl (such as methyl or ethyl e.g. methyl) and $R^7$ is selected from hydroxy$C_{1-6}$alkyl and —$(CH_2)$—O—$C_{1-6}$alkyl, In one embodiment, $R^8$ is methyl and $R^7$ is selected from methyl, —$CH_2$—OH and —$CH_2$—$OCH_3$. In one embodiment $R^6$ is methyl and $R^7$ is methyl, ethyl, or propyl. In one embodiment $R^6$ is methyl and $R^7$ is methyl.

In one embodiment, $R^6$ is $C_{1-6}$alkyl or halo$C_{1-6}$alkyl (e.g. methyl, monofluoromethyl, trifluoromethyl or ethyl).

In one embodiment, $R^5$ is $C_{3-8}$ cycloalkyl such as $C_{3-6}$cycloalkyl (e.g. cyclopropyl).

In one embodiment $R^6$ is $C_{1-6}$alkyl (such as methyl or ethyl e.g. ethyl) and $R^7$ is selected from:
(point of attachment represented by dashed bond or bond terminus marked "*"):

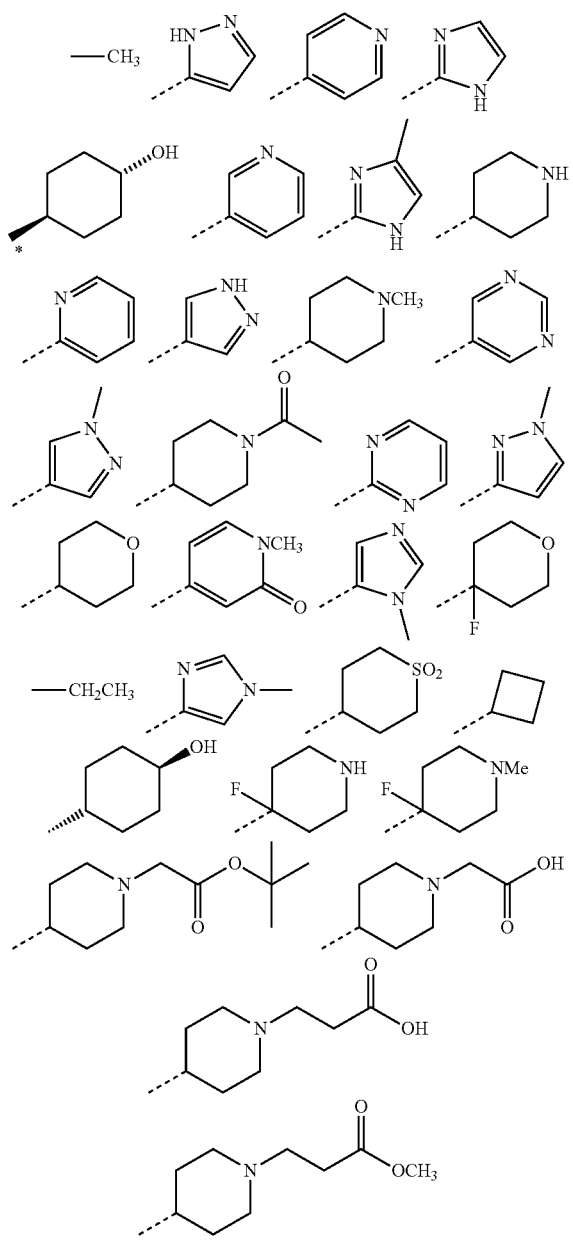

In one embodiment $R^6$ is $C_{1-6}$alkyl (such as methyl or ethyl e.g. ethyl) and $R^7$ is selected from:

(point of attachment represented by dashed bond or bond terminus marked "*"):

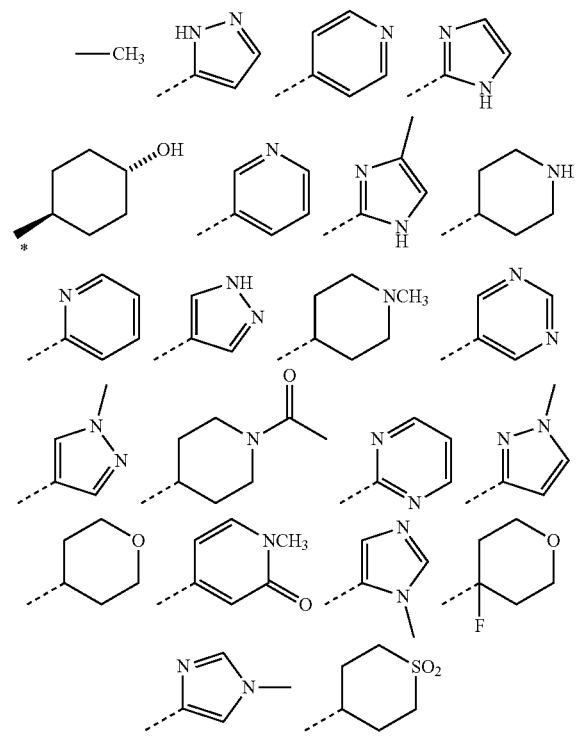

In particular, $R^7$ is:
(point of attachment represented by dashed bond):

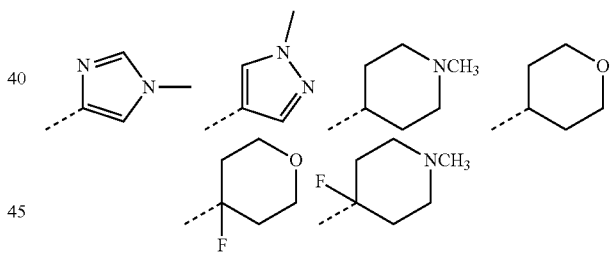

In one embodiment, $R^6$ is $C_{1-6}$alkyl (such as methyl or ethyl e.g. methyl) and $R^7$ is oxanyl, and the compound of formula (I°) is a compound of formula (Iw):

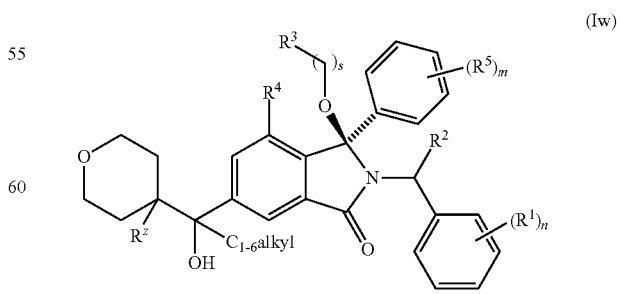

In one embodiment of formula (Iw) $R_z$ is hydrogen or fluorine.

In one embodiment, $R^7$ is imidazolyl and the compound of formula (I°) is a compound of formula (Ix) or a tautomer or a solvate or a pharmaceutically acceptable salt thereof:

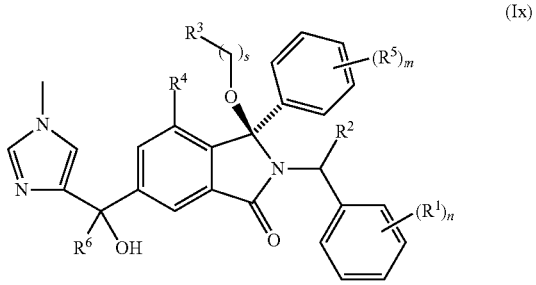
(Ix)

In one embodiment, $R^7$ is N-methyl piperidinyl and the compound of formula (I°) is a compound of formula (Ix') or a tautomer or a solvate or a pharmaceutically acceptable salt thereof:

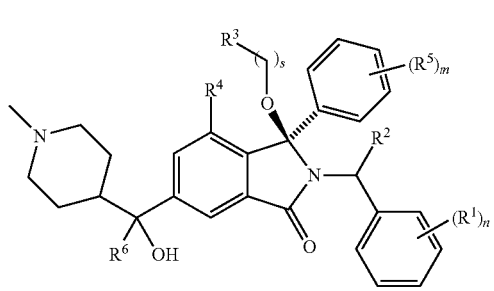
(Ix')

In one embodiment, $R^7$ is 4-fluoro-1-methylpiperidin-4-yl and the compound of formula (I°) is a compound of formula (Ix'') or a tautomer or a solvate or a pharmaceutically acceptable salt thereof:

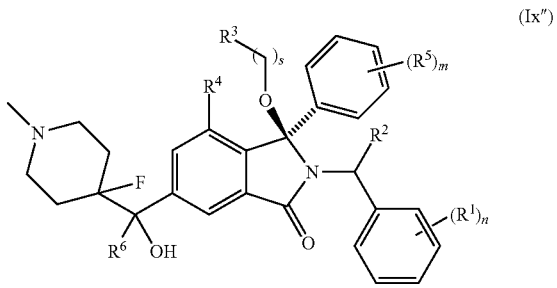
(Ix'')

In one embodiment, $R^7$ is pyrazolyl optionally substituted by one or more $R^z$ groups (e.g. methyl). In one embodiment, $R^7$ is N-methylpyrazol-3-yl or N-methylpyrazol-4-yl.

In one embodiment, $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxyl).

In one embodiment, $R^7$ is selected from piperidinyl optionally substituted by one or more $R^z$ groups (e.g. methyl, fluorine, or hydroxyl, in particular methyl and fluorine).

In one embodiment, the compound of formula (I°) is a compound of formula (Ix) and $R^5$ is $C_{1-4}$alkyl.

In one embodiment, $R^5$ is $C_{1-6}$alkyl (e.g. —CH$_3$, —CH$_2$CH$_3$ or —CH$_2$CH$_2$CH$_3$ such as methyl or ethyl e.g. ethyl) and $R^7$ is a heterocyclic group with 3 to 7 ring members optionally substituted by one or more $R^z$ groups.

In one embodiment, $R^5$ is $C_{1-6}$alkyl (e.g. —CH$_3$, —CH$_2$CH$_3$ or —CH$_2$CH$_2$CH$_3$ such as methyl or ethyl e.g. ethyl) and $R^7$ is imidazolyl optionally substituted by one or more $R^z$ groups (e.g. methyl imidazolyl).

In one embodiment, RB is $C_{1-6}$alkyl (e.g. —CH$_3$, —CH$_2$CH$_3$ or —CH$_2$CH$_2$CH$_3$ such as methyl or ethyl e.g. ethyl) and $R^7$ is piperidinyl optionally substituted by one or more $R^z$ groups (e.g. methyl piperidinyl).

In one embodiment $R^6$ is $C_{1-6}$alkyl (e.g. —CH$_3$, —CH$_2$CH$_3$ or —CH$_2$CH$_2$CH$_3$ such as methyl or ethyl e.g. ethyl) and $R^7$ is $C_{1-4}$alkyl, hydroxyl$C_{1-4}$alkyl, methoxy$C_{1-4}$alkyl, a heterocyclic group with 5 or 6 ring members or $C_{3-6}$cycloalkyl, wherein the heterocyclic group or $C_{3-6}$cycloalkyl group is optionally substituted by one or more $R^z$ (e.g. methyl, halogen (such as fluorine), C(=O)Me, or —OH).

In one embodiment $R^5$ is $C_{1-6}$alkyl (e.g. —CH$_3$, —CH$_2$CH$_3$ or —CH$_2$CH$_2$CH$_3$ such as methyl or ethyl e.g. ethyl) and $R^7$ is methyl, ethyl, hydroxylmethyl, hydroxyethyl, methoxymethyl, piperidinyl, oxanyl, imidazolyl, pyrazolyl, cyclobutyl, cyclohexyl, optionally substituted by one or more $R^z$ (e.g. methyl, halogen (such as fluorine), C(=O)Me, or —OH).

In one embodiment, $R^6$ and $R^7$ are both the same. In one embodiment, $R^6$ and $R^7$ are both methyl, and the compound of formula (I°) is a compound of formula (Iy) or a tautomer or a solvate or a pharmaceutically acceptable salt thereof:

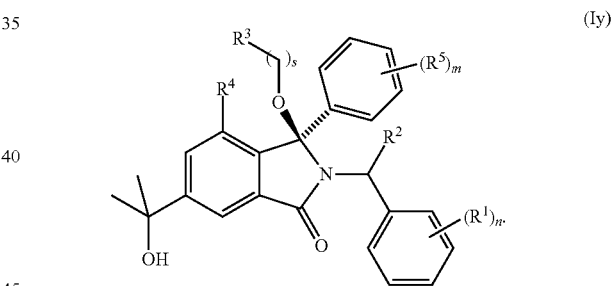
(Iy)

In one embodiment the group —CR$^6$R$^7$OH is other than —C(CH$_3$)$_{20}$H.

In one embodiment, $R^7$ is selected from the group consisting of:

(point of attachment represented by dashed bond)

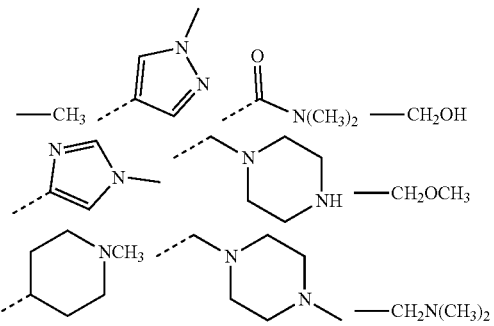

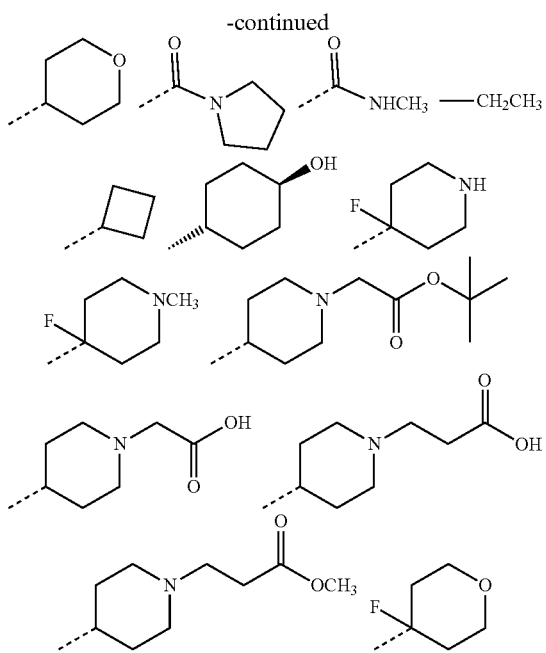

In one embodiment, R⁷ is selected from the group consisting of:
(point of attachment represented by dashed bond)

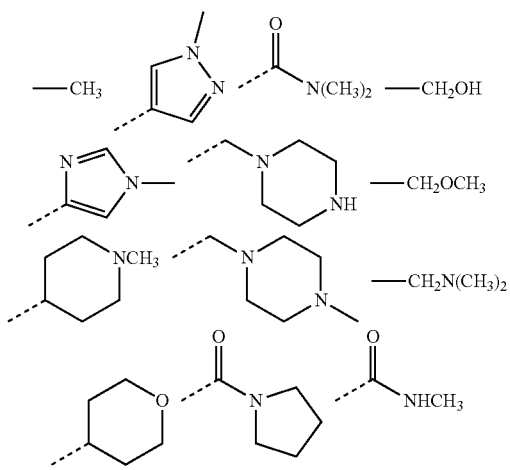

In one embodiment R$^z$ is independently selected from halogen, nitro, nitrile, $C_{1-6}$ alkyl, halo$C_{1-6}$alkyl, $C_{2-6}$alkenyl, $C_{2-6}$alkynyl, =O, hydroxy, hydroxy$C_{1-6}$alkyl, $C_{1-8}$ alkoxy, —(CH$_2$)$_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_k$—CO$_2$C$_{1-6}$ alkyl, —(CH$_2$)$_r$—CO$_2$H, —NH(C$_{1-4}$alkyl), —N(C$_{1-4}$alkyl)$_2$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$ alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$ cycloalkyl and C$_{3-8}$ cycloalkenyl.

In another embodiment R$^z$ is independently selected from halogen, nitro, nitrile, C$_{1-6}$alkyl, haloC$_{1-6}$alkyl, C$_{2-6}$alkenyl, C$_{2-6}$ alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O) C$_{1-6}$ alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_r$—CO$_2$C$_{1-8}$alkyl, —(CH$_2$)$_r$—CO$_2$H, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$ cycloalkyl and C$_{3-8}$ cycloalkenyl.

In another embodiment when R⁷ contains a saturated heterocyclic group then R¹ is independently selected from halogen, nitro, nitrile, C$_{1-6}$alkyl, haloC$_{1-6}$alkyl, C$_{2-6}$alkenyl, C$_{2-6}$ alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O) C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_r$—CO$_2$C$_{1-6}$alkyl, —(CH$_2$)$_r$—CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$ alkyl, heterocyclyl group with 3 to 6 ring members substituted by —C(=O) OC$_{1-4}$ alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$ cycloalkenyl.

Subformulae

In one embodiment, the compound of formulae (I°) is a compound of formulae (II) or a tautomer or a solvate or a pharmaceutically acceptable salt thereof:

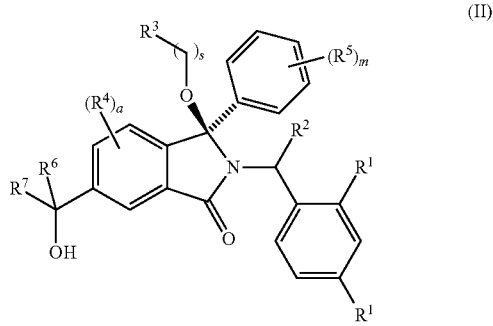

(II)

wherein R¹, R², R³, R⁴, R⁵, R⁶, R⁷, a, m and s are as defined herein.

In one embodiment, R¹ is chloro, nitrile, methyl or methoxy. In one embodiment, R¹ is hydroxy or hydroxyC$_{1-4}$ alkyl (e.g. hydroxyl).

In one embodiment, R¹ is O$_{0,1}$(CR$^x$R$^y$)$_x$COOH (e.g. —COOH, —CH$_2$COOH, —OCH$_2$COOH or —C(CH$_3$)$_2$ COOH.

In another embodiment, R¹ is chloro or nitrile and the compound of formula (II) is a compound of formula (IIa) or (IIb) or a tautomer or a solvate or a pharmaceutically acceptable salt thereof:

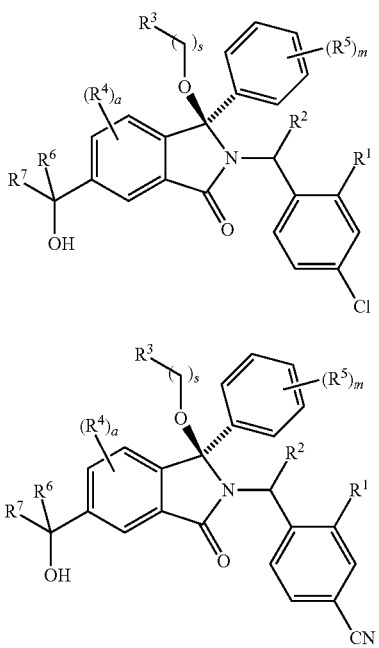
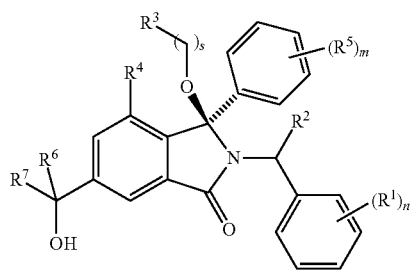

wherein $R^2$, $R^3$, $R^4$, $R^5$, $R^7$, m and s are as defined herein.
In one embodiment, $R^1$ is —$SO_2$—$R^x$. In particular, $R^x$ is —$SO_2$—$C_{1-4}$alkyl, for example —$SO_2$—$CH_3$ or —$SO_2$-heterocyclic group with 5 to 6 ring members (e.g. —$SO_2$-morpholinyl, typically —$SO_2$-(1-morpholinyl). In another embodiment In one embodiment, $R^1$ is hydroxy or hydroxy$C_{1-4}$alkyl (e.g. —$CH_2OH$ or OH).

In one embodiment, $R^6$ is methyl or ethyl, and the compound of formula (I°) is a compound of formula (IIIa) or (IIIb) or a tautomer or a solvate or a pharmaceutically acceptable salt thereof:

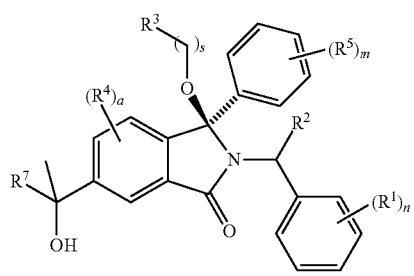

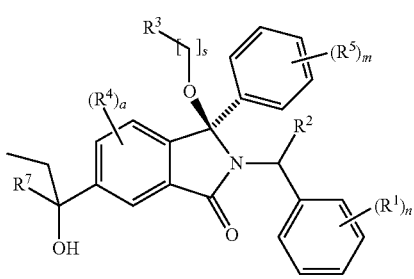

wherein $R^1$, $R^2$, $R^3$, $R^4$, $R^5$, $R^7$, a, m and s are as defined herein.

In one embodiment, a is 1 and the compound of formula (I°) is a compound of formula (IVa) or a tautomer or a solvate or a pharmaceutically acceptable salt thereof:

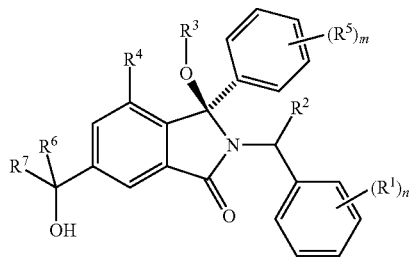

wherein $R^1$, $R^2$, $R^3$, $R^4$, $R^5$, $R^7$, a, m and s are as defined herein.

In one embodiment, s is 0 and the compound of formula (I°) is a compound of formula (IVb) or a tautomer or a solvate or a pharmaceutically acceptable salt thereof:

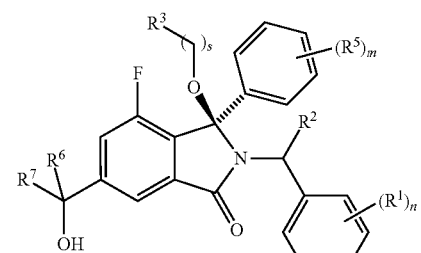

wherein $R^1$, $R^2$, $R^3$, $R^4$, $R^5$, $R^7$, a, m and s are as defined herein.

In one embodiment, $R^4$ is F and the compound of formula (IVa) is a compound of formula (V) or a tautomer or a solvate or a pharmaceutically acceptable salt thereof:

(V)

wherein $R^1$, $R^2$, $R^3$, $R^5$, $R^7$, m and s are as defined herein.

In one embodiment, m is 1 and the substituent $R^4$ is at the 4-position of the phenyl group, and the compound of formula (I°) is a compound of formula (VI) or a tautomer or a solvate or a pharmaceutically acceptable salt thereof:

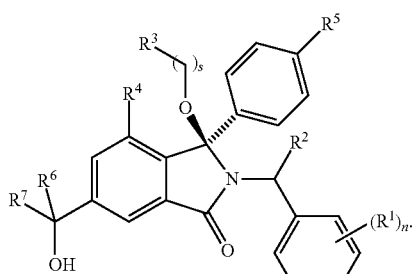

(VI)

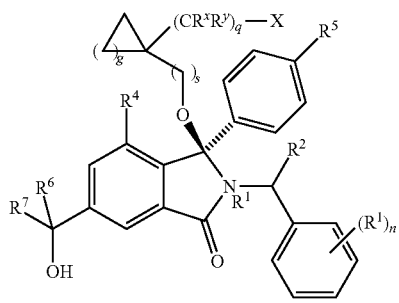

(VIIa)

In one embodiment, $R^5$ is chloro and the compound of formula (VI) is a compound of formula (VIa) or a tautomer or a solvate or a pharmaceutically acceptable salt thereof:

In one embodiment, g is 1, and so the cycloalkyl group is a cyclopropyl group and the compound of formula (VIIa) is a compound of formula (VIIb) or a tautomer or a solvate or a pharmaceutically acceptable salt thereof:

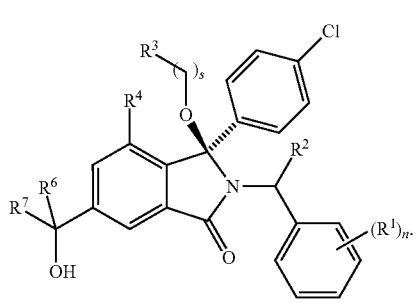

(VIa)

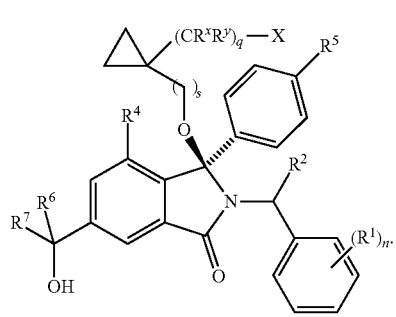

(VIIb)

In one embodiment, A is a $C_{3-6}$cycloalkyl group (g is 1, 2 or 3) and t is 1, and the compound of formula (VI) is a compound of formula (VII) or a tautomer or a solvate or a pharmaceutically acceptable salt thereof:

In one embodiment, s is 1, and the compound of formula (VIIb) is a compound of formula (VIIc) or a tautomer or a solvate or a pharmaceutically acceptable salt thereof:

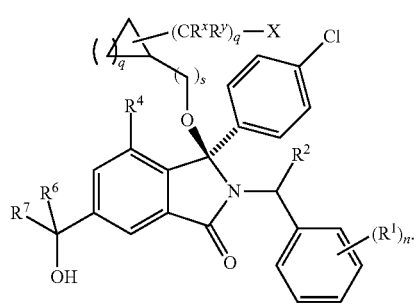

(VII)

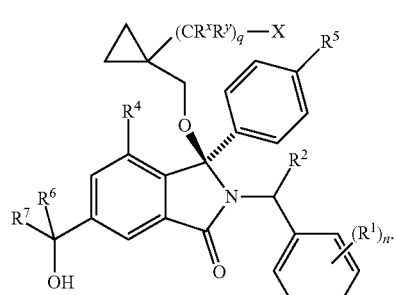

(VIIc)

In one embodiment, A is a $C_{3-6}$ cycloalkyl group (g is 1, 2 or 3) and t is 1, and the cycloalkyl group is geminally disubstituted (i.e. the group —($CR^xR^y$)—X and the $CH_2$ group (where s is 1) or the oxygen atom (where s is 0) are both attached to the same atom of the cycloalkyl group, and the compound of formula (VII) is a compound of formula (VIIa) or a tautomer or a solvate or a pharmaceutically acceptable salt thereof:

In one embodiment, $R^x$ and $R^y$ are hydrogen (including $^1H$ and $^2H$) and q is 1 and the compound of formula (VIIc) is a compound of (VIId) or a tautomer or a solvate or a pharmaceutically acceptable salt thereof:

In one embodiment, the compound of formula (VIId) is a compound of (VIId') or a tautomer or a solvate or a pharmaceutically acceptable salt thereof:

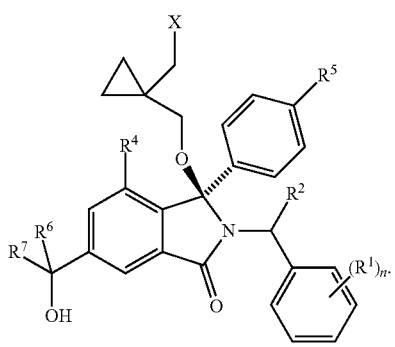
(VIId)

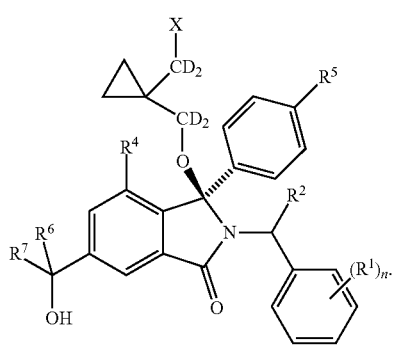
(VIId')

In one embodiment, the compound of formula (VIId) is a compound of (VIId') and X is hydroxy.

In one embodiment, X is hydroxy, and the compound of formula (VIId) is a compound of the formula (VIIe) or a tautomer or a solvate or a pharmaceutically acceptable salt thereof:

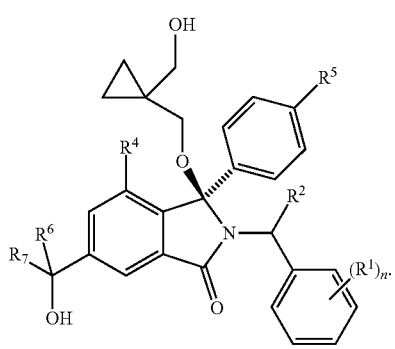
(VIIe)

In one embodiment, X is —C(=O)NH$_2$ and the compound of formula (VIIe) is a compound of the formula (VIIe') or a tautomer or a solvate or a pharmaceutically acceptable salt thereof:

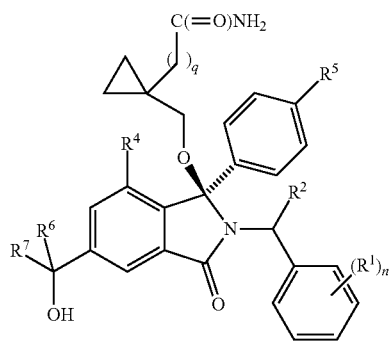
(VIIe')

wherein q is 0 or 1, and in particular q is 0.

In one embodiment, X is —CN and the compound of formula (VIId) is a compound of the formula (VIIe") or a tautomer or a solvate or a pharmaceutically acceptable salt thereof:

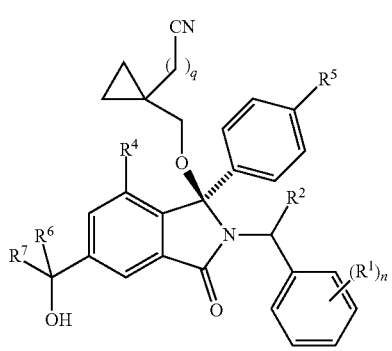
(VIIe")

wherein q is 0 or 1, and in particular q is 0.

In one embodiment, R$^3$ is methyl, and the compound of formula (VI) is a compound of formula (VIIf) or a tautomer or a solvate or a pharmaceutically acceptable salt thereof:

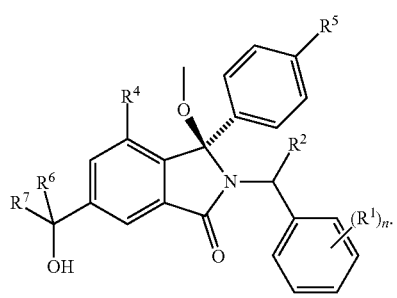
(VIIf)

In one embodiment of Formula (VIIa-e') R$^6$ is methyl. In one embodiment of Formula (VIIa-e') R$^6$ is ethyl.

In one embodiment of Formula (VIIe") or (VIIf) R$^6$ is methyl. In one embodiment of Formula (VIIe") or (VIIf) R$^5$ is ethyl.

In one embodiment of Formula (VIIe") or (VIIf) R$^5$ is methyl. In one embodiment of Formula (VIIe") or (VIIf) R$^6$ is ethyl.

In one embodiment of the compound of formula (VIIa-e'), R$^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (VIIa-e'), $R^7$ is selected from oxanyl and methyl.

In one embodiment of the compound of formula (VIIe") or (VIIf), $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (VIIe") or (VIIf), $R^7$ is selected from oxanyl and methyl.

In one embodiment of the compound of formula (VIIa-f), $R^7$ is selected from piperidinyl optionally substituted by one or more $R^z$ groups (e.g. methyl, fluorine, or hydroxy).

In another embodiment, the compound of formula (I°) is a compound of formula (a) or a tautomer or a solvate or a pharmaceutically acceptable salt thereof:

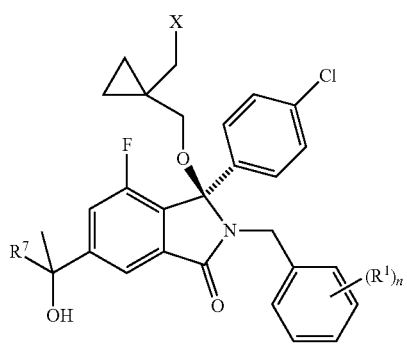

(a)

wherein $R^1$ is chloro or nitrile, when s is 1 then X is hydroxyl or when s is 0 then X is —C(=O)NH$_2$.

In another embodiment, the compound of formula (I°) is a compound of formula (a') or a tautomer or a solvate or a pharmaceutically acceptable salt thereof:

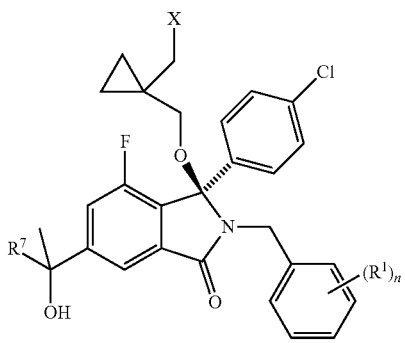

(a')

wherein $R^1$ is chloro or nitrile, when s is 1 then X is hydroxyl or when s is 0 then X is —CN.

In another embodiment, the compound of formula (I°) is a compound of formula (a") or a tautomer or a solvate or a pharmaceutically acceptable salt thereof:

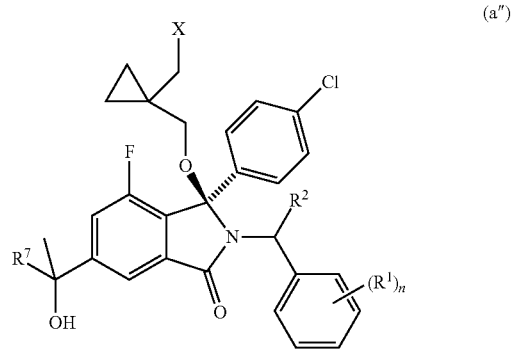

(a")

wherein $R^1$ is chloro or nitrile, when s is 1 then X is hydroxyl or when s is 0 then X is —C(=O)NH$_2$.

In another embodiment, the compound of formula (I°) is a compound of formula (a''') or a tautomer or a solvate or a pharmaceutically acceptable salt thereof:

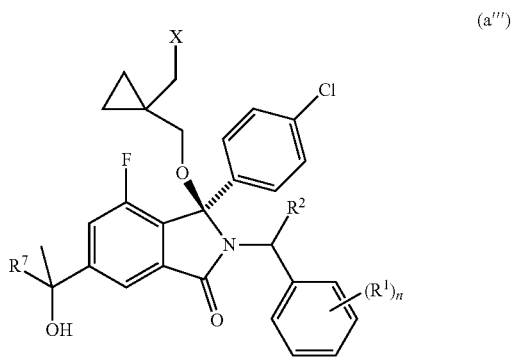

(a''')

wherein $R^1$ is chloro or nitrile, when s is 1 then X is hydroxyl or when s is 0 then X is —CN.

In one embodiment of the compound of formula (a), $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (a), $R^7$ is oxanyl or methyl.

In one embodiment of the compound of formula (a), $R^7$ is piperidinyl, optionally substituted with $C_{1-6}$ alkyl (e.g. methyl) and/or halo (e.g. fluoro).

In one embodiment of the compound of formula (a'), (a") or (a''') $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (a'), (a") or (a''') $R^7$ is oxanyl or methyl.

In one embodiment of the compound of formula (a'), (a") or (a''') $R^7$ is piperidinyl, optionally substituted with $C_{1-6}$ alkyl (e.g. methyl) and/or halo (e.g. fluoro).

In one embodiment, A is a heterocyclyl group with 3 to 6 ring members, wherein the heterocyclic group comprises one or more (e.g. 1, 2, or 3) heteroatoms selected from N, O, S and oxidised forms thereof (t is 1; g is 1, 2, 3 or 4; Z represents N, O, S and oxidised forms thereof; i is 1, 2, or 3; and i+g=2, 3, 4 or 5), and the compound of formula (VI)

is a compound of formula (b) or a tautomer or a solvate or a pharmaceutically acceptable salt thereof:

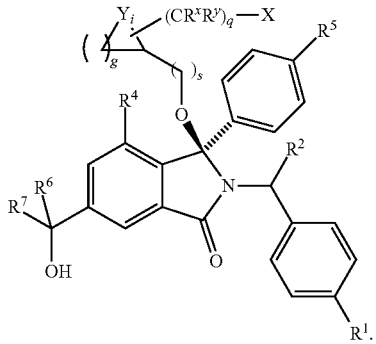

(b)

In one embodiment, Y is 0 and i is 1 and the compound of formula (b) is a compound of formula (ba) or a tautomer or a solvate or a pharmaceutically acceptable salt thereof:

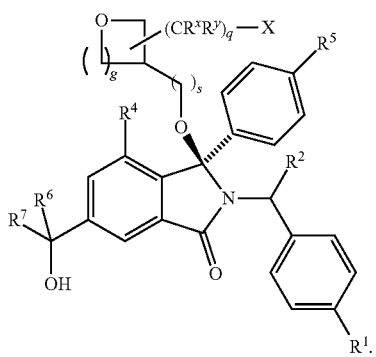

(ba)

In one embodiment, s is 0, g is 2, q is 0 and X is hydrogen, and the compound of formula (b) is a compound of formula (bb) or a tautomer or a solvate or a pharmaceutically acceptable salt thereof:

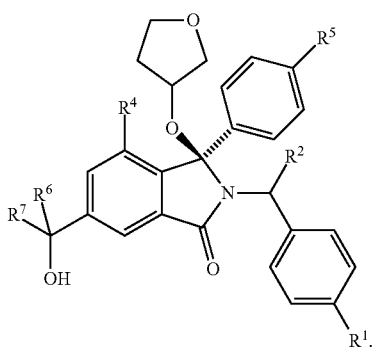

(bb)

In one embodiment, s is 0, g is 1, Y is 0 and i is 1 and the compound of formula (b) is a compound of formula (bc) or a tautomer or a solvate or a pharmaceutically acceptable salt thereof:

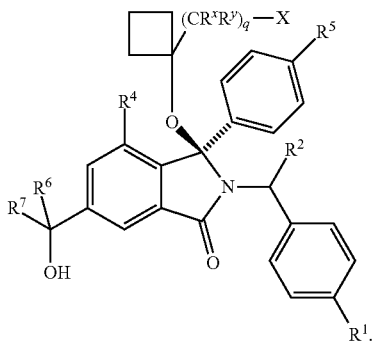

(bc)

In one embodiment, the compound of formula (bc) is where q is 0 and X is fluorine.

In another embodiment, the compound of formula (I°) is a compound of formula (c) or a tautomer or a solvate or a pharmaceutically acceptable salt thereof:

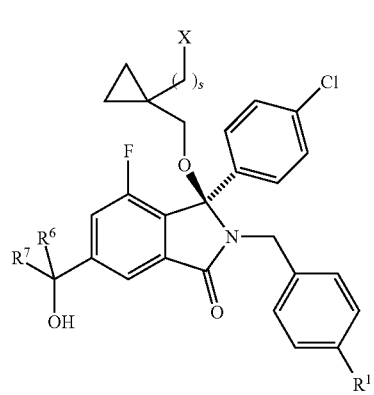

(c)

wherein $R^1$ is chloro or nitrile, s is 1 and X is hydroxyl or s is 0 and X is —C(=O)NH$_2$.

In another embodiment, the compound of formula (I°) is a compound of formula (c') or a tautomer or a solvate or a pharmaceutically acceptable salt thereof:

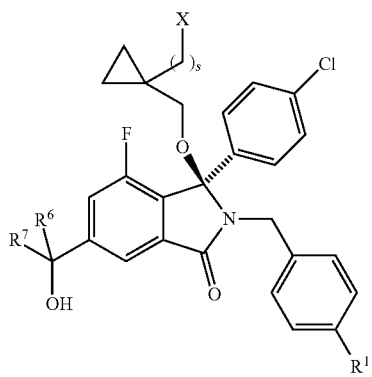

(c')

wherein $R^1$ is chloro or nitrite, s is 1 and X is hydroxyl or s is 0 and X is —CN.

In another embodiment, the compound of formula (I°) is a compound of formula (c") or a tautomer or a solvate or a pharmaceutically acceptable salt thereof:

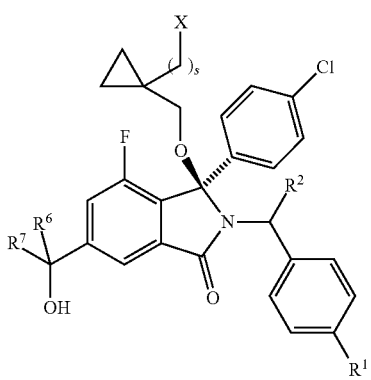

(c″)

wherein R¹ is chloro or nitrile, s is 1 and X is hydroxyl or s is 0 and X is —C(=O)NH₂.

In another embodiment, the compound of formula (I°) is a compound of formula (c‴) or a tautomer or a solvate or a pharmaceutically acceptable salt thereof:

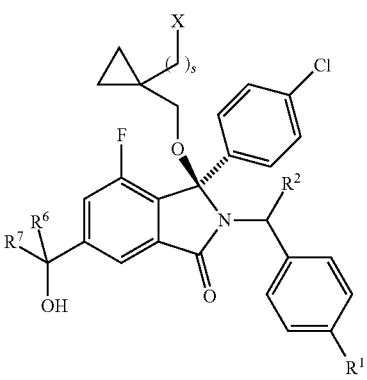

(c‴)

wherein R¹ is chloro or nitrile, s is 1 and X is hydroxyl or s is 0 and X is —CN.

In one embodiment of the compound of formula (c), R⁷ is selected from methyl, oxanyl, pyrazolyl, imidazolyl, piperidinyl, and cyclohexyl wherein said cycloalkyl and heterocyclic groups are optionally substituted by one or more R$^z$ groups (e.g. methyl, fluorine, or hydroxy).

In one embodiment of the compound of formula (c), R⁷ is oxanyl or methyl.

In one embodiment of the compound of formula (c), R⁷ is piperidinyl, optionally substituted with $C_{1-6}$alkyl (e.g. methyl) and/or halo (e.g. fluoro).

In one embodiment of the compound of formula (c'), (c″) or (c‴) R⁷ is selected from methyl, oxanyl, pyrazolyl, imidazolyl, piperidinyl, and cyclohexyl wherein said cycloalkyl and heterocyclic groups are optionally substituted by one or more R$^z$ groups (e.g. methyl, fluorine, or hydroxy).

In one embodiment of the compound of formula (c'), (c″) or (c‴) R⁷ is oxanyl or methyl.

In one embodiment of the compound of formula (c'), (c″) or (c‴) R⁷ is piperidinyl, optionally substituted with $C_{1-6}$alkyl (e.g. methyl) and/or halo (e.g. fluoro).

In another embodiment of the subsformulae described hereinabove, R² is selected from hydrogen and —(R$^x$R$^y$)$_u$—CO₂H (e.g. —COOH, —CH₂COOH, —CH₂CH₂—CO₂H, —(CH(CH₃))—CO₂H and —(C(CH₃)₂—CO₂H).

In another embodiment of the subsformulae described hereinabove, R² is selected from —(CH(CH₃))—CO₂H and —(C(CH₃)₂—CO₂H).

In another embodiment, R² is selected from —(CH(CH₃))—CO₂H and —(C(CH₃)₂—CO₂H)

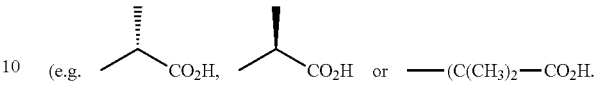

In one embodiment, the invention provides a combination comprising the compound of formula (I°) or a tautomer or a solvate or a pharmaceutically acceptable salt thereof wherein:

R¹ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, and $C_{2-4}$ alkynyl;

R² is selected from hydrogen, $C_{1-4}$ alkyl, $C_{2-6}$ alkenyl, hydroxy$C_{1-4}$alkyl and —CH₂CO₂H;

R³ is hydrogen or -(A)$_t$-(CR$^x$R$^y$)$_q$—X;

s and t are independently selected from 0 and 1;

q is selected from 0, 1 and 2;

wherein when R³ is -(A)$_t$-(CR$^x$R$^y$)$_q$—X then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR⁹, —(CH₂)$_v$—CO₂H, —(CH₂)$_v$—CO₂$C_{1-4}$alkyl, —NR$^x$R$^y$, —NHSO₂R$^x$, —NR$^x$COR$^y$; and —C(=O)NR$^x$R$^y$;

R⁴ and R⁵ are independently selected from halogen, nitrile, $C_{1-4}$ alkyl, halo$C_{1-4}$alkyl, $C_{1-4}$alkoxy and halo$C_{1-4}$alkoxy;

R⁶ and R⁷ are independently selected from hydrogen, $C_{1-6}$alkyl, $C_{2-6}$ alkenyl, $C_{2-6}$ alkynyl, hydroxy, hydroxy$C_{1-4}$alkyl, —CO$_0$$C_{1-6}$alkyl, heterocyclic group with 3 to 7 ring members, —CH₂-heterocyclic group with 3 to 7 ring members, —CH₂—O-heterocyclic group with 3 to 7 ring members, —CH₂—NH-heterocyclic group with 3 to 7 ring members, —CH₂—N($C_{1-6}$alkyl)-heterocyclic group with 3 to 7 ring members, —C(=O)NH-heterocyclic group with 3 to 7 ring members, $C_{3-8}$cycloalkyl, —CH₂—$C_{3-8}$cycloalkyl, —CH₂—O—$C_{3-8}$ cycloalkyl, and $C_{3-6}$cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

R⁹ is selected from hydrogen, $C_{1-6}$alkyl, halo$C_{1-6}$alkyl, hydroxy$C_{1-6}$alkyl, —(CH₂)$_k$—O—$C_{1-4}$alkyl, —(CH₂)$_k$—O-(hydroxy$C_{1-6}$alkyl), hydroxy$C_{1-6}$alkoxy, —(CH₂)$_k$—CO₂$C_{1-4}$alkyl, —(CH₂)$_k$—CO₂H, —$C_{1-6}$alkyl-N(H)$_e$($C_{1-4}$ alkyl)$_{2-e}$, —(CH₂)j-$C_{3-8}$cycloalkyl and —(CH₂)$_j$—$C_{3-8}$ cycloalkenyl;

R$^x$ and R$^y$ are independently selected from hydrogen, halogen, nitro, nitrile, $C_{1-6}$alkyl, halo$C_{1-6}$alkyl, $C_{2-6}$alkenyl, 02-6alkynyl, hydroxy, hydroxy$C_{1-6}$alkyl, $C_{1-6}$alkoxy, —(CH₂)$_k$—O—$C_{1-6}$alkyl, hydroxy$C_{1-6}$alkoxy, —COO$C_{1-6}$ alkyl, —N(H)$_e$($C_{1-4}$alkyl)$_{2-e}$, —$C_{1-6}$alkyl-N(H)$_e$($C_{1-4}$ alkyl)$_{2-e}$, —(CH₂)$_k$—C(=O)N(H)$_e$($C_{1-6}$alkyl)$_{2-e}$ $C_{3-8}$ cycloalkyl and $C_{3-8}$cycloalkenyl;

R$^z$ is independently selected from halogen, nitro, nitrile, halo$C_{1-6}$alkyl, $C_{2-6}$ alkenyl, $C_{2-6}$ alkynyl, =O, hydroxy, hydroxy$C_{1-6}$alkyl, $C_{1-6}$alkoxy, —(CH₂)$_k$—O—$C_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$ alkyl-N(H)$_e$(C$_{1-4}$alkyl)$_{2-e}$, —C(=O)N(H)$_e$(C$_{1-4}$alkyl)$_{2-e}$, —(CH$_2$)$_r$—CO$_2$C$_{1-6}$ alkyl, —(CH$_2$)$_r$—CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$cycloalkenyl;

n, e, r and j are independently selected from 0, 1 and 2;
k and m are independently selected from 1 and 2; and
v and a are independently selected from 0 and 1.

In one embodiment, the invention provides a combination comprising the compound of formula (I°) or a tautomer or a solvate or a pharmaceutically acceptable salt thereof, wherein:

R$^1$ is independently selected from hydroxy, halogen, nitro, nitrile and C$_{1-4}$alkyl;
R$^2$ is selected from hydrogen, C$_{1-4}$ alkyl, C$_{2-6}$alkenyl, hydroxyC$_{1-4}$alkyl and CH$_2$CO$_2$H;
R$^3$ is hydrogen or -(A)$_t$-(CR$^x$R$^y$)$_q$—X;
s and t are independently selected from 0 and 1;
q is selected from 0, 1 and 2;
wherein when R$^3$ is -(A)$_t$-(CR$^x$R$^y$)$_q$—X then (i) at least one of s, t and q is other than 0 and (ii) when t is 0 then s is 1 and q is other than 0;
A is a C$_{3-8}$cycloalkyl group or a heterocyclic group with 3 to 6 ring members, wherein the heterocyclic group comprises one or more (e.g. 1, 2, or 3) heteroatoms selected from N, O, S and oxidised forms thereof;
X is selected from hydrogen, halogen, —CN, —OR$^9$, —(CH$_2$)$_v$—CO$_2$H, —(CH$_2$)CO$_2$C$_{1-4}$alkyl, —C(=O)—C$_{1-4}$alkyl, —NR$^x$R$^y$, —NHSO$_2$R$^x$, —NR$^x$COR$^y$; and —C(=O)NR$^x$R$^y$;
R$^4$ and R$^5$ are independently selected from halogen, nitrile and C$_{1-4}$ alkyl;
R$^6$ is selected from hydrogen, C$_{1-6}$alkyl, C$_{2-6}$ alkenyl, and C$_{2-6}$alkynyl;
R$^7$ is selected from hydrogen, C$_{1-6}$alkyl, haloC$_{1-6}$alkyl, C$_{2-6}$alkenyl, C$_{2-6}$ alkynyl, hydroxy, hydroxyC$_{1-6}$alkyl, —COOC$_{1-6}$alkyl, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, C$_{3-8}$ cycloalkyl, acycloalkyl, —CH$_2$—O—C$_{3-8}$ cycloalkyl, and C$_{3-8}$ cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;
R$^9$ is selected from hydrogen, C$_{1-6}$alkyl, haloC$_{1-6}$alkyl, hydroxyC$_{1-6}$alkyl, —(CH$_2$)$_k$—O—C$_{1-6}$ alkyl, —(CH$_2$)$_k$—O-(hydroxyC$_{1-6}$alkyl), hydroxyC$_{1-6}$alkoxy, —(CH$_2$)$_k$—CO$_2$C$_{1-6}$alkyl, —(CH$_2$)$_k$—CO$_2$H, —C$_{1-6}$ alkyl-N(H)$_e$(C$_{1-4}$alkyl)$_{2-e}$, —(CH$_2$)j-C$_{3-8}$cycloalkyl and —(CH$_2$)$_j$—C$_{3-8}$cycloalkenyl;
R$^x$ and R$^y$ are independently selected from hydrogen, halogen, nitro, nitrile, C$_{1-6}$alkyl, haloC$_{1-6}$alkyl, C$_{2-6}$alkenyl, C$_{2-6}$alkynyl, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —COOC$_{1-6}$alkyl, —N(H)$_e$(C$_{1-4}$alkyl)$_{2-e}$, —C$_{1-4}$alkyl-N(H)$_e$(C$_{1-4}$alkyl)$_{2-e}$, —(CH$_2$)$_k$—C(=O)N(H)$_e$(C$_{1-4}$alkyl)$_{2-e}$, C$_{3-8}$ cycloalkyl and C$_{3-8}$ cycloalkenyl;
R$^z$ is independently selected from halogen, nitro, nitrile, C$_{1-6}$alkyl, haloC$_{1-6}$alkyl, C$_{2-6}$ alkenyl, C$_{2-8}$ alkynyl, =O, hydroxy, hydroxyC$_{1-6}$alkyl, C$_{1-6}$alkoxy, —(CH$_2$)$_k$—O—C$_{1-6}$ alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_r$—CO$_2$C$_{1-6}$ alkyl, —(CH$_2$)$_r$—CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$ cycloalkenyl;

n, e, r and j are independently selected from 0, 1 and 2;
k and m are independently selected from 1 and 2; and
v and a are independently selected from 0 and 1.

In one embodiment, the invention provides a combination comprising the compound of formula (I°) or a tautomer or a solvate or a pharmaceutically acceptable salt thereof, wherein:

R$^1$ is independently selected from hydroxy, halogen, nitro, nitrile and C$_{1-4}$alkyl;
R$^2$ is selected from hydrogen, C$_{1-4}$ alkyl, C$_{2-6}$alkenyl, hydroxyC$_{1-4}$alkyl and —CH$_2$CO$_2$H;
R$^3$ is hydrogen or -(A)$_t$-(CR$^x$R$^y$)$_q$—X;
s and t are independently selected from 0 and 1;
q is selected from 0, 1 and 2;
wherein when R$^3$ is -(A)$_t$-(CR$^x$R$^y$)$_q$—X then (i) at least one of s, t and q is other than 0 and (ii) when t is 0 then s is 1 and q is other than 0;
A is a heterocyclic group with 3 to 6 ring members, wherein the heterocyclic group comprises one or more (e.g. 1, 2, or 3) heteroatoms selected from N, O, S and oxidised forms thereof;
X is selected from hydrogen, halogen, —CN and —OR$^9$;
R$^4$ and R$^5$ are independently selected from halogen, nitrile and C$_{1-4}$ alkyl;
R$^6$ is selected from hydrogen and C$_{1-6}$alkyl;
R$^7$ is selected from heterocyclic group with 3 to 7 ring members, —CH$_2$-heterocyclic group with 3 to 7 ring members, C$_{3-8}$ cycloalkyl, and —CH$_2$—C$_{3-8}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;
R$^9$ is selected from hydrogen and C$_{1-6}$ alkyl;
R$^x$ and R$^y$ are independently selected from hydrogen and C$_{1-6}$alkyl;
R$^z$ is independently selected from halogen, nitro, nitrile, C$_{1-6}$alkyl, haloC$_{1-6}$alkyl, C$_{2-6}$alkenyl, hydroxy, hydroxyC$_{1-6}$ alkyl, C$_{1-6}$alkoxy, —C(=O)C$_{1-6}$alkyl, and —N(H)$_e$(C$_{1-4}$alkyl)$_{2-e}$;
n and e are independently selected from 0, 1 and 2
m is selected from 1 and 2; and
a is selected from 0 and 1.

In one embodiment, the invention provides a combination comprising the compound of formula (I°) or a tautomer or a solvate or a pharmaceutically acceptable salt thereof, wherein:

R$^1$ is independently selected from halogen, hydroxy and nitrile;
R$^2$ is selected from hydrogen, C$_{1-4}$ alkyl and —CH$_2$CO$_2$H;

$R^3$ is -(A)$_t$-(CR$^x$R$^y$)$_q$—X;

A is a heterocyclic group with 3 to 6 ring members, wherein the heterocyclic group comprises one or more (e.g. 1, 2, or 3) heteroatoms selected from N, O, S and oxidised forms thereof;

s and t are independently selected from 0 and 1;

q is selected from 0, 1 and 2;

wherein (i) at least one of s, t and q is other than 0 and (ii) when t is 0 then s is 1 and q is other than 0;

X is selected from hydrogen, halogen or —OR$^9$;

$R^4$ and $R^5$ are independently selected from halogen;

$R^6$ is selected from hydrogen and C$_{1-6}$alkyl;

$R^7$ is selected from heterocyclic group with 3 to 7 ring members, —CH$_2$-heterocyclic group with 3 to 7 ring members, C$_{3-6}$cycloalkyl, and —CH$_2$—C$_{3-8}$ cycloalkyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

$R^9$ is selected from hydrogen and C$_{1-6}$alkyl;

$R^x$ and $R^y$ are independently selected from hydrogen and C$_{1-6}$alkyl;

$R^z$ is independently selected from halogen, nitro, nitrile, and C$_{1-6}$alkyl;

n is 1 and m is 1; and a is selected from 0 and 1.

In one embodiment, the invention provides a combination comprising the compound of formula (I°) or a tautomer or a solvate or a pharmaceutically acceptable salt thereof, wherein:

$R^1$ is independently selected from halogen, hydroxy and nitrile;

$R^2$ is selected from hydrogen, C$_{1-4}$ alkyl and CH$_2$CO$_2$H;

$R^3$ is -(A)$_t$-(CR$^x$R$^y$)$_q$—X;

A is a heterocyclic group with 3 to 6 ring members, wherein the heterocyclic group comprises one or more (e.g. 1, 2, or 3) heteroatoms selected from N, O, S and oxidised forms thereof;

s and t are independently selected from 0 and 1;

q is selected from 0, 1 and 2;

wherein (i) at least one of s, t and q is other than 0 and (ii) when t is 0 then s is 1 and q is other than 0;

X is selected from hydrogen, halogen and —OR$^9$;

$R^4$ and $R^5$ are independently selected from halogen;

$R^6$ is selected from hydrogen and C$_{1-6}$alkyl;

$R^7$ is a heterocyclic group with 3 to 7 ring members optionally substituted by one or more R$^z$ groups;

$R^9$ is selected from hydrogen and C$_{1-6}$alkyl;

$R^x$ and $R^y$ are independently selected from hydrogen and C$_{1-6}$alkyl;

$R^z$ is independently selected from halogen and C$_{1-6}$alkyl; and n is, 1 and m is 1; and a is 1.

In one embodiment, the invention provides a combination comprising the compound of formula (I°) or a tautomer or a solvate or a pharmaceutically acceptable salt thereof, wherein:

$R^1$ is halogen (e.g. Cl), C$_{1-4}$alkynyl (e.g. —C≡CH), nitrile, hydroxyC$_{1-4}$alkyl (e.g. —CH$_2$OH), —O$_{0,1}$(CR$^x$R$^y$)$_v$COOH (e.g. —COOH, —CH$_2$COOH, —OCH$_2$COOH or —C(CH$_3$)$_2$ COOH, —S(O)$_d$—C$_{1-4}$alkyl (e.g. SCH$_3$, SOCH$_3$, or SO$_2$CH$_3$), —SO$_2$-(1-morpholinyl) or —P(=O)(R$^x$)$_2$, (e.g. —P(=O)(CH$_3$)$_2$);

n is 1 or 2;

$R^2$ is hydrogen, C$_{1-4}$ alkyl (e.g. —CH$_3$), hydroxyC$_{1-4}$alkyl (e.g. CH$_2$OH) or —(CH$_2$)$_v$COOH (e.g. —CH$_2$COOH, —CH$_2$CH$_2$—CO$_2$H or —(CH(CH$_3$))—CO$_2$H);

the moiety —(CH$_2$)$_s$R$^3$ is selected from:

(point of attachment to the oxygen represented by dashed bond or bond terminus indicated by *):

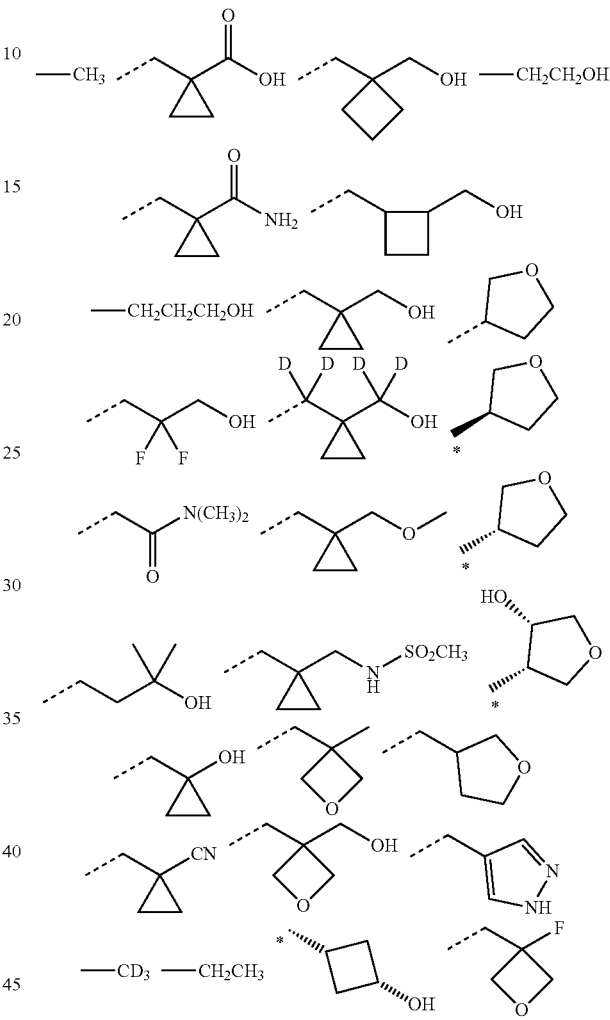

$R^4$ is halogen (e.g. F);

a is 0 or 1;

$R^5$ is halogen (e.g. Cl);

m is 1;

$R^6$ is hydrogen or C$_{1-6}$alkyl (e.g. —CH$_3$ or —CH$_2$CH$_3$);

$R^7$ is C$_{1-6}$alkyl (e.g. —CH$_3$ or —CH$_2$CH$_3$), hydroxyC$_{1-4}$alkyl (e.g. —CH$_2$OH), —C$_{1-6}$alkyl-NR$^x$R$^y$ (e.g. —CH$_2$N(CH$_3$)$_2$), —(CR$^x$R$^y$)$_p$—CONR$^x$R$^y$ (e.g. —C(=O)N(CH$_3$)$_2$ or —C(=O)NHCH$_3$ or

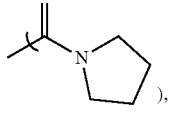

),

—(CH$_2$)$_j$—O—C$_{1-6}$alkyl (e.g. —CH$_2$OCH$_3$), C$_{3-8}$cycloalkyl (e.g. cyclobutyl or cyclohexyl), heterocyclic group with 3 to 7 ring members e.g.

(point of attachment represented by dashed bond)

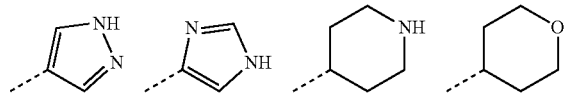

or —CH$_2$-heterocyclic group with 3 to 7 ring members e.g. (point of attachment represented by dashed bond)

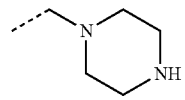

wherein when the moiety R$^7$ comprises a heterocyclic or cycloalkyl group, the heterocyclic group may be optionally substituted by one or more R$^z$ groups selected from C$_{1-6}$alkyl (e.g. methyl), hydroxy, halogen (e.g. fluoro), —C(═O)C$_{1-6}$ alkyl (e.g. —C(═O)C(CH$_3$)$_3$), —(CH$_2$)$_r$—CO$_2$H (e.g. —CH$_2$COOH or CH$_2$CH$_2$COOH or —(CH$_2$)$_r$—CO$_2$C$_{1-6}$ alkyl (e.g. CH$_2$CH$_2$COOCH$_3$).

In one embodiment, the invention provides a combination comprising the compound of formula (I°) or a tautomer or a solvate or a pharmaceutically acceptable salt thereof, wherein:

R$^1$ is halogen (e.g. Cl), C$_{1-4}$alkynyl (e.g. —C≡CH), nitrile, hydroxyC$_{1-4}$alkyl (e.g. CH$_2$OH), —(CH$_2$)$_v$COOH (e.g. —COOH), —S(O)$_d$—C$_{1-4}$alkyl (e.g. SCH$_3$, SOCH$_3$, or SO$_2$CH$_3$), —SO$_2$-(1-morpholinyl) or —P(═O)(R$^x$)$_2$, (e.g. —P(═O)(CH$_3$)$_2$);

n is 1 or 2;

R$^2$ is hydrogen, C$_{1-4}$ alkyl (e.g. —CH$_3$), hydroxyC$_{1-4}$alkyl (e.g. CH$_2$OH) or —(CH$_2$)$_u$COOH (e.g. —CH$_2$COOH);

the moiety —(CH$_2$)$_s$R$^3$ is selected from:

(point of attachment to the oxygen represented by dashed bond or bond terminus indicated by *):

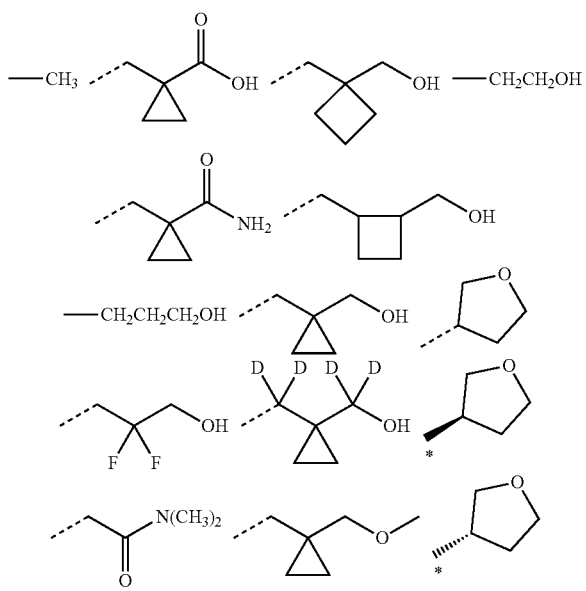

R$^4$ is halogen (e.g. F);
a is 0 or 1;
R$^5$ is halogen (e.g. Cl);
m is 1;
R$^6$ is hydrogen or C$_{1-6}$alkyl (e.g. —CH$_3$ or —CH$_2$CH$_3$);
R$^7$ is C$_{1-6}$ alkyl (e.g. —CH$_3$), hydroxyC$_{1-6}$alkyl (e.g. —CH$_2$OH), —(CH$_2$)$_j$—O—C$_{1-6}$alkyl (e.g. —CH$_2$OCH$_3$), —C$_{1-6}$alkyl-NR$^x$R$^y$ (e.g. —CH$_2$N(CH$_3$)$_2$), —(CR$^x$R$^y$)$_p$—CONR$^x$R$^y$ (e.g. —C(═O)N(CH$_3$)$_2$ or —C(═O)NHCH$_3$) or

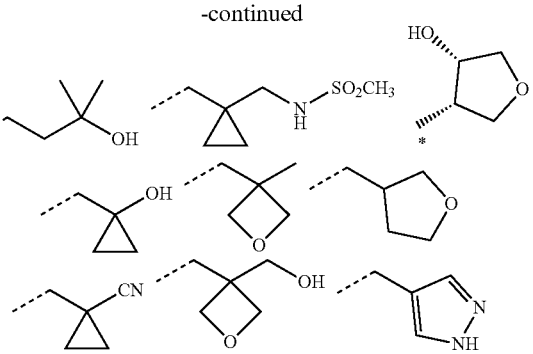

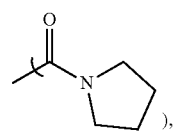

), heterocyclic group with 3 to 7 ring members e.g. (point of attachment represented by dashed bond)

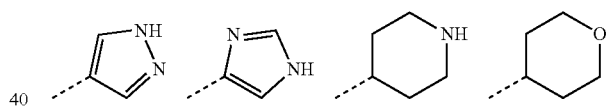

or —CH$_2$-heterocyclic group with 3 to 7 ring members e.g. (point of attachment represented by dashed bond)

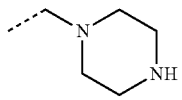

wherein when R$^7$ comprises a heterocyclic group, the heterocyclic group may be optionally substituted by one or more R$^z$ groups selected from C$_{1-6}$alkyl (e.g. methyl).

In one embodiment of formula (I°) R$^7$ is a heterocyclic group with 3 to 7 ring members e.g.
(point of attachment represented by dashed bond)

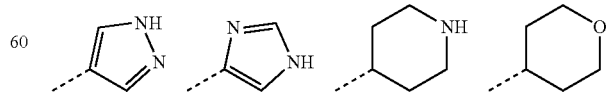

In one embodiment of formula wherein when R$^7$ comprises a heterocyclic group, the heterocyclic group may be R$^7$ is a heterocyclic group with 3 to 7 ring members optionally substituted by one or more R$^z$ groups e.g.

(point of attachment represented by dashed bond)

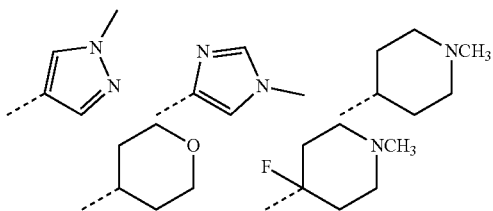

or a —CH$_2$-heterocyclic group with 3 to 7 ring members optionally substituted by one or more R$^z$ groups e.g. (point of attachment represented by dashed bond)

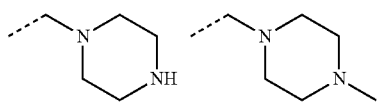

In one embodiment of formula wherein when R$^7$ comprises a heterocyclic group, the heterocyclic group may be R$^7$ is a heterocyclic group with 3 to 7 ring members optionally substituted by one or more R$^z$ groups e.g. (point of attachment represented by dashed bond)

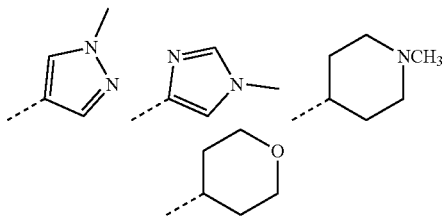

or a —CH$_2$-heterocyclic group with 3 to 7 ring members optionally substituted by one or more R$^z$ groups e.g. (point of attachment represented by dashed bond)

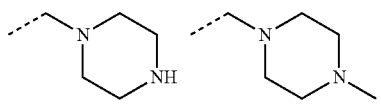

In one embodiment, the invention provides a combination comprising the compound of formula (I°) or a tautomer or a solvate or a pharmaceutically acceptable salt thereof, wherein:
R$^1$ is —Cl, —CN, —OH or —OCH$_3$;
n is 1;
R$^2$ is hydrogen;
R$^3$ is hydrogen or -(A)$_t$-(CR$^x$R$^y$)$_q$—X;
s is 0 or 1, and t is 1;
A is selected from cyclopropyl, oxetanyl and tetrahydrofuranyl;
X is selected from hydrogen, fluorine, —CN, —OH and —C(=O)NH$_2$;
q is 0 or 1 and R$^x$ and R$^y$ are hydrogen or deuterium;
a is 0 or 1 and R$^4$ is halogen (e.g. fluorine);
R$^5$ is halogen (e.g. Cl);
m is 1;
R$^6$ is C$_{1-4}$alkyl (e.g. methyl or ethyl);

R$^7$ is C$_{1-4}$alkyl (e.g. methyl or ethyl), hydroxylC$_{1-4}$alkyl (e.g. hydroxylmethyl or hydroxyethyl), methoxyC$_{1-4}$alkyl (e.g. methoxymethyl), a heterocyclic group with 5 or 6 ring members (e.g. piperidinyl, oxanyl, imidazolyl or pyrazolyl) or C$_{3-6}$cycloalkyl (e.g. cyclobutyl or cyclohexyl) wherein said heterocyclic group with 5 or 6 ring members and C$_{3-8}$ cycloalkyl groups may be optionally substituted with one or two R$^z$ groups independently selected from methyl, halogen (such as fluorine), —C(=O)Me, and —OH.

In one embodiment, the invention provides a combination comprising the compound of formula (I°) or a tautomer or a solvate or a pharmaceutically acceptable salt thereof, wherein:
R$^1$ is —Cl, —CN, —OH or —OCH$_3$;
n is 1;
R$^2$ is hydrogen or —(CH$_2$)$_u$—CO$_2$H wherein u is independently selected from 0 and 1;
R$^3$ is hydrogen and s is 1 or R$^3$ is -(A)$_t$-(CR$^x$R$^y$)$_q$—X and t is 1 and q is 1;
A is selected from cyclopropyl;
X is —OH;
R$^x$ and R$^y$ are hydrogen or deuterium;
a is 0 or 1 and R$^4$ is halogen (e.g. fluorine);
R$^5$ is halogen (e.g. Cl);
m is 1;
R$^6$ is C$_{1-4}$alkyl (e.g. methyl or ethyl);
R$^7$ is C$_{1-4}$alkyl (e.g. methyl or ethyl), hydroxylC$_{1-4}$alkyl (e.g. hydroxylmethyl or hydroxyethyl), methoxyC$_{1-4}$alkyl (e.g. methoxymethyl), a heterocyclic group with 5 or 6 ring members (e.g. piperidinyl, oxanyl, imidazolyl or pyrazolyl) or C$_{3-8}$ cycloalkyl (e.g. cyclobutyl or cyclohexyl);
wherein said heterocyclic group with 5 or 6 ring members and C$_{3-6}$ cycloalkyl groups may be optionally substituted with one or two R$^z$ groups independently selected from methyl, halogen (such as fluorine), —C(=O)Me, and —OH.

In one embodiment, the invention provides a combination comprising the compound of formula (I°) or a tautomer or a solvate or a pharmaceutically acceptable salt thereof, wherein:
R$^1$ is halogen (e.g. Cl) or nitrile;
n is 1;
R$^2$ is hydrogen or —(CH$_2$)$_u$COOH (e.g. —CH$_2$COOH);
R$^3$ is hydrogen and s is 1 or R$^3$ is -(A)$_t$-(CR$^x$R$^y$)$_q$—X and t is 1 and q is 1;
A is selected from cyclopropyl;
X is —OH;
R$^x$ and R$^y$ are hydrogen or deuterium (e.g. hydrogen);
R$^4$ is halogen (e.g. F);
a is 0 or 1;
R$^5$ is halogen (e.g. Cl);
m is 1;
R$^6$ is hydrogen or C$_{1-4}$alkyl (e.g. —CH$_3$ or —CH$_2$CH$_3$);
R$^7$ is C$_{1-4}$alkyl (e.g. methyl), hydroxylC$_{1-4}$alkyl (e.g. hydroxylmethyl), methoxyC$_{1-4}$alkyl (e.g. methoxymethyl), a heterocyclic group with 5 or 6 ring members (e.g. piperidinyl, oxanyl, imidazolyl or pyrazolyl));
wherein said heterocyclic group with 5 or 6 ring members may be optionally substituted with one or two R$^z$ groups independently selected from C$_{1-4}$alkyl (e.g. methyl).

In one embodiment, the invention provides a combination comprising the compound of formula (I°) or a tautomer or a solvate or a pharmaceutically acceptable salt thereof, wherein:
R$^1$ is halogen (e.g. Cl), nitrile, O$_{0-1}$(CR$^x$R$^y$)$_v$COOH (e.g. —COOH, —CH$_2$COOH, —OCH$_2$COOH or —C(CH$_3$)$_2$COOH;

n is 1 or 2;
R² is selected from hydrogen and —(R$^x$R$^y$)$_u$—CO$_2$H (e.g. —COOH, —CH$_2$COOH, —CH$_2$CH$_2$—CO$_2$H, —(CH(CH$_3$))—CO$_2$H and —(C(CH$_3$)$_2$—CO$_2$H).
R³ is hydrogen and s is 1;
R⁴ is halogen (e.g. F);
R⁵ is halogen (e.g. Cl);
m is 1;
R⁶ is hydrogen or C$_{1-6}$alkyl (e.g. —CH$_3$ or —CH$_2$CH$_3$);
R⁷ is C$_{1-4}$ alkyl (e.g. methyl), hydroxylC$_{1-4}$alkyl (e.g. hydroxylmethyl), methoxyC$_{1-4}$alkyl (e.g. methoxymethyl), a heterocyclic group with 5 or 6 ring members (e.g. piperidinyl, oxanyl, imidazolyl or pyrazolyl));
wherein said heterocyclic group with 5 or 6 ring members may be optionally substituted with one or two R$^z$ groups independently selected from C$_{1-4}$alkyl (e.g. methyl).

In one embodiment, the invention provides a combination comprising a compound of formula (I°) which is one of the Examples 1-137 or is selected from the Examples 1-137 or a tautomer, N-oxide, pharmaceutically acceptable salt or solvate thereof.

In one embodiment, the invention provides a combination comprising the compound of formula (I°) which is one of the Examples 1-97 or is selected from the Examples 1-97 or a tautomer, N-oxide, pharmaceutically acceptable salt or solvate thereof.

In one embodiment, the invention provides a combination comprising a compound of formula (I°) which is selected from the following compounds, or a tautomer, N-oxide, pharmaceutically acceptable salt or solvate thereof:
4-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}benzonitrile; and
(3S)-3-(4-chlorophenyl)-3-[(1R)-1-(4-chlorophenyl)-7-fluoro-5-[1-hydroxy-1-(oxan-4-yl)ethyl]-1-methoxy-3-oxo-2,3-dihydro-1H-isoindol-2-yl]propanoic acid.

In one embodiment, the invention provides a combination comprising a compound of formula (I°) which is selected from the following compounds, or a tautomer, N-oxide, pharmaceutically acceptable salt or solvate thereof:
4-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}benzonitrile; and
(3S)-3-(4-chlorophenyl)-3-[(1R)-1-(4-chlorophenyl)-7-fluoro-5-[1-hydroxy-1-(oxan-4-yl)ethyl]-1-methoxy-3-oxo-2,3-dihydro-1H-isoindol-2-yl]propanoic acid.

In one embodiment, the invention provides a combination comprising a compound of formula (I°) which is diastereoisomer 2B and is selected from the following compounds, or a tautomer, N-oxide, pharmaceutically acceptable salt or solvate thereof:
4-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}benzonitrile; and
(3S)-3-(4-chlorophenyl)-3-[(1R)-1-(4-chlorophenyl)-7-fluoro-5-[1-hydroxy-1-(oxan-4-yl)ethyl]-1-methoxy-3-oxo-2,3-dihydro-1H-isoindol-2-yl]propanoic acid.

In one embodiment, the compound of formula (I°) is 2-(5-chloro-2-{[(1R)-1-(4-chlorophenyl)-7-fluoro-5-[(1S)-1-hydroxy-1-(oxan-4-yl) propyl]-1-methoxy-3-oxo-2,3-dihydro-1H-isoindol-2-yl]methyl}phenyl)-2-methylpropanoic acid, or a tautomer, N-oxide, pharmaceutically acceptable salt or solvate thereof.

In one embodiment, the invention provides a combination comprising the compound of formula (I°) which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, or a tautomer, N-oxide, pharmaceutically acceptable salt or solvate thereof.

For the avoidance of doubt, it is to be understood that each general and specific embodiment and example for one substituent may be combined with each general and specific embodiment and example for one or more, in particular all, other substituents as defined herein and that all such embodiments are embraced by this application.

Compounds of Formula (I°) Wherein Cyc is a Heterocyclic Group Het
Het
Het is pyridinyl, pyrimidinyl, pyrazinyl or pyridazinyl, or an N-oxide thereof.

In one embodiment Het is pyridinyl, pyrimidinyl or pyridazinyl, or an N-oxide thereof.

In one embodiment Het is pyridinyl or pyrimidinyl, or an N-oxide thereof. In one embodiment Het is pyridinyl or pyrimidinyl. In one embodiment, Het is optionally substituted pyrimidin-2-yl.

In one embodiment, the point of attachment of the Het group is at the 2-position of the Het group and the Het is pyridin-2-yl, pyrimidin-2-yl, or pyridazin-2yl. In other words, the Het ring is attached to the rest of the molecule by a carbon atom adjacent to a nitrogen atom in the Het ring.

In one embodiment, Het is pyridinyl. In particular, Het may be pyridin-2-yl and the compound of formula (I°) is a compound of formula (Ia) or a tautomer or a solvate or a pharmaceutically acceptable salt thereof, or pyridin-3-yl and the compound of formula (I°) is a compound of formula (Ib) or a tautomer or a solvate or a pharmaceutically acceptable salt thereof:

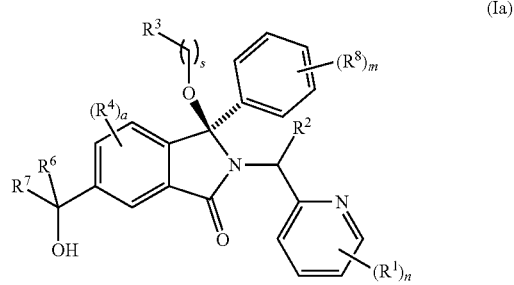

(Ia)

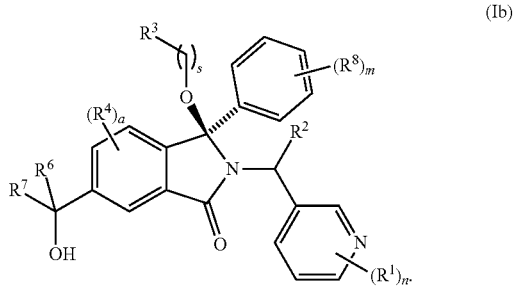

(Ib)

In one embodiment, Het is N-oxide pyridinyl. In particular, Het may be N-oxide pyridin-2-yl and the compound of formula (I°) is a compound of formula (Ia) or a tautomer or a solvate or a pharmaceutically acceptable salt thereof:

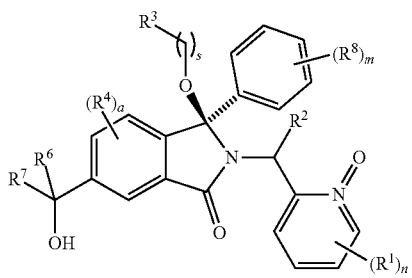

(Ia')

In one embodiment, Het is pyrimidinyl. In particular, Het may be pyrimidin-2-yl and the compound of formula (I°) is a compound of formula (Ic) or a tautomer or a solvate or a pharmaceutically acceptable salt thereof:

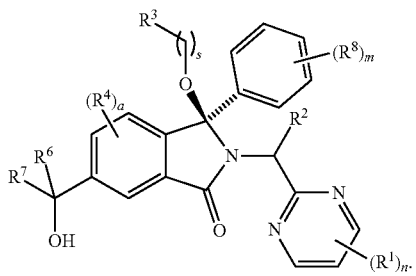

(Ic)

In one embodiment the compound of formula (I°) can be pyridin-2-yl or pyrimidin-2-yl and the compound of formula (I°) is a compound of formula (Id) or a tautomer or a solvate or a pharmaceutically acceptable salt thereof:

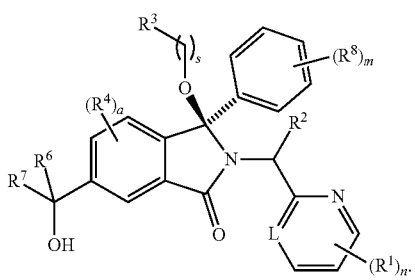

(Id)

wherein L is $CR^1$, CH or N. In one embodiment of formula (Ic) L is CH or N.

In one embodiment Het is pyrid-2-yl or pyrimidin-2-yl.

In one embodiment, Het is selected from the group consisting of (dashed line represents connection to carbon atom bound to $CHR^2$ group):

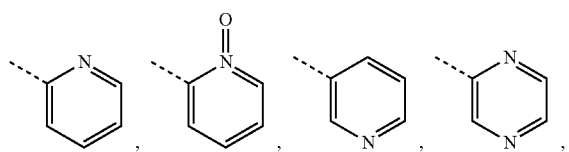

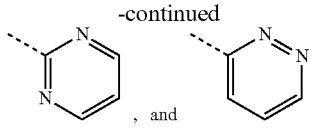

, and .

In one embodiment, Het is selected from the group consisting of (dashed line represents connection to carbon atom bound to $CHR^2$ group):

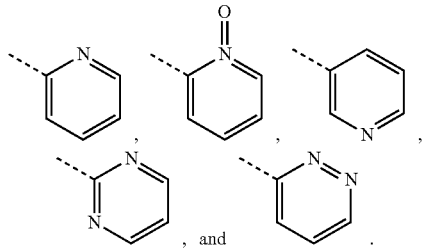

, and .

$R^1$ and n $R^1$ is the substituent(s) on the Het group. $R^1$ is attached to a carbon atom (not a nitrogen atom) of the Het group.

n is 0, 1, 2 or 3. In other words, the Het group may have 0, 1, 2 or 3 substituents $R^1$.

In one embodiment n is 1, 2 or 3. In one embodiment n is 1 or 2. In another embodiment n is 1.

When n is 2 or 3 (i.e. the Het group is substituted with more than one $R^1$) the substituents $R^1$ may be the same or different (i.e. are independently selected from the definitions of $R^1$).

$R^1$ may be attached to a carbon atom at the ortho (or o-), meta (or m-) or para (or p-) position of the 6-membered Het group, wherein the position is defined relative to the point of attachment of the 6-membered Het group to the group —$CHR^2$—.

$R^1$ is independently selected from hydroxy, halogen, nitro, nitrile, $C_{1-4}$ alkyl, halo$C_{1-4}$alkyl, hydroxy$C_{1-4}$alkyl, $C_{2-6}$ alkenyl, $C_{1-4}$ alkoxy, halo$C_{1-4}$alkoxy, $C_{2-4}$ alkynyl, —$O_{0.1}$—$(CR^xR^y)_v$—$CO_2H$, —$(CR^xR^y)_v$—$CO_2C_{1-4}$alkyl, —$(CR^xR^y)_v$—$CON(C_{1-4}alkyl)_2$, —P(=O)$(R^x)_2$, —S(O)$_d$—$R^x$, —S(O)$_d$-heterocyclic group with 3 to 6 ring members and —S(O)$_d$—$N(R^8)_2$.

In one embodiment, $R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$ alkoxy, halo$C_{1-4}$alkoxy, $C_{2-4}$alkynyl, —$(CR^xR^y)_v$—$CO_2H$, —$(CR^xR^y)_v$—$CO_2C_{1-4}$alkyl, —$(CR^xR^y)_v$—$CON(C_{1-4}alkyl)_2$, —P(=O)$(R^x)_2$, —S(O)$_d$—$R^x$, —S(O)$_d$-heterocyclic group with 3 to 6 ring members and —S(O)$_d$—$N(R^8)_2$.

In one embodiment, $R^1$ is attached to a carbon atom and is independently selected from hydroxy, halogen, nitro, nitrile, $C_{1-4}$alkyl, hydroxy$C_{1-4}$alkyl, $C_{2-6}$ alkenyl, $C_{1-4}$alkoxy, halo$C_{1-4}$alkoxy, $C_{2-4}$alkynyl, —$(CR^xR^y)_v$—$CO_2C_{1-4}$alkyl, —$(CR^xR^y)_v$—$CON(C_{1-4}alkyl)_2$, —P(=O)$(R^x)_2$, —S(O)$_d$—$R^x$, —S(O)$_d$-heterocyclic group with 3 to 6 ring members and —S(O)$_d$—$N(R^8)_2$;

In one embodiment, $R^1$ is independently selected from halogen, hydroxy, nitrile, $C_{1-4}$alkyl, $C_{2-4}$alkynyl, or $C_{1-4}$ alkoxy, for example $R^1$ is independently selected from fluoro, chloro, hydroxy, nitrile, methyl or methoxy.

In one embodiment $R^1$ is independently selected from halogen (e.g. chloro), $C_{1-4}$alkyl (e.g. methyl), $C_{1-4}$alkoxy (e.g. methoxy), —$O_{0.1}$—$(CR^xR^y)_v$—$CO_2H$ (e.g. —$CO_2H$, —(CH$_2$)—CO$_2$H, —(C(CH$_3$)$_2$)—CO$_2$H, or —O(CH$_2$)—CO$_2$H) or —S(O)$_d$—R$^x$ (e.g. SO$_2$CH$_3$).

In one embodiment R$^1$ is O$_{0.1}$—(CR$^x$R$^y$)$_v$—CO$_2$H in particular —CO$_2$H, —(CH$_2$)—CO$_2$H, —(C(CH$_3$)$_2$)—CO$_2$H, or —O(CH$_2$)—CO$_2$H), such as —(C(CH$_3$)$_2$)—CO$_2$H.

In one embodiment, R$^1$ is chloro or nitrile, in particular chloro.

In one embodiment, R$^1$ is nitro (i.e. p-NO$_2$).

In one embodiment, R$^1$ is nitro at the ortho or meta position.

In another embodiment, n is 1 and R$^1$ is chloro or nitrile.

In another embodiment, n is 1 and R$^1$ is chloro.

In another embodiment, n is 1 and R$^1$ is nitrile.

In one embodiment, one of the R$^1$ groups or the R$^1$ group (where n=1) is at the para-position (i.e. para to the point of attachment of the six-membered ring). In one embodiment n is 1 and R$^1$ is p-chloro or p-nitrile.

In one embodiment, n is 1 and R$^1$ is halogen (e.g. Cl or F), nitrile, C$_{1-4}$alkoxy (e.g. —OCH$_3$) or C$_{1-4}$alkyl (e.g. CH$_3$).

In one embodiment, n is 2. In one embodiment when n is 2, the Het group is substituted with (i) o-(-S(O)$_d$—C$_{1-4}$alkyl) or o-(-S(O)$_d$-heterocyclic group with 3 to 6 ring members) and (ii) halogen (e.g. Cl or F), nitrile, or C$_{1-4}$ alkyl, in particular chloro, nitrile or methyl.

In another embodiment, one or more R$^1$ is —SO$_2$CH$_3$, or —SO$_2$-heterocyclic group with 6 ring members e.g. —SO$_2$-(morpholinyl), in particular —SO$_2$-(1-morpholinyl).

In one embodiment, R$^1$ is o-(-S(O)$_d$—C$_{1-4}$alkyl) or o-(-S(O)$_d$-heterocyclic group with 3 to 6 ring members).

In one embodiment, n is 2 and R$^1$ is (i) —SO$_2$CH$_3$ and (ii) chloro.

In one embodiment n is 2 and R$^1$ is (i) —SO$_2$CH$_3$ and (ii) chloro, nitrile or methyl.

In one embodiment, Het and R$^1$ form a group:

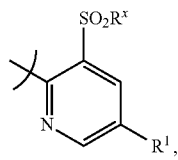

wherein in particular, R$^1$ is halogen (for example chloro), nitrile or C$_{1-4}$alkyl (for example —CH$_3$) and R$^x$ is C$_{1-4}$alkyl (for example —CH$_3$).

In one embodiment, Het and R$^1$ form a group:

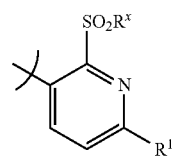

wherein in particular, R$^1$ is C$_{1-4}$alkyl (for example —CH$_3$) and R$^x$ is C$_{1-4}$alkyl (for example —CH$_3$).

In one embodiment when n is 2, the Het group is substituted with (i) o-OH or o-CH$_2$OH and (ii) halogen (e.g. Cl or F), nitrile, or C$_{1-4}$ alkyl, in particular chloro, or nitrile. In one embodiment, when n is 2, the Het group is substituted with (i) hydroxy and (ii) halogen (e.g. Cl or F) or nitrile, in particular chloro or nitrile. In one embodiment, when n is 2, the Het group is substituted with (i) o-hydroxy and (ii) p-Cl or p-CN (e.g. p-Cl).

In one embodiment, n is 2 and R$^1$ is fluorine (e.g. at the ortho and para positions of the Het group).

In one embodiment, R$^1$ is halogen (e.g. Cl or F), C$_{1-4}$alkynyl (e.g. —C≡CH), nitrile, —(CH$_2$)$_v$COOH (e.g. —COOH) or —SO$_2$C$_{1-4}$alkyl (e.g. SO$_2$CH$_3$) and n is 1 or 2.

In one embodiment, n is 1 and R$^1$ is Cl (e.g. p-Cl), CN (e.g. p-CN), F e.g. (p-F), CH$_3$ (e.g. p-CH$_3$), or OCH$_3$ (p-OCH$_3$), or n is 2 and (i) R$^1$ is p-F; o-F, or (ii) p-CH$_3$; o-OCH$_3$; or (iii) p-Cl, o-SO$_2$CH$_3$ or (iv) p-Cl, o-OH.

In one embodiment, n is 1 and R$^1$ is Cl (e.g. p-Cl), CN (e.g. p-CN), F e.g. (p-F), CH$_3$ (e.g. p-CH$_3$), or OCH$_3$ (p-OCH$_3$).

In one embodiment, n is 2 and (i) R$^1$ is p-F; o-F, or (ii) p-CH$_3$; o-OCH$_3$; or (iii) p-Cl, o-SO$_2$CH$_3$ or (iv) p-Cl, o-OH.

In one embodiment, n is 2 and R$^1$ is p-Cl and o-OH.

In one embodiment, R$^1$ is —O$_{0.1}$(CR$^x$R$^y$)$_v$COOH (e.g. —COOH, —CH$_2$COOH, —OCH$_2$COOH or —C(CH$_3$)$_2$COOH).

In one embodiment, n is 2 and R$^1$ is p-Cl and o-O$_{0.1}$(CR$^x$R$^y$)$_v$COOH (e.g. —COOH, —CH$_2$COOH, —OCH$_2$COOH or —O—C(CH$_3$)$_2$COOH).

In one embodiment n is 1 and R$^1$ is —Cl, —CN, OMe, —O$_{0.1}$(CR$^x$R$^y$)$_v$COOH (e.g. —COOH) or C$_{1-4}$alkyl (e.g. —CH$_3$) (e.g. p-Cl, p-CN or p-OMe). In one embodiment n is 1 and R$^1$ is —Cl or —CN (e.g. p-Cl or p-CN).

In one embodiment n is 1 and R$^1$ is —Cl, —CN or —OMe (e.g. p-Cl, p-CN or p-OMe). In one embodiment n is 1 and R$^1$ is —Cl or —CN (e.g. p-Cl or p-CN).

In one embodiment, R$^1$ is independently selected from hydroxy, halogen (e.g. chlorine), nitrile, C$_{1-4}$alkyl (e.g. methyl), C$_{1-4}$alkoxy (e.g. methoxy), and —O$_{0.1}$—(CR$^x$R$^y$)$_u$—CO$_2$H (e.g. —CO$_2$H).

In one embodiment R$^1$ is O$_{0.1}$—(CR$^x$R$^y$)$_v$—CO$_2$H in particular —CO$_2$H, —(CH$_2$)—CO$_2$H, —(C(CH$_3$)$_2$)—CO$_2$H, or —O(CH$_2$)—CO$_2$H), such as —CO$_2$H.

R$^2$

R$^2$ is selected from hydrogen, C$_{1-4}$ alkyl, C$_{2-6}$alkenyl, hydroxyC$_{1-4}$alkyl, —(CR$^x$R$^y$)$_u$—CO$_2$H, —(CR$^x$R$^y$)$_u$—CO$_2$C$_{1-4}$alkyl, and —(CR$^x$R$^y$)$_u$—CONR$^x$R$^y$.

In one embodiment u is selected from 0, 1, or 2. In one embodiment u is selected from 0 or 1.

In one embodiment, R$^2$ is selected from hydrogen, C$_{1-4}$ alkyl, C$_{2-6}$alkenyl, hydroxyC$_{1-4}$alkyl and —(CR$^x$R$^y$)$_u$—CO$_2$H. In one embodiment, R$^2$ is selected from hydrogen, C$_{1-4}$ alkyl, hydroxyC$_{1-4}$alkyl and —(CR$^x$R$^y$)$_u$—CO$_2$H. In one embodiment, R$^2$ is selected from hydrogen, C$_{1-4}$ alkyl, C$_{2-6}$alkenyl, and hydroxyC$_{1-4}$alkyl. In another embodiment R$^2$ is selected from hydrogen and —(CH$_2$)$_u$—CO$_2$H (e.g. —CH$_2$—CO$_2$H).

In one embodiment, R$^2$ is hydrogen, C$_{1-4}$ alkyl (e.g. —CH$_3$), hydroxyC$_{1-4}$alkyl (e.g. CH$_2$OH) or —(CH$_2$)$_u$COOH (e.g. —COOH, —CH$_2$COOH, —CH$_2$CH$_2$—CO$_2$H, —(CH(CH$_3$))—CO$_2$H or —(C(CH$_3$)$_2$—CO$_2$H, such as —COOH, —CH$_2$COOH, —CH$_2$CH$_2$—CO$_2$H, or —(CH(CH$_3$))—CO$_2$H).

In one embodiment, R$^2$ is selected from hydrogen, C$_{1-4}$alkyl, C$_{2-6}$alkenyl, and hydroxyC$_{1-4}$alkyl.

In one embodiment, R$^2$ is hydrogen, C$_{1-4}$ alkyl (e.g. —CH$_3$), hydroxyC$_{1-4}$alkyl (e.g. CH$_2$OH) or —(CH$_2$)$_u$COOH (e.g. —CH$_2$COOH).

In one embodiment, R$^2$ is selected from hydrogen, —CH$_3$, —CH$_2$OH, and —CH(OH)CH$_2$OH.

In one embodiment, R$^2$ is selected from hydrogen, —CH$_3$, —CH$_2$OH, —CH=CH$_2$ and —CH(OH)CH$_2$OH.

In one embodiment, R$^2$ is selected from hydrogen, —CH$_3$, —CH$_2$OH, and —CH$_2$CO$_2$H.

In one embodiment, $R^2$ is hydrogen or $C_{1-4}$ alkyl (e.g. —$CH_3$ or —$CH_2CH_3$).

In one embodiment, $R^2$ is selected from hydrogen, —$CH_3$ and —$CH_2CH_3$. In one embodiment, $R^2$ is selected from hydrogen and methyl.

In one embodiment, $R^2$ is selected from hydrogen and —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$.

In one embodiment, $R^2$ is —$(R^xR^y)_u$COOH (e.g. —$CH_2COOH$, —$CH_2CH_2$—$CO_2H$

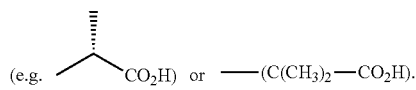

(e.g. CO₂H) or —(C(CH₃)₂—CO₂H).

In one embodiment, $R^2$ is hydrogen, $C_{1-6}$ alkyl (e.g. —$CH_3$) or —$(CH_2)_v$COOH (e.g. —$CH_2COOH$, —$CH_2CH_2$—$CO_2H$ or —$(CH(CH_3))$—$CO_2H$).

In one embodiment, $R^2$ is hydrogen, $C_{1-4}$ alkyl (e.g. —$CH_3$) or —$(CH_2)_u$COOH (e.g. —$CH_2COOH$).

In one embodiment, $R^2$ is —$(CR^xR^y)_u$—$CO_2H$ (e.g. —$CH_2$—$CO_2H$).

In another embodiment, $R^2$ is selected from —$(CH(CH_3))$—$CO_2H$ and —$(C(CH_3)_2$—$CO_2H)$

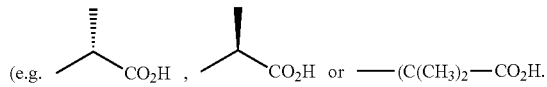

(e.g. CO₂H, CO₂H or —(C(CH₃)₂—CO₂H.

In another embodiment, $R^2$ is hydrogen and the compound of formula ($I^o$) is a compound of formula (Ie) or a tautomer or a solvate or a pharmaceutically acceptable salt thereof:

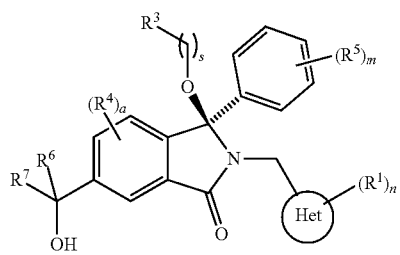

(Ie)

When $R^2$ is other than hydrogen, the compound of formula ($I^o$) can exist as at least two diastereoisomers:

Diastereoisomer 1A

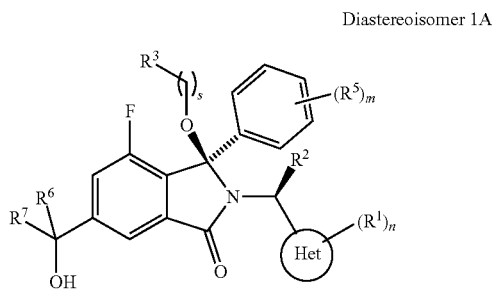

-continued

Diastereoisomer 1B

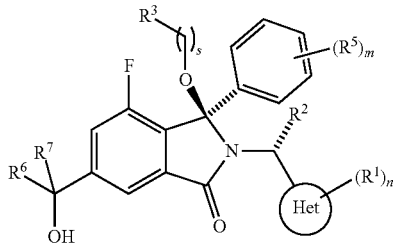

For the avoidance of doubt, the general formula ($I^o$) and all subformulae cover both individual diastereoisomers and mixtures of the diastereoisomers which are related as epimers at the —$CHR^2$— group. In one embodiment the compound of formula I is diastereoisomer 1A or a tautomer or a solvate or a pharmaceutically acceptable salt thereof. In one embodiment the compound of formula I is diastereoisomer 1B or a tautomer or a solvate or a pharmaceutically acceptable salt thereof.

In one embodiment, the compound is diastereoisomer 1A and $R^2$ is selected from:
  i. $C_{1-4}$ alkyl, $C_{2-6}$ alkenyl, hydroxy$C_{1-4}$alkyl, —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$, —$(CH_2)_u$—$CO_2C_{1-4}$ alkyl, and —$(CH_2)_u$—$CONR^xR^y$; or
  ii. $C_{1-4}$ alkyl, $C_{2-6}$ alkenyl, and hydroxy$C_{1-4}$alkyl.

In one embodiment, the compound is diastereoisomer 1A and $R^2$ is selected from:
  i. $C_{1-4}$ alkyl, $C_{2-6}$alkenyl, hydroxy$C_{1-4}$alkyl, —$(CH_2)_u$—$CO_2H$, —$(CH_2)_u$—$CO_2C_{1-4}$alkyl, and —$(CH_2)_u$—$CONR^xR^y$; or
  ii. $C_{1-4}$ alkyl, $C_{2-6}$ alkenyl, and hydroxy$C_{1-4}$alkyl.

In another embodiment $R^2$ is selected from hydrogen and —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$, In another embodiment $R^2$ is selected from hydrogen and —$(CH_2)_u$—$CO_2H$ (e.g. —$CH_2$—$CO_2H$).

In one embodiment, the compound is diastereoisomer 1A and $R^2$ is selected from:
  iv. —$CH_3$, —$CH_2OH$, —$CH$=$CH_2$ and —$CH(OH)CH_2OH$; or
  v. $C_{1-4}$ alkyl (e.g. —$CH_3$ or —$CH_2CH_3$); or
  vi. —$CH_3$ and —$CH_2CH_3$.

In one embodiment, the compound is diastereoisomer 1B and $R^2$ is selected from:
  i. $C_{1-4}$ alkyl, $C_{2-6}$alkenyl, hydroxy$C_{1-4}$alkyl, —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$, —$(CH_2)_u$—$CO_2C_{1-4}$alkyl, and —$(CH_2)_u$—$CONR^xR^y$; or
  ii. $C_{1-4}$ alkyl, $C_{2-6}$alkenyl, and hydroxy$C_{1-4}$alkyl.

In one embodiment, the compound is diastereoisomer 1B and $R^2$ is selected from:
  i. $C_{1-4}$ alkyl, $C_{2-6}$alkenyl, hydroxy$C_{1-4}$alkyl, —$(CH_2)_u$—$CO_2H$, —$(CH_2)_u$—$CO_2C_{1-4}$ alkyl, and —$(CH_2)_u$—$CONR^xR^y$; or
  ii. $C_{1-4}$ alkyl, $C_{2-6}$alkenyl, and hydroxy$C_{1-4}$alkyl.

In another embodiment $R^2$ is selected from hydrogen and —$(CH_2)_u$—$CO_2H$ (e.g. —$CH_2$—$CO_2H$).

In one embodiment, the compound is diastereoisomer 1B and $R^2$ is selected from:

iv. —CH$_3$, —CH$_2$OH, —CH=CH$_2$ and —CH(OH)CH$_2$OH; or v. C$_{1-4}$alkyl (e.g. —CH$_3$ or —CH$_2$CH$_3$); or vi. —CH$_3$ and —CH$_2$CH$_3$.

In another embodiment R$^2$ is selected from hydrogen and —(R$^x$R$^y$)$_u$—CO$_2$H (e.g. —COOH, —CH$_2$COOH, —CH$_2$CH$_2$—CO$_2$H, —(CH(CH$_3$))—CO$_2$H and —C(CH$_3$)$_2$—CO$_2$H), In one embodiment R$^2$ is selected from C$_{1-4}$alkyl, hydroxyC$_{1-4}$alkyl, —(CH$_2$)$_u$—CO$_2$H, —(CH$_2$)$_u$—CO$_2$C$_{1-4}$alkyl, and —(CH$_2$)$_w$—CONR$^x$R$^y$ (in particular —CH$_2$—CO$_2$H) and the compound is diastereoisomer 1A.

In one embodiment R$^2$ is selected from C$_{1-4}$ alkyl, hydroxyC$_{1-4}$alkyl, —(CH$_2$)$_u$—CO$_2$H, —(CH$_2$)$_u$—CO$_2$C$_{1-4}$alkyl, and —(CH$_2$)$_u$—CONR$^x$R$^y$ (in particular —CH$_2$—CO$_2$H) and the compound is diastereoisomer 1B.

In one embodiment R$^2$ is hydroxyC$_{1-4}$alkyl (e.g. —CH$_2$OH) and the compound is diastereoisomer 1A.

In one embodiment R$^2$ is —(CH$_2$)$_u$—CO$_2$H (e.g. —CH$_2$—CO$_2$H) and the compound is diastereoisomer 1A.

In one embodiment R$^2$ and the hydrogen on the carbon to which it is attached are $^2$H (i.e. deuterium).

R$^3$ and s

R$^3$ is hydrogen or -(A)$_t$-(CR$^x$R$^y$)$_q$—X;

s is selected from 0 and 1;

t is selected from 0 and 1;

q is selected from 0, 1 and 2;

wherein when R$^3$ is -(A)$_t$-(CR$^x$R$^y$)$_u$—X then (i) at least one of s, t and q is other than 0 and (ii) when t is 0 then s is 1 and q is other than 0;

A is a C$_{3-6}$ cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$alkyl, —S(O)$_d$—R$^x$, —C(=O)—C$_{1-4}$ alkyl, —S(O)$_d$—N(H)$_e$(C$_{1-4}$alkyl)$_{2-e}$, —NR$^x$R$^y$, —NHSO$_2$R$^x$, —NR$^x$COR$^y$, and —C(=O)NR$^x$R$^y$;

R$^9$ is independently selected from hydrogen, C$_{1-6}$alkyl, hydroxyC$_{1-6}$alkyl, —(CH$_2$)$_k$—O—C$_{1-6}$alkyl, —(CH$_2$)$_k$—O-(hydroxyC$_{1-6}$alkyl), hydroxyC$_{1-6}$alkoxy, —(CH$_2$)$_k$—CO$_2$C$_{1-6}$ alkyl, —(CH$_2$)$_k$—CO$_2$H, —C$_{1-43}$ alkyl-N(H)$_e$(C$_{1-4}$alkyl)$_{2-e}$, —(CH$_2$)$_j$—C$_{3-8}$cycloalkyl and —(CH$_2$)$_j$—C$_{3-8}$ cycloalkenyl;

R$^x$ and R$^y$ are independently selected from hydrogen, halogen, nitro, nitrile, C$_{1-6}$alkyl, haloC$_{1-6}$alkyl, C$_{2-6}$alkenyl, C$_{2-6}$alkynyl, hydroxy, hydroxyC$_{1-6}$alkyl, C$_{1-6}$alkoxy, —(CH$_2$)$_k$—O—C$_{1-6}$ alkyl, hydroxyC$_{1-6}$alkoxy, —CO$_0$C$_{1-6}$ alkyl, —N(H)$_e$(C$_{1-4}$alkyl)$_{2-e}$, —C$_{1-6}$alkyl-N(H)$_e$(C$_{1-4}$alkyl)$_{2-e}$, —(CH$_2$)$_k$—C(=O)N(H)$_e$(C$_{1-4}$alkyl)$_{2-e}$, C$_{3-8}$cycloalkyl and C$_{3-8}$ cycloalkenyl;

or the R$^x$ and R$^y$ groups, together with the carbon or nitrogen atom to which they are attached, can join to form a C$_{3-6}$ cycloalkyl or saturated heterocyclyl group with 3 to 6 ring members which may be optionally fused to an aromatic heterocyclyl group of 3 to 5 ring members or can join to form a =CH group;

j, d, and e are independently selected from 0, 1 and 2;

k is selected from 1 and 2; and v is independently selected from 0 and 1.

In one embodiment when t is 1 the group —(CR$^x$R$^y$)$_q$—X and the rest of the molecule are attached to the same carbon atom in the group A. In one embodiment when t is 1 the group (CR$^x$R$^y$)$_q$—X and the rest of the molecule are attached to different carbon atoms in the group A.

In one embodiment, R$^3$ is hydrogen or -(A)$_t$-(CR$^x$R$^y$)$_q$—X;

s is selected from 0 and 1;

t is selected from 0 and 1;

q is selected from 0, 1 and 2;

wherein when R$^3$ is -(A)$_t$-(CR$^x$R$^y$)$_q$—X then (i) at least one of s, t and q is other than 0 and (ii) when t is 0 then s is 1 and q is other than 0;

A is a C$_{3-6}$ cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_u$—CO$_2$C$_{1-4}$ alkyl, —S(O)$_d$—R$^x$, —C(=O)—C$_{1-4}$alkyl, —S(O)$_d$—N(H)$_e$(C$_{1-4}$alkyl)$_{2-e}$, —NR$^x$R$^y$, —NHSO$_2$R$^x$, —NR$^x$COR$^y$, and —C(=O)NR$^x$R$^y$;

R$^9$ is independently selected from hydrogen and C$_{1-6}$alkyl;

R$^x$ and R$^y$ are independently selected from hydrogen and C$_{1-6}$alkyl;

d and e are independently selected from 0, 1 and 2;

v is independently selected from 0 and 1.

In one embodiment, R$^3$ is hydrogen or -(A)$_t$-(CR$^x$R$^y$)$_q$—X;

s is selected from 0 and 1;

t is selected from 0 and 1;

q is selected from 0, 1 and 2;

wherein when R$^3$ is -(A)$_t$-(CR$^x$R$^y$)$_q$—X then (i) at least one of s, t and q is other than 0 and (ii) when t is 0 then s is 1 and q is other than 0;

A is a C$_{3-6}$ cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$alkyl, —C(=O)—C$_{1-4}$alkyl, —NR$^x$R$^y$, —NR$^x$COR$^y$, and —C(=O)NR$^x$R$^y$;

R$^9$ is independently selected from hydrogen and C$_{1-6}$alkyl;

R$^x$ and R$^y$ are independently selected from hydrogen and C$_{1-6}$alkyl;

v is independently selected from 0 and 1.

In one embodiment, R$^3$ is hydrogen or -(A)$_t$-(CR$^x$R$^y$)$_q$—X;

s is selected from 0 and 1;

t is selected from 0 and 1;

q is selected from 0, 1 and 2;

wherein when R$^3$ is -(A)$_t$-(CR$^x$R$^y$)$_q$—X then (i) at least one of s, t and q is other than 0 and (ii) when t is 0 then s is 1 and q is other than 0;

A is a C$_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —NR$^x$COR$^y$, and —C(=O)NR$^x$R$^y$;

R$^9$ is independently selected from hydrogen and C$_{1-6}$ alkyl;

R$^x$ and R$^y$ are independently selected from hydrogen and C$_{1-6}$alkyl;

v is independently selected from 0 and 1.

In one embodiment, R$^3$ is hydrogen or -(A)$_t$-(CR$^x$R$^y$)$_q$—X;

s is selected from 0 and 1;

t is selected from 0 and 1;

q is selected from 0, 1 and 2;

wherein when R$^3$ is -(A)$_t$-(CR$^x$R$^y$)$_q$—X then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;
X is selected from hydrogen, halogen (e.g. fluoro), —OR$^9$, —NR$^x$COR$^y$; and —C(=O)NR$^x$R$^y$;
R$^9$ is independently selected from hydrogen and $C_{1-6}$alkyl;
R$^x$ and R$^y$ are independently selected from hydrogen and $C_{1-6}$alkyl;
v is independently selected from 0 and 1.

In one embodiment, R$^3$ is hydrogen and s is 1 i.e. the moiety —(CH$_2$)$_s$R$^3$ is —CH$_3$.

In one embodiment, R$^3$ is hydrogen and s is 0 i.e. the moiety —(CH$_2$)$_s$R$^3$ is —H.

In one embodiment, t is 1 and A is a $C_{3-6}$cycloalkyl group or a heterocyclic group with 3 to 6 ring members, wherein the heterocyclic group comprises one or more (e.g. 1 or 2) heteroatoms selected from N, O, S and oxidised forms thereof.

In one embodiment, t is 1 and A is a $C_{3-6}$cycloalkyl group. In one embodiment, A is a $C_{3-5}$cycloalkyl group. For example, A is selected from a cyclopropyl group, a cyclobutyl group and a cyclopentyl group.

In one embodiment, A is a cyclopropyl group. In one embodiment, A is a cyclobutyl group.

In particular, t is 1 and A is cyclopropyl.

In one embodiment, t is 1 and A is a heterocyclic group with 3 to 6 ring members, wherein the heterocyclic group comprises one or more (e.g. 1, 2, or 3) heteroatoms selected from N, O, S and oxidised forms thereof.

In one embodiment, t is 1 and A is a heterocyclic group with 3 to 5 ring members, wherein the heterocyclic group comprises one or more (e.g. 1, 2, or 3) heteroatoms selected from N, O, S and oxidised forms thereof.

In one embodiment, t is 1 and A is an unsaturated heterocyclic group with 3 to 5 ring members, wherein the heterocyclic group comprises one or more (e.g. 1, 2, or 3) heteroatoms selected from N, O, S and oxidised forms thereof, in particular O.

In one embodiment, t is 1 and A is a saturated heterocyclic group with 3 to 5 ring members, wherein the heterocyclic group comprises one or more (e.g. 1, 2, or 3) heteroatoms selected from N, O, S and oxidised forms thereof, in particular O.

In one embodiment, t is 1 and A is a heterocyclic group which is selected from morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, oxetanyl, pyranyl (2H-pyran or 4H-pyran), dihydrothienyl, dihydropyranyl, dihydrofuranyl, dihydrothiazolyl, tetrahydrofuranyl (e.g. tetrahydrofuran-3-yl), tetrahydrothienyl, dioxanyl, oxanyl (e.g. oxan-4-yl), imidazolinyl, imidazolidinonyl, oxazolinyl, thiazolinyl, pyrazolin-2-yl, pyrazolidinyl, piperazinonyl, piperazinyl, and N-alkyl piperazines such as N-methyl piperazinyl.

In one embodiment, t is 1 and A is a heterocyclic group which is selected from morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, oxetanyl, pyranyl (2H-pyran or 4H-pyran), dihydropyranyl, dihydrofuranyl, dihydrothiazolyl, tetrahydrofuranyl (e.g. tetrahydrofuran-3-yl), dioxanyl, oxanyl (e.g. oxan-4-yl), imidazolinyl, imidazolidinonyl, oxazolinyl, pyrazolin-2-yl, pyrazolidinyl, piperazinonyl, piperazinyl, and N-alkyl piperazines such as N-methyl piperazinyl.

In particular, t is 1 and A is a heterocyclic group which is oxetanyl (e.g. oxetan-3-yl).

In particular, t is 1 and A is a heterocyclic group which is tetrahydrofuranyl (e.g. tetrahydrofuran-3-yl).

In one embodiment, X is hydrogen, s is 0 and q is 0, and R$^3$ is a heterocyclic group with 3 to 6 ring members, wherein the heterocyclic group comprises one or more (e.g. 1, 2, or 3) heteroatoms selected from N, O, S and oxidised forms thereof. In particular, R$^3$ is tetrahydrofuranyl (e.g. tetrahydrofuran-3-yl).

In one embodiment, s is 0 and t is 1 and A is attached directly to the oxygen atom bound to the isoindolinone. In one embodiment s is 1 and the cycloalkyl group is attached via a methylene group (i.e. —CH$_2$—) to the oxygen atom bound to the isoindolinone.

In one embodiment, A is tetrahydrofuranyl and X is hydrogen.

In one embodiment A is selected from cyclopropyl, oxetanyl and tetrahydrofuranyl.

In one embodiment, A is oxetanyl and X is fluorine.

In one embodiment, q is 0. In one embodiment, q is 1. In one embodiment, q is 2.

When q is not 0, R$^x$ and R$^y$ are selected from hydrogen, halogen (e.g. fluorine), hydroxy and methyl e.g. hydrogen and methyl, in particular hydrogen.

In one embodiment, q is 1 and at least one R$^x$ and R$^y$ is hydrogen. In one embodiment, q is 2 and at least two R$^x$ and R$^y$ are hydrogen e.g. three R$^x$ and R$^y$ are hydrogen.

In one embodiment, —(CR$^x$R$^y$)$_q$— is selected from —CH$_2$— and —CH$_2$CH$_2$—.

In one embodiment, R$^x$ and R$^y$ together form a saturated heterocyclyl group with 3 to 6 ring members. In one embodiment t is 0 and —(CR$^x$R$^y$)$_q$— is —CH$_2$—. In one embodiment t is 0, s is 0, —(CR$^x$R$^y$)$_q$— is —CH$_2$— and X is hydroxy.

In one embodiment, X is selected from —CN, —OH, —O—$C_{1-4}$ alkyl, —O-hydroxy$C_{1-4}$alkyl, —S(O)$_d$—$C_{1-4}$alkyl, —C(=O)—$C_{1-4}$alkyl, —NR$^x$R$^y$, —NR$^x$COR$^y$ and —C(=O)NR$^x$R$^y$.

In one embodiment, X is selected from —CN, —OH, —O—CH$_2$CH$_2$OH, —S(O)$_d$—$C_{1-4}$alkyl and —C(=O)NR$^x$R$^y$ (e.g. —C(=O)NH$_2$ or —C(=O)NH(CH$_3$)). In one embodiment X is selected from —CN, —OH, —C(=O)NH$_2$ or —C(=O)NH(CH$_3$).

In one embodiment, X is selected from hydrogen, halogen, —CN, —OR$^9$, and —C(=O)NR$^x$R$^y$. In another embodiment, X is selected from hydrogen, halogen, —CN, —OH, —OCH$_3$, and —C(=O)NH$_2$. In another embodiment, X is selected from hydrogen, fluorine, —CN, —OH, and —C(=O)NH$_2$.

In one embodiment, X is selected from hydrogen, fluorine, —CN, —OH and —C(=O)NH$_2$. In one embodiment, X is selected from hydrogen, —CN, —OH and —C(=O)NH$_2$. In one embodiment, X is selected from —CN, —OH and —C(=O)NH$_2$.

In one embodiment X is selected from —OH and —C(=O)NH$_2$ e.g. —OH.

In one embodiment, X is —C(=O)NR$^x$R$^y$ (e.g. —C(=O)NH$_2$ or —C(=O)NH(CH$_3$)).

In one embodiment, R$^x$ and R$^y$ are hydrogen, halogen (e.g. fluorine), hydroxy and methyl. In one embodiment, R$^x$ and R$^y$ are hydrogen and methyl. In one embodiment, R$^x$ and R$^y$ together form a saturated heterocyclyl group with 3 to 6 ring members.

In one embodiment, A is a $C_{3-6}$cycloalkyl group (i.e. g is 1, 2 or 3) and t is 1 and s is 0 or 1, and the compound of formula (I°) is a compound of formula (If) or a tautomer or a solvate or a pharmaceutically acceptable salt thereof:

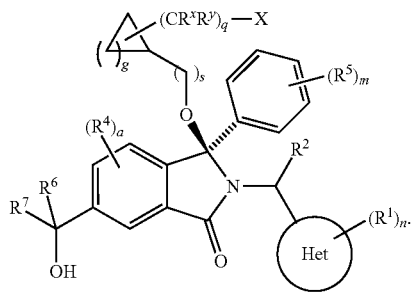

(If)

In one embodiment, A is a $C_{3-6}$ cycloalkyl group (i.e. g is 1, 2 or 3) and t is 1 and s is 1, and the compound of formula (I°) is a compound of formula (Ig) or a tautomer or a solvate or a pharmaceutically acceptable salt thereof:

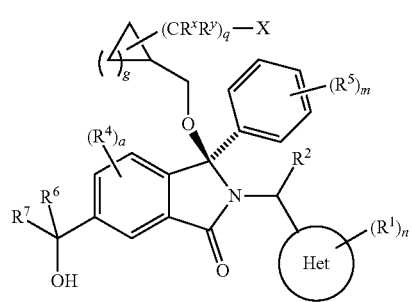

(Ig)

In one embodiment, A is a $C_{3-6}$ cycloalkyl group (i.e. g is 1, 2 or 3) and t is 1 and s is 0, and the compound of formula (I°) is a compound of formula (Ig') or a tautomer or a solvate or a pharmaceutically acceptable salt thereof:

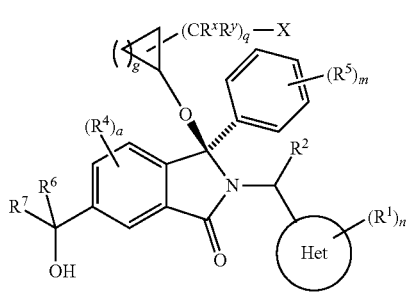

(Ig')

In one embodiment, the compound of formula (I°) is a compound of formula (Ig') and g is 2.

In one embodiment, A is a $C_{3-6}$ cycloalkyl group (i.e. g is 1, 2 or 3) and t is 1 and s is 1, and the cycloalkyl group is geminally disubstituted (i.e. the group —$(CR^xR^y)_q$—X and the —$CH_2$—O-isoindolinone group are both attached to the same atom of the cycloalkyl group), and the compound of formula (I°) is a compound of formula (Ih) or a tautomer or a solvate or a pharmaceutically acceptable salt thereof:

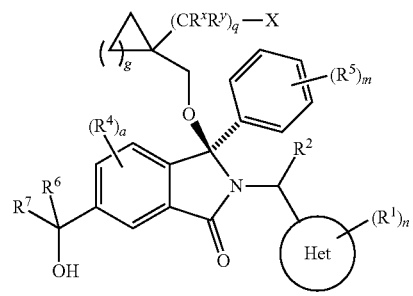

(Ih)

In one embodiment, A is a cyclopropyl group (i.e. g is 1), t is 1 and s is 1. Therefore the cycloalkyl group is a cyclopropyl group and the compound of formula (I°) is a compound of formula (Ii) or a tautomer or a solvate or a pharmaceutically acceptable salt thereof:

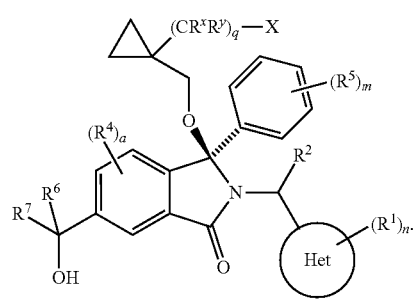

(Ii)

In one embodiment, A is a $C_{3-6}$ cycloalkyl group (i.e. g is 1, 2 or 3), t is 1, s is 1 and X is hydroxy, and the compound of formula (I°) is a compound of the formula (Ij) or a tautomer or a solvate or a pharmaceutically acceptable salt thereof:

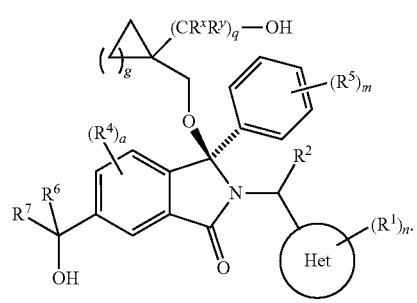

(Ij)

In one embodiment, A is a $C_{3-6}$ cycloalkyl group (i.e. g is 1, 2 or 3), t is 1, s is 1 and X is —C(=O)NH$_2$ and the compound of formula (I°) is a compound of the formula (Ik) or a tautomer or a solvate or a pharmaceutically acceptable salt thereof:

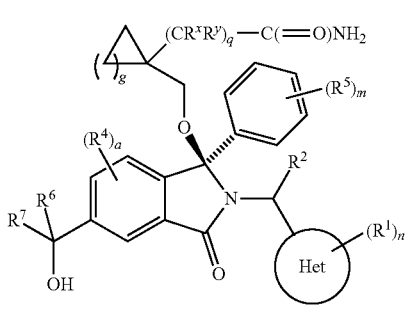
(Ik)

In one embodiment, A is a $C_{3-6}$cycloalkyl group (i.e. g is 1, 2 or 3), t is 1, s is 1 and X is CN and the compound of formula (I°) is a compound of the formula (Ik') or a tautomer or a solvate or a pharmaceutically acceptable salt thereof:

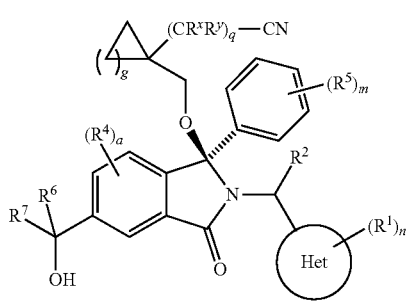
(Ik')

In another embodiment, A is a $C_{3-6}$ cycloalkyl group (i.e. g is 1, 2 or 3), t is 1, s is 1 and $R^x$ and $R^y$ are hydrogen (including $^1H$ and $^2H$) and the compound of formula (I°) is a compound of formula (IL) or a tautomer or a solvate or a pharmaceutically acceptable salt thereof:

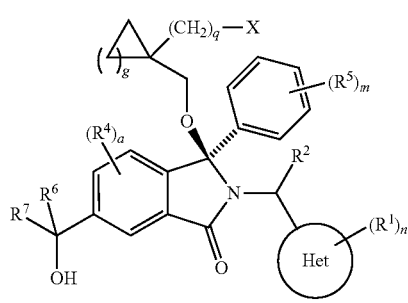
(IL)

In one embodiment, A is a cyclopropyl or cyclobutyl group (i.e. g is 1 or 2), t is 1, s is 1 and X is hydroxy and the compound of formula (IL) is a compound of formula (Im) or a tautomer or a solvate or a pharmaceutically acceptable salt thereof:

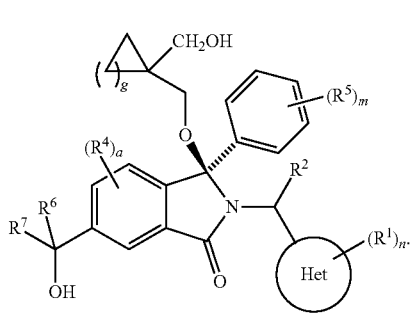
(Im)

In one embodiment, g is 1 and the compound of formula (Im) is a compound of the formula (Im') or a tautomer or a solvate or a pharmaceutically acceptable salt thereof:

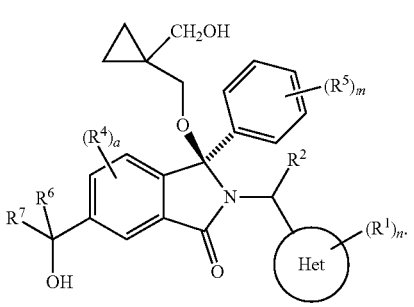
(Im')

In one embodiment, A is a $C_3$-cycloalkyl group (i.e. g is 1), t is 1, s is 1 and X is —C(=O)NH$_2$ and the compound of formula (I°) is a compound of formula (In) or a tautomer or a solvate or a pharmaceutically acceptable salt thereof:

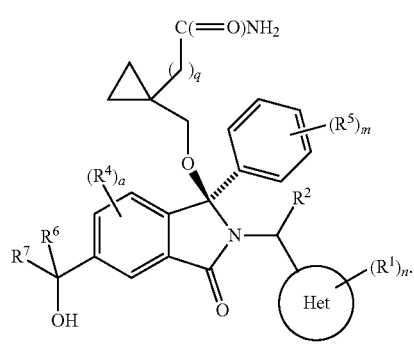
(In)

wherein q is 0 or 1. In one embodiment of the compound (In), q is 0.

In one embodiment, A is a $C_3$-cycloalkyl group (i.e. g is 1), t is 1, s is 1 and X is —CN and the compound of formula (I°) is a compound of formula (In') or a tautomer or a solvate or a pharmaceutically acceptable salt thereof:

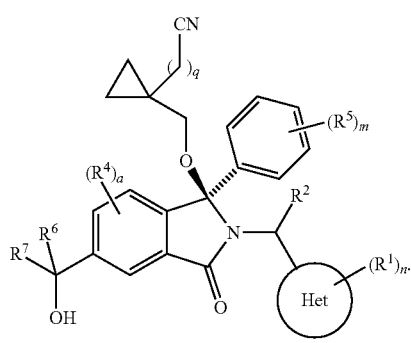

(In′)

wherein q is 0 or 1. In one embodiment of the compound (In), q is O.

In one embodiment of formula (I°) and subformulae thereof, the hydrogens in the —(CR$^x$R$^y$)— group of R$^3$ are $^2$H (i.e. deuterium, D). In one embodiment, the hydrogens in the group —CH$_2$—O group are $^2$H (i.e. deuterium, D). In one embodiment, the hydrogens in the —(CR$^x$R$^y$)— and —CH$_2$—O groups are $^2$H (i.e. deuterium, D).

In one embodiment q is 0 or 1 and R$^x$ and R$^y$ are hydrogen or deuterium.

In one embodiment, A is cyclopropyl (i.e. g is 1), t is 1, s is 1, X is hydroxy and the hydrogens in the —(CR$^x$R$^y$)— and —CH$_2$—O groups are $^2$H (or D), and the compound of formula (I°) is a compound of formula (Io) or a tautomer or a solvate or a pharmaceutically acceptable salt thereof:

(Io)

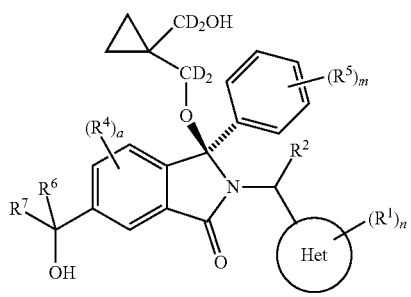

In one embodiment the compound of formula (I°) is a compound of formula (Io′) or (Io″) or a tautomer or a solvate or a pharmaceutically acceptable salt thereof:

(Io′)

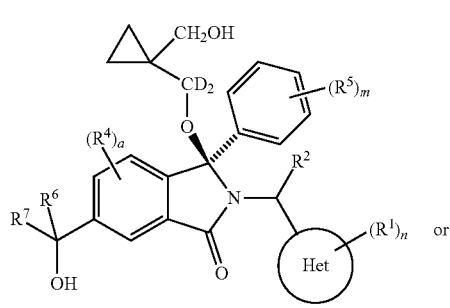

or

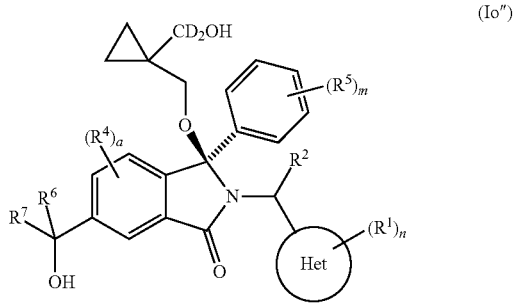

(Io″)

In one embodiment, R$^3$ is —(CR$^x$R$^y$)$_q$—X and s is 1, t is 0 and q is 1 or 2, and the compound of formula (I°) is a compound of the formula (Ip):

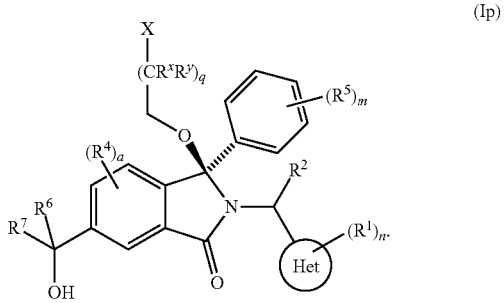

(Ip)

In one embodiment, R$^x$ and R$^y$ are H, and the compound of formula (Ip) is a compound of the formula (Ip′) or a tautomer or a solvate or a pharmaceutically acceptable salt thereof:

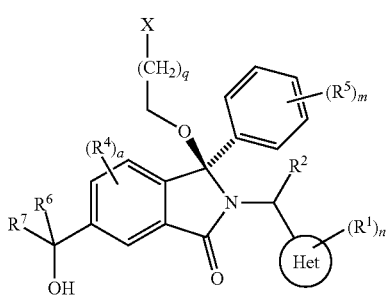

(Ip′)

In one embodiment, A is a C$_{3-6}$cycloalkyl group or saturated heterocyclic group with 3 to 6 ring members, wherein t is 1, and s is 1, Y is independently selected from —CH$_2$—, O, or SO$_2$, i is 0 or 1, g is 1, 2, 3 or 4 and i+g is 1, 2, 3 or 4 and the compound of formula (I°) is a compound of the formula (Iq) or a tautomer or a solvate or a pharmaceutically acceptable salt thereof:

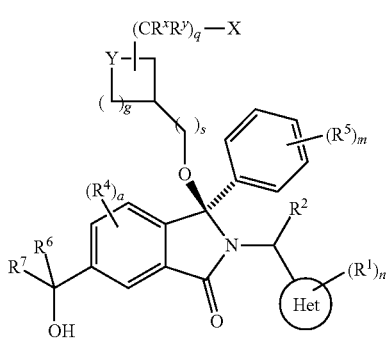

(Iq)

In one embodiment the compound of formula (I°) is a compound of the formula (Iq) or a tautomer or a solvate or a pharmaceutically acceptable salt thereof:

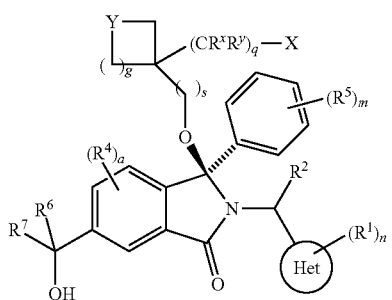

(Iq')

In one embodiment the compound of (10 is where q is 1 and $R^x$, $R^y$ and X are hydrogen.

In one embodiment of the compound of formula (Iq'), q is 1, RX and $R^y$ are hydrogen, and X is hydroxy.

In one embodiment of the compound of formula (Iq'), q is 1, $R^x$ and $R^y$ are hydrogen, and X is fluorine.

In one embodiment of the compound of formula (Iq'), q is 0. In one embodiment of the compound of formula (Iq'), q is 0 and X is fluorine.

In one embodiment q is 0 and X is F and the compound of formula (Iq') is a compound of the formula (Iq") or a tautomer or a solvate or a pharmaceutically acceptable salt thereof:

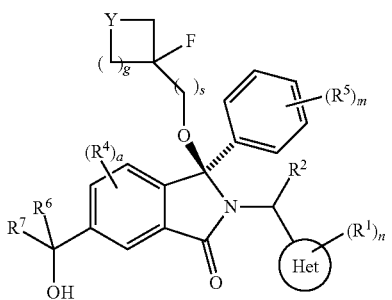

(Iq")

In one embodiment of the compound of (Iq') or the compound of (Iq"), g is 1, i is 1 and Y is 0.

In one embodiment g is 1, i is 1, Y is 0, q is 0 and X is F and the compound of formula (Iq') is a compound of the formula (IC) or a tautomer or a solvate or a pharmaceutically acceptable salt thereof:

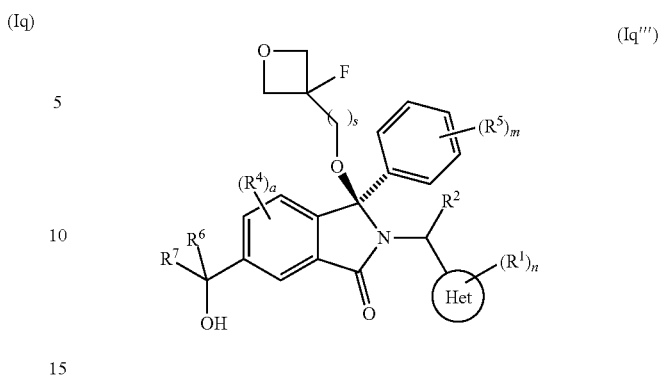

(Iq''')

In one embodiment, i is 1 and Y is 0 or $SO_2$, in particular O. In one embodiment, the compound of formula (Iq) is a compound of formula (Iq''') or a tautomer or a solvate or a pharmaceutically acceptable salt thereof:

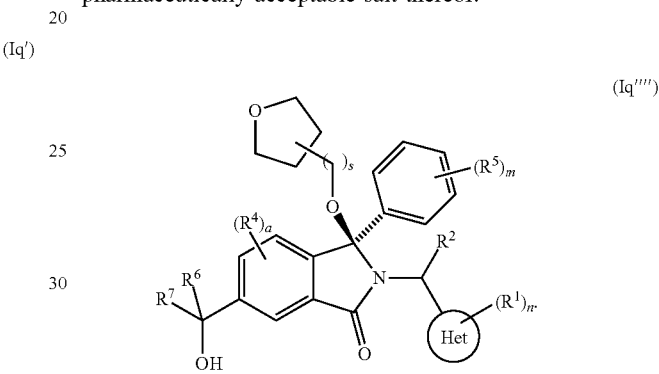

(Iq'''')

In one embodiment, s is 0, t is 1, A is tetrahydofuranyl, q is 0 and X is hydrogen. In one embodiment, $R^3$ is tetrahydrofuranyl and s is 0.

In one embodiment, —$(CH_2)_s R^3$ is selected from the following table (point of attachment to the oxygen represented by dashed bond or bond terminus marked "*"):

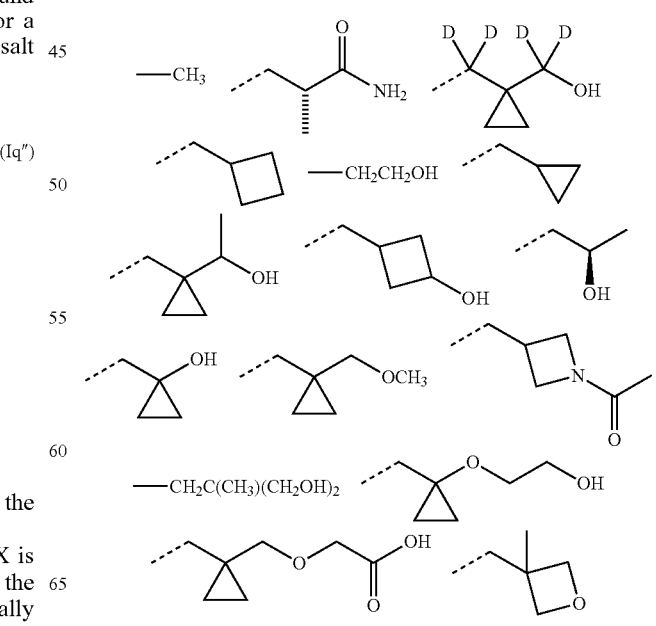

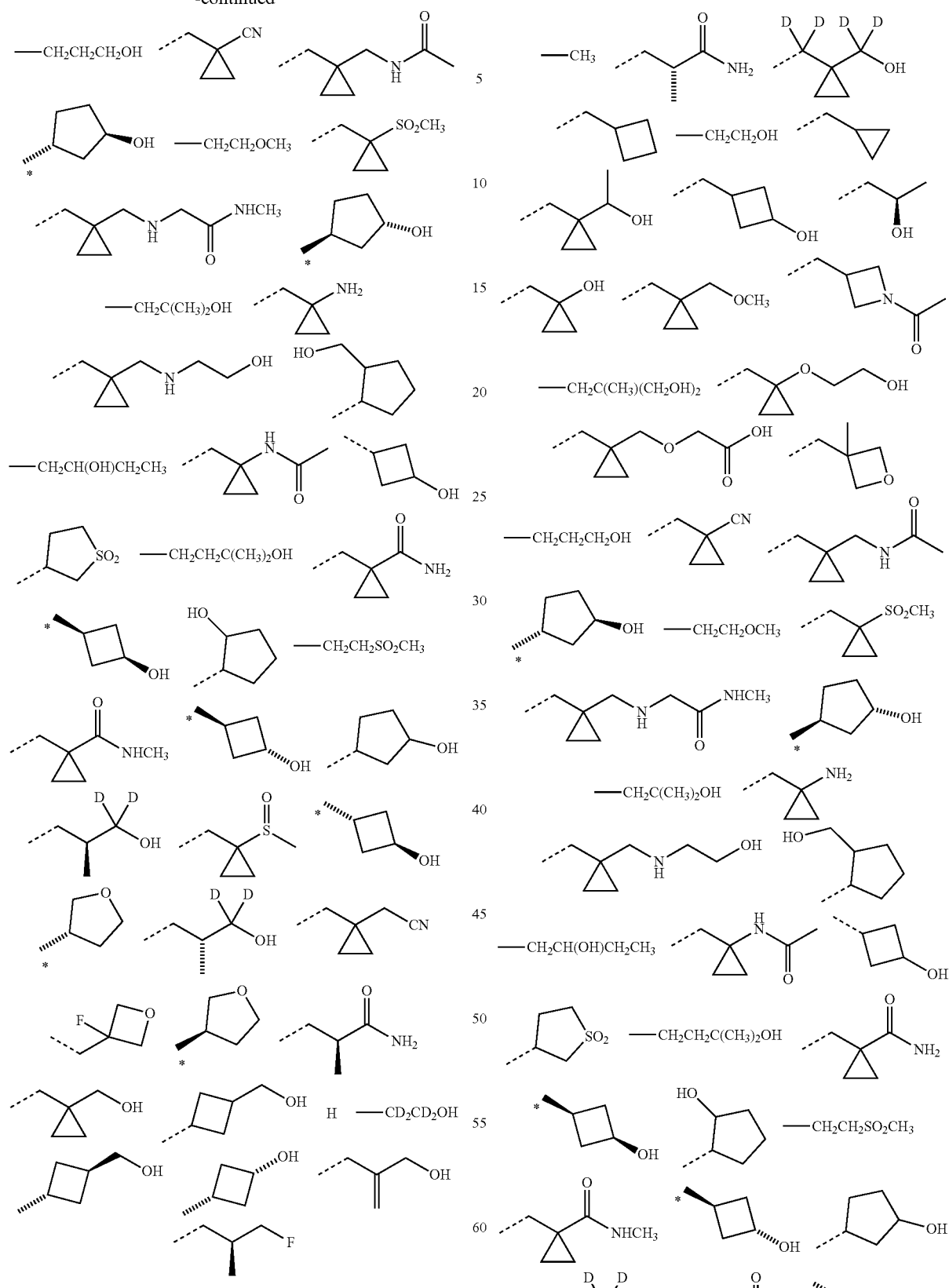
In one embodiment, —(CH$_2$)$_5$R$^3$ is selected from the following table (point of attachment to me oxygen represented by dashed bond or bond terminus marked "*"):

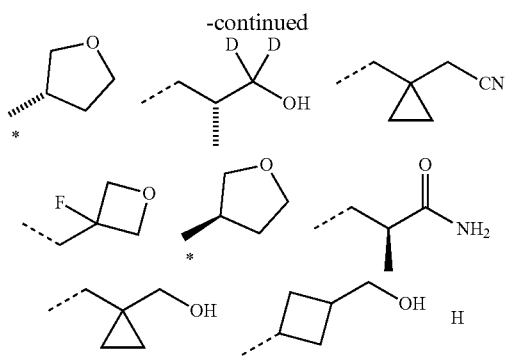

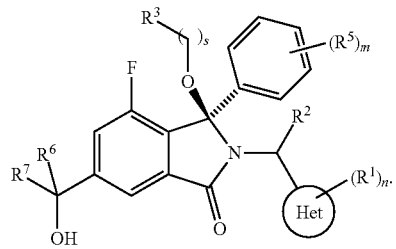

In one embodiment A is cyclopropyl, t is 1, s is 1, $R^x$ and $R^y$ are hydrogen and X is —OH.

In one embodiment A is cyclopropyl, t is 1, s is 1, $R^x$ and $R^y$ are hydrogen and X is —CN.

In one embodiment $R^3$ is hydrogen and s is 1. In one embodiment, X is hydrogen and s, t, and q are 0.

$R^4$ and a a is 0, 1, 2 or 3. In other words, the phenyl group of the isoindolin-1-one may have 0, 1, 2 or 3 substituents $R^4$.

In one embodiment a is 0 or 1. In another embodiment a is 0. In another embodiment a is 1.

When a is 2 or 3 (i.e. the phenyl group of the isoindolin-1-one is substituted with more than one $R^4$) the substituents $R^4$ may be the same or different (i.e. are independently selected from the definitions of $R^4$).

In one embodiment, a is 1 and the substituent $R^4$ is at the 4-position of the isoindolin-1-one, and the compound of formula (I°) is a compound of formula (Ir) or a tautomer or a solvate or a pharmaceutically acceptable salt thereof:

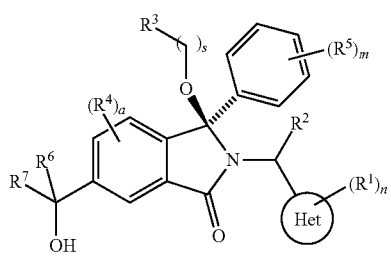

$R^4$ is independently selected from halogen, nitrile, $C_{1-4}$ alkyl, halo$C_{1-4}$alkyl, $C_{1-4}$alkoxy and halo$C_{1-4}$alkoxy.

In one embodiment, $R^4$ is halogen. In one embodiment, $R^4$ is fluoro or chloro. In another embodiment, $R^4$ is fluoro.

In one embodiment, a is 1, the substituent $R^4$ is at the 4-position of the isoindolin-1-one, and $R^4$ is F and the compound of formula (I°) is a compound of formula (Is) or a tautomer or a solvate or a pharmaceutically acceptable salt thereof:

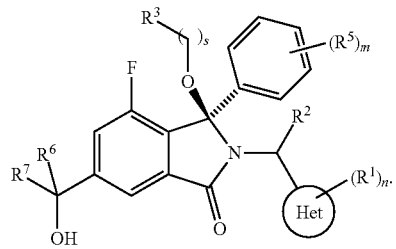

In one embodiment, a is 0, and the compound of formula (I°) is a compound of formula (If) or a tautomer or a solvate or a pharmaceutically acceptable salt thereof:

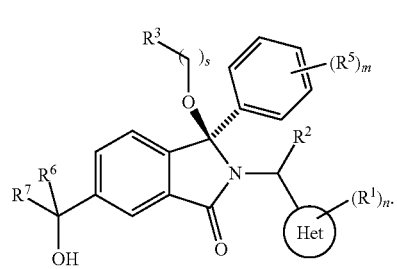

In one embodiment, $R^4$ is $C_{1-4}$ alkyl (e.g. —CH$_3$), or halogen (e.g. F or Cl) and a is 1.

In one embodiment, a is 0 and $R^4$ is absent (i.e. hydrogen).

In one embodiment a is 0 or 1 and $R^4$ is halogen (e.g. fluorine).

$R^5$ and m m is 1 or 2. In other words, the phenyl group may have 1 or 2 substituents $R^5$.

In one embodiment, m is 1 and the phenyl group has one substituent.

$R^5$ may be attached at the ortho (or o-), meta (or m-) or para (or p-) position of the phenyl group, wherein the position is defined relative to the point of attachment of the phenyl group to the 3-position of the isoindolin-1-one ring.

When m is 2 (i.e. the phenyl group is substituted with more than one $R^5$) the substituents $R^5$ may be the same or different (i.e. are independently selected from the definitions of $R^5$).

In one embodiment, m is 1 and the substituent $R^4$ is at the p-position of the phenyl group, and the compound of formula (I°) is a compound of formula (Iu) or a tautomer or a solvate or a pharmaceutically acceptable salt thereof:

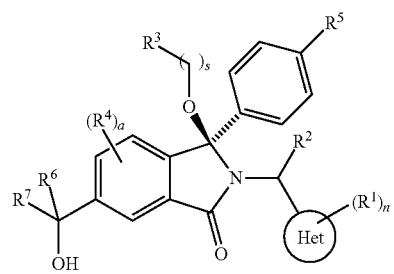

$R^5$ is independently selected from halogen, nitrile, $C_{1-4}$ alkyl, halo$C_{1-4}$alkyl, $C_{1-4}$alkoxy and halo$C_{1-4}$alkoxy.

In one embodiment, $R^5$ is halogen, $C_{1-4}$ alkyl, halo$C_{1-6}$ alkyl or $C_{1-4}$ alkoxy. In another embodiment $R^5$ is halogen (e.g. chloro).

In one embodiment, $R^5$ is halogen (e.g. Cl or F), $C_{1-4}$ alkyl (e.g. —CH$_2$CH$_3$), nitrile, halo$C_{1-4}$alkyl (e.g. —CF$_3$, or —CF$_2$CH$_3$), or halo$C_{1-4}$alkoxy (e.g. —OCF$_3$), and m is 1 or 2.

In one embodiment, m is 1 and $R^5$ is selected from halogen, nitrile, $C_{1-4}$ alkyl, halo$C_{1-4}$alkyl, $C_{1-4}$alkoxy and halo$C_{1-4}$alkoxy.

In one embodiment, m=1 and $R^5$ is —Cl (e.g. p-Cl), —F (e.g. p-F), —CN (e.g. p-CN), —CF$_3$ (e.g. p-CF$_3$), —OCF$_3$ (e.g. p-OCF$_3$), CF$_2$CH$_3$ (e.g. p-CF$_2$CH$_3$) or —CH$_2$CH$_3$ (e.g. p-CH$_2$CH$_3$), or m=2 and $R^5$ is p-F or m-F.

$R^6$ and $R^7$ $R^6$ and $R^7$ are independently selected from hydrogen, $C_{1-6}$alkyl, halo$C_{1-6}$alkyl, $C_{2-6}$alkenyl, $C_{2-6}$ alkynyl, hydroxy, hydroxy$C_{1-6}$alkyl, —COO$C_{1-6}$alkyl, —(CH$_2$)$_j$—O—$C_{1-6}$alkyl, —(CH$_2$)$_j$—O-(hydroxy$C_{1-6}$alkyl), —$C_{1-6}$alkyl-NR$^x$R$^y$, —(CR$^x$R$^y$)$_p$—CONR$^x$R$^y$, —(CR$^x$R$^y$)$_p$—NR$^x$COR$^y$, —(CR$^x$R$^y$)$_p$—O—CH$_2$—CONR$^x$R$^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N($C_{1-6}$alkyl)-heterocyclic group with 3 to 7 ring members, —C(=O)NH-heterocyclic group with 3 to 7 ring members, $C_{3-8}$cycloalkyl, —CH$_2$—$C_{3-8}$cycloalkyl, —CH$_2$—O—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

or the $R^6$ and $R^7$ groups, together with the carbon atom to which they are attached, can join to form a $C_{3-8}$ cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-8}$cycloalkyl and heterocyclyl groups may be optionally substituted by one or more $R^z$ groups;

$R^x$ and $R^y$ are independently selected from hydrogen, halogen, nitro, nitrile, halo$C_{1-6}$alkyl, $C_{2-6}$alkenyl, $C_{2-6}$ alkynyl, hydroxy, hydroxy$C_{1-6}$alkyl, $C_{1-6}$alkoxy, —(CH$_2$)$_k$—O—$C_{1-6}$ alkyl, hydroxy$C_{1-6}$alkoxy, —COO$C_{1-3}$alkyl, —N(H)$_e$($C_{1-4}$alkyl)$_{2-e}$, —$C_{1-6}$alkyl-N(H)$_e$($C_{1-4}$alkyl)$_{2-e}$, —(CH$_2$)$_k$—C(=O)N(H)$_e$($C_{1-4}$a141)$_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$ cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =CH$_2$ group;

$R^z$ is independently selected from halogen, nitro, nitrile, $C_{1-6}$alkyl, $C_{2-6}$ alkenyl, $C_{2-6}$alkynyl, =O, hydroxy, hydroxy$C_{1-6}$alkyl, $C_{1-6}$ alkoxy, —(CH$_2$)$_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$ alkyl-N(H)$_e$($C_{1-4}$alkyl)$_{2-e}$, —C(=O)N(H)$_e$($C_{1-4}$alkyl)$_{2-e}$, —(CH$_2$)$_r$—CO$_2$$C_{1-6}$alkyl, —(CH$_2$)$_r$—CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$ alkyl, heterocyclyl group with 3 to 6 ring members substituted by —C(=O)O$C_{1-4}$ alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$ cycloalkyl and $C_{3-8}$cycloalkenyl, wherein if $R^7$ is pyridine then $R^z$ is other then —NH$_2$;

j, e, r and p are independently selected from 0, 1 and 2; and k is selected from 1 and 2.

In one embodiment, $R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-4}$alkyl, —(CH$_2$)$_j$—O—$C_{1-6}$ alkyl, —(CH$_2$)$_j$—O-(hydroxy$C_{1-6}$alkyl), —$C_{1-6}$alkyl-NR$^x$R$^y$, —(CR$^x$R$^y$)$_p$—CONR$^x$R$^y$, —(CR$^x$R$^y$)$_p$—NR$^x$COR$^y$, —(CR$^x$R$^y$)$_p$—O—CH$_2$—CONR$^x$R$^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N($C_{1-6}$alkyl)-heterocyclic group with 3 to 7 ring members, —C(=O)NH-heterocyclic group with 3 to 7 ring members, $C_{3-8}$ cycloalkyl, —CH$_2$—$C_{3-6}$cycloalkyl, —CH$_2$—O—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

In one embodiment $R^7$ is a cycloalkyl, cycloalkenyl or heterocyclic group optionally substituted by one or more $R^z$ selected from $C_{1-6}$alkyl (e.g. methyl), $C_{1-6}$alkoxy (e.g. methoxy) and —C(=O)$C_{1-6}$alkyl (e.g. —C(=O)CH$_3$).

In one embodiment $R^7$ is a cycloalkyl or cycloalkenyl group optionally substituted by one or more $R^z$ groups wherein $R^z$ is hydroxy.

$R^6$ and $R^7$ may be the same or different.

When $R^6$ and $R^7$ are different, the compound of formula (I°) can exist as at least two diastereoisomers:

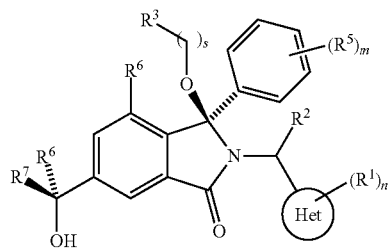

Diastereoisomer 2A

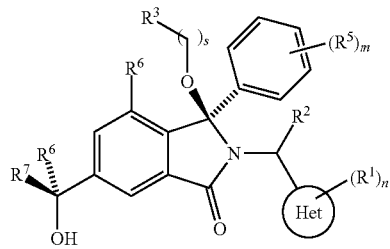

Diastereoisomer 2B

For the avoidance of doubt, the general formula (I°) and all subformulae cover both individual diastereoisomers and mixtures of the diastereoisomers which are related as epimers at the —CR$^6$R$^7$OH group.

In one embodiment of the compound of formula (I°) $R^6$ and $R^7$ are different and the compound is diastereoisomer 2A or a tautomer or a solvate or a pharmaceutically acceptable salt thereof.

In one embodiment of the compound of formula (I°) $R^6$ and $R^7$ are different and the compound is diastereoisomer 2B or a tautomer or a solvate or a pharmaceutically acceptable salt thereof.

In one embodiment, $R^6$ is methyl and the compound of formula (I°) is a compound of formula (Iv) or a tautomer or a solvate or a pharmaceutically acceptable salt thereof:

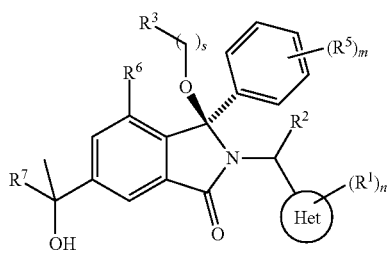

(Iv)

In one embodiment, $R^6$ is ethyl and the compound of formula (I°) is a compound of formula (Iv') or a tautomer or a solvate or a pharmaceutically acceptable salt thereof:

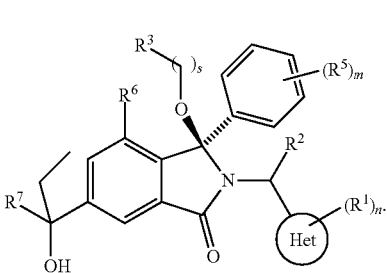

(Iv')

In one embodiment, $R^7$ is selected from $C_{1-6}$alkyl or halo$C_{1-6}$ alkyl. In one embodiment $R^7$ is a $C_{1-6}$cycloalkyl (e.g. cyclopropyl, cyclobutyl or cyclohexyl) optionally substituted by one or more $R^z$ groups (e.g. —OH).

In one embodiment, $R^7$ is selected from $C_{1-6}$alkyl, hydroxy$C_{1-6}$alkyl, —$(CH_2)_j$—O—$C_{1-6}$ alkyl, —$(CH_2)_j$—O—(hydroxy$C_{1-6}$alkyl), —$C_{1-6}$alkyl-$NR^xR^y$ (e.g. —$C_{1-6}$alkyl-N(H)$_e$($C_{1-4}$alkyl)$_{2-e}$), —$(CR^xR^y)_p$—$NR^xCOR^y$, heterocyclic group with 3 to 7 ring members, —$CH_2$-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$ cycloalkyl, and —$CH_2$—$C_{3-8}$cycloalkyl, wherein said cycloalkyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof.

In one embodiment, $R^7$ is selected from $C_{1-6}$alkyl, hydroxy$C_{1-6}$alkyl, —$(CH_2)_j$—O—$C_{1-6}$alkyl, —$(CH_2)_j$—O—(hydroxy$C_{1-6}$alkyl), —$C_{1-6}$alkyl-N(H)$_e$($C_{1-4}$alkyl)$_{2-e}$), heterocyclic group with 3 to 7 ring members, —$CH_2$-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$ cycloalkyl, and —$CH_2$—$C_{3-8}$ cycloalkyl, wherein said cycloalkyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof.

In one embodiment, $R^7$ is selected from heterocyclic group with 3 to 7 ring members, —$CH_2$-heterocyclic group with 3 to 7 ring members, —$CH_2$—NH-heterocyclic group with 3 to 7 ring members, —$CH_2$—N($CH_3$)-heterocyclic group with 3 to 7 ring members, —C(=O)NH-heterocyclic group with 3 to 7 ring members, $C_{3-6}$cycloalkyl, and —$CH_2$—$C_{3-6}$cycloalkyl, wherein said cycloalkyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof.

In one embodiment, $R^7$ is selected from heterocyclic group with 3 to 7 ring members and —$CH_2$-heterocyclic group with 3 to 7 ring members, wherein said heterocyclic groups may be optionally substituted by one or more $R^z$ groups, and wherein in each instance the heterocyclic group comprises one or more (e.g. 1, or 2) heteroatoms selected from N, O, S and oxidised forms thereof.

In embodiment, the heterocyclic group is saturated. In one embodiment, $R^7$ is saturated heterocyclic group with 3 to 6 ring members or —$CH_2$-(saturated heterocyclic group with 3 to 6 ring members) such as wherein the heterocyclic group is selected from oxetanyl, oxanyl, piperidinyl, piperazinyl, morpholinyl, pyrrolidinyl, imidazolinyl, azetidinyl, thiomorpolinyl, such as oxanyl, piperdinyl or piperazinyl.

In one embodiment, $R^7$ is selected from saturated heterocyclic group with 3 to 6 ring members and —$CH_2$-saturated heterocyclic group with 3 to 6 ring members, wherein said heterocyclic groups may be optionally substituted by one or more $R^z$ groups, and wherein in each instance the heterocyclic group comprises one or more (e.g. 1, 2, or 3) heteroatoms selected from N, O, S. In one embodiment, $R^7$ is selected from a nitrogen containing saturated heterocyclic group with 3 to 6 ring member and —$CH_2$-(nitrogen containing saturated heterocyclic group with 3 to 6 ring members), wherein said heterocyclic groups may be optionally substituted by one or more $R^z$ groups, and wherein the heterocyclic group may optionally contain one or more (e.g. 1, 2, or 3) additional heteroatoms selected from N, O, S.

In one embodiment, $R^7$ is nitrogen containing saturated heterocyclic group with 3 to 7 ring members or —$CH_2$-(nitrogen containing saturated heterocyclic group with 3 to 7 ring members), wherein said nitrogen containing saturated heterocyclic groups may be optionally substituted by one or more $R^z$ groups and wherein the nitrogen containing saturated heterocyclic group may optionally contain one or more (e.g. 1, 2, or 3) additional heteroatoms selected from N, O, S. In one embodiment the nitrogen containing saturated heterocyclic group with 3 to 7 ring members (such as 3 to 6 ring members) is selected from piperidinyl, piperazinyl, morpholinyl, pyrrolidinyl, imidazolinyl, azetidinyl, thiomorpolinyl, such as piperdinyl or piperazinyl.

In one embodiment, $R^7$ is nitrogen containing aromatic heterocyclic group with 3 to 6 ring members or —$CH_2$-(nitrogen containing aromatic heterocyclic group with 3 to 6 ring members), wherein said heterocyclic groups may be optionally substituted by one or more $R^z$ groups and wherein the heterocyclic group may optionally contain one or more (e.g. 1, 2, or 3) additional heteroatoms selected from N, O, S.

In another embodiment, $R^7$ is nitrogen containing aromatic heterocyclic group with 3 to 6 ring members, wherein said heterocyclic group may be unsubsituted or substituted by one or more $R^z$ groups, for example selected from halogen (e.g. fluorine), $C_{1-6}$alkyl (e.g. methyl), $C_{1-6}$alkoxy (e.g. methoxy), and —C(=O)$C_{1-6}$alkyl (e.g. —C(=O)CH$_3$).

In one embodiment, $R^7$ is oxygen containing aromatic heterocyclic group with 3 to 6 ring members or —CH$_2$-(oxygen containing aromatic heterocyclic group with 3 to 6 ring members), wherein said heterocyclic groups may be optionally substituted by one or more $R^z$ groups and wherein the heterocyclic group may optionally contain one or more (e.g. 1, 2, or 3) additional heteroatoms selected from N, O, S.

In another embodiment, $R^7$ is oxygen containing aromatic heterocyclic group with 3 to 6 ring members, wherein said heterocyclic group may be unsubsituted or substituted by one or more $R^z$ groups, for example $R^z$ groups selected from halogen (e.g. fluorine), $C_{1-6}$alkyl (e.g. methyl), $C_{1-6}$alkoxy (e.g. methoxy), and —C(=O)$C_{1-6}$alkyl (e.g. —C(=O)CH$_3$).

In one embodiment $R^7$ is selected from heterocyclyl groups containing 5 or 6 ring members optionally substituted by one or more R.

In one embodiment $R^7$ is selected from aromatic heterocyclyl groups containing 5 ring members optionally substituted by one or more $R^z$. In one embodiment $R^7$ is selected from an aromatic nitrogen containing (e.g. diaza) heteterocyclyl group containing 5 ring members optionally substituted by one or more $R^z$. In one embodiment $R^7$ is pyrazolyl (e.g. pyrazol-4-yl or pyrazol-3-yl).

In one embodiment $R^7$ is selected from a saturated heterocyclyl group containing 6 ring members optionally substituted by one or more $R^z$. In one embodiment $R^7$ is selected from a saturated oxygen or nitrogen containing heteterocyclyl group containing 6 ring members optionally substituted by one or more $R^z$.

In one embodiment $R^7$ is selected from oxanyl, piperidinyl, pyrazolyl or imidazolyl optionally substituted by one or more $R^z$. In one embodiment $R^7$ is selected from oxanyl, piperidinyl, pyrazolyl or imidazolyl optionally substituted by one or more $R^z$, where $R^z$ is selected from halo (e.g. —F) or $C_{1-4}$alkyl (e.g. methyl).

In one embodiment $R^7$ is selected from oxanyl (also known as tetrahydropyranyl) or piperidinyl optionally substituted by one or more $R^z$. In one embodiment $R^7$ is selected from oxanyl or piperidinyl unsubstituted or substituted by one or more $R^z$, where $R^z$ is selected from halo (e.g. —F) or $C_{1-4}$alkyl (e.g. methyl), in particular halo (e.g. —F).

In one embodiment, $R^7$ is $C_{3-8}$cycloalkyl such as $C_{3-6}$cycloalkyl (e.g. cyclobutyl or cyclohexyl) optionally substituted by one or more $R^z$, for example where $R^z$ is hydroxy. In one embodiment, $R^7$ is cyclohexyl optionally substituted by one or more hydroxy. In one embodiment $R^7$ is cyclohexyl optionally substituted by one or more hydroxyl, in the trans stereochemistry (e.g. trans-4-hydroxycyclohexane).

In one embodiment $R^7$ is selected from —CH$_2$—NH-heterocyclic group with 3 to 7 ring members (e.g. —CH$_2$—NH-oxanyl and —CH$_2$—N($C_{1-6}$alkyl)-heterocyclic group with 3 to 7 ring members (e.g. —CH$_2$NCH$_3$-(piperidinyl) optionally substituted by one or more $R^z$ groups (e.g. methyl, —COCH$_3$).

In one embodiment, $R^7$ is —(CR$^x$R$^y$)$_p$—CONR$^x$R$^y$ or —C(=O)NH-heterocyclic group with 3 to 7 ring members. In one embodiment, $R^7$ is —C(=O)NH-heterocyclic group with 4 to 6 ring members (e.g. piperidinyl, pyrazolyl, or azetidinyl).

In one embodiment, $R^7$ is —(CR$^x$R$^y$)$_p$—CONR$^x$R$^y$. In one embodiment $R^7$ is —(CR$^x$R$^y$)$_p$—CONH($C_{1-4}$alkyl), in particular —(CO)NHCH$_3$, —(CO)NHCH$_2$CH$_3$ or —(CO)NH(CH(CH$_3$)$_2$).

In one embodiment $R^7$ is —C(=O)NH-heterocyclic group with 3 to 7 ring members (e.g. —C(=O)NH-piperidinyl, —C(=O)NH-azetidinyl or —C(=O)NH-pyrazolyl) optionally substituted by one or more $R^z$ groups (e.g. methyl, —COCH$_3$).

In one embodiment, $R^7$ is —$C_{1-6}$alkyl-NR$^x$R$^y$ (e.g. —$C_{1-6}$alkyl-N(H)$_e$($C_{1-4}$alkyl)$_{2-e}$). In one embodiment $R^7$ is —CH$_2$NH$_2$, —CH$_2$NHCH$_3$, or —CH$_2$N(CH$_3$)$_2$. In one embodiment $R^7$ is —$C_{1-6}$alkyl-NR$^x$R$^y$ wherein RX is $C_{3-8}$cycloalkyl. In one embodiment $R^7$ is —$C_{1-2}$alkyl-NH—$C_{3-6}$ cycloalkyl (e.g. —CH$_2$—NH-cyclopropyl).

In one embodiment, $R^7$ is —$C_{1-6}$alkyl-NR$^x$R$^y$ wherein the $R^x$ and $R^y$ groups, together with the nitrogen atom to which they are attached, can join to form a $C_{3-6}$cycloalkyl or heterocyclyl group with 3 to 6 ring members. In one embodiment, $R^x$ and $R^y$ together form a saturated heterocyclyl group with 3 to 6 ring members e.g. piperazinyl.

In one embodiment $R^7$ is —$C_{1-6}$alkyl-NR$^x$R$^y$, wherein the $R^x$ and $R^y$ groups, together with the nitrogen atom to which they are attached, join to form a $C_{3-6}$cycloalkyl or saturated heterocyclyl group with 3 to 6 ring members which may be optionally fused to an aromatic heterocyclyl group of 3 to 5 ring members.

In one embodiment $R^7$ is —$C_{1-6}$ alkyl-NR$^x$R$^y$, wherein the $R^x$ and $R^y$ groups, together with the nitrogen atom to which they are attached, join to form a saturated heterocyclyl group with 3 to 6 ring members which is fused to an aromatic heterocyclyl group of 3 to 5 ring members. $R^z$ is independently selected from halogen, nitro, nitrile, $C_{1-8}$ alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —(CH$_2$)$_k$—O—$C_{1-6}$alkyl, hydroxy$C_{1-6}$alkoxy, —C(=O)$C_{1-6}$ alkyl, —C(=O)$C_{1-6}$alkyl-OH, —C(=O)$C_{1-6}$ alkyl-N(H)$_e$($C_{1-4}$alkyl)$_{2-e}$, —C(=O)N(H)$_e$($C_{1-4}$alkyl)$_{2-e}$, —(CH$_2$)$_r$—CO$_2$$C_{1-6}$ alkyl, —(CH$_2$)$_r$—CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$ alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl.

In one embodiment $R^z$ is independently selected from halogen (e.g. fluorine), $C_{1-6}$alkyl (e.g. methyl), $C_{1-6}$alkoxy (e.g. methoxy), and —C(=O)$C_{1-6}$alkyl (e.g. —C(=O)CH$_3$).

In one embodiment $R^z$ is independently selected from $C_{1-6}$alkyl (e.g. methyl), $C_{1-6}$alkoxy (e.g. methoxy), and —C(=O)$C_{1-6}$alkyl (e.g. —C(=O)CH$_3$).

In one embodiment, $R^z$ is $C_{1-6}$alkyl (e.g. methyl or ethyl), halo$C_{1-6}$alkyl (e.g. trifluoromethyl), $C_{2-6}$ alkenyl (e.g. $C_2$alkenyl), hydroxy$C_{1-6}$alkyl (e.g. —CH$_2$OH, —CH$_2$CH$_2$OH), —$C_{1-6}$alkyl-NR$^x$R$^y$ (e.g. —CH$_2$NH$_2$, —CH$_2$NHCH$_3$, —CH$_2$N(CH$_3$)$_2$, or —CH$_2$—NH-cyclopropyl), —(CR$^x$R$^y$)$_p$—CONR$^x$R$^y$ (e.g. —(CO)NHCH$_3$, —(CO)NHCH$_2$CH$_3$, —(CO)NHCH$_2$CH$_2$NH$_2$ or —(CO)NH(CH(CH$_3$)$_2$), —(CH$_2$)$_j$—O—$C_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHCOCH$_3$), —(CR$^x$R$^y$)$_p$—O—CH$_2$—CONR$^x$R$^y$ (e.g. —CH$_2$—O—CH$_2$CON(CH$_3$)$_2$), —(CH$_2$)$_j$—O-(hydroxy$C_{1-6}$alkyl) (e.g. —CH$_2$—O—CH$_2$CH$_2$OH,), —C(=O)NH-heterocyclic group with 3 to 7 ring members, $C_{3-6}$cycloalkyl, heterocyclic group with 3 to 7 ring members (e.g. oxanyl), or —$CH_2$-heterocyclic group with 3 to 7 ring members wherein the cycloalkyl or heterocyclic group comprises one or more (e.g. 1, 2, or 3) heteroatoms selected from N, O, S and oxidised forms and may be optionally substituted by one or more $R^z$ groups (for example selected from $C_{1-6}$alkyl (e.g. methyl), $C_{1-6}$alkoxy (e.g. methoxy) and —C(=O)$C_{1-6}$alkyl (e.g. —C(=O)$CH_3$)). In one embodiment, $R^6$ is methyl or ethyl and $R^7$ is $C_{1-6}$alkyl (e.g. methyl), hydroxy$C_{1-6}$alkyl, —$C_{1-6}$alkyl-$NR^xR^y$, —$(CR^xR^y)_p$—$CONR^xR^y$, —$(CR^xR^y)_p$—$NR^xCOR^y$, —$(CR^xR^y)_p$—O—$CH_2$—$CONR^xR^y$, —$(CH_2)_j$—O-(hydroxy$C_{1-6}$alkyl), heterocyclic group with 3 to 7 ring members (e.g. oxanyl), or —$CH_2$-heterocyclic group with 3 to 7 ring members wherein the heterocyclic group comprises one or more (e.g. 1, 2, or 3) heteroatoms selected from N, O, S and oxidised forms and may be optionally substituted by one or more $R^z$ groups selected from $C_{1-6}$alkyl (e.g. methyl), $C_{1-6}$alkoxy (e.g. methoxy) and —C(=O)$C_{1-6}$alkyl (e.g. —C(=O)$CH_3$).

In one embodiment, $R^6$ is selected from hydrogen, $C_{1-6}$alkyl (e.g. —$CH_3$, —$CH_2CH_3$ or —$CH_2CH_2CH_3$), $C_{2-6}$alkenyl (e.g. —CH=$CH_2$) and halo$C_{1-6}$alkyl (e.g. —$CF_3$).

In one embodiment, $R^6$ is selected from hydrogen, $C_{1-6}$alkyl (e.g. —$CH_3$ or —$CH_2CH_3$), $C_{2-6}$alkenyl (e.g. —CH=$CH_2$) and halo$C_{1-6}$alkyl (e.g. —$CF_3$).

In one embodiment, $R^7$ is $C_{1-6}$alkyl (e.g. —$CH_3$ or —$CH_2CH_3$), $C_{3-8}$cycloalkyl (e.g. cyclopropyl, cyclobutyl or cyclohexyl), $C_{2-6}$alkenyl (e.g. —CH=$CH_2$), halo$C_{1-6}$alkyl (e.g. —$CF_3$), hydroxy$C_{1-4}$alkyl (e.g. —$CH_2OH$ or —$CH_2CH_2OH$), —$C_{1-6}$alkyl-$NR^xR^y$ (e.g. —$CH_2NH_2$, —$CH_2N(CH_3)_2$, —$CH_2NHCH_3$, or —$CH_2NH$(cyclopropyl)), —$(CR^xR^y)_p$—$CONR^xR^y$ (e.g. —C(=O)$NHCH_3$, —(CO)$NHCH_2CH_3$, —(CO)$NHCH_2CH_2NH_2$, —C(=O)NH(CH(CH_3)_2)), Or —$(CH_2)_j$—O—$C_{1-6}$alkyl (e.g. —$CH_2OCH_3$, —$CH_2OCH_2CH_3$ or —$CH_2OCD_3$), —$(CR^xR^y)_p$—$NR^xCOR^y$ (e.g. —$CH_2NHC$(=O)$CH_3$), —$(CR^xR^y)_p$—O—$CH_2$—$CONR^xR^y$ (e.g. —$CH_2OCH_2C$(=O)$N(CH_3)_2$), —$(CH_2)_j$—O-(hydroxy$C_{1-6}$alkyl) (e.g. —$CH_2OCH_2CH_2OH$), heterocyclic group with 3 to 7 ring members e.g.
(point of attachment represented by dashed bond):

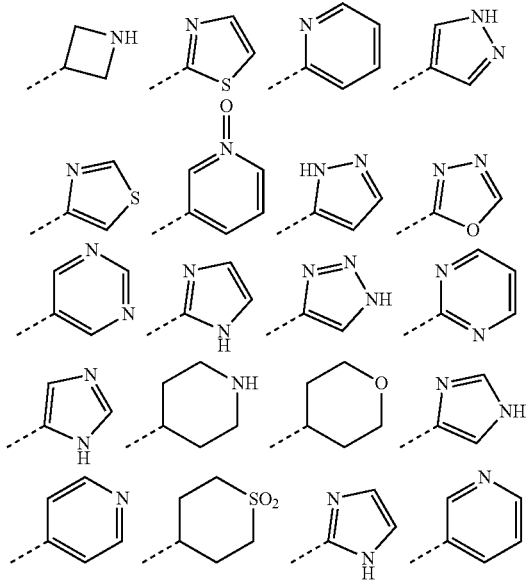

or —$CH_2$-heterocyclic group with 3 to 7 ring members e.g. (point of attachment represented by dashed bond)

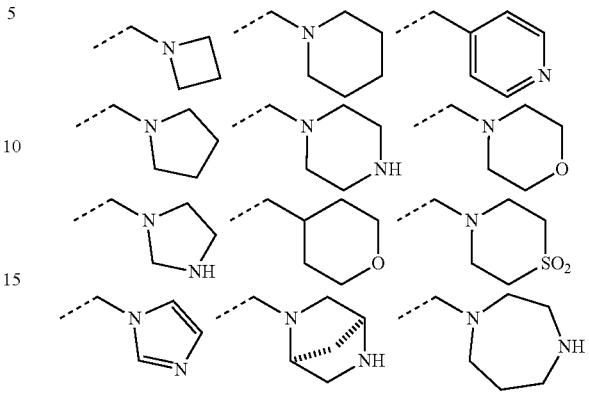

wherein when the moiety $R^7$ comprises a heterocyclic group, the heterocyclic group may be optionally substituted by one or more $R^z$ groups selected from $C_{1-6}$alkyl (e.g. methyl), hydroxyalkyl (e.g. —$CH_2CH_2OH$), halogen (e.g. fluoro), =O, $C_{1-6}$alkoxy (e.g. methoxy), —C(=O)$C_{1-6}$ alkyl (e.g. —C(=O)$CH_3$), —C(=O)hydroxy$C_{1-6}$alkyl (e.g. —C(=O)$CH_2OH$), heterocyclyl group with 3 to 6 ring members (e.g. oxetanyl or pyrimidinyl), and —$S(O)_d$—$C_{1-4}$alkyl wherein d is selected from 0, 1 and 2 (e.g. —$SO_2$—$CH_3$).

In one embodiment, $R^7$ is $C_{1-6}$ alkyl (e.g. —$CH_3$ or —$CH_2CH_3$), $C_{3-8}$cycloalkyl (e.g. cyclopropyl, cyclobutyl or cyclohexyl), $C_{2-6}$alkenyl (e.g. —CH=$CH_2$), halo$C_{1-6}$alkyl (e.g. —$CF_3$), hydroxy$C_{1-6}$alkyl (e.g. —$CH_2OH$ or —$CH_2CH_2OH$), —$C_{1-6}$alkyl-$NR^xR^y$ (e.g. —$CH_2NH_2$, —$CH_2N(CH_3)_2$, —$CH_2NHCH_3$, or —$CH_2NH$(cyclopropyl)), —$(CR^xR^y)_p$—$CONR^xR^y$ (e.g. —C(=O)$NHCH_3$, —(CO)$NHCH_2CH_3$, —(CO)$NHCH_2CH_2NH_2$, —C(=O)NH(CH(CH_3)_2)), or —$(CH_2)_j$—O—$C_{1-6}$ alkyl (e.g. —$CH_2OCH_3$, —$CH_2OCH_2CH_3$ or —$CH_2OCD_3$), —$(CR^xR^y)_p$—$NR^xCOR^y$ (e.g. —$CH_2NHC$(=O)$CH_3$), —$(CR^xR^y)_p$—O—$CH_2$—$CONR^xR^y$ (e.g. —$CH_2OCH_2C$(=O)$N(CH_3)_2$), —$(CH_2)_r$—O-(hydroxy$C_{1-6}$alkyl) (e.g. —$CH_2OCH_2CH_2OH$), heterocyclic group with 3 to 7 ring members e.g.
(point of attachment represented by dashed bond):

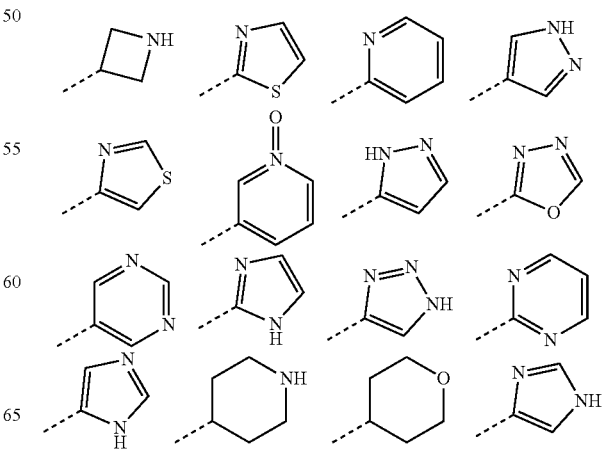

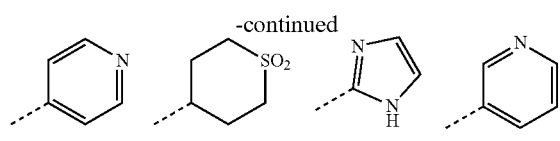

or —CH$_2$-heterocyclic group with 3 to 7 ring members e.g. (point of attachment represented by dashed bond)

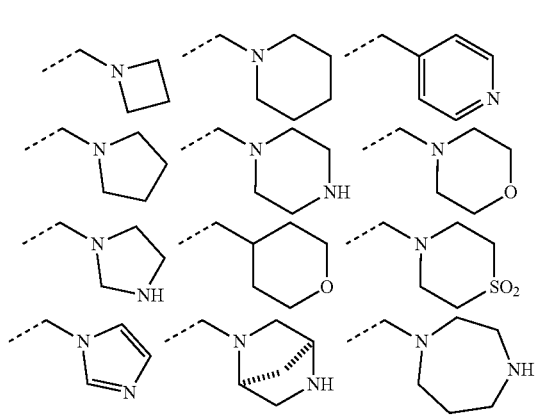

wherein when the moiety R$^7$ comprises a heterocyclic group, the heterocyclic group may be optionally substituted by one or more R$^z$ groups selected from C$_{1-6}$alkyl (e.g. methyl), halogen (e.g. fluoro), =O, C$_{1-6}$alkoxy (e.g. methoxy), —C(=O)C$_{1-8}$alkyl (e.g. —C(=O)CH$_3$), —C(=O)hydroxyC$_{1-6}$alkyl (e.g. —C(=O)CH$_2$OH), heterocyclyl group with 3 to 6 ring members (e.g. pyrimidinyl), and —S(O)$_d$—C$_{1-4}$alkyl wherein d is selected from 0, 1 and 2 (e.g. —SO$_2$—CH$_3$).

In one embodiment of formula (I°) R$^7$ is a heterocyclic group with 3 to 7 ring members optionally substituted by one or more R$^z$ groups e.g. (point of attachment represented by dashed bond)

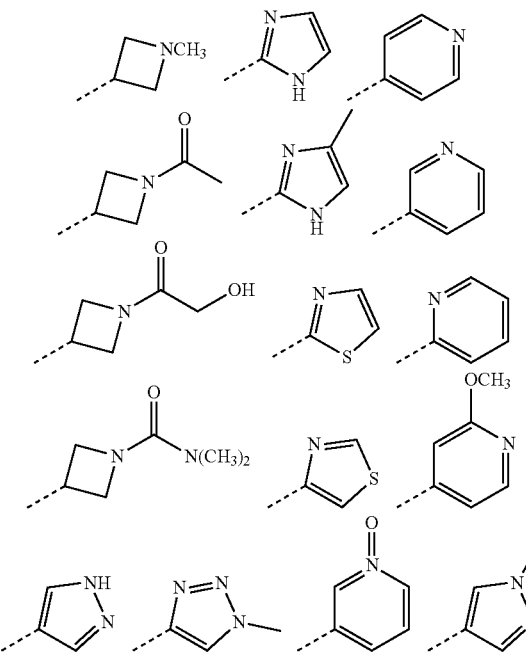
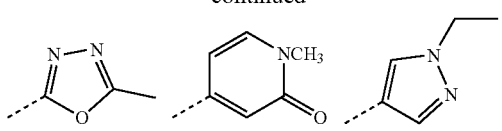
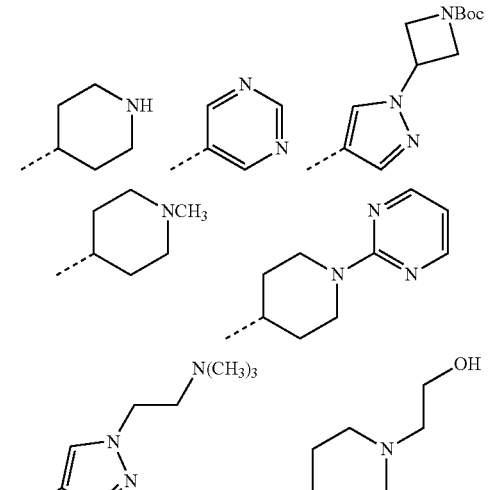
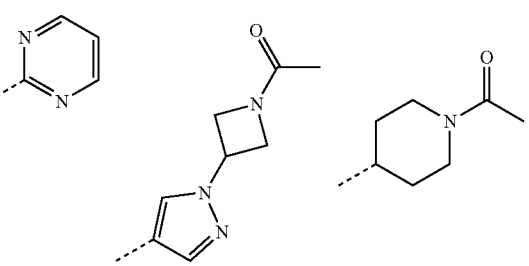
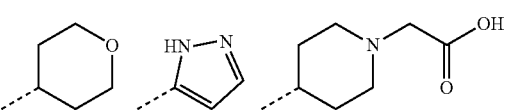
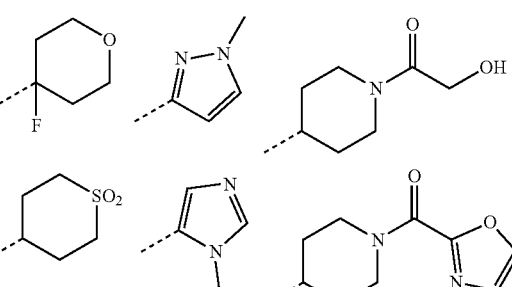
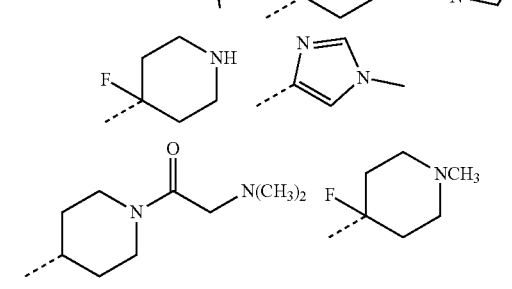
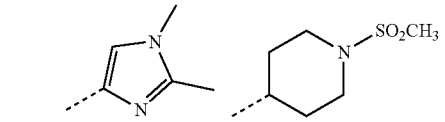

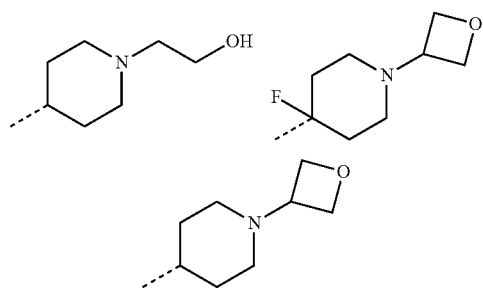
In one embodiment of formula (I°) R[7] is a heterocyclic group with 3 to 7 ring members optionally substituted by one or more R[z] groups e.g.
(point of attachment represented by dashed bond)
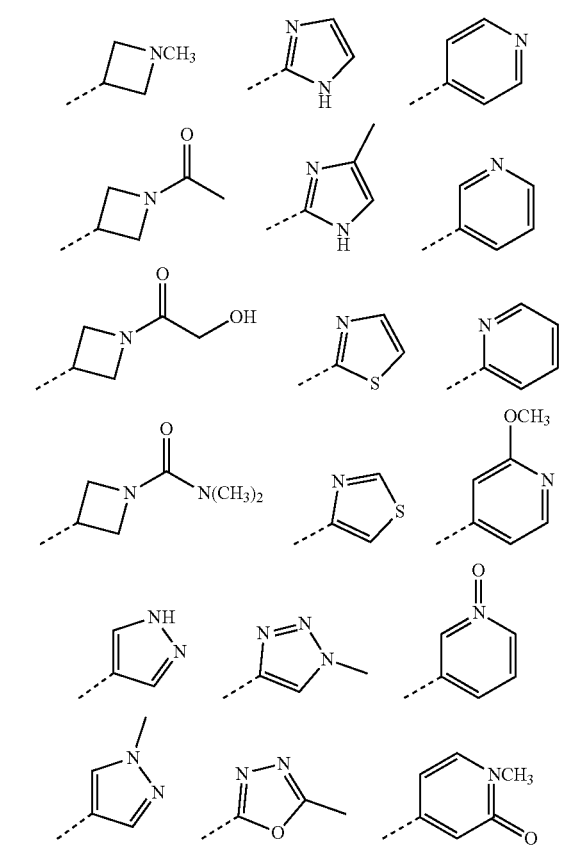
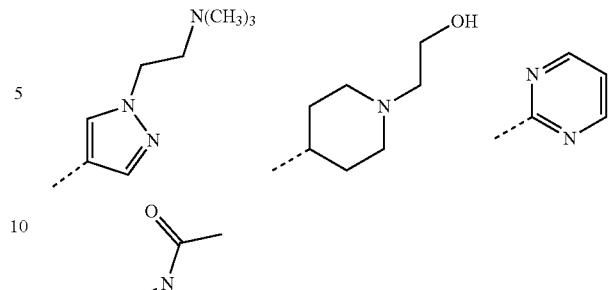
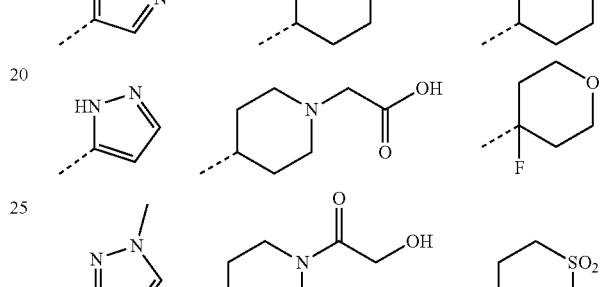
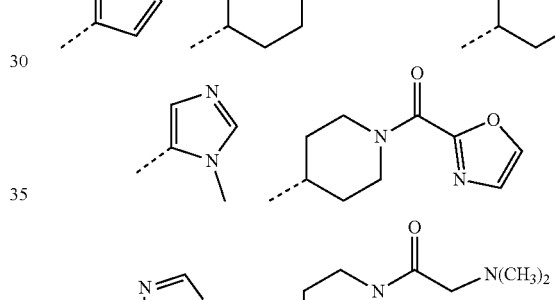
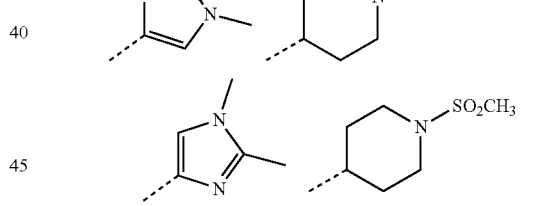
In one embodiment, R[7] is a —CH$_2$-heterocyclic group with 3 to 7 ring members optionally substituted by by one or more R[z] groups e.g.
(point of attachment represented by dashed bond)
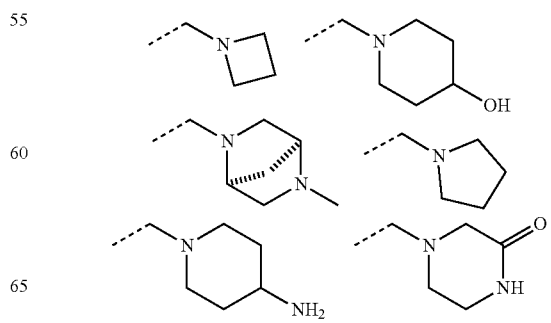
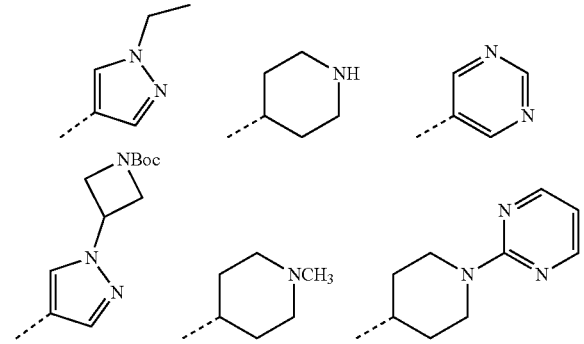

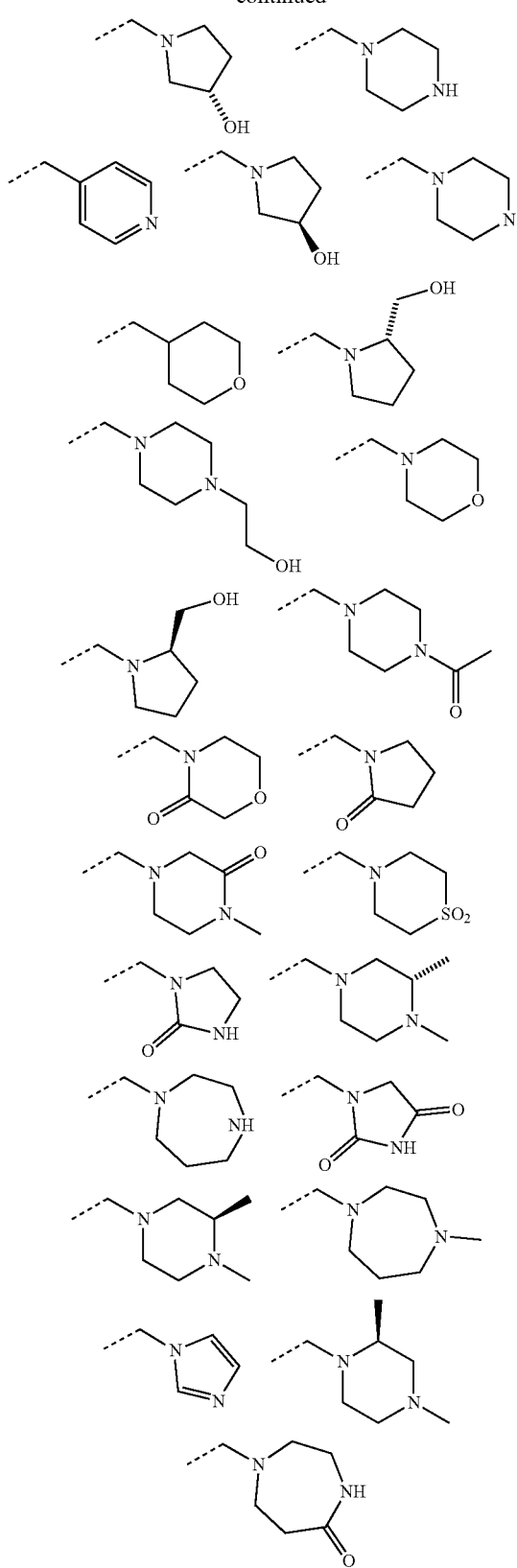
In one embodiment $R^7$ is selected from:
(point of attachment represented by dashed bond):
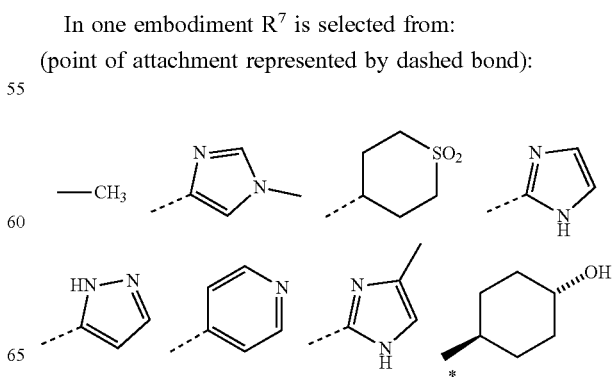
In one embodiment $R^7$ is selected from:
(point of attachment represented by dashed bond):

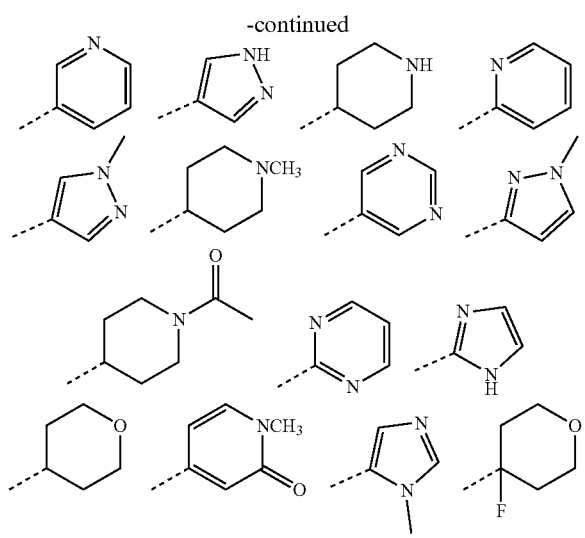

In one embodiment $R^7$ is selected from:
(point of attachment represented by dashed bond):

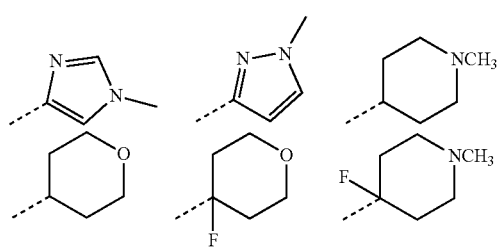

In one embodiment $R^7$ is selected from:
(point of attachment represented by dashed bond):

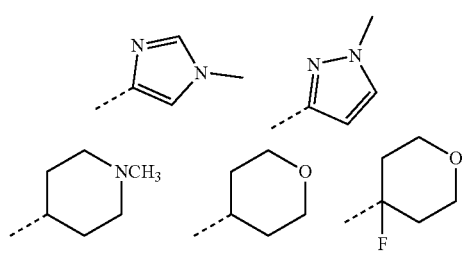

In one embodiment, $R^6$ is hydrogen or $C_{1-6}$alkyl (such as —CH$_3$, —CH$_2$CH$_3$ or —CH$_2$CH$_2$CH$_3$, e.g. —CH$_3$ or —CH$_2$CH$_3$). In one embodiment, $R^6$ is $C_{1-6}$alkyl. In one embodiment, $R^6$ is methyl or ethyl. In one embodiment, $R^6$ is ethyl.

In one embodiment, $R^6$ is $C_{1-6}$alkyl (such as methyl or ethyl e.g. methyl) and $R^7$ is selected from hydroxyC$_{1-6}$alkyl and —(CH$_2$)—O—C$_{1-6}$alkyl, In one embodiment, $R^6$ is methyl and $R^7$ is selected from methyl, —CH$_2$—OH and —CH$_2$—OCH$_3$. In one embodiment $R^6$ is methyl and $R^7$ is methyl, ethyl, or propyl. In one embodiment $R^6$ is methyl and $R^7$ is methyl.

In one embodiment, $R^5$ is $C_{1-6}$alkyl or haloC$_{1-6}$alkyl (e.g. methyl, monofluoromethyl, trifluoromethyl or ethyl).

In one embodiment, $R^5$ is $C_{3-8}$ cycloalkyl such as $C_{3-8}$cycloalkyl (e.g. cyclopropyl).

In one embodiment $R^5$ is $C_{1-4}$alkyl (e.g. —CH$_3$, —CH$_2$CH$_3$ or —CH$_2$CH$_2$CH$_3$ such as methyl or ethyl e.g. ethyl) and $R^7$ is selected from:
(point of attachment represented by dashed bond or bond terminus marked "*"):

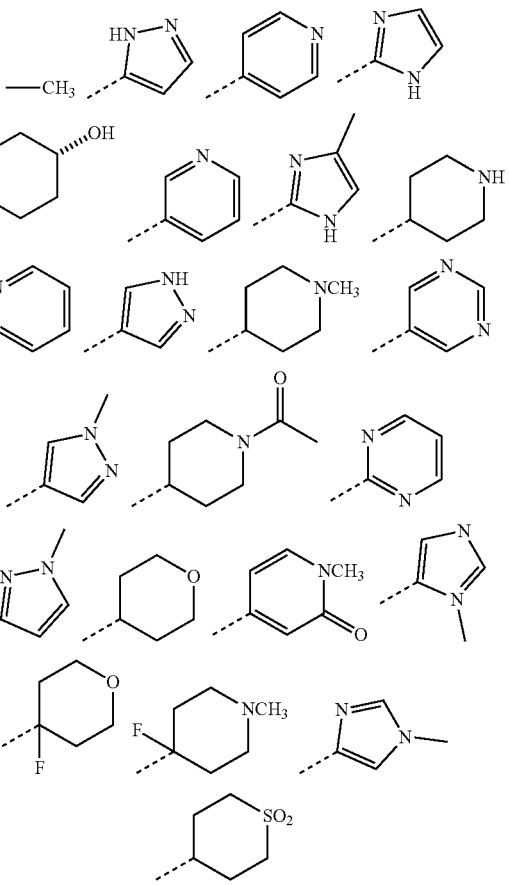

In one embodiment $R^5$ is $C_{1-6}$alkyl (e.g. —CH$_3$, —CH$_2$CH$_3$ or —CH$_2$CH$_2$CH$_3$ such as methyl or ethyl e.g. ethyl) and $R^7$ is selected from:
(point of attachment represented by dashed bond or bond terminus marked "*"):

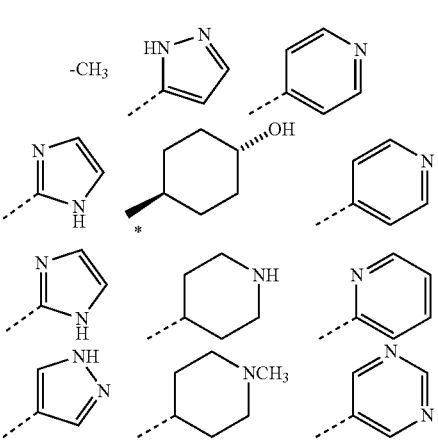

-continued

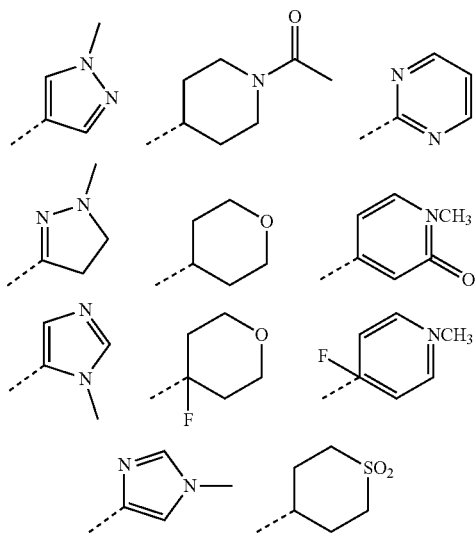

In particular, $R^7$ is:
(point of attachment represented by dashed bond):

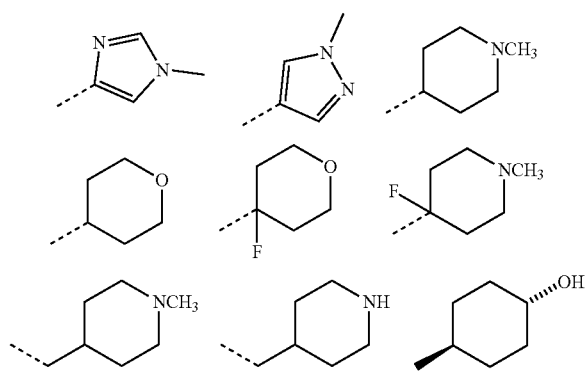

In particular, $R^7$ is:
(point of attachment represented by dashed bond):

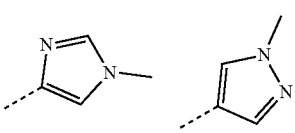

In one embodiment, $R^6$ is $C_{1-6}$alkyl (e.g. —$CH_3$, —$CH_2CH_3$ or —$CH_2CH_2CH_3$) such as methyl or ethyl e.g. methyl) and $R^7$ is oxanyl, and the compound of formula (I°) is a compound of formula (Iw):

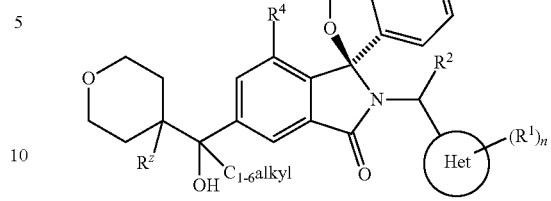

In one embodiment of formula (Iw) $R^z$ is hydrogen or fluorine.

In one embodiment, $R^7$ is imidazolyl and the compound of formula (I°) is a compound of formula (Ix) or a tautomer or a solvate or a pharmaceutically acceptable salt thereof:

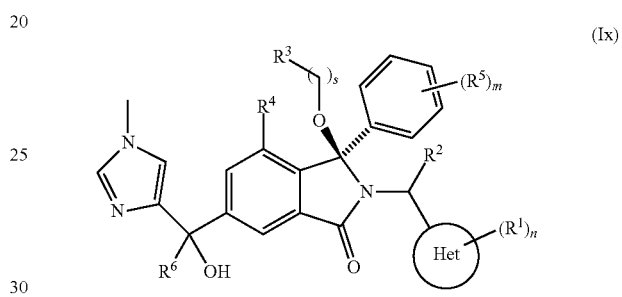

In one embodiment, $R^7$ is N-methyl piperidinyl and the compound of formula (I°) is a compound of formula (Ix') or a tautomer or a solvate or a pharmaceutically acceptable salt thereof:

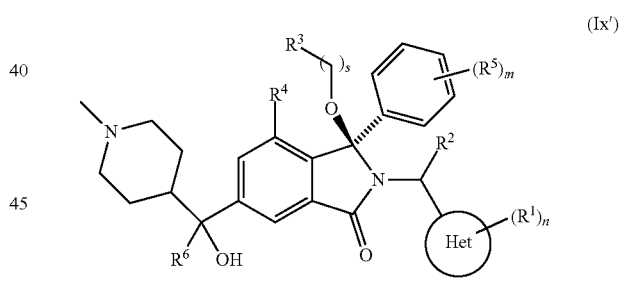

In one embodiment, $R^7$ is 4-fluoro-1-methylpiperidin-4-yl and the compound of formula (I°) is a compound of formula (Ix") or a tautomer or a solvate or a pharmaceutically acceptable salt thereof:

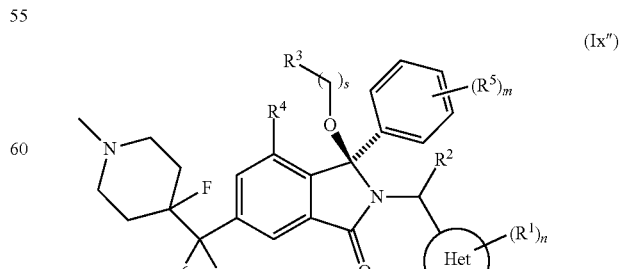

In one embodiment, $R^7$ is pyrazolyl optionally substituted by one or more $R^z$ groups (e.g. methyl). In one embodiment, $R^7$ is N-methylpyrazol-3-yl or N-methylpyrazol-4-yl.

In one embodiment, $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxyl).

In one embodiment, $R^7$ is selected from piperidinyl optionally substituted by one or more $R^z$ groups (e.g. methyl, fluorine, or hydroxyl, in particular methyl and fluorine).

In one embodiment, the compound of formula (I°) is a compound of formula (Ix) and $R^6$ is $C_{1-4}$alkyl.

In one embodiment, $R^8$ is $C_{1-6}$alkyl (e.g. —$CH_3$, —$CH_2CH_3$ or —$CH_2CH_2CH_3$ such as methyl or ethyl e.g. ethyl) and $R^7$ is a heterocyclic group with 3 to 7 ring members optionally substituted by one or more $R^z$ groups.

In one embodiment, $R^8$ is $C_{1-6}$alkyl (e.g. —$CH_3$, —$CH_2CH_3$ or —$CH_2CH_2CH_3$ such as methyl or ethyl e.g. ethyl) and $R^7$ is imidazolyl optionally substituted by one or more $R^z$ groups (e.g. methyl imidazolyl).

In one embodiment, $R^8$ is $C_{1-6}$alkyl (e.g. —$CH_3$, —$CH_2CH_3$ or —$CH_2CH_2CH_3$ such as methyl or ethyl e.g. ethyl) and $R^7$ is piperidinyl optionally substituted by one or more $R^z$ groups (e.g. methyl piperidinyl).

In one embodiment $R^8$ is $C_{1-6}$alkyl (e.g. —$CH_3$, —$CH_2CH_3$ or —$CH_2CH_2CH_3$ such as methyl or ethyl e.g. ethyl) and $R^7$ is $C_{1-4}$alkyl, hydroxyl$C_{1-4}$alkyl, methoxy$C_{1-4}$alkyl, a heterocyclic group with 5 or 6 ring members or $C_{3-8}$cycloalkyl, wherein the heterocyclic group or $C_{3-6}$cycloalkyl group is optionally substituted by one or more $R^z$ (e.g. methyl, halogen (such as fluorine), C(=O)Me, or —OH).

In one embodiment $R^6$ is $C_{1-4}$alkyl (e.g. —$CH_3$, —$CH_2CH_3$ or —$CH_2CH_2CH_3$ such as methyl or ethyl e.g. ethyl) and $R^7$ is methyl, ethyl, hydroxylmethyl, hydroxyethyl, methoxymethyl, piperidinyl, oxanyl, imidazolyl, pyrazolyl, cyclobutyl, cyclohexyl, optionally substituted by one or more $R^z$ (e.g. methyl, halogen (such as fluorine), C(=O)Me, or —OH).

In one embodiment, $R^6$ and $R^7$ are both the same. In one embodiment, $R^6$ and $R^7$ are both methyl, and the compound of formula (I°) is a compound of formula (Iy) or a tautomer or a solvate or a pharmaceutically acceptable salt thereof:

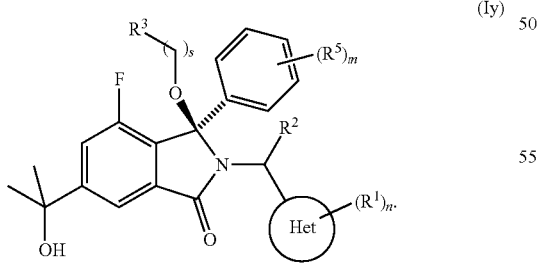

(Iy)

In one embodiment the group —$CR^6R^7OH$ is other than —$C(CH_3)_2OH$.

In one embodiment, $R^7$ is selected from the group consisting of:
(point of attachment represented by dashed bond or bond terminus indicated by "*"):

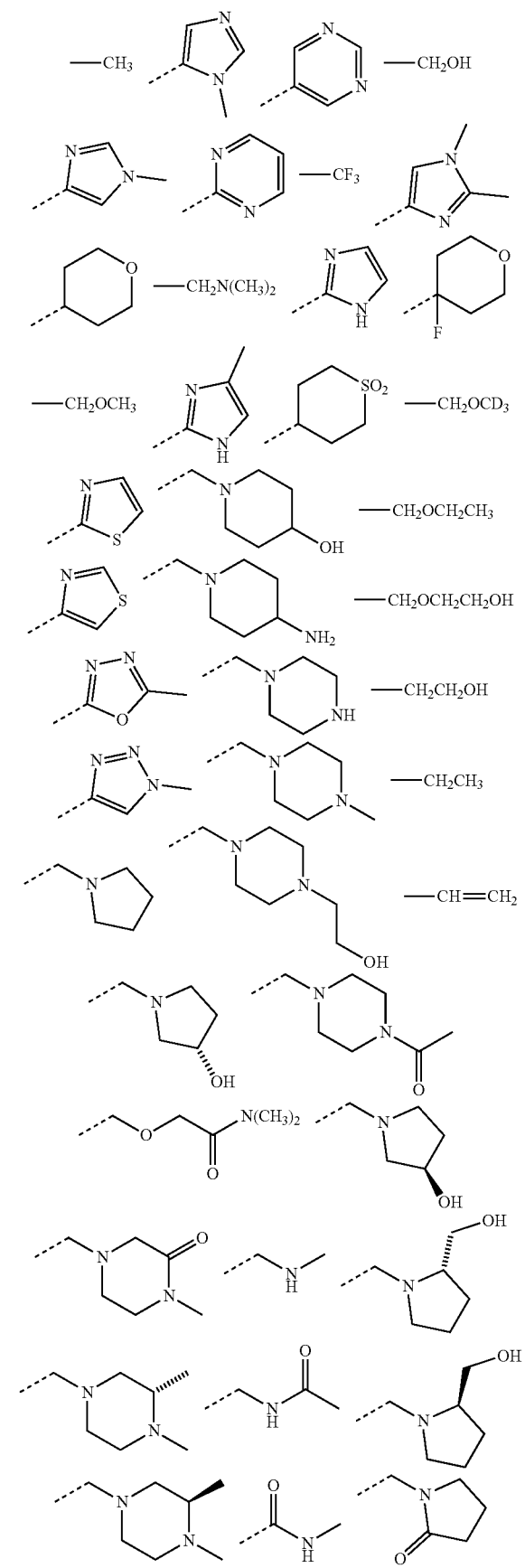

-continued
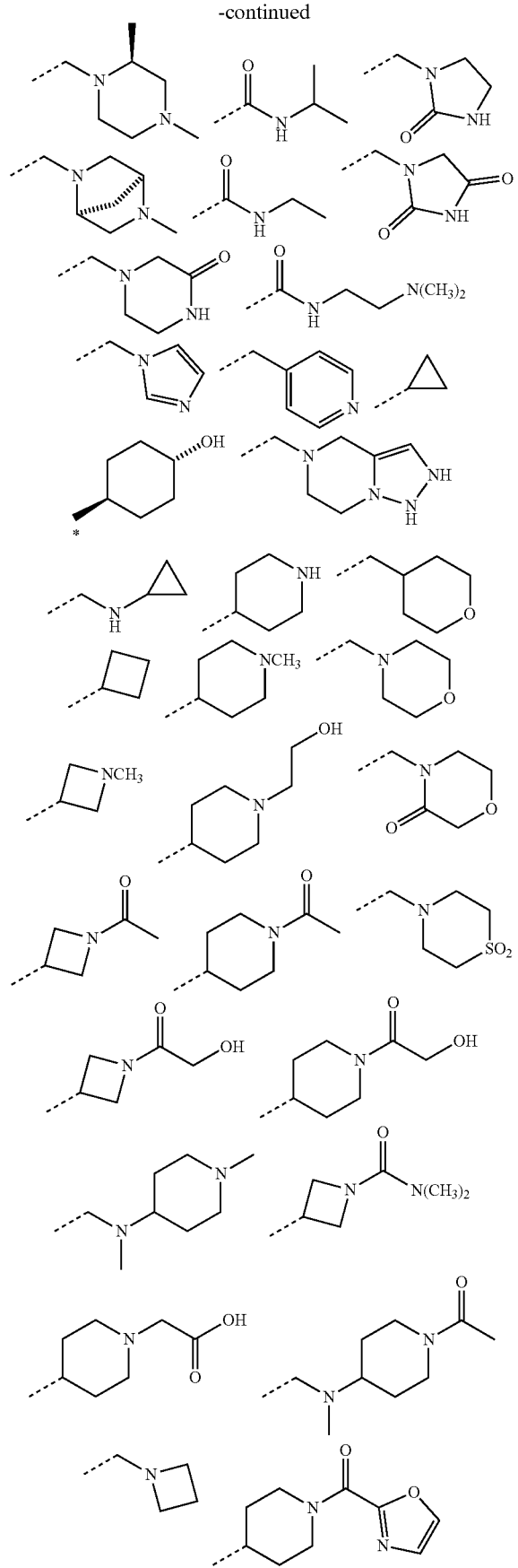
-continued
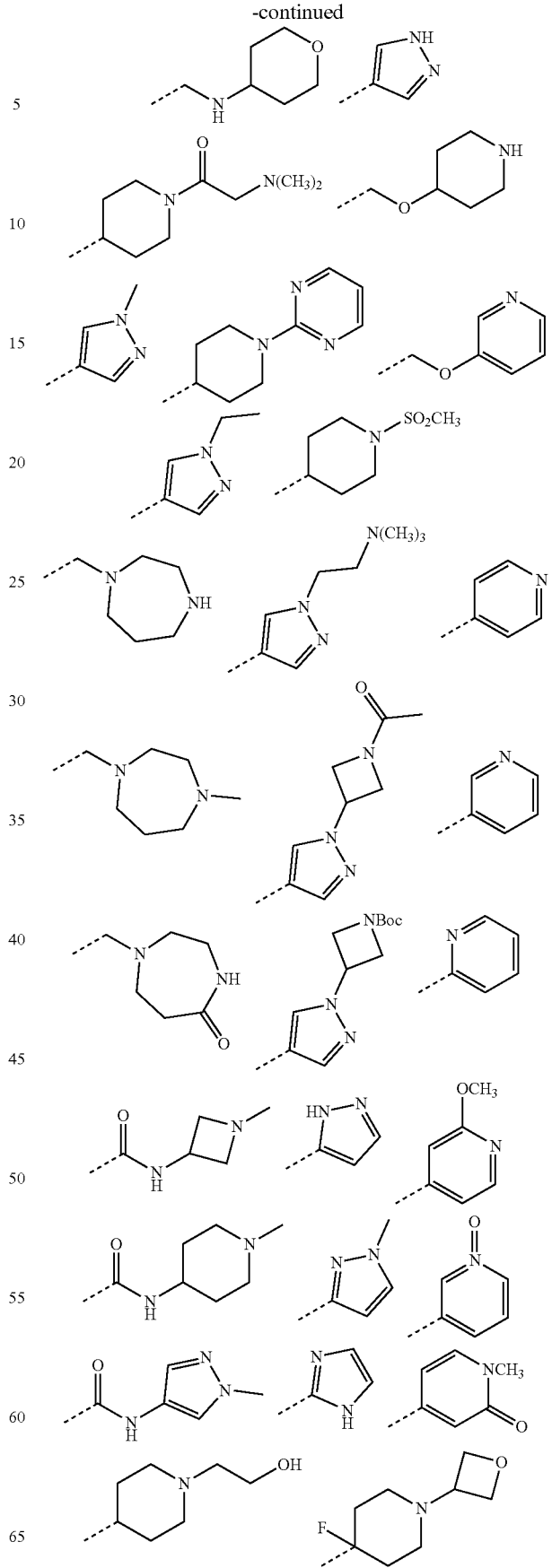

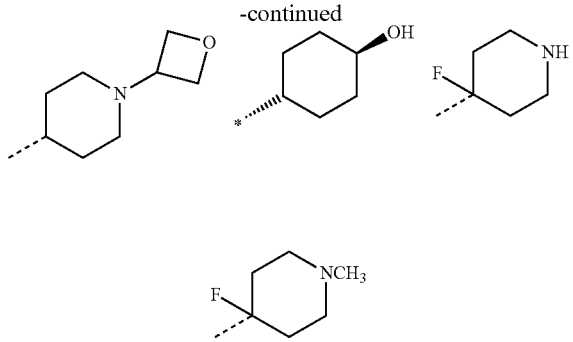

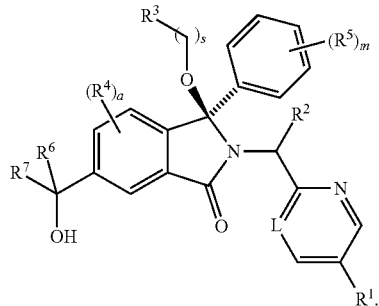
(II)

In one embodiment R$^z$ is independently selected from halogen, nitro, nitrile, C$_{1-6}$alkyl, haloC$_{1-6}$alkyl, C$_{2-6}$alkenyl, C$_{2-6}$ alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$ alkyl-OH, —C(=O)C$_{1-6}$alkyl-N(H)$_e$(C$_{1-4}$alkyl)$_{2-e}$, —C(=O)N(H)$_e$(C$_{1-4}$ alkyl)$_{2-e}$, —(CH$_2$)$_k$—CO$_2$C$_{1-6}$alkyl, —(CH$_2$)$_r$—CO$_2$H, —NH(C$_{1-4}$alkyl), —N(C$_{1-4}$alkyl)$_2$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$ alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-6}$cycloalkenyl.

In another embodiment R$^z$ is independently selected from halogen, nitro, nitrile, C$_{1-6}$alkyl, haloC$_{1-6}$alkyl, C$_{2-6}$ alkenyl, C$_{2-6}$alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_1$—CO$_2$H, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$ alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$ cycloalkyl and C$_{3-8}$cycloalkenyl.

In another embodiment when R$^7$ contains a saturated heterocyclic group then R$^z$ is independently selected from halogen, nitro, nitrile, C$_{1-6}$alkyl, haloC$_{1-6}$alkyl, C$_{2-6}$alkenyl, C$_{2-6}$alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_r$—CO$_2$C$_{1-6}$alkyl, —(CH$_2$)$_r$—CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$ alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$cycloalkenyl.

Subformulae

In one embodiment, the compound of formulae (I°) is a compound of formulae (II) or a tautomer or a solvate or a pharmaceutically acceptable salt thereof:

wherein L is CR$^1$, CH or N and R$^1$, R$^2$, R$^3$, R$^4$, R$^5$, R$^6$, R$^7$, a, m and s are as defined herein. In one embodiment L is CH. In one embodiment L is N. In one embodiment L is CR$^1$ such as C—OH or C-hydroxyC$_{1-4}$alkyl (e.g. C—OH or C—CH$_2$OH).

In one embodiment, R$^1$ is chloro, nitrile, methyl or methoxy. In one embodiment, R$^1$ is hydroxy or hydroxyC$_{1-4}$ alkyl (e.g. hydroxyl).

In one embodiment, R$^1$ is O$_{0,1}$(CR$^x$R$^y$)$_v$COOH (e.g. —COOH, —CH$_2$COOH, —OCH$_2$COOH or —C(CH$_3$)$_2$COOH.

In another embodiment, R$^1$ is chloro or nitrile and the compound of formula (II) is a compound of formula (IIa) or (11b) or a tautomer or a solvate or a pharmaceutically acceptable salt thereof:

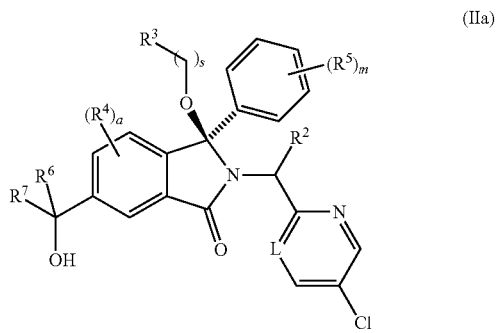
(IIa)

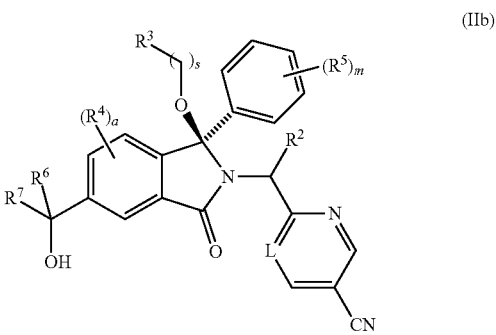
(IIb)

wherein R$^1$, R$^2$, R$^3$, R$^4$, R$^5$, R$^7$, m and s are as defined herein.

In one embodiment, R$^6$ is methyl or ethyl, and the compound of formula (II) is a compound of formula (IIIa) or (IIIb) or a tautomer or a solvate or a pharmaceutically acceptable salt thereof:

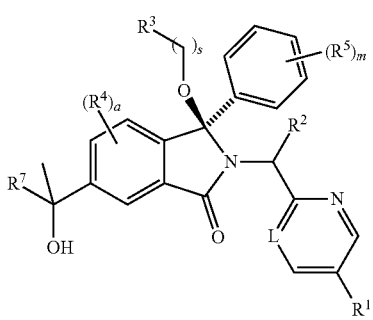

(IIIa)

wherein $R^1$, $R^2$, $R^3$, $R^4$, $R^5$, $R^7$, m and s are as defined herein.

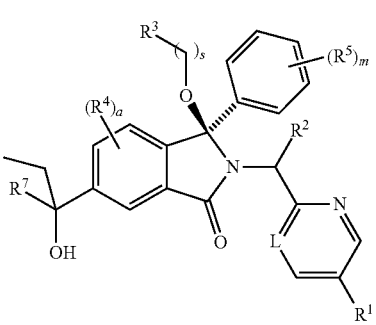

(IIIb)

wherein $R^1$, $R^2$, $R^3$, $R^4$, $R^5$, $R^7$, a, m and s are as defined herein.

In one embodiment, a is 1 and the compound of formula (II) is a compound of formula (IVa) or a tautomer or a solvate or a pharmaceutically acceptable salt thereof:

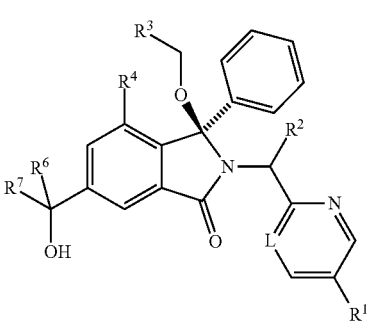

(IVa)

wherein $R^1$, $R^2$, $R^3$, $R^4$, $R^5$, $R^7$, m and s are as defined herein.

In one embodiment, s is 0 and the compound of formula (II) is a compound of formula (IVb) or a tautomer or a solvate or a pharmaceutically acceptable salt thereof:

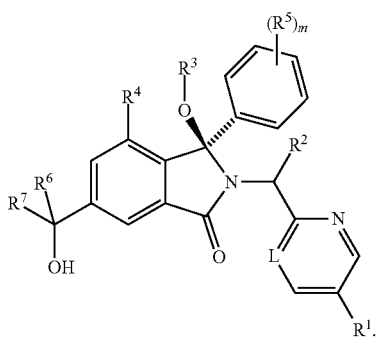

(IVb)

wherein $R^1$, $R^2$, $R^3$, $R^4$, $R^5$, $R^7$, m and s are as defined herein.

In one embodiment, $R^4$ is F and the compound of formula (I°) is a compound of formula (V) or a tautomer or a solvate or a pharmaceutically acceptable salt thereof:

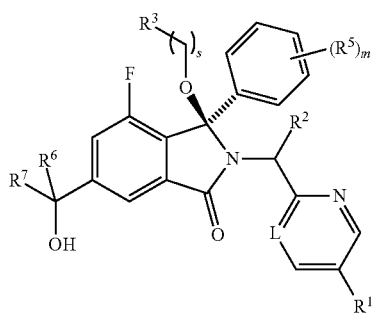

(V)

wherein $R^1$, $R^2$, $R^3$, $R^5$, $R^7$, m and s are as defined herein.

In one embodiment, m is 1 and the substituent $R^4$ is at the 4-position of the phenyl group, and the compound of formula (II) is a compound of formula (VI) or a tautomer or a solvate or a pharmaceutically acceptable salt thereof:

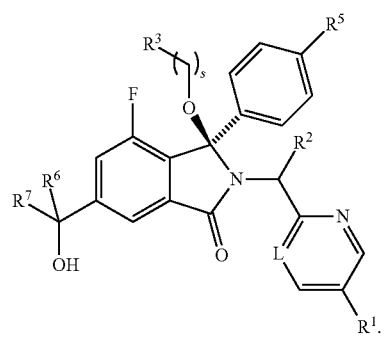

(VI)

In one embodiment, $R^5$ is chloro and the compound of formula (VI) is a compound of formula (Via) or a tautomer or a solvate or a pharmaceutically acceptable salt thereof:

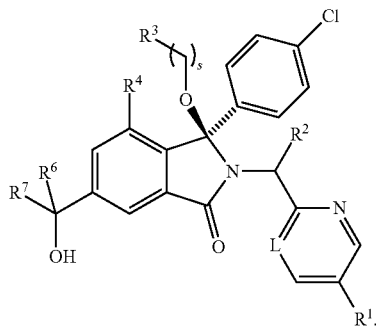
(VIa)

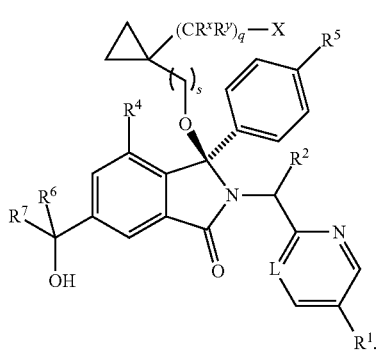
(VIIb)

In one embodiment, A is a $C_{3-6}$ cycloalkyl group (g is 1, 2 or 3) and t is 1, and the compound of formula (VI) is a compound of formula (VII) or a tautomer or a solvate or a pharmaceutically acceptable salt thereof:

In one embodiment, s is 1, and the compound of formula (VIIb) is a compound of formula (VIIc) or a tautomer or a solvate or a pharmaceutically acceptable salt thereof:

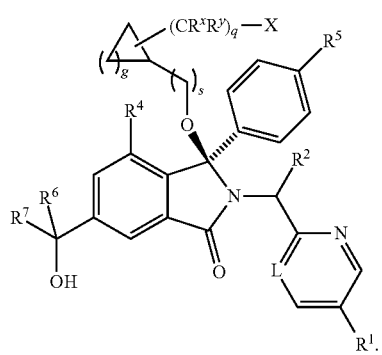
(VII)

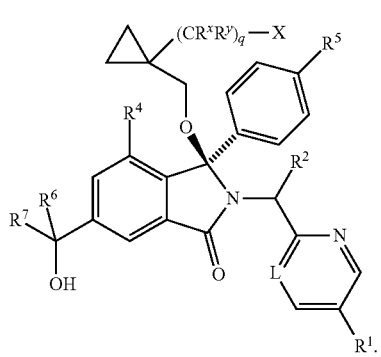
(VIIc)

In one embodiment, A is a $C_{3-6}$ cycloalkyl group (g is 1, 2 or 3) and t is 1, and the cycloalkyl group is geminally disubstituted (i.e. the group —$(CR^xR^y)$—X and the CH$_2$ group (where s is 1) or the oxygen atom (where s is 0) are both attached to the same atom of the cycloalkyl group, and the compound of formula (VII) is a compound of formula (VIIa) or a tautomer or a solvate or a pharmaceutically acceptable salt thereof:

In one embodiment, $R^x$ and $R^y$ are hydrogen (including $^1$H and $^2$H) and q is 1 and the compound of formula (VIIc) is a compound of (VIId) or a tautomer or a solvate or a pharmaceutically acceptable salt thereof:

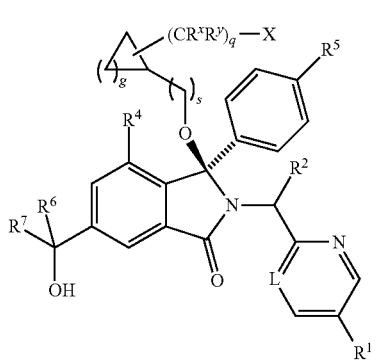
(VIIa)

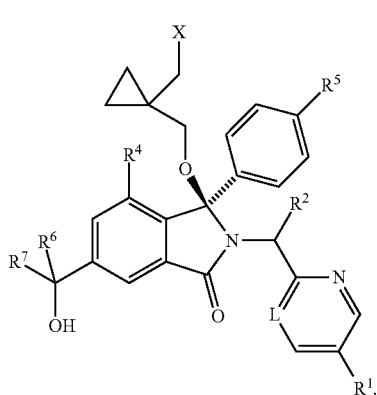
(VIId)

In one embodiment, g is 1, and so the cycloalkyl group is a cyclopropyl group and the compound of formula (VIIa) is a compound of formula (VIIb) or a tautomer or a solvate or a pharmaceutically acceptable salt thereof:

In one embodiment, the compound of formula (VIId) is a compound of (VIId') or a tautomer or a solvate or a pharmaceutically acceptable salt thereof:

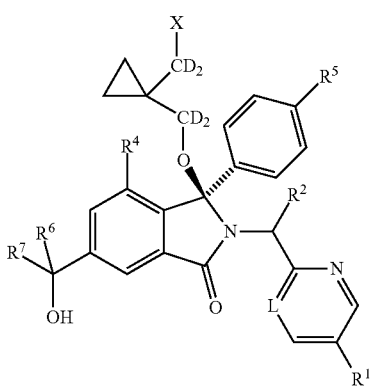

(VIId')

In one embodiment, the compound of formula (VIId) is a compound of (VIId') and X is hydroxy.

In one embodiment, X is hydroxy, and the compound of formula (VIId) is a compound of the formula (VIIe) or a tautomer or a solvate or a pharmaceutically acceptable salt thereof:

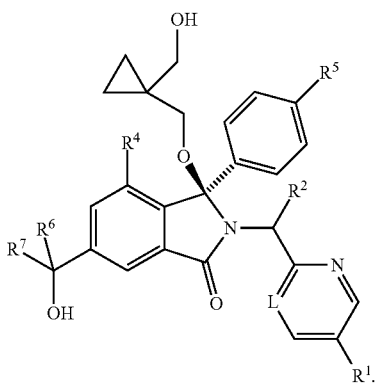

(VIIe)

In one embodiment, X is —C(=O)NH$_2$ and the compound of formula (VIIe) is a compound of the formula (VIIe') or a tautomer or a solvate or a pharmaceutically acceptable salt thereof:

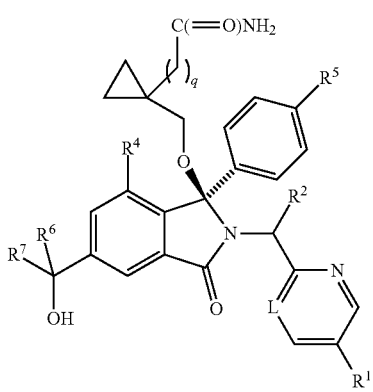

(VIIe')

wherein q is 0 or 1, and in particular q is 0.

In one embodiment, X is —CN and the compound of formula (VIId) is a compound of the formula (VIIe") or a tautomer or a solvate or a pharmaceutically acceptable salt thereof:

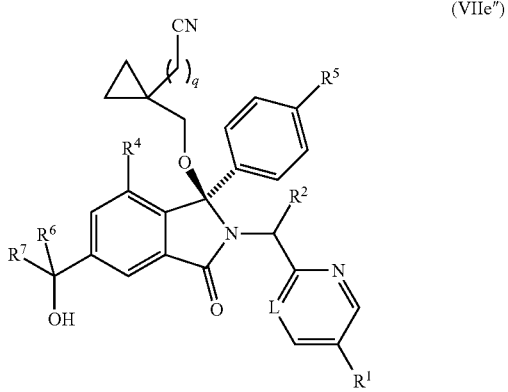

(VIIe")

wherein q is 0 or 1, and in particular q is 0.

In one embodiment, R$^3$ is methyl, and the compound of formula (VI) is a compound of formula (VIIf) or a tautomer or a solvate or a pharmaceutically acceptable salt thereof:

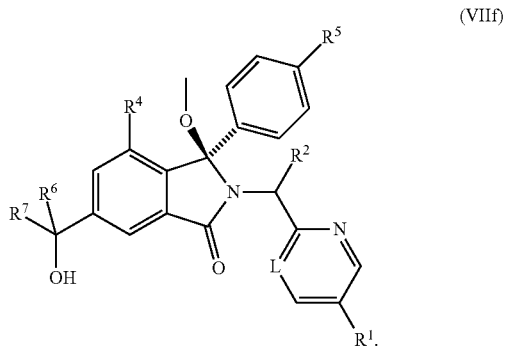

(VIIf)

In one embodiment of Formula (VIIa-e') R$^6$ is methyl. In one embodiment of Formula (VIIa-e') R$^6$ is ethyl.

In one embodiment of Formula (VIIe") or (VIIf) R$^6$ is methyl. In one embodiment of Formula (VIIe") or (VIIf) R$^6$ is ethyl.

In one embodiment of Formula (VIIe") or (VIIf) R$^6$ is methyl. In one embodiment of Formula (VIIe") or (VIIf) R$^6$ is ethyl.

In one embodiment of the compound of formula (VIIa-e'), R$^7$ is selected from methyl, oxanyl, pyrazolyl, imidazolyl, piperidinyl, and cyclohexyl wherein said cycloalkyl and heterocyclic groups are optionally substituted by one or more R$^z$ groups (e.g. methyl, fluorine, or hydroxy).

In one embodiment of the compound of formula (VIIa-e'), R$^7$ is selected from oxanyl and methyl.

In one embodiment of the compound of formula (VIIe") or (VIIf), R$^7$ is selected from methyl, oxanyl, pyrazolyl, imidazolyl, piperidinyl, and cyclohexyl wherein said cycloalkyl and heterocyclic groups are optionally substituted by one or more R$^z$ groups (e.g. methyl, fluorine, or hydroxy).

In one embodiment of the compound of formula (VIIe") or (VIIf), R$^7$ is selected from oxanyl and methyl.

In one embodiment of the compound of formula (VIIa-t), R⁷ is selected from piperidinyl optionally substituted by one or more R^z groups (e.g. methyl, fluorine, or hydroxy).

In another embodiment, the compound of formula (I°) is a compound of formula (a) or a tautomer or a solvate or a pharmaceutically acceptable salt thereof:

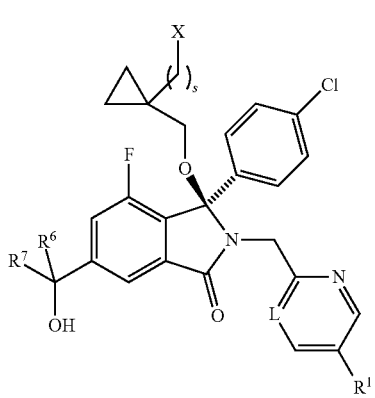

(a)

wherein R¹ is chloro or nitrile, X is hydroxyl when s is 1 or X is —C(=O)NH₂ when s is 0.

In another embodiment, the compound of formula (I°) is a compound of formula (a') or a tautomer or a solvate or a pharmaceutically acceptable salt thereof:

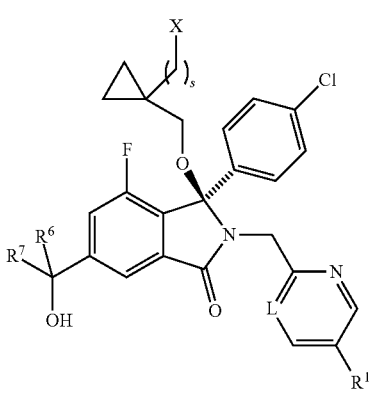

(a')

wherein R¹ is chloro or nitrile, X is hydroxyl when s is 1 or X is —CN when s is 0.

In one embodiment of the compound of formula (a), R⁷ is selected from methyl, oxanyl, pyrazolyl, imidazolyl, piperidinyl, and cyclohexyl wherein said cycloalkyl and heterocyclic groups are optionally substituted by one or more R^z groups (e.g. methyl, fluorine, or hydroxy).

In one embodiment of the compound of formula (a), R⁷ is oxanyl or methyl.

In one embodiment of the compound of formula (a), R⁷ is piperidinyl, optionally substituted with $C_{1-6}$alkyl (e.g. methyl) and/or halo (e.g. fluoro).

In one embodiment of the compound of formula (a'), R⁷ is selected from methyl, oxanyl, pyrazolyl, imidazolyl, piperidinyl, and cyclohexyl wherein said cycloalkyl and heterocyclic groups are optionally substituted by one or more R^z groups (e.g. methyl, fluorine, or hydroxy).

In one embodiment of the compound of formula (a'), R⁷ is oxanyl or methyl.

In one embodiment of the compound of formula (a'), R⁷ is piperidinyl, optionally substituted with $C_{1-6}$ alkyl (e.g. methyl) and/or halo (e.g. fluoro).

In one embodiment, A is a heterocyclyl group with 3 to 6 ring members, wherein the heterocyclic group comprises one or more (e.g. 1, 2, or 3) heteroatoms selected from N, O, S and oxidised forms thereof (t is 1; g is 1, 2, 3 or 4; Z represents N, O, S and oxidised forms thereof; i is 1, 2, or 3; and i+g=2, 3, 4 or 5), and the compound of formula (VI) is a compound of formula (b) or a tautomer or a solvate or a pharmaceutically acceptable salt thereof:

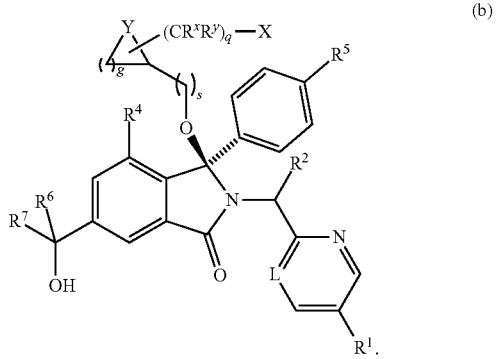

(b)

In one embodiment, Y is O and i is 1 and the compound of formula (b) is a compound of formula (ba) or a tautomer or a solvate or a pharmaceutically acceptable salt thereof:

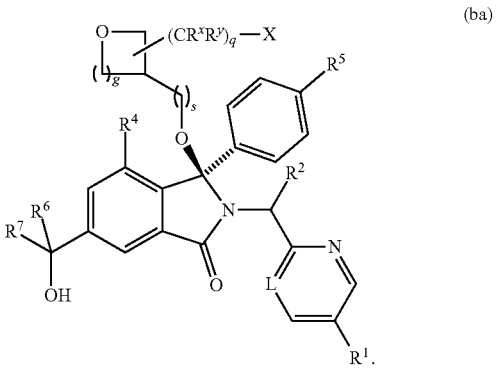

(ba)

In one embodiment, s is 0, g is 2, q is 0 and X is hydrogen, and the compound of formula (b) is a compound of formula (bb) or a tautomer or a solvate or a pharmaceutically acceptable salt thereof:

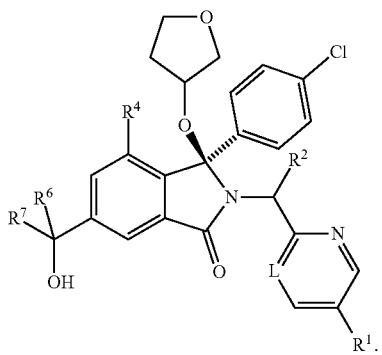

(bb)

In one embodiment, s is 0, g is 1, Y is 0 and i is 1 and the compound of formula (b) is a compound of formula (bc) or a tautomer or a solvate or a pharmaceutically acceptable salt thereof:

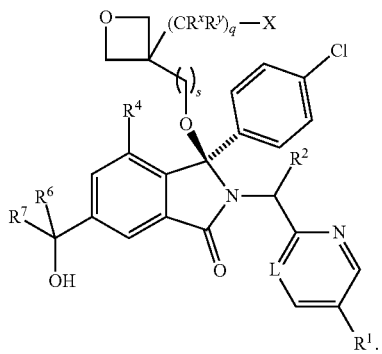

(bc)

In one embodiment, the compound of formula (bc) is where q is 0 and X is fluorine.

In another embodiment, the compound of formula (I°) is a compound of formula (c) or a tautomer or a solvate or a pharmaceutically acceptable salt thereof:

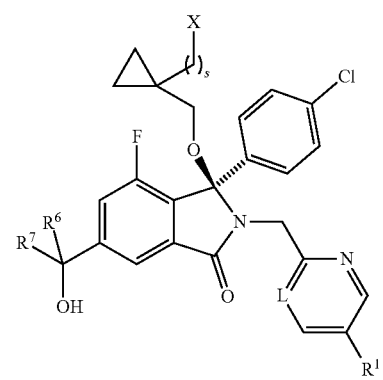

(c)

wherein $R^1$ is chloro or nitrile, s is 1 and X is hydroxyl or s is 0 and X is —C(=O)NH$_2$.

In another embodiment, the compound of formula (I°) is a compound of formula (c') or a tautomer or a solvate or a pharmaceutically acceptable salt thereof:

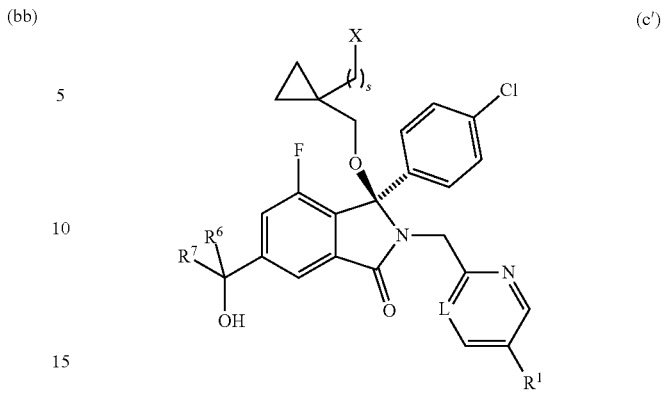

(c')

wherein $R^1$ is chloro or nitrile, s is 1 and X is hydroxyl or s is 0 and X is —CN.

In one embodiment of the compound of formula (c), $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (c), $R^7$ is oxanyl or methyl.

In one embodiment of the compound of formula (c), $R^7$ is piperidinyl, optionally substituted with $C_{1-6}$alkyl (e.g. methyl) and/or halo (e.g. fluoro).

In one embodiment of the compound of formula (c'), $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (c'), $R^7$ is oxanyl or methyl.

In one embodiment of the compound of formula (c'), $R^7$ is piperidinyl, optionally substituted with $C_{1-6}$alkyl (e.g. methyl) and/or halo (e.g. fluoro).

In one embodiment the compound of formula (I°) is a compound of formula (II), (IIa), (IIb), (IIIa), (IIIb), (IVa), (IVb), (V), (VI), (Via), (VII), (VIIa), (VIIb), (VIIc), (VIId), (VIId'), (VIIe), (VIIe'), (a), (b), (ba), (bb), (bc) or (c) and L is CH. In one embodiment the compound of formula (I°) is a compound of formula (II), (IIa), (IIb), (IIIa), (IIIb), (IVa), (IVb), (V), (VI), (Via), (VII), (VIIa), (VIIb), (VIIc), (VI Id), (VIId'), (VIIe), (VIIe'), (a), (b), (ba), (bb), (bc) or (c) and L is N.

In one embodiment the compound of formula (I°) is a compound of formula (II), (IIa), (IIb), (IIIa), (IIIb), (IVa), (IVb), (V), (VI), (Via), (VII), (VIIa), (VIIb), (VIIc), (VIId), (VIId'), (VIIe), (VIIe'), (VIIe"), (VIIf), (a), (a'), (b), (ba), (bb), (bc), (c) or (c') and L is CH. In one embodiment the compound of formula (I°) is a compound of formula (II), (IIa), (IIb), (IIIa), (IIIb), (IVa), (IVb), (V), (VI), (Via), (VII), (VIIa), (VIIb), (VIIc), (VIId), (VIId'), (VIIe), (VIIe'), (a), (b), (ba), (bb), (bc) or (c) and L is N.

In one embodiment, the invention provides a combination comprising the compound of formula (I°) or a tautomer or a solvate or a pharmaceutically acceptable salt thereof wherein:

Het is pyridinyl, pyrimidinyl, or pyridazinyl, or an N-oxide thereof $R^1$ is attached to a carbon atom and is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, and $C_{2-4}$alkynyl;

$R^2$ is selected from hydrogen, $C_{1-4}$ alkyl, $C_{2-6}$ alkenyl, hydroxy$C_{1-4}$alkyl and —$CH_2CO_2H$;

$R^3$ is hydrogen or -$(A)_t$-$(CR^xR^y)_q$—X;

s and t are independently selected from 0 and 1;

q is selected from 0, 1 and 2;

wherein when $R^3$ is -$(A)_t$-$(CR^xR^y)_q$—X then (i) at least one of s, t and q is other than 0 and (ii) when t is 0 then s is 1 and q is other than 0;

A is a $C_{3-6}$ cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —$OR^9$, —$(CH_2)_v$—$CO_2H$, —$(CH_2)_v$—$CO_2C_{1-4}$ alkyl, —C(=O)—$C_{1-4}$alkyl, —$NR^xR^y$, —$NHSO_2R^x$, —$NR^xCOR^y$; and —$C(=O)NR^xR^y$;

$R^4$ and $R^5$ are independently selected from halogen, nitrile, $C_{1-4}$ alkyl, halo$C_{1-4}$alkyl, $C_{1-4}$ alkoxy and halo$C_{1-4}$alkoxy;

$R^6$ and $R^7$ are independently selected from hydrogen, $C_{1-6}$alkyl, halo$C_{1-6}$alkyl, $C_{2-6}$ alkenyl, $C_{2-6}$ alkynyl, hydroxy, hydroxy$C_{1-6}$alkyl, —$COOC_{1-6}$alkyl, heterocyclic group with 3 to 7 ring members, —$CH_2$-heterocyclic group with 3 to 7 ring members, —$CH_2$—O-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$cycloalkyl, —$CH_2$—$C_{3-8}$ cycloalkyl, —$CH_2$—O—$C_{3-8}$ cycloalkyl, and $C_{3-13}$ cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

$R^9$ is selected from hydrogen, $C_{1-6}$alkyl, hydroxy$C_{1-6}$alkyl, —$(CH_2)_k$—O—$C_{1-6}$ alkyl, —$(CH_2)_k$—O-(hydroxy$C_{1-6}$alkyl), hydroxy$C_{1-6}$alkoxy, —$(CH_2)_k$—$CO_2C_{1-8}$ alkyl, —$(CH_2)_k$—$CO_2H$, —$C_{1-6}$alkyl-N(H)$_e$($C_{1-4}$alkyl)$_{2-e}$, —$(CH_2)j$-$C_{3-8}$cycloalkyl and —$(CH_2)_j$—$C_{3-8}$ cycloalkenyl;

$R^x$ and $R^y$ are independently selected from hydrogen, halogen, nitro, nitrile, halo$C_{1-6}$alkyl, $C_{2-6}$alkenyl, $C_{2-8}$ alkynyl, hydroxy, hydroxy$C_{1-6}$alkyl, $C_{1-6}$alkoxy, —$(CH_2)_k$—O—$C_{1-6}$ alkyl, hydroxy$C_{1-6}$alkoxy, —$COOC_{1-6}$ alkyl, —N(H)$_e$($C_{1-4}$alkyl)$_{2-e}$, —$C_{1-6}$alkyl-N(H)$_e$($C_{1-4}$ alkyl)$_{2-e}$, —$(CH_2)_k$—C(=O)N(H)$_e$($C_{1-4}$ alkyl)$_{2-e}$ $C_{3-8}$cycloalkyl and $C_{3-8}$ cycloalkenyl;

$R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$ alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_r CO_2C_{1-6}$alkyl, —$(CH_2)_r$—$CO_2H$, —N(H)$_e$($C_{1-4}$alkyl)$_{2-e}$, heterocyclyl group with 3 to 6 ring members, heterocyclyl group with 3 to 6 ring members substituted by —C(=O)$C_{1-4}$ alkyl, heterocyclyl group with 3 to 6 ring members substituted by —C(=O)$OC_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$ cycloalkyl and $C_{3-8}$ cycloalkenyl;

n, e, r and j are independently selected from 0, 1 and 2;

k and m are independently selected from 1 and 2; and v and a are independently selected from 0 and 1.

In one embodiment, the invention provides a combination comprising the compound of formula (I$^o$) or a tautomer or a solvate or a pharmaceutically acceptable salt thereof, wherein:

Het is pyridinyl or pyrimidinyl;

$R^1$ is attached to a carbon atom and is independently selected from hydroxy, halogen, nitro, nitrile and $C_{1-4}$alkyl;

$R^2$ is selected from hydrogen, $C_{1-4}$ alkyl, $C_{2-6}$alkenyl, hydroxy$C_{1-4}$alkyl and $CH_2CO_2H$;

$R^3$ is hydrogen or -$(A)_t$-$(CR^xR^y)_q$—X;

s and t are independently selected from 0 and 1;

q is selected from 0, 1 and 2;

wherein when $R^3$ is -$(A)_t$-$(CR^xR^y)_q$—X then (i) at least one of s, t and q is other than 0 and (ii) when t is 0 then s is 1 and q is other than 0;

A is a $C_{3-6}$ cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —$OR^9$, —$(CH_2)_v$—$CO_2H$, —$(CH_2)_v$—$CO_2C_{1-4}$alkyl, —C(=O)—$C_{1-4}$alkyl, —$NR^xR^y$, —$NHSO_2R^x$, —$NR^xCOR^y$; and —$C(=O)NR^xR^y$;

$R^4$ and $R^5$ are independently selected from halogen, nitrile and $C_{1-4}$ alkyl;

$R^6$ is selected from hydrogen, $C_{1-6}$alkyl, halo$C_{1-6}$alkyl, $C_{2-6}$alkenyl, and $C_{2-8}$alkynyl;

$R^7$ is selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —$COOC_{1-6}$alkyl, heterocyclic group with 3 to 7 ring members, —$CH_2$-heterocyclic group with 3 to 7 ring members, —$CH_2$—O-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$ cycloalkyl, —$CH_2$—$C_{3-8}$cycloalkyl, —$CH_2$—O—$C_{3-6}$cycloalkyl, and $C_{3-8}$ cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

$R^9$ is selected from hydrogen, $C_{1-6}$alkyl, halo$C_{1-6}$alkyl, hydroxy$C_{1-6}$alkyl, —$(CH_2)_k$—O—$C_{1-6}$ alkyl, —$(CH_2)_k$—O-(hydroxy$C_{1-6}$alkyl), hydroxy$C_{1-6}$alkoxy, —$(CH_2)_k$—$CO_2C_{1-6}$alkyl, —$(CH_2)_k$—$CO_2H$, —$C_{1-6}$ alkyl-N(H)$_e$($C_{1-4}$alkyl)$_{2-e}$, —$(CH_2)j$-$C_{3-8}$cycloalkyl and —$(CH_2)_j$—$C_{3-8}$cycloalkenyl;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-8}$alkynyl, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —$COOC_{1-6}$ alkyl, —N(H)$_e$($C_{1-4}$alkyl)$_{2-e}$, —$C_{1-6}$alkyl-N(H)$_e$($C_{1-4}$ alkyl)$_{2-e}$, —$(CH_2)_1$c-C(=O)N(H)$_e$($C_{1-4}$alkyl)$_{2-e}$, $C_{3-8}$cycloalkyl and $C_{3-8}$ cycloalkenyl;

$R^z$ is independently selected from halogen, nitro, nitrile, $C_{1-6}$alkyl, halo$C_{1-6}$alkyl, $C_{2-6}$ alkenyl, $C_{2-8}$alkynyl, =O, hydroxy, hydroxy$C_{1-6}$alkyl, $C_{1-6}$alkoxy, —$(CH_2)_k$—O—$C_{1-6}$ alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_r$—$CO_2C_{1-6}$ alkyl, —$(CH_2)_r$—$CO_2H$, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$ alkyl, heterocyclyl group with 3 to 6 ring members substituted by —C(=O)$OC_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl;

n, e, r and j are independently selected from 0, 1 and 2;
k and m are independently selected from 1 and 2; and
v and a are independently selected from 0 and 1.

In one embodiment, the invention provides a combination comprising the compound of formula (I°) or a tautomer or a solvate or a pharmaceutically acceptable salt thereof, wherein:
Het is pyridinyl or pyrimidinyl
$R^1$ is attached to a carbon atom and is independently selected from hydroxy, halogen, nitro, nitrile and $C_{1-4}$alkyl;
$R^2$ is selected from hydrogen, $C_{1-4}$ alkyl, $C_{2-8}$alkenyl, hydroxy$C_{1-4}$alkyl and —$CH_2CO_2H$;
$R^3$ is hydrogen or -(A)$_t$-(CR$^x$R$^y$)$_q$—X;
s and t are independently selected from 0 and 1;
q is selected from 0, 1 and 2;
wherein when $R^3$ is -(A)$_t$-(CR$^x$R$^y$)$_q$—X then (i) at least one of s, t and q is other than 0 and (ii) when t is 0 then s is 1 and q is other than 0;
A is a heterocyclic group with 3 to 6 ring members, wherein the heterocyclic group comprises one or more (e.g. 1, 2, or 3) heteroatoms selected from N, O, S and oxidised forms thereof;
X is selected from hydrogen, halogen, —CN and —OR$^9$;
$R^4$ and $R^5$ are independently selected from halogen, nitrile and $C_{1-4}$ alkyl;
$R^5$ is selected from hydrogen and $C_{1-6}$alkyl;
$R^7$ is selected from heterocyclic group with 3 to 7 ring members, —$CH_2$-heterocyclic group with 3 to 7 ring members, $C_{3-8}$ cycloalkyl, and —$CH_2$—$C_{3-8}$ cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;
$R^9$ is selected from hydrogen and $C_{1-6}$alkyl;
$R^x$ and $R^y$ are independently selected from hydrogen and $C_{1-6}$alkyl;
$R^z$ is independently selected from halogen, nitro, nitrile, $C_{2-6}$ alkenyl, hydroxy, hydroxy$C_{1-6}$alkyl, $C_{1-6}$alkoxy, —C(=O) $C_{1-8}$ alkyl, and —N(H)$_e$($C_{1-4}$alkyl)$_{2-e}$;
n and e are independently selected from 0, 1 and 2;
m is selected from 1 and 2; and
a is selected from 0 and 1.

In one embodiment, the invention provides a combination comprising the compound of formula (I°) or a tautomer or a solvate or a pharmaceutically acceptable salt thereof, wherein:
Het is pyridinyl or pyrimidinyl
$R^1$ is attached to a carbon atom and is independently selected from halogen, hydroxy and nitrile;
$R^2$ is selected from hydrogen, $C_{1-4}$ alkyl and —$CH_2CO_2H$;
$R^3$ is hydrogen or -(A)$_t$-(CR$^x$R$^y$)$_q$—X;
A is a heterocyclic group with 3 to 6 ring members, wherein the heterocyclic group comprises one or more (e.g. 1, 2, or 3) heteroatoms selected from N, O, S and oxidised forms thereof;
s and t are independently selected from 0 and 1;
q is selected from 0, 1 and 2;
wherein when $R^3$ is -(A)$_t$-(CR$^x$R$^y$)$_q$—X then (i) at least one of s, t and q is other than 0 and (ii) when t is 0 then s is 1 and q is other than 0;
X is selected from hydrogen, halogen or —OR$^9$;
$R^4$ and $R^5$ are independently selected from halogen;
$R^5$ is selected from hydrogen and $C_{1-6}$alkyl;
$R^7$ is selected from heterocyclic group with 3 to 7 ring members, —$CH_2$-heterocyclic group with 3 to 7 ring members, $C_{3-8}$ cycloalkyl, and —$CH_2$—$C_{3-8}$cycloalkyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;
$R^9$ is selected from hydrogen and $C_{1-6}$alkyl;
$R^x$ and $R^y$ are independently selected from hydrogen and $C_{1-6}$alkyl;
$R^z$ is independently selected from halogen, nitro, nitrile, and $C_{1-4}$alkyl;
n is 1 and m is 1; and
a is selected from 0 and 1.

In one embodiment, the invention provides a combination comprising the compound of formula (I°) or a tautomer or a solvate or a pharmaceutically acceptable salt thereof, wherein:
Het is pyridinyl or pyrimidinyl
$R^1$ is attached to a carbon atom and is independently selected from halogen, hydroxy and nitrile;
$R^2$ is selected from hydrogen, $C_{1-4}$ alkyl and $CH_2CO_2H$;
$R^3$ is -(A)$_t$-(CR$^x$R$^y$)$_q$—X;
A is a heterocyclic group with 3 to 6 ring members, wherein the heterocyclic group comprises one or more (e.g. 1, 2, or 3) heteroatoms selected from N, O, S and oxidised forms thereof;
s and t are independently selected from 0 and 1;
q is selected from 0, 1 and 2;
wherein (i) at least one of s, t and q is other than 0 and (ii) when t is 0 then s is 1 and q is other than 0;
X is selected from hydrogen, halogen and —OR$^6$;
$R^4$ and $R^5$ are independently selected from halogen;
$R^6$ is selected from hydrogen and $C_{1-6}$alkyl;
$R^7$ is a heterocyclic group with 3 to 7 ring members optionally substituted by one or more R$^z$ groups;
$R^9$ is selected from hydrogen and $C_{1-6}$alkyl;
$R^x$ and $R^y$ are independently selected from hydrogen and $C_{1-6}$alkyl;
$R^z$ is independently selected from halogen and $C_{1-6}$alkyl;
n is, 1 and m is 1 and
a is 1.

In one embodiment, the invention provides a combination comprising the compound of formula (I°) or a tautomer or a solvate or a pharmaceutically acceptable salt thereof, wherein:
Het is pyridinyl or pyrimidinyl
$R^1$ is attached to a carbon atom and is independently selected from halogen, hydroxy and nitrile;
$R^2$ is selected from hydrogen, $C_{1-4}$ alkyl and —$CH_2CO_2H$;
$R^3$ is hydrogen and s is 1;
wherein (i) at least one of s, t and q is other than 0 and (ii) when t is 0 then s is 1 and q is other than 0;
$R^4$ and $R^5$ are independently selected from halogen;
$R^6$ is selected from hydrogen and $C_{1-6}$alkyl;
$R^7$ is a heterocyclic group with 3 to 7 ring members optionally substituted by one or more R$^z$ groups;
$R^9$ is selected from hydrogen and $C_{1-6}$alkyl;
$R^z$ is independently selected from halogen and $C_{1-6}$alkyl;
n is, 1 and m is 1 and
a is 1.

In one embodiment, the invention provides a combination comprising the compound of formula (I°) or a tautomer or a solvate or a pharmaceutically acceptable salt thereof, wherein:
Het is pyridinyl, pyrimidinyl, or pyridazinyl, or an N-oxide thereof;
$R^1$ is halogen (e.g. Cl), nitrile, hydroxy, $C_{1-4}$alkoxy (e.g. —$OCH_3$), $C_{1-4}$ alkyl (e.g. $CH_3$) or —S(O)$_d$—$C_{1-4}$alkyl;

n is 1 or 2;

R² is selected from hydrogen, C₁₋₄ alkyl (e.g. —CH₃), hydroxyC₁₋₄alkyl (e.g. —CH₂OH or —CH(OH)CH₂OH), —CH₂CO₂H and C₂₋₆alkenyl (e.g. —CH═CH₂);

the moiety —(CH₂)$_s$R³ is selected from:

(point of attachment to the oxygen represented by dashed bond or bond terminus indicated by *):

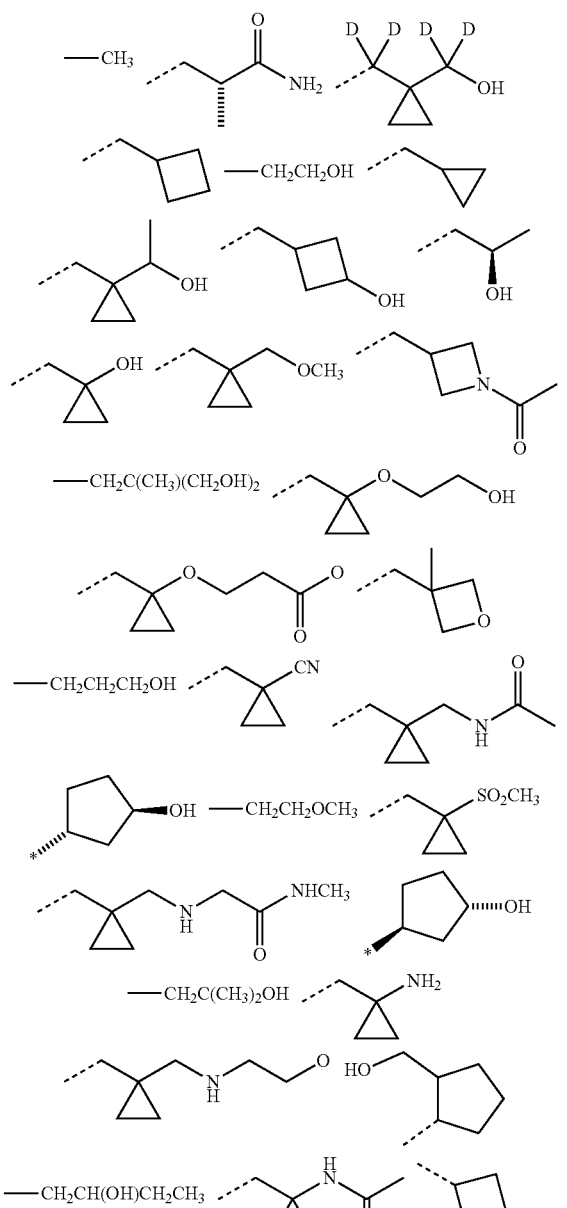

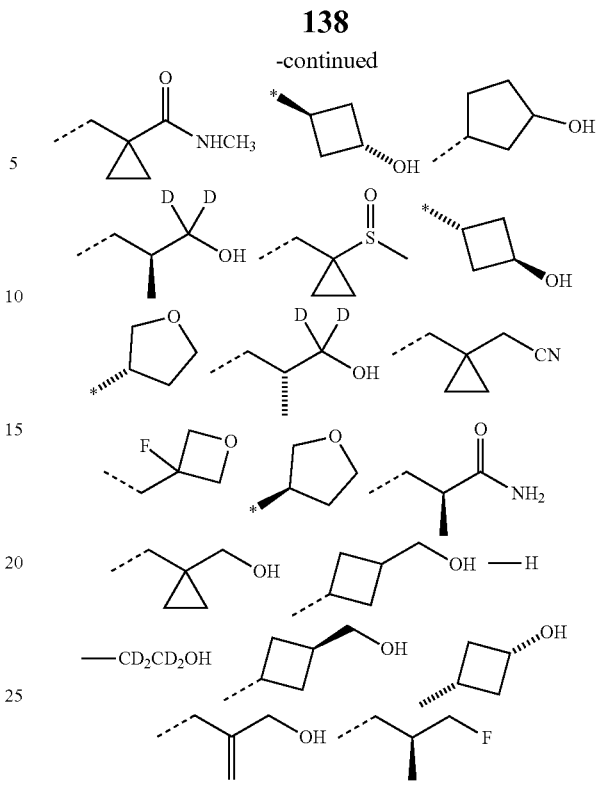

R⁴ is C₁₋₄alkyl (e.g. —CH₃), or halogen (e.g. F or Cl);
a is 0 or 1;
R⁵ is halogen (e.g. Cl or F), C₁₋₄ alkyl (e.g. —CH₂CH₃), nitrile, haloC₁₋₄alkyl (e.g. —CF₃, or —CF₂CH₃), or haloC₁₋₄ alkoxy (e.g. —OCF₃);
m is 1 or 2;
R⁶ is hydrogen, C₁₋₆alkyl (e.g. —CH₃ or —CH₂CH₃), C₂₋₈ alkenyl (e.g. —CH═CH₂) and haloC₁₋₆alkyl (e.g. —CF₃ or —CH₂F);
R⁷ is C₁₋₈ alkyl (e.g. —CH₃ or —CH₂CH₃), C₃₋₈cycloalkyl (e.g. cyclopropyl, cyclobutyl or cyclohexyl), C₂₋₆alkenyl (e.g. —CH═CH₂), haloC₁₋₆ alkyl (e.g. —CF₃), hydroxyC₁₋₆ alkyl (e.g. —CH₂OH or —CH₂CH₂OH), —C₁₋₆ alkyl-NR$^x$R$^y$ (e.g. —CH₂NH₂, —CH₂N(CH₃)₂, —CH₂NHCH₃, or —CH₂NH(cyclopropyl)), —(CR$^x$R$^y$)$_p$—CONR$^x$R$^y$ (e.g. —C(═O)NHCH₃, —(CO)NHCH₂CH₃, —(CO)NHCH₂CH₂NH₂, —C(═O)NH(CH(CH₃)₂)), or —(CH₂)$_r$—O—C₁₋₆alkyl (e.g. —CH₂OCH₃, —CH₂OCH₂CH₃ or —CH₂OCD₃), —(CR$^x$R$^y$)$_p$—NR$^x$COR$^y$ (e.g. —CH₂NHC(═O)CH₃), —(CR$^x$R$^y$)$_p$—O—CH₂—CONR$^x$R$^y$ (e.g. —CH₂OCH₂C(═O)N(CH₃)₂), —(CH₂)$_j$—O-(hydroxyC₁₋₆alkyl) (e.g. —CH₂OCH₂CH₂OH), heterocyclic group with 3 to 7 ring members e.g.

(point of attachment represented by dashed bond):

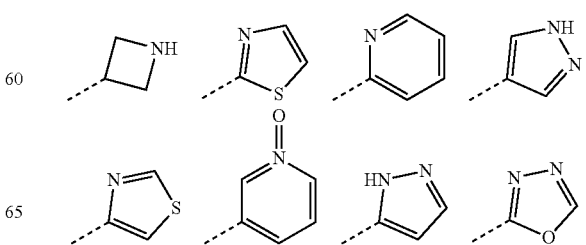

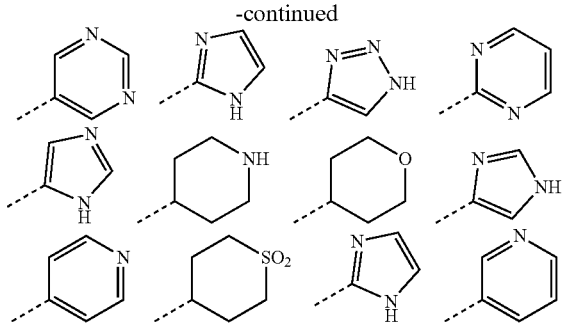

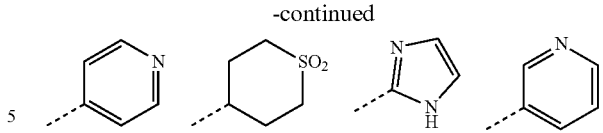

In one embodiment of formula (I°) R⁷ is a heterocyclic group with 3 to 7 ring members optionally substituted by one or more R$^z$ groups e.g.

(point of attachment represented by dashed bond)

or —CH₂-heterocyclic group with 3 to 7 ring members e.g. (point of attachment represented by dashed bond)

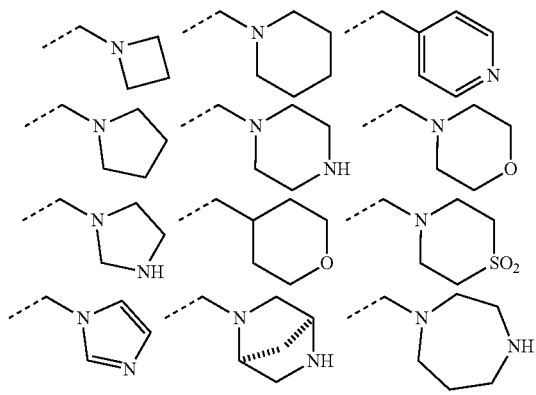

wherein when the moiety R⁷ comprises a heterocyclic group, the heterocyclic group may be optionally substituted by one or more R$^z$ groups selected from $C_{1-6}$alkyl (e.g. methyl), hydroxyalkyl (e.g. —CH₂CH₂OH), halogen (e.g. fluoro), =O, $C_{1-6}$alkoxy (e.g. methoxy), —C(=O)$C_{1-6}$alkyl (e.g. —C(=O)CH₃), —C(=O)hydroxy$C_{1-6}$alkyl (e.g. —C(=O)CH₂OH), heterocyclyl group with 3 to 6 ring members (e.g. oxetanyl or pyrimidinyl), and —S(O)$_d$—$C_{1-4}$ alkyl wherein d is selected from 0, 1 and 2 (e.g. —SO₂—CH₃).

In one embodiment of formula (I°) R⁷ is a heterocyclic group with 3 to 7 ring members e.g.

(point of attachment represented by dashed bond)

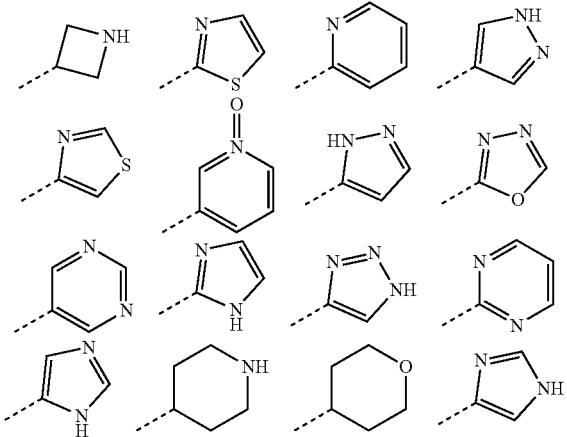

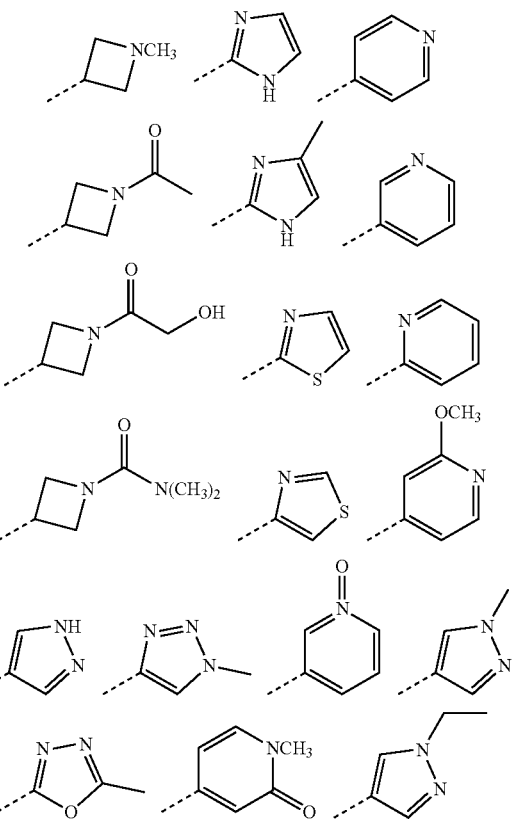

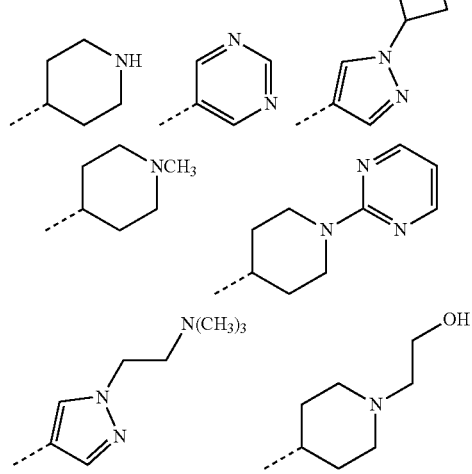

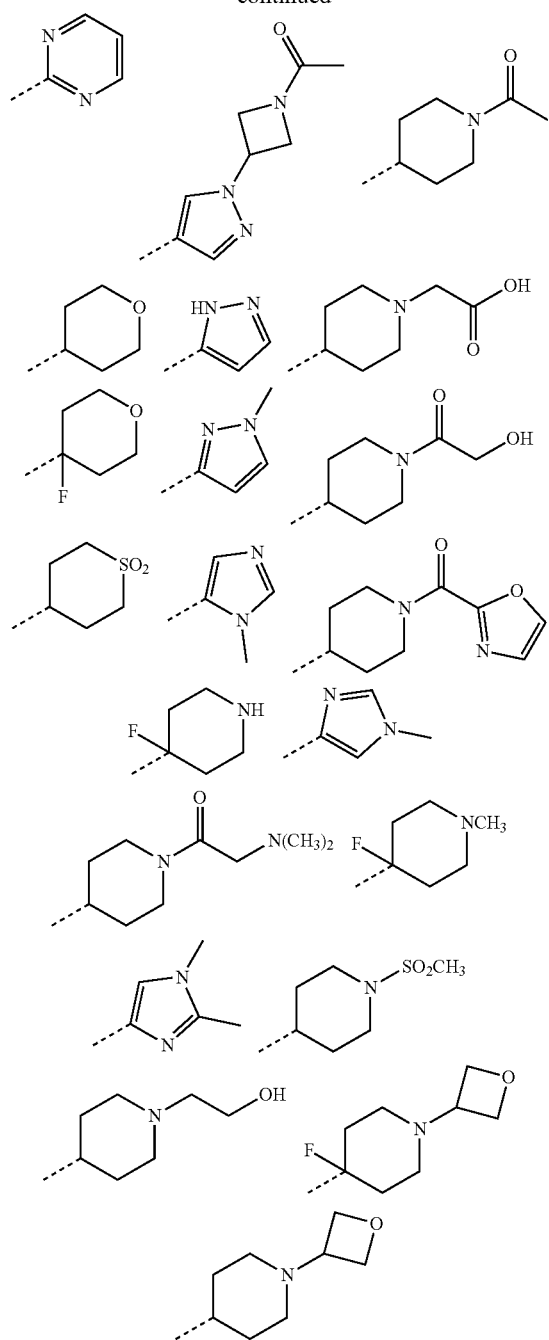
or a —CH$_2$-heterocyclic group with 3 to 7 ring members optionally substituted by one or more R$^z$ groups e.g. (point of attachment represented by dashed bond)
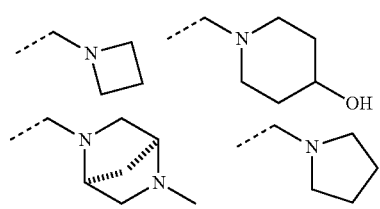
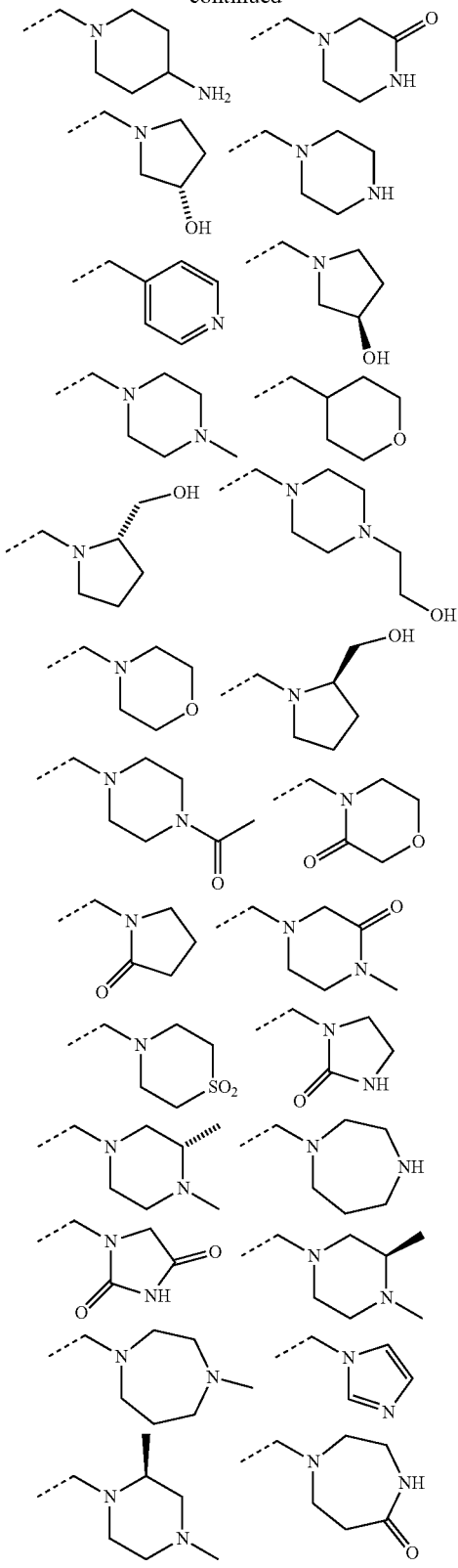
In one embodiment, the invention provides a combination comprising the compound of formula (I°) or a tautomer or a solvate or a pharmaceutically acceptable salt thereof, wherein:

Het is pyridinyl, pyrimidinyl, or pyridazinyl, or an N-oxide thereof;

$R^1$ is halogen (e.g. Cl), nitrile, hydroxy, $C_{1-4}$alkoxy (e.g. —OCH$_3$), $C_{1-4}$alkyl (e.g. CH$_3$) or —S(O)$_d$—C$_{1-4}$alkyl;

n is 1 or 2;

$R^2$ is selected from hydrogen, $C_{1-4}$ alkyl (e.g. —CH$_3$), hydroxyC$_{1-4}$alkyl (e.g. —CH$_2$OH or —CH(OH)CH$_2$OH), CH$_2$CO$_2$H and C$_{2-6}$alkenyl (e.g. —CH=CH$_2$);

the moiety —(CH$_2$)$_s$R$^3$ is selected from:

(point of attachment to the oxygen represented by dashed bond or bond terminus indicated by *):

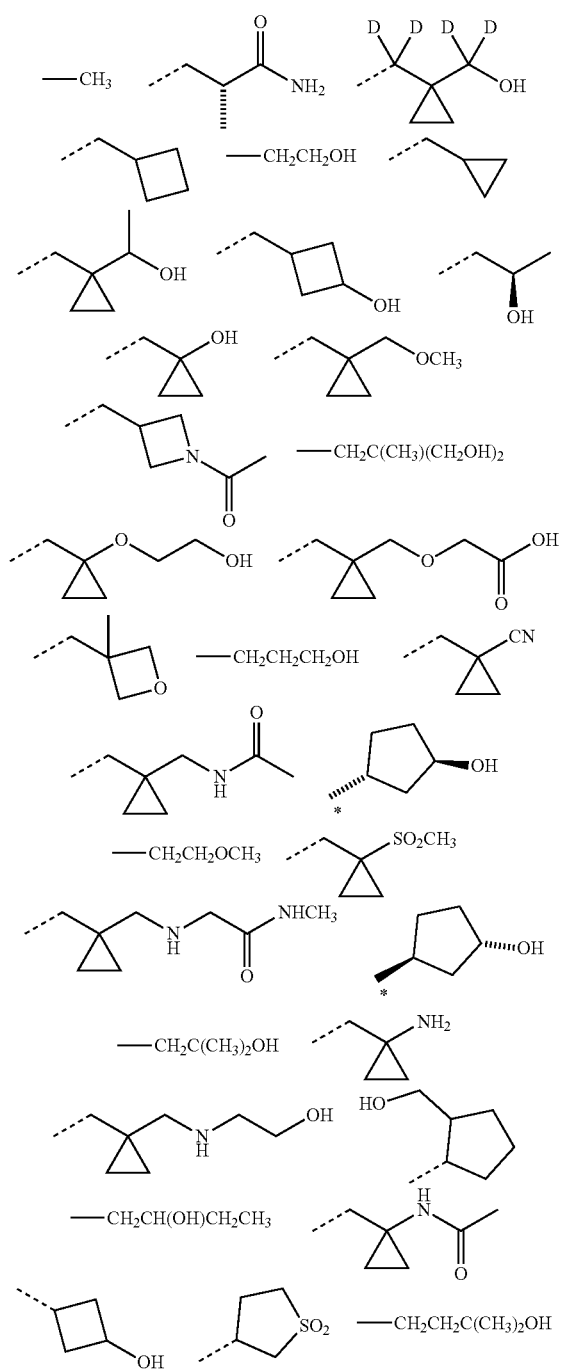
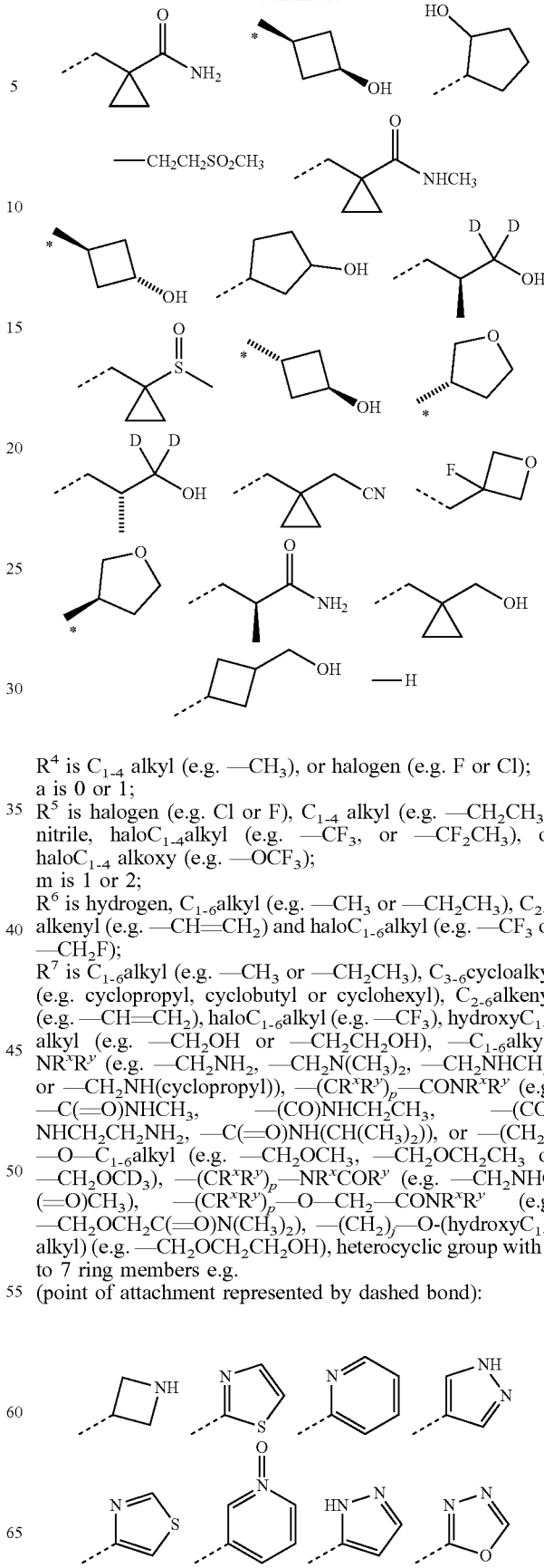

$R^4$ is $C_{1-4}$ alkyl (e.g. —CH$_3$), or halogen (e.g. F or Cl); a is 0 or 1;

$R^5$ is halogen (e.g. Cl or F), $C_{1-4}$ alkyl (e.g. —CH$_2$CH$_3$), nitrile, haloC$_{1-4}$alkyl (e.g. —CF$_3$, or —CF$_2$CH$_3$), or haloC$_{1-4}$ alkoxy (e.g. —OCF$_3$);

m is 1 or 2;

$R^6$ is hydrogen, $C_{1-6}$alkyl (e.g. —CH$_3$ or —CH$_2$CH$_3$), $C_{2-6}$ alkenyl (e.g. —CH=CH$_2$) and haloC$_{1-6}$alkyl (e.g. —CF$_3$ or —CH$_2$F);

$R^7$ is $C_{1-6}$alkyl (e.g. —CH$_3$ or —CH$_2$CH$_3$), $C_{3-6}$cycloalkyl (e.g. cyclopropyl, cyclobutyl or cyclohexyl), $C_{2-6}$alkenyl (e.g. —CH=CH$_2$), haloC$_{1-6}$alkyl (e.g. —CF$_3$), hydroxyC$_{1-6}$ alkyl (e.g. —CH$_2$OH or —CH$_2$CH$_2$OH), —C$_{1-6}$alkyl-NR$^x$R$^y$ (e.g. —CH$_2$NH$_2$, —CH$_2$N(CH$_3$)$_2$, —CH$_2$NHCH$_3$, or —CH$_2$NH(cyclopropyl)), —(CR$^x$R$^y$)$_p$—CONR$^x$R$^y$ (e.g. —C(=O)NHCH$_3$, —(CO)NHCH$_2$CH$_3$, —(CO) NHCH$_2$CH$_2$NH$_2$, —C(=O)NH(CH(CH$_3$)$_2$)), or —(CH$_2$)$_j$ —O—C$_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHC (=O)CH$_3$), —(CR$^x$R$^y$)$_p$—O—CH$_2$—CONR$^x$R$^y$ (e.g. —CH$_2$OCH$_2$C(=O)N(CH$_3$)$_2$), —(CH$_2$)$_j$—O-(hydroxyC$_{1-6}$ alkyl) (e.g. —CH$_2$OCH$_2$CH$_2$OH), heterocyclic group with 3 to 7 ring members e.g.

(point of attachment represented by dashed bond):

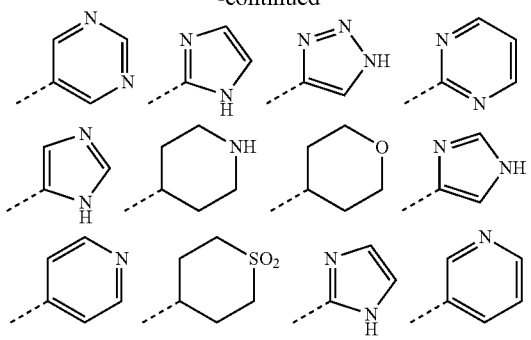

or —CH$_2$-heterocyclic group with 3 to 7 ring members e.g.
(point of attachment represented by dashed bond)

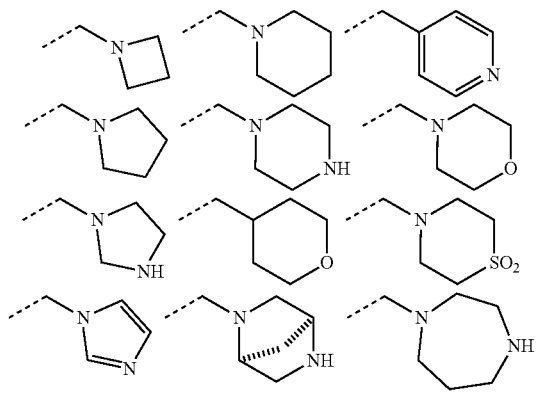

wherein when R$^7$ comprises a heterocyclic group, the heterocyclic group may be optionally substituted by one or more R$^z$ groups selected from C$_{1-6}$alkyl (e.g. methyl), halogen (e.g. fluoro), =O, C$_{1-6}$alkoxy (e.g. methoxy), —C(=O)C$_{1-6}$alkyl (e.g. —C(=O)CH$_3$), —C(=O)hydroxyC$_{1-6}$alkyl (e.g. —C(=O)CH$_2$OH), heterocyclyl group with 3 to 6 ring members (e.g. pyrimidinyl), and —S(O)$_d$—C$_{1-4}$alkyl wherein d is selected from 0, 1 and 2 (e.g. —SO$_2$—CH$_3$).

In one embodiment of formula (I°) R$^7$ is a heterocyclic group with 3 to 7 ring members e.g.
(point of attachment represented by dashed bond)

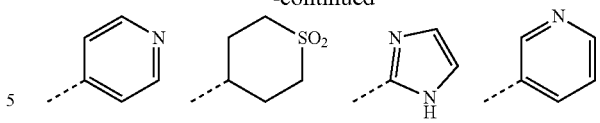

In one embodiment of formula (I°) R$^7$ is a heterocyclic group with 3 to 7 ring members optionally substituted by one or more R$^z$ groups e.g.
(point of attachment represented by dashed bond)

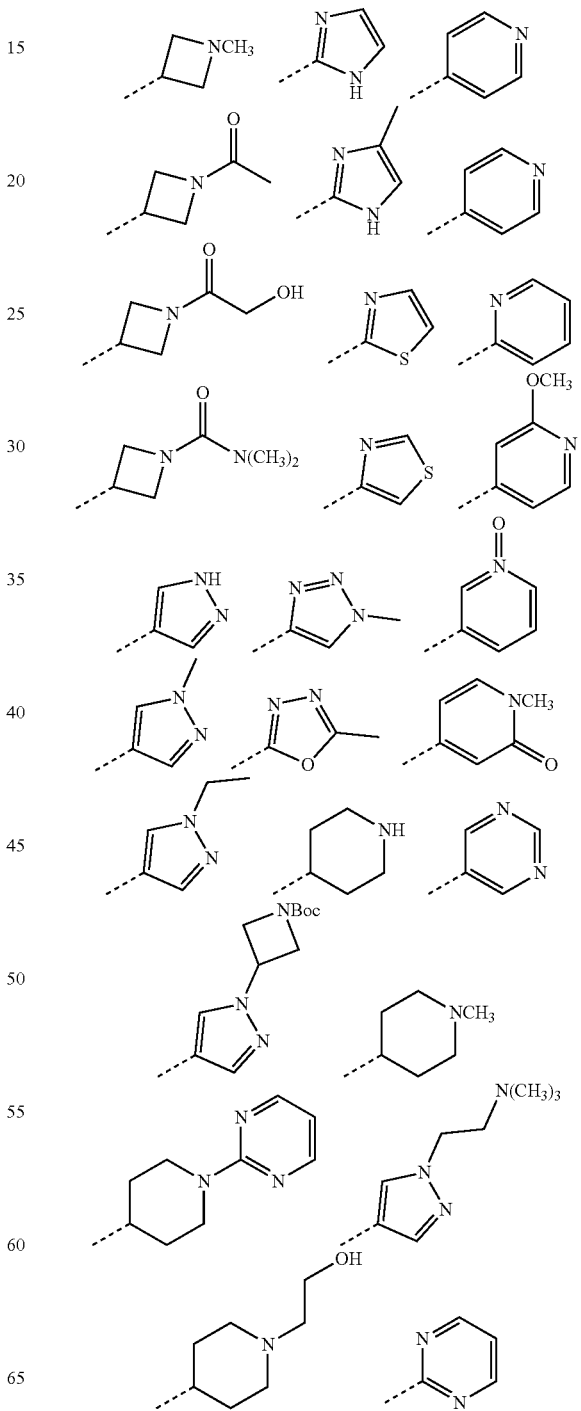

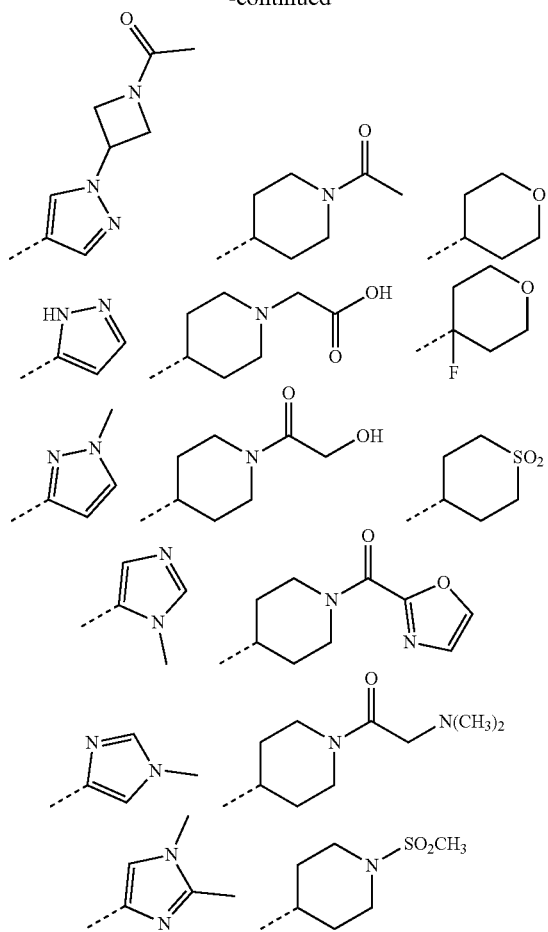

or a —CH₂-heterocyclic group with 3 to 7 ring members optionally substituted by one or more $R^z$ groups e.g. (point of attachment represented by dashed bond)

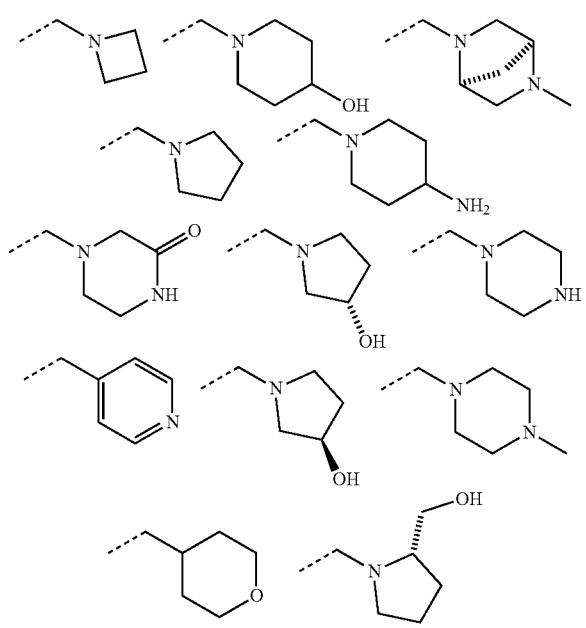

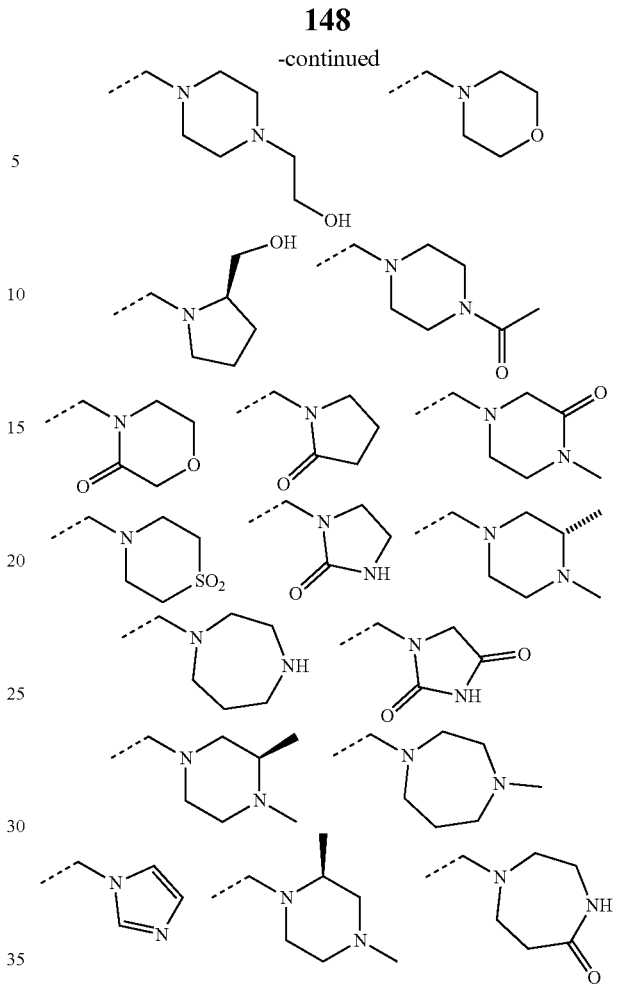

In one embodiment, the invention provides a combination comprising the compound of formula (I°) or a tautomer or a solvate or a pharmaceutically acceptable salt thereof, wherein:

Het is pyridin-2-yl or pyrimidin-2-yl;
$R^1$ is —Cl, —CN, —OH or —OMe;
n is 1;
$R^2$ is hydrogen;
$R^3$ is -(A)$_s$-(CR$^x$R$^y$)$_q$—X;
s is 0 or 1;
t is 1;
A is selected from cyclopropyl, oxetanyl and tetrahydrofuranyl;
X is selected from hydrogen, fluorine, —CN, —OH and —C(=O)NH₂,
q is 0 or 1 and $R^x$ and $R^y$ are hydrogen or deuterium;
a is 0 or 1 and $R^4$ is halogen (e.g. fluorine);
$R^5$ is halogen (e.g. Cl);
m is 1;
$R^6$ is $C_{1-4}$alkyl (e.g. methyl or ethyl);
$R^7$ is $C_{1-4}$ alkyl (e.g. methyl or ethyl), hydroxyl$C_{1-4}$alkyl (e.g. hydroxylmethyl or hydroxyethyl), methoxy$C_{1-4}$alkyl (e.g. methoxymethyl), a heterocyclic group with 5 or 6 ring members (e.g. piperidinyl, oxanyl, imidazolyl or pyrazolyl) or $C_{3-6}$cycloalkyl (e.g. cyclobutyl or cyclohexyl) wherein said heterocyclic group with 5 or 6 ring members and $C_{3-6}$cycloalkyl groups may be optionally substituted with one or two $R^z$ groups independently selected from methyl, halogen (such as fluorine), —C(=O)Me, and —OH.

In one embodiment, the invention provides a combination comprising the compound of formula (I°) or a tautomer or a solvate or a pharmaceutically acceptable salt thereof, wherein:
Het is pyridin-2-yl or pyrimidin-2-yl;
$R^1$ is —Cl, —CN, —OH or —OMe;
n is 1;
$R^2$ is hydrogen;
$R^3$ is hydrogen and s is 1;
a is 0 or 1 and $R^4$ is halogen (e.g. fluorine);
$R^5$ is halogen (e.g. Cl);
m is 1;
$R^6$ is $C_{1-4}$alkyl (e.g. methyl or ethyl);
$R^7$ is $C_{1-4}$alkyl (e.g. methyl or ethyl), hydroxyl$C_{1-4}$alkyl (e.g. hydroxylmethyl or hydroxyethyl), methoxy$C_{1-4}$alkyl (e.g. methoxymethyl), a heterocyclic group with 5 or 6 ring members (e.g. piperidinyl, oxanyl, imidazolyl or pyrazolyl) or $C_{3-6}$cycloalkyl (e.g. cyclobutyl or cyclohexyl) wherein said heterocyclic group with 5 or 6 ring members and $C_{3-13}$ cycloalkyl groups may be optionally substituted with one or two $R^z$ groups independently selected from methyl, halogen (such as fluorine), —C(=O)Me, and —OH.

In one embodiment, the invention provides a compound of formula (I°) which is one of the Examples 1-580 or is selected from the Examples 1-580 or a tautomer, N-oxide, pharmaceutically acceptable salt or solvate thereof.

In one embodiment, the invention provides a compound of formula (I°) which is one of the Examples 1-460 or is selected from the Examples 1-460 or a tautomer, N-oxide, pharmaceutically acceptable salt or solvate thereof.

In one embodiment, the invention provides a compound of formula (I°) which is one of the Examples 1-459 or is selected from the Examples 1-459 or a tautomer, N-oxide, pharmaceutically acceptable salt or solvate thereof.

In one embodiment, the invention provides a compound of formula (I°) which is selected from the following compounds, or a tautomer, N-oxide, pharmaceutically acceptable salt or solvate thereof:
(3R)-3-(4-chlorophenyl)-2-[(5-chloropyrimidin-2-yl) methyl]-4-fluoro-6-{1-hydroxy-1-[trans-4-hydroxycyclohexyl]ethyl}-3-{[1-(hydroxymethyl)cyclopropyl] methoxy}-2,3-dihydro-1H-isoindol-1-one;
2-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl] methyl}pyrimidine-5-carbonitrile;
(3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one;
6-{[(1R)-1-(4-chlorophenyl)-7-fluoro-5-[1-(4-fluorooxan-4-yl)-1-hydroxypropyl]-3-oxo-1-[(3S)-oxolan-3-yloxy]-2,3-dihydro-1H-isoindol-2-yl]methyl}pyridine-3-carbonitrile;
6-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl] methyl}pyridine-3-carbonitrile;
6-{[(1R)-1-(4-chlorophenyl)-7-fluoro-1-({1-[hydroxy($^2H_2$) methyl]cyclopropyl}($^2H_2$)methoxy)-5-[1-hydroxy-1-(1-methyl-1H-imidazol-4-yl)propyl]-3-oxo-2,3-dihydro-1H-isoindol-2-yl]methyl}pyridine-3-carbonitrile; and
(3R)-3-(4-chlorophenyl)-2-[(5-chloropyrimidin-2-yl) methyl]-4-fluoro-6-[1-hydroxy-1-(1-methylpiperidin-4-yl)propyl]-3-[(3S)-oxolan-3-yloxy]-2,3-dihydro-1H-isoindol-1-one.

In one embodiment, the invention provides a combination comprising the compound of formula (I°) which is diastereoisomer 2A and is selected from the following compounds, or a tautomer, N-oxide, pharmaceutically acceptable salt or solvate thereof:
(3R)-3-(4-chlorophenyl)-2-[(5-chloropyrimidin-2-yl) methyl]-4-fluoro-6-{1-hydroxy-1-[trans-4-hydroxycyclohexyl]ethyl}-3-{[1-(hydroxymethyl)cyclopropyl] methoxy}-2,3-dihydro-1H-isoindol-1-one;
2-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl] methyl}pyrimidine-5-carbonitrile;
(3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one;
6-{[(1R)-1-(4-chlorophenyl)-7-fluoro-5-[1-(4-fluorooxan-4-yl)-1-hydroxypropyl]-3-oxo-1-[(3S)-oxolan-3-yloxy]-2,3-dihydro-1H-isoindol-2-yl]methyl}pyridine-3-carbonitrile;
6-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl] methyl}pyridine-3-carbonitrile;
6-{[(1R)-1-(4-chlorophenyl)-7-fluoro-1-({1-[hydroxy($^2H_2$) methyl]cyclopropyl}($^2H_2$)meth oxy)-5-[1-hydroxy-1-(1-methyl-1H-imidazol-4-yl)propyl]-3-oxo-2,3-dihydro-1H-isoindol-2-yl]methyl}pyridine-3-carbonitrile; and
(3R)-3-(4-chlorophenyl)-2-[(5-chloropyrimidin-2-yl) methyl]-4-fluoro-6-[1-hydroxy-1-(1-methylpiperidin-4-yl)propyl]-3-[(3S)-oxolan-3-yloxy]-2,3-dihydro-1H-isoindol-1-one.

In one embodiment, the invention provides a combination comprising the compound of formula (I°) which is diastereoisomer 2B and is selected from the following compounds, or a tautomer, N-oxide, pharmaceutically acceptable salt or solvate thereof:
(3R)-3-(4-chlorophenyl)-2-[(5-chloropyrimidin-2-yl) methyl]-4-fluoro-6-{1-hydroxy-1-[trans-4-hydroxycyclohexyl]ethyl}-3-{[1-(hydroxymethyl)cyclopropyl]neth oxy}-2,3-dihydro-1H-isoindol-1-one;
2-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl] methyl}pyrimidine-5-carbonitrile;
(3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one;
6-{[(1R)-1-(4-chlorophenyl)-7-fluoro-5-[1-(4-fluorooxan-4-yl)-1-hydroxypropyl]-3-oxo-1-[(3S)-oxolan-3-yloxy]-2,3-dihydro-1H-isoindol-2-yl]methyl}pyridine-3-carbonitrile;
6-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl] methyl}pyridine-3-carbonitrile;
6-{[(1R)-1-(4-chlorophenyl)-7-fluoro-1-({1-[hydroxy($^2H_2$) methyl]cyclopropyl}($^2H_2$)meth oxy)-5-[1-hydroxy-1-(1-methyl-1H-imidazol-4-yl)propyl]-3-oxo-2,3-dihydro-1H-isoindol-2-yl]methyl}pyridine-3-carbonitrile; and
(3R)-3-(4-chlorophenyl)-2-[(5-chloropyrimidin-2-yl) methyl]-4-fluoro-6-[1-hydroxy-1-(1-methylpiperidin-4-yl)propyl]-3-[(3S)-oxolan-3-yloxy]-2,3-dihydro-1H-isoindol-1-one.

In one embodiment, the invention provides a combination comprising the compound of formula (I°) which is selected from the following compounds, or a tautomer, N-oxide, pharmaceutically acceptable salt or solvate thereof:
(3R)-3-(4-chlorophenyl)-2-[(5-chloropyrimidin-2-yl)methyl]-4-fluoro-6-[2-hydroxy-1-(4-methylpiperazin-1-yl)butan-2-yl]-3-[(3S)-oxolan-3-yloxy]-2,3-dihydro-1H-isoindol-1-one;
(3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one;
1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile;
(3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[cis-3-hydroxycyclobutoxy]-2,3-dihydro-1H-isoindol-1-one; and
(3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[(2R)-2-hydroxypropoxy]-2,3-dihydro-1H-isoindol-1-one.

In one embodiment, the invention provides a combination comprising the compound of formula (I°) which is 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile, or a tautomer, N-oxide, pharmaceutically acceptable salt or solvate thereof.

In one embodiment, the invention provides a combination comprising the compound of formula (I°) which is (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one, or a tautomer, N-oxide, pharmaceutically acceptable salt or solvate thereof.

In one embodiment, the invention provides a combination comprising the compound of formula (I°) which is diastereoisomer 2A and is 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile, or a tautomer, N-oxide, pharmaceutically acceptable salt or solvate thereof.

In one embodiment, the invention provides a combination comprising the compound of formula (I°) which is diastereoisomer 2A and is (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one, or a tautomer, N-oxide, pharmaceutically acceptable salt or solvate thereof.

In one embodiment, the invention provides a combination comprising the compound of formula (I°) which is diastereoisomer 2B and is 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile, or a tautomer, N-oxide, pharmaceutically acceptable salt or solvate thereof.

In one embodiment, the invention provides a combination comprising the compound of formula (I°) which is diastereoisomer 2B and is (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one, or a tautomer, N-oxide, pharmaceutically acceptable salt or solvate thereof.

In one embodiment the compound of formula (I°) is (3R)-3-(4-chlorophenyl)-2-[(5-chloropyrimidin-2-yl)methyl]-4-fluoro-6-[(1S)-1-(4-fluoro-1-methylpiperidin-4-yl)-1-hydroxypropyl]-3-methoxy-2,3-dihydro-1H-isoindol-1-one, or a tautomer, N-oxide, pharmaceutically acceptable salt or solvate thereof.

In one embodiment the compound of formula (I°) is (3R)-3-(4-chlorophenyl)-2-[(5-chloropyrimidin-2-yl)methyl]-4-fluoro-6-[(1R)-1-(4-fluoro-1-methylpiperidin-4-yl)-1-hydroxypropyl]-3-methoxy-2,3-dihydro-1H-isoindol-1-one, or a tautomer, N-oxide, pharmaceutically acceptable salt or solvate thereof.

In one embodiment the compound of formula (I°) is 1-({[(1R)-1-(4-chlorophenyl)-2-[(5-chloropyrimidin-2-yl)methyl]-7-fluoro-5-[(1S)-1-(4-fluoro-1-methylpiperidin-4-yl)-1-hydroxypropyl]-3-oxo-2,3-dihydro-1H-isoindol-1-yl]oxy}methyl)cyclopropane-1-carbonitrile, or a tautomer, N-oxide, pharmaceutically acceptable salt or solvate thereof.

In one embodiment the compound of formula (I°) is 1-({[(1R)-1-(4-chlorophenyl)-2-[(5-chloropyrimidin-2-yl)methyl]-7-fluoro-5-[(1R)-1-(4-fluoro-1-methylpiperidin-4-yl)-1-hydroxypropyl]-3-oxo-2,3-dihydro-1H-isoindol-1-yl]oxy}methyl)cyclopropane-1-carbonitrile, or a tautomer, N-oxide, pharmaceutically acceptable salt or solvate thereof.

For the avoidance of doubt, it is to be understood that each general and specific embodiment and example for one substituent may be combined with each general and specific embodiment and example for one or more, in particular all, other substituents as defined herein and that all such embodiments are embraced by this application.

The combinations include a compound which is SGI-110:

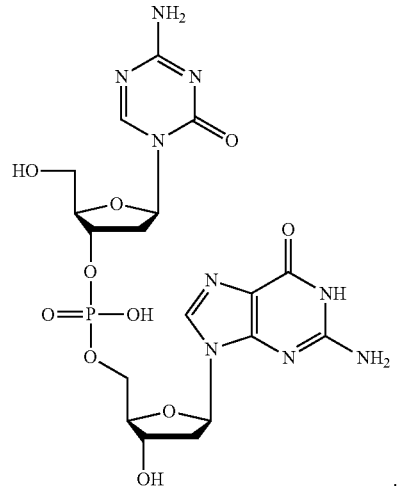

(SGI-110)

SGI-110 is 2'-deoxy-5-azacytidylyl-(3'5')-2'-deoxyguanosine or guadecitabine.

In particular, SGI-110 is present as the sodium salt. Alternatively, SGI-110 is present as the free compound i.e. is not a pharmaceutically acceptable salt.

Particular Combination

In particular, the invention provides a combination comprising: (i) (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, or a tautomer, N-oxide, pharmaceutically acceptable salt or solvate thereof; and (ii) SGI-110 or a tautomer, N-oxide, pharmaceutically acceptable salt or solvate thereof.

Salts, Solvates, Tautomers, Isomers, N-Oxides, Esters, Prodrugs and Isotopes

A reference to any compound herein also includes ionic forms, salts, solvates, isomers (including geometric and stereochemical isomers unless specified), tautomers, N-oxides, esters, prodrugs, isotopes and protected forms thereof, for example, as discussed below; in particular, the salts or tautomers or isomers or N-oxides or solvates thereof; and more particularly the salts or tautomers or N-oxides or solvates thereof. In one embodiment reference to a compound also includes the salts or tautomers or solvates thereof.

Salts

The compounds can exist in the form of salts, for example acid addition salts or, in certain cases salts of organic and inorganic bases such as carboxylate, sulfonate and phosphate salts. All such salts are within the scope of this invention, and references to compounds of the formula (I°) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), a-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)- DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

In one embodiment, the compound of formula (I°) is the tris(hydroxymethyl)aminomethane (TRIS) salt.

If the compound is anionic, or has a functional group which may be anionic (e.g., —COOH may be —COO⁻ and —OH may be —O⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

In one embodiment, SGI-110 is the sodium salt.

Where the compounds contain an amine function, these may form quaternary ammonium salts, for example by reaction with an alkylating agent according to methods well known to the skilled person. Such quaternary ammonium compounds are within the scope of formula (I°).

The compounds may exist as mono- or di-salts depending upon the pKa of the acid from which the salt is formed.

The salt forms of the compounds are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms, which may be useful, for example, in the purification or separation of the compounds of the invention, also form part of the invention.

In one embodiment of the invention, there is provided a pharmaceutical composition comprising a solution (e.g. an aqueous solution) containing a compound as described herein in the form of a salt in a concentration of greater than 10 mg/ml, typically greater than 15 mg/ml and typically greater than 20 mg/ml.

N-Oxides

Compounds containing an amine function may also form N-oxides. A reference herein to a compound that contains an amine function also includes the N-oxide.

Where a compound contains several amine functions one, or more than one, nitrogen atom may be oxidised to form an N-oxide. Particular examples of N-oxides are the N-oxides of a tertiary amine or a nitrogen atom of a nitrogen-containing heterocyclic group.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

In one embodiment of the invention, the compound is an N-oxide, e.g. from a nitrogen atom on the $R^6$ or $R^7$ group, for example a pyridine N-oxide.

Geometric Isomers and Tautomers

The compounds may exist in a number of different geometric isomeric, and tautomeric forms and references to compounds of the formula (I°) include all such forms. For the avoidance of doubt, where a compound can exist in one of several geometric isomeric or tautomeric forms and only one is specifically described or shown, all others are nevertheless embraced by the invention.

For example, certain heteroaryl rings can exist in the two tautomeric forms such as A and B shown below. For simplicity, a formula may illustrate one form but the formula is to be taken as embracing both tautomeric forms.

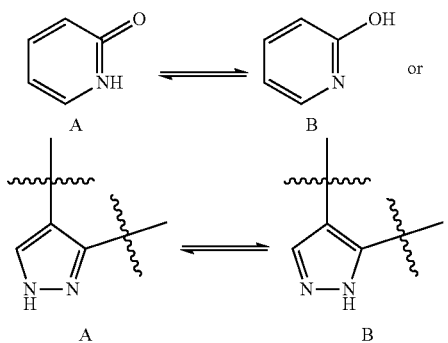

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

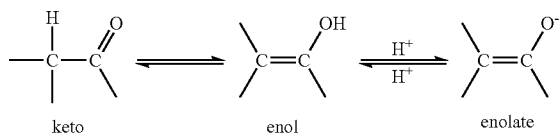

Stereoisomers

Unless otherwise mentioned or indicated, the chemical designation of compounds denotes the mixture of all possible stereochemically isomeric forms.

Compounds of Formula (I°)

Stereocentres are illustrated in the usual fashion, using 'hashed' or 'solid' wedged lines. e.g.

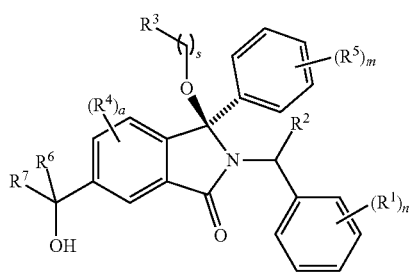

Where a compound is described as a mixture of two diastereoisomers/epimers, the configuration of the stereocentre is not specified and is represented by straight lines.

Where compounds contain one or more chiral centres, and can exist in the form of two or more optical isomers, references to compounds include all optical isomeric forms thereof (e.g. enantiomers, epimers and diastereoisomers), either as individual optical isomers, or mixtures (e.g. racemic or scalemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomers by preferential crystallisation, and then dissociating the salts to give the individual enantiomer of the free base.

Additionally enantiomeric separation can be achieved by covalently linking a enantiomerically pure chiral auxiliary onto the compound and then performing diastereoisomer separation using conventional methods such as chromatography. This is then followed by cleavage of the aforementioned covalent linkage to generate the appropriate enantiomerically pure product.

Where compounds exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, the invention provides compositions containing a compound of the invention having one or more chiral centres, wherein at least 55% (e.g. at least 60%, 65%, 70%, 75%, 80%, 85%, 90% or 95%) of the compound of the formula (I°) is present as a single optical isomer (e.g. enantiomer or diastereoisomer). In one general embodiment, 99% or more (e.g. substantially all) of the total amount of the compound of the formula (I°) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds which are stereochemically pure. When a compound is for instance specified as R, this means that the compound is substantially free of the S isomer. If a compound is for instance specified as E, this means that the compound is substantially free of the Z isomer. The terms cis, trans, R, S, E and Z are well known to a person skilled in the art.

SGI-110

The compound SGI-110 (2'-deoxy-5-azacytidylyl-(3"→5)-2'-deoxy-guanosine or guadecitabine) is a single stereoisomer, with its chirality depicted in the standard way herein:

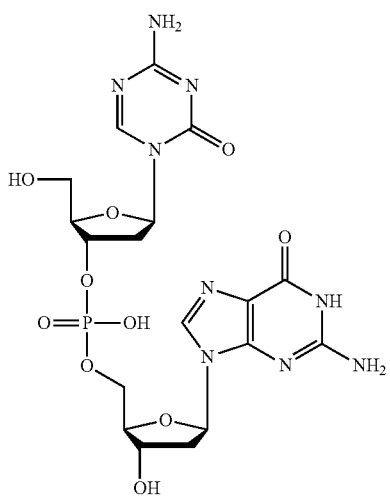

Isotopic Variations

The present invention includes all pharmaceutically acceptable isotopically-labeled compounds, i.e. compounds, wherein one or more atoms are replaced by atoms having the same atomic number, but an atomic mass or mass number different from the atomic mass or mass number usually found in nature.

Examples of isotopes suitable for inclusion in the compounds comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds, for example, those incorporating a radioactive isotope, are useful in drug and/or substrate tissue distribution studies. The compounds can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be used in some circumstances.

In particular, every reference to hydrogen in the application should be constructed to cover $^1$H and $^2$H, whether hydrogen is defined explicitly, or hydrogen is present implicitly to satisfy the relevant atom's (in particular carbon's) valency.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters, acyloxy esters and phosphate esters of the compounds bearing a carboxylic acid group or a hydroxyl group are also embraced. Examples of esters are compounds containing the group —C(=O)OR, wherein R is an ester substituent, for example, a $C_{1-7}$ alkyl group, a $C_{3-12}$ heterocyclyl group, or a $C_{5-12}$ aryl group, typically a $C_{1-6}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-6}$ alkyl group, a $C_{3-12}$ heterocyclyl group, or a $C_{5-12}$ aryl group, typically a $C_{1-6}$ alkyl group. Particular examples of acyloxy groups include, but are not limited to, —OC(=O)CH$_3$ (acetoxy), —OC(=O)CH$_2$CH$_3$, —OC(=O)C($C_{1-13}$)$_3$, —OC(=O)Ph, and —OC(=O)CH$_2$Ph. Examples of phosphate esters are those derived from phosphoric acid.

In one embodiment of the invention, the compounds include esters of the compounds bearing a carboxylic acid group or a hydroxyl group. In another embodiment of the invention, the compounds do not include within their scope esters of the compounds bearing a carboxylic acid group or a hydroxyl group.

Solvates and Crystalline Forms

Also encompassed by the compounds are any polymorphic forms of the compounds, and solvates such as hydrates, alcoholates and the like.

The compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation conditions that include an amount of the solvent required for the particular solvate. Thereafter the standard methods described herein, can be used to establish whether solvates had formed.

Furthermore, the compounds of the present invention may have one or more polymorph or amorphous crystalline forms and as such are intended to be included in the scope of the invention.

Complexes

The compounds also includes within their scope complexes (e.g. inclusion complexes or clathrates with compounds such as cyclodextrins, or complexes with metals) of the compounds. Inclusion complexes, clathrates and metal complexes can be formed by means of methods well known to the skilled person.

Prodrugs

Also encompassed by the compounds are any pro-drugs of the compounds. By "prodrugs" is meant for example any compound that is converted in vivo into the biologically active compounds.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is: $C_{1-7}$alkyl (e.g., -Me, -Et, -nPr, -iPr, -nBu, -sBu, -iBu, -tBu);

$C_{1-7}$ aminoalkyl (e.g., aminoethyl; 2-(N,N-diethylamino) ethyl; 2-(4-morpholino)ethyl); and acyloxy-$C_{1-7}$ alkyl (e.g., acyloxymethyl; acyloxyethyl; pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-oxanyloxy) carbonyloxymethyl; 1-(4-oxanyloxy)carbonyloxyethyl; (4-oxanyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative. In one embodiment formula (I°) does not include pro-drugs of the compounds of the formula (I°) within its scope.

Methods for the Preparation of Compounds of the Invention

Compounds of the Formula (I°)

In this section, as in all other sections of this application unless the context indicates otherwise, references to formula I° also include all other subformulae and examples thereof as defined herein, unless the context indicates otherwise.

Compounds of the formula (I°) can be prepared in accordance with synthetic methods well known to the skilled person.

The required intermediates are either commercially available, known in the literature, prepared by methods analogous to those in the literature or prepared by methods analogous to those described in the example experimental procedures below. Other compounds may be prepared by functional group interconversion of the groups using methods well known in the art.

General processes for preparing, isolating and purifying the compounds wherein cyc is phenyl can be found in international patent application no PCT/GB2016/053042 which was published as WO 2017/055860 on Jun. 4, 2017:

General processes for preparing, isolating and purifying the compounds wherein cyc is Het can be found in international patent application no PCT/GB2016/053041 which was published as WO 2017/055859 on Jun. 4, 2017:

SGI-110

The sodium salt of SGI-110 was prepared as described in U.S. Pat. No. 7,700,567 (the content of which is hereby incorporated by reference) by coupling a protected 2'-deoxyguanosine (where $R_1$=carbamate protective group) with a phosphoramidite building block:

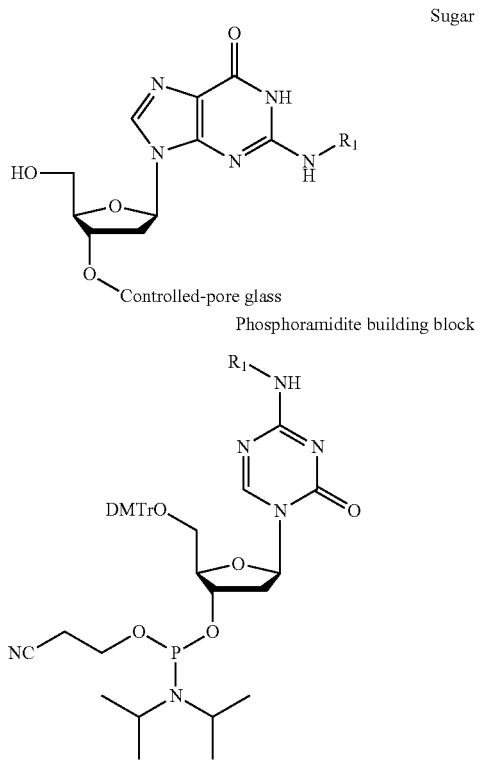

Biological Effects

The compounds of formula (I°), subgroups and examples thereof, have been shown to inhibit the interaction of p53 with MDM2. Such inhibition leads to cell proliferative arrest and apoptosis, which may be useful in preventing or treating disease states or conditions.

The compounds have been shown to be good inhibitors of the formation of MDM2-p53 complex. The antagonist compounds of formula (I°) are capable of binding to MDM2 and exhibiting potency for MDM2. The efficacies of the compounds have been determined against MDM2/p53 using the assay protocol described herein and other methods known in the art. More particularly, the compounds of the formula (I°) and sub-groups thereof have affinity for MDM2/p53.

Certain compounds of the invention are those having $IC_{50}$ values of less than 0.1 µM in particular less than 0.01 or 0.001 µM.

MDM2/p53 function has been implicated in many diseases due to its role in a variety of process for example vascular remodelling and antiangiogenic processes and regulation of metabolic pathways, as well as in oncogenesis.

As a consequence of their affinity for MDM2 it is anticipated that the compounds may prove useful in treating or preventing a range of diseases or conditions including autoimmune conditions; diabetes mellitus; chronic inflammatory diseases, for example lupus nephritis, systemic lupus erythematosus (SLE), autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; hyperkeratotic diseases such as autosomal recessive congenital ichthyosis (ARCI); kidney diseases including glomerular disorders, chronic kidney disease (CKD) renal inflammation, podocyte loss, glomerulosclerosis, proteinuria, and progressive kidney disease; cardiovascular diseases for example cardiac hypertrophy, restenosis, arrhythmia, atherosclerosis; ischemic injury associated myocardial infarctions, vascular injury, stroke and reperfusion injury; vascular proliferative diseases; ocular diseases such as age-related macular degeneration in particular wet form of age-related macular degeneration, ischemic proliferative retinopathies such as retinopathy of prematurity (ROP) and diabetic retinopathy, and hemangioma.

SGI-110 is a DNA hypomethylating agent (HMA) that induces global and gene-specific DNA hypomethylation.

Thus, it is envisaged that the combinations will be useful in medicine or therapy. For example, the combinations of the invention are expected to be useful in treating the diseases and conditions discussed below and the diseases and conditions described in the "Background of the Invention" section above.

Thus, for example, it is envisaged that the combinations may be useful in alleviating or reducing the incidence of cancer.

The combinations may be useful for the treatment of the adult population. The combinations may be useful for the treatment of the pediatric population.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, bowel, colorectal, rectum and anus), liver (hepatocellular carcinoma), gall bladder and biliary system, exocrine pancreas, kidney (for example renal cell carcinoma), lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, testes, cervix, myometrium, endometrium, thyroid (for example thyroid follicular carcinoma), brain, adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas (e.g. gliomas), neuromas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Growth of cells is a closely controlled function. Cancer, a condition of abnormal cell growth, results when cells replicate in an uncontrolled manner (increasing in number), uncontrollably grow (getting larger) and/or experience reduced cell death by apoptosis (programmed cell death), necrosis, or annoikis. In one embodiment abnormal cell growth is selected from uncontrolled cell proliferation, excessive cell growth or reduced programmed cell death. In particular, the condition or disease of abnormal cell growth is a cancer.

Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. Compounds of the invention may therefore be useful in preventing and disrupting initiation of tumour angiogenesis.

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage. In diabetes (and in many different eye diseases), new vessels invade the macula or retina or other ocular structures, and may cause blindness. The process of atherosclerosis has been linked to angiogenesis. Tumor growth and metastasis have been found to be angiogenesis-dependent. The combinations may be beneficial in the treatment of diseases such as cancer and metastasis, ocular diseases, arthritis and hemangioma.

Therefore, the combinations may be useful in the treatment of metastasis and metastatic cancers. Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body. In particular, the compounds of the invention may be useful in the treatment of metastasis and metastatic cancers.

In one embodiment the haematological malignancies is a leukaemia. In another embodiment the haematological malignancies is a lymphoma. In one embodiment the cancer is AML. In another embodiment the cancer is CLL.

In one embodiment the combination is for use in the prophylaxis or treatment of leukemia, such as acute or chronic leukaemia, in particular acute myeloid leukaemia (AML), acute lymphocytic leukaemia (ALL), chronic lymphocytic leukaemia (CLL), or chronic myeloid leukaemia (CML). In one embodiment the compound of the invention is for use in the prophylaxis or treatment of lymphoma, such as acute or chronic lymphoma, in particular Burkitt lymphoma, Hodgkin lymphoma, non-Hodgkin lymphoma or difuse large B-cell lymphoma.

In one embodiment the combination is for use in the prophylaxis or treatment of acute myeloid leukaemia (AML) or acute lymphocytic leukaemia (ALL).

In one embodiment the combination is for use in the prophylaxis or treatment of acute myeloid leukaemia (AML). In another embodiment the patient to be treated is selected from a sub-population possessing cancers which are p53 wild type.

In another embodiment the combination is used to treat biphenotypic B myelomonocytic leukemia.

One embodiment includes a combination for use in the prophylaxis or treatment of cancer in a patient selected from a sub-population possessing cancers which are p53 wild-type or have an MDM2 amplification The cancers may be cancers which are sensitive to treatment with MDM2 inhibitors. The cancers may be cancers which overexpress MDM2. The cancer may be cancers which are p53 wild-type.

Particular cancers include those with an MDM2 amplification and/or MDM2 overexpression, for example, hepatocellular carcinoma, lung, sarcomas, osteosarcomas, and Hodgkin disease.

Particular cancers include those with wild-type p53. Particulars cancers include those cancer cells with wild-type p53, particularly but not exclusively, if MDM2 is highly expressed.

In one embodiment the cancer is a p53 functional tumours. In one embodiment this disease to be treated is p53 functional solid and haematological malignancies. In another embodiment the patient to be treated has p53 mutant tumour for example AML patients with p53 mutant tumour.

In one embodiment the cancer is a tumour of the brain, for example glioma, or neuroblastoma.

In one embodiment the cancer is a cancer of the skin, for example melanoma.

In one embodiment the cancer is a cancer of the lung, for example mesothelioma. In one embodiment the mesothelioma is malignant peritoneal mesothelioma or malignant pleural mesothelioma.

In one embodiment the cancer is a cancer of the gastrointestinal tract, for example GIST, gastric, colorectal or bowel.

In one embodiment the cancer is osteosarcoma.

In one embodiment the cancer is liposarcoma.

In one embodiment the cancer is Ewing's sarcoma.

In one embodiment, the cancer is liposarcoma, soft tissue sarcoma, osteosarcoma, oesophageal cancer, and certain paediatric malignancies including B-cell malignancies.

In one embodiment, the cancer is colorectal, breast, lung and brain

In one embodiment, the cancer is a paediatric cancer.

Whether a particular cancer is one which is sensitive to MDM2 inhibitors, may be determined by a method as set out in the section headed "Methods of Diagnosis".

A further aspect provides the use of a combination for the manufacture of a medicament for the treatment of a disease or condition as described herein, in particular cancer.

Certain cancers are resistant to treatment with particular drugs. This can be due to the type of the tumour (most common epithelial malignancies are inherently chemoresistant and prostate is relatively resistant to currently available regimens of chemotherapy or radiation therapy) or resistance can arise spontaneously as the disease progresses or as a result of treatment. In this regard, references to prostate includes prostate with resistance towards anti-androgen therapy, in particular abiraterone or enzalutamide, or castrate-resistant prostate. Similarly references to multiple myeloma includes bortezomib-insensitive multiple myeloma or refractory multiple myeloma and references to chronic myelogenous leukemia includes imitanib-insensitive chronic myelogenous leukemia and refractory chronic myelogenous leukemia. In this regard, references to mesothelioma includes mesothelioma with resistance towards topoisomerase poisons, alkylating agents, antitubulines, antifolates, platinum compounds and radiation therapy, in particular cisplatin-resistant mesothelioma.

The compounds may also be useful in the treatment of tumour growth, pathogenesis, resistance to chemo- and radio-therapy by sensitising cells to chemotherapy and as an anti-metastatic agent.

Therapeutic anticancer interventions of all types necessarily increase the stresses imposed on the target tumour cells. Inhibitors of MDM2/p53 represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

In one embodiment the invention provides a combination for use in the treatment of a disease or condition which is mediated by MDM2. In a further embodiment the disease or condition which is mediated by MDM2 is a cancer which is characterised by overexpression and/or increased activity of MDM2, or high copy number MDM2 and/or wildtype p53.

A further aspect provides the use of a combination for the manufacture of a medicament for the treatment of a disease or condition as decribed herein, in particular cancer.

In one embodiment there is provided a combination for use in the prophylaxis or treatment of a disease or condition mediated by MDM2/p53. In one embodiment there is provided a combination for inhibiting the interaction between of MDM2 protein with p53.

In one embodiment there is provided a pharmaceutical composition comprising an effective amount of at least one combination as defined.

In one embodiment there is provided a method for the prophylaxis or treatment of cancer comprising the steps of administering to a mammal a medicament comprising at least one combination as defined herein.

In particular, the combinations of the invention are useful for the prophylaxis or treatment of acute myeloid leukaemia (AML).

Myelodysplastic syndromes (MDS) are heterogeneous clonal haematopoietic stem cell disorders associated with the presence of dysplastic changes in one or more of the haematopoietic lineages, including dysplastic changes in the myeloid, erythroid, and megakaryocytic series. These changes result in cytopenias in one or more of the three lineages. Subjects afflicted with MDS typically develop complications related to anaemia, neutropenia (infections), or thrombocytopenia (bleeding). Generally, from about 10% to about 70% of subjects with MDS develop acute leukemia. Representative myelodysplastic syndromes include acute myeloid leukemia, acute promyelocytic leukemia, acute lymphoblastic leukemia, and chronic myelogenous leukemia.

Acute myeloid leukemia (AML) is the most common type of acute leukemia in adults. Several inherited genetic disorders and immunodeficiency states are associated with an increased risk of AML. These include disorders with defects in DNA stability leading to random chromosomal breakage, such as Bloom's syndrome, Fanconi's anaemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15; 17 chromosomal translocation. This translocation leads to the generation of a fusion transcript comprising a retinoic acid receptor sequence and a promyelocytic leukemia sequence.

Acute lymphoblastic leukemia (ALL) is a heterogeneous disease with distinct clinical features displayed by various subtypes. Reoccurring cytogenetic abnormalities have been demonstrated in ALL. The most common associated cytogenetic abnormality is the 9; 22 translocation leading to development of the Philadelphia chromosome.

Chronic myelogenous leukemia (CML) is a clonal myeloproliferative disorder of a pluripotent stem cell, generally caused by ionizing radiation. CML is characterized by a specific chromosomal abnormality involving the translocation of chromosomes 9 and 22, creating the Philadelphia chromosome.

Combinations disclosed hererin can be used to provide therapy for a MDS. In some embodiments, a combination thereof can provide therapy for more than one MDS in a single administration.

In some embodiments, the invention provides a method for treating a myelodysplastic syndrome (MDS).

In some embodiments, the invention provides a method for treating one or more myelodysplastic syndromes, leukemia, or solid tumours. In some embodiments, the invention provides a method for treating acute myeloid leukemia (AML). In some embodiments, the invention provides a method for treating acute promyelocytic leukemia (APML) in a subject. In some embodiments, the invention provides a method for treating acute lymphoblastic leukemia (ALL). In some embodiments, the invention provides a method for treating chronic myelogenous leukemia (CML).

In some embodiments, the myelodysplastic syndrome is acute myeloid leukemia (AML), acute promyelocytic leukemia (APL), acute lymphoblastic leukemia (ALL), or chronic myelogenous leukemia (CML).

In some embodiments, the administration is subcutaneous.

Methods of Diagnosis

Prior to administration of a combination, a patient may be screened to determine whether a disease or condition from which the patient is or may be suffering is one which would be susceptible to treatment with a combination of the invention. The term 'patient' includes human and veterinary subjects such as primates, in particular human patients.

For example, a biological sample taken from a patient may be analysed to determine whether a condition or disease, such as cancer, that the patient is or may be suffering from is one which is characterised by a genetic abnormality or abnormal protein expression which leads to up-regulation of the levels of MDM2 or to upregulation of a biochemical pathway downstream of MDM2/p53.

Examples of such abnormalities that result in activation or sensitisation of MDM2, loss of, or inhibition of regulatory pathways impacting on MDM2 expression, up-regulation of receptors or their ligands, cytogenetic aberrations or presence of mutant variants of the receptors or ligands. Tumours with up-regulation of MDM2/p53, in particular over-expression of MDM2 or exhibit wild-type p53, may be particularly sensitive to inhibitors of MDM2/p53. For example, amplification of MDM2 and/or deletion of its negative regulator such as p14ARF has been identified in a range of cancers as discussion in the Introduction section.

The term up-regulation includes elevated expression or over-expression, including gene amplification (i.e. multiple gene copies), cytogenetic aberration and increased expression by a transcriptional or posttranslational effect. Thus, the patient may be subjected to a diagnostic test to detect a marker characteristic of up-regulation of MDM2. The term diagnosis includes screening. By marker we include genetic markers including, for example, the measurement of DNA composition to identify presence of mutations in p53 or amplification MDM2 or deletion (loss) of p14ARF. The term marker also includes markers which are characteristic of up regulation of MDM2/p53, including protein levels, protein state and mRNA levels of the aforementioned proteins. Gene amplification includes greater than 7 copies, as well as gains of between 2 and 7 copies.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal smears, skin biopsy or urine.

Methods of identification and analysis of cytogenetic aberration, genetic amplification, mutations and up-regulation of proteins are known to a person skilled in the art. Screening methods could include, but are not limited to, standard methods such as DNA sequence analysis by conventional Sanger or next-generation sequencing methods, reverse-transcriptase polymerase chain reaction (RT-PCR), RNA sequencing (RNAseq), nanostring hybridisation proximity RNA nCounter assays, or in-situ hybridization such as fluorescence in situ hybridization (FISH) or allele-specific polymerase chain reaction (PCR).

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Certain probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), BMC Cancer, 3:3). Briefly, the protocol is as follows: double-stranded cDNA is synthesized from total RNA using a (dT)24 oligomer for priming first-strand cDNA synthesis from polyadenylated mRNA, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight to gene-specific oligonucleotide probes on Human Genome Arrays. Alternatively, single nucleotide polymorphism (SNP) arrays, a type of DNA microarray, can be used to detect polymorphisms within a population.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins e.g. capillary electrophoresis. Detection methods would include the use of site specific antibodies. The skilled person will recognize that all such well-known techniques can be used for detection of upregulation of MDM2 and p53, detection of MDM2 or p53 variants or mutants, or loss of negative regulators of MDM2 in the present case.

Abnormal levels of proteins such as MDM2 or p53 can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured. Assay methods also include the use of markers.

In other words, p53 and MDM2 overexpression can be measured by tumour biopsy.

Methods for assessing gene copy changes include techniques commoly used in cytogenetic laboratories such as MLPA (Multiplex Ligation-dependent Probe Amplification) a multiplex PCR method detecting abnormal copy numbers, or other PCR techniques which can detect gene amplification, gain and deletion.

Ex-functional assays could also be utilised where appropriate, for example measurement of circulating leukemia cells in a cancer patient, to assess the response to challenge with an MDM2/p53 inhibitor.

Therefore all of these techniques could also be used to identify tumours particularly suitable for treatment with the compounds of the invention.

Therefore in a further aspect of the invention includes use of a combination according to the invention for the manufacture of a medicament for the treatment or prophylaxis of a disease state or condition in a patient who has been screened and has been determined as suffering from, or being at risk of suffering from, a disease or condition which would be susceptible to treatment with an MDM2/p53 inhibitor.

Another aspect of the invention includes a combination of the invention for use in the prophylaxis or treatment of cancer in a patient selected from a sub-population possessing amplification of MDM2.

Another aspect of the invention includes a combination of the invention for use in the prophylaxis or treatment of cancer in a patient selected from a sub-population possessing p53 wild-type.

Another aspect of the invention includes a combination of the invention for use in the prophylaxis or treatment of cancer in a patient possessing loss of a MDM2 negative regulator such as p14ARF.

MRI determination of vessel normalization (e.g. using MRI gradient echo, spin echo, and contrast enhancement to measure blood volume, relative vessel size, and vascular permeability) in combination with circulating biomarkers may also be used to identify patients suitable for treatment with a compound of the invention.

Thus a further aspect of the invention is a method for the diagnosis and treatment of a disease state or condition mediated by MDM2/p53, which method comprises (i) screening a patient to determine whether a disease or condition from which the patient is or may be suffering is one which would be susceptible to treatment with MDM2/p53 inhibitor; and (ii) where it is indicated that the disease or condition from which the patient is thus susceptible, thereafter administering to the patient a combination as defined herein.

Advantages of the Combinations

The combinations of the invention may have a number of advantages over prior art compounds and combinations.

Each compound in the combinations of the invention may have particular advantage in one or more of the following aspects:

(i) Superior potency;
(ii) Superior in vivo efficacy
(iii) Superior PK;
(iv) Superior metabolic stability;
(v) Superior oral bioavailabilty; and
(vi) Superior physiochemical properties.

Superior Potency and In Vivo Efficacy

The compounds of the formula (I°) have increased affinity for MDM2 and in particular increased cell potency against cell lines known to be sensitive to MDM2 antagonists.

Enhanced target engagement is a highly desirable property in a pharmaceutical compound as it allows for a reduced dosage of drug and a good separation ('therapeutic window') between MDM2 activity and toxic effects.

The compounds of the formula (I°) have improved cell potency and/or improved selectivity for p53 WT vs mutant p53 cell lines. As a result of increased potency against MDM2 compounds of the invention may have increased in vivo efficacy in cancer cell lines and in vivo models. In addition the compounds show selectivity for MDM2 over MDMX, despite the close sequence, structural and functional similarity between these genetic paralogues.

Superior PK and Metabolic Stability

The compounds of the combination may have advantageous ADMET properties for example better metabolic stability (for example as determined with mouse liver microsomes), a better P450 profile, short half-life and/or beneficial clearance (e.g. low or high clearance). It has also been found that many compounds have an improved PK profile.

These features could confer the advantage of having more drug available in the systemic circulation to reach the appropriate site of action to exert its therapeutic effect. Increased drug concentrations to exert pharmacological action in tumours potentially leads to improved efficacy which thereby allows reduced dosages to be administered. Thus, the compounds should exhibit reduced dosage requirements and should be more readily formulated and administered.

This results in a good separation ('therapeutic window') between MDM2 activity and toxic effects. Many compounds of the formula (I°) have a reduction in Cmax required for efficacy (due to better MDM2 potency and/or PK).

Superior Oral Bioavailability

Potentially the compounds of the combination have physiochemical properties suitable for oral exposure (oral exposure or AUC). In particular, compounds may exhibit improved oral bioavailability or improved reproducibility of oral absorption. Oral bioavailability can be defined as the ratio (F) of the plasma exposure of a compound when dosed by the oral route to the plasma exposure of the compound when dosed by the intravenous (i.v.) route, expressed as a percentage.

Compounds having an oral bioavailability (F value) of greater than 10%, 20% or 30%, more particularly greater than 40%, are particularly advantageous in that they may be administered orally rather than, or as well as, by parenteral administration.

Superior Physiochemical Properties

The compounds of the combination may have advantageous physiochemical properties in particular chemical stability in acidic conditions and reduced lipophilicity.

Lipophilicity can be measured using a partition-coefficient (logP) or a distribution-coefficient (logD). The partition coefficient is a ratio of concentrations of un-ionized compound between two immiscible phases (n-octanol and water) at equilibrium whereas the distribution coefficient is the ratio of the sum of the concentrations of all forms of the compound (ionized plus un-ionized) in each of the two phases. High lipophilicity is associated with poor drug like properties such us low aqueous solubility, poor pharmacokinetics properties (low oral bioavailability), undesired drug metabolism and high promiscuity. Compounds with optimal lipophilicity might have greater chances of success in drug development. However redued logP (or calculated logP, clogP) can be challenging to achieve whilst retaining an acceptable level of potency for inhibition of protein-protein interactions (PPIs) due to the lipophilic nature of the targets involved.

Pharmaceutical Formulations

While it is possible for the active compounds in the combinations of the invention to be administered without any accompanying pharmaceutical excipients or carriers, it is preferable to present them in the form of pharmaceutical compositions (e.g. formulations). As such, they may be formulated for simultaneous or sequential administration.

Where they are intended for sequential administration, they will typically be formulated in separate compositions which may be of the same type or a different type. Thus, for example, the components of the combination may be formulated for delivery by the same route (e.g. both by the oral route or both by injection) or they may be formulated for administration by different routes (e.g. one by the oral route and another by a parenteral route such as by i.v. injection or infusion). In a preferred embodiment the compound (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid and salts therof, is administered sequentially (either before or after) or simultaneously with the ancillary compound. Preferably the compound (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid and salts therof is administered using an i.v. formulation as defined herein.

When they are intended for simultaneous administration, they may be formulated together or separately and, as above, may be formulated for administration by the same route or by different routes.

Thus, the present invention further provides pharmaceutical compositions, as defined above, and methods of making a pharmaceutical composition comprising (e.g. admixing) at least one compound of the invention, together with one or more pharmaceutically acceptable excipients and optionally other therapeutic or prophylactic agents as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions.

Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short-term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient in a bottle for subsequent reconstitution using an appropriate diluent.

The pharmaceutical formulation can be prepared by lyophilising a compound of the invention, or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening materials such as lecithin, by the maintenance of the required particle size in the case of dispersions, and by the use of surfactants.

The compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one typical embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another typical embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of the invention may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% active ingredient and from 99% (w/w) to 5% (w/w) of a pharmaceutically acceptable excipient or combination of excipients. Typically, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, typically from approximately 20% to approximately 90%, active ingredient. Pharmaceutical compositions according to the invention may be, for example, in unit dose form, such as in the form of ampoules, vials, suppositories, pre-filled syringes, dragees, tablets or capsules.

The pharmaceutically acceptable excipient(s) can be selected according to the desired physical form of the formulation and can, for example, be selected from diluents (e.g. solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) polymers (depending on dose). The film coats of the tablet or capsule typically contain 0-10% (w/w) release-controlling (e.g. delaying) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described herein. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Formulations Comprising SGI-110

Suitable formulations can be solutions or suspensions of a compound in a solvent or a mixture of solvents. Non-limiting examples of suitable solvents include propylene glycol, glycerin, ethanol, and any combination of the foregoing. The formulations can be prepared as non-aqueous formulations. The formulations can be anhydrous or substantially anhydrous.

A mixture of solvents can contain a percentage of propylene glycol on either a mass or a volume basis. In some embodiments, the percentage of propylene glycol can be at least 10%, at least 20%, at least 30%, at least 40%, at least 50%, at least about 10%, at least about 20%, at least about 30%, at least about 40%, or at least about 50%. In some embodiments, the percentage of propylene glycol can be at most 90%, at most 80%, at most 70%, at most 60%, at most about 90%, at most about 80%, at most about 70%, or at most about 60%. In some embodiments, the percentage of propylene glycol can be 30% to 90%, 45% to 85%, 55% to 75%, 60% to 70%, about 30% to about 90%, about 45% to about 85%, about 55% to about 75%, or about 60% to about 70%. In some embodiments, the percentage of propylene glycol can be 30%, 35%, 40%, 45%, 50%, 55%, 60%, 65%, 70%, 75%, 80%, 85%, 90%, about 30%, about 35%, about 40%, about 45%, about 50%, about 55%, about 60%, about 65%, about 70%, about 75%, about 80%, about 85%, or about 90%.

A mixture of solvents can contain a percentage of glycerin on either a mass or a volume basis. In some embodiments, the percentage of glycerin can be at least 5%, at least 10%, at least 15%, at least 25%, at least 30%, at least about 5%, at least about 10%, at least about 15%, at least about 25%, or at least about 30%. In some embodiments, the percentage of glycerin can be at most 70%, at most 60%, at most 50%, at most 40%, at most 30%, at most about 70%, at most about 60%, at most about 50%, at most about 40%, or at most about 30%. In some embodiments, the percentage of glycerin can be 0% to 50%, 5% to 45%, 15% to 35%, 20% to 30%, 0% to about 50%, about 5% to about 45%, about 15% to about 35%, or about 20% to about 30%. In some embodiments, the percentage of glycerin can be 0%, 5%, 10%, 15%, 20%, 25%, 30%, 35%, 40%, 45%, 50%, about 5%, about 10%, about 15%, about 20%, about 25%, about 30%, about 35%, about 40%, about 45%, or about 50%.

A mixture of solvents can contain a percentage of ethanol on either a mass or a volume basis. In some embodiments, the percentage of ethanol can be at least 1%, at least 3%, at least 5%, at least 10%, at least 15%, at least about 1%, at least about 3%, at least about 5%, at least about 10%, or at least about 15%. In some embodiments, the percentage of ethanol can be at most 30%, at most 25%, at most 20%, at most 15%, at most 10%, at most about 30%, at most about 25%, at most about 20%, at most about 15%, or at most about 10%. In some embodiments, the percentage of ethanol can be 0% to 30%, 0% to 25%, 0% to 20%, 5% to 15%, 0% to about 30%, 0% to about 25%, 0% to about 20%, or about 5% to about 15%. In some embodiments, the percentage of ethanol can be 0%, 1%, 2%, 3%, 4%, 5%, 6%, 7%, 8%, 9%, 10%, 11%, 12%, 13%, 14%, 15%, about 1%, about 2%, about 3%, about 4%, about 5%, about 6%, about 7%, about 8%, about 9%, about 10%, about 11%, about 12%, about 13%, about 14%, or about 15%.

In some embodiments, a solvent or a mixture of solvents comprises 45% to 85% propylene glycol, 5% to 45% glycerin, and 0% to 30% ethanol. In some embodiments, a solvent or a mixture of solvents comprises about 45% to about 85% propylene glycol, about 5% to about 45% glycerin, and 0% to about 30% ethanol. In some embodiments, a solvent or a mixture of solvents consists essentially of 45% to 85% propylene glycol, 5% to 45% glycerin, and 0% to 30% ethanol. In some embodiments, a solvent or a mixture of solvents consists essentially of about 45% to about 85% propylene glycol, about 5% to about 45% glycerin, and 0% to about 30% ethanol. In some embodiments, a solvent or a mixture of solvents is 45% to 85% propylene glycol, 5% to 45% glycerin, and 0% to 30% ethanol. In some embodiments, a solvent or a mixture of solvents is about 45% to about 85% propylene glycol, about 5% to about 45% glycerin, and 0% to about 30% ethanol.

In some embodiments, a solvent or a mixture of solvents comprises 55% to 75% propylene glycol, 15% to 35% glycerin, and 0% to 20% ethanol. In some embodiments, a solvent or a mixture of solvents comprises about 55% to about 75% propylene glycol, about 15% to about 35% glycerin, and 0% to about 20% ethanol. In some embodiments, a solvent or a mixture of solvents consists essentially of 55% to 75% propylene glycol, 15% to 35% glycerin, and 0% to 20% ethanol. In some embodiments, a solvent or a mixture of solvents consists essentially of about 55% to about 75% propylene glycol, about 15% to about 35% glycerin, and 0% to about 20% ethanol. In some embodiments, a solvent or a mixture of solvents is 55% to 75% propylene glycol, 15% to 35% glycerin, and 0% to 20% ethanol. In some embodiments, a solvent or a mixture of solvents is about 55% to about 75% propylene glycol, about 15% to about 35% glycerin, and 0% to about 20% ethanol.

In some embodiments, a solvent or a mixture of solvents comprises 60% to 70% propylene glycol; 20% to 30% glycerin; and 5% to 15% ethanol. In some embodiments, a solvent or a mixture of solvents comprises about 60% to about 70% propylene glycol; about 20% to about 30% glycerin; and about 5% to about 15% ethanol. In some embodiments, a solvent or a mixture of solvents consists essentially of 60% to 70% propylene glycol; 20% to 30% glycerin; and 5% to 15% ethanol. In some embodiments, a solvent or a mixture of solvents consists essentially of about 60% to about 70% propylene glycol; about 20% to about 30% glycerin; and about 5% to about 15% ethanol. In some embodiments, a solvent or a mixture of solvents is 60% to 70% propylene glycol; 20% to 30% glycerin; and 5% to 15% ethanol. In some embodiments, a solvent or a mixture of solvents is about 60% to about 70% propylene glycol; about 20% to about 30% glycerin; and about 5% to about 15% ethanol.

In some embodiments, a solvent or a mixture of solvents comprises 65% propylene glycol; 25% glycerin; and 10% ethanol. In some embodiments, a solvent or a mixture of solvents comprises about 65% propylene glycol; about 25% glycerin; and about 10% ethanol. In some embodiments, a solvent or a mixture of solvents consists essentially of 65% propylene glycol; 25% glycerin; and 10% ethanol. In some embodiments, a solvent or a mixture of solvents consists essentially of about 65% propylene glycol; about 25% glycerin; and about 10% ethanol. In some embodiments, a solvent or a mixture of solvents is 65% propylene glycol; 25% glycerin; and 10% ethanol. In some embodiments, a solvent or a mixture of solvents is about 65% propylene glycol; about 25% glycerin; and about 10% ethanol.

Formulations for use in the combinations of the invention can be prepared, stored, transported, and handled in anhydrous or substantially-anhydrous form. A solvent can be dried prior to preparing a formulation, and a compound can be dried, for example, by lyophilization. A drying agent, or desiccant, can be used during preparation, storage, transportation, or handling to regulate water content. Non-limiting examples of drying agents include silica gel, calcium sulfate, calcium chloride, calcium phosphate, sodium chloride, sodium bicarbonate, sodium sulfate, sodium phosphate, montmorillonite, molecular sieves (beads or powdered), alumina, titania, zirconia, and sodium pyrophosphate. A drying agent can contact a formulation directly, be inserted into the formulation in the form of a packet with a permeable membrane, or be stored with the formulation in a sealed environment, such as a dessicator, such that the drying agent and the formulation are simultaneously exposed to the same controlled atmosphere. A drying agent can be removed from a formulation, for example, by filtration or cannulation. Additionally, a formulation can be stored in a sealed container within a controlled atmosphere consisting essentially of, or enriched in, nitrogen or argon.

Anhydrous or substantially-anhydrous conditions benefit the shelf-life of a formulation disclosed herein at both ambient and reduced temperatures. This benefit reduces the costs associated with the storage, transportation, and spoilage of a formulation, increases the convenience of storage and handling, and avoids the need to administer cold formulations, thereby improving subject tolerance and compliance to a regimen of a formulation of the invention.

The formulations can further include a pharmaceutically-acceptable excipient. Non-limiting examples of excipients include mannitol, sorbitol, lactose, dextrose, and cyclodextrins. Excipients can be added to modulate the density, rheology, uniformity, and viscosity of the formulation.

The formulations can include acidic or basic excipients to modulate the acidity or basicity of the formulation. Non limiting examples of acids suitable to increase the acidity of a formulation include hydrochloric acid, hydrobromic acid, hydroiodic acid, sulfuric acid, phosphoric acid, nitric acid, ascorbic acid, citric acid, tartaric acid, lactic acid, oxalic acid, formic acid, benzenesulphonic acid, benzoic acid, maleic acid, glutamic acid, succinic acid, aspartic acid, diatrizoic acid, and acetic acid. Non limiting examples of bases suitable to increase the basicity of a formulation include lithium hydroxide, sodium hydroxide, potassium hydroxide, sodium carbonate, sodium bicarbonate, sodium phosphate, potassium phosphate, sodium acetate, sodium benzoate, tetrabutylammonium acetate, tetrabutylammonium benzoate, and trialkyl amines. Polyfunctional excipients, such as ethylene diamine tetraacetic acid (EDTA), or a salt thereof, can also be used to modulate acidity or basicity.

SGI-110 as hereinbefore defined can be present in a formulation in any amount. In some embodiments, the compound is present in a concentration of 1 mg/mL to 130 mg/mL, 10 mg/mL to 130 mg/mL, 40 mg/mL to 120 mg/mL, 80 mg/mL to 110 mg/mL, about 1 mg/mL to about 130 mg/mL, about 10 mg/mL to about 130 mg/mL, about 40 mg/mL to about 120 mg/mL, or about 80 mg/mL to about 110 mg/mL. In some embodiments, the compound is present in a concentration of 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, or about 200 mg/mL. In some embodiments, the compound is present in a concentration of 100 mg/mL. In some embodiments, the compound is present in a concentration of about 100 mg/mL.

The formulation can be prepared by contacting a compound described herein with a solvent or a mixture of solvents. Alternatively, the compound can be contacted with a single solvent, and other solvents can be added subsequently, as a mixture, or sequentially. When the final formulation is a solution, complete solvation can be achieved at whatever step of the process is practical for manufacturing. Optional excipients can be added to the formulation at whatever step is practical for manufacturing.

Preparation of the formulation can be optionally promoted by agitation, heating, or extension of the dissolution period. Non-limiting examples of agitation include shaking, sonication, mixing, stirring, vortex, and combinations thereof.

In some embodiments, the formulation is optionally sterilized. Non-limiting examples of sterilization techniques include filtration, chemical disinfection, irradiation, and heating.

The use of DMSO as a solvent in the preparation of the formulations for use in the SGI-110 formulations permit reduction in bulk solution and fill volumes (both bulk and fill volumes can be reduced to $\frac{1}{5}^{th}$ of those used with aqueous systems) and relieves time and temperature restrictions on scale-up. Moreover, the use of substantially anhydrous DMSO greatly increases stability: increasing water concentration is correlated with a decrease in stability (as shown in FIG. 4 of WO 2013/033176, which shows the % change in total related substances of the sodium salt of a compound of Formula I-1 when stored in DMSO or DMSO/water (water for injection, "WFI") at 25° C./60% RH for 24 hours).

Any source of DMSO can be used according to the invention. In some embodiments, the DMSO source is suitable for healthcare and drug delivery applications, for example conforming to USP or Ph. Eur monographs, and be manufactured under cGMP and API guidelines. Grades such as anhydrous or Pharma Solvent can be used according to the invention.

The DMSO for use according to the invention can have impurities in very low levels, for example <0.2% water by KF, <0.01% non-volatile residue and <0.1% of related compounds.

In some embodiments, DMSO can include isosteres thereof, including in particular DMSO isosteres in which one or more atom(s) is(are) replaced by a cognate isotope, for example hydrogen by deuterium.

Suitable doses of formulations can be administered to a subject by methods known in the art, and exemplary dosing and administration parameters are described in WO2007/041071, which teaching is hereby incorporated by reference in its entirety.

Thus, non-limiting examples of methods of administration include subcutaneous injection, intravenous injection, and infusion. In some embodiments, a subject is in need or want of the formulation. In some embodiments, the administration is subcutaneous administration.

A therapeutically effective amount of SGI-110 can be expressed as mg of the compound per kg of subject body mass. In some embodiments, a therapeutically effective amount is 1-1,000 mg/kg, 1-500 mg/kg, 1-250 mg/kg, 1-100 mg/kg, 1-50 mg/kg, 1-25 mg/kg, or 1-10 mg/kg. In some embodiments, a therapeutically-effective amount is 5 mg/kg, 10 mg/kg, 25 mg/kg, 50 mg/kg, 75 mg/kg, 100 mg/kg, 150 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1,000 mg/kg, about 5 mg/kg, about 10 mg/kg, about 25 mg/kg, about 50 mg/kg, about 75 mg/kg, about 100 mg/kg, about 150 mg/kg, about 200 mg/kg, about 250 mg/kg, about 300 mg/kg, about 400 mg/kg, about 500 mg/kg, about 600 mg/kg, about 700 mg/kg, about 800 mg/kg, about 900 mg/kg, or about 1,000 mg/kg.

A therapeutically effective amount of SGI-110 can also be expressed as mg of the compound per square metre of subject body area. In some embodiments, the combinations of the invention can be administered subcutaneously in a range of doses, for example 1 to 1500 mg (0.6 to 938 mg/m2), or 2 to 800 mg (1.25 to 500 mg/m2), or 5 to 500 mg (3.1 to 312 mg/m2), or 2 to 200 mg (1.25 to 125 mg/m2) or 10 to 1000 mg (6.25 to 625 mg/m2), particular examples of doses including 10 mg (6.25 mg/m2), 20 mg (12.5 mg/m2), 50 mg (31.3 mg/m2), 80 mg (50 mg/m2), 100 mg (62.5 mg/m2), 200 mg (125 mg/m2), 300 mg (187.5 mg/m2), 400 mg (250 mg/m2), 500 mg (312.5 mg/m2), 600 mg (375 mg/m2), 700 mg (437.5 mg/m2), 800 mg (500 mg/m2), 900 mg (562.5 mg/m2) and 1000 mg (625 mg/m2).

SGI-110 can be administered once or more than once each day. SGI-110 is typically administered continuously (i.e. taken every day without a break for the duration of the treatment regimen).

In some embodiments, a therapeutically effective amount can be administered 1-35 times per week, 1-14 times per week, or 1-7 times per week. In some embodiments, a therapeutically-effective amount can be administered 1-10 times per day, 1-5 times per day, 1 time, 2 times, or 3 times per day.

In some embodiments, the materials of the invention can be administered according to a dosage regimen of: (a) once, twice, three times, four times, five times, six times or seven times a week; or (b) every day for 5, 6, 7, 8, 9 or 10 days; or (c) every day for up to 10 days; or (d) every day for between 5 and 10 days; or (e) every day for 5 days, immediately followed by two dose-free days and then every day for the next 5 days. In some embodiments, administration is subcutaneous.

In one embodiment, SGI-110 is formulated in a subcutaneous formulation.

In particular, SGI-110 is dissolved in a substantially anhydrous solvent comprising about 45% to about 85% propylene glycol; about 5% to about 45% glycerin; and 0% to about 30% ethanol. In such embodiments, said solvent can comprise about 65% to about 70% propylene glycol; about 25% to about 30% glycerin, and 0% to about 10% ethanol, for example: (a) 65% to 70% propylene glycol and 25% to 30% glycerin, any balance being ethanol; (b) about 65% propylene glycol; about 25% glycerin; and about 10% ethanol; (c) 65% propylene glycol; 25% glycerin; and 10% ethanol; (d) about 70% propylene glycol and about 30% glycerin, ethanol being absent; (e) 45% to 85% propylene glycol; 5% to 45% glycerin; and 0% to 30% ethanol; (f) 65% to 70% propylene glycol; 25% to 30% glycerin, and 0% to 10% ethanol. The formulation can further comprise DMSO, optionally at a DMSO:compound ratio of 2:1; 1:1; 0.5:1; 0.3:1 or 0.2-0.3:1. The combination can be suitable for administration by subcutaneous injection.

When present as part of a formulation, SGI-110 can be present at a concentration of about 80 mg/mL to about 110 mg/mL, optionally about 100 mg/mL.

In some embodiments, the invention provides a kit comprising:
(a) a first vessel containing SGl-110 or salt thereof;
(b) a second vessel containing a substantially anhydrous solvent as described herein; and
(c) one or more ancillary therapeutic component(s).

The compound can be present in the kit in the form of a substantially anhydrous powder, for example being lyophilized. In some embodiments, the first vessel can contain about 80 mg to about 110 mg of SGI-110, for example about 100 mg of SGI-110, and can further comprise instructions for administration by subcutaneous injection.

In some embodiments, the invention provides a process for preparing a pharmaceutical composition, the process comprising dissolving SGI-110 or salt thereof as defined above in a substantially anhydrous solvent as also defined above, and then combining the dissolved compound with one or more ancillary therapeutic component(s) as also defined above. In some embodiments, the process further comprises the preliminary steps of:
(a) dissolving SGl-110 in DMSO to produce a solution of said compound in DMSO; and
(b) lyophilizing said solution of step (a) to provide said compound as a substantially anhydrous powder.

In some embodiments, the invention provides a process for producing a pharmaceutical composition comprising SGI-110 or salt thereof as defined above in the form of a substantially anhydrous powder, the process comprising dissolving SGI-110 in DMSO to produce a solution in DMSO, lyophilizing said solution to provide SGI-110 as a substantially anhydrous powder and then combining the powder with one or more ancillary therapeutic component (s). In some embodiments, said substantially anhydrous powder comprises residual DMSO, for example: (a) present in an amount of 52000, or about 0.1 to about 2000 mg/g of said compound; or (b) present in an amount of 51000, or about 0.1 to about 1000 mg/g; 5600, or about 0.1 to about 600 mg/g; 5500, or about 0.1 to about 500 mg/g; 5400, or about 0.1 to about 400 mg/g; 0.5300, or about 0.1 to about 300 mg/g; or about 200 about 300 mg/g of said compound; or (c) present in an amount of 200-300 mg/g of said compound.

In some embodiments, the invention provides a substantially anhydrous powder consisting essentially of SGI-110 or salt thereof as defined above and DMSO, the DMSO being present in an amount of 5200, or about 0.1% to about 200% w/w, in combination with one or more ancillary therapeutic component(s) as defined above. In such embodiments, the DMSO is present in an amount of 5100%, or about 0.1% to about 100%, ≤60%, or about 0.1% to about 60%, 5.50%, or about 0.1% to about 50%, ≤40%, or about 0.1% to about 40%, or ≤30%, or about 0.1% to about 30% w/w DMSO/compound, for example in an amount of about 20-about 30% w/w DMSO/compound.

Particular formulations of SGI-110 are disclosed in WO2017/004538 and WO2017/004538, the contents of which are incorporated herein in their entirety.

General

In one embodiment the compound of formula (I°) is formulated in a manner suitable for oral administration.

In one embodiment the compound of formula (I°) is formulated in a manner suitable for I.V. administration.

In one embodiment SGI-110 is formulated in a manner suitable for subcutaneous administration.

Methods of Treatment

The combinations defined herein may be useful in the prophylaxis or treatment of a range of disease states or conditions. Examples of such disease states and conditions are set out above.

The combinations are generally administered to a subject in need of such administration, for example a human or animal patient, typically a human.

The combinations will typically be administered in amounts that are therapeutically or prophylactically useful and which generally are non-toxic. However, in certain situations (for example in the case of life threatening diseases), the benefits of administering a combination may outweigh the disadvantages of any toxic effects or side effects, in which case it may be considered desirable to administer compounds in amounts that are associated with a degree of toxicity.

The combinations may be administered over a prolonged term to maintain beneficial therapeutic effects or may be administered for a short period only. Alternatively, they may be administered in a continuous manner or in a manner that provides intermittent dosing (e.g. a pulsatile manner).

The compounds of the combination can be administered simultaneously or sequentially. When administered sequentially, they can be administered at closely spaced intervals (for example over a period of 5-10 minutes) or at longer intervals (for example 1, 2, 3, 4 or more hours apart, or even longer periods, e.g. 1, 2, 3, 4, 5, 6, or 7 days, apart where required), the precise dosage regimen being commensurate with the properties of the therapeutic agent(s). With sequential administration, the delay in administering the second (or additional) active ingredient should not be such as to lose the advantageous benefit of the efficacious effect of the combination of the active ingredients. In addition, the delay in administering the second (or additional) active ingredient is typically timed so as to allow for any adverse side effects of the first compound to subside to an acceptable level before administration of the second compound, whilst not losing the advantageous benefit of the efficacious effect of the combination of the active ingredients.

The compounds may be given in individually varying dose schedules and via the same or different routes.

For example, one compound may be administered by the oral route and the other compound administered by parenteral administration such as administration by injection (e.g. i.v.) or infusion. In an alternative, both compounds may be administered by injection or infusion. In a further alternative, both compounds may be given orally. In one particular embodiment, one compound is administered by injection or infusion and the other compound is adminstered orally.

When administered at different times, the administration of one component of the combination may alternate with or interleaf with administration of the other component or the components of the combination may be administered in sequential blocks of therapy. As indicated above, the administration of the components of the combination may be spaced apart in time, for example by one or more hours, or days, or even weeks, provided that they form part of the same overall treatment.

In one embodiment of the invention, the compound of the formula (I°) and sub-groups thereof as defined herein is administered sequentially or simultaneously with SG1-110.

In another embodiment of the invention, the compound of the formula (I°) and sub-groups thereof as defined herein is administered sequentially with SGI-110 in either order.

In a further embodiment, SGI-110 is administered prior to the compound of the formula (I°) and sub-groups thereof as defined herein.

In another embodiment, SGI-110 is administered after the compound of the formula (I°) and sub-groups thereof as defined herein.

In another embodiment of the invention, the compound of the formula (I°) and sub-groups thereof as defined herein and SGI-110 are administered simultaneously.

In another embodiment, the compound of the formula (I°) and sub-groups thereof as defined herein and SGI-110 are each administered in a therapeutically effective amount with respect to the individual components; in other words, the compound of the formula (I°) and sub-groups thereof as defined herein and SGI-110 are administered in amounts that would be therapeutically effective even if the components were administered other than in combination.

In another embodiment, the compound of the formula (I°) and sub-groups thereof as defined herein and SGI-110 are each administered in a sub-therapeutic amount with respect to the individual components; in other words, the compound of the formula (I°) and sub-groups thereof as defined herein and SGI-110 are administered in amounts that would be therapeutically ineffective if the components were administered other than in combination.

Preferably, the compound of the formula (I°) and sub-groups thereof as defined herein and SGI-110 interact in a synergistic or additive manner.

A typical daily dose of each compound of the combination can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I°) can be administered on a daily basis or on a repeat basis every 2, or 3, or 4, or 5, or 6, or 7, or 10 or 14, or 21, or 28 days for example.

Dosages may also be expressed as the amount of drug administered relative to the body surface area of the patient (mg/m$^2$). A typical daily dose of the compound of formula (I°) can be in the range from 3700 pg/m$^2$ to 3700 mg/m$^2$, more typically 185 ng/m$^2$ to 925 mg/m$^2$, and more usually 370 ng/m$^2$ to 555 mg/m$^2$ (e.g. 370 ng/m$^2$ to 370 mg/m$^2$, and more typically 37 mg/m$^2$ to 740 mg/m$^2$, for example 37 mg/m$^2$ to 370 mg/m$^2$) although higher or lower doses may be administered where required. The compounds can be administered on a daily basis or on a repeat basis every 2, or 3, or 4, or 5, or 6, or 7, or 10 or 14, or 21, or 28 days for example.

Each compound of the combination may be administered orally in a range of doses, for example 0.1 to 5000 mg, or 1 to 1500 mg, 2 to 800 mg, or 5 to 500 mg, e.g. 2 to 200 mg or 10 to 1000 mg, particular examples of doses including 10, 20, 50 and 80 mg. Each compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles. This discontinuous treatment can also be based upon numbers of days rather than a full week. For example, the treatment can comprise daily dosing for 1 to 6 days, no dosing for 1 to 6 days with this pattern repeating during the treatment protocol. The number of days (or weeks) wherein the compounds of the invention are not dosed do not necessarily have to equal the number of days (or weeks) wherein the compounds of the invention are dosed.

In one embodiment, the compounds of the invention can be administered in amounts from 3 mg/m$^2$ to 125 mg/m$^2$ daily. Treatment can be by continuous daily dosing or more usually consist of multiple cycles of treatment separated by treatment breaks. One example of a single treatment cycle is 5 consecutive daily doses followed by 3 weeks without treatment.

One particular dosing regimen is once a day (e.g. orally) fora week (e.g. 5 days of treatment), followed by a treatment break of 1, 2, or 3 weeks. An alternative dosing regimen is once a week (e.g. orally), for 1, 2, 3 or 4 weeks.

In one particular dosing schedule, a patient will be given an infusion of a compound for periods of one hour daily for up to ten days in particular up to five days for one week, and the treatment repeated at a desired interval such as two to four weeks, in particular every three weeks.

More particularly, a patient may be given an infusion of a compound for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

The compounds of the invention can also be administered by bolus or continuous infusion. The compound of the invention can be given daily to once every week, or once every two weeks, or once every three weeks, or once every four weeks during the treatment cycle. If administered daily during a treatment cycle, this daily dosing can be discontinuous over the number of weeks of the treatment cycle: for example, dosed for a week (or a number of days), no dosing for a week (or a number of days, with the pattern repeating during the treatment cycle.

In a further particular dosing schedule, a patient is given a continuous infusion for a period of 12 hours to 5 days, and in particular a continuous infusion of 24 hours to 72 hours.

Ultimately, however, the quantity of compound administered and the type of composition used will be commensurate with the nature of the disease or physiological condition being treated and will be at the discretion of the physician.

It may be beneficial to use the combination of the invention alone or to combine the combination with a further agent which acts via a different mechanism to regulate cell growth thus treating two of the characteristic features of cancer development.

The combinations as defined herein can be administered alone or they can be administered with one or more further compounds (or therapies) for treatment of a particular disease state, for example a neoplastic disease such as a cancer as hereinbefore defined. For the treatment of the above conditions, the combinations of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the combinations of the invention include but are not limited to:
  Topoisomerase I inhibitors
  Antimetabolites
  Tubulin targeting agents
  DNA binder and topoisomerase II inhibitors
  Alkylating Agents
  Monoclonal Antibodies.
  Anti-Hormones
  Signal Transduction Inhibitors
  Proteasome Inhibitors
  DNA methyl transferase inhibitors
  Cytokines and retinoids
  Chromatin targeted therapies
  Radiotherapy, and,
  Other therapeutic or prophylactic agents.

Particular examples of anti-cancer agents or adjuvants (or salts thereof), include but are not limited to any of the agents selected from groups (i)-(xlviii), and optionally group (xlix), below:
(i) Platinum compounds, for example cisplatin (optionally combined with amifostine), carboplatin or oxaliplatin;
(ii) Taxane compounds, for example paclitaxel, paclitaxel protein bound particles (Abraxane™) docetaxel, cabazitaxel or larotaxel;
(iii) Topoisomerase I inhibitors, for example camptothecin compounds, for example camptothecin, irinotecan (CPT11), SN-38, or topotecan;
(iv) Topoisomerase II inhibitors, for example anti-tumour epipodophyllotoxins or podophyllotoxin derivatives for example etoposide, or teniposide;
(v) Vinca alkaloids, for example vinblastine, vincristine, liposomal vincristine (Onco-TCS), vinorelbine, vindesine, vinflunine or vinvesir;
(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;
(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);

(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);

(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;

(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;

(xi) DNA methyl transferase inhibitors, for example temozolomide, azacytidine, or decitabine;

(xii) Antifolates, for example methotrexate, pemetrexed disodium, or raltitrexed;

(xiii) Cytotoxic antibiotics, for example antinomycin D, bleomycin, mitomycin C, dactinomycin, carminomycin, daunomycin, levamisole, plicamycin, or mithramycin;

(xiv) Tubulin-binding agents, for example combrestatin, colchicines or nocodazole;

(xv) Signal Transduction inhibitors such as Kinase inhibitors for example receptor tyrosine kinase inhibitors (e.g. EGFR (epithelial growth factor receptor) inhibitors, VEGFR (vascular endothelial growth factor receptor) inhibitors, PDGFR (platelet-derived growth factor receptor) inhibitors, Axl inhibitors, MTKI (multi target kinase inhibitors), Raf inhibitors, ROCK inhibitors, mTOR inhibitors, MEK inhibitors or P13K Inhibitors) for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), vemurafenib (PLX4032 or RG7204), dabrafenib, encorafenib, selumetinib (AZD6244), trametinib (GSK121120212), dactolisib (BEZ235), buparlisib (BKM-120; NVP-BKM-120), BYL719, copanlisib (BAY-80-6946), ZSTK-474, CUDC-907, apitolisib (GDC-0980; RG-7422), pictilisib (pictrelisib, GDC-0941, RG-7321), GDC-0032, GDC-0068, GSK-2636771, idelalisib (formerly CAL-101, GS 1101, GS-1101), MLN1117 (INK1117), MLN0128 (INK128), IPI-145 (INK1197), LY-3023414, ipatasertib, afuresertib, MK-2206, MK-8156, LY-3023414, LY294002, SF1126 or PI-103, sonolisib (PX-866), or AT13148.

(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;

(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, ZK-304709, or AZD-5438 and including CDK4 inhibitors such as palbociclib (PD332991) and ribociclib (LEE-011);

(xviii) PKA/B inhibitors and PKB (akt) pathway inhibitors for example AT13148, AZ-5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);

(xix) Hsp90 inhibitors for example onalespib (AT13387), herbimycin, geldanamycin (GA), 17-a Ilylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (B116-021 an oral purine), ganetespib (STA-9090), SNX-5422 (SC-102112) or IPI-504;

(xx) Monoclonal Antibodies (unconjugated or conjugated to radioisotopes, toxins or other agents), antibody derivatives and related agents, such as anti-CD, anti-VEGFR, anti-HER2 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), catumaxumab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (IL6) or immunomodulating agents such as CTLA-4 blocking antibodies and/or antibodies against PD-1 and PD-L1 and/or PD-L2 for example ipilimumab (CTLA4), MK-3475 (pembrolizumab, formerly lambrolizumab, anti-PD-1), nivolumab (a anti-PD-1), BMS-936559 (anti-PD-L1), MPDL320A, AMP-514 or MEDI4736 (anti-PD-L1), or tremelimumab (formerly ticilimumab, CP-675, 206, anti-CTLA-4); (xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;

(xxii) Aromatase inhibitors and related drugs, such as exemestane, anastrozole, letrazole, testolactone aminoglutethimide, mitotane or vorozole;

(xxiii) Antiandrogens (i.e. androgen receptor antagonists) and related agents for example bicalutamide, nilutamide, flutamide, cyproterone, or ketoconazole;

(xxiv) Hormones and analogues thereof such as medroxyprogesterone, diethylstilbestrol (a.k.a. diethylstilboestrol) or octreotide;

(xxv) Steroids for example dromostanolone propionate, megestrol acetate, nandrolone (decanoate, phenpropionate), fluoxymestrone or gossypol, (xxvi) Steroidal cytochrome P450 17alpha-hydroxylase-17, 20-lyase inhibitor (CYP17), e.g. abiraterone;

(xxvii) Gonadotropin releasing hormone agonists or antagonists (GnRAs) for example abarelix, goserelin acetate, histrelin acetate, leuprolide acetate, triptorelin, buserelin, or deslorelin; (xxviii) Glucocorticoids, for example prednisone, prednisolone, dexamethasone;

(xxix) Differentiating agents, such as retinoids, rexinoids, vitamin D or retinoic acid and retinoic acid metabolism blocking agents (RAMBA) for example accutane, alitretinoin, bexarotene, or tretinoin;

(xxx) Farnesyltransferase inhibitors for example tipifarnib;

(xxxi) Chromatin targeted therapies such as histone deacetylase (HDAC) inhibitors for example sodium butyrate, suberoylanilide hydroxamic acid (SAHA), depsipeptide (FR 901228), dacinostat (NVP-LAQ824), R306465/JNJ-16241199, JNJ-26481585, trichostatin A, vorinostat, chlamydocin, A-173, JNJ-MGCD-0103, PXD-101, or apicidin;

(xxxii) Drugs targeting the ubiquitin-proteasome pathway including proteasome Inhibitors for example bortezomib, carfilzomib, CEP-18770, MLN-9708, or ONX-0912; NEDD8 inhibitors; HDM2 antagonist and deubiquitinases (DUBS);

(xxxiii) Photodynamic drugs for example porfimer sodium or temoporfin;

(xxxiv) Marine organism-derived anticancer agents such as trabectidin;

(xxxv) Radiolabelled drugs for radioimmunotherapy for example with a beta particle-emitting isotope (e.g., Iodine -131, Yittrium -90) or an alpha particle-emitting isotope (e.g., Bismuth-213 or Actinium-225) for example ibritumomab or Iodine tositumomab or alpha radium 223;

(xxxvi) Telomerase inhibitors for example telomestatin;

(xxxvii) Matrix metalloproteinase inhibitors for example batimastat, marimastat, prinostat or metastat;

(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;

(xxxix) Selective immunoresponse modulators for example thalidomide, or lenalidomide;

(xl) Therapeutic Vaccines such as sipuleucel-T (Provenge) or OncoVex;

(xli) Cytokine-activating agents include Picibanil, Romurtide, Sizofiran, Virulizin, or Thymosin;

(xlii) Arsenic trioxide;

(xliii) Inhibitors of G-protein coupled receptors (GPCR) for example atrasentan;

(xliv) Enzymes such as L-asparaginase, pegaspargase, rasburicase, or pegademase;

(xlv) DNA repair inhibitors such as PARP inhibitors for example, olaparib, velaparib, iniparib, INO-1001, AG-014699, or ON0-2231;

(xlvi) Agonists of Death receptor (e.g. TNF-related apoptosis inducing ligand (TRAIL) receptor), such as mapatumumab (formerly HGS-ETR1), conatumumab (formerly AMG 655), PRO95780, lexatumumab, dulanermin, CS-1008, apomab or recombinant TRAIL ligands such as recombinant Human TRAILJApo2 Ligand;

(xlvii) Immunotherapies such as immune checkpoint inhibitors; cancer vaccines and CAR-T cell therapy;

(xlviii) Regulators of Cell death (apoptosis) including Bcl-2 (B-cell lymphoma 2) antagonists such as venetoclax (ABT-199 or GDC-0199), ABT-737, ABT-263, TW-37, sabutoclax, obatoclax, and MIMI and IAP antagonists including LCL-161 (Novartis), Debio-1143 (Debiopharma /Ascenta), AZD5582, Birinapant/TL-32711 (TetraLogic), CUDC-427/GDC-0917/RG-7459 (Genentech), JP1201 (Joyant), T-3256336 (Takeda), GDC-0152 (Genentech) or HGS-1029/AEG-40826 (HGS/Aegera);

(xlix) Prophylactic agents (adjuncts); i.e. agents that reduce or alleviate some of the side effects associated with chemotherapy agents, for example
anti-emetic agents,
agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim),
agents that inhibit bone resorption such as denosumab or bisphosphonates e.g. zoledronate, zoledronic acid, pamidronate and ibandronate,
agents that suppress inflammatory responses such as dexamethasone, prednisone, and prednisolone,
agents used to reduce blood levels of growth hormone and IGF-I (and other hormones) in patients with acromegaly or other rare hormone-producing tumours, such as synthetic forms of the hormone somatostatin e.g. octreotide acetate,
antidote to drugs that decrease levels of folic acid such as leucovorin, or folinic acid,
agents for pain e.g. opiates such as morphine, diamorphine and fentanyl,
non-steroidal anti-inflammatory drugs (NSAID) such as COX-2 inhibitors for example celecoxib, etoricoxib and lumiracoxib,
agents for mucositis e.g. palifermin,
agents for the treatment of side-effects including anorexia, cachexia, oedema or thromoembolic episodes, such as megestrol acetate.

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen. Examples of standard combination regimens are provided below.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($ring/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 mg/m², for gemcitabine in a dosage of about 800 to 1200 mg/m² and for capecitabine in about 1000 to 2500 mg/m² per course of treatment.

The alkylating agents such as nitrogen mustard or nitrosourea is advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, typically 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment.

Where the combination is administered in combination therapy with one, two, three, four or more other therapeutic agents (typically one or two, more typically one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the typical method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the each compound of the combination and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I°) and another anticancer agent may range from 1/10 to 10/1, more in particular from 1/5 to 5/1, even more in particular from 1/3 to 3/1.

The combinations of the invention may also be administered in conjunction with non-chemotherapeutic treatments such as radiotherapy, photodynamic therapy, gene therapy; surgery and controlled diets. Radiotherapy may be for radical, palliative, adjuvant, neoadjuvant or prophylactic purposes.

The combinations of the present invention also have therapeutic applications in sensitising tumour cells for radiotherapy and chemotherapy. Hence the combinations of the present invention can be used as "radiosensitizer" and/or "chemosensitizer" or can be given in combination with another "radiosensitizer" and/or "chemosensitizer". In one embodiment the combination of the invention is for use as chemosensitiser.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

Examples

The invention will now be illustrated, but not limited, by reference to the specific embodiments described in the following examples. Compounds are named using an automated naming package such as AutoNom (MDL) or ChemAxon Structure to Name or are as named by the chemical supplier.

The following first set of examples, in which cyc is phenyl, can be prepared as decribed in international patent application no PCT/GB2016/053042 which was published as WO 2017/055860 on Jun. 4,2017:

| Ex. | Structure | Name |
| --- | --- | --- |
| 1 | 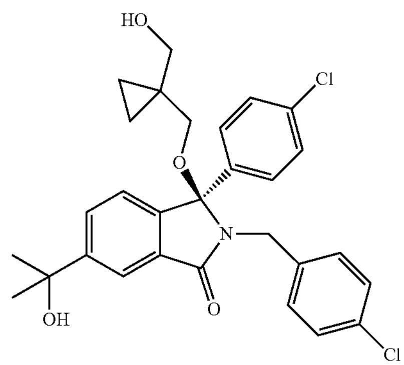 [SMILES: CC(C)(O)c1ccc2c(c1)C(=O)N(Cc1ccc(Cl)cc1)[C@@]2(OCC1(CO)CC1)c1ccc(Cl)cc1] | (3R)-3-(4-chlorophenyl)-2-[(4-chlorophenyl)methyl]-3-{[1-(hydroxymethyl)cyclopropyl]methoxy}-6-(2-hydroxypropan-2-yl)-2,3-dihydro-1H-isoindol-1-one |
| 2 | 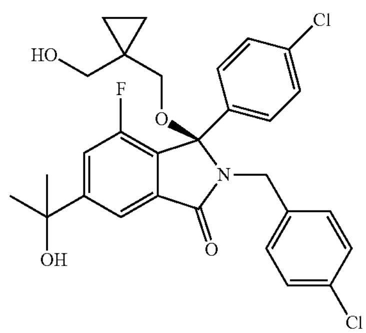 [SMILES: CC(C)(O)c1cc(F)c2c(c1)C(=O)N(Cc1ccc(Cl)cc1)[C@@]2(OCC1(CO)CC1)c1ccc(Cl)cc1] | (3R)-3-(4-chlorophenyl)-2-[(4-chlorophenyl)methyl]-4-fluoro-3-{[1-(hydroxymethyl)cyclopropyl]methoxy}-6-(2-hydroxypropan-2-yl)-2,3-dihydro-1H-isoindol-1-one |
| 3 | 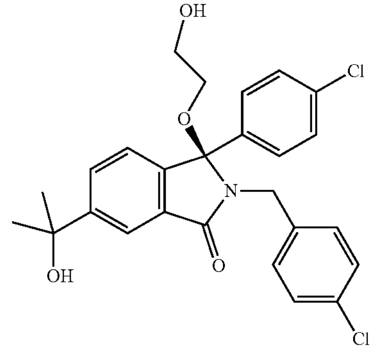 [SMILES: CC(C)(O)c1ccc2c(c1)C(=O)N(Cc1ccc(Cl)cc1)[C@@]2(OCCO)c1ccc(Cl)cc1] | (3R)-3-(4-chlorophenyl)-2-[(4-chlorophenyl)methyl]-3-(2-hydroxyethoxy)-6-(2-hydroxypropan-2-yl)-2,3-dihydro-1H-isoindol-1-one |

-continued

| Ex. | Structure | Name |
|---|---|---|
| 4 | 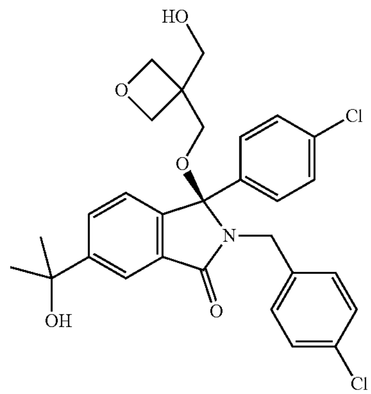 [SMILES: CC(C)(O)c1ccc2c(c1)C(=O)N(Cc1ccc(Cl)cc1)[C@@]2(OCC1(CO)COC1)c1ccc(Cl)cc1] | (3R)-3-(4-chlorophenyl)-2-[(4-chlorophenyl)methyl]-3-{[3-(hydroxymethyl)oxetan-3-yl]methoxy}-6-(2-hydroxypropan-2-yl)-2,3-dihydro-1H-isoindol-1-one |
| 5 | 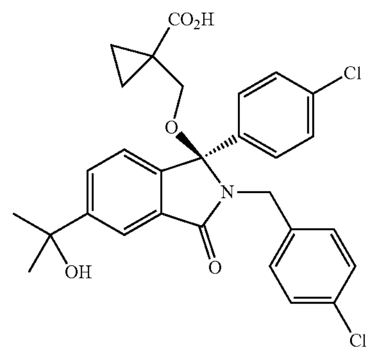 [SMILES: CC(C)(O)c1ccc2c(c1)C(=O)N(Cc1ccc(Cl)cc1)[C@@]2(OCC1(C(=O)O)CC1)c1ccc(Cl)cc1] | 1-({[(1R)-1-(4-chlorophenyl)-2-[(4-chlorophenyl)methyl]-5-(2-hydroxypropan-2-yl)-3-oxo-2,3-dihydro-1H-isoindol-1-yl]oxy}methyl)cyclopropane-1-carboxylic acid |
| 6 | (*as a mixture of isomers at the position shown) | (3R)-3-(4-chlorophenyl)-2-[(1S)-1-(4-chlorophenyl)ethyl]-3-(2,3-dihydroxy-2-methylpropoxy)-6-(2-hydroxypropan-2-yl)-2,3-dihydro-1H-isoindol-1-one |
| 7 | 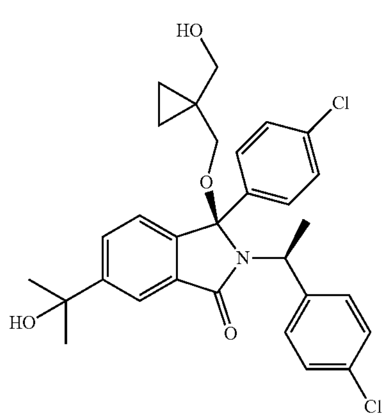 [SMILES: C[C@@H](c1ccc(Cl)cc1)N1C(=O)c2cc(C(C)(C)O)ccc2[C@]1(OCC1(CO)CC1)c1ccc(Cl)cc1] | (3R)-3-(4-chlorophenyl)-2-[(1S)-1-(4-chlorophenyl)ethyl]-3-{[1-(hydroxymethyl)cyclopropyl]methoxy}-6-(2-hydroxypropan-2-yl)-2,3-dihydro-1H-isoindol-1-one |

-continued

| Ex. | Structure | Name |
|---|---|---|
| 8 and 9 | 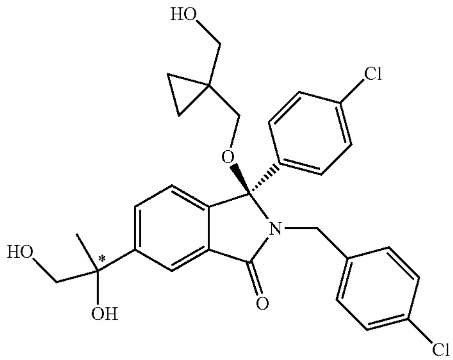 | (3R)-3-(4-chlorophenyl)-2-[(4-chlorophenyl)methyl]-6-(1,2-dihydroxypropan-2-yl)-3-{[1-(hydroxymethyl)cyclopropyl]methoxy}-2,3-dihydro-1H-isoindol-1-one |
| | *The two separate epimers at the position shown | |
| 10 and 11 | 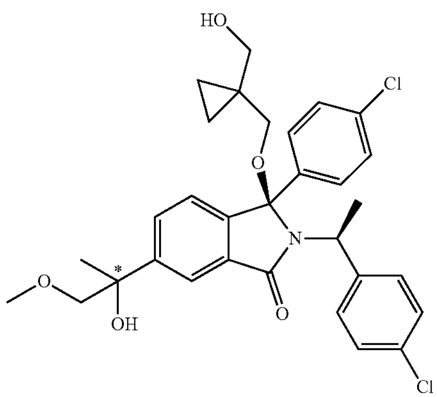 | (3R)-3-(4-chlorophenyl)-2-[(1S)-1-(4-chlorophenyl)ethyl]-6-(2-hydroxy-1-methoxypropan-2-yl)-3-{[1-(hydroxymethyl)cyclopropyl]methoxy}-2,3-dihydro-1H-isoindol-1-one |
| | *The two separate epimers at the position shown | |
| 12 and 13 | 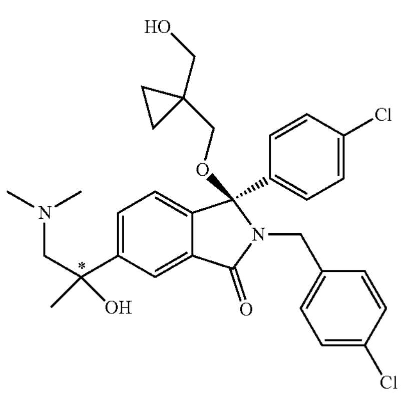 | (3R)-3-(4-chlorophenyl)-2-[(4-chlorophenyl)methyl]-6-[1-(dimethylamino)-2-hydroxypropan-2-yl]-3-{[1-(hydroxymethyl)cyclopropyl]methoxy}-2,3-dihydro-1H-isoindol-1-one |
| | (*Two isomers at the position shown) | |

-continued

| Ex. | Structure | Name |
|---|---|---|
| 14 | 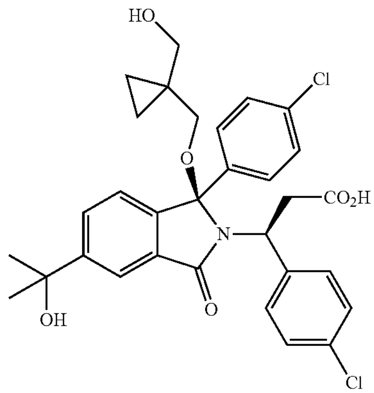 [SMILES: CC(C)(O)c1ccc2c(c1)C(=O)N([C@@H](CC(=O)O)c1ccc(Cl)cc1)[C@@]2(OCC1(CO)CC1)c1ccc(Cl)cc1] | (3S)-3-(4-chlorophenyl)-3-[(1R)-1-(4-chlorophenyl)-1-{[1-(hydroxymethyl)cyclopropyl]methoxy}-5-(2-hydroxypropan-2-yl)-3-oxo-2,3-dihydro-1H-isoindol-2-yl]propanoic acid |
| 15 | 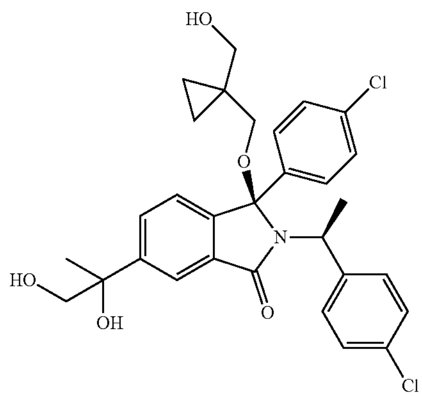 [SMILES: C[C@@H](c1ccc(Cl)cc1)N1C(=O)c2cc(C(C)(O)CO)ccc2[C@]1(OCC1(CO)CC1)c1ccc(Cl)cc1] | (3R)-3-(4-chlorophenyl)-2-[(1S)-1-(4-chlorophenyl)ethyl]-6-(1,2-dihydroxypropan-2-yl)-3-{[1-(hydroxymethyl)cyclopropyl]methoxy}-2,3-dihydro-1H-isoindol-1-one |
| 16 | 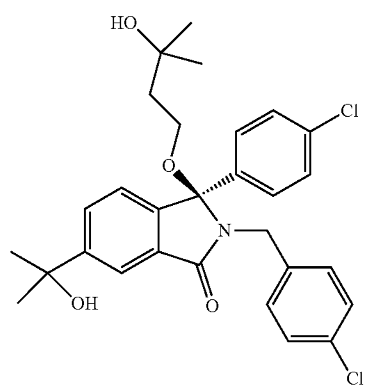 [SMILES: CC(C)(O)CCO[C@]1(c2ccc(Cl)cc2)c2ccc(C(C)(C)O)cc2C(=O)N1Cc1ccc(Cl)cc1] | (3R)-3-(4-chlorophenyl)-2-[(4-chlorophenyl)methyl]-3-(3-hydroxy-3-methylbutoxy)-6-(2-hydroxypropan-2-yl)-2,3-dihydro-1H-isoindol-1-one |
| 17 | 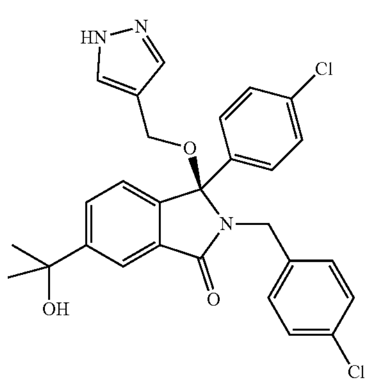 [SMILES: CC(C)(O)c1ccc2c(c1)C(=O)N(Cc1ccc(Cl)cc1)[C@@]2(OCc1cn[nH]c1)c1ccc(Cl)cc1] | (3R)-3-(4-chlorophenyl)-2-[(4-chlorophenyl)methyl]-6-(2-hydroxypropan-2-yl)-3-[(1H-pyrazol-4-yl)methoxy]-2,3-dihydro-1H-isoindol-1-one |

| Ex. | Structure | Name |
|---|---|---|
| 18 | 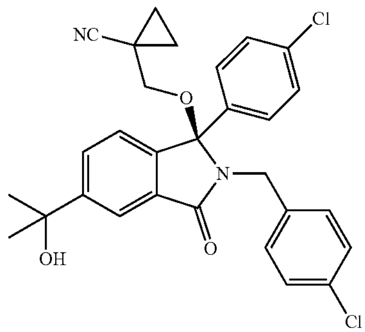 [SMILES: CC(C)(O)c1ccc2c(c1)C(=O)N(Cc1ccc(Cl)cc1)[C@@]2(OCC1(C#N)CC1)c1ccc(Cl)cc1] | 1-({[(1R)-1-(4-chlorophenyl)-2-[(4-chlorophenyl)methyl]-5-(2-hydroxypropan-2-yl)-3-oxo-2,3-dihydro-1H-isoindol-1-yl]oxy}methyl)cyclopropane-1-carbonitrile |
| 19 | 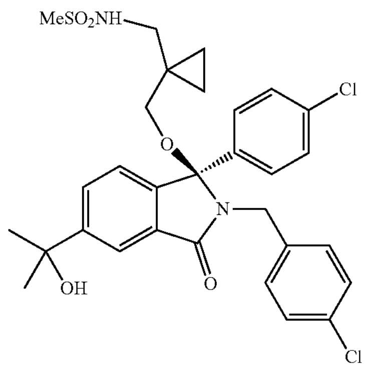 | N-{[1-({[(1R)-1-(4-chlorophenyl)-2-[(4-chlorophenyl)methyl]-5-(2-hydroxypropan-2-yl)-3-oxo-2,3-dihydro-1H-isoindol-1-yl]oxy}methyl)cyclopropyl]methyl}methanesulfonamide |
| 20 | 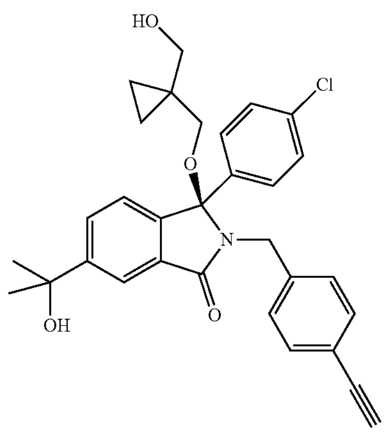 [SMILES: C#Cc1ccc(CN2C(=O)c3cc(C(C)(C)O)ccc3[C@]2(OCC2(CO)CC2)c2ccc(Cl)cc2)cc1] | (3R)-3-(4-chlorophenyl)-2-[(4-ethynylphenyl)methyl]-3-{[1-(hydroxymethyl)cyclopropyl]methoxy}-6-(2-hydroxypropan-2-yl)-2,3-dihydro-1H-isoindol-1-one |
| 21 | 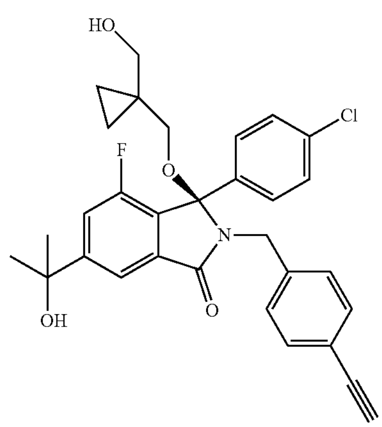 [SMILES: C#Cc1ccc(CN2C(=O)c3cc(C(C)(C)O)cc(F)c3[C@]2(OCC2(CO)CC2)c2ccc(Cl)cc2)cc1] | (3R)-3-(4-chlorophenyl)-2-[(4-ethynylphenyl)methyl]-4-fluoro-3-{[1-(hydroxymethyl)cyclopropyl]methoxy}-6-(2-hydroxypropan-2-yl)-2,3-dihydro-1H-isoindol-1-one |

-continued

| Ex. | Structure | Name |
|---|---|---|
| 22 and 23 | 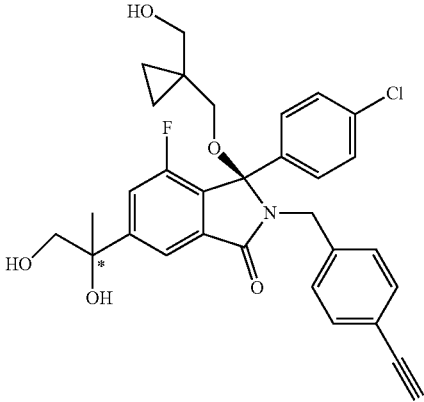 (*Two isomers at position shown) | (3R)-3-(4-chlorophenyl)-6-(1,2-dihydroxypropan-2-yl)-2-[(4-ethynylphenyl)methyl]-4-fluoro-3-{[1-(hydroxymethyl)cyclopropyl]methoxy}-2,3-dihydro-1H-isoindol-1-one |
| 24 | 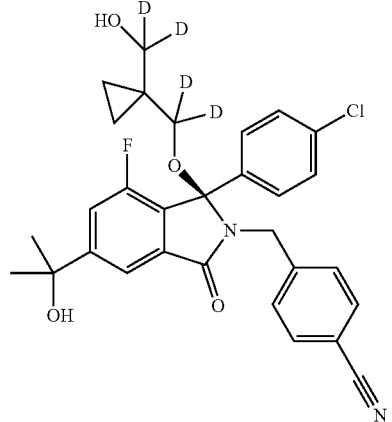 [SMILES: [2H]C([2H])(O)C1(C([2H])([2H])O[C@]2(c3ccc(Cl)cc3)c3c(F)cc(C(C)(C)O)cc3C(=O)N2Cc2ccc(C#N)cc2)CC1] | 4-{[(1R)-1-(4-chlorophenyl)-7-fluoro-1-({1-[hydroxy($^2$H$_2$)methyl]cyclopropyl}($^2$H$_2$)methoxy)-5-(2-hydroxypropan-2-yl)-3-oxo-2,3-dihydro-1H-isoindol-2-yl]methyl}benzonitrile |
| 25 | 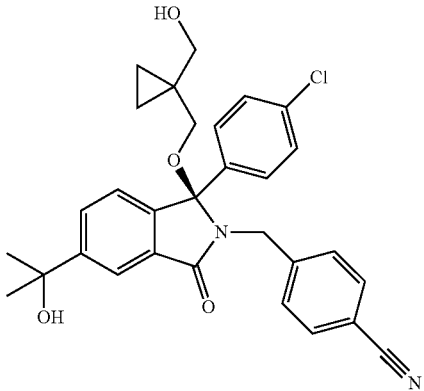 [SMILES: CC(C)(O)c1ccc2c(c1)C(=O)N(Cc1ccc(C#N)cc1)[C@@]2(OCC1(CO)CC1)c1ccc(Cl)cc1] | 4-{[(1R)-1-(4-chlorophenyl)-1-{[1-(hydroxymethyl)cyclopropyl]methoxy}-5-(2-hydroxypropan-2-yl)-3-oxo-2,3-dihydro-1H-isoindol-2-yl]methyl}benzonitrile |

-continued

| Ex. | Structure | Name |
|---|---|---|
| 26 | 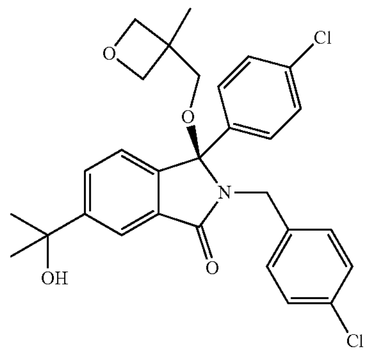 [SMILES: CC1(CO[C@]2(c3ccc(Cl)cc3)c3ccc(C(C)(C)O)cc3C(=O)N2Cc2ccc(Cl)cc2)COC1] | (3R)-3-(4-chlorophenyl)-2-[(4-chlorophenyl)methyl]-6-(2-hydroxypropan-2-yl)-3-[(3-methyloxetan-3-yl)methoxy]-2,3-dihydro-1H-isoindol-1-one |
| 27 and 28 | (*both isomers at position shown) | 4-{[(1R)-1-(4-chlorophenyl)-5-(1,2-dihydroxypropan-2-yl)-1-{[1-(hydroxymethyl)cyclopropyl]methoxy}-3-oxo-2,3-dihydro-1H-isoindol-2-yl]methyl}benzonitrile |
| 29 | 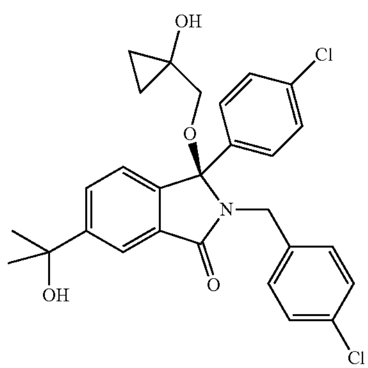 [SMILES: CC(C)(O)c1ccc2c(c1)C(=O)N(Cc1ccc(Cl)cc1)[C@@]2(OCC1(O)CC1)c1ccc(Cl)cc1] | (3R)-3-(4-chlorophenyl)-2-[(4-chlorophenyl)methyl]-3-[(1-hydroxycyclopropyl)methoxy]-6-(2-hydroxypropan-2-yl)-2,3-dihydro-1H-isoindol-1-one |
| 30 | 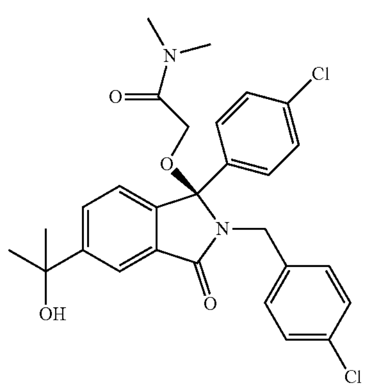 [SMILES: CN(C)C(=O)CO[C@]1(c2ccc(Cl)cc2)c2ccc(C(C)(C)O)cc2C(=O)N1Cc1ccc(Cl)cc1] | 2-{[(1R)-1-(4-Chlorophenyl)-2-[(4-chlorophenyl)methyl]-5-(2-hydroxypropan-2-yl)-3-oxo-2,3-dihydro-1H-isoindol-1-yl]oxy}-N,N-dimethylacetamide |

| Ex. | Structure | Name |
|---|---|---|
| 31 | 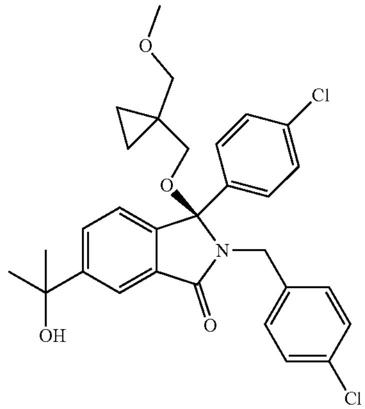 [SMILES: COCC1(CO[C@]2(c3ccc(Cl)cc3)c3ccc(C(C)(C)O)cc3C(=O)N2Cc2ccc(Cl)cc2)CC1] | (3R)-3-(4-Chlorophenyl)-2-[(4-chlorophenyl)methyl]-6-(2-hydroxypropan-2-yl)-3-{[1-(methoxymethyl)cyclopropyl]methoxy}-2,3-dihydro-1H-isoindol-1-one |
| 32 | 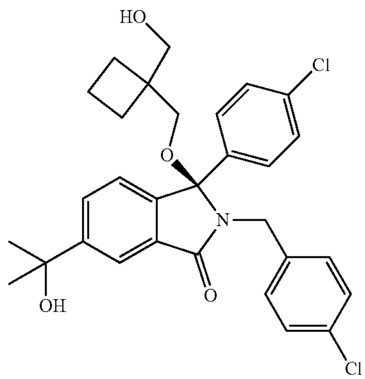 [SMILES: CC(C)(O)c1ccc2c(c1)C(=O)N(Cc1ccc(Cl)cc1)[C@@]2(OCC1(CO)CCC1)c1ccc(Cl)cc1] | (3R)-3-(4-Chlorophenyl)-2-[(4-chlorophenyl)methyl]-3-{[1-(hydroxymethyl)cyclobutyl]methoxy}-6-(2-hydroxypropan-2-yl)-2,3-dihydro-1H-isoindol-1-one |
| 33 | 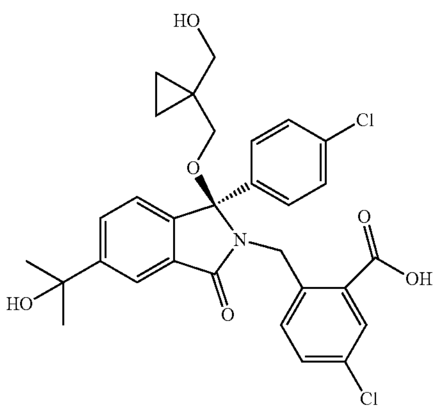 [SMILES: CC(C)(O)c1ccc2c(c1)C(=O)N(Cc1ccc(Cl)cc1C(=O)O)[C@@]2(OCC1(CO)CC1)c1ccc(Cl)cc1] | 5-chloro-2-{[(1R)-1-(4-chlorophenyl)-1-{[1-(hydroxymethyl)cyclopropyl]methoxy}-5-(2-hydroxypropan-2-yl)-3-oxo-2,3-dihydro-1H-isoindol-2-yl]methyl}benzoic acid |
| 34 | 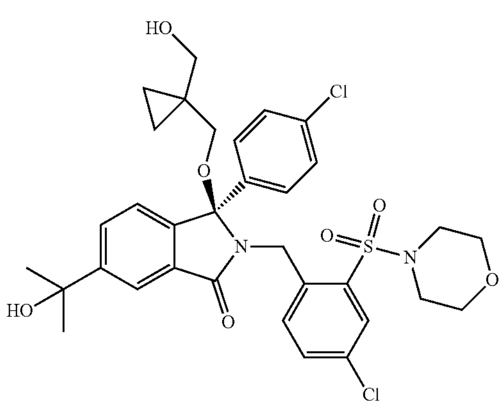 [SMILES: CC(C)(O)c1ccc2c(c1)C(=O)N(Cc1ccc(Cl)cc1S(=O)(=O)N1CCOCC1)[C@@]2(OCC1(CO)CC1)c1ccc(Cl)cc1] | (3R)-2-{[4-chloro-2-(morpholine-4-sulfonyl)phenyl]methyl}-3-(4-chlorophenyl)-3-{[1-(hydroxymethyl)cyclopropyl]methoxy}-6-(2-hydroxypropan-2-yl)-2,3-dihydro-1H-isoindol-1-one |

-continued

| Ex. | Structure | Name |
|---|---|---|
| 35 | 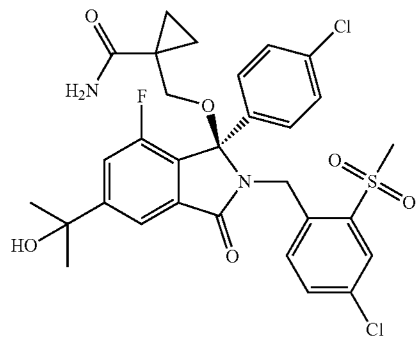 [SMILES: CC(C)(O)c1cc(F)c2c(c1)C(=O)N(Cc1ccc(Cl)cc1S(C)(=O)=O)[C@@]2(OCC1(C(N)=O)CC1)c1ccc(Cl)cc1] | 1-({[(1R)-2-[(4-chloro-2-methanesulfonylphenyl)methyl]-1-(4-chlorophenyl)-7-fluoro-5-(2-hydroxypropan-2-yl)-3-oxo-2,3-dihydro-1H-isoindol-1-yl]oxy}methyl)cyclopropane-1-carboxamide |
| 36 | 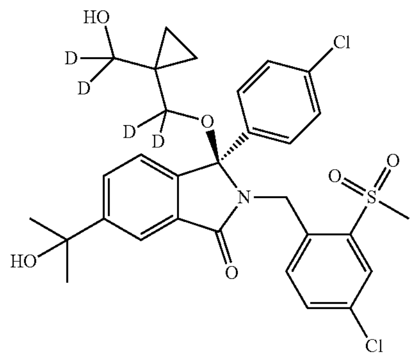 [SMILES: [2H]C([2H])(O)C1(C([2H])([2H])O[C@]2(c3ccc(Cl)cc3)c3ccc(C(C)(C)O)cc3C(=O)N2Cc2ccc(Cl)cc2S(C)(=O)=O)CC1] | (3R)-2-[(4-chloro-2-methanesulfonylphenyl)methyl]-3-(4-chlorophenyl)-3-({1-[hydroxy(²H₂)methyl]cyclopropyl}(²H₂)methoxy)-6-(2-hydroxypropan-2-yl)-2,3-dihydro-1H-isoindol-1-one |
| 37 and 38 | (*both isomers at the position shown) | (3R)-3-(4-Chlorophenyl)-2-[(4-chlorophenyl)methyl]-6-(2-hydroxypropan-2-yl)-3-(oxolan-3-yloxy)-2,3-dihydro-1H-isoindol-1-one |
| 39 and 40 | (*both isomers at the position shown) | (3R)-3-(4-chlorophenyl)-2-[(4-chlorophenyl)methyl]-6-(2-hydroxypropan-2-yl)-3-[(oxolan-3-yl)methoxy]-2,3-dihydro-1H-isoindol-1-one |

| Ex. | Structure | Name |
|---|---|---|
| 41 and 42 | (*both isomers at the position shown) | (3R)-2-[(4-chloro-2-methanesulfonylphenyl)methyl]-3-(4-chlorophenyl)-4-fluoro-6-[1-hydroxy-1-(oxan-4-yl)ethyl]-3-{[1-(hydroxymethyl)cyclopropyl]methoxy}-2,3-dihydro-1H-isoindol-1-one |
| 43 and 44 | (*both isomers at the position shown) | (3R)-2-[(4-chloro-2-methanesulfonylphenyl)methyl]-3-(4-chlorophenyl)-4-fluoro-6-[2-hydroxy-1-(piperazin-1-yl)propan-2-yl]-3-{[1-(hydroxymethyl)cyclopropyl]methoxy}-2,3-dihydro-1H-isoindol-1-one<br>Ex. 43 is the faster eluting isomer<br>Ex. 44 is the slower eluting isomer |
| 45 | 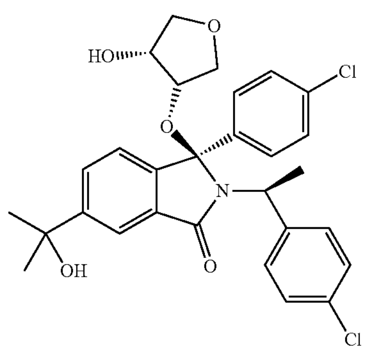 | (3R)-3-(4-Chlorophenyl)-2-[(1S)-1-(4-chlorophenyl)ethyl]-3-{[(3S,4R)-4-hydroxyoxolan-3-yl]oxy}-6-(2-hydroxypropan-2-yl)-2,3-dihydro-1H-isoindol-1-one |
| 46 | 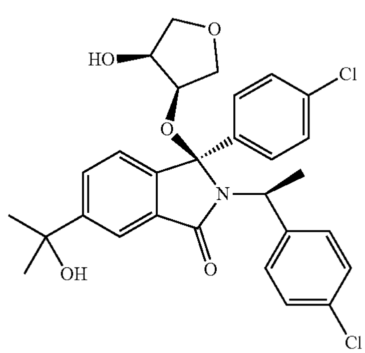 [SMILES: C[C@@H](c1ccc(Cl)cc1)N1C(=O)c2cc(C(C)(C)O)ccc2[C@]1(O[C@@H]1COC[C@@H]1O)c1ccc(Cl)cc1] | (3R)-3-(4-chlorophenyl)-2-[(1S)-1-(4-chlorophenyl)ethyl]-3-{[(3R,4S)-4-hydroxyoxolan-3-yl]oxy}-6-(2-hydroxypropan-2-yl)-2,3-dihydro-1H-isoindol-1-one |

-continued

| Ex. | Structure | Name |
| --- | --- | --- |
| 47 | 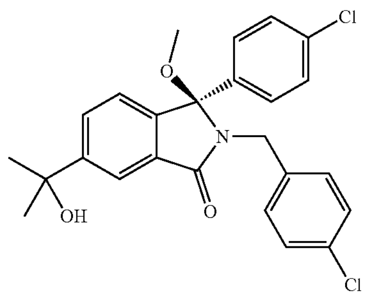 [SMILES: CO[C@]1(c2ccc(Cl)cc2)c2ccc(C(C)(C)O)cc2C(=O)N1Cc1ccc(Cl)cc1] | (3R)-3-(4-Chlorophenyl)-2-[(4-chlorophenyl)methyl]-6-(2-hydroxypropan-2-yl)-3-methoxy-2,3-dihydro-1H-isoindol-1-one |
| 48 | 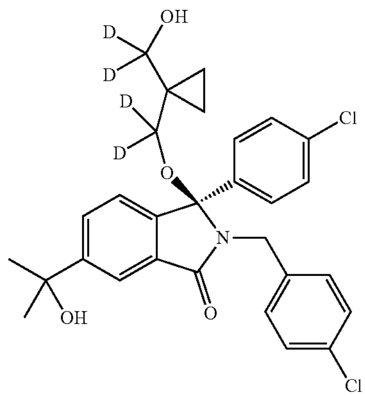 [SMILES: [2H]C([2H])(O)C1(C([2H])([2H])O[C@]2(c3ccc(Cl)cc3)c3ccc(C(C)(C)O)cc3C(=O)N2Cc2ccc(Cl)cc2)CC1] | (3R)-3-(4-Chlorophenyl)-2-[(4-chlorophenyl)methyl]-3-({1-[hydroxy($^2$H$_2$)methyl]cyclopropyl}($^2$H$_2$)methoxy)-6-(2-hydroxypropan-2-yl)-2,3-dihydro-1H-isoindol-1-one |
| 49 | 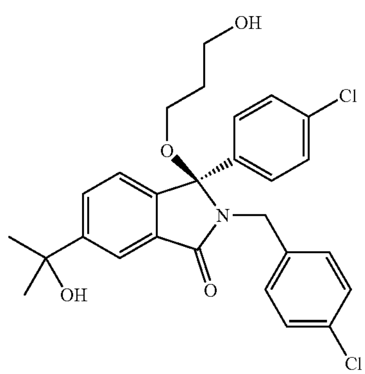 [SMILES: CC(C)(O)c1ccc2c(c1)C(=O)N(Cc1ccc(Cl)cc1)[C@@]2(OCCCO)c1ccc(Cl)cc1] | (3R)-3-(4-Chlorophenyl)-2-[(4-chlorophenyl)methyl]-6-(2-hydroxypropan-2-yl)-3-(3-hydroxypropoxy)-2,3-dihydro-1H-isoindol-1-one |
| 50 | 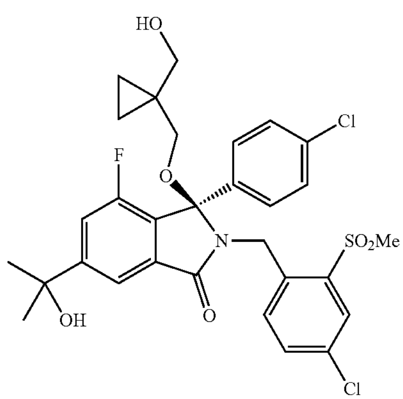 [SMILES: CC(C)(O)c1cc(F)c2c(c1)C(=O)N(Cc1ccc(Cl)cc1S(C)(=O)=O)[C@@]2(OCC1(CO)CC1)c1ccc(Cl)cc1] | (3R)-2-[(4-chloro-2-methanesulfonylphenyl)methyl]-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one |

| Ex. | Structure | Name |
|---|---|---|
| 51 | 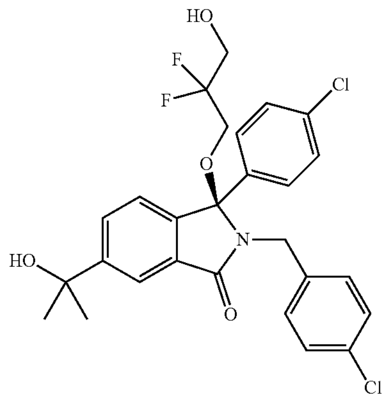 [SMILES: CC(C)(O)c1ccc2c(c1)C(=O)N(Cc1ccc(Cl)cc1)[C@@]2(OCC(F)(F)CO)c1ccc(Cl)cc1] | (3R)-3-(4-Chlorophenyl)-2-[(4-chlorophenyl)methyl]-3-(2,2-difluoro-3-hydroxypropoxy)-6-(2-hydroxypropan-2-yl)-2,3-dihydro-1H-isoindol-1-one |
| 52 and 53 | (both isomers as shown) | (3R)-3-(4-Chlorophenyl)-2-[(4-chlorophenyl)methyl]-3-{[2-(hydroxymethyl)cyclobutyl]methoxy}-6-(2-hydroxypropan-2-yl)-2,3-dihydro-1H-isoindol-1-one |
| 54 and 55 | (*Both isomers at the position shown) | (3R)-3-(4-chlorophenyl)-2-[(4-chlorophenyl)methyl]-6-[2-hydroxy-1-oxo-1-(pyrrolidin-1-yl)propan-2-yl]-3-{[1-(hydroxymethyl)cyclopropyl]methoxy}-2,3-dihydro-1H-isoindol-1-one |

-continued

| Ex. | Structure | Name |
|---|---|---|
| 56 and 57 | (*both isomers at the position highlighted) | 2-[(1R)-1-(4-chlorophenyl)-2-[(4-chlorophenyl)methyl]-1-{[1-(hydroxymethyl)cyclopropyl]methoxy}-3-oxo-2,3-dihydro-1H-isoindol-5-yl]-2-hydroxy-N,N-dimethylpropanamide |
| 58 and 59 | (*both isomers at the position highlighted) | 2-[(1R)-1-(4-Chlorophenyl)-2-[(4-chlorophenyl)methyl]-1-{[1-(hydroxymethyl)cyclopropyl]methoxy}-3-oxo-2,3-dihydro-1H-isoindol-5-yl]-2-hydroxy-N-methylpropanamide |
| 60 | 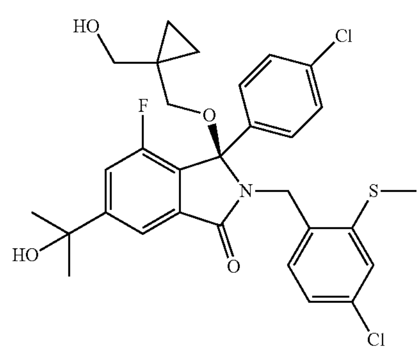 [SMILES: CSc1cc(Cl)ccc1CN1C(=O)c2cc(C(C)(C)O)cc(F)c2[C@]1(OCC1(CO)CC1)c1ccc(Cl)cc1] | (3R)-2-{[4-chloro-2-(methylsulfanyl)phenyl]methyl}-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one |

-continued

| Ex. | Structure | Name |
|---|---|---|
| 61 and 62 | 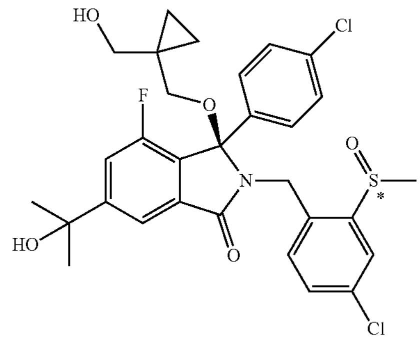 | (3R)-2-[(4-Chloro-2-methanesulfinylphenyl)methyl]-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one<br><br>(*both isomers at position highlighted) |
| 63 and 64 | 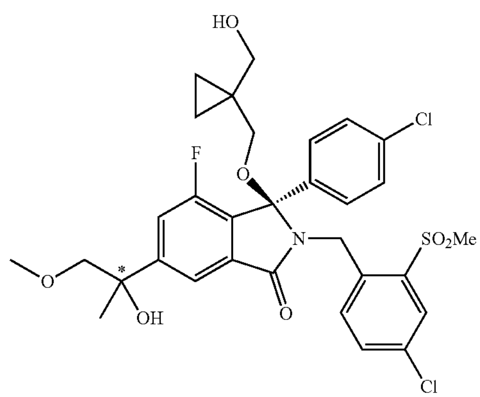 | (3R)-2-[(4-Chloro-2-methanesulfonylphenyl)methyl]-3-(4-chlorophenyl)-4-fluoro-6-(2-hydroxy-1-methoxypropan-2-yl)-3-{[1-(hydroxymethyl)cyclopropyl]methoxy}-2,3-dihydro-1H-isoindol-1-one<br>Ex. 63 is the faster eluting isomer<br>Ex. 64 is the slower eluting isomer<br><br>(*both isomers at position highlighted) |
| 65 and 66 | 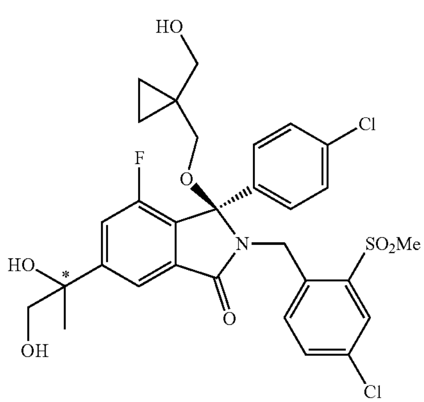 | (3R)-2-[(4-Chloro-2-methanesulfonylphenyl)methyl]-3-(4-chlorophenyl)-6-(1,2-dihydroxypropan-2-yl)-4-fluoro-3-{[1-(hydroxymethyl)cyclopropyl]methoxy}-2,3-dihydro-1H-isoindol-1-one<br>Ex. 65 is the faster eluting isomer<br>Ex. 66 is the slower eluting isomer<br><br>(*both isomers at position shown) |

| Ex. | Structure | Name |
|---|---|---|
| 67 and 68 | (*both isomers at position shown) | (3R)-2-[(4-Chloro-2-methanesulfonylphenyl)methyl]-3-(4-chlorophenyl)-4-fluoro-6-[2-hydroxy-1-(4-methylpiperazin-1-yl)propan-2-yl]-3-[(3R)-oxolan-3-yloxy]-2,3-dihydro-1H-isoindol-1-one<br>Ex. 67 is the faster eluting isomer<br>Ex. 68 is the slower eluting isomer |
| 69 and 70 | (*both isomers at position shown) | (3R)-2-[(4-Chloro-2-methanesulfonylphenyl)methyl]-3-(4-chlorophenyl)-4-fluoro-6-[2-hydroxy-1-(4-methylpiperazin-1-yl)propan-2-yl]-3-[(3S)-oxolan-3-yloxy]-2,3-dihydro-1H-isoindol-1-one<br>Ex. 69 is the faster eluting isomer<br>Ex. 70 is the slower eluting isomer |
| 71 | 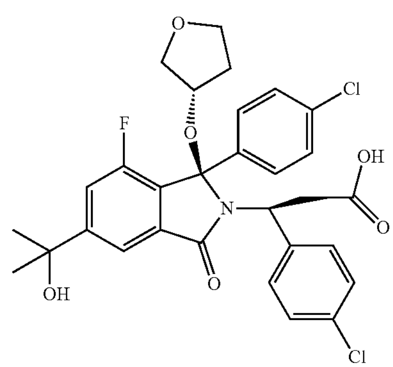 [SMILES: CC(C)(O)c1cc(F)c2c(c1)C(=O)N([C@@H](CC(=O)O)c1ccc(Cl)cc1)[C@@]2(O[C@H]1CCOC1)c1ccc(Cl)cc1] | (3S)-3-(4-Chlorophenyl)-3-[(1R)-1-(4-chlorophenyl)-7-fluoro-5-(2-hydroxypropan-2-yl)-3-oxo-1-[(3S)-oxolan-3-yloxy]-2,3-dihydro-1H-isoindol-2-yl]propanoic acid |
| 72 | 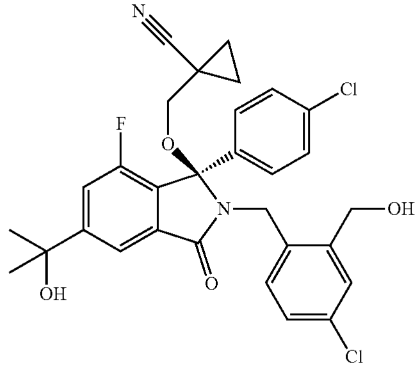 [SMILES: CC(C)(O)c1cc(F)c2c(c1)C(=O)N(Cc1ccc(Cl)cc1CO)[C@@]2(OCC1(C#N)CC1)c1ccc(Cl)cc1] | 1-({[(1R)-2-{[4-Chloro-2-(hydroxymethyl)phenyl]methyl}-1-(4-chlorophenyl)-7-fluoro-5-(2-hydroxypropan-2-yl)-3-oxo-2,3-dihydro-1H-isoindol-1-yl]oxy}methyl)cyclopropane-1-carbonitrile |

-continued

| Ex. | Structure | Name |
|---|---|---|
| 73 and 74 | (*both isomers at position shown) | 1-({[(1R)-2-[(4-chloro-2-methanesulfonylphenyl)methyl]-1-(4-chlorophenyl)-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide<br>Ex. 73 is the faster eluting isomer<br>Ex. 74 is the slower eluting isomer |
| 75 and 76 | (*both isomers at position shown) | (3R)-2-[(4-chloro-2-methanesulfonylphenyl)methyl]-3-(4-chlorophenyl)-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one<br>Ex. 75 is the slower eluting isomer<br>Ex. 76 is the faster eluting isomer |
| 77 and 78 | (*both isomers at position shown) | (3R)-2-[(4-chloro-2-methanesulfonylphenyl)methyl]-3-(4-chlorophenyl)-4-fluoro-6-[2-hydroxy-1-(4-methylpiperazin-1-yl)propan-2-yl]-3-{[1-(hydroxymethyl)cyclopropyl]methoxy}-2,3-dihydro-1H-isoindol-1-one<br>Ex. 77 is the faster eluting isomer<br>Ex. 78 is the slower eluting isomer |

| Ex. | Structure | Name |
| --- | --- | --- |
| 79 | 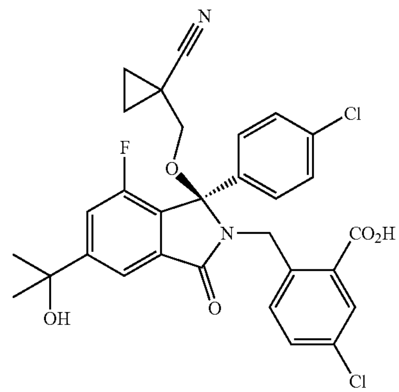 [SMILES: CC(C)(O)c1cc(F)c2c(c1)C(=O)N(Cc1ccc(Cl)cc1C(=O)O)[C@@]2(OCC1(C#N)CC1)c1ccc(Cl)cc1] | 5-chloro-2-{[(1R)-1-(4-chlorophenyl)-1-[(1-cyanocyclopropyl)methoxy]-7-fluoro-5-(2-hydroxypropan-2-yl)-3-oxo-2,3-dihydro-1H-isoindol-2-yl]methyl}benzoic acid |
| 80 and 81 | (*both isomers at position shown) | (3R)-2-[(4-chloro-2-methanesulfonylphenyl)methyl]-3-(4-chlorophenyl)-4-fluoro-6-[1-hydroxy-1-(1-methylpiperidin-4-yl)ethyl]-3-{[1-(hydroxymethyl)cyclopropyl]methoxy}-2,3-dihydro-1H-isoindol-1-one |
| 82 | 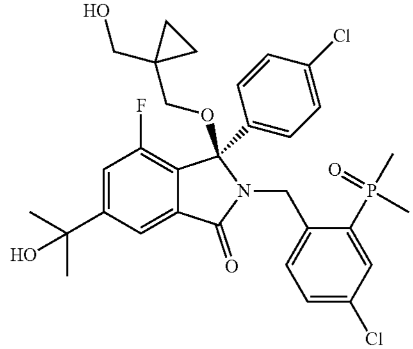 [SMILES: CC(C)(O)c1cc(F)c2c(c1)C(=O)N(Cc1ccc(Cl)cc1P(C)(C)=O)[C@@]2(OCC1(CO)CC1)c1ccc(Cl)cc1] | (3R)-2-{[4-chloro-2-(dimethylphosphoryl)phenyl]methyl}-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one |

| Ex. | Structure | Name |
|---|---|---|
| 83 and 84 | 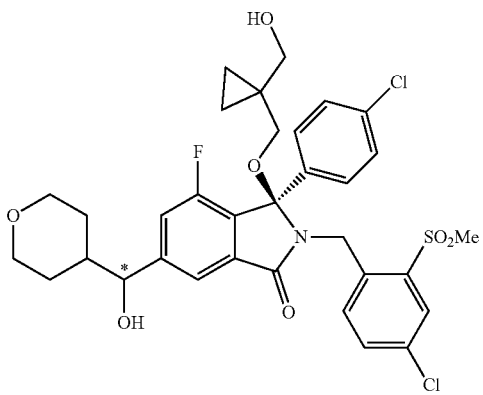<br>(*both isomers at position shown) | (3R)-2-[(4-chloro-2-methanesulfonylphenyl)methyl]-3-(4-chlorophenyl)-4-fluoro-6-[hydroxy(oxan-4-yl)methyl]-3-{[1-(hydroxymethyl)cyclopropyl]methoxy}-2,3-dihydro-1H-isoindol-1-one<br>Ex. 83 is the slower eluting isomer<br>Ex. 84 is the faster eluting isomer |
| 85 and 86 | 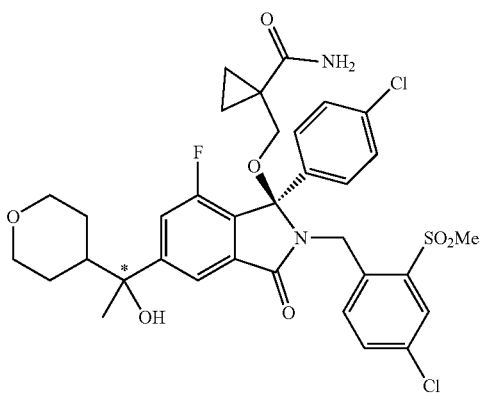<br>(*both isomers at position shown) | 1-({[(1R)-2-[(4-chloro-2-methanesulfonylphenyl)methyl]-1-(4-chlorophenyl)-7-fluoro-5-[1-hydroxy-1-(oxan-4-yl)ethyl]-3-oxo-2,3-dihydro-1H-isoindol-1-yl]oxy}methyl)cyclopropane-1-carboxamide<br>Ex. 85 is the slower eluting isomer<br>Ex. 86 is the faster eluting isomer |
| 87 | 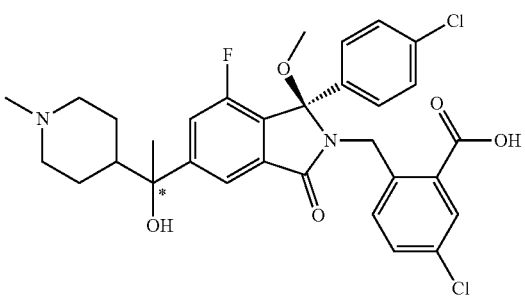<br>(Example isolated as a single isomer at the position shown*) | 5-chloro-2-{[(1R)-1-(4-chlorophenyl)-7-fluoro-5-[1-hydroxy-1-(1-methylpiperidin-4-yl)ethyl]-1-methoxy-3-oxo-2,3-dihydro-1H-isoindol-2-yl]methyl}benzoic acid |

| Ex. | Structure | Name |
|---|---|---|
| 88 and 89 | 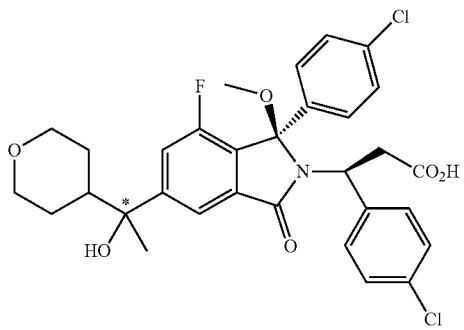 (*both isomers separated and isolated) | (3S)-3-(4-chlorophenyl)-3-[(1R)-1-(4-chlorophenyl)-7-fluoro-5-[1-hydroxy-1-(oxan-4-yl)ethyl]-1-methoxy-3-oxo-2,3-dihydro-1H-isoindol-2-yl]propanoic acid<br>Ex. 88 is the faster eluting isomer<br>Ex. 89 is the slower eluting isomer |
| 90 and 91 | 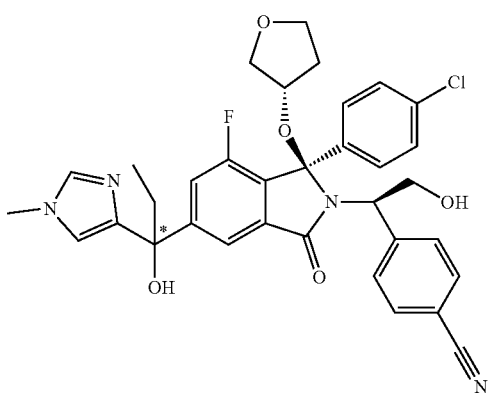 (*both isomers separated and isolated) | 4-[(1R)-1-[(1R)-1-(4-Chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]-2-hydroxyethyl]benzonitrile |
| 92 and 93 | 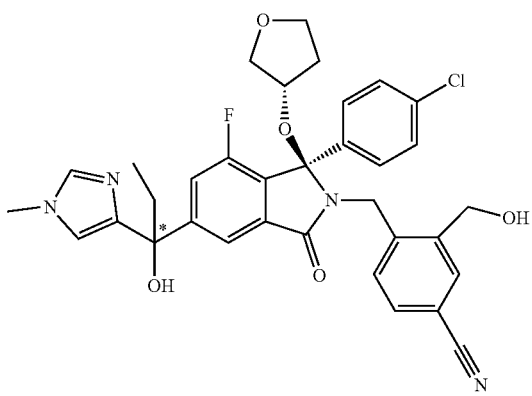 (*both isomers separated and isolated) | 4-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}-3-(hydroxymethyl)benzonitrile<br>Ex. 92 is the faster eluting isomer<br>Ex. 93 is the slower eluting isomer |

-continued

| Ex. | Structure | Name |
|---|---|---|
| 94 and 95 | 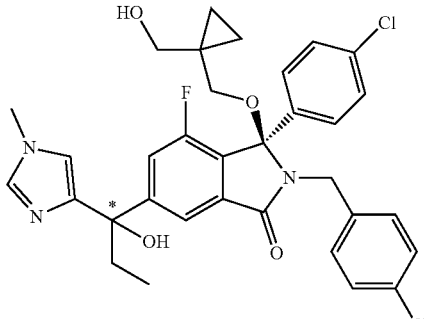<br>(*both isomers separated and isolated) | 4-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}benzonitrile<br>Ex. 94 is the faster eluting isomer<br>Ex. 95 is the slower eluting isomer |
| 96 and 97 | 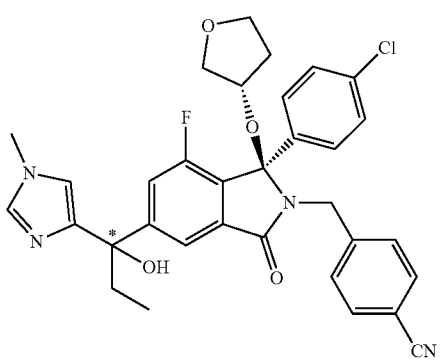<br>(*both isomers separated and isolated) | 4-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}benzonitrile |
| 98 and 99 | 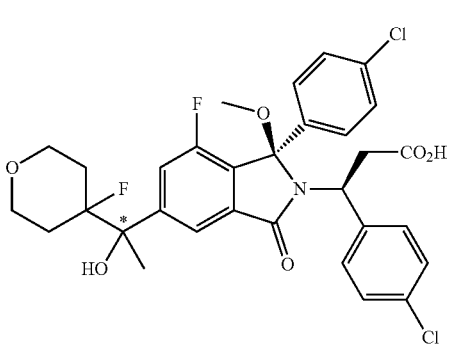<br>(*both isomers separated and isolated) | (3S)-3-(4-chlorophenyl)-3-[(1R)-1-(4-chlorophenyl)-7-fluoro-5-[1-(4-fluorooxan-4-yl)-1-hydroxyethyl]-1-methoxy-3-oxo-2,3-dihydro-1H-isoindol-2-yl]propanoic acid<br>Ex. 98 is the faster eluting isomer<br>Ex. 99 is the slower eluting isomer |
| 100 | 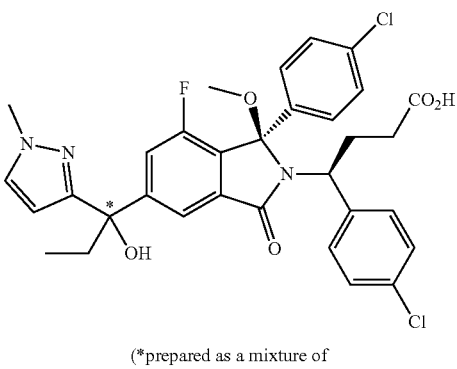<br>(*prepared as a mixture of epimers at the position shown) | (4S)-4-(4-chlorophenyl)-4-[(1R)-1-(4-chlorophenyl)-7-fluoro-5-[1-hydroxy-1-(1-methyl-1H-pyrazol-3-yl)propyl]-1-methoxy-3-oxo-2,3-dihydro-1H-isoindol-2-yl]butanoic acid |

| Ex. | Structure | Name |
|---|---|---|
| 101 and 102 | 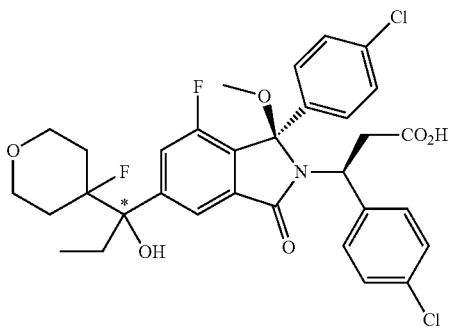 (*both isomers separated and isolated) | (3S)-3-(4-chlorophenyl)-3-[(1R)-1-(4-chlorophenyl)-7-fluoro-5-[1-(4-fluorooxan-4-yl)-1-hydroxypropyl]-1-methoxy-3-oxo-2,3-dihydro-1H-isoindol-2-yl]propanoic acid<br>Ex. 101 is the faster eluting isomer<br>Ex. 102 is the slower eluting isomer |
| 103 and 104 | 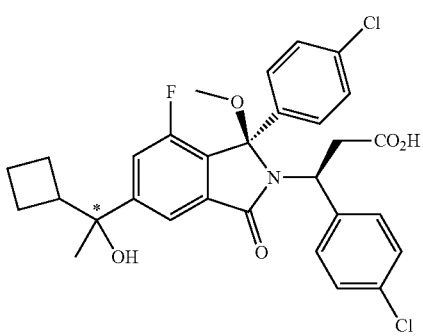 (*both isomers separated and isolated) | (3S)-3-(4-chlorophenyl)-3-[(1R)-1-(4-chlorophenyl)-5-(1-cyclobutyl-1-hydroxyethyl)-7-fluoro-1-methoxy-3-oxo-2,3-dihydro-1H-isoindol-2-yl]propanoic acid<br>Ex. 103 is the faster eluting isomer<br>Ex. 104 is the slower eluting isomer |
| 105 | 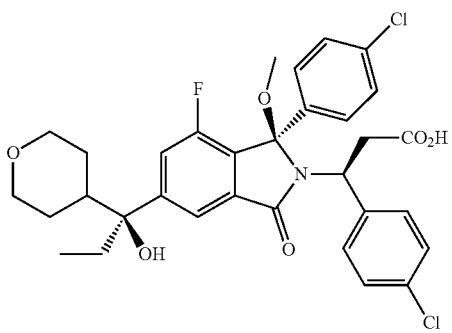 [SMILES: CC[C@@](O)(c1cc(F)c2c(c1)C(=O)N([C@@H](CC(=O)O)c1ccc(Cl)cc1)[C@@]2(OC)c1ccc(Cl)cc1)C1CCOCC1] | (3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]propanoic acid |
| 106 | 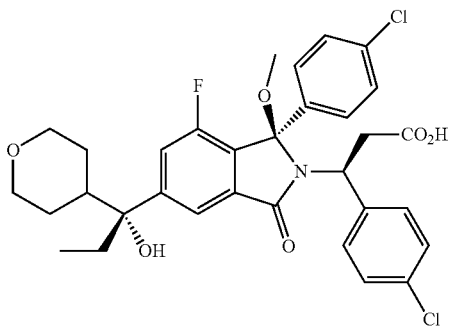 [SMILES: CC[C@](O)(c1cc(F)c2c(c1)C(=O)N([C@@H](CC(=O)O)c1ccc(Cl)cc1)[C@@]2(OC)c1ccc(Cl)cc1)C1CCOCC1] | (3S)-3-(4-chlorophenyl)-3-[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]propanoic acid |

| Ex. | Structure | Name |
|---|---|---|
| 107 | 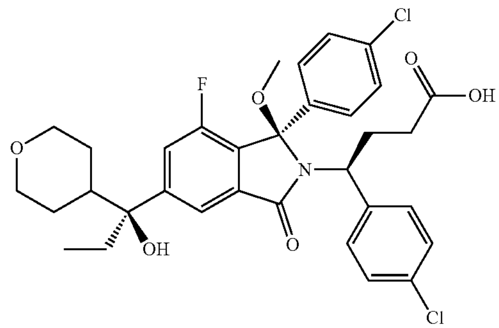 [SMILES: CC[C@@](O)(c1cc(F)c2c(c1)C(=O)N([C@@H](CCC(=O)O)c1ccc(Cl)cc1)[C@@]2(OC)c1ccc(Cl)cc1)C1CCOCC1] | (4S)-4-(4-chlorophenyl)-4-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]butanoic acid |
| 108 | 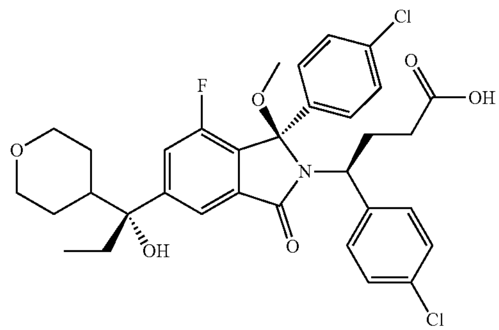 [SMILES: CC[C@](O)(c1cc(F)c2c(c1)C(=O)N([C@@H](CCC(=O)O)c1ccc(Cl)cc1)[C@@]2(OC)c1ccc(Cl)cc1)C1CCOCC1] | (4S)-4-(4-chlorophenyl)-4-[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]butanoic acid |
| 109 | 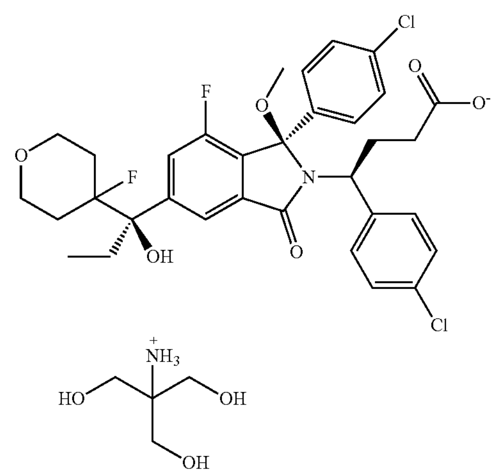 [SMILES: CC[C@@](O)(c1cc(F)c2c(c1)C(=O)N([C@@H](CCC(=O)[O-])c1ccc(Cl)cc1)[C@@]2(OC)c1ccc(Cl)cc1)C1(F)CCOCC1 ; NC(CO)(CO)CO] | (4S)-4-(4-Chlorophenyl)-4-[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]butanoic acid (tris(hydroxymethyl)aminomethane salt) |
| 110 | 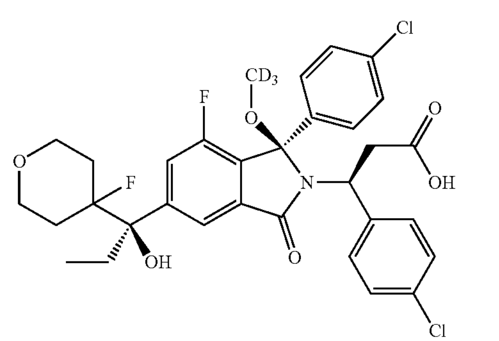 [SMILES: [2H]C([2H])([2H])O[C@]1(c2ccc(Cl)cc2)c2c(F)cc([C@](O)(CC)C3(F)CCOCC3)cc2C(=O)N1[C@@H](CC(=O)O)c1ccc(Cl)cc1] | (3S)-3-(4-chlorophenyl)-3-[(1R)-1-(4-chlorophenyl)-7-fluoro-5-[(1R)-1-(4-fluorooxan-4-yl)-1-hydroxypropyl]-1-trideuteromethoxy-3-oxo-2,3-dihydro-1H-isoindol-2-yl]propanoic acid |

-continued

| Ex. | Structure | Name |
|---|---|---|
| 111 | 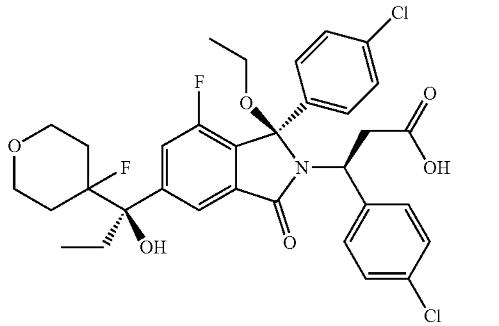 [SMILES: CCO[C@]1(c2ccc(Cl)cc2)c2c(F)cc([C@](O)(CC)C3(F)CCOCC3)cc2C(=O)N1[C@@H](CC(=O)O)c1ccc(Cl)cc1] | (3S)-3-(4-chlorophenyl)-3-[(1R)-1-(4-chlorophenyl)-1-ethoxy-7-fluoro-5-[(1R)-1-(4-fluorooxan-4-yl)-1-hydroxypropyl]-3-oxo-2,3-dihydro-1H-isoindol-2-yl]propanoic acid |
| 113 | 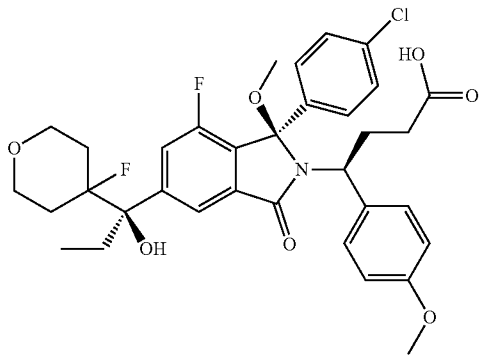 [SMILES: CC[C@@](O)(c1cc(F)c2c(c1)C(=O)N([C@@H](CCC(=O)O)c1ccc(OC)cc1)[C@@]2(OC)c1ccc(Cl)cc1)C1(F)CCOCC1] | 4S)-4-[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]-4-(4-methoxyphenyl)butanoic acid |
| 114 | (*Example prepared and isolated as a single isomer at the position shown*) | (4S)-4-(4-chlorophenyl)-4-[(1R)-1-(4-chlorophenyl)-7-fluoro-5-{1-hydroxy-1-[trans-4-hydroxycyclohexyl]propyl}-1-methoxy-3-oxo-2,3-dihydro-1H-isoindol-2-yl]butanoic acid |
| 115 | 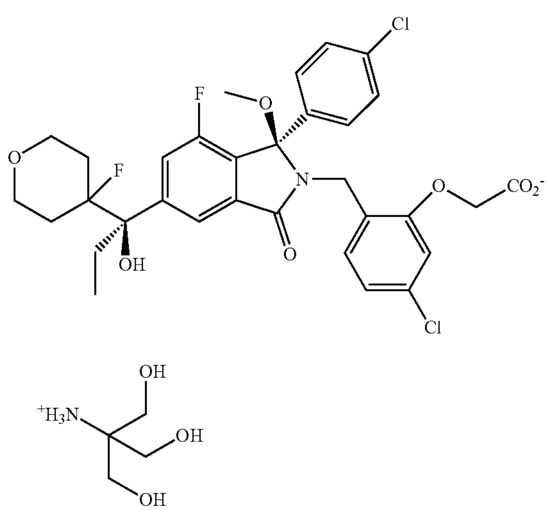 | 2-(5-chloro-2-{[1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}phenoxy)acetic acid (tris(hydroxymethyl)aminomethane salt) |

| Ex. | Structure | Name |
|---|---|---|
| 116 | 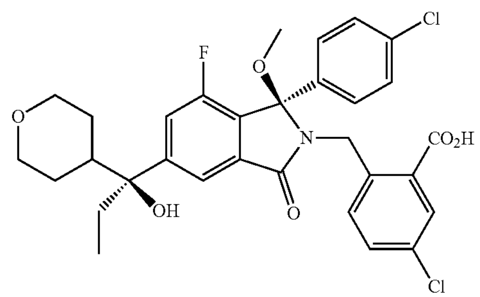 [SMILES: CC[C@@](O)(c1cc(F)c2c(c1)C(=O)N(Cc1ccc(Cl)cc1C(=O)O)[C@@]2(OC)c1ccc(Cl)cc1)C1CCOCC1] | 5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}benzoic acid |
| 117 | 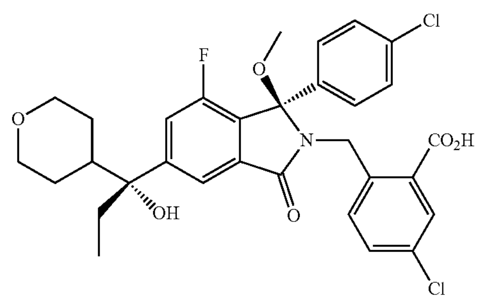 [SMILES: CC[C@](O)(c1cc(F)c2c(c1)C(=O)N(Cc1ccc(Cl)cc1C(=O)O)[C@@]2(OC)c1ccc(Cl)cc1)C1CCOCC1] | 5-chloro-2-{[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]methyl}benzoic acid |
| 118 | 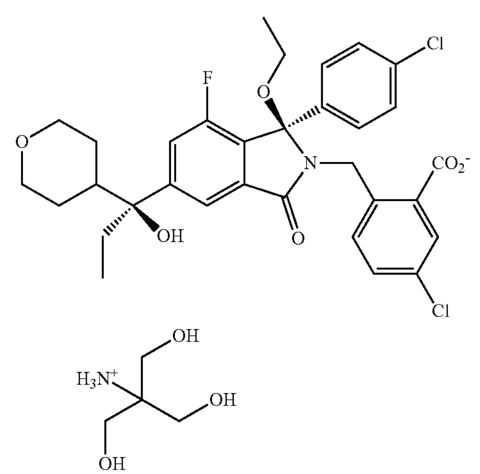 | 5-chloro-2-{[(1R)-1-(4-chlorophenyl)-1-ethoxy-7-fluoro-5-[(1S)-1-hydroxy-1-(oxan-4-yl)propyl]-3-oxo-2,3-dihydro-1H-isoindol-2-yl]methyl}benzoic acid-(tris(hydroxymethyl)aminomethane salt) |
| 119 | 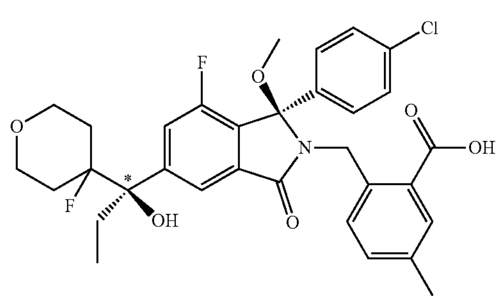 [SMILES: CC[C@@](O)(c1cc(F)c2c(c1)C(=O)N(Cc1ccc(C)cc1C(=O)O)[C@@]2(OC)c1ccc(Cl)cc1)C1(F)CCOCC1] | 2-{[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}-5-methylbenzoic acid |

-continued

| Ex. | Structure | Name |
|---|---|---|
| 120 | 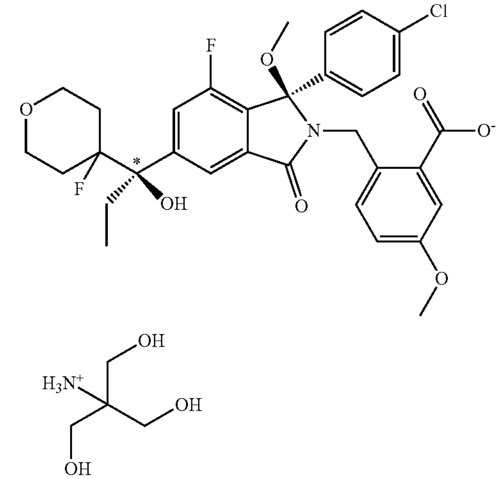 [SMILES: CC[C@@](O)(c1cc(F)c2c(c1)C(=O)N(Cc1ccc(OC)cc1C(=O)[O-])[C@@]2(OC)c1ccc(Cl)cc1)C1(F)CCOCC1 ; [NH3+]C(CO)(CO)CO] | 2-{[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}-5-methoxybenzoic acid-tris(hydroxymethyl)aminomethane salt |
| 121 | 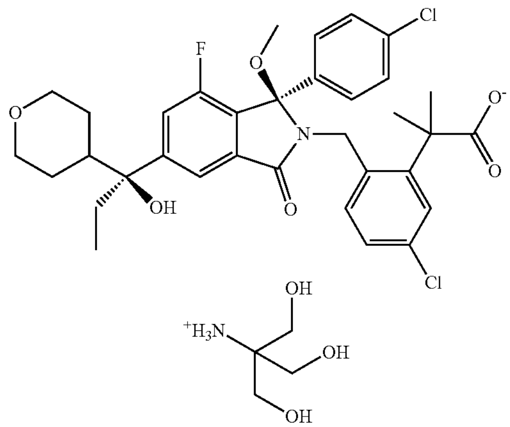 [SMILES: CC[C@@](O)(c1cc(F)c2c(c1)C(=O)N(Cc1ccc(Cl)cc1C(C)(C)C(=O)[O-])[C@@]2(OC)c1ccc(Cl)cc1)C1CCOCC1 ; [NH3+]C(CO)(CO)CO] | 2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl)-2-methylpropanoic acid (tris(hydroxymethyl)aminomethane salt) |
| 122 | 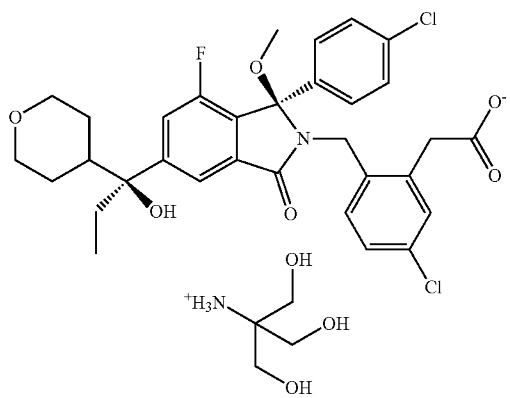 [SMILES: CC[C@@](O)(c1cc(F)c2c(c1)C(=O)N(Cc1ccc(Cl)cc1CC(=O)[O-])[C@@]2(OC)c1ccc(Cl)cc1)C1CCOCC1 ; [NH3+]C(CO)(CO)CO] | 2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl)acetic acid (tris(hydroxymethyl)aminomethane salt) |
| 123 | 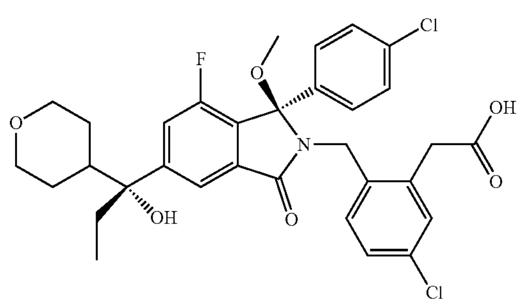 [SMILES: CC[C@](O)(c1cc(F)c2c(c1)C(=O)N(Cc1ccc(Cl)cc1CC(=O)O)[C@@]2(OC)c1ccc(Cl)cc1)C1CCOCC1] | 2-(5-chloro-2-{[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]methyl}phenyl)acetic acid |

-continued

| Ex. | Structure | Name |
|---|---|---|
| 124 | 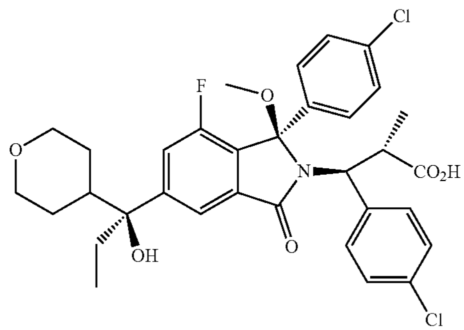 [SMILES: CC[C@@](O)(c1cc(F)c2c(c1)C(=O)N([C@H](c1ccc(Cl)cc1)[C@H](C)C(=O)O)[C@@]2(OC)c1ccc(Cl)cc1)C1CCOCC1] | (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid |
| 124 a | 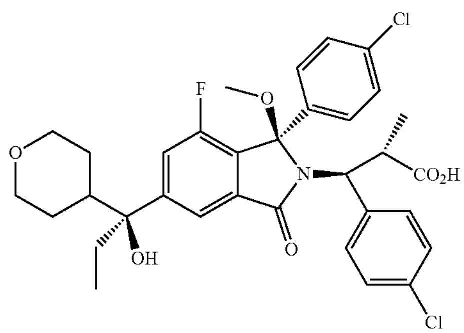 [SMILES: CC[C@@](O)(c1cc(F)c2c(c1)C(=O)N([C@H](c1ccc(Cl)cc1)[C@H](C)C(=O)O)[C@@]2(OC)c1ccc(Cl)cc1)C1CCOCC1] | (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (tris(hydroxymethyl)aminomethane salt) |
| 125 and 126 | (*both isomers separated and isolated) | (3S)-3-(4-chlorophenyl)-3-[(1R)-1-(4-chlorophenyl)-7-fluoro-1-[(3-fluorooxetan-3-yl)methoxy]-5-(2-hydroxybutan-2-yl)-3-oxo-2,3-dihydro-1H-isoindol-2-yl]propanoic acid<br>Ex. 125 is the faster eluting isomer<br>Ex. 126 is the slower eluting isomer |
| 127 and 128 | (*both isomers separated and isolated) | (3S)-3-(4-chlorophenyl)-3-[(1R)-1-(4-chlorophenyl)-7-fluoro-5-[1-hydroxy-1-(pyridin-2-yl)propyl]-1-methoxy-3-oxo-2,3-dihydro-1H-isoindol-2-yl]propanoic acid<br>Ex. 127 is the faster eluting isomer<br>Ex. 128 is the slower eluting isomer |

-continued

| Ex. | Structure | Name |
|---|---|---|
| 129 | 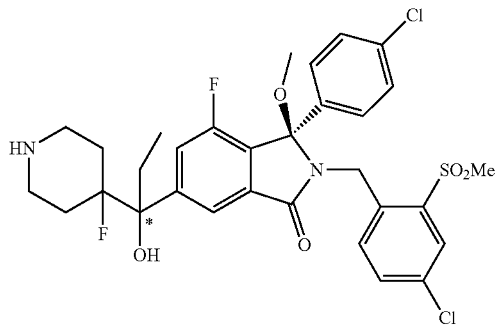 | (3R)-2-[(4-chloro-2-methanesulfonylphenyl)methyl]-3-(4-chlorophenyl)-4-fluoro-6-[1-(4-fluoropiperidin-4-yl)-1-hydroxypropyl]-3-methoxy-2,3-dihydro-1H-isoindol-1-one |
|  | (Example isolated as a single isomer at the position shown*) | |
| 130 | 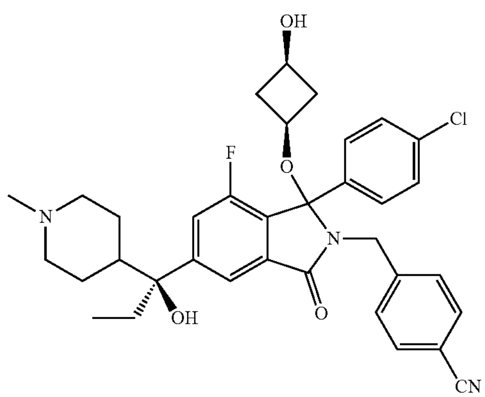 [SMILES: CC[C@@](O)(c1cc(F)c2c(c1)C(=O)N(Cc1ccc(C#N)cc1)C2(O[C@H]1C[C@@H](O)C1)c1ccc(Cl)cc1)C1CCN(C)CC1] | 4-{[(1R)-1-(4-chlorophenyl)-7-fluoro-5-[(1S)-1-hydroxy-1-(1-methylpiperidin-4-yl)propyl]-3-oxo-1-[cis-3-hydroxycyclobutoxy]-2,3-dihydro-1H-isoindol-2-yl]methyl}benzonitrile |
| 131 | 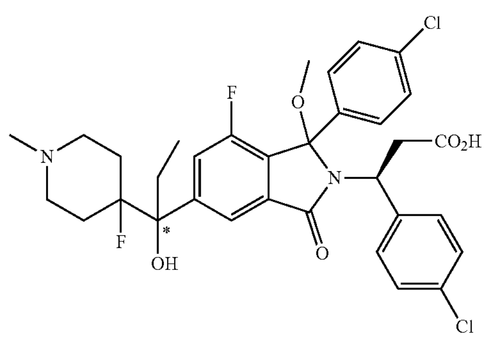 | (3S)-3-(4-chlorophenyl)-3-[(1R)-1-(4-chlorophenyl)-7-fluoro-5-[1-(4-fluoro-1-methylpiperidin-4-yl)-1-hydroxypropyl]-1-methoxy-3-oxo-2,3-dihydro-1H-isoindol-2-yl]propanoic acid |
|  | (*single isomer separated and isolated) | |
| 132 and 133 | 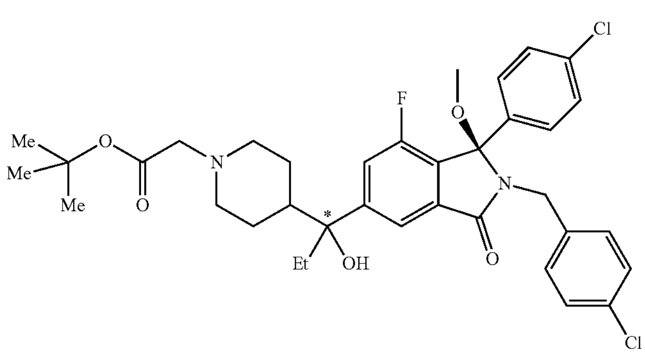 | tert-butyl 2-{4-[(1S)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetate and tert-butyl 2-{4-[(1R)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetate Ex. 132 is the faster eluting isomer Ex. 133 is the slower eluting isomer |
|  | (*both isomers separated and isolated) | |

-continued

| Ex. | Structure | Name |
|---|---|---|
| 134 | (*prepared and isolated as a single isomers) | 2-{4-[(1S)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetic acid |
| 135 | (*prepared and isolated as a single isomers) | 2-{4-[(1R)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetic acid |
| 136 | 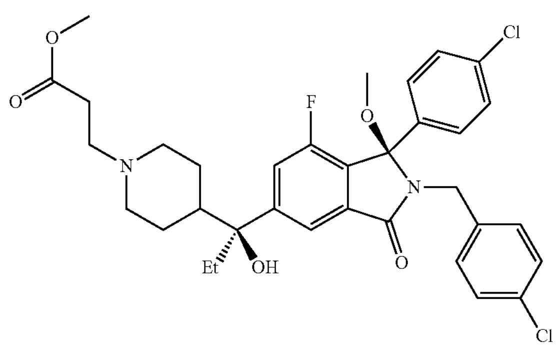 [SMILES: CC[C@@](O)(c1cc(F)c2c(c1)C(=O)N(Cc1ccc(Cl)cc1)[C@@]2(OC)c1ccc(Cl)cc1)C1CCN(CCC(=O)OC)CC1] | Methyl 3-{4-[(1S)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}propanoate |
| 137 | 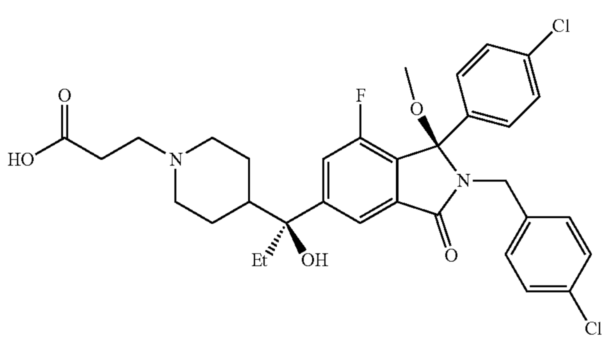 [SMILES: CC[C@@](O)(c1cc(F)c2c(c1)C(=O)N(Cc1ccc(Cl)cc1)[C@@]2(OC)c1ccc(Cl)cc1)C1CCN(CCC(=O)O)CC1] | 3-{4-[(1S)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}propanoic acid |

The following second set of examples, in which cyc is Het, can be prepared as decribed in international patent application no PCT/GB2016/053041 which was published as WO 2017/055859 on Jun. 4, 2017:

| Ex. | Structure | Name |
|---|---|---|
| 1 | 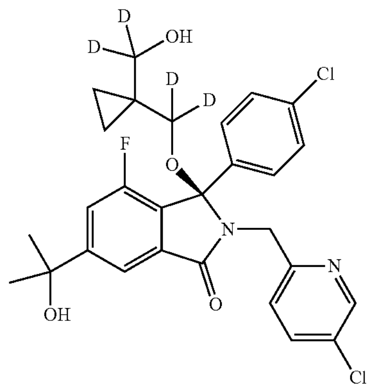 [SMILES: [2H]C([2H])(O)C1(C([2H])([2H])O[C@]2(c3ccc(Cl)cc3)c3c(F)cc(C(C)(C)O)cc3C(=O)N2Cc2ccc(Cl)cn2)CC1] | (3R)-3-(4-chlorophenyl)-2-[(5-chloropyridin-2-yl)methyl]-4-fluoro-3-({1-[hydroxy($^2$H$_2$)methyl]cyclopropyl}($^2$H$_2$)methoxy)-6-(2-hydroxypropan-2-yl)-2,3-dihydro-1H-isoindol-1-one |
| 2 | 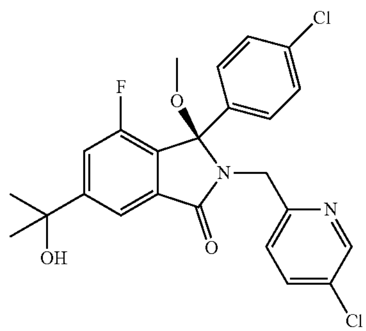 [SMILES: CO[C@]1(c2ccc(Cl)cc2)c2c(F)cc(C(C)(C)O)cc2C(=O)N1Cc1ccc(Cl)cn1] | (3R)-3-(4-Chlorophenyl)-2-[(5-chloropyridin-2-yl)methyl]-4-fluoro-6-(2-hydroxypropan-2-yl)-3-methoxy-2,3-dihydro-1H-isoindol-1-one |
| 3 | 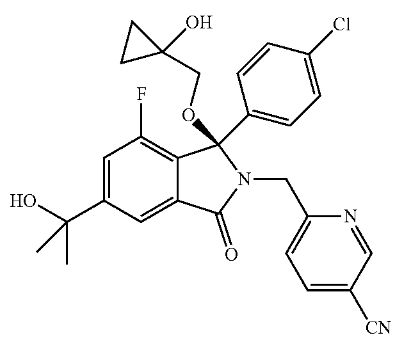 [SMILES: CC(C)(O)c1cc(F)c2c(c1)C(=O)N(Cc1ccc(C#N)cn1)[C@@]2(OCC1(O)CC1)c1ccc(Cl)cc1] | 6-{[(1R)-1-(4-chlorophenyl)-7-fluoro-1-[(1-hydroxycyclopropyl)methoxy]-5-(2-hydroxypropan-2-yl)-3-oxo-2,3-dihydro-1H-isoindol-2-yl]methyl}pyridine-3-carbonitrile |
| 4 | 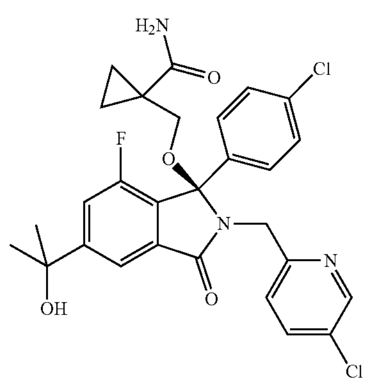 [SMILES: CC(C)(O)c1cc(F)c2c(c1)C(=O)N(Cc1ccc(Cl)cn1)[C@@]2(OCC1(C(N)=O)CC1)c1ccc(Cl)cc1] | 1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropane-1-carboxamide |

| Ex. | Structure | Name |
|---|---|---|
| 5 | 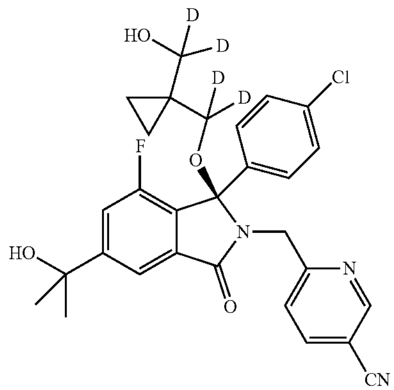 [SMILES: [2H]C([2H])(O)C1(C([2H])([2H])O[C@]2(c3ccc(Cl)cc3)c3c(F)cc(C(C)(C)O)cc3C(=O)N2Cc2ccc(C#N)cn2)CC1] | 6-{[(1R)-1-(4-Chlorophenyl)-7-fluoro-1-({1-[hydroxy($^2$H$_2$)methyl]cyclopropyl}($^2$H$_2$)methoxy)-5-(2-hydroxypropan-2-yl)-3-oxo-2,3-dihydro-1H-isoindol-2-yl]methyl}pyridine-3-carbonitrile |
| 6 | 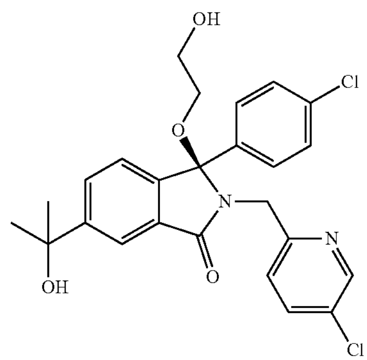 [SMILES: CC(C)(O)c1ccc2c(c1)C(=O)N(Cc1ccc(Cl)cn1)[C@@]2(OCCO)c1ccc(Cl)cc1] | (3R)-3-(4-chlorophenyl)-2-[(5-chloropyridin-2-yl)methyl]-3-(2-hydroxyethoxy)-6-(2-hydroxypropan-2-yl)-2,3-dihydro-1H-isoindol-1-one |
| 7 | 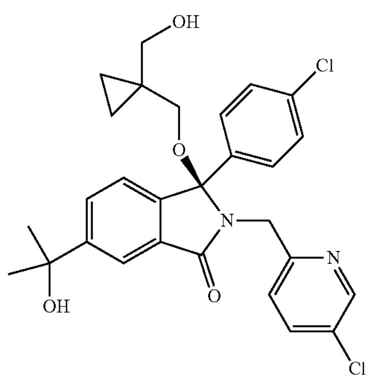 [SMILES: CC(C)(O)c1ccc2c(c1)C(=O)N(Cc1ccc(Cl)cn1)[C@@]2(OCC1(CO)CC1)c1ccc(Cl)cc1] | (3R)-3-(4-Chlorophenyl)-2-[(5-chloropyridin-2-yl)methyl]-3-{[1-(hydroxymethyl)cyclopropyl]methoxy}-6-(2-hydroxypropan-2-yl)-2,3-dihydro-1H-isoindol-1-one |
| 8 | 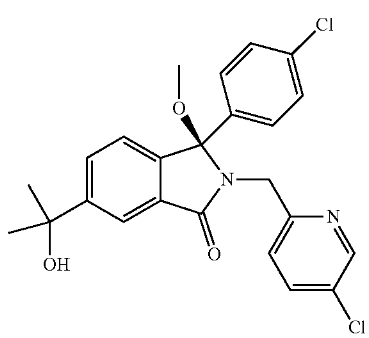 [SMILES: CO[C@]1(c2ccc(Cl)cc2)c2ccc(C(C)(C)O)cc2C(=O)N1Cc1ccc(Cl)cn1] | (3R)-3-(4-Chlorophenyl)-2-[(5-chloropyridin-2-yl)methyl]-6-(2-hydroxypropan-2-yl)-3-methoxy-2,3-dihydro-1H-isoindol-1-one |

| Ex. | Structure | Name |
|---|---|---|
| 9 | 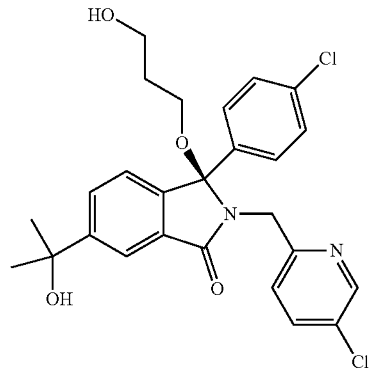 [SMILES: CC(C)(O)c1ccc2c(c1)C(=O)N(Cc1ccc(Cl)cn1)[C@@]2(OCCCO)c1ccc(Cl)cc1] | (3R)-3-(4-Chlorophenyl)-2-[(5-chloropyridin-2-yl)methyl]-6-(2-hydroxypropan-2-yl)-3-(3-hydroxypropoxy)-2,3-dihydro-1H-isoindol-1-one |
| 10 | 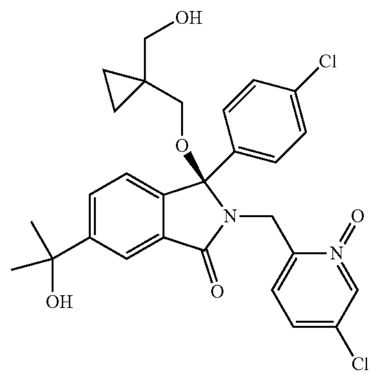 [SMILES: CC(C)(O)c1ccc2c(c1)C(=O)N(Cc1ccc(Cl)c[n+]1[O-])[C@@]2(OCC1(CO)CC1)c1ccc(Cl)cc1] | (3R)-2-[(5-Chloro-1-oxo-1λ⁵-pyridin-2-yl)methyl]-3-(4-chlorophenyl)-3-{[1-(hydroxymethyl)cyclopropyl]methoxy}-6-(2-hydroxypropan-2-yl)-2,3-dihydro-1H-isoindol-1-one |
| 11 | 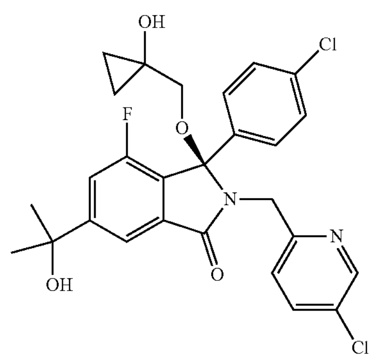 [SMILES: CC(C)(O)c1cc(F)c2c(c1)C(=O)N(Cc1ccc(Cl)cn1)[C@@]2(OCC1(O)CC1)c1ccc(Cl)cc1] | (3R)-3-(4-Chlorophenyl)-2-[(5-chloropyridin-2-yl)methyl]-4-fluoro-3-[(1-hydroxycyclopropyl)methoxy]-6-(2-hydroxypropan-2-yl)-2,3-dihydro-1H-isoindol-1-one |
| 12 | 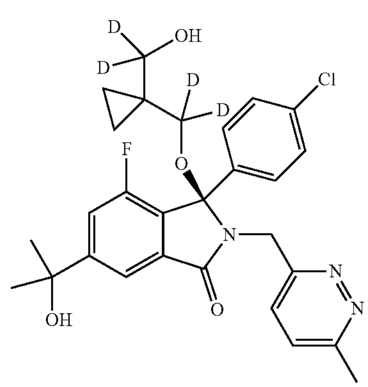 [SMILES: [2H]C([2H])(O)C1(C([2H])([2H])O[C@]2(c3ccc(Cl)cc3)c3c(F)cc(C(C)(C)O)cc3C(=O)N2Cc2ccc(C)nn2)CC1] | (3R)-3-(4-Chlorophenyl)-4-fluoro-3-({1-[hydroxy(²H₂)methyl]cyclopropyl}(²H₂)methoxy)-6-(2-hydroxypropan-2-yl)-2-[(6-methylpyridazin-3-yl)methyl]-2,3-dihydro-1H-isoindol-1-one |

| Ex. | Structure | Name |
|---|---|---|
| 13 | 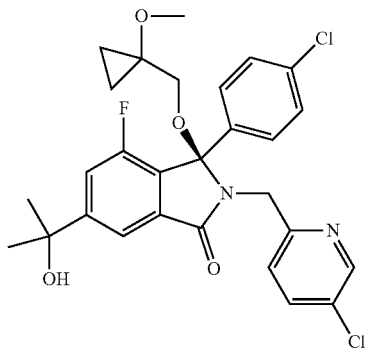 [SMILES: COC1(CO[C@]2(c3ccc(Cl)cc3)c3c(F)cc(C(C)(C)O)cc3C(=O)N2Cc2ccc(Cl)cn2)CC1] | (3R)-3-(4-Chlorophenyl)-2-[(5-chloropyridin-2-yl)methyl]-4-fluoro-6-(2-hydroxypropan-2-yl)-3-[(1-methoxycyclopropyl)methoxy]-2,3-dihydro-1H-isoindol-1-one |
| 14 and 15 | 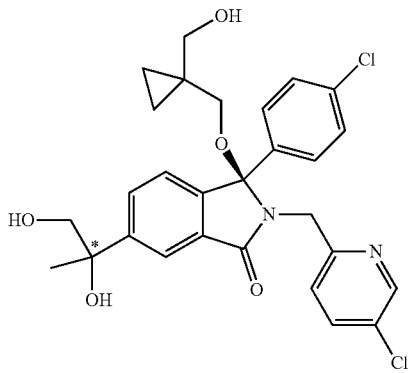<br>(*both isomers separated and isolated) | (3R)-3-(4-Chlorophenyl)-2-[(5-chloropyridin-2-yl)methyl]-6-(1,2-dihydroxypropan-2-yl)-3-{[1-(hydroxymethyl)cyclopropyl]methoxy}-2,3-dihydro-1H-isoindol-1-one |
| 16 and 17 | 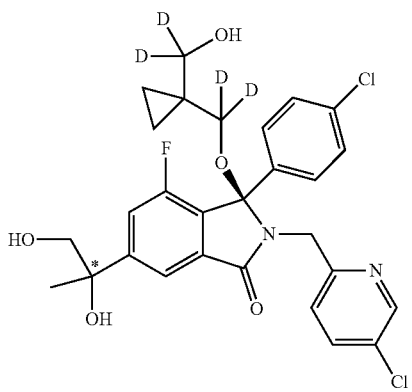<br>(*both isomers separated and isolated) | (3R)-3-(4-Chlorophenyl)-2-[(5-chloropyridin-2-yl)methyl]-6-(1,2-dihydroxypropan-2-yl)-4-fluoro-3-({1-[hydroxy($^{2}H_2$)methyl]cyclopropyl}($^{2}H_2$)methoxy)-2,3-dihydro-1H-isoindol-1-one |

-continued

| Ex. | Structure | Name |
|---|---|---|
| 18 and 19 | 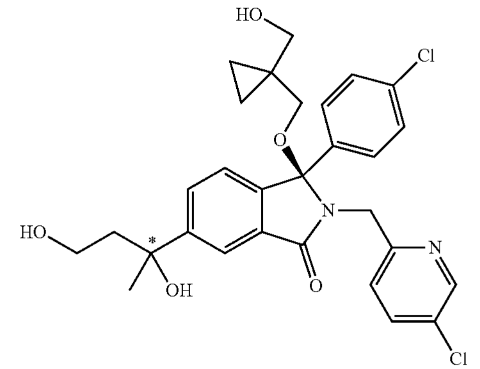 | (3R)-3-(4-Chlorophenyl)-2-[(5-chloropyridin-2-yl)methyl]-6-(2,4-dihydroxybutan-2-yl)-3-{[1-(hydroxymethyl)cyclopropyl]methoxy}-2,3-dihydro-1H-isoindol-1-one |
| | (*both isomers separated and isolated) | |
| 20 and 21 | 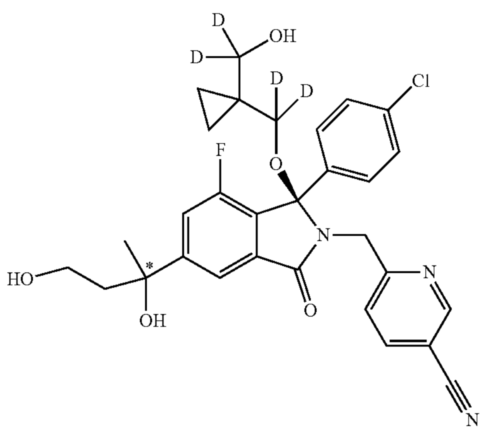 | 6-{[(1R)-1-(4-Chlorophenyl)-5-(2,4-dihydroxybutan-2-yl)-7-fluoro-1-({1-[hydroxy($^2$H$_2$)methyl]cyclopropyl}($^2$H$_2$)methoxy)-3-oxo-2,3-dihydro-1H-isoindol-2-yl]methyl}pyridine-3-carbonitrile |
| | (*both isomers separated and isolated) | |
| 22 and 23 | 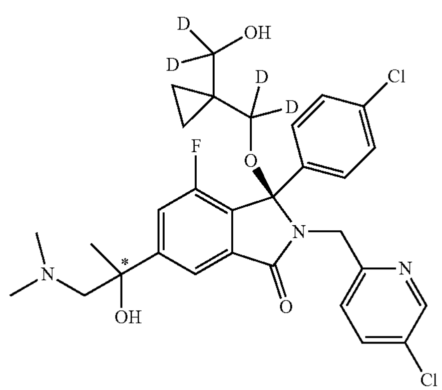 | (3R)-3-(4-Chlorophenyl)-2-[(5-chloropyridin-2-yl)methyl]-6-[1-(dimethylamino)-2-hydroxypropan-2-yl]-4-fluoro-3-({1-[hydroxy($^2$H$_2$)methyl]cyclopropyl}($^2$H$_2$)methoxy)-2,3-dihydro-1H-isoindol-1-one |
| | (*both isomers separated and isolated) | |

-continued

| Ex. | Structure | Name |
|---|---|---|
| 24 and 25 | 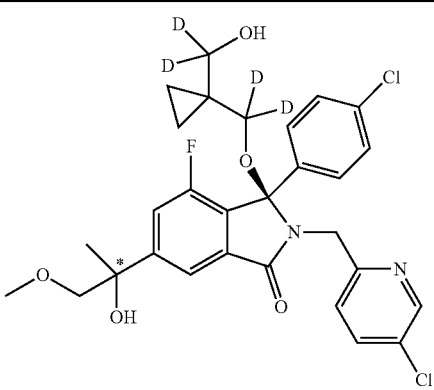 (*both isomers separated and isolated) | (3R)-3-(4-Chlorophenyl)-2-[(5-chloropyridin-2-yl)methyl]-4-fluoro-3-({1-[hydroxy($^2$H$_2$)methyl]cyclopropyl}($^2$H$_2$)methoxy)-6-(2-hydroxy-1-methoxypropan-2-yl)-2,3-dihydro-1H-isoindol-1-one |
| 26 | 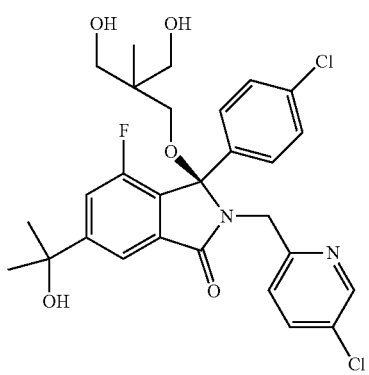 [SMILES: CC(CO)(CO)CO[C@]1(c2ccc(Cl)cc2)c2c(F)cc(C(C)(C)O)cc2C(=O)N1Cc1ccc(Cl)cn1] | (3R)-3-(4-Chlorophenyl)-2-[(5-chloropyridin-2-yl)methyl]-4-fluoro-3-[3-hydroxy-2-(hydroxymethyl)-2-methylpropoxy]-6-(2-hydroxypropan-2-yl)-2,3-dihydro-1H-isoindol-1-one |
| 27 | 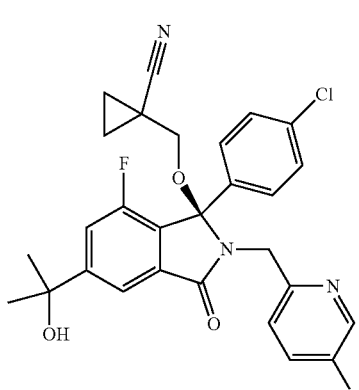 | 1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropane-1-carbonitrile |
| 28 | 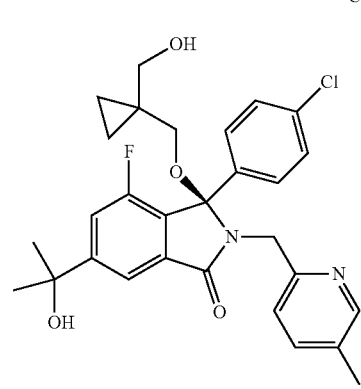 | (3R)-3-(4-Chlorophenyl)-4-fluoro-3-{[1-(hydroxymethyl)cyclopropyl]methoxy}-6-(2-hydroxypropan-2-yl)-2-[(5-methylpyridin-2-yl)methyl]-2,3-dihydro-1H-isoindol-1-one |

-continued

| Ex. | Structure | Name |
|---|---|---|
| 29 | 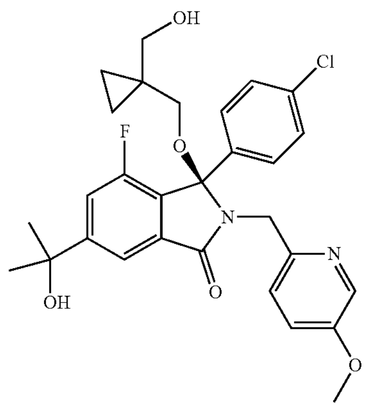 [SMILES: COc1ccc(CN2C(=O)c3cc(C(C)(C)O)cc(F)c3[C@]2(OCC2(CO)CC2)c2ccc(Cl)cc2)nc1] | (3R)-3-(4-Chlorophenyl)-4-fluoro-3-{[1-(hydroxymethyl)cyclopropyl]methoxy}-6-(2-hydroxypropan-2-yl)-2-[(5-methoxypyridin-2-yl)methyl]-2,3-dihydro-1H-isoindol-1-one |
| 30 | 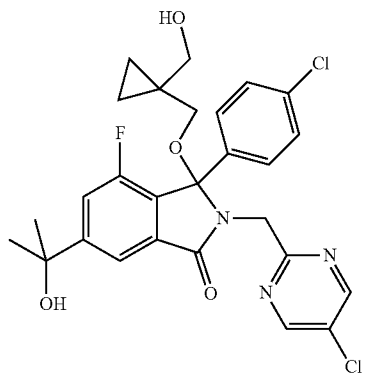 [SMILES: CC(C)(O)c1cc(F)c2c(c1)C(=O)N(Cc1ncc(Cl)cn1)C2(OCC1(CO)CC1)c1ccc(Cl)cc1] | 3-(4-Chlorophenyl)-2-[(5-chloropyrimidin-2-yl)methyl]-4-fluoro-3-{[1-(hydroxymethyl)cyclopropyl]methoxy}-6-(2-hydroxypropan-2-yl)-2,3-dihydro-1H-isoindol-1-one |
| 31 | 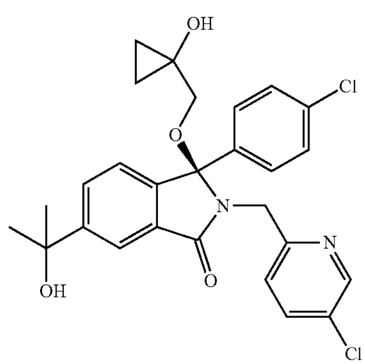 [SMILES: CC(C)(O)c1ccc2c(c1)C(=O)N(Cc1ccc(Cl)cn1)[C@@]2(OCC1(O)CC1)c1ccc(Cl)cc1] | (3R)-3-(4-chlorophenyl)-2-[(5-chloropyridin-2-yl)methyl]-3-[(1-hydroxycyclopropyl)methoxy]-6-(2-hydroxypropan-2-yl)-2,3-dihydro-1H-isoindol-1-one |
| 32 | 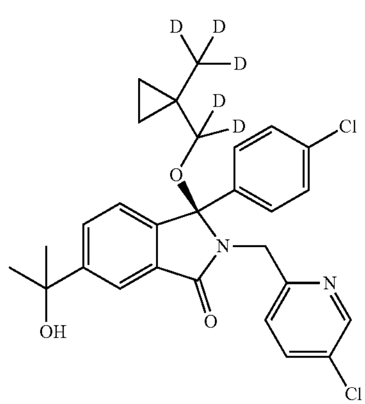 [SMILES: [2H]C([2H])([2H])C1(C([2H])([2H])O[C@]2(c3ccc(Cl)cc3)c3ccc(C(C)(C)O)cc3C(=O)N2Cc2ccc(Cl)cn2)CC1] | (3R)-3-(4-Chlorophenyl)-2-[(5-chloropyridin-2-yl)methyl]-3-({1-[hydroxy($^2H_2$)methyl]cyclopropyl}($^2H_2$)methoxy)-6-(2-hydroxypropan-2-yl)-2,3-dihydro-1H-isoindol-1-one |

| Ex. | Structure | Name |
|---|---|---|
| 33 | 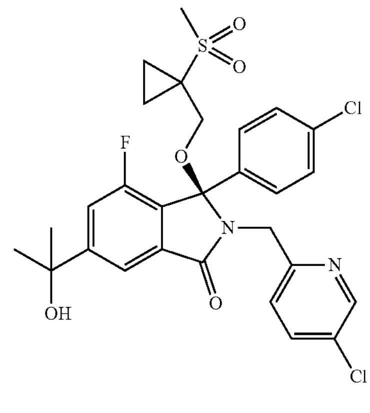 [SMILES: CC(C)(O)c1cc(F)c2c(c1)C(=O)N(Cc1ccc(Cl)cn1)[C@@]2(OCC1(S(C)(=O)=O)CC1)c1ccc(Cl)cc1] | (3R)-3-(4-chlorophenyl)-2-[(5-chloropyridin-2-yl)methyl]-4-fluoro-6-(2-hydroxypropan-2-yl)-3-[(1-methanesulfonylcyclopropyl)methoxy]-2,3-dihydro-1H-isoindol-1-one |
| 34 | 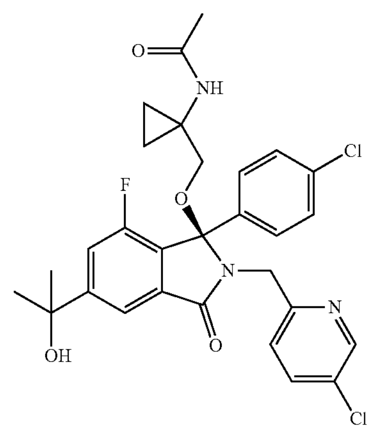 [SMILES: CC(=O)NC1(CO[C@]2(c3ccc(Cl)cc3)c3c(F)cc(C(C)(C)O)cc3C(=O)N2Cc2ccc(Cl)cn2)CC1] | N-[1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]acetamide |
| 35 | 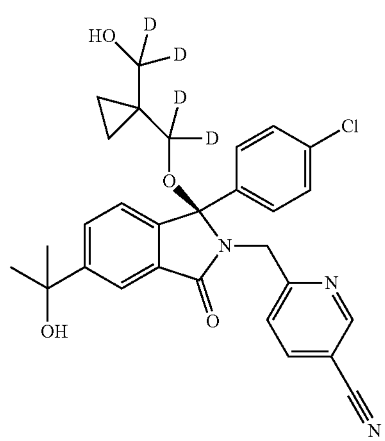 [SMILES: [2H]C([2H])(O)C1(C([2H])([2H])O[C@]2(c3ccc(Cl)cc3)c3ccc(C(C)(C)O)cc3C(=O)N2Cc2ccc(C#N)cn2)CC1] | 6-{[(1R)-1-(4-Chlorophenyl)-1-({1-[hydroxy($^2$H$_2$)methyl]cyclopropyl}($^2$H$_2$)methoxy)-5-(2-hydroxypropan-2-yl)-3-oxo-2,3-dihydro-1H-isoindol-2-yl]methyl}pyridine-3-carbonitrile |

| Ex. | Structure | Name |
| --- | --- | --- |
| 36 | 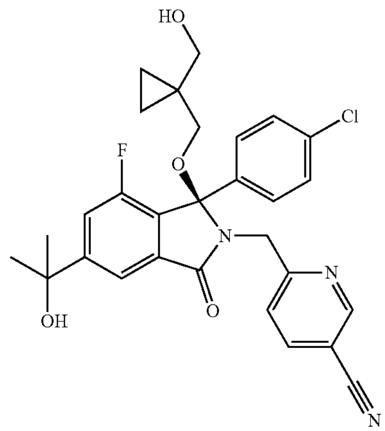 [SMILES: CC(C)(O)c1cc(F)c2c(c1)C(=O)N(Cc1ccc(C#N)cn1)[C@@]2(OCC1(CO)CC1)c1ccc(Cl)cc1] | 6-{[(1R)-1-(4-chlorophenyl)-7-fluoro-1-{[1-(hydroxymethyl)cyclopropyl]methoxy}-5-(2-hydroxypropan-2-yl)-3-oxo-2,3-dihydro-1H-isoindol-2-yl]methyl}pyridine-3-carbonitrile |
| 37 | 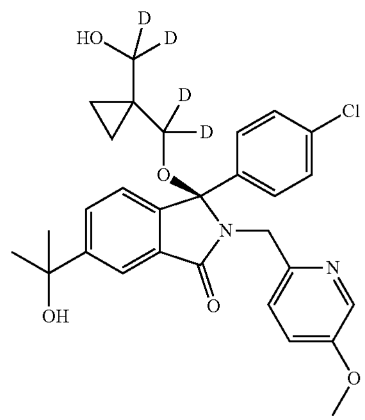 [SMILES: [2H]C([2H])(O)C1(C([2H])([2H])O[C@]2(c3ccc(Cl)cc3)c3ccc(C(C)(C)O)cc3C(=O)N2Cc2ccc(OC)cn2)CC1] | (3R)-3-(4-Chlorophenyl)-4-fluoro-3-({1-[hydroxy($^2$H$_2$)methyl]cyclopropyl}($^2$H$_2$)methoxy)-6-(2-hydroxypropan-2-yl)-2-[(6-methoxypyridin-3-yl)methyl]-2,3-dihydro-1H-isoindol-1-one |
| 38 and 39 | 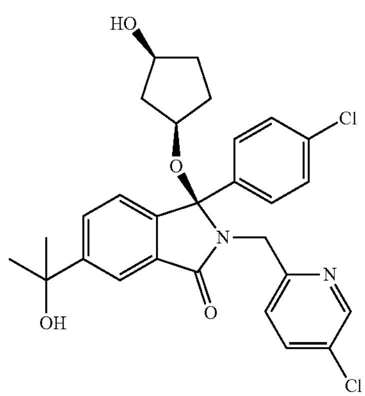 [SMILES: CC(C)(O)c1ccc2c(c1)C(=O)N(Cc1ccc(Cl)cn1)[C@@]2(O[C@@H]1CC[C@H](O)C1)c1ccc(Cl)cc1] | (3R)-3-(4-chlorophenyl)-2-[(5-chloropyridin-2-yl)methyl]-3-{[(1S,3R)-3-hydroxycyclopentyl]oxy}-6-(2-hydroxypropan-2-yl)-2,3-dihydro-1H-isoindol-1-one and (3R)-3-(4-chlorophenyl)-2-[(5-chloropyridin-2-yl)methyl]-3-{[(1R,3S)-3-hydroxycyclopentyl]oxy}-6-(2-hydroxypropan-2-yl)-2,3-dihydro-1H-isoindol-1-one |

| Ex. | Structure | Name |
|---|---|---|
| | 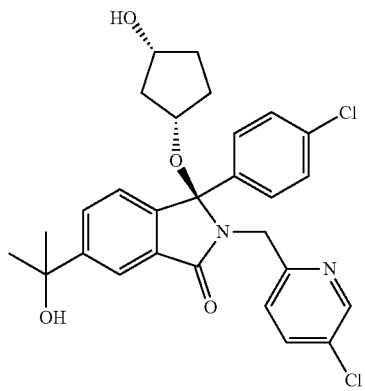<br>(Both isomers as shown) | |
| 40 and 41 | 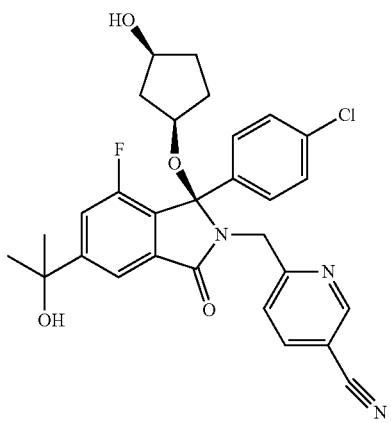 [SMILES: CC(C)(O)c1cc(F)c2c(c1)C(=O)N(Cc1ccc(C#N)cn1)[C@@]2(O[C@@H]1CC[C@H](O)C1)c1ccc(Cl)cc1] | 6-{[(1R)-1-(4-chlorophenyl)-7-fluoro-1-{[(1S,3R)-3-hydroxycyclopentyl]oxy}-5-(2-hydroxypropan-2-yl)-3-oxo-2,3-dihydro-1H-isoindol-2-yl]methyl}pyridine-3-carbonitrile and 6-{[(1R)-1-(4-chlorophenyl)-7-fluoro-1-{[(1R,3S)-3-hydroxycyclopentyl]oxy}-5-(2-hydroxypropan-2-yl)-3-oxo-2,3-dihydro-1H-isoindol-2-yl]methyl}pyridine-3-carbonitrile |
| | 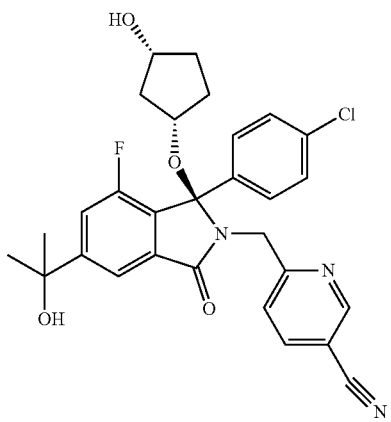 [SMILES: CC(C)(O)c1cc(F)c2c(c1)C(=O)N(Cc1ccc(C#N)cn1)[C@@]2(O[C@@H]1CC[C@@H](O)C1)c1ccc(Cl)cc1]<br>(Both isomers as shown) | |

| Ex. | Structure | Name |
|---|---|---|
| 42 and 43 | 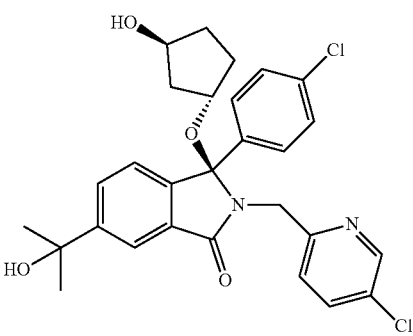 [SMILES: CC(C)(O)c1ccc2c(c1)C(=O)N(Cc1ccc(Cl)cn1)[C@@]2(O[C@H]1CC[C@H](O)C1)c1ccc(Cl)cc1]<br>(Both isomers as shown) | 6-{[(1R)-1-(4-chlorophenyl)-7-fluoro-1-[(3-hydroxycyclopentyl)oxy]-5-(2-hydroxypropan-2-yl)-3-oxo-2,3-dihydro-1H-isoindol-2-yl]methyl}pyridine-3-carbonitrile |
| 44 and 45 | 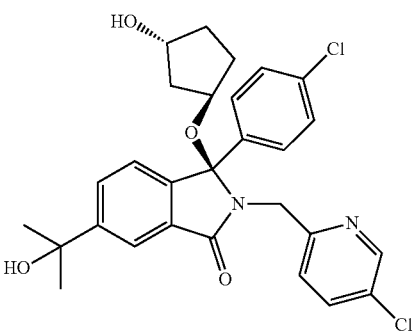<br>(Both isomers as shown) | (3R)-3-(4-chlorophenyl)-2-[(5-chloropyridin-2-yl)methyl]-3-{[(1R,3R)-3-hydroxycyclopentyl]oxy}-6-(2-hydroxypropan-2-yl)-2,3-dihydro-1H-isoindol-1-one and (3R)-3-(4-chlorophenyl)-2-[(5-chloropyridin-2-yl)methyl]-3-{[(1S,3S)-3-hydroxycyclopentyl]oxy}-6-(2-hydroxypropan-2-yl)-2,3-dihydro-1H-isoindol-1-one |

| Ex. | Structure | Name |
|---|---|---|
| 46 | 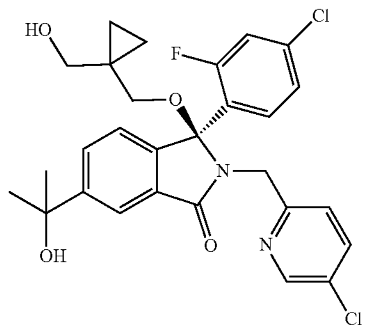 [SMILES: CC(C)(O)c1ccc2c(c1)C(=O)N(Cc1ccc(Cl)cn1)[C@@]2(OCC1(CO)CC1)c1ccc(Cl)cc1F] | (3S)-3-(4-Chloro-2-fluorophenyl)-2-[(5-chloropyridin-2-yl)methyl]-3-{[1-(hydroxymethyl)cyclopropyl]methoxy}-6-(2-hydroxypropan-2-yl)-2,3-dihydro-1H-isoindol-1-one |
| 47 | 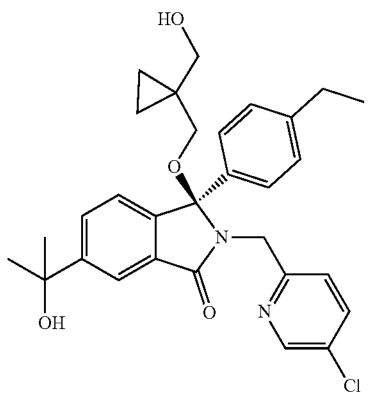 [SMILES: CCc1ccc([C@@]2(OCC3(CO)CC3)c3ccc(C(C)(C)O)cc3C(=O)N2Cc2ccc(Cl)cn2)cc1] | ((3R)-2-[(5-chloropyridin-2-yl)methyl]-3-(4-ethylphenyl)-3-{[1-(hydroxymethyl)cyclopropyl]methoxy}-6-(2-hydroxypropan-2-yl)-2,3-dihydro-1H-isoindol-1-one |
| 48 | 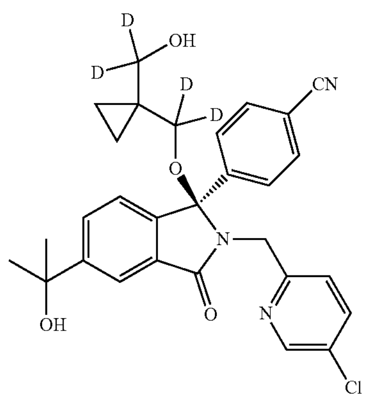 [SMILES: [2H]C([2H])(O)C1(C([2H])([2H])O[C@]2(c3ccc(C#N)cc3)c3ccc(C(C)(C)O)cc3C(=O)N2Cc2ccc(Cl)cn2)CC1] | 4-[(1R)-2-[(5-Chloropyridin-2-yl)methyl]-1-({1-[hydroxy($^2$H$_2$)methyl]cyclopropyl}($^2$H$_2$)methoxy)-5-(2-hydroxypropan-2-yl)-3-oxo-2,3-dihydro-1H-isoindol-1-yl]benzonitrile |
| 49 | 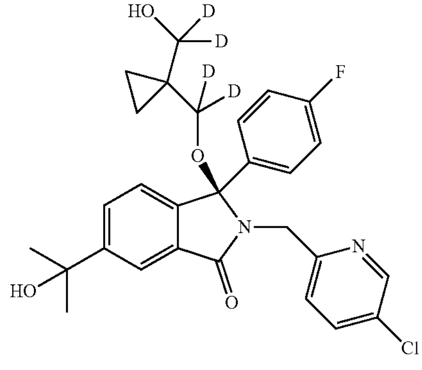 [SMILES: [2H]C([2H])(O)C1(C([2H])([2H])O[C@]2(c3ccc(F)cc3)c3ccc(C(C)(C)O)cc3C(=O)N2Cc2ccc(Cl)cn2)CC1] | (3R)-2-[(5-Chloropyridin-2-yl)methyl]-3-(4-fluorophenyl)-3-({1-[hydroxy($^2$H$_2$)methyl]cyclopropyl}($^2$H$_2$)methoxy)-6-(2-hydroxypropan-2-yl)-2,3-dihydro-1H-isoindol-1-one |

| Ex. | Structure | Name |
|---|---|---|
| 50 | 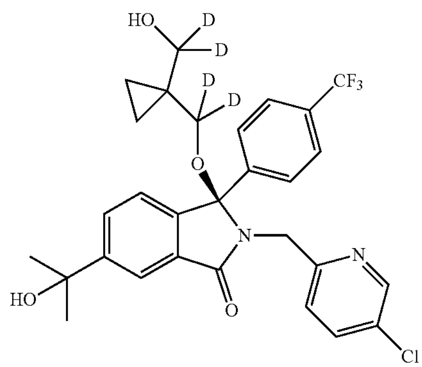 [SMILES: [2H]C([2H])(O)C1(C([2H])([2H])O[C@]2(c3ccc(C(F)(F)F)cc3)c3ccc(C(C)(C)O)cc3C(=O)N2Cc2ccc(Cl)cn2)CC1] | (3R)-2-[(5-Chloropyridin-2-yl)methyl]-3-({1-[hydroxy($^2H_2$)methyl]cyclopropyl}($^2H_2$)methoxy)-6-(2-hydroxypropan-2-yl)-3-[4-(trifluoromethyl)phenyl]-2,3-dihydro-1H-isoindol-1-one |
| 51 | 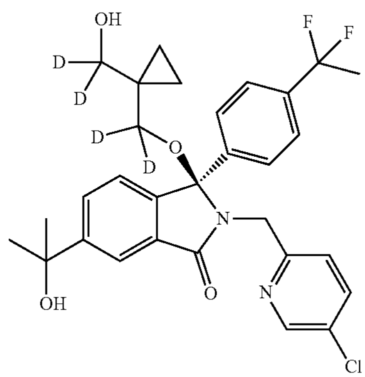 [SMILES: [2H]C([2H])(O)C1(C([2H])([2H])O[C@]2(c3ccc(C(C)(F)F)cc3)c3ccc(C(C)(C)O)cc3C(=O)N2Cc2ccc(Cl)cn2)CC1] | (3R)-2-[(5-chloropyridin-2-yl)methyl]-3-[4-(1,1-difluoroethyl)phenyl]-3-{[1-(hydroxymethyl)cyclopropyl]methoxy}-6-(2-hydroxypropan-2-yl)-2,3-dihydro-1H-isoindol-1-one |
| 52 | 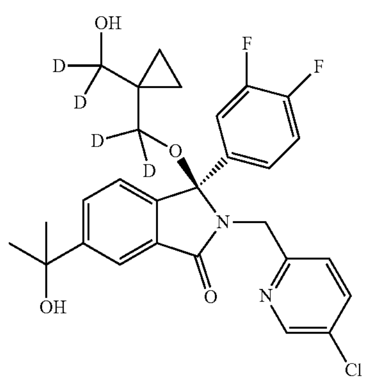 [SMILES: [2H]C([2H])(O)C1(C([2H])([2H])O[C@]2(c3ccc(F)c(F)c3)c3ccc(C(C)(C)O)cc3C(=O)N2Cc2ccc(Cl)cn2)CC1] | (3R)-2-[(5-chloropyridin-2-yl)methyl]-3-(3,4-difluorophenyl)-3-({1-[hydroxy($^2H_2$)methyl]cyclopropyl}($^2H_2$)methoxy)-6-(2-hydroxypropan-2-yl)-2,3-dihydro-1H-isoindol-1-one |
| 53 | 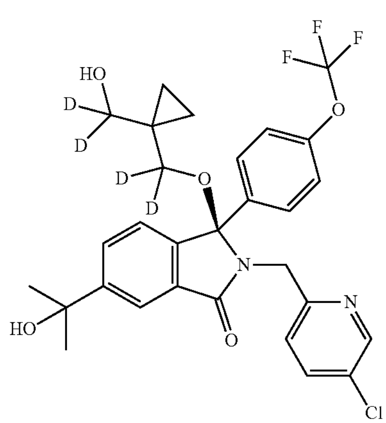 [SMILES: [2H]C([2H])(O)C1(C([2H])([2H])O[C@]2(c3ccc(OC(F)(F)F)cc3)c3ccc(C(C)(C)O)cc3C(=O)N2Cc2ccc(Cl)cn2)CC1] | (3R)-2-[(5-chloropyridin-2-yl)methyl]-3-({1-[hydroxy($^2H_2$)methyl]cyclopropyl}($^2H_2$)methoxy)-6-(2-hydroxypropan-2-yl)-3-[4-(trifluoromethoxy)phenyl]-2,3-dihydro-1H-isoindol-1-one |

| Ex. | Structure | Name |
|---|---|---|
| 54 | 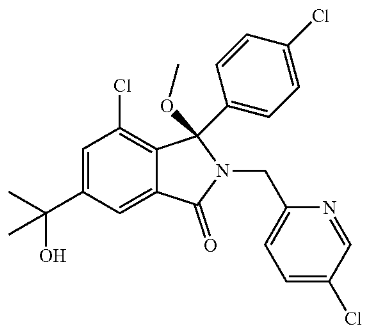 [SMILES: CO[C@]1(c2ccc(Cl)cc2)c2c(Cl)cc(C(C)(C)O)cc2C(=O)N1Cc1ccc(Cl)cn1] | (3R)-4-Chloro-3-(4-chlorophenyl)-2-[(5-chloropyridin-2-yl)methyl]-6-(2-hydroxypropan-2-yl)-3-methoxy-2,3-dihydro-1H-isoindol-1-one |
| 55 and 56 | (*both isomers separated and isolated) | (3R)-3-(4-Chlorophenyl)-2-[(5-chloropyridin-2-yl)methyl]-6-[1-hydroxy-1-(1H-pyrazol-4-yl)ethyl]-3-methoxy-2,3-dihydro-1H-isoindol-1-one |
| 57 and 58 | (*both isomers separated and isolated) | (3R)-3-(4-chlorophenyl)-2-[(5-chloropyridin-2-yl)methyl]-6-[1-hydroxy-1-(1-methyl-1H-pyrazol-4-yl)ethyl]-3-methoxy-2,3-dihydro-1H-isoindol-1-one<br>Ex. 57 is the faster eluting isomer<br>Ex. 58 is the slower eluting isomer |
| 59 | 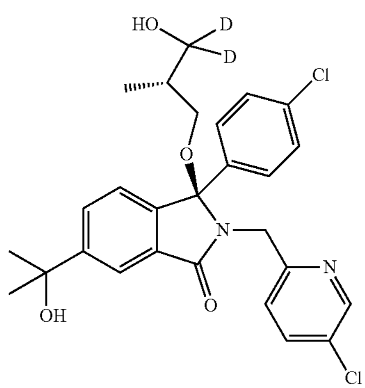 [SMILES: [2H]C([2H])(O)[C@@H](C)CO[C@]1(c2ccc(Cl)cc2)c2ccc(C(C)(C)O)cc2C(=O)N1Cc1ccc(Cl)cn1] | (3R)-3-(4-Chlorophenyl)-2-[(5-chloropyridin-2-yl)methyl]-3-[(2S)-3-hydroxy-2-methyl(3,3-$^2$H$_2$)propoxy]-6-(2-hydroxypropan-2-yl)-2,3-dihydro-1H-isoindol-1-one |

| Ex. | Structure | Name |
|---|---|---|
| 60 | 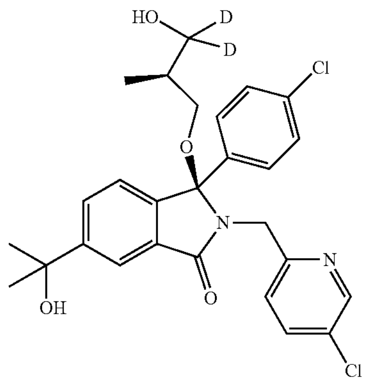 [SMILES: [2H]C([2H])(O)[C@H](C)CO[C@]1(c2ccc(Cl)cc2)c2ccc(C(C)(C)O)cc2C(=O)N1Cc1ccc(Cl)cn1] | (3R)-3-(4-Chlorophenyl)-2-[(5-chloropyridin-2-yl)methyl]-3-[(2R)-3-hydroxy-2-methyl(3,3-$^2$H$_2$)propoxy]-6-(2-hydroxypropan-2-yl)-2,3-dihydro-1H-isoindol-1-one |
| 61 | 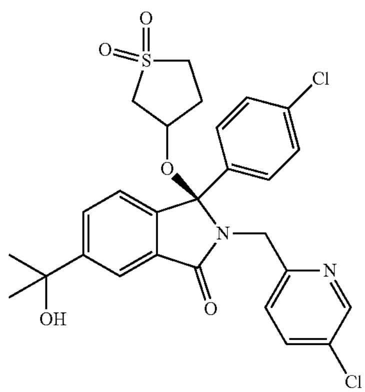 [SMILES: CC(C)(O)c1ccc2c(c1)C(=O)N(Cc1ccc(Cl)cn1)[C@@]2(OC1CCS(=O)(=O)C1)c1ccc(Cl)cc1] | 3-{[(1R)-1-(4-Chlorophenyl)-2-[(5-chloropyridin-2-yl)methyl]-5-(2-hydroxypropan-2-yl)-3-oxo-2,3-dihydro-1H-isoindol-1-yl]oxy}-1$\lambda^6$-thiolane-1,1-dione-Isomer 1 |
| 62 | 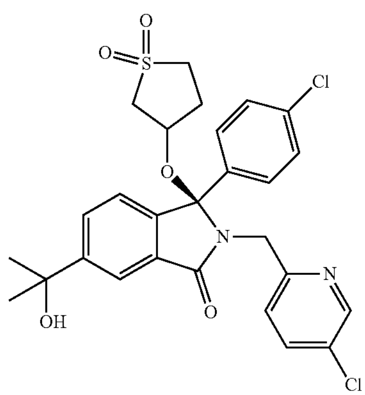 [SMILES: CC(C)(O)c1ccc2c(c1)C(=O)N(Cc1ccc(Cl)cn1)[C@@]2(OC1CCS(=O)(=O)C1)c1ccc(Cl)cc1] | 3-{[(1R)-1-(4-Chlorophenyl)-2-[(5-chloropyridin-2-yl)methyl]-5-(2-hydroxypropan-2-yl)-3-oxo-2,3-dihydro-1H-isoindol-1-yl]oxy}-1$\lambda^6$-thiolane-1,1-dione-Isomer 2 |
| 63 | 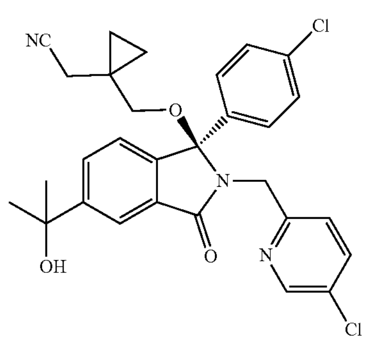 [SMILES: CC(C)(O)c1ccc2c(c1)C(=O)N(Cc1ccc(Cl)cn1)[C@@]2(OCC1(CC#N)CC1)c1ccc(Cl)cc1] | 2-[1-({[(1R)-1-(4-chlorophenyl)-2-[(5-chloropyridin-2-yl)methyl]-5-(2-hydroxypropan-2-yl)-3-oxo-2,3-dihydro-1H-isoindol-1-yl]oxy}methyl)cyclopropyl]acetonitrile |

-continued

| Ex. | Structure | Name |
|---|---|---|
| 64 | 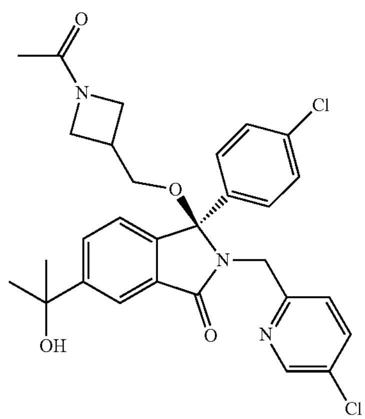 [SMILES: CC(=O)N1CC(CO[C@]2(c3ccc(Cl)cc3)c3ccc(C(C)(C)O)cc3C(=O)N2Cc2ccc(Cl)cn2)C1] | (3R)-3-[(1-acetylazetidin-3-yl)methoxy]-3-(4-chlorophenyl)-2-[(5-chloropyridin-2-yl)methyl]-6-(2-hydroxypropan-2-yl)-2,3-dihydro-1H-isoindol-1-one |
| 65 | 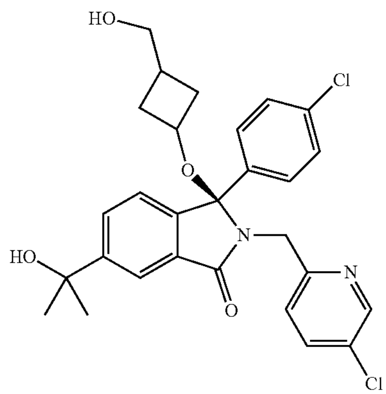 [SMILES: CC(C)(O)c1ccc2c(c1)C(=O)N(Cc1ccc(Cl)cn1)[C@@]2(OC1CC(CO)C1)c1ccc(Cl)cc1] | (3R)-3-(4-chlorophenyl)-2-[(5-chloropyridin-2-yl)methyl]-3-[3-(hydroxymethyl)cyclobutoxy]-6-(2-hydroxypropan-2-yl)-2,3-dihydro-1H-isoindol-1-one |
| 66 | 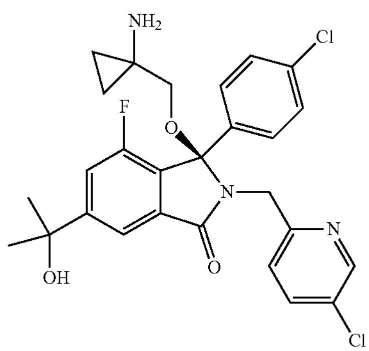 [SMILES: CC(C)(O)c1cc(F)c2c(c1)C(=O)N(Cc1ccc(Cl)cn1)[C@@]2(OCC1(N)CC1)c1ccc(Cl)cc1] | (3R)-3-[(1-Aminocyclopropyl)methoxy]-3-(4-chlorophenyl)-2-[(5-chloropyridin-2-yl)methyl]-4-fluoro-6-(2-hydroxypropan-2-yl)-2,3-dihydro-1H-isoindol-1-one |
| 67 | 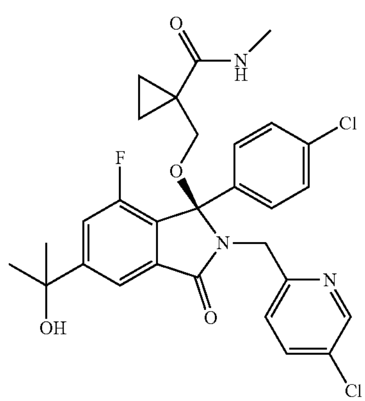 [SMILES: CNC(=O)C1(CO[C@]2(c3ccc(Cl)cc3)c3c(F)cc(C(C)(C)O)cc3C(=O)N2Cc2ccc(Cl)cn2)CC1] | 1-({[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)-N-methylcyclopropane-1-carboxamide |

| Ex. | Structure | Name |
|---|---|---|
| 68 and 69 | (*both isomers separated and isolated) | 1-({[(1R)-1-(4-Chlorophenyl)-2-[(5-chloropyridin-2-yl)methyl]-7-fluoro-5-[2-hydroxy-1-(piperazin-1-yl)propan-2-yl]-3-oxo-2,3-dihydro-1H-isoindol-1-yl]oxy}methyl)cyclopropane-1-carboxamide |
| 70 and 71 | | 1-({[(1R)-1-(4-chlorophenyl)-2-[(1S)-1-(5-chloropyridin-2-yl)ethyl]-7-fluoro-5-(2-hydroxypropan-2-yl)-3-oxo-2,3-dihydro-1H-isoindol-1-yl]oxy}methyl)cyclopropane-1-carboxamide and 1-({[(1R)-1-(4-chlorophenyl)-2-[(1R)-1-(5-chloropyridin-2-yl)ethyl]-7-fluoro-5-(2-hydroxypropan-2-yl)-3-oxo-2,3-dihydro-1H-isoindol-1-yl]oxy}methyl)cyclopropane-1-carboxamide |
| 72 | 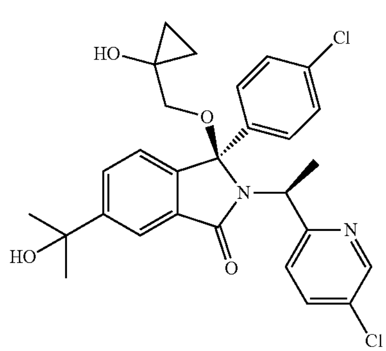 [SMILES: C[C@@H](c1ccc(Cl)cn1)N1C(=O)c2cc(C(C)(C)O)ccc2[C@]1(OCC1(O)CC1)c1ccc(Cl)cc1] | (3R)-3-(4-Chlorophenyl)-2-[(1S)-1-(5-chloropyridin-2-yl)ethyl]-3-[(1-hydroxycyclopropyl)methoxy]-6-(2-hydroxypropan-2-yl)-2,3-dihydro-1H-isoindol-1-one |

| Ex. | Structure | Name |
|---|---|---|
| 73 | 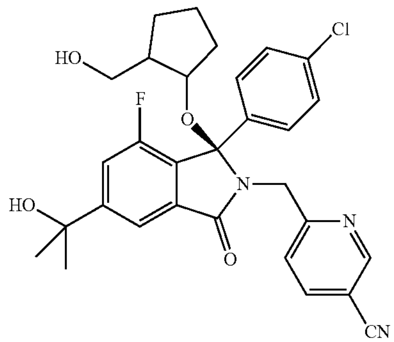 [SMILES: CC(C)(O)c1cc(F)c2c(c1)C(=O)N(Cc1ccc(C#N)cn1)[C@@]2(OC1CCCC1CO)c1ccc(Cl)cc1] | 6-{[(1R)-1-(4-chlorophenyl)-7-fluoro-1-{[2-(hydroxymethyl)cyclopentyl]oxy}-5-(2-hydroxypropan-2-yl)-3-oxo-2,3-dihydro-1H-isoindol-2-yl]methyl}pyridine-3-carbonitrile |
| 74 | 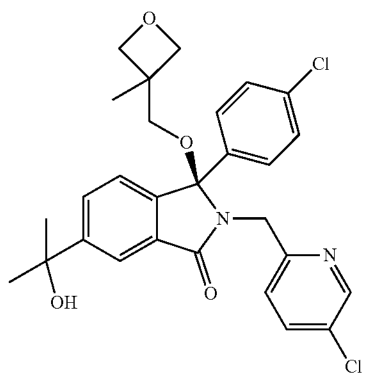 [SMILES: CC1(CO[C@]2(c3ccc(Cl)cc3)c3ccc(C(C)(C)O)cc3C(=O)N2Cc2ccc(Cl)cn2)COC1] | (3R)-3-(4-Chlorophenyl)-2-[(5-chloropyridin-2-yl)methyl]-6-(2-hydroxypropan-2-yl)-3-[(3-methyloxetan-3-yl)methoxy]-2,3-dihydro-1H-isoindol-1-one |
| 75 | 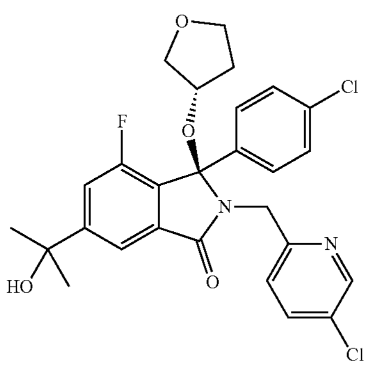 [SMILES: CC(C)(O)c1cc(F)c2c(c1)C(=O)N(Cc1ccc(Cl)cn1)[C@@]2(O[C@H]1CCOC1)c1ccc(Cl)cc1] | (3R)-3-(4-chlorophenyl)-2-[(5-chloropyridin-2-yl)methyl]-4-fluoro-6-(2-hydroxypropan-2-yl)-3-[(3S)-oxolan-3-yloxy]-2,3-dihydro-1H-isoindol-1-one |
| 76 | 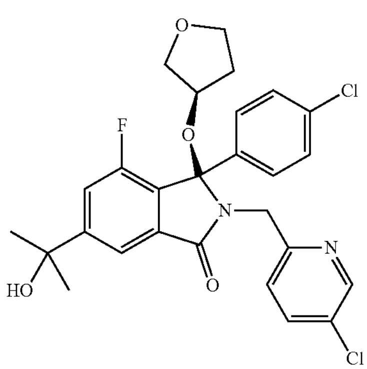 | (3R)-3-(4-chlorophenyl)-2-[(5-chloropyridin-2-yl)methyl]-4-fluoro-6-(2-hydroxypropan-2-yl)-3-[(3R)-oxolan-3-yloxy]-2,3-dihydro-1H-isoindol-1-one |

| Ex. | Structure | Name |
|---|---|---|
| 77 and 78 | (*both isomers separated and isolated) | (3R)-3-(4-chlorophenyl)-2-[(5-chloropyridin-2-yl)methyl]-6-[1-hydroxy-1-(pyridin-3-yl)ethyl]-3-methoxy-2,3-dihydro-1H-isoindol-1-one<br>Ex. 77 is the faster eluting isomer<br>Ex. 78 is the slower eluting isomer |
| 79 and 80 | (*both isomers separated and isolated) | (3R)-3-(4-chlorophenyl)-2-[(5-chloropyridin-2-yl)methyl]-6-[1-hydroxy-1-(oxan-4-yl)ethyl]-3-methoxy-2,3-dihydro-1H-isoindol-1-one<br>Ex. 79 is the faster eluting isomer<br>Ex. 80 is the slower eluting isomer |
| 81 | 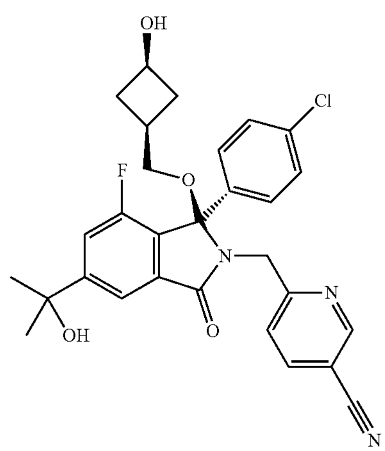 | 6-{[(1R)-1-(4-chlorophenyl)-7-fluoro-1-[(cis-3-hydroxycyclobutyl)methoxy]-5-(2-hydroxypropan-2-yl)-3-oxo-2,3-dihydro-1H-isoindol-2-yl]methyl}pyridine-3-carbonitrile |

-continued

| Ex. | Structure | Name |
|---|---|---|
| 82 and 83 | (*both isomers separated and isolated) | 1-({[(1R)-1-(4-chlorophenyl)-2-[(5-chloropyridin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide<br>Ex. 82 is the faster eluting isomer<br>Ex. 83 is the slower eluting isomer |
| 84 | 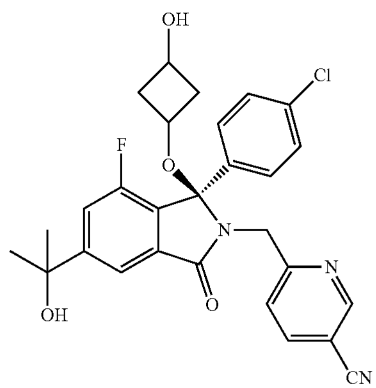 [SMILES: CC(C)(O)c1cc(F)c2c(c1)C(=O)N(Cc1ccc(C#N)cn1)[C@@]2(OC1CC(O)C1)c1ccc(Cl)cc1] | 6-{[(1R)-1-(4-chlorophenyl)-7-fluoro-1-(3-hydroxycyclobutoxy)-5-(2-hydroxypropan-2-yl)-3-oxo-2,3-dihydro-1H-isoindol-2-yl]methyl}pyridine-3-carbonitrile |
| 85 and 86 | (*both isomers separated and isolated) | (3R)-6-[1-(1-acetylpiperidin-4-yl)-1-hydroxyethyl]-3-(4-chlorophenyl)-2-[(5-chloropyridin-2-yl)methyl]-3-methoxy-2,3-dihydro-1H-isoindol-1-one<br>Ex. 85 is the faster eluting isomer<br>Ex. 86 is the slower eluting isomer |
| 87 | 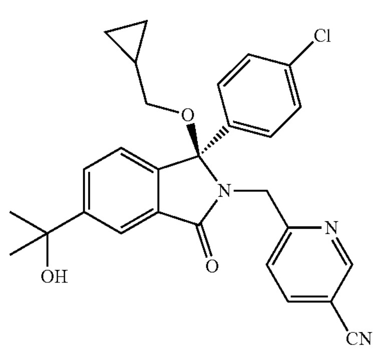 [SMILES: CC(C)(O)c1ccc2c(c1)C(=O)N(Cc1ccc(C#N)cn1)[C@@]2(OCC1CC1)c1ccc(Cl)cc1] | 6-{[(1R)-1-(4-chlorophenyl)-1-(cyclopropylmethoxy)-5-(2-hydroxypropan-2-yl)-3-oxo-2,3-dihydro-1H-isoindol-2-yl]methyl}pyridine-3-carbonitrile |

| Ex. | Structure | Name |
|---|---|---|
| 88 | 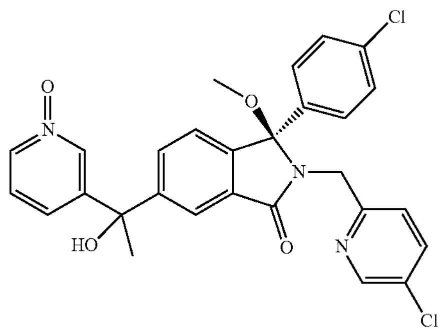 [SMILES: CO[C@]1(c2ccc(Cl)cc2)c2ccc(C(C)(O)c3ccc[n+]([O-])c3)cc2C(=O)N1Cc1ccc(Cl)cn1] | (3R)-3-(4-Chlorophenyl)-2-[(5-chloropyridin-2-yl)methyl]-6-[1-hydroxy-1-(1-oxo-1λ⁵-pyridin-3-yl)ethyl]-3-methoxy-2,3-dihydro-1H-isoindol-1-one |
| 89 and 90 | (*both isomers separated and isolated) | 6-{[(1R)-1-(4-chlorophenyl)-7-fluoro-5-[1-hydroxy-1-(oxan-4-yl)ethyl]-1-{[1-(hydroxymethyl)cyclopropyl]methoxy}-3-oxo-2,3-dihydro-1H-isoindol-2-yl]methyl}pyridine-3-carbonitrile<br>Ex. 89 is the faster eluting isomer<br>Ex. 90 is the slower eluting isomer |
| 91 and 92 | (*both isomers separated and isolated) | (3R)-3-(4-chlorophenyl)-2-[(5-chloropyridin-2-yl)methyl]-6-[2-hydroxy-1-(oxan-4-yl)propan-2-yl]-3-methoxy-2,3-dihydro-1H-isoindol-1-one<br>Ex. 91 is the faster eluting isomer<br>Ex. 92 is the slower eluting isomer |
| 93 | 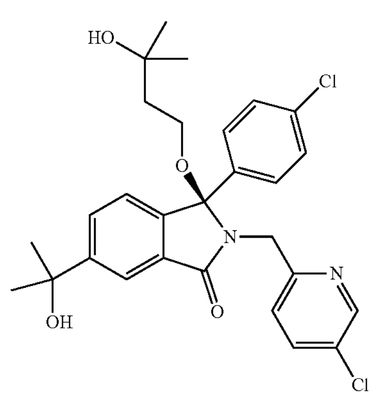 [SMILES: CC(C)(O)CCO[C@]1(c2ccc(Cl)cc2)c2ccc(C(C)(C)O)cc2C(=O)N1Cc1ccc(Cl)cn1] | (3R)-3-(4-Chlorophenyl)-2-[(5-chloropyridin-2-yl)methyl]-3-(3-hydroxy-3-methylbutoxy)-6-(2-hydroxypropan-2-yl)-2,3-dihydro-1H-isoindol-1-one |

| Ex. | Structure | Name |
|---|---|---|
| 94 | 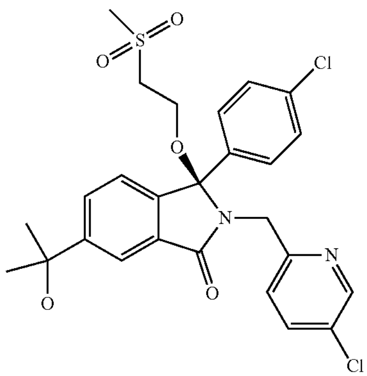 [SMILES: CC(C)(O)c1ccc2c(c1)C(=O)N(Cc1ccc(Cl)cn1)[C@@]2(OCCS(C)(=O)=O)c1ccc(Cl)cc1] | (3R)-3-(4-Chlorophenyl)-2-[(5-chloropyridin-2-yl)methyl]-6-(2-hydroxypropan-2-yl)-3-(2-methanesulfonylethoxy)-2,3-dihydro-1H-isoindol-1-one |
| 95 | 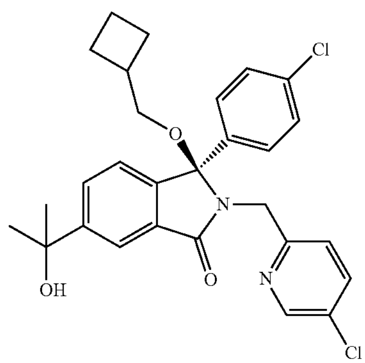 [SMILES: CC(C)(O)c1ccc2c(c1)C(=O)N(Cc1ccc(Cl)cn1)[C@@]2(OCC1CCC1)c1ccc(Cl)cc1] | (3R)-3-(4-chlorophenyl)-2-[(5-chloropyridin-2-yl)methyl]-3-(cyclobutylmethoxy)-6-(2-hydroxypropan-2-yl)-2,3-dihydro-1H-isoindol-1-one |
| 96 | 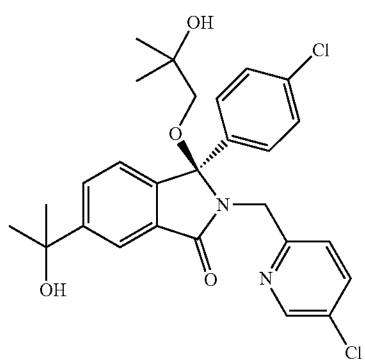 [SMILES: CC(C)(O)CO[C@]1(c2ccc(Cl)cc2)c2ccc(C(C)(C)O)cc2C(=O)N1Cc1ccc(Cl)cn1] | (3R)-3-(4-chlorophenyl)-2-[(5-chloropyridin-2-yl)methyl]-3-(2-hydroxy-2-methylpropoxy)-6-(2-hydroxypropan-2-yl)-2,3-dihydro-1H-isoindol-1-one |
| 97 and 98 | (*both isomers separated and isolated) | (3R)-3-(4-chlorophenyl)-2-[(5-chloropyridin-2-yl)methyl]-4-fluoro-3-(2-hydroxybutoxy)-6-(2-hydroxypropan-2-yl)-2,3-dihydro-1H-isoindol-1-one |

-continued

| Ex. | Structure | Name |
|---|---|---|
| 99 and 100 | 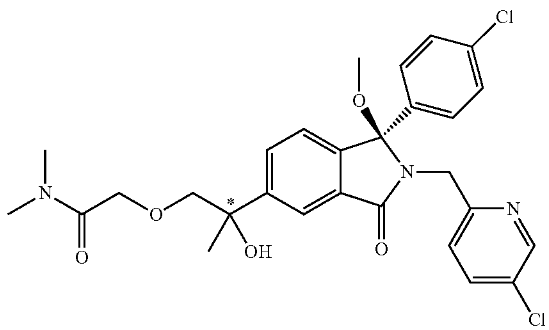 [SMILES: CO[C@]1(c2ccc(Cl)cc2)c2ccc(C(C)(O)COCC(=O)N(C)C)cc2C(=O)N1Cc1ccc(Cl)cn1] | 2-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropoxy}-N,N-dimethylacetamide<br>Ex. 99 is the faster eluting isomer<br>Ex. 100 is the slower eluting isomer |
| 101 | 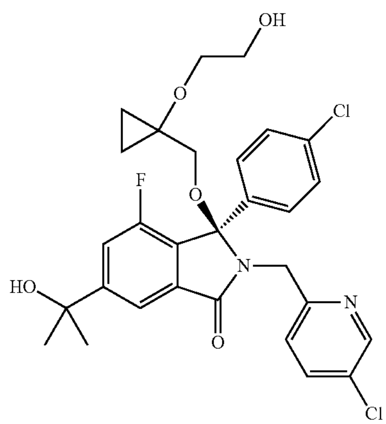 [SMILES: CC(C)(O)c1cc(F)c2c(c1)C(=O)N(Cc1ccc(Cl)cn1)[C@@]2(OCC1(OCCO)CC1)c1ccc(Cl)cc1] | (3R)-3-(4-chlorophenyl)-2-[(5-chloropyridin-2-yl)methyl]-4-fluoro-3-{[1-(2-hydroxyethoxy)cyclopropyl]methoxy}-6-(2-hydroxypropan-2-yl)-2,3-dihydro-1H-isoindol-1-one |
| 102 and 103 | (*both isomers separated and isolated) | (3R)-3-(4-chlorophenyl)-2-[(5-chloropyridin-2-yl)methyl]-6-[2-hydroxy-1-(2-hydroxyethoxy)propan-2-yl]-3-methoxy-2,3-dihydro-1H-isoindol-1-one<br>Ex. 102 is the faster eluting isomer<br>Ex. 103 is the slower eluting isomer |
| 104 and 105 | (*both isomers separated and isolated) | (3R)-3-(4-chlorophenyl)-2-[(5-chloropyridin-2-yl)methyl]-6-[2-hydroxy-1-(piperazin-1-yl)propan-2-yl]-3-methoxy-2,3-dihydro-1H-isoindol-1-one<br>Ex. 104 is the faster eluting isomer<br>Ex. 105 is the slower eluting isomer |

-continued

| Ex. | Structure | Name |
|---|---|---|
| 106 and 107 | (*both isomers separated and isolated) | (3R)-3-(4-chlorophenyl)-2-[(5-chloropyridin-2-yl)methyl]-6-[2-hydroxy-1-(morpholin-4-yl)propan-2-yl]-3-methoxy-2,3-dihydro-1H-isoindol-1-one<br>Ex. 106 is the faster eluting isomer<br>Ex. 107 is the slower eluting isomer |
| 108 and 109 | (*both isomers separated and isolated) | (3R)-3-(4-chlorophenyl)-2-[(5-chloropyridin-2-yl)methyl]-6-[2-hydroxy-1-(methylamino)propan-2-yl]-3-methoxy-2,3-dihydro-1H-isoindol-1-one<br>Ex. 108 is the faster eluting isomer<br>Ex. 109 is the slower eluting isomer |
| 110 and 111 | (*both isomers separated and isolated) | (3R)-3-(4-chlorophenyl)-2-[(5-chloropyridin-2-yl)methyl]-6-[1-(cyclopropylamino)-2-hydroxypropan-2-yl]-3-methoxy-2,3-dihydro-1H-isoindol-1-one<br>Ex. 110 is the faster eluting isomer<br>Ex. 111 is the slower eluting isomer |
| 112 and 113 | (*both isomers separated and isolated) | (3R)-3-(4-chlorophenyl)-2-[(5-chloropyridin-2-yl)methyl]-6-[2-hydroxy-1-(4-methyl-3-oxopiperazin-1-yl)propan-2-yl]-3-methoxy-2,3-dihydro-1H-isoindol-1-one<br>Ex. 112 is the faster eluting isomer<br>Ex. 113 is the slower eluting isomer |

| Ex. | Structure | Name |
|---|---|---|
| 114 and 115 | 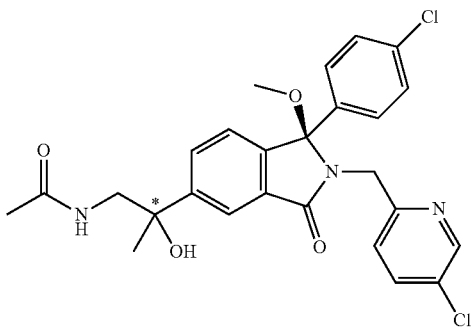<br>(*both isomers separated and isolated) | N-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropyl}acetamide<br>Ex. 114 is the faster eluting isomer<br>Ex. 115 is the slower eluting isomer |
| 116 and 117 | 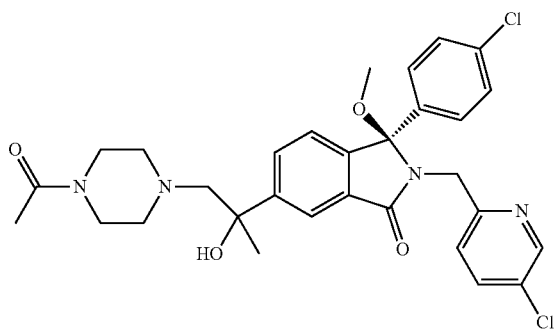<br>(*both isomers separated and isolated) | (3R)-6-[1-(4-acetylpiperazin-1-yl)-2-hydroxypropan-2-yl]-3-(4-chlorophenyl)-2-[(5-chloropyridin-2-yl)methyl]-3-methoxy-2,3-dihydro-1H-isoindol-1-one<br>Ex. 116 is the faster eluting isomer<br>Ex. 117 is the slower eluting isomer |
| 118 and 119 | 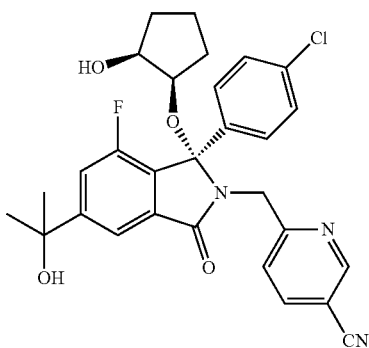 [SMILES: CC(C)(O)c1cc(F)c2c(c1)C(=O)N(Cc1ccc(C#N)cn1)[C@@]2(O[C@@H]1CCC[C@@H]1O)c1ccc(Cl)cc1]<br>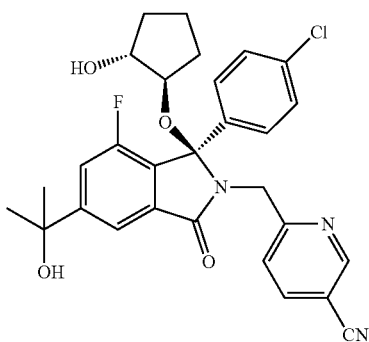 [SMILES: CC(C)(O)c1cc(F)c2c(c1)C(=O)N(Cc1ccc(C#N)cn1)[C@@]2(O[C@@H]1CCC[C@H]1O)c1ccc(Cl)cc1] | 6-{[(1R)-1-(4-chlorophenyl)-7-fluoro-1-[(2-hydroxycyclopentyl)oxy]-5-(2-hydroxypropan-2-yl)-3-oxo-2,3-dihydro-1H-isoindol-2-yl]methyl}pyridine-3-carbonitrile |

| Ex. | Structure | Name |
|---|---|---|
| 120 and 121 | 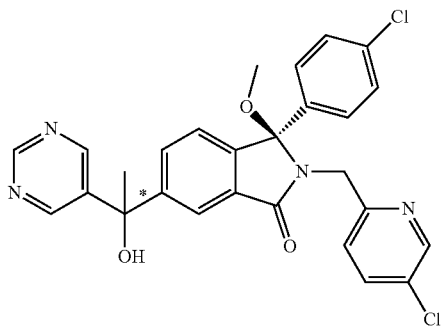<br>(*both isomers separated and isolated) | (3R)-3-(4-chlorophenyl)-2-[(5-chloropyridin-2-yl)methyl]-6-[1-hydroxy-1-(pyrimidin-5-yl)ethyl]-3-methoxy-2,3-dihydro-1H-isoindol-1-one<br>Ex. 120 is the faster eluting isomer<br>Ex. 121 is the slower eluting isomer |
| 122 and 123 | 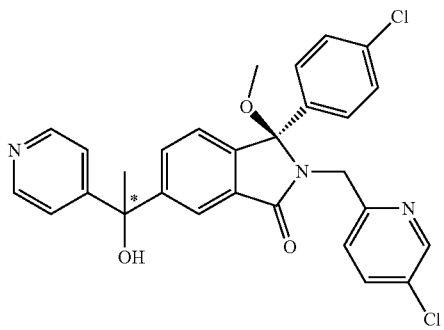<br>(*both isomers separated and isolated) | (3R)-3-(4-chlorophenyl)-2-[(5-chloropyridin-2-yl)methyl]-6-[1-hydroxy-1-(pyridin-4-yl)ethyl]-3-methoxy-2,3-dihydro-1H-isoindol-1-one<br>Ex. 122 is the faster eluting isomer<br>Ex. 123 is the slower eluting isomer |
| 124 | 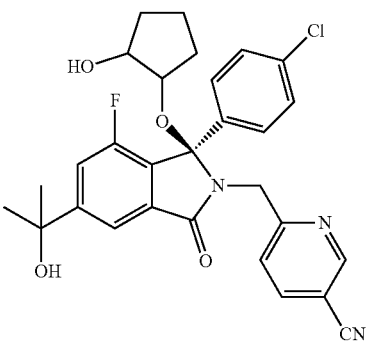 [SMILES: CC(C)(O)c1cc(F)c2c(c1)C(=O)N(Cc1ccc(C#N)cn1)[C@@]2(OC1CCCC1O)c1ccc(Cl)cc1] | 6-{[(1R)-1-(4-chlorophenyl)-7-fluoro-1-[(2-hydroxycyclopentyl)oxy]-5-(2-hydroxypropan-2-yl)-3-oxo-2,3-dihydro-1H-isoindol-2-yl]methyl}pyridine-3-carbonitrile |
| 125 and 126 | 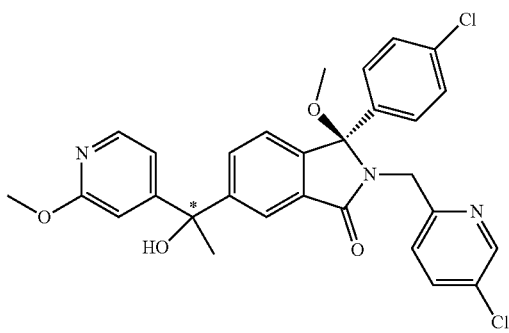<br>(*both isomers separated and isolated) | (3R)-3-(4-chlorophenyl)-2-[(5-chloropyridin-2-yl)methyl]-6-[1-hydroxy-1-(2-methoxypyridin-4-yl)ethyl]-3-methoxy-2,3-dihydro-1H-isoindol-1-one<br>Ex. 125 is the faster eluting isomer<br>Ex. 126 is the slower eluting isomer |

-continued

| Ex. | Structure | Name |
|---|---|---|
| 127 | 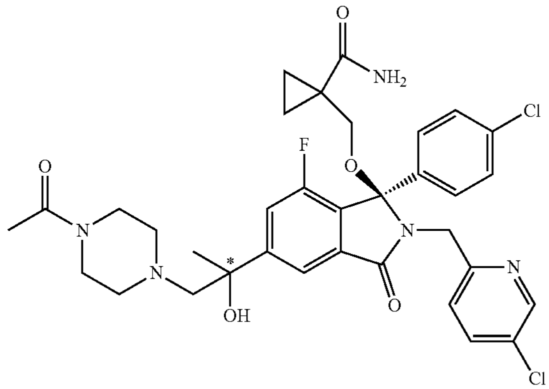 | 1-({[(1R)-5-[1-(4-Acetylpiperazin-1-yl)-2-hydroxypropan-2-yl]-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carboxamide<br><br>(Example isolated as a single isomer at the position shown*) |
| 128 and 129 | 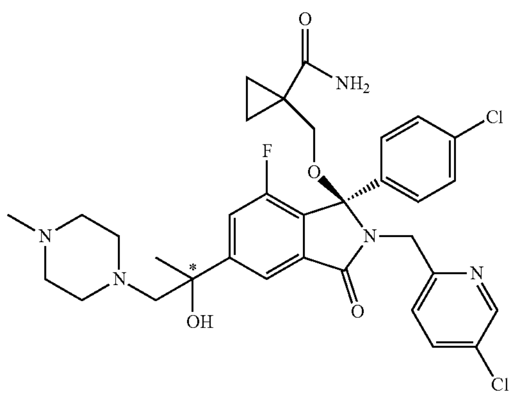 | 1-({[(1R)-1-(4-Chlorophenyl)-2-[(5-chloropyridin-2-yl)methyl]-7-fluoro-5-[2-hydroxy-1-(4-methylpiperazin-1-yl)propan-2-yl]-3-oxo-2,3-dihydro-1H-isoindol-1-yl]oxy}methyl)cyclopropane-1-carboxamide<br>Ex. 128 is the faster eluting isomer<br>Ex. 129 is the slower eluting isomer<br><br>(*both isomers separated and isolated) |
| 130 and 131 | 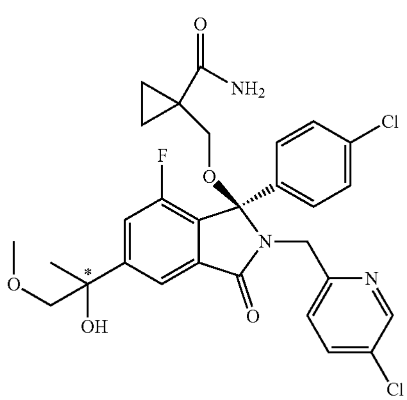 | 1-({[(1R)-1-(4-Chlorophenyl)-2-[(5-chloropyridin-2-yl)methyl]-7-fluoro-5-(2-hydroxy-1-methoxypropan-2-yl)-3-oxo-2,3-dihydro-1H-isoindol-1-yl]oxy}methyl)cyclopropane-1-carboxamide<br>Ex. 130 is the faster eluting isomer<br>Ex. 131 is the slower eluting isomer<br><br>(*both isomers separated and isolated) |

| Ex. | Structure | Name |
|---|---|---|
| 132 and 133 | 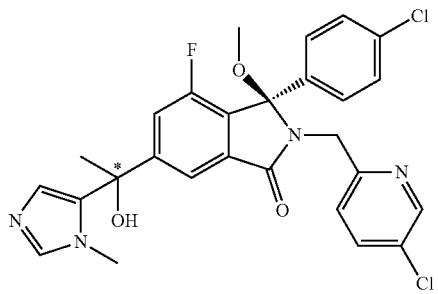<br>(*both isomers separated and isolated) | (3R)-3-(4-Chlorophenyl)-2-[(5-chloropyridin-2-yl)methyl]-6-[1-hydroxy-1-(1-methyl-1H-imidazol-5-yl)ethyl]-3-methoxy-2,3-dihydro-1H-isoindol-1-one<br>Ex. 132 is the faster eluting isomer<br>Ex. 133 is the slower eluting isomer |
| 134 and 135 | 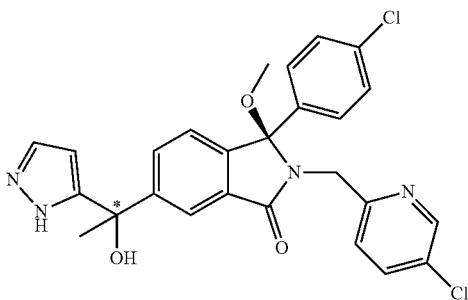<br>(*both isomers separated and isolated) | (3R)-3-(4-Chlorophenyl)-2-[(5-chloropyridin-2-yl)methyl]-6-[1-hydroxy-1-(1H-pyrazol-5-yl)ethyl]-3-methoxy-2,3-dihydro-1H-isoindol-1-one<br>Ex. 134 is the faster eluting isomer<br>Ex. 135 is the slower eluting isomer |
| 136 and 137 | 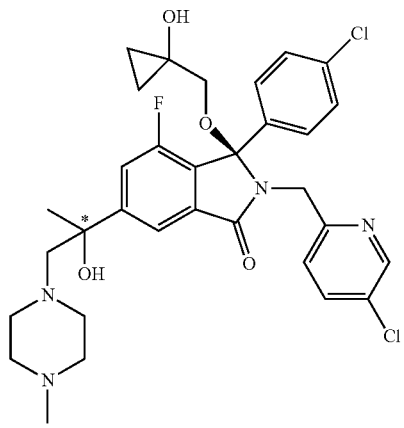<br>(*both isomers separated and isolated) | (3R)-3-(4-Chlorophenyl)-2-[(5-chloropyridin-2-yl)methyl]-4-fluoro-6-[2-hydroxy-1-(4-methylpiperazin-1-yl)propan-2-yl]-3-[(1-hydroxycyclopropyl)methoxy]-2,3-dihydro-1H-isoindol-1-one<br>Ex. 136 is the faster eluting isomer<br>Ex. 137 is the slower eluting isomer |

| Ex. | Structure | Name |
|---|---|---|
| 138 and 139 | 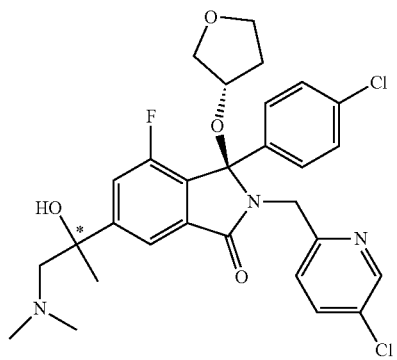 (*both isomers separated and isolated) | (3R)-3-(4-Chlorophenyl)-2-[(5-chloropyridin-2-yl)methyl]-6-[1-(dimethylamino)-2-hydroxypropan-2-yl]-4-fluoro-3-[(3S)-oxolan-3-yloxy]-2,3-dihydro-1H-isoindol-1-one<br>Ex. 138 is the faster eluting isomer<br>Ex. 139 is the slower eluting isomer |
| 140 and 141 | 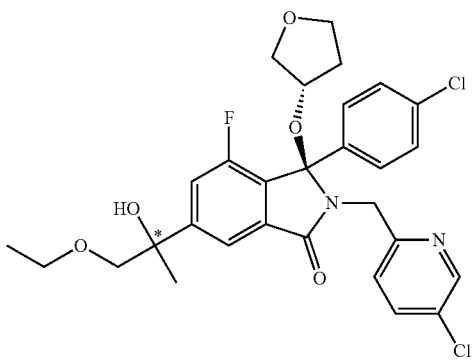 (*both isomers separated and isolated) | (3R)-3-(4-Chlorophenyl)-2-[(5-chloropyridin-2-yl)methyl]-6-(1-ethoxy-2-hydroxypropan-2-yl)-4-fluoro-3-[(3S)-oxolan-3-yloxy]-2,3-dihydro-1H-isoindol-1-one<br>Ex. 140 is the faster eluting isomer<br>Ex. 141 is the slower eluting isomer |
| 142 and 143 | 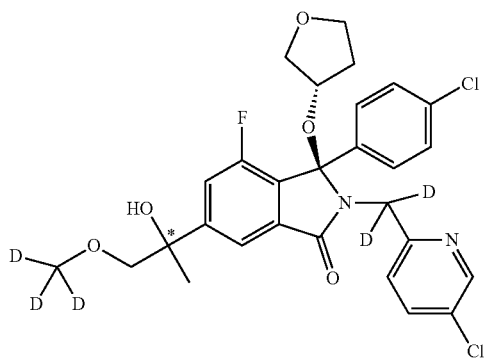 (*both isomers separated and isolated) | (3R)-3-(4-Chlorophenyl)-2-[(5-chloropyridin-2-yl)($^2$H$_2$)methyl]-4-fluoro-6-[2-hydroxy-1-($^2$H$_3$)methoxypropan-2-yl]-3-[(3S)-oxolan-3-yloxy]-2,3-dihydro-1H-isoindol-1-one<br>Ex. 142 is the faster eluting isomer<br>Ex. 143 is the slower eluting isomer |

-continued

| Ex. | Structure | Name |
|---|---|---|
| 144 | 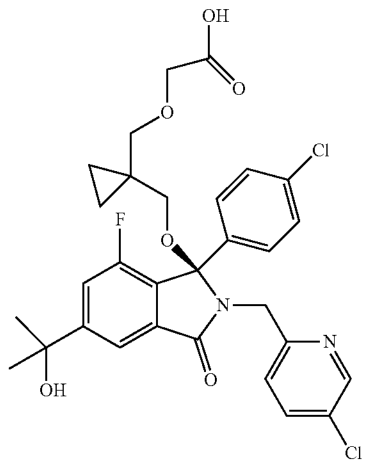 [SMILES: CC(C)(O)c1cc(F)c2c(c1)C(=O)N(Cc1ccc(Cl)cn1)[C@@]2(OCC1(COCC(=O)O)CC1)c1ccc(Cl)cc1] | 2-{[1-({[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]methoxy}acetic acid |
| 145 and 146 | (*both isomers separated and isolated) | 2-[(1R)-1-(4-Chlorophenyl)-2-[(5-chloropyridin-2-yl)methyl]-1-methoxy-3-oxo-2,3-dihydro-1H-isoindol-5-yl]-2-hydroxy-N-methylpropanamide<br>Ex. 145 is the faster eluting isomer<br>Ex. 146 is the slower eluting isomer |
| 147 and 148 | (*both isomers separated and isolated) | 2-[(1R)-1-(4-Chlorophenyl)-2-[(5-chloropyridin-2-yl)methyl]-1-methoxy-3-oxo-2,3-dihydro-1H-isoindol-5-yl]-N-ethyl-2-hydroxypropanamide<br>Ex. 147 is the faster eluting isomer<br>Ex. 148 is the slower eluting isomer |
| 149 and 150 | (*both isomers separated and isolated) | 2-[(1R)-1-(4-Chlorophenyl)-2-[(5-chloropyridin-2-yl)methyl]-1-methoxy-3-oxo-2,3-dihydro-1H-isoindol-5-yl]-N-[2-(dimethylamino)ethyl]-2-hydroxypropanamide<br>Ex. 149 is the faster eluting isomer<br>Ex. 150 is the slower eluting isomer |

| Ex. | Structure | Name |
|---|---|---|
| 151 and 152 | 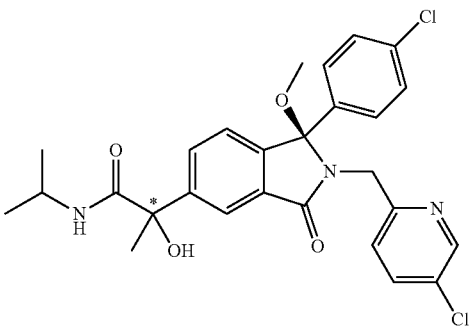<br>(*both isomers separated and isolated) | 2-[(1R)-1-(4-Chlorophenyl)-2-[(5-chloropyridin-2-yl)methyl]-1-methoxy-3-oxo-2,3-dihydro-1H-isoindol-5-yl]-2-hydroxy-N-(propan-2-yl)propanamide<br>Ex. 151 is the faster eluting isomer<br>Ex. 152 is the slower eluting isomer |
| 153 and 154 | 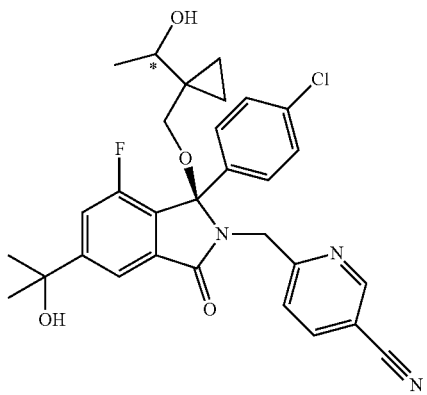<br>(*both isomers separated and isolated) | 6-{[(1R)-1-(4-Chlorophenyl)-7-fluoro-1-{[1-(1-hydroxyethyl)cyclopropyl]methoxy}-5-(2-hydroxypropan-2-yl)-3-oxo-2,3-dihydro-1H-isoindol-2-yl]methyl}pyridine-3-carbonitrile<br>Ex. 153 is the faster eluting isomer<br>Ex. 154 is the slower eluting isomer |
| 155 | 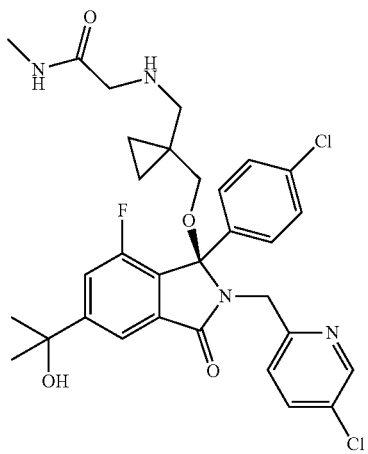 [SMILES: CNC(=O)CNCC1(CO[C@]2(c3ccc(Cl)cc3)c3c(F)cc(C(C)(C)O)cc3C(=O)N2Cc2ccc(Cl)cn2)CC1] | 2-({[1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]methyl}amino)-N-methylacetamide |

| Ex. | Structure | Name |
|---|---|---|
| 156 | 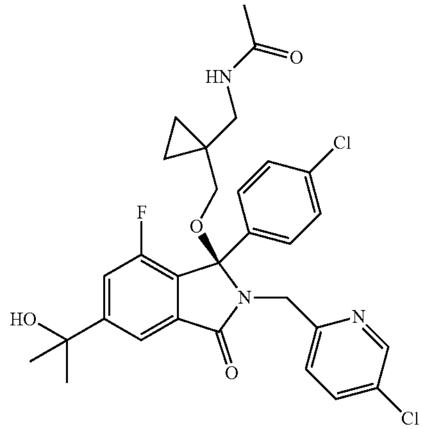 [SMILES: CC(=O)NCC1(CO[C@]2(c3ccc(Cl)cc3)c3c(F)cc(C(C)(C)O)cc3C(=O)N2Cc2ccc(Cl)cn2)CC1] | N-{[1-({[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]methyl} acetamide |
| 157 and 158 | (*both isomers separated and isolated) | (3R)-3-(4-Chlorophenyl)-2-[(5-chloropyridin-2-yl)methyl]-6-[2-hydroxy-1-(2-oxoimidazolidin-1-yl)propan-2-yl]-3-methoxy-2,3-dihydro-1H-isoindol-1-one |
| 159 and 160 | (*both isomers separated and isolated) | (3R)-3-(4-Chlorophenyl)-2-[(5-chloropyridin-2-yl)methyl]-6-[2-hydroxy-1-(1H-imidazol-1-yl)propan-2-yl]-3-methoxy-2,3-dihydro-1H-isoindol-1-one |
| 161 and 162 | (*both isomers separated and isolated) | (3R)-3-(4-Chlorophenyl)-2-[(5-chloropyridin-2-yl)methyl]-6-[1-(1,2-dimethyl-1H-imidazol-4-yl)-1-hydroxyethyl]-4-fluoro-3-methoxy-2,3-dihydro-1H-isoindol-1-one |

-continued

| Ex. | Structure | Name |
|---|---|---|
| 163 and 164 | (*both isomers separated and isolated) | (3R)-3-(4-chlorophenyl)-2-[(5-chloropyridin-2-yl)methyl]-4-fluoro-6-[1-hydroxy-1-(1H-imidazol-2-yl)ethyl]-3-methoxy-2,3-dihydro-1H-isoindol-1-one<br>Ex. 163 is the faster eluting isomer<br>Ex. 164 is the slower eluting isomer |
| 165 and 166 | (*both isomers separated and isolated) | (3R)-3-(4-Chlorophenyl)-2-[(5-chloropyridin-2-yl)methyl]-4-fluoro-6-[1-hydroxy-1-(1,3-thiazol-2-yl)ethyl]-3-methoxy-2,3-dihydro-1H-isoindol-1-one<br>Ex. 165 is the faster eluting isomer<br>Ex. 166 is the slower eluting isomer |
| 167 | 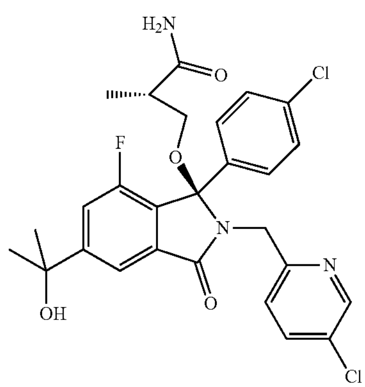 [SMILES: C[C@@H](CO[C@]1(c2ccc(Cl)cc2)c2c(F)cc(C(C)(C)O)cc2C(=O)N1Cc1ccc(Cl)cn1)C(N)=O] | (2S)-3-{[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}-2-methylpropanamide |
| 168 | 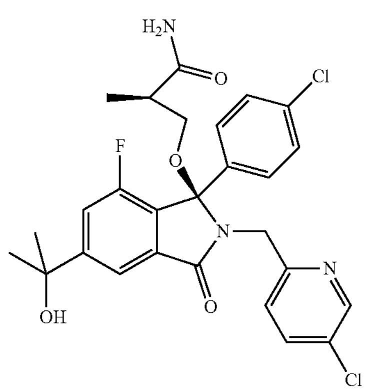 [SMILES: C[C@H](CO[C@]1(c2ccc(Cl)cc2)c2c(F)cc(C(C)(C)O)cc2C(=O)N1Cc1ccc(Cl)cn1)C(N)=O] | (2R)-3-{[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}-2-methylpropanamide |

-continued

| Ex. | Structure | Name |
|---|---|---|
| 169 | 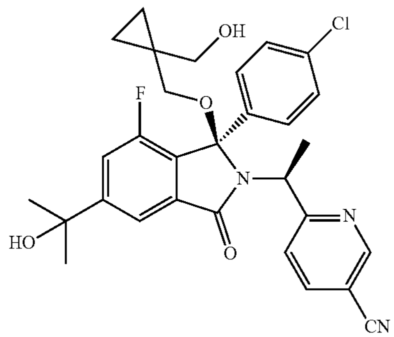 [SMILES: C[C@@H](c1ccc(C#N)cn1)N1C(=O)c2cc(C(C)(C)O)cc(F)c2[C@]1(OCC1(CO)CC1)c1ccc(Cl)cc1] | 6-[(1S)-1-[(1R)-1-(4-Chlorophenyl)-7-fluoro-1-{[1-(hydroxymethyl)cyclopropyl]methoxy}-5-(2-hydroxypropan-2-yl)-3-oxo-2,3-dihydro-1H-isoindol-2-yl]ethyl]pyridine-3-carbonitrile |
| 170 | 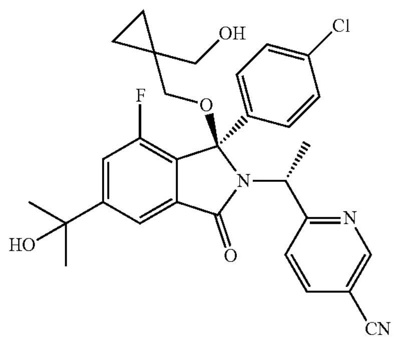 [SMILES: C[C@H](c1ccc(C#N)cn1)N1C(=O)c2cc(C(C)(C)O)cc(F)c2[C@]1(OCC1(CO)CC1)c1ccc(Cl)cc1] | 6-[(1R)-1-[(1R)-1-(4-Chlorophenyl)-7-fluoro-1-{[1-(hydroxymethyl)cyclopropyl]methoxy}-5-(2-hydroxypropan-2-yl)-3-oxo-2,3-dihydro-1H-isoindol-2-yl]ethyl]pyridine-3-carbonitrile |
| 171 and 172 | (*both isomers separated and isolated) | (3R)-3-(4-Chlorophenyl)-2-[(5-chloropyridin-2-yl)methyl]-4-fluoro-6-(2-hydroxypropan-2-yl)-3-[(1-methanesulfinylcyclopropyl)methoxy]-2,3-dihydro-1H-isoindol-1-one |
| 173 | 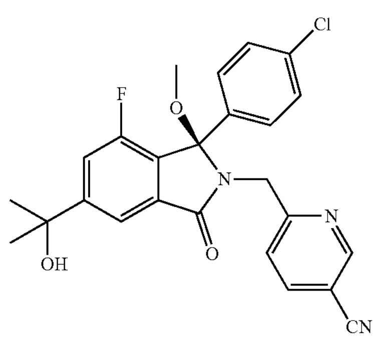 [SMILES: CO[C@]1(c2ccc(Cl)cc2)c2c(F)cc(C(C)(C)O)cc2C(=O)N1Cc1ccc(C#N)cn1] | 6-{[(1R)-1-(4-Chlorophenyl)-7-fluoro-5-(2-hydroxypropan-2-yl)-1-methoxy-3-oxo-2,3-dihydro-1H-isoindol-2-yl]methyl}pyridine-3-carbonitrile. |

| Ex. | Structure | Name |
|---|---|---|
| 174 | 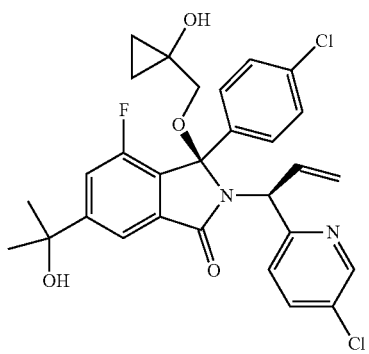 [SMILES: C=C[C@@H](c1ccc(Cl)cn1)N1C(=O)c2cc(C(C)(C)O)cc(F)c2[C@]1(OCC1(O)CC1)c1ccc(Cl)cc1] | (3R)-3-(4-Chlorophenyl)-2-[(1S)-1-(5-chloropyridin-2-yl)prop-2-en-1-yl]-4-fluoro-3-[(1-hydroxycyclopropyl)methoxy]-6-(2-hydroxypropan-2-yl)-2,3-dihydro-1H-isoindol-1-one |
| 175 and 176 | 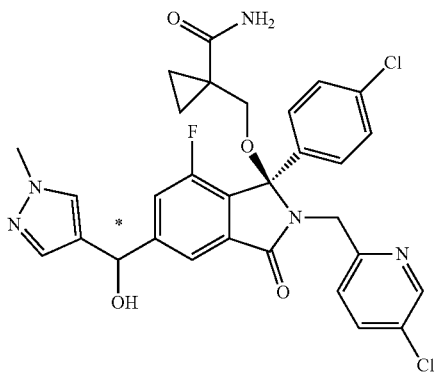<br>(*both isomers separated and isolated) | 1-({[(1R)-1-(4-Chlorophenyl)-2-[(5-chloropyridin-2-yl)methyl]-7-fluoro-5-[hydroxy(1-methyl-1H-pyrazol-4-yl)methyl]-3-oxo-2,3-dihydro-1H-isoindol-1-yl]oxy}methyl)cyclopropane-1-carboxamide<br>Ex. 175 is the faster eluting isomer<br>Ex. 176 is the slower eluting isomer |
| 177 and 178 | 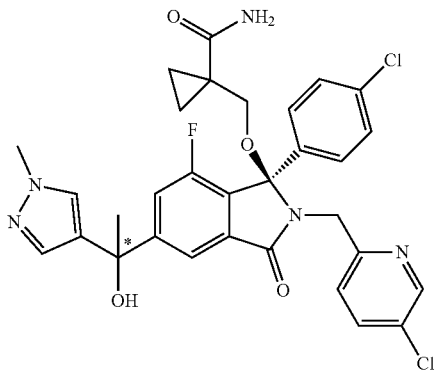<br>(*both isomers separated and isolated) | 1-({[(1R)-1-(4-Chlorophenyl)-2-[(5-chloropyridin-2-yl)methyl]-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide<br>Ex. 177 is the faster eluting isomer<br>Ex. 178 is the slower eluting isomer |

| Ex. | Structure | Name |
|---|---|---|
| 179 and 180 | 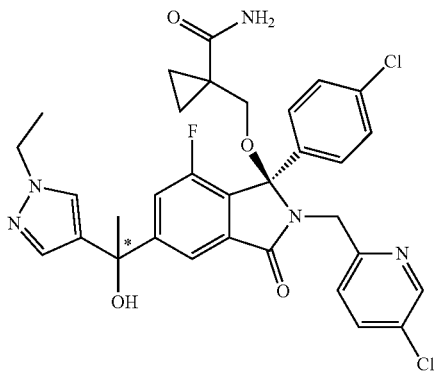 (*both isomers separated and isolated) | 1-({[(1R)-1-(4-Chlorophenyl)-2-[(5-chloropyridin-2-yl)methyl]-5-[1-(1-ethyl-1H-pyrazol-4-yl)-1-hydroxyethyl]-7-fluoro-3-oxo-2,3-dihydro-1H-isoindol-1-yl]oxy}methyl)cyclopropane-1-carboxamide<br>Ex. 179 is the faster eluting isomer<br>Ex. 180 is the slower eluting isomer |
| 181 and 182 | 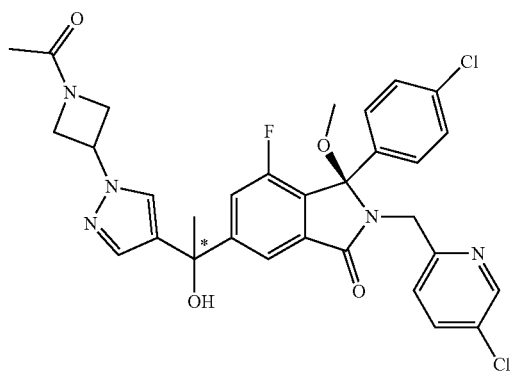 (*both isomers separated and isolated | (3R)-6-{1-[1-(1-Acetylazetidin-3-yl)-1H-pyrazol-4-yl]-1-hydroxyethyl}-3-(4-chlorophenyl)-2-[(5-chloropyridin-2-yl)methyl]-4-fluoro-3-methoxy-2,3-dihydro-1H-isoindol-1-one |
| 183 and 184 | 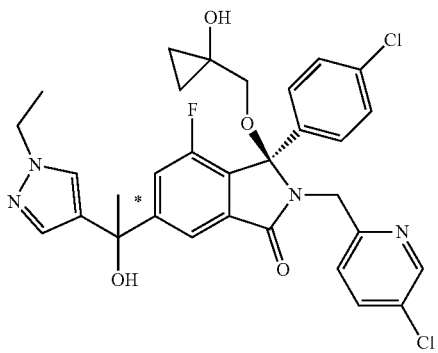 (*both isomers separated and isolated) | (3R)-3-(4-Chlorophenyl)-2-[(5-chloropyridin-2-yl)methyl]-6-[1-(1-ethyl-1H-pyrazol-4-yl)-1-hydroxyethyl]-4-fluoro-3-[(1-hydroxycyclopropyl)methoxy]-2,3-dihydro-1H-isoindol-1-one<br>Ex. 183 is the faster eluting isomer<br>Ex. 184 is the slower eluting isomer |

| Ex. | Structure | Name |
|---|---|---|
| 185 and 186 | 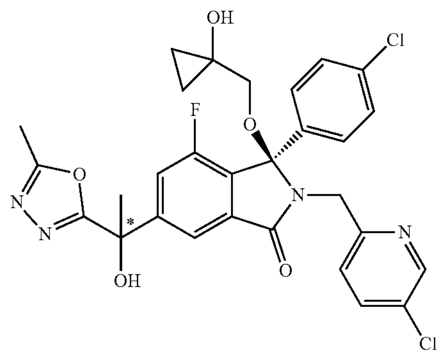 | (3R)-3-(4-Chlorophenyl)-2-[(5-chloropyridin-2-yl)methyl]-4-fluoro-6-[1-hydroxy-1-(5-methyl-1,3,4-oxadiazol-2-yl)ethyl]-3-[(1-hydroxycyclopropyl)methoxy]-2,3-dihydro-1H-isoindol-1-one<br>Ex. 185 is the faster eluting isomer<br>Ex. 186 is the slower eluting isomer |
| 187 and 188 | 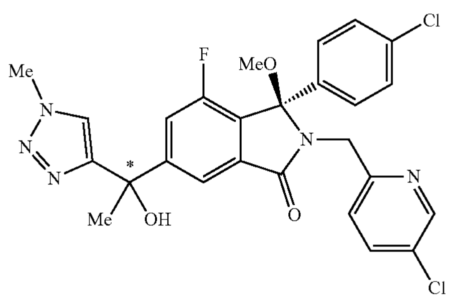 | (3R)-3-(4-Chlorophenyl)-2-[(5-chloropyridin-2-yl)methyl]-4-fluoro-6-[1-hydroxy-1-(1-methyl-1H-1,2,3-triazol-4-yl)ethyl]-3-methoxy-2,3-dihydro-1H-isoindol-1-one<br>Ex. 187 is the faster eluting isomer<br>Ex. 188 is the slower eluting isomer |
| 189 and 190 | 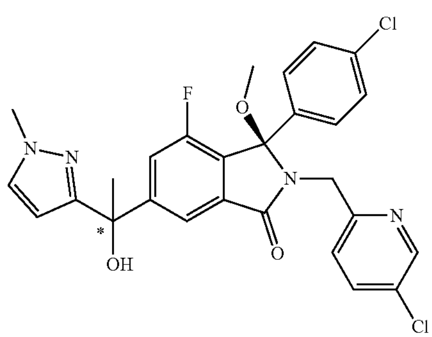 | (3R)-3-(4-Chlorophenyl)-2-[(5-chloropyridin-2-yl)methyl]-4-fluoro-6-[1-hydroxy-1-(1-methyl-1H-pyrazol-3-yl)ethyl]-3-methoxy-2,3-dihydro-1H-isoindol-1-one<br>Ex. 189 is the faster eluting isomer<br>Ex. 190 is the slower eluting isomer |
| 191 and 192 | 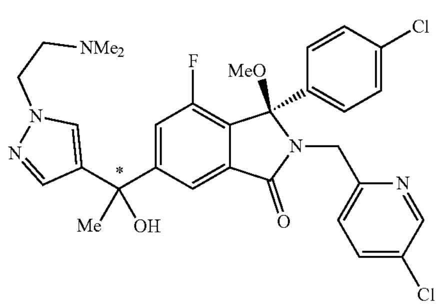 | (3R)-3-(4-Chlorophenyl)-2-[(5-chloropyridin-2-yl)methyl]-6-(1-{1-[2-(dimethylamino)ethyl]-1H-pyrazol-4-yl}-1-hydroxyethyl)-4-fluoro-3-methoxy-2,3-dihydro-1H-isoindol-1-one |

| Ex. | Structure | Name |
|---|---|---|
| 193 and 194 | 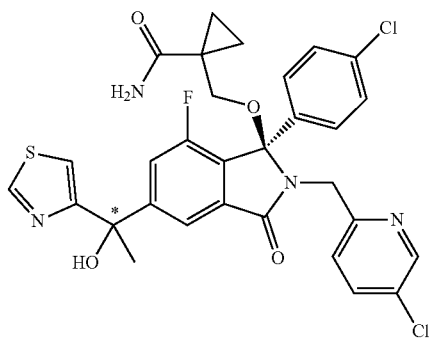<br>(*both isomers separated and isolated) | 1-({[(1R)-1-(4-chlorophenyl)-2-[(5-chloropyridin-2-yl)methyl]-7-fluoro-5-[1-hydroxy-1-(1,3-thiazol-4-yl)ethyl]-3-oxo-2,3-dihydro-1H-isoindol-1-yl]oxy}methyl)cyclopropane-1-carboxamide<br>Ex. 193 is the faster eluting isomer<br>Ex. 194 is the slower eluting isomer |
| 195 and 196 | 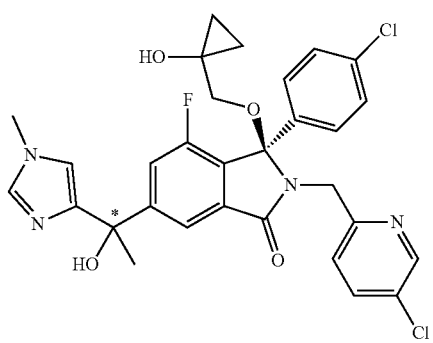<br>(*both isomers separated and isolated) | (3R)-3-(4-chlorophenyl)-2-[(5-chloropyridin-2-yl)methyl]-4-fluoro-6-[1-hydroxy-1-(1-methyl-1H-imidazol-4-yl)ethyl]-3-[(1-hydroxycyclopropyl)methoxy]-2,3-dihydro-1H-isoindol-1-one<br>Ex. 195 is the faster eluting isomer<br>Ex. 196 is the slower eluting isomer |
| 197 and 198 | 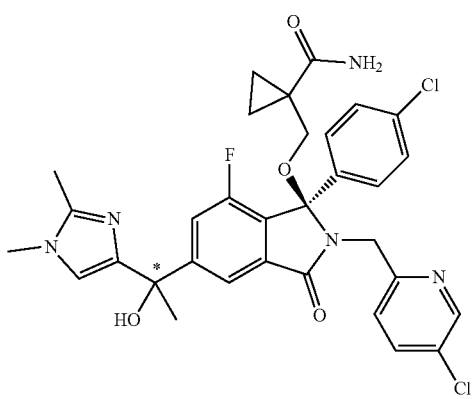<br>(*both isomers separated and isolated) | 1-({[(1R)-1-(4-chlorophenyl)-2-[(5-chloropyridin-2-yl)methyl]-5-[1-(1,2-dimethyl-1H-imidazol-4-yl)-1-hydroxyethyl]-7-fluoro-3-oxo-2,3-dihydro-1H-isoindol-1-yl]oxy}methyl)cyclopropane-1-carboxamide<br>Ex. 197 is the faster eluting isomer<br>Ex. 198 is the slower eluting isomer |

-continued

| Ex. | Structure | Name |
|---|---|---|
| 199 and 200 | 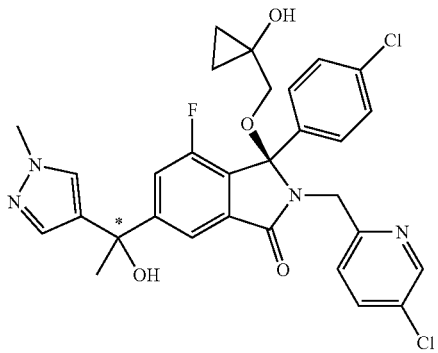<br>(*both isomers separated and isolated) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one<br>Ex. 199 is the faster eluting isomer<br>Ex. 200 is the slower eluting isomer |
| 201 and 202 | 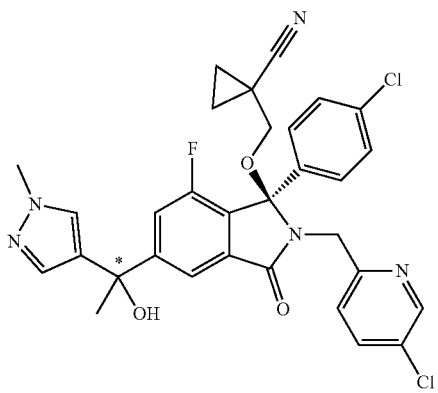<br>(*both isomers separated and isolated) | 1-({[(1R)-1-(4-chlorophenyl)-2-[(5-chloropyridin-2-yl)methyl]-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carbonitrile<br>Ex. 201 is the faster eluting isomer<br>Ex. 202 is the slower eluting isomer |
| 203 and 204 | 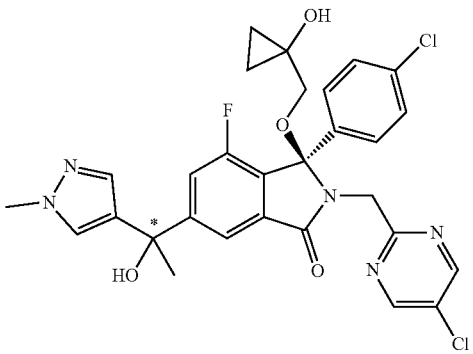<br>(*both isomers separated and isolated) | (3R)-3-(4-chlorophenyl)-2-[(5-chloropyrimidin-2-yl)methyl]-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one<br>Ex. 203 is the slower eluting isomer<br>Ex. 204 is the faster eluting isomer |

-continued

| Ex. | Structure | Name |
|---|---|---|
| 205 | 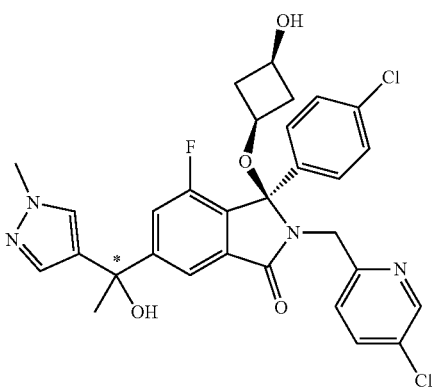<br>(isolated as a single isomer at the position shown) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[cis-3-hydroxycyclobutoxy]-2,3-dihydro-1H-isoindol-1-one |
| 206 | 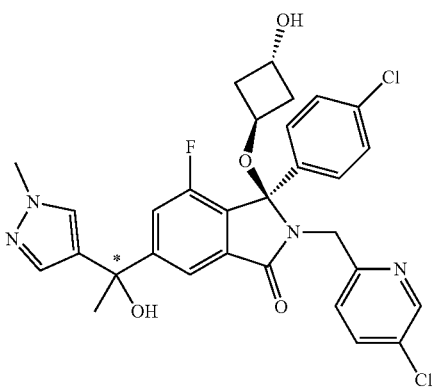<br>(isolated as a single isomer at the position shown) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[trans-3-hydroxycyclobutoxy]-2,3-dihydro-1H-isoindol-1-one |
| 207 | 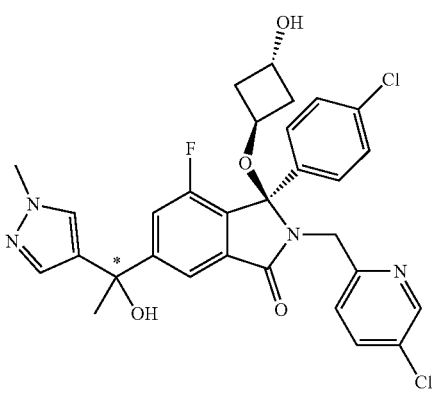<br>(isolated as a single isomer at the position shown) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[trans-3-hydroxycyclobutoxy]-2,3-dihydro-1H-isoindol-1-one |

| Ex. | Structure | Name |
|---|---|---|
| 208 | 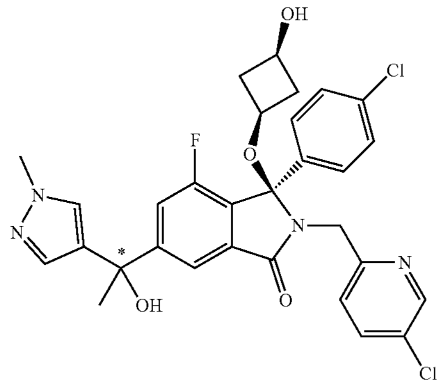 | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[cis-3-hydroxycyclobutoxy]-2,3-dihydro-1H-isoindol-1-one<br><br>(isolated as a single isomer at the position shown) |
| 209 | 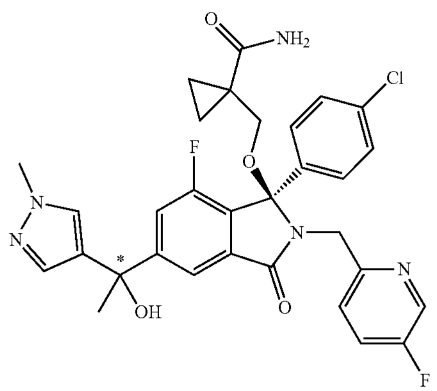 | 1-({[(1R)-1-(4-chlorophenyl)-7-fluoro-2-[(5-fluoropyridin-2-yl)methyl]-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide<br><br>(isolated as a single isomer at the position shown) |
| 210 | 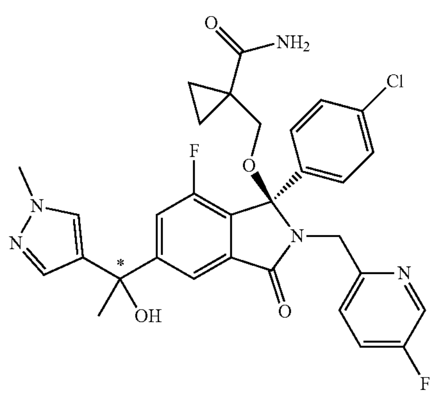 | 1-({[(1R)-1-(4-chlorophenyl)-7-fluoro-2-[(5-fluoropyridin-2-yl)methyl]-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide<br><br>(isolated as a single isomer at the position shown) |

| Ex. | Structure | Name |
|---|---|---|
| 211 | (isolated as a single isomer at the position shown) | 6-{[(1R)-1-(4-chlorophenyl)-1-[(1-cyanocyclopropyl)methoxy]-7-fluoro-5-[1-hydroxy-1-(1-methyl-1H-pyrazol-4-yl)ethyl]-3-oxo-2,3-dihydro-1H-isoindol-2-yl]methyl}pyridine-3-carbonitrile |
| 212 | (isolated as a single isomer at the position shown) | 6-{[(1R)-1-(4-chlorophenyl)-1-[(1-cyanocyclopropyl)methoxy]-7-fluoro-5-[1-hydroxy-1-(1-methyl-1H-pyrazol-4-yl)ethyl]-3-oxo-2,3-dihydro-1H-isoindol-2-yl]methyl}pyridine-3-carbonitrile |
| 213 | (isolated as a single isomer at the position shown) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-(2-hydroxyethoxy)-2,3-dihydro-1H-isoindol-1-one |

-continued

| Ex. | Structure | Name |
|---|---|---|
| 214 | (isolated as a single isomer at the position shown) | 1-({[(1R)-1-(4-chlorophenyl)-2-[(5-chloropyrimidin-2-yl)methyl]-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide |
| 215 | (isolated as a single isomer at the position shown) | 1-({[(1R)-1-(4-chlorophenyl)-2-[(5-chloropyrimidin-2-yl)methyl]-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide |
| 216 | (isolated as a single isomer at the position shown) | 1-({[(1R)-1-(4-chlorophenyl)-7-fluoro-5-[1-hydroxy-1-(1-methyl-1H-pyrazol-4-yl)ethyl]-2-[(6-methoxypyridin-3-yl)methyl]-3-oxo-2,3-dihydro-1H-isoindol-1-yl]oxy}methyl)cyclopropane-1-carboxamide |

-continued

| Ex. | Structure | Name |
|---|---|---|
| 217 | 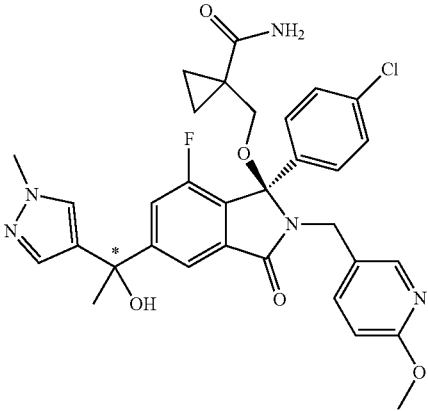<br>(isolated as a single isomer at the position shown) | 1-({[(1R)-1-(4-chlorophenyl)-7-fluoro-5-[1-hydroxy-1-(1-methyl-1H-pyrazol-4-yl)ethyl]-2-[(6-methoxypyridin-3-yl)methyl]-3-oxo-2,3-dihydro-1H-isoindol-1-yl]oxy}methyl)cyclopropane-1-carboxamide |
| 218 | 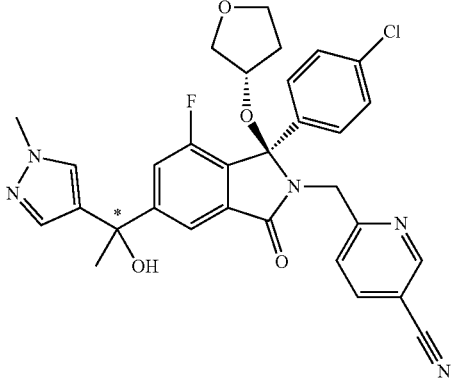<br>(isolated as a single isomer at the position shown) | 6-{[(1R)-1-(4-chlorophenyl)-7-fluoro-5-[1-hydroxy-1-(1-methyl-1H-pyrazol-4-yl)ethyl]-3-oxo-1-[(3S)-oxolan-3-yloxy]-2,3-dihydro-1H-isoindol-2-yl]methyl}pyridine-3-carbonitrile |
| 219 | 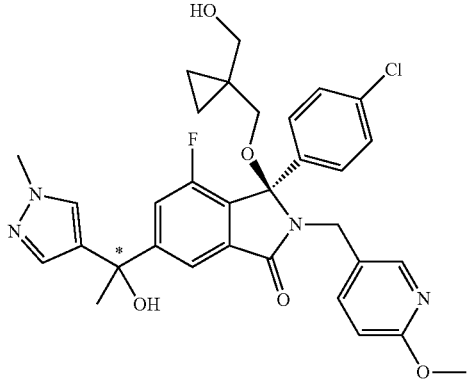<br>(isolated as a single isomer at the position shown) | (3R)-3-(4-chlorophenyl)-4-fluoro-6-[1-hydroxy-1-(1-methyl-1H-pyrazol-4-yl)ethyl]-3-{[1-(hydroxymethyl)cyclopropyl]methoxy}-2-[(6-methoxypyridin-3-yl)methyl]-2,3-dihydro-1H-isoindol-1-one |

| Ex. | Structure | Name |
| --- | --- | --- |
| 220 | 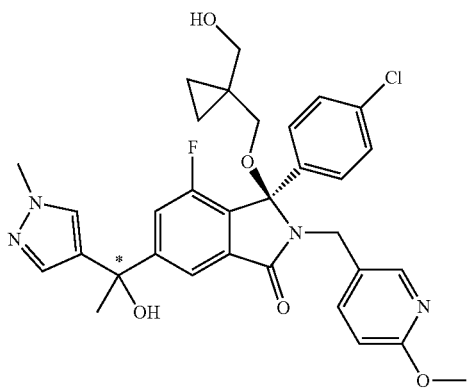<br>(isolated as a single isomer at the position shown) | (3R)-3-(4-chlorophenyl)-4-fluoro-6-[1-hydroxy-1-(1-methyl-1H-pyrazol-4-yl)ethyl]-3-{[1-(hydroxymethyl)cyclopropyl]methoxy}-2-[(6-methoxypyridin-3-yl)methyl]-2,3-dihydro-1H-isoindol-1-one |
| 221 | 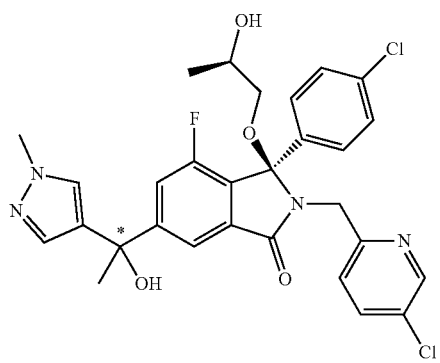<br>(isolated as a single isomer at the position shown) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(2R)-2-hydroxypropoxy]-2,3-dihydro-1H-isoindol-1-one |
| 222 | 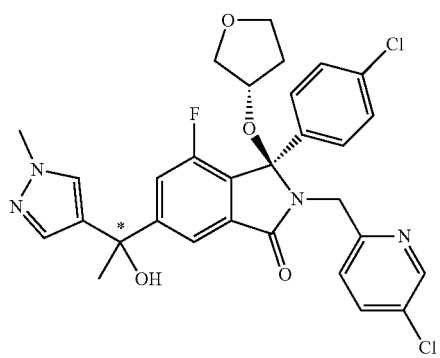<br>(isolated as a single isomer at the position shown) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(3S)-oxolan-3-yloxy]-2,3-dihydro-1H-isoindol-1-one |

| Ex. | Structure | Name |
|---|---|---|
| 223 | 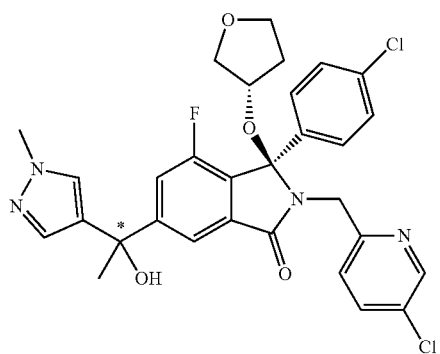<br>(isolated as a single isomer at the position shown) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(3S)-oxolan-3-yloxy]-2,3-dihydro-1H-isoindol-1-one |
| 224 | 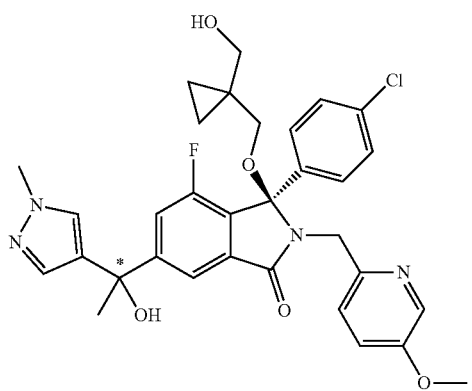<br>(isolated as a single isomer at the position shown) | (3R)-3-(4-chlorophenyl)-4-fluoro-6-[1-hydroxy-1-(1-methyl-1H-pyrazol-4-yl)ethyl]-3-{[1-(hydroxymethyl)cyclopropyl]methoxy}-2-[(5-methoxypyridin-2-yl)methyl]-2,3-dihydro-1H-isoindol-1-one |
| 225 | 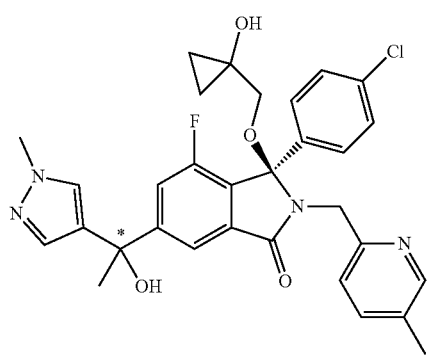<br>(isolated as a single isomer at the position shown) | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(5-methylpyridin-2-yl)methyl]-2,3-dihydro-1H-isoindol-1-one |

| Ex. | Structure | Name |
|---|---|---|
| 226 | 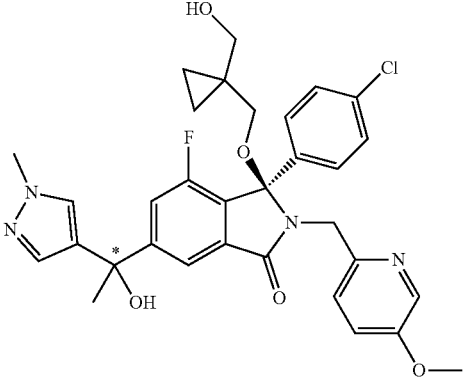<br>(isolated as a single isomer at the position shown) | (3R)-3-(4-chlorophenyl)-4-fluoro-6-[1-hydroxy-1-(1-methyl-1H-pyrazol-4-yl)ethyl]-3-{[1-(hydroxymethyl)cyclopropyl]methoxy}-2-[(5-methoxypyridin-2-yl)methyl]-2,3-dihydro-1H-isoindol-1-one |
| 227 | 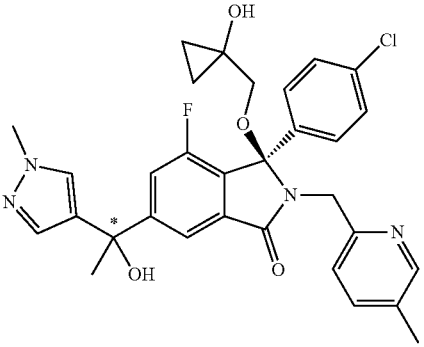<br>(isolated as a single isomer at the position shown) | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(5-methylpyridin-2-yl)methyl]-2,3-dihydro-1H-isoindol-1-one |
| 228 | 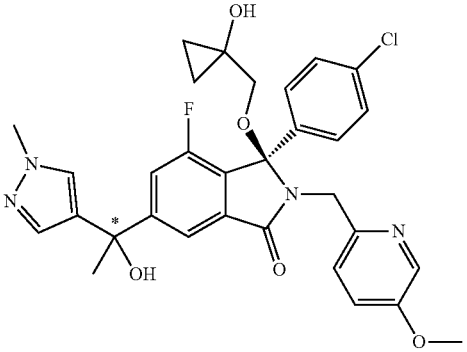<br>(isolated as a single isomer at the position shown) | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(5-methoxypyridin-2-yl)methyl]-2,3-dihydro-1H-isoindol-1-one |

| Ex. | Structure | Name |
|---|---|---|
| 229 | (isolated as a single isomer at the position shown) | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(6-methoxypyridin-3-yl)methyl]-2,3-dihydro-1H-isoindol-1-one |
| 230 | (isolated as a single isomer at the position shown) | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(6-methoxypyridin-3-yl)methyl]-2,3-dihydro-1H-isoindol-1-one |
| 231 | (isolated as a single isomer at the position shown) | (3R)-3-(4-chlorophenyl)-4-fluoro-2-[(5-fluoropyridin-2-yl)methyl]-6-[1-hydroxy-1-(1-methyl-1H-pyrazol-4-yl)ethyl]-3-[(1-hydroxycyclopropyl)methoxy]-2,3-dihydro-1H-isoindol-1-one |

| Ex. | Structure | Name |
|---|---|---|
| 232 | (isolated as a single isomer at the position shown) | (3R)-3-(4-chlorophenyl)-4-fluoro-2-[(5-fluoropyridin-2-yl)methyl]-6-[1-hydroxy-1-(1-methyl-1H-pyrazol-4-yl)ethyl]-3-[(1-hydroxycyclopropyl)methoxy]-2,3-dihydro-1H-isoindol-1-one |
| 233 and 234 | (*both isomers separated and isolated) | (3R)-3-(4-chlorophenyl)-2-[(5-chloropyridin-2-yl)methyl]-6-[2-hydroxy-1-(pyridin-3-yloxy)propan-2-yl]-3-methoxy-2,3-dihydro-1H-isoindol-1-one<br>Ex. 233 is the faster eluting isomer<br>Ex. 234 is the slower eluting isomer |
| 235 | (isolated as a single isomer at the position shown) | (3R)-3-(4-chlorophenyl)-2-[(5-chloropyridin-2-yl)methyl]-6-(1-ethoxy-2-hydroxypropan-2-yl)-3-methoxy-2,3-dihydro-1H-isoindol-1-one |
| 236 | (isolated as a single isomer at the position shown) | (3R)-3-(4-chlorophenyl)-2-[(5-chloropyridin-2-yl)methyl]-6-(1-ethoxy-2-hydroxypropan-2-yl)-3-methoxy-2,3-dihydro-1H-isoindol-1-one |

-continued

| Ex. | Structure | Name |
|---|---|---|
| 237 | (isolated as a single isomer at the position shown) | (3R)-3-(4-chlorophenyl)-2-[(5-chloropyridin-2-yl)methyl]-6-{2-hydroxy-1-[4-(2-hydroxyethyl)piperazin-1-yl]propan-2-yl}-3-methoxy-2,3-dihydro-1H-isoindol-1-one |
| 238 | (isolated as a single isomer at the position shown) | (3R)-3-(4-chlorophenyl)-2-[(5-chloropyridin-2-yl)methyl]-6-[2-hydroxy-1-(4-hydroxypiperidin-1-yl)propan-2-yl]-3-methoxy-2,3-dihydro-1H-isoindol-1-one |
| 239 | (isolated as a single isomer at the position shown) | (3R)-3-(4-chlorophenyl)-2-[(5-chloropyridin-2-yl)methyl]-6-{2-hydroxy-1-[methyl(1-methylpiperidin-4-yl)amino]propan-2-yl}-3-methoxy-2,3-dihydro-1H-isoindol-1-one |
| 240 | (isolated as a single isomer at the position shown) | (3R)-3-(4-chlorophenyl)-2-[(5-chloropyridin-2-yl)methyl]-6-{2-hydroxy-1-[(oxan-4-yl)amino]propan-2-yl}-3-methoxy-2,3-dihydro-1H-isoindol-1-one |

-continued

| Ex. | Structure | Name |
|---|---|---|
| 241 | (isolated as a single isomer at the position shown) | (3R)-3-(4-chlorophenyl)-2-[(5-chloropyridin-2-yl)methyl]-6-[2-hydroxy-1-(3-oxopiperazin-1-yl)propan-2-yl]-3-methoxy-2,3-dihydro-1H-isoindol-1-one |
| 242 | (isolated as a single isomer at the position shown) | (3R)-3-(4-chlorophenyl)-2-[(5-chloropyridin-2-yl)methyl]-6-[1-(1,4-diazepan-1-yl)-2-hydroxypropan-2-yl]-3-methoxy-2,3-dihydro-1H-isoindol-1-one |
| 243 | (isolated as a single isomer at the position shown) | (3R)-3-(4-chlorophenyl)-2-[(5-chloropyridin-2-yl)methyl]-6-[1-(1,4-diazepan-1-yl)-2-hydroxypropan-2-yl]-3-methoxy-2,3-dihydro-1H-isoindol-1-one |
| 244 | (isolated as a single isomer at the position shown) | (3R)-3-(4-chlorophenyl)-2-[(5-chloropyridin-2-yl)methyl]-6-{2-hydroxy-1-[(oxan-4-yl)amino]propan-2-yl}-3-methoxy-2,3-dihydro-1H-isoindol-1-one |

| Ex. | Structure | Name |
|---|---|---|
| 245 | (isolated as a single isomer at the position shown) | (3R)-3-(4-chlorophenyl)-2-[(5-chloropyridin-2-yl)methyl]-6-[2-hydroxy-1-(3-oxopiperazin-1-yl)propan-2-yl]-3-methoxy-2,3-dihydro-1H-isoindol-1-one |
| 246 | (isolated as a single isomer at the position shown) | (3R)-3-(4-chlorophenyl)-2-[(5-chloropyridin-2-yl)methyl]-6-{2-hydroxy-1-[4-(2-hydroxyethyl)piperazin-1-yl]propan-2-yl}-3-methoxy-2,3-dihydro-1H-isoindol-1-one |
| 247 | (isolated as a single isomer at the position shown) | (3R)-3-(4-chlorophenyl)-2-[(5-chloropyridin-2-yl)methyl]-6-[2-hydroxy-1-(4-hydroxypiperidin-1-yl)propan-2-yl]-3-methoxy-2,3-dihydro-1H-isoindol-1-one |
| 248 | (isolated as a single isomer at the position shown) | (3R)-3-(4-chlorophenyl)-2-[(5-chloropyridin-2-yl)methyl]-6-{2-hydroxy-1-[methyl(1-methylpiperidin-4-yl)amino]propan-2-yl}-3-methoxy-2,3-dihydro-1H-isoindol-1-one |

-continued

| Ex. | Structure | Name |
|---|---|---|
| 249 | (isolated as a single isomer at the position shown) | 4-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropyl}-1λ6-thiomorpholine-1,1-dione |
| 250 | (isolated as a single isomer at the position shown) | (3R)-3-(4-chlorophenyl)-2-[(5-chloropyridin-2-yl)methyl]-6-{2-hydroxy-1-[(2S)-2-(hydroxymethyl)pyrrolidin-1-yl]propan-2-yl}-3-methoxy-2,3-dihydro-1H-isoindol-1-one |
| 251 | (isolated as a single isomer at the position shown) | (3R)-3-(4-chlorophenyl)-2-[(5-chloropyridin-2-yl)methyl]-6-{2-hydroxy-1-[(2S)-2-(hydroxymethyl)pyrrolidin-1-yl]propan-2-yl}-3-methoxy-2,3-dihydro-1H-isoindol-1-one |
| 252 | (isolated as a single isomer at the position shown) | 4-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropyl}-1λ6-thiomorpholine-1,1-dione |

-continued

| Ex. | Structure | Name |
|---|---|---|
| 253 | 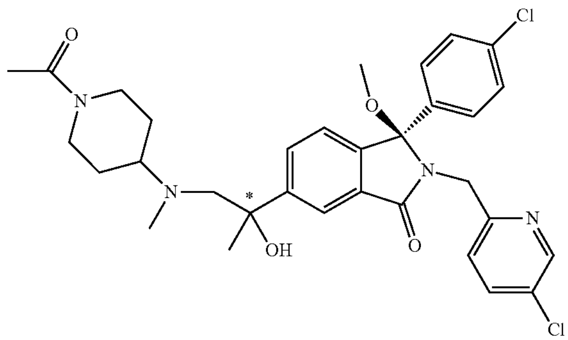 | (3R)-6-{1-[(1-acetylpiperidin-4-yl)(methyl)amino]-2-hydroxypropan-2-yl}-3-(4-chlorophenyl)-2-[(5-chloropyridin-2-yl)methyl]-3-methoxy-2,3-dihydro-1H-isoindol-1-one |
| | (isolated as a single isomer at the position shown) | |
| 253 a | 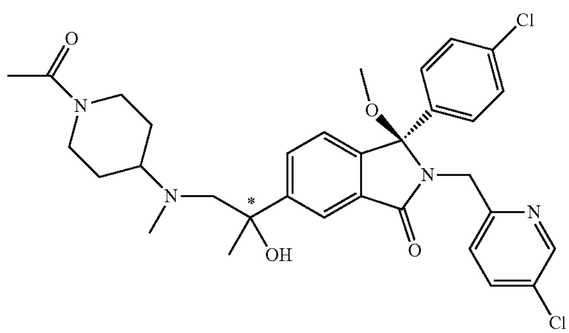 | (3R)-6-{1-[(1-acetylpiperidin-4-yl)(methyl)amino]-2-hydroxypropan-2-yl}-3-(4-chlorophenyl)-2-[(5-chloropyridin-2-yl)methyl]-3-methoxy-2,3-dihydro-1H-isoindol-1-one |
| | (isolated as a single isomer at the position shown) | |
| 254 | 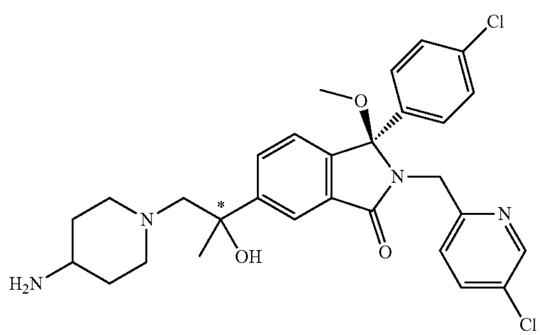 | (3R)-6-[1-(4-aminopiperidin-1-yl)-2-hydroxypropan-2-yl]-3-(4-chlorophenyl)-2-[(5-chloropyridin-2-yl)methyl]-3-methoxy-2,3-dihydro-1H-isoindol-1-one |
| | (isolated as a single isomer at the position shown) | |
| 255 | 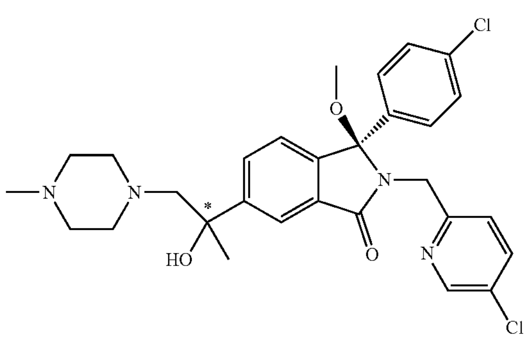 | (3R)-3-(4-chlorophenyl)-2-[(5-chloropyridin-2-yl)methyl]-6-[2-hydroxy-1-(4-methylpiperazin-1-yl)propan-2-yl]-3-methoxy-2,3-dihydro-1H-isoindol-1-one |
| | (isolated as a single isomer at the position shown) | |

| Ex. | Structure | Name |
|---|---|---|
| 256 | (isolated as a single isomer at the position shown) | (3R)-3-(4-chlorophenyl)-2-[(5-chloropyridin-2-yl)methyl]-6-[2-hydroxy-1-(4-methylpiperazin-1-yl)propan-2-yl]-3-methoxy-2,3-dihydro-1H-isoindol-1-one |
| 257 | (isolated as a single isomer at the position shown) | (3R)-3-(4-chlorophenyl)-2-[(5-chloropyridin-2-yl)methyl]-6-[2-hydroxy-1-(2-oxopyrrolidin-1-yl)propan-2-yl]-3-methoxy-2,3-dihydro-1H-isoindol-1-one |
| 258 | (isolated as a single isomer at the position shown) | (3R)-3-(4-chlorophenyl)-2-[(5-chloropyridin-2-yl)methyl]-6-[2-hydroxy-1-(2-oxopyrrolidin-1-yl)propan-2-yl]-3-methoxy-2,3-dihydro-1H-isoindol-1-one |
| 259 | (isolated as a single isomer at the position shown) | (3R)-6-[1-(4-aminopiperidin-1-yl)-2-hydroxypropan-2-yl]-3-(4-chlorophenyl)-2-[(5-chloropyridin-2-yl)methyl]-3-methoxy-2,3-dihydro-1H-isoindol-1-one |

-continued

| Ex. | Structure | Name |
|---|---|---|
| 260 | (isolated as a single isomer at the position shown) | (3R)-3-(4-chlorophenyl)-2-[(5-chloropyridin-2-yl)methyl]-6-[2-hydroxy-1-(5-oxo-1,4-diazepan-1-yl)propan-2-yl]-3-methoxy-2,3-dihydro-1H-isoindol-1-one |
| 261 | (isolated as a single isomer at the position shown) | (3R)-3-(4-chlorophenyl)-2-[(5-chloropyridin-2-yl)methyl]-6-[2-hydroxy-1-(5-oxo-1,4-diazepan-1-yl)propan-2-yl]-3-methoxy-2,3-dihydro-1H-isoindol-1-one |
| 262 | (isolated as a single isomer at the position shown) | (3R)-3-(4-chlorophenyl)-2-[(5-chloropyridin-2-yl)methyl]-6-(2-hydroxy-1-{4H,5H,6H,7H-[1,2,3]triazolo[1,5-a]pyrazin-5-yl}propan-2-yl)-3-methoxy-2,3-dihydro-1H-isoindol-1-one |
| 263 | (isolated as a single isomer at the position shown) | (3R)-3-(4-chlorophenyl)-2-[(5-chloropyridin-2-yl)methyl]-6-{2-hydroxy-1-[(1S,4S)-5-methyl-2,5-diazabicyclo[2.2.1]heptan-2-yl]propan-2-yl}-3-methoxy-2,3-dihydro-1H-isoindol-1-one |

-continued

| Ex. | Structure | Name |
|---|---|---|
| 264 | (isolated as a single isomer at the position shown) | (3R)-3-(4-chlorophenyl)-2-[(5-chloropyridin-2-yl)methyl]-6-{2-hydroxy-1-[(1S,4S)-5-methyl-2,5-diazabicyclo[2.2.1]heptan-2-yl]propan-2-yl}-3-methoxy-2,3-dihydro-1H-isoindol-1-one |
| 265 | (isolated as a single isomer at the position shown) | (3R)-3-(4-chlorophenyl)-2-[(5-chloropyridin-2-yl)methyl]-6-{2-hydroxy-1-[(2R)-2-(hydroxymethyl)pyrrolidin-1-yl]propan-2-yl}-3-methoxy-2,3-dihydro-1H-isoindol-1-one |
| 266 | (isolated as a single isomer at the position shown) | (3R)-3-(4-chlorophenyl)-2-[(5-chloropyridin-2-yl)methyl]-6-[2-hydroxy-1-(4-methyl-1,4-diazepan-1-yl)propan-2-yl]-3-methoxy-2,3-dihydro-1H-isoindol-1-one |
| 267 | (isolated as a single isomer at the position shown) | (3R)-3-(4-chlorophenyl)-2-[(5-chloropyridin-2-yl)methyl]-6-{2-hydroxy-1-[(2R)-2-(hydroxymethyl)pyrrolidin-1-yl]propan-2-yl}-3-methoxy-2,3-dihydro-1H-isoindol-1-one |

| Ex. | Structure | Name |
|---|---|---|
| 268 | (isolated as a single isomer at the position shown) | (3R)-3-(4-chlorophenyl)-2-[(5-chloropyridin-2-yl)methyl]-6-[2-hydroxy-1-(4-methyl-1,4-diazepan-1-yl)propan-2-yl]-3-methoxy-2,3-dihydro-1H-isoindol-1-one |
| 269 | (isolated as a single isomer at the position shown) | (3R)-6-[1-(azetidin-1-yl)-2-hydroxypropan-2-yl]-3-(4-chlorophenyl)-2-[(5-chloropyridin-2-yl)methyl]-3-methoxy-2,3-dihydro-1H-isoindol-1-one |
| 270 | (isolated as a single isomer at the position shown) | (3R)-6-[1-(azetidin-1-yl)-2-hydroxypropan-2-yl]-3-(4-chlorophenyl)-2-[(5-chloropyridin-2-yl)methyl]-3-methoxy-2,3-dihydro-1H-isoindol-1-one |
| 271 | (isolated as a single isomer at the position shown) | (3R)-3-(4-chlorophenyl)-2-[(5-chloropyridin-2-yl)methyl]-6-{1-[(3S)-3,4-dimethylpiperazin-1-yl]-2-hydroxypropan-2-yl}-3-methoxy-2,3-dihydro-1H-isoindol-1-one |

-continued

| Ex. | Structure | Name |
|---|---|---|
| 272 | (isolated as a single isomer at the position shown) | (3R)-3-(4-chlorophenyl)-2-[(5-chloropyridin-2-yl)methyl]-6-{1-[(3R)-3,4-dimethylpiperazin-1-yl]-2-hydroxypropan-2-yl}-3-methoxy-2,3-dihydro-1H-isoindol-1-one |
| 273 | (isolated as a single isomer at the position shown) | (3R)-3-(4-chlorophenyl)-2-[(5-chloropyridin-2-yl)methyl]-6-{1-[(3R)-3,4-dimethylpiperazin-1-yl]-2-hydroxypropan-2-yl}-3-methoxy-2,3-dihydro-1H-isoindol-1-one |
| 274 | (isolated as a single isomer at the position shown) | (3R)-3-(4-chlorophenyl)-2-[(5-chloropyridin-2-yl)methyl]-6-{1-[(2S)-2,4-dimethylpiperazin-1-yl]-2-hydroxypropan-2-yl}-3-methoxy-2,3-dihydro-1H-isoindol-1-one |
| 275 | (isolated as a single isomer at the position shown) | (3R)-3-(4-chlorophenyl)-2-[(5-chloropyridin-2-yl)methyl]-6-(2-hydroxy-1-{4H,5H,6H,7H-[1,2,3]triazolo[1,5-a]pyrazin-5-yl}propan-2-yl)-3-methoxy-2,3-dihydro-1H-isoindol-1-one |

| Ex. | Structure | Name |
|---|---|---|
| 276 and 277 | 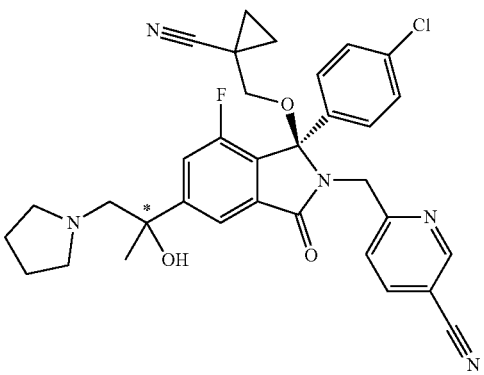 [SMILES: CC(O)(CN1CCCC1)c1cc(F)c2c(c1)C(=O)N(Cc1ccc(C#N)cn1)[C@@]2(OCC1(C#N)CC1)c1ccc(Cl)cc1] | 6-{[(1R)-1-(4-chlorophenyl)-1-[(1-cyanocyclopropyl)methoxy]-7-fluoro-5-[2-hydroxy-1-(pyrrolidin-1-yl)propan-2-yl]-3-oxo-2,3-dihydro-1H-isoindol-2-yl]methyl}pyridine-3-carbonitrile<br>Ex. 276 is the faster eluting isomer<br>Ex. 277 is the slower eluting isomer |
| 278 and 279 | 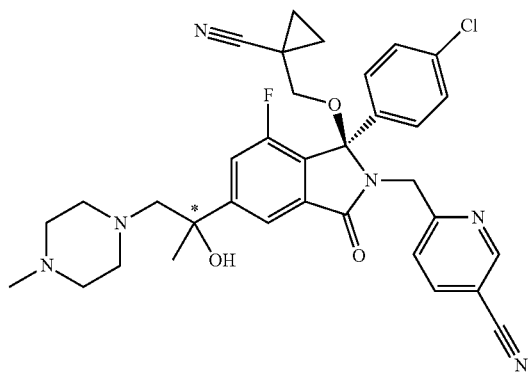 [SMILES: CN1CCN(CC(C)(O)c2cc(F)c3c(c2)C(=O)N(Cc2ccc(C#N)cn2)[C@@]3(OCC2(C#N)CC2)c2ccc(Cl)cc2)CC1] | 6-{[(1R)-1-(4-chlorophenyl)-1-[(1-cyanocyclopropyl)methoxy]-7-fluoro-5-[2-hydroxy-1-(4-methylpiperazin-1-yl)propan-2-yl]-3-oxo-2,3-dihydro-1H-isoindol-2-yl]methyl}pyridine-3-carbonitrile<br>Ex. 278 is the faster eluting isomer<br>Ex. 279 is the slower eluting isomer |
| 280 | 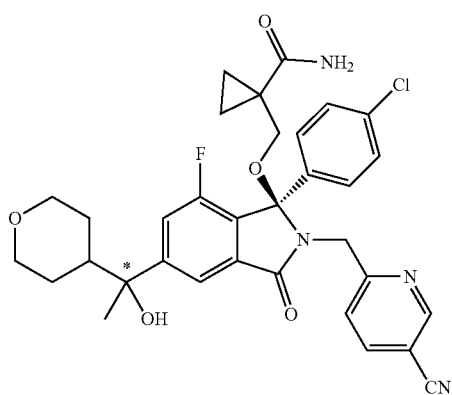(isolated as a single isomer at the position shown) | 1-({[(1R)-1-(4-chlorophenyl)-2-[(5-cyanopyridin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide |

| Ex. | Structure | Name |
|---|---|---|
| 281 | (*single isomer separated and isolated) | 1-({[(1R)-1-(4-chlorophenyl)-2-[(5-cyanopyridin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide |
| 282 and 283 | (examples were prepared and isolated as a single isomer) | 6-{[(1R)-1-(4-chlorophenyl)-1-[(1-cyanocyclopropyl)methoxy]-7-fluoro-5-[1-hydroxy-1-(oxan-4-yl)ethyl]-3-oxo-2,3-dihydro-1H-isoindol-2-yl]methyl}pyridine-3-carbonitrile |
| 284 and 285 | (examples were prepared and isolated as a single isomer) | 1-({[(1R)-1-(4-chlorophenyl)-2-[(5-chloropyrimidin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide |

| Ex. | Structure | Name |
|---|---|---|
| 286 | 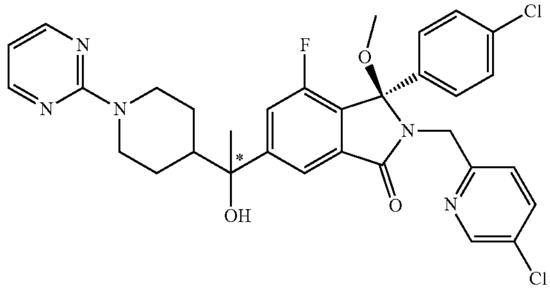 | (3R)-3-(4-chlorophenyl)-2-[(5-chloropyridin-2-yl)methyl]-4-fluoro-6-{1-hydroxy-1-[1-(pyrimidin-2-yl)piperidin-4-yl]ethyl}-3-methoxy-2,3-dihydro-1H-isoindol-1-one<br>Ex. 286 is the slower eluting isomer<br>(*single isomer separated and isolated) |
| 287 | 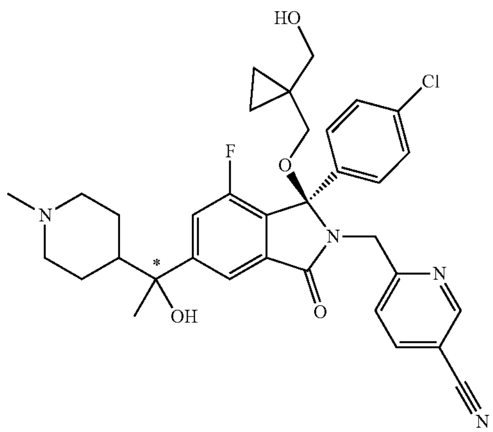 | 6-{[(1R)-1-(4-chlorophenyl)-7-fluoro-5-[1-hydroxy-1-(1-methylpiperidin-4-yl)ethyl]-1-{[1-(hydroxymethyl)cyclopropyl]methoxy}-3-oxo-2,3-dihydro-1H-isoindol-2-yl]methyl}pyridine-3-carbonitrile<br>Ex. 287 is the faster eluting isomer<br>(*single isomer separated and isolated) |
| 288 | 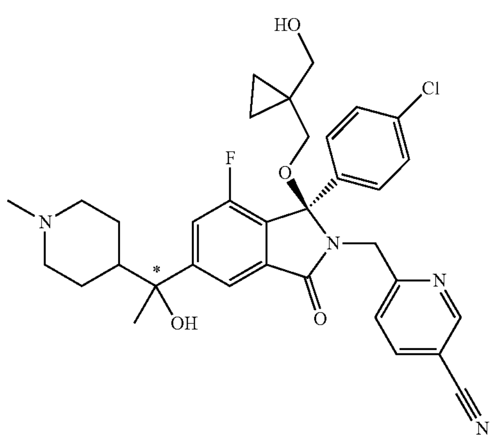 | 6-{[(1R)-1-(4-chlorophenyl)-7-fluoro-5-[1-hydroxy-1-(1-methylpiperidin-4-yl)ethyl]-1-{[1-(hydroxymethyl)cyclopropyl]methoxy}-3-oxo-2,3-dihydro-1H-isoindol-2-yl]methyl}pyridine-3-carbonitrile<br>(*single isomer separated and isolated) |

-continued

| Ex. | Structure | Name |
|---|---|---|
| 289 and 290 | 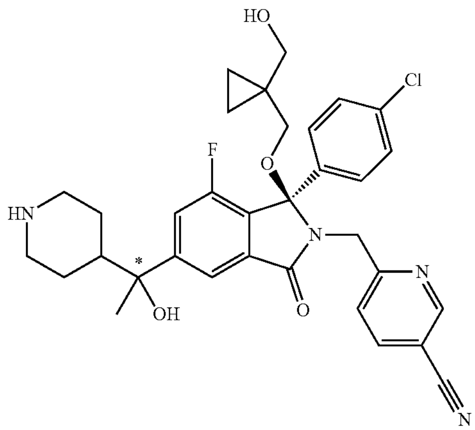 [SMILES: CC(O)(c1cc(F)c2c(c1)C(=O)N(Cc1ccc(C#N)cn1)[C@@]2(OCC1(CO)CC1)c1ccc(Cl)cc1)C1CCNCC1] | 6-{[(1R)-1-(4-chlorophenyl)-7-fluoro-5-[1-hydroxy-1-(piperidin-4-yl)ethyl]-1-{[1-(hydroxymethyl)cyclopropyl]methoxy}-3-oxo-2,3-dihydro-1H-isoindol-2-yl]methyl}pyridine-3-carbonitrile<br>Ex. 289 is the slower eluting isomer<br>Ex. 290 is the faster eluting isomer |
| 291 and 292 | 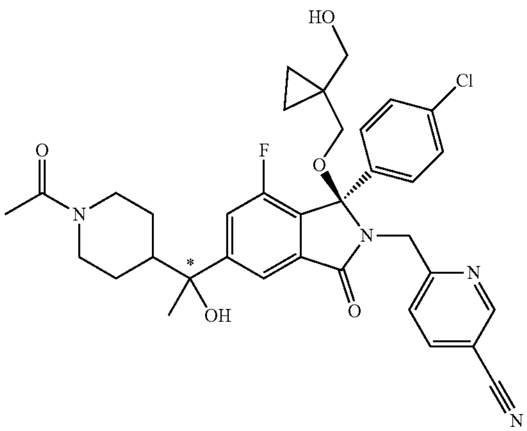 [SMILES: CC(=O)N1CCC(C(C)(O)c2cc(F)c3c(c2)C(=O)N(Cc2ccc(C#N)cn2)[C@@]3(OCC2(CO)CC2)c2ccc(Cl)cc2)CC1] | 6-{[(1R)-5-[1-(1-acetylpiperidin-4-yl)-1-hydroxyethyl]-1-(4-chlorophenyl)-7-fluoro-1-{[1-(hydroxymethyl)cyclopropyl]methoxy}-3-oxo-2,3-dihydro-1H-isoindol-2-yl]methyl}pyridine-3-carbonitrile<br>Ex. 291 is the slower eluting isomer<br>Ex. 292 is the faster eluting isomer |
| 293 | (example isolated as a single isomer at the position shown*) | (3R)-6-[1-(1-acetylpiperidin-4-yl)-1-hydroxyethyl]-3-(4-chlorophenyl)-2-[(5-chloropyridin-2-yl)methyl]-4-fluoro-3-methoxy-2,3-dihydro-1H-isoindol-1-one<br>Ex. 293 is the slower eluting isomer |
| 294 | (example isolated as a single isomer at the position shown*) | (3R)-3-(4-chlorophenyl)-2-[(5-chloropyridin-2-yl)methyl]-4-fluoro-6-[1-hydroxy-1-(1-methanesulfonylpiperidin-4-yl)ethyl]-3-methoxy-2,3-dihydro-1H-isoindol-1-one |

-continued

| Ex. | Structure | Name |
|---|---|---|
| 295 | 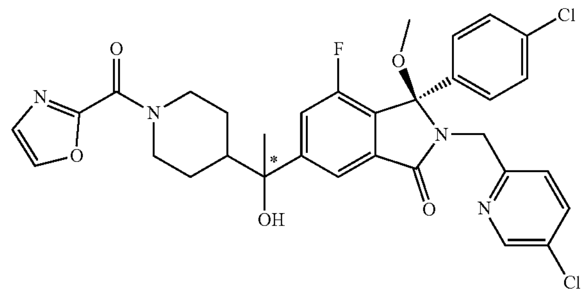 | (3R)-3-(4-chlorophenyl)-2-[(5-chloropyridin-2-yl)methyl]-4-fluoro-6-{1-hydroxy-1-[1-(1,3-oxazole-2-carbonyl)piperidin-4-yl]ethyl}-3-methoxy-2,3-dihydro-1H-isoindol-1-one<br>Ex. 295 is the slower eluting isomer<br>(example isolated as a single isomer at the position shown*) |
| 296 | 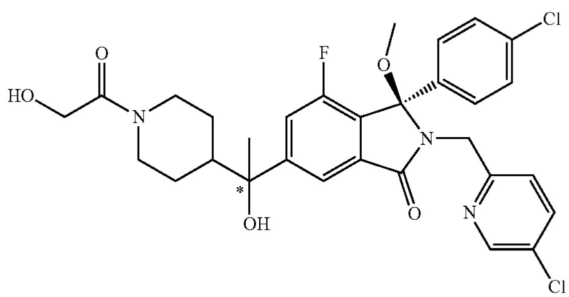 | (3R)-3-(4-chlorophenyl)-2-[(5-chloropyridin-2-yl)methyl]-4-fluoro-6-{1-hydroxy-1-[1-(2-hydroxyacetyl)piperidin-4-yl]ethyl}-3-methoxy-2,3-dihydro-1H-isoindol-1-one<br>Ex. 296 is the faster eluting isomer<br>(example isolated as a single isomer at the position shown*) |
| 297 | 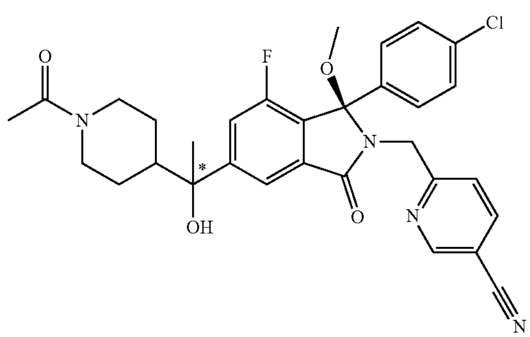 | 6-{[(1R)-5-[1-(1-acetylpiperidin-4-yl)-1-hydroxyethyl]-1-(4-chlorophenyl)-7-fluoro-1-methoxy-3-oxo-2,3-dihydro-1H-isoindol-2-yl]methyl}pyridine-3-carbonitrile<br>Ex. 297 is the slower eluting isomer<br>(example isolated as a single isomer at the position shown*) |
| 298 and 299 | 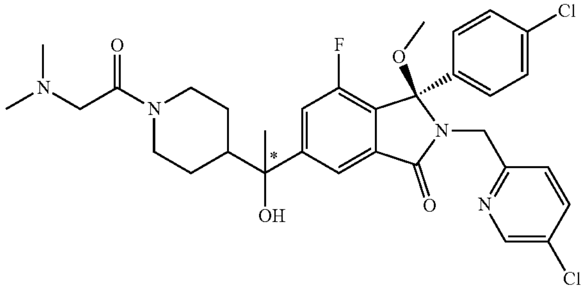 | (3R)-3-(4-chlorophenyl)-2-[(5-chloropyridin-2-yl)methyl]-6-(1-{1-[2-(dimethylamino)acetyl]piperidin-4-yl}-1-hydroxyethyl)-4-fluoro-3-methoxy-2,3-dihydro-1H-isoindol-1-one<br>Ex. 298 is the faster eluting isomer<br>Ex. 299 is the slower eluting isomer<br>(example isolated as a single isomer at the position shown*) |

-continued

| Ex. | Structure | Name |
|---|---|---|
| 300 | 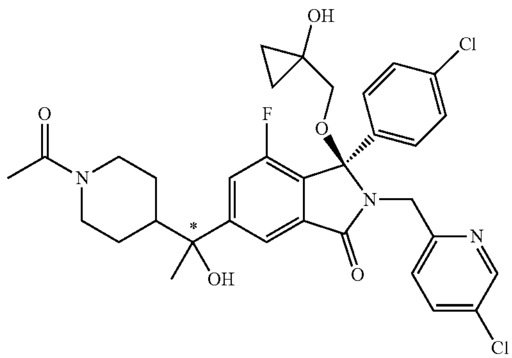 | (3R)-6-[1-(1-acetylpiperidin-4-yl)-1-hydroxyethyl]-3-(4-chlorophenyl)-2-[(5-chloropyridin-2-yl)methyl]-4-fluoro-3-[(1-hydroxycyclopropyl)methoxy]-2,3-dihydro-1H-isoindol-1-one<br><br>(example isolated as a single isomer at the position shown*) |
| 301 | 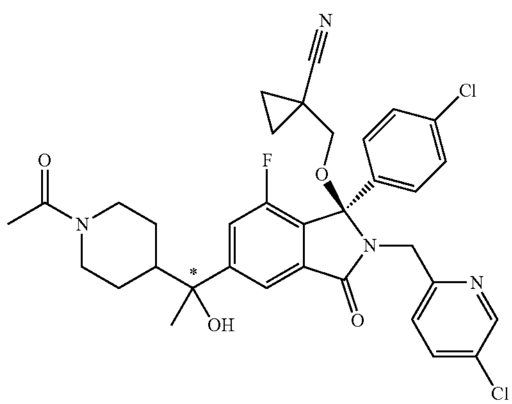 | 1-({[(1R)-5-[1-(1-acetylpiperidin-4-yl)-1-hydroxyethyl]-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carbonitrile<br><br>(example isolated as a single isomer at the position shown*) |
| 302 and 303 | 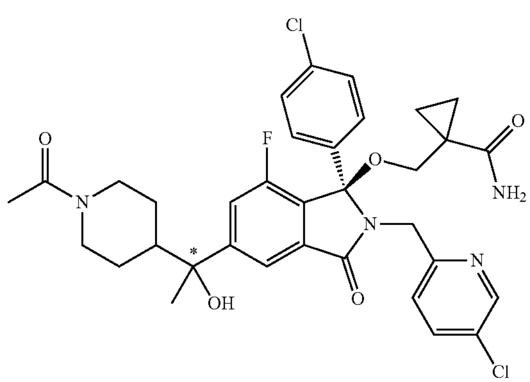 | 1-({[(1R)-5-[1-(1-acetylpiperidin-4-yl)-1-hydroxyethyl]-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carboxamide<br>Ex. 302 is the faster eluting isomer<br>Ex. 303 is the slower eluting isomer<br><br>(example isolated as a single isomer at the position shown*) |

| Ex. | Structure | Name |
|---|---|---|
| 304 | 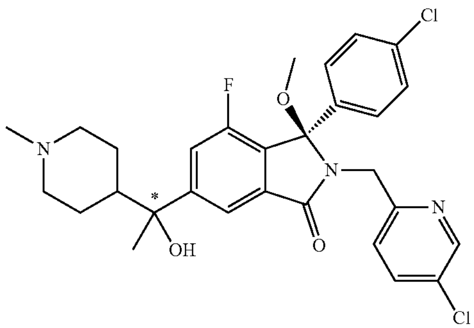 | (3R)-3-(4-chlorophenyl)-2-[(5-chloropyridin-2-yl)methyl]-4-fluoro-6-[1-hydroxy-1-(1-methylpiperidin-4-yl)ethyl]-3-methoxy-2,3-dihydro-1H-isoindol-1-one<br><br>(example isolated as a single isomer at the position shown*) |
| 305 | 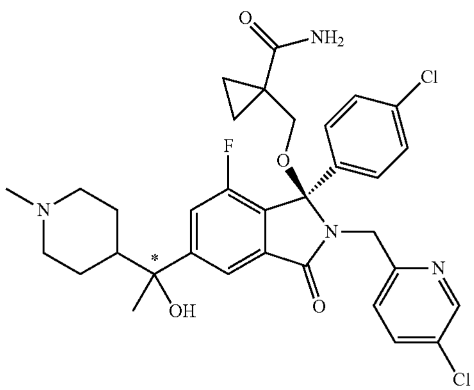 | 1-({[(1R)-1-(4-chlorophenyl)-2-[(5-chloropyridin-2-yl)methyl]-7-fluoro-5-[1-hydroxy-1-(1-methylpiperidin-4-yl)ethyl]-3-oxo-2,3-dihydro-1H-isoindol-1-yl]oxy}methyl)cyclopropane-1-carboxamide<br>Ex. 305 is the slower eluting isomer<br><br>(example isolated as a single isomer at the position shown*) |
| 306 | 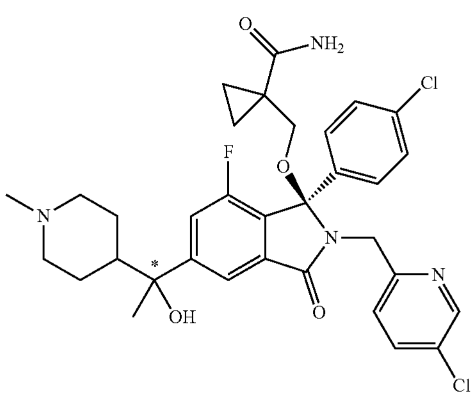 | 1-({[(1R)-1-(4-chlorophenyl)-2-[(5-chloropyridin-2-yl)methyl]-7-fluoro-5-[1-hydroxy-1-(1-methylpiperidin-4-yl)ethyl]-3-oxo-2,3-dihydro-1H-isoindol-1-yl]oxy}methyl)cyclopropane-1-carboxamide<br>Ex. 306 is the slower eluting isomer<br><br>(example isolated as a single isomer at the position shown*) |

-continued

| Ex. | Structure | Name |
|---|---|---|
| 307 and 308 | 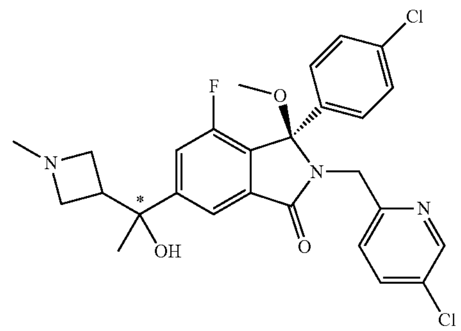 | (3R)-3-(4-chlorophenyl)-2-[(5-chloropyridin-2-yl)methyl]-4-fluoro-6-[1-hydroxy-1-(1-methylazetidin-3-yl)ethyl]-3-methoxy-2,3-dihydro-1H-isoindol-1-one |
| | (*both isomers separated and isolated) | |
| 309 and 310 | 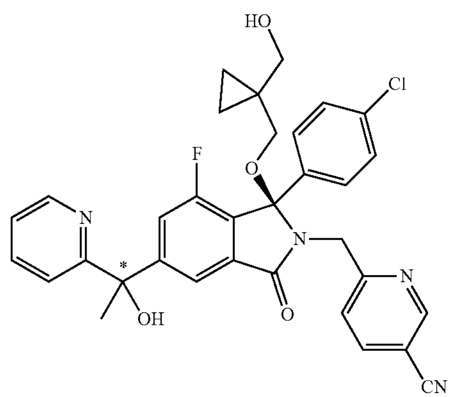 | 6-{[(1R)-1-(4-chlorophenyl)-7-fluoro-5-[1-hydroxy-1-(pyridin-2-yl)ethyl]-1-{[1-(hydroxymethyl)cyclopropyl]methoxy}-3-oxo-2,3-dihydro-1H-isoindol-2-yl]methyl}pyridine-3-carbonitrile |
| | (*both isomers separated and isolated) | |
| 311 and 312 | 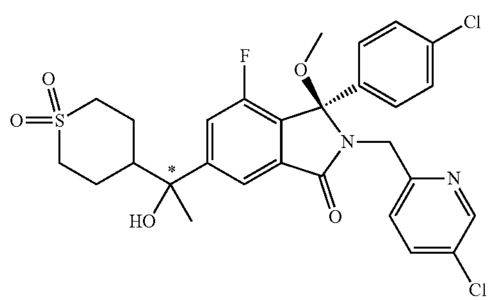 | 4-{1-[(1R)-1-(4-chlorophenyl)-2-[(5-chloropyridin-2-yl)methyl]-7-fluoro-1-methoxy-3-oxo-2,3-dihydro-1H-isoindol-5-yl]-1-hydroxyethyl}-1λ6-thiane-1,1-dione<br>Ex. 311 is the slower eluting isomer<br>Ex. 312 is the faster eluting isomer |
| | (*both isomers separated and isolated) | |
| 313 and 314 | 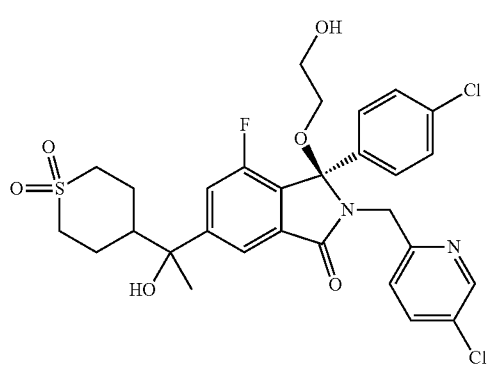 | 4-{1-[(1R)-1-(4-chlorophenyl)-2-[(5-chloropyridin-2-yl)methyl]-7-fluoro-1-(2-hydroxyethoxy)-3-oxo-2,3-dihydro-1H-isoindol-5-yl]-1-hydroxyethyl}-1λ6-thiane-1,1-dione<br>Ex. 313 is the slower eluting isomer<br>Ex. 314 is the faster eluting isomer |
| | (*both isomers separated and isolated) | |

-continued

| Ex. | Structure | Name |
|---|---|---|
| 315 | 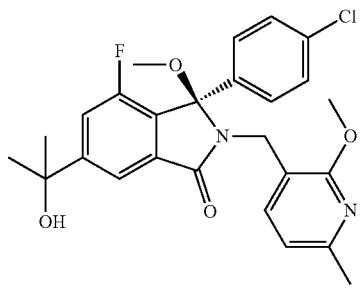 [SMILES: COc1nc(C)ccc1CN1C(=O)c2cc(C(C)(C)O)cc(F)c2[C@]1(OC)c1ccc(Cl)cc1] | (3R)-3-(4-chlorophenyl)-4-fluoro-6-(2-hydroxypropan-2-yl)-3-methoxy-2-[(2-methoxy-6-methylpyridin-3-yl)methyl]-2,3-dihydro-1H-isoindol-1-one |
| 316 and 317 | 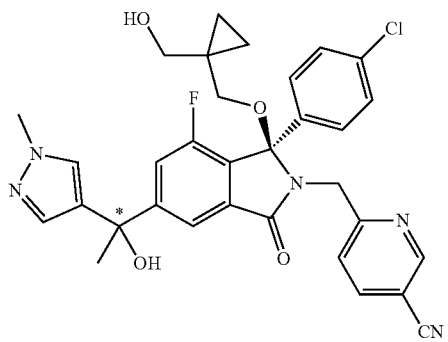 (*both isomers separated and isolated) | 6-{[(1R)-1-(4-chlorophenyl)-7-fluoro-5-[1-hydroxy-1-(1-methyl-1H-pyrazol-4-yl)ethyl]-1-{[1-(hydroxymethyl)cyclopropyl]methoxy}-3-oxo-2,3-dihydro-1H-isoindol-2-yl]methyl}pyridine-3-carbonitrile<br>Ex. 316 is the faster eluting isomer<br>Ex. 317 is the slower eluting isomer |
| 318 and 319 | 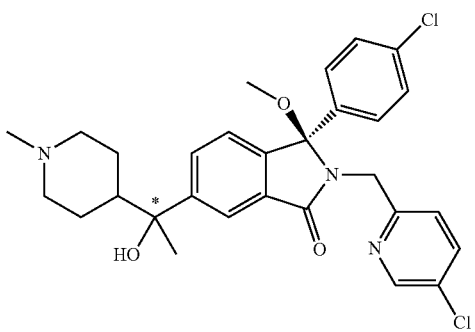 (*both isomers separated and isolated) | (3R)-3-(4-chlorophenyl)-2-[(5-chloropyridin-2-yl)methyl]-6-[1-hydroxy-1-(1-methylpiperidin-4-yl)ethyl]-3-methoxy-2,3-dihydro-1H-isoindol-1-one<br>Ex. 318 is the faster eluting isomer<br>Ex. 319 is the slower eluting isomer |
| 320 and 321 | 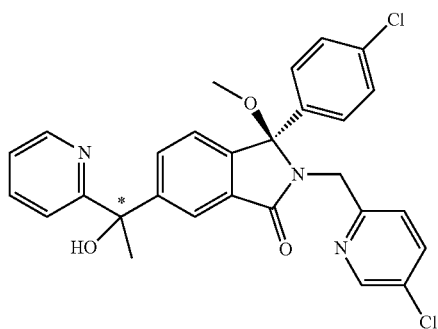 (*both isomers separated and isolated) | (3R)-3-(4-chlorophenyl)-2-[(5-chloropyridin-2-yl)methyl]-6-[1-hydroxy-1-(pyridin-2-yl)ethyl]-3-methoxy-2,3-dihydro-1H-isoindol-1-one<br>Ex. 320 is the faster eluting isomer<br>Ex. 321 is the slower eluting isomer |

-continued

| Ex. | Structure | Name |
|---|---|---|
| 322 and 323 | 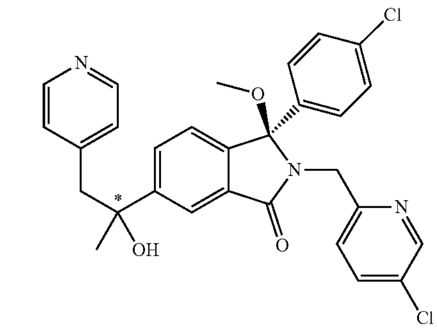 [SMILES: CO[C@]1(c2ccc(Cl)cc2)c2ccc(C(C)(O)Cc3ccncc3)cc2C(=O)N1Cc1ccc(Cl)cn1] | (3R)-3-(4-chlorophenyl)-2-[(5-chloropyridin-2-yl)methyl]-6-[2-hydroxy-1-(pyridin-4-yl)propan-2-yl]-3-methoxy-2,3-dihydro-1H-isoindol-1-one<br>Ex. 322 is the faster eluting isomer<br>Ex. 323 is the slower eluting isomer |
| 324 and 325 | (*both isomers separated and isolated) | (3R)-3-(4-chlorophenyl)-2-[(5-chloropyridin-2-yl)methyl]-6-[1-(1,2-dimethyl-1H-imidazol-4-yl)-1-hydroxyethyl]-4-fluoro-3-[(1-hydroxycyclopropyl)methoxy]-2,3-dihydro-1H-isoindol-1-one<br>Ex. 324 is the faster eluting isomer<br>Ex. 325 is the slower eluting isomer |
| 326 | 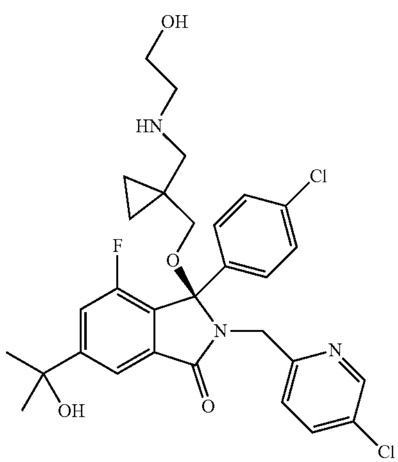 [SMILES: CC(C)(O)c1cc(F)c2c(c1)C(=O)N(Cc1ccc(Cl)cn1)[C@@]2(OCC1(CNCCO)CC1)c1ccc(Cl)cc1] | (3R)-3-(4-chlorophenyl)-2-[(5-chloropyridin-2-yl)methyl]-4-fluoro-3-[(1-{[(2-hydroxyethyl)amino]methyl}cyclopropyl)methoxy]-6-(2-hydroxypropan-2-yl)-2,3-dihydro-1H-isoindol-1-one |
| 327 and 328 | (*both isomers separated and isolated) | (3R)-3-(4-Chlorophenyl)-2-[(5-chloropyridin-2-yl)methyl]-6-[2-hydroxy-1-(3-oxomorpholin-4-yl)propan-2-yl]-3-methoxy-2,3-dihydro-1H-isoindol-1-one |

-continued

| Ex. | Structure | Name |
|---|---|---|
| 329 and 330 | (*both isomers separated and isolated) | 1-{2-[(1R)-1-(4-Chlorophenyl)-2-[(5-chloropyridin-2-yl)methyl]-1-methoxy-3-oxo-2,3-dihydro-1H-isoindol-5-yl]-2-hydroxypropyl}imidazolidine-2,4-dione |
| 331 | 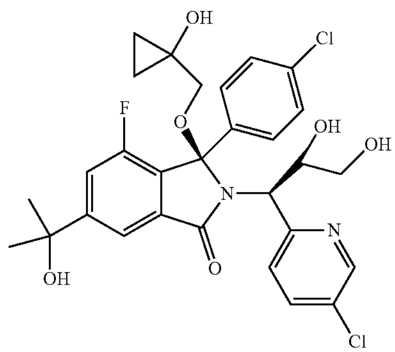 [SMILES: CC(C)(O)c1cc(F)c2c(c1)C(=O)N([C@H](c1ccc(Cl)cn1)C(O)CO)[C@@]2(OCC1(O)CC1)c1ccc(Cl)cc1] | (3R)-3-(4-Chlorophenyl)-2-[(1R)-1-(5-chloropyridin-2-yl)-2,3-dihydroxypropyl]-4-fluoro-3-[(1-hydroxycyclopropyl)methoxy]-6-(2-hydroxypropan-2-yl)-2,3-dihydro-1H-isoindol-1-one |
| 332 | (*Example 332 was isolated as a mixture of 2 isomers) | (3R)-3-(4-chlorophenyl)-2-[(5-chloropyridin-2-yl)methyl]-4-fluoro-6-[1-hydroxy-1-(4-methyl-1H-imidazol-2-yl)ethyl]-3-[(1-hydroxycyclopropyl)methoxy]-2,3-dihydro-1H-isoindol-1-one |
| 333 and 334 | (*both isomers separated and isolated) | 6-{[(1R)-1-(4-Chlorophenyl)-7-fluoro-5-[1-hydroxy-1-(1,3-thiazol-4-yl)propyl]-1-(2-hydroxyethoxy)-3-oxo-2,3-dihydro-1H-isoindol-2-yl]methyl}pyridine-3-carbonitrile<br>Ex. 333 is the faster eluting isomer<br>Ex. 334 is the slower eluting isomer |

-continued

| Ex. | Structure | Name |
|---|---|---|
| 335 and 336 | 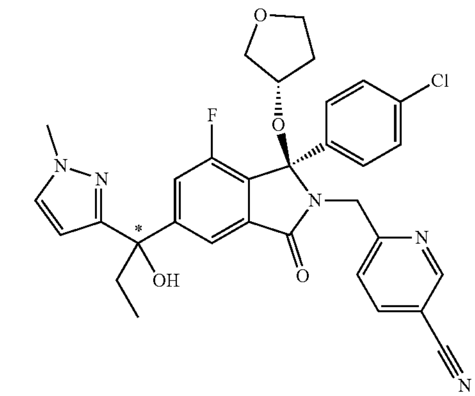 | 6-{[1-(4-chlorophenyl)-7-fluoro-5-[1-hydroxy-1-(1-methyl-1H-pyrazol-3-yl)propyl]-3-oxo-1-[(3S)-oxolan-3-yloxy]-2,3-dihydro-1H-isoindol-2-yl]methyl}pyridine-3-carbonitrile<br>Ex. 335 is the faster eluting isomer<br>Ex. 336 is the slower eluting isomer |
| 337 and 338 | 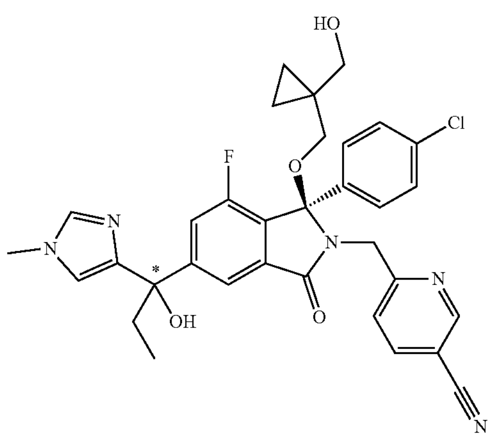 | -{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}pyridine-3-carbonitrile<br>Ex. 337 is the faster eluting isomer<br>Ex. 338 is the slower eluting isomer |
| 339 | 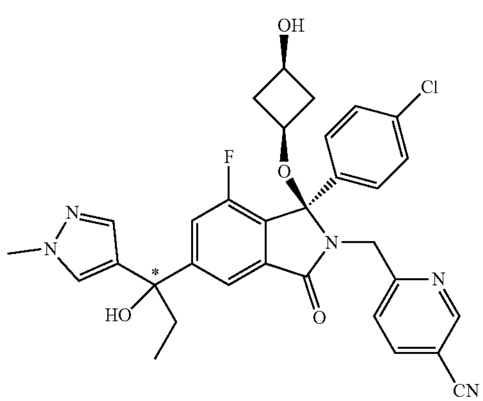 | 6-{[(1R)-1-(4-chlorophenyl)-7-fluoro-5-[1-hydroxy-1-(1-methyl-1H-pyrazol-4-yl)propyl]-3-oxo-1-[cis-3-hydroxycyclobutoxy]-2,3-dihydro-1H-isoindol-2-yl]methyl}pyridine-3-carbonitrile |

| Ex. | Structure | Name |
|---|---|---|
| 340 | (*isolated as a single isomer at the position shown) | 6-{[(1R)-1-(4-chlorophenyl)-7-fluoro-5-[1-hydroxy-1-(1-methyl-1H-pyrazol-4-yl)ethyl]-1-[(1-hydroxycyclopropyl)methoxy]-3-oxo-2,3-dihydro-1H-isoindol-2-yl]methyl}pyridine-3-carbonitrile |
| 341 | (*isolated as a single isomer at the position shown) | 6-{[(1R)-1-(4-chlorophenyl)-7-fluoro-5-[1-hydroxy-1-(1-methyl-1H-pyrazol-4-yl)ethyl]-1-[(1-hydroxycyclopropyl)methoxy]-3-oxo-2,3-dihydro-1H-isoindol-2-yl]methyl}pyridine-3-carbonitrile |
| 342 | (*isolated as a single isomer at the position shown) | 6-{[(1R)-1-(4-chlorophenyl)-7-fluoro-5-[1-hydroxy-1-(1-methyl-1H-pyrazol-4-yl)propyl]-3-oxo-1-[cis-3-hydroxycyclobutoxy]-2,3-dihydro-1H-isoindol-2-yl]methyl}pyridine-3-carbonitrile |

| Ex. | Structure | Name |
|---|---|---|
| 343 | (*isolated as a single isomer at the position shown) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-(2-hydroxyethoxy)-2,3-dihydro-1H-isoindol-1-one |
| 344 | (*isolated as a single isomer at the position shown) | 6-{[(1R)-1-(4-chlorophenyl)-7-fluoro-5-[1-hydroxy-1-(1-methyl-1H-pyrazol-4-yl)ethyl]-3-oxo-1-[(3S)-oxolan-3-yloxy]-2,3-dihydro-1H-isoindol-2-yl]methyl}pyridine-3-carbonitrile |
| 345 | (*isolated as a single isomer at the position shown) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one |

| Ex. | Structure | Name |
|---|---|---|
| 346 | (*isolated as a single isomer at the position shown) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one |
| 347 | (*isolated as a single isomer at the position shown) | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(5-methoxypyridin-2-yl)methyl]-2,3-dihydro-1H-isoindol-1-one |
| 348 | (*isolated as a single isomer at the position shown) | (3R)-3-(4-chlorophenyl)-2-[(5-chloropyrimidin-2-yl)methyl]-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one<br>Ex. 348 is the slower eluting isomer |

| Ex. | Structure | Name |
|---|---|---|
| 349 | 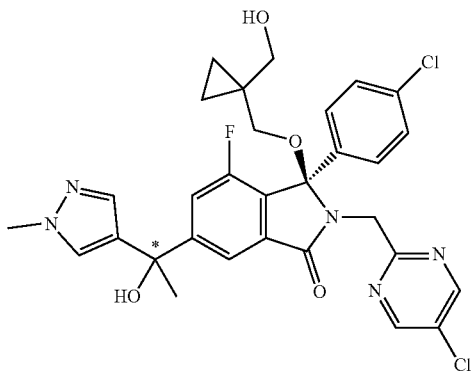 (*isolated as a single isomer at the position shown) | (3R)-3-(4-chlorophenyl)-2-[(5-chloropyrimidin-2-yl)methyl]-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one<br>Ex. 349 is the faster eluting isomer |
| 350 | 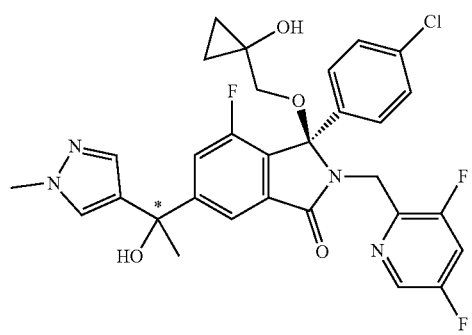 (*isolated as a single isomer at the position shown) | (3R)-3-(4-chlorophenyl)-2-[(3,5-difluoropyridin-2-yl)methyl]-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one<br>Ex. 350 is the slower eluting isomer |
| 351 | 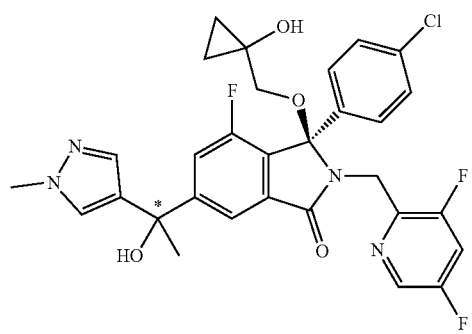 (*isolated as a single isomer at the position shown) | (3R)-3-(4-chlorophenyl)-2-[(3,5-difluoropyridin-2-yl)methyl]-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one<br>Ex. 351 is the faster eluting isomer |

| Ex. | Structure | Name |
|---|---|---|
| 352 | 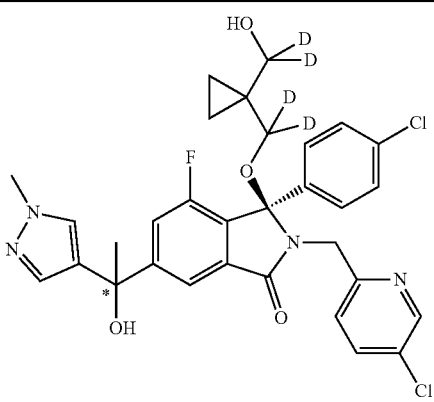 (*isolated as a single isomer at the position shown) | 6-{[(1R)-1-(4-chlorophenyl)-7-fluoro-1-({1-[hydroxy($^2H_2$)methyl]cyclopropyl}($^2H_2$)methoxy)-5-[1-hydroxy-1-(1-methyl-1H-pyrazol-4-yl)ethyl]-3-oxo-2,3-dihydro-1H-isoindol-2-yl]methyl}pyridine-3-carbonitrile<br>Ex. 352 is the faster eluting isomer |
| 353 | 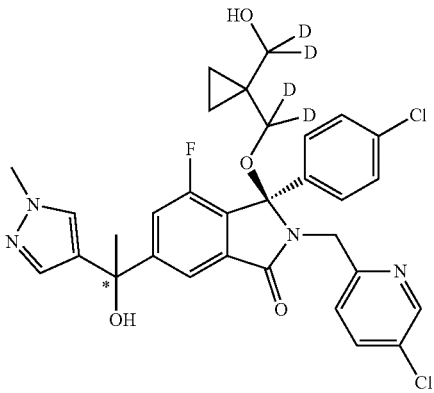 (*isolated as a single isomer at the position shown) | 6-{[(1R)-1-(4-chlorophenyl)-7-fluoro-1-({1-[hydroxy($^2H_2$)methyl]cyclopropyl}($^2H_2$)methoxy)-5-[1-hydroxy-1-(1-methyl-1H-pyrazol-4-yl)ethyl]-3-oxo-2,3-dihydro-1H-isoindol-2-yl]methyl}pyridine-3-carbonitrile<br>Ex. 353 is the slower eluting isomer |
| 354 | 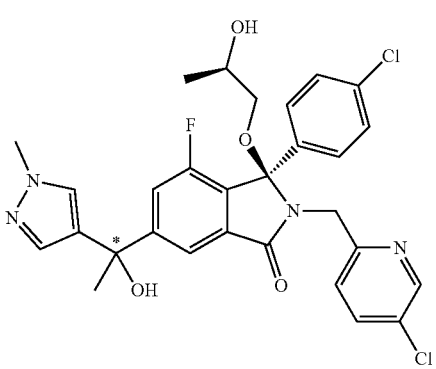 (*isolated as a single isomer at the position shown) | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(2R)-2-hydroxypropoxy]-2,3-dihydro-1H-isoindol-1-one<br>Ex. 354 is the faster eluting isomer |

| Ex. | Structure | Name |
|---|---|---|
| 355 | 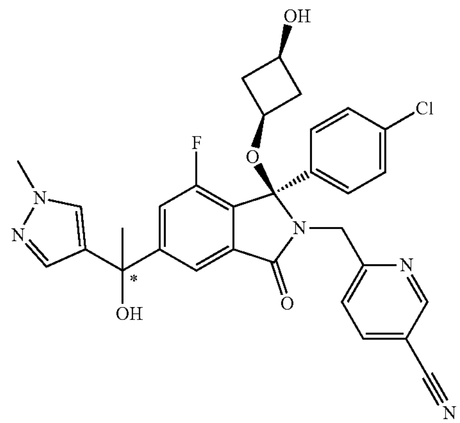 | 6-{[1-(4-chlorophenyl)-7-fluoro-5-[1-hydroxy-1-(1-methyl-1H-pyrazol-4-yl)ethyl]-3-oxo-1-[cis-3-hydroxycyclobutoxy]-2,3-dihydro-1H-isoindol-2-yl]methyl}pyridine-3-carbonitrile<br>Ex. 355 is the faster eluting isomer |
| 356 | 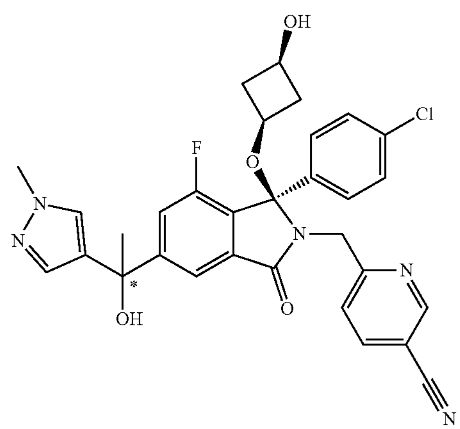 | 6-{[1-(4-chlorophenyl)-7-fluoro-5-[1-hydroxy-1-(1-methyl-1H-pyrazol-4-yl)ethyl]-3-oxo-1-[cis-3-hydroxycyclobutoxy]-2,3-dihydro-1H-isoindol-2-yl]methyl}pyridine-3-carbonitrile<br>Ex. 356 is the slower eluting isomer |
| 357 | 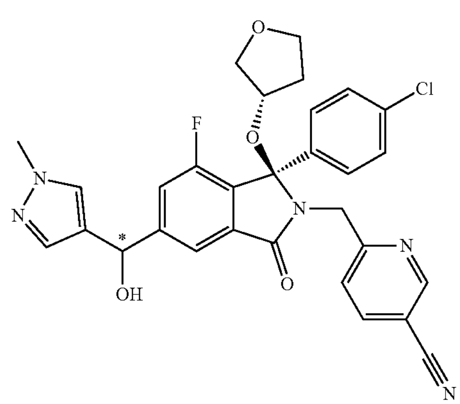 | 6-{[(1R)-1-(4-chlorophenyl)-7-fluoro-5-[hydroxy(1-methyl-1H-pyrazol-4-yl)methyl]-3-oxo-1-[(3S)-oxolan-3-yloxy]-2,3-dihydro-1H-isoindol-2-yl]methyl}pyridine-3-carbonitrile<br>Ex. 357 is the slower eluting isomer |

| Ex. | Structure | Name |
|---|---|---|
| 358 | 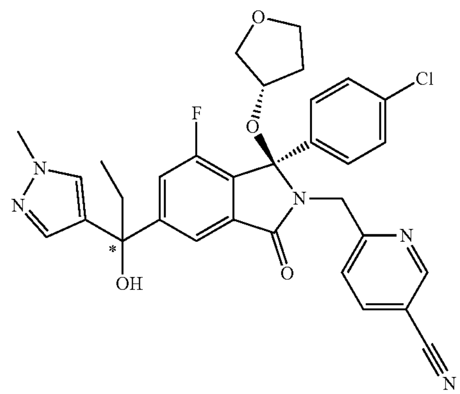 | 6-{[(1R)-1-(4-chlorophenyl)-7-fluoro-5-[1-hydroxy-1-(1-methyl-1H-pyrazol-4-yl)propyl]-3-oxo-1-[(3S)-oxolan-3-yloxy]-2,3-dihydro-1H-isoindol-2-yl]methyl}pyridine-3-carbonitrile<br>Ex. 358 is the slower eluting isomer |
| 359 | 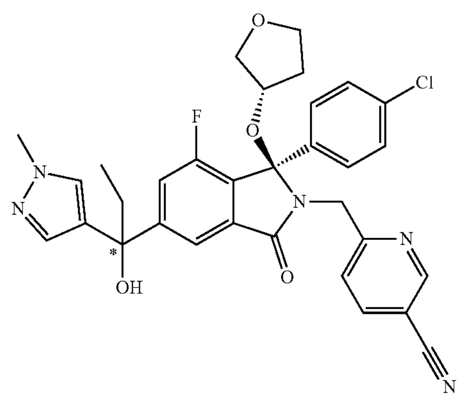 | 6-{[(1R)-1-(4-chlorophenyl)-7-fluoro-5-[1-hydroxy-1-(1-methyl-1H-pyrazol-4-yl)propyl]-3-oxo-1-[(3S)-oxolan-3-yloxy]-2,3-dihydro-1H-isoindol-2-yl]methyl}pyridine-3-carbonitrile<br>Ex. 359 is the faster eluting isomer |
| 360 | 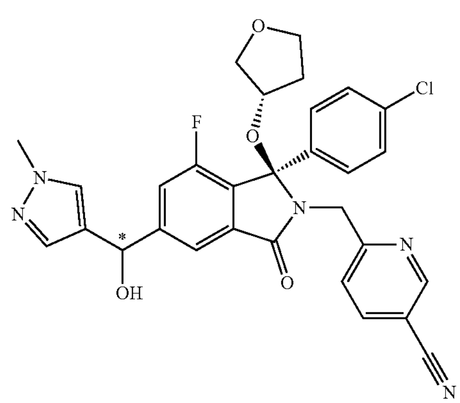 | 6-{[(1R)-1-(4-chlorophenyl)-7-fluoro-5-[hydroxy(1-methyl-1H-pyrazol-4-yl)methyl]-3-oxo-1-[(3S)-oxolan-3-yloxy]-2,3-dihydro-1H-isoindol-2-yl]methyl}pyridine-3-carbonitrile<br>Ex. 360 is the faster eluting isomer |

| Ex. | Structure | Name |
|---|---|---|
| 361 | 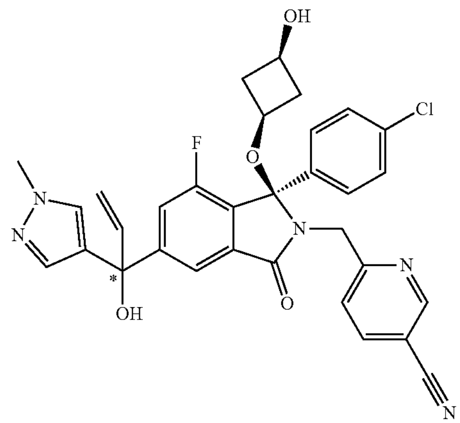 | 6-{[(1R)-1-(4-chlorophenyl)-7-fluoro-5-[1-hydroxy-1-(1-methyl-1H-pyrazol-4-yl)prop-2-en-1-yl]-3-oxo-1-[cis-3-hydroxycyclobutoxy]-2,3-dihydro-1H-isoindol-2-yl]methyl}pyridine-3-carbonitrile<br>Ex. 361 is the slower eluting isomer |
| 362 | 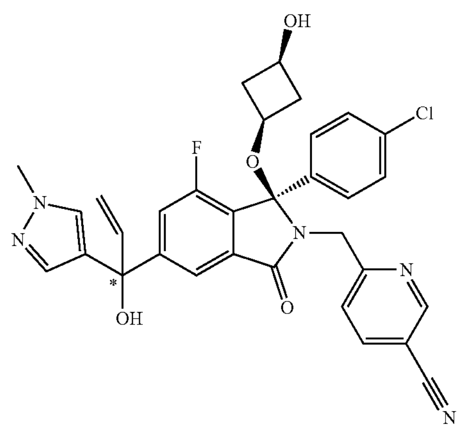 | 6-{[(1R)-1-(4-chlorophenyl)-7-fluoro-5-[1-hydroxy-1-(1-methyl-1H-pyrazol-4-yl)prop-2-en-1-yl]-3-oxo-1-[cis-3-hydroxycyclobutoxy]-2,3-dihydro-1H-isoindol-2-yl]methyl}pyridine-3-carbonitrile<br>Ex. 362 is the faster eluting isomer |
| 363 | 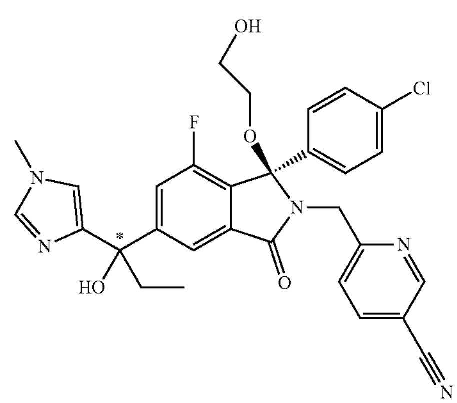 | 6-{[(1R)-1-(4-chlorophenyl)-7-fluoro-5-[1-hydroxy-1-(1-methyl-1H-imidazol-4-yl)propyl]-1-(2-hydroxyethoxy)-3-oxo-2,3-dihydro-1H-isoindol-2-yl]methyl}pyridine-3-carbonitrile |

| Ex. | Structure | Name |
|---|---|---|
| 364 | (*isolated as a single isomer at the position shown) | 6-{[(1R)-1-(4-chlorophenyl)-7-fluoro-5-[1-hydroxy-1-(1-methyl-1H-imidazol-4-yl)propyl]-1-(2-hydroxyethoxy)-3-oxo-2,3-dihydro-1H-isoindol-2-yl]methyl}pyridine-3-carbonitrile |
| 365 | (*isolated as a single isomer at the position shown) | 6-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyridine-3-carbonitrile |
| 366 | (*isolated as a single isomer at the position shown) | 6-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyridine-3-carbonitrile |

-continued

| Ex. | Structure | Name |
|---|---|---|
| 367 | 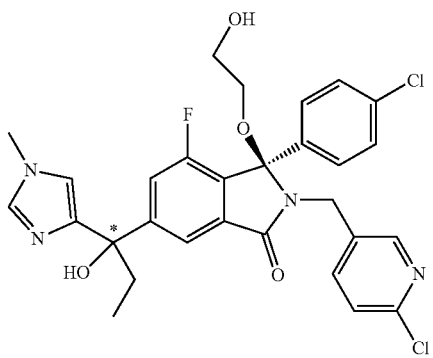 (*isolated as a single isomer at the position shown) | (3R)-3-(4-chlorophenyl)-2-[(6-chloropyridin-3-yl)methyl]-4-fluoro-6-[1-hydroxy-1-(1-methyl-1H-imidazol-4-yl)propyl]-3-(2-hydroxyethoxy)-2,3-dihydro-1H-isoindol-1-one |
| 368 | 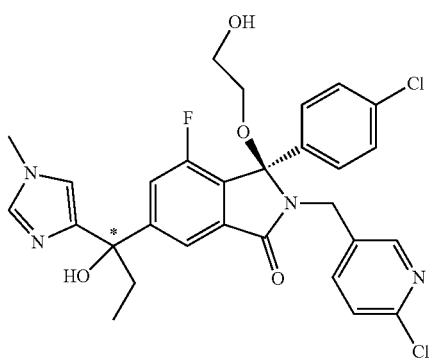 (*isolated as a single isomer at the position shown) | (3R)-3-(4-chlorophenyl)-2-[(6-chloropyridin-3-yl)methyl]-4-fluoro-6-[1-hydroxy-1-(1-methyl-1H-imidazol-4-yl)propyl]-3-(2-hydroxyethoxy)-2,3-dihydro-1H-isoindol-1-one |
| 369 | 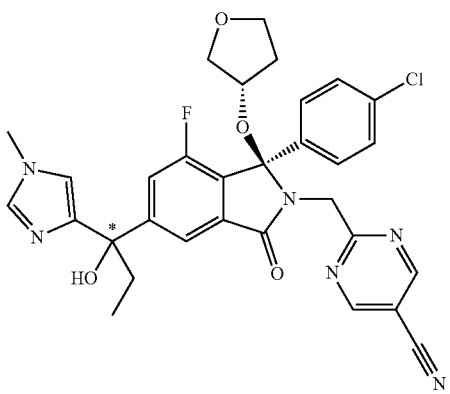 (*isolated as a single isomer at the position shown) | 2-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyrimidine-5-carbonitrile<br>Ex. 369 is the slower eluting isomer |

| Ex. | Structure | Name |
|---|---|---|
| 370 | (*isolated as a single isomer at the position shown) | 2-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyrimidine-5-carbonitrile<br>Ex. 370 is the faster eluting isomer |
| 371 | (*isolated as a single isomer at the position shown) | 6-{[(1R)-1-(4-chlorophenyl)-7-fluoro-3-oxo-1-[(3S)-oxolan-3-yloxy]-5-[2,2,2-trifluoro-1-hydroxy-1-(1-methyl-1H-pyrazol-4-yl)ethyl]-2,3-dihydro-1H-isoindol-2-yl]methyl}pyridine-3-carbonitrile |
| 372 | (*isolated as a single isomer at the position shown) | (3R)-2-[(5-chloro-3-methanesulfonylpyridin-2-yl)methyl]-3-(4-chlorophenyl)-4-fluoro-6-[1-hydroxy-1-(1-methyl-1H-pyrazol-4-yl)ethyl]-3-methoxy-2,3-dihydro-1H-isoindol-1-one |

| Ex. | Structure | Name |
|---|---|---|
| 373 | 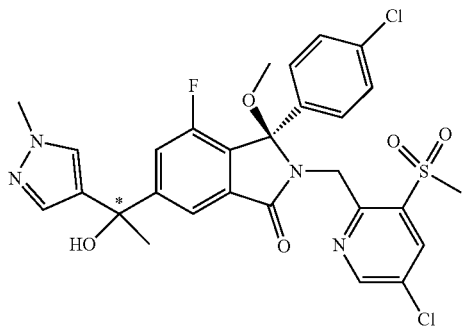<br>(*isolated as a single isomer at the position shown) | (3R)-2-[(5-chloro-3-methanesulfonylpyridin-2-yl)methyl]-3-(4-chlorophenyl)-4-fluoro-6-[1-hydroxy-1-(1-methyl-1H-pyrazol-4-yl)ethyl]-3-methoxy-2,3-dihydro-1H-isoindol-1-one |
| 374 and 375 | 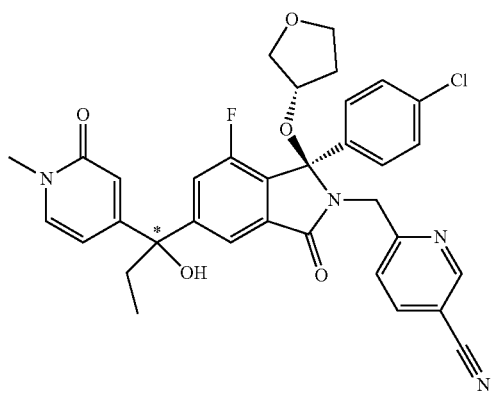<br>(*both isomers separated and isolated) | 6-{[(1R)-1-(4-chlorophenyl)-7-fluoro-5-[1-hydroxy-1-(1-methyl-2-oxo-1,2-dihydropyridin-4-yl)propyl]-3-oxo-1-[(3S)-oxolan-3-yloxy]-2,3-dihydro-1H-isoindol-2-yl]methyl}pyridine-3-carbonitrile |
| 376 | 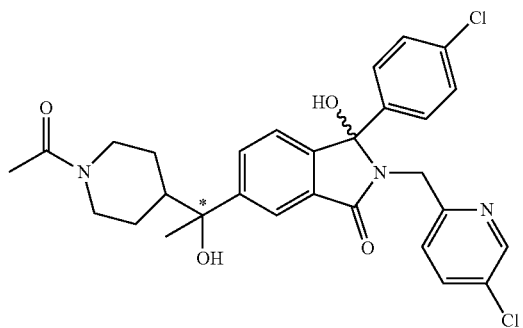<br>(*single configuration at position shown*. Mixture of epimers at the 3-position) | 6-[1-(1-Acetylpiperidin-4-yl)-1-hydroxyethyl]-3-(4-chlorophenyl)-2-[(5-chloropyridin-2-yl)methyl]-4-fluoro-3-hydroxy-2,3-dihydro-1H-isoindol-1-one |

-continued

| Ex. | Structure | Name |
|---|---|---|
| 377 and 378 | 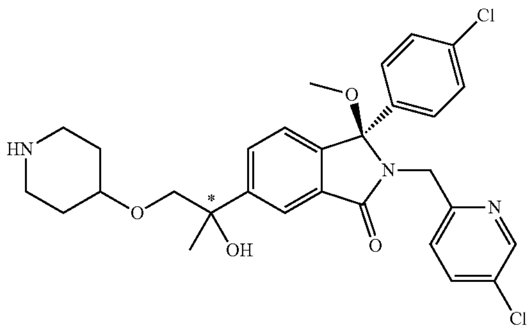 | (3R)-3-(4-chlorophenyl)-2-[(5-chloropyridin-2-yl)methyl]-6-[2-hydroxy-1-(piperidin-4-yloxy)propan-2-yl]-3-methoxy-2,3-dihydro-1H-isoindol-1-one<br>Ex. 377 is the faster eluting isomer<br>Ex. 378 is the slower eluting isomer<br>(*both isomers separated and isolated) |
| 379 | 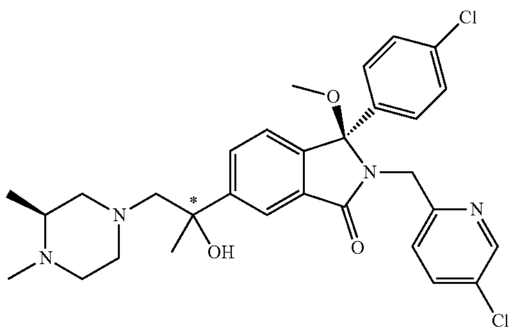 | (3R)-3-(4-chlorophenyl)-2-[(5-chloropyridin-2-yl)methyl]-6-{1-[(3S)-3,4-dimethylpiperazin-1-yl]-2-hydroxypropan-2-yl}-3-methoxy-2,3-dihydro-1H-isoindol-1-one<br>(*isolated as a single isomer at the position shown) |
| 380 | 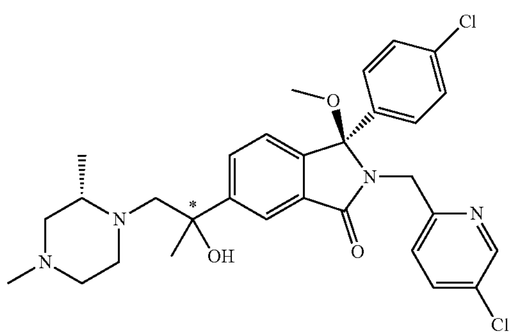 | (3R)-3-(4-chlorophenyl)-2-[(5-chloropyridin-2-yl)methyl]-6-{1-[(2S)-2,4-dimethylpiperazin-1-yl]-2-hydroxypropan-2-yl}-3-methoxy-2,3-dihydro-1H-isoindol-1-one<br>(*isolated as a single isomer at the position shown) |
| 381 | 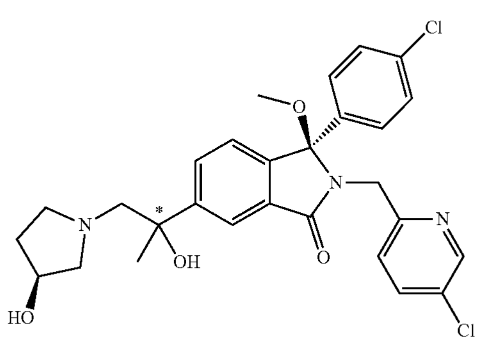 | (3R)-3-(4-chlorophenyl)-2-[(5-chloropyridin-2-yl)methyl]-6-{2-hydroxy-1-[(3S)-3-hydroxypyrrolidin-1-yl]propan-2-yl}-3-methoxy-2,3-dihydro-1H-isoindol-1-one<br>(*isolated as a single isomer at the position shown) |

-continued

| Ex. | Structure | Name |
|---|---|---|
| 382 | (*isolated as a single isomer at the position shown) | (3R)-3-(4-chlorophenyl)-2-[(5-chloropyridin-2-yl)methyl]-6-{2-hydroxy-1-[(3S)-3-hydroxypyrrolidin-1-yl]propan-2-yl}-3-methoxy-2,3-dihydro-1H-isoindol-1-one |
| 383 | (*isolated as a single isomer at the position shown) | (3R)-3-(4-chlorophenyl)-2-[(5-chloropyridin-2-yl)methyl]-6-{2-hydroxy-1-[(3R)-3-hydroxypyrrolidin-1-yl]propan-2-yl}-3-methoxy-2,3-dihydro-1H-isoindol-1-one |
| 384 | (*isolated as a single isomer at the position shown) | (3R)-3-(4-chlorophenyl)-2-[(5-chloropyridin-2-yl)methyl]-6-{2-hydroxy-1-[(3R)-3-hydroxypyrrolidin-1-yl]propan-2-yl}-3-methoxy-2,3-dihydro-1H-isoindol-1-one |
| 385 | (*isolated as a single isomer at the position shown) | (3R)-3-(4-chlorophenyl)-2-[(5-chloropyrimidin-2-yl)methyl]-4-fluoro-6-[1-(4-fluorooxan-4-yl)-1-hydroxyethyl]-3-[(1-hydroxycyclopropyl)methoxy]-2,3-dihydro-1H-isoindol-1-one |

| Ex. | Structure | Name |
|---|---|---|
| 386 | 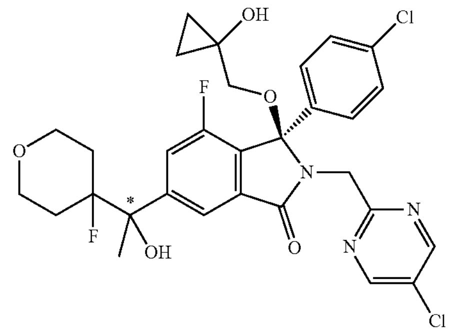 | (3R)-3-(4-chlorophenyl)-2-[(5-chloropyrimidin-2-yl)methyl]-4-fluoro-6-[1-(4-fluorooxan-4-yl)-1-hydroxyethyl]-3-[(1-hydroxycyclopropyl)methoxy]-2,3-dihydro-1H-isoindol-1-one |
| | (*isolated as a single isomer at the position shown) | |
| 387 | 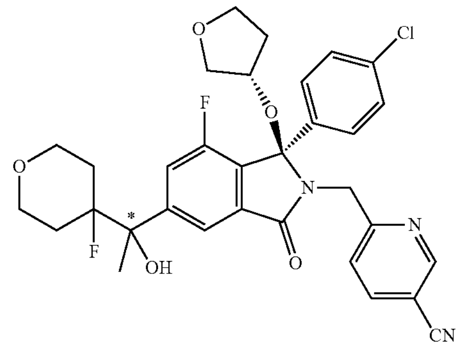 | 6-{[(1R)-1-(4-chlorophenyl)-7-fluoro-5-[1-(4-fluorooxan-4-yl)-1-hydroxyethyl]-3-oxo-1-[(3S)-oxolan-3-yloxy]-2,3-dihydro-1H-isoindol-2-yl]methyl}pyridine-3-carbonitrile |
| | (*isolated as a single isomer at the position shown) | |
| 388 | 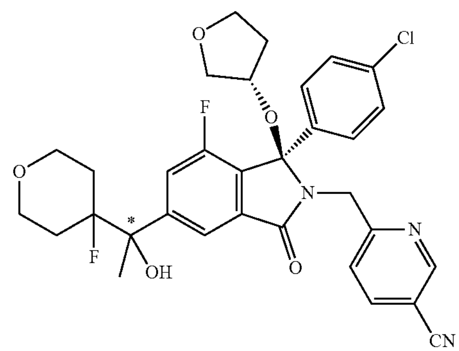 | 6-{[(1R)-1-(4-chlorophenyl)-7-fluoro-5-[1-(4-fluorooxan-4-yl)-1-hydroxyethyl]-3-oxo-1-[(3S)-oxolan-3-yloxy]-2,3-dihydro-1H-isoindol-2-yl]methyl}pyridine-3-carbonitrile |
| | (*isolated as a single isomer at the position shown) | |
| 389 and 390 | 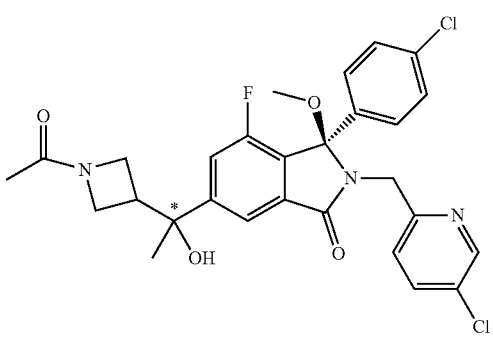 | (3R)-6-[1-(1-acetylazetidin-3-yl)-1-hydroxyethyl]-3-(4-chlorophenyl)-2-[(5-chloropyridin-2-yl)methyl]-4-fluoro-3-methoxy-2,3-dihydro-1H-isoindol-1-one |
| | (*examples were isolated as a single isomers) | |

| Ex. | Structure | Name |
|---|---|---|
| 391 and 392 | 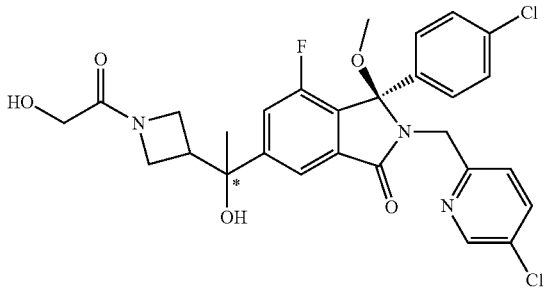 (*examples were isolated as single isomers) | (3R)-3-(4-chlorophenyl)-2-[(5-chloropyridin-2-yl)methyl]-4-fluoro-6-{1-hydroxy-1-[1-(2-hydroxyacetyl)azetidin-3-yl]ethyl}-3-methoxy-2,3-dihydro-1H-isoindol-1-one |
| 393 and 394 | 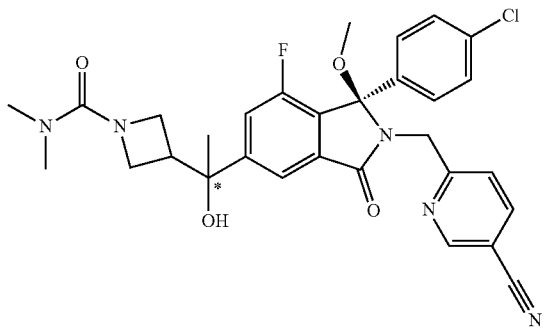 (*examples were isolated as single isomers) | 3-{1-[(1R)-1-(4-chlorophenyl)-2-[(5-cyanopyridin-2-yl)methyl]-7-fluoro-1-methoxy-3-oxo-2,3-dihydro-1H-isoindol-5-yl]-1-hydroxyethyl}-N,N-dimethylazetidine-1-carboxamide |
| 395 and 396 | 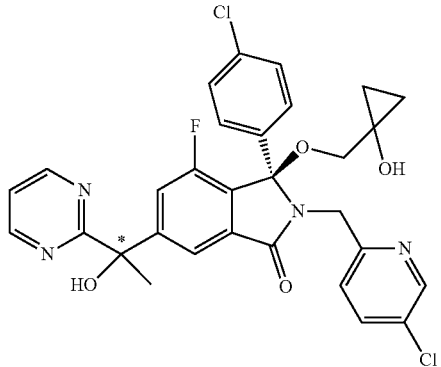 (*both isomers separated and isolated) | (3R)-3-(4-chlorophenyl)-2-[(5-chloropyridin-2-yl)methyl]-4-fluoro-6-[1-hydroxy-1-(pyrimidin-2-yl)ethyl]-3-[(1-hydroxycyclopropyl)methoxy]-2,3-dihydro-1H-isoindol-1-one<br>Ex. 395 is the slower eluting isomer<br>Ex. 396 is the faster eluting isomer |

| Ex. | Structure | Name |
|---|---|---|
| 397 and 398 | 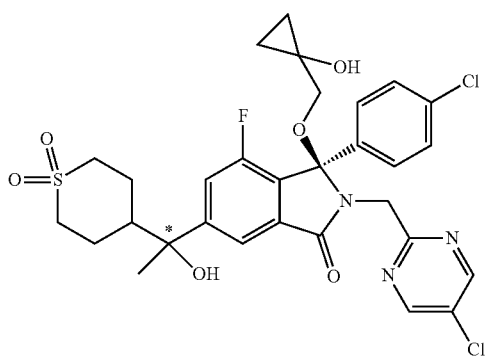 (*both isomers separated and isolated) | 4-{1-[(1R)-1-(4-chlorophenyl)-2-[(5-chloropyrimidin-2-yl)methyl]-7-fluoro-1-[(1-hydroxycyclopropyl)methoxy]-3-oxo-2,3-dihydro-1H-isoindol-5-yl]-1-hydroxyethyl}-1λ6-thiane-1,1-dione Ex. 397 is the slower eluting isomer Ex. 398 is the faster eluting isomer |
| 399 and 400 | 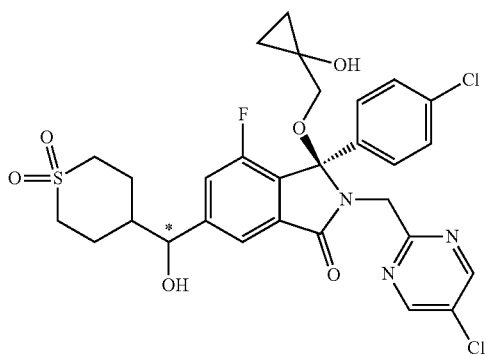 (*both isomers separated and isolated) | 4-{[(1R)-1-(4-chlorophenyl)-2-[(5-chloropyrimidin-2-yl)methyl]-7-fluoro-1-[(1-hydroxycyclopropyl)methoxy]-3-oxo-2,3-dihydro-1H-isoindol-5-yl](hydroxy)methyl}-1λ6-thiane-1,1-dione |
| 401 and 402 | 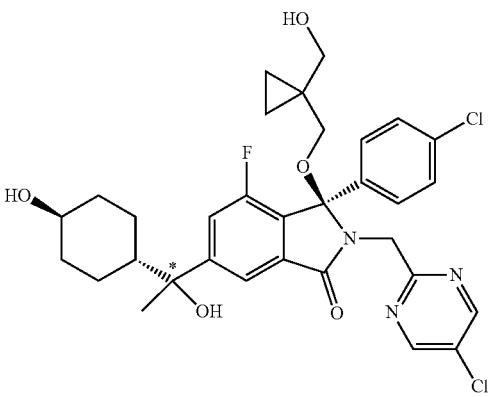 (*both isomers separated and isolated) | (3R)-3-(4-chlorophenyl)-2-[(5-chloropyrimidin-2-yl)methyl]-4-fluoro-6-{1-hydroxy-1-[trans-4-hydroxycyclohexyl]ethyl}-3-{[1-(hydroxymethyl)cyclopropyl]methoxy}-2,3-dihydro-1H-isoindol-1-one |

-continued

| Ex. | Structure | Name |
|---|---|---|
| 403 and 404 | (*both isomers separated and isolated) | 1-({[(1R)-1-(4-chlorophenyl)-2-[(5-chloropyrimidin-2-yl)methyl]-5-(1-cyclobutyl-1-hydroxyethyl)-7-fluoro-3-oxo-2,3-dihydro-1H-isoindol-1-yl]oxy}methyl)cyclopropane-1-carboxamide<br>Ex. 403 is the slower eluting isomer<br>Ex. 404 is the faster eluting isomer |
| 405 and 406 | (*both isomers separated and isolated) | 6-{[(1R)-1-(4-chlorophenyl)-5-(1-cyclobutyl-1-hydroxyethyl)-7-fluoro-1-(2-hydroxyethoxy)-3-oxo-2,3-dihydro-1H-isoindol-2-yl]methyl}pyridine-3-carbonitrile<br>Ex. 405 is the slower eluting isomer<br>Ex. 406 is the faster eluting isomer |
| 407 | (*isolated as a single isomer at the position shown) | (3R)-2-[(5-chloro-1-oxo-1λ⁵-pyridin-2-yl)methyl]-3-(4-chlorophenyl)-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one |

| Ex. | Structure | Name |
|---|---|---|
| 408 | 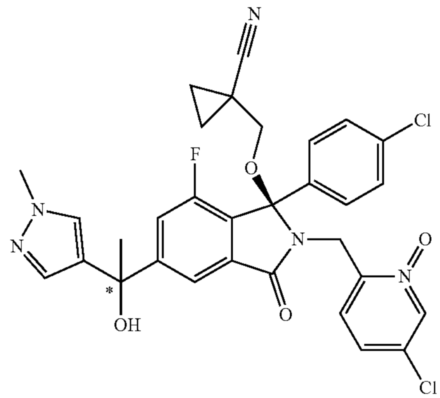 | 1-({[(1R)-2-[(5-chloro-1-oxo-1λ$^5$-pyridin-2-yl)methyl]-1-(4-chlorophenyl)-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carbonitrile |
| | (*isolated as a single isomer at the position shown) | |
| 409 | 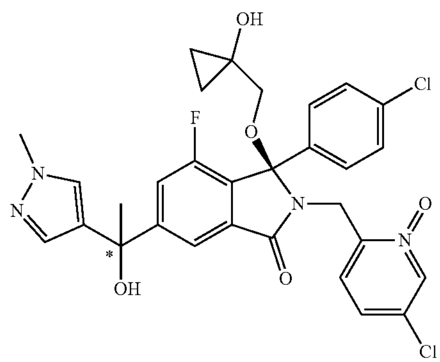 | (3R)-2-[(5-chloro-1-oxo-1λ$^5$-pyridin-2-yl)methyl]-3-(4-chlorophenyl)-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one |
| | (*isolated as a single isomer at the position shown) | |
| 410 | 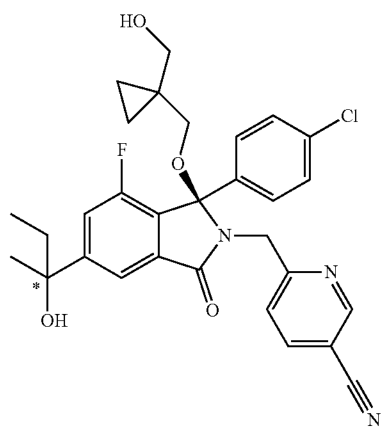 | 6-{[(1R)-1-(4-chlorophenyl)-7-fluoro-5-(2-hydroxybutan-2-yl)-1-{[1-(hydroxymethyl)cyclopropyl]methoxy}-3-oxo-2,3-dihydro-1H-isoindol-2-yl]methyl}pyridine-3-carbonitrile |
| | (*isolated as a single isomer at the position shown) | |

| Ex. | Structure | Name |
|---|---|---|
| 411 | 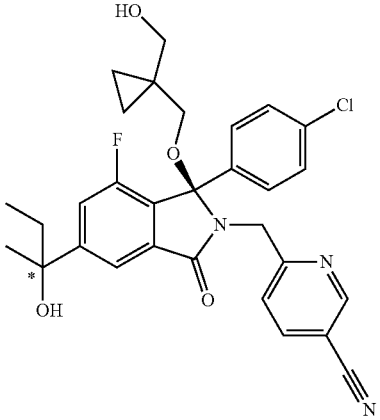<br>(*isolated as a single isomer at the position shown) | 6-{[(1R)-1-(4-chlorophenyl)-7-fluoro-5-(2-hydroxybutan-2-yl)-1-{[1-(hydroxymethyl)cyclopropyl]methoxy}-3-oxo-2,3-dihydro-1H-isoindol-2-yl]methyl}pyridine-3-carbonitrile |
| 412 | 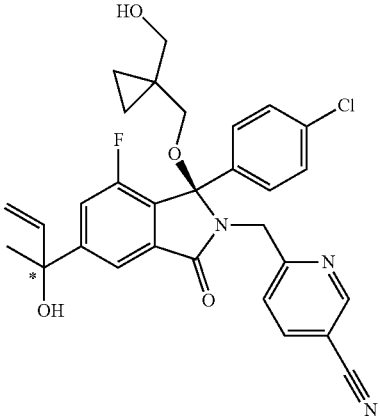<br>(*isolated as a single isomer at the position shown) | 6-{[(1R)-1-(4-Chlorophenyl)-7-fluoro-5-(2-hydroxybut-3-en-2-yl)-1-{[1-(hydroxymethyl)cyclopropyl]methoxy}-3-oxo-2,3-dihydro-1H-isoindol-2-yl]methyl}pyridine-3-carbonitrile |
| 413 | 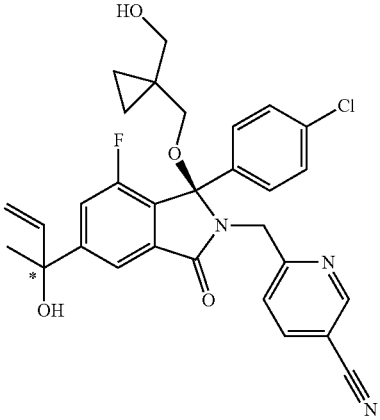<br>(*isolated as a single isomer at the position shown) | 6-{[(1R)-1-(4-Chlorophenyl)-7-fluoro-5-(2-hydroxybut-3-en-2-yl)-1-{[1-(hydroxymethyl)cyclopropyl]methoxy}-3-oxo-2,3-dihydro-1H-isoindol-2-yl]methyl}pyridine-3-carbonitrile |

| Ex. | Structure | Name |
|---|---|---|
| 414 | 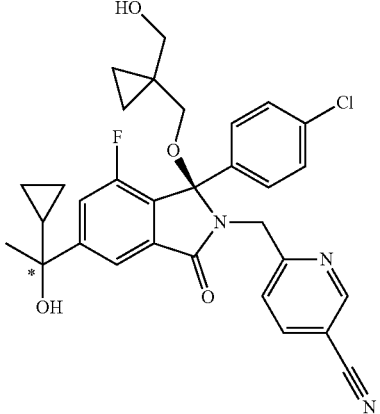 (*isolated as a single isomer at the position shown) | 6-{[(1R)-1-(4-Chlorophenyl)-5-(1-cyclopropyl-1-hydroxyethyl)-7-fluoro-1-{[1-(hydroxymethyl)cyclopropyl]methoxy}-3-oxo-2,3-dihydro-1H-isoindol-2-yl]methyl}pyridine-3-carbonitrile |
| 415 | 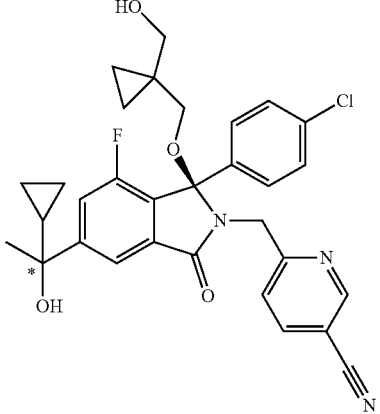 (*isolated as a single isomer at the position shown) | 6-{[(1R)-1-(4-Chlorophenyl)-5-(1-cyclopropyl-1-hydroxyethyl)-7-fluoro-1-{[1-(hydroxymethyl)cyclopropyl]methoxy}-3-oxo-2,3-dihydro-1H-isoindol-2-yl]methyl}pyridine-3-carbonitrile |
| 416 | 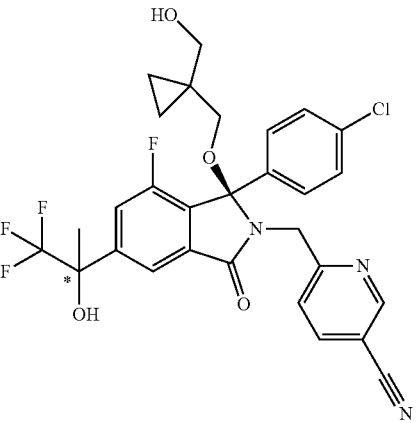 (*isolated as a single isomer at the position shown) | 6-{[(1R)-1-(4-chlorophenyl)-7-fluoro-1-{[1-(hydroxymethyl)cyclopropyl]methoxy}-3-oxo-5-(1,1,1-trifluoro-2-hydroxypropan-2-yl)-2,3-dihydro-1H-isoindol-2-yl]methyl}pyridine-3-carbonitrile |

| Ex. | Structure | Name |
|---|---|---|
| 417 | 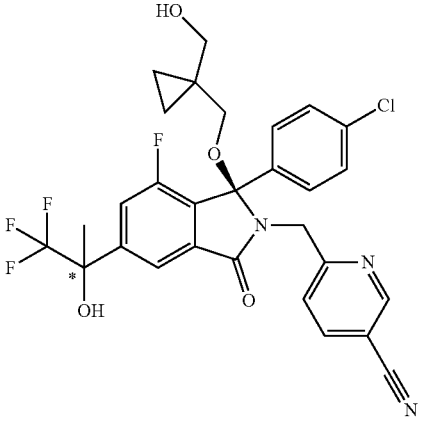 (*isolated as a single isomer at the position shown) | 6-{[(1R)-1-(4-chlorophenyl)-7-fluoro-1-{[1-(hydroxymethyl)cyclopropyl]methoxy}-3-oxo-5-(1,1,1-trifluoro-2-hydroxypropan-2-yl)-2,3-dihydro-1H-isoindol-2-yl]methyl}pyridine-3-carbonitrile |
| 418 | 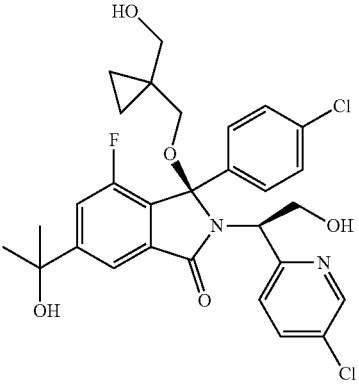 [SMILES: CC(C)(O)c1cc(F)c2c(c1)C(=O)N([C@@H](CO)c1ccc(Cl)cn1)[C@@]2(OCC1(CO)CC1)c1ccc(Cl)cc1] | (3R)-3-(4-Chlorophenyl)-2-[(1R)-1-(5-chloropyridin-2-yl)-2-hydroxyethyl]-4-fluoro-3-{[1-(hydroxymethyl)cyclopropyl]methoxy}-6-(2-hydroxypropan-2-yl)-2,3-dihydro-1H-isoindol-1-one |
| 419 | 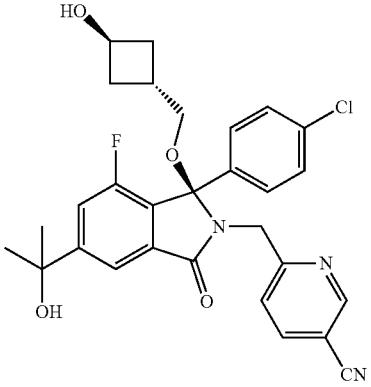 [SMILES: CC(C)(O)c1cc(F)c2c(c1)C(=O)N(Cc1ccc(C#N)cn1)[C@@]2(OC[C@H]1C[C@H](O)C1)c1ccc(Cl)cc1] | 6-{[(1R)-1-(4-chlorophenyl)-7-fluoro-5-(2-hydroxypropan-2-yl)-3-oxo-1-{[(trans-3-hydroxycyclobutyl]methoxy}-2,3-dihydro-1H-isoindol-2-yl]methyl}pyridine-3-carbonitrile |

| Ex. | Structure | Name |
|---|---|---|
| 420 | 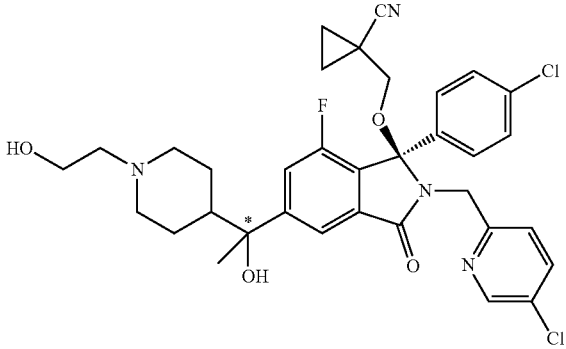<br>(example isolated as a single isomer at the position shown*) | 1-({[(1R)-1-(4-chlorophenyl)-2-[(5-pchloropyridin-2-yl)methyl]-7-fluoro-5-{1-hydroxy-1-[1-(2-hydroxyethyl)piperidin-4-yl]ethyl}-3-oxo-2,3-dihydro-1H-isoindol-1-yl]oxy}methyl)cyclopropane-1-carbonitrile |
| 421 | 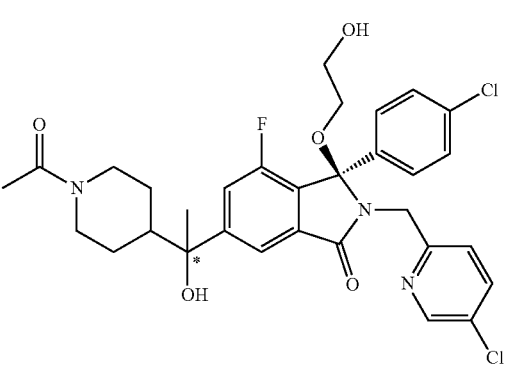<br>(example isolated as a single isomer at the position shown*) | (3R)-6-[1-(1-acetylpiperidin-4-yl)-1-hydroxyethyl]-3-(4-chlorophenyl)-2-[(5-chloropyridin-2-yl)methyl]-4-fluoro-3-(2-hydroxyethoxy)-2,3-dihydro-1H-isoindol-1-one |
| 422 | 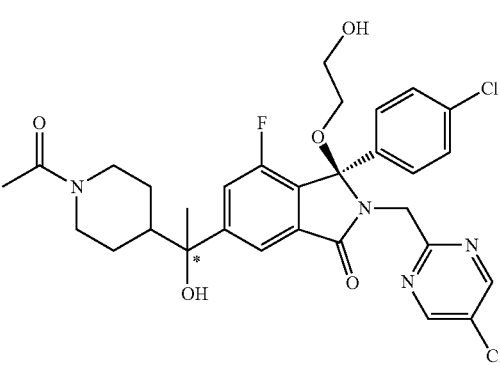<br>(example isolated as a single isomer at the position shown*) | (3R)-6-[1-(1-acetylpiperidin-4-yl)-1-hydroxyethyl]-3-(4-chlorophenyl)-2-[(5-chloropyrimidin-2-yl)methyl]-4-fluoro-3-(2-hydroxyethoxy)-2,3-dihydro-1H-isoindol-1-one |

| Ex. | Structure | Name |
|---|---|---|
| 423 | 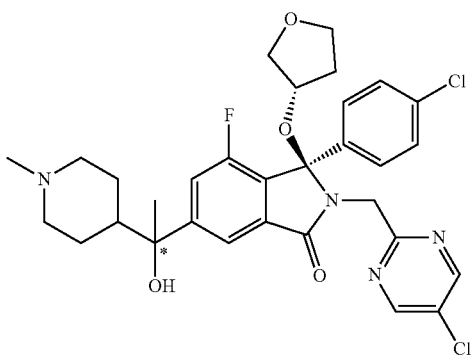 (example isolated as a single isomer at the position shown*) | (3R)-3-(4-chlorophenyl)-2-[(5-chloropyrimidin-2-yl)methyl]-4-fluoro-6-[1-hydroxy-1-(1-methylpiperidin-4-yl)ethyl]-3-[(3S)-oxolan-3-yloxy]-2,3-dihydro-1H-isoindol-1-one |
| 424 | 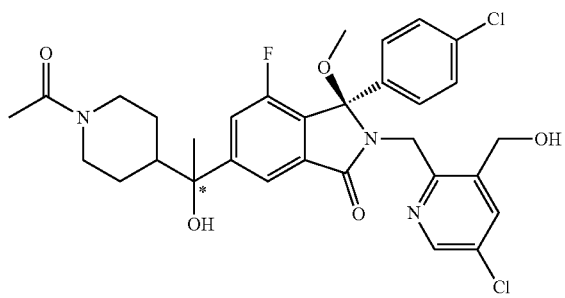 (example isolated as a single isomer at the position shown*) | (3R)-6-[1-(1-acetylpiperidin-4-yl)-1-hydroxyethyl]-2-{[5-chloro-3-(hydroxymethyl)pyridin-2-yl]methyl}-3-(4-chlorophenyl)-4-fluoro-3-methoxy-2,3-dihydro-1H-isoindol-1-one<br>Ex. 424 is the faster eluting isomer |
| 425 | 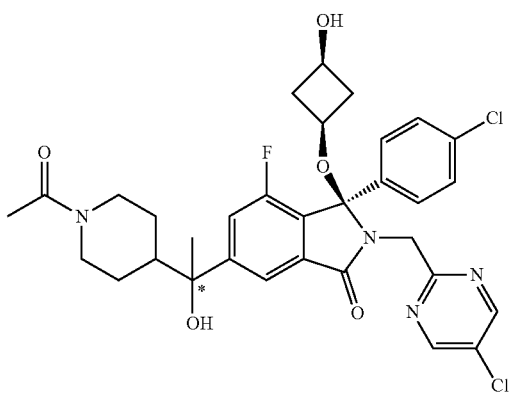 (example isolated as a single isomer at the position shown*) | (3R)-6-[1-(1-acetylpiperidin-4-yl)-1-hydroxyethyl]-3-(4-chlorophenyl)-2-[(5-chloropyrimidin-2-yl)methyl]-4-fluoro-3-[cis-3-hydroxycyclobutoxy]-2,3-dihydro-1H-isoindol-1-one<br>Ex. 425 is the slower eluting isomer |

| Ex. | Structure | Name |
|---|---|---|
| 426 | 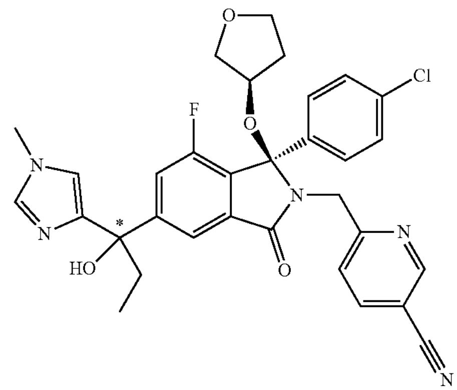 | 6-{[(1R)-1-(4-chlorophenyl)-7-fluoro-5-[1-hydroxy-1-(1-methyl-1H-imidazol-4-yl)propyl]-3-oxo-1-[(3R)-oxolan-3-yloxy]-2,3-dihydro-1H-isoindol-2-yl]methyl}pyridine-3-carbonitrile<br><br>(*isolated as a single isomer at the position shown) |
| 427 | 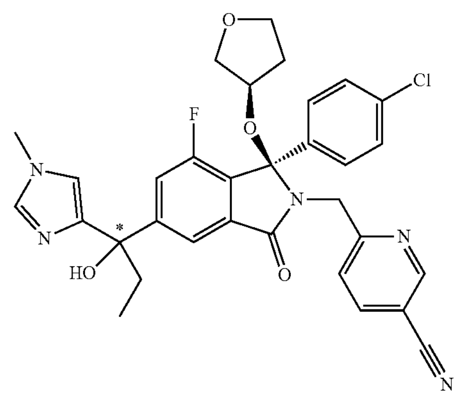 | 6-{[(1R)-1-(4-chlorophenyl)-7-fluoro-5-[1-hydroxy-1-(1-methyl-1H-imidazol-4-yl)propyl]-3-oxo-1-[(3R)-oxolan-3-yloxy]-2,3-dihydro-1H-isoindol-2-yl]methyl}pyridine-3-carbonitrile<br><br>(*isolated as a single isomer at the position shown) |
| 428 | 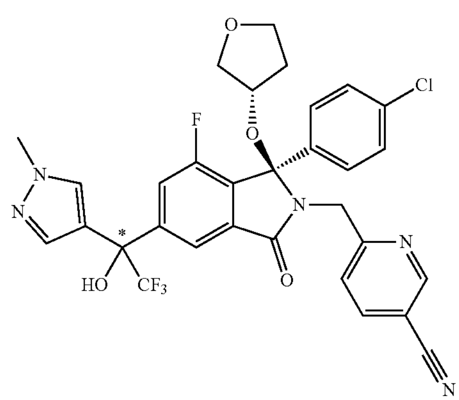 | 6-{[(1R)-1-(4-chlorophenyl)-7-fluoro-3-oxo-1-[(3S)-oxolan-3-yloxy]-5-[2,2,2-trifluoro-1-hydroxy-1-(1-methyl-1H-pyrazol-4-yl)ethyl]-2,3-dihydro-1H-isoindol-2-yl]methyl}pyridine-3-carbonitrile<br><br>(*isolated as a single isomer at the position shown) |

| Ex. | Structure | Name |
|---|---|---|
| 429 | 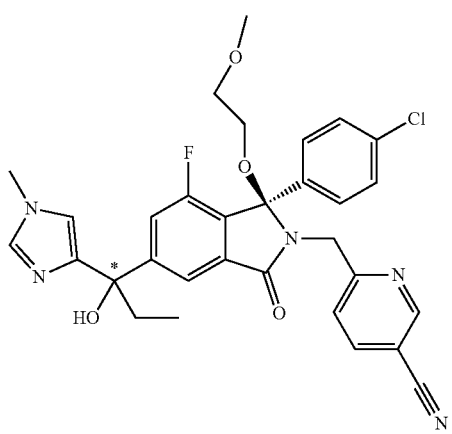 (*isolated as a single isomer at the position shown | 6-{[(1R)-1-(4-chlorophenyl)-7-fluoro-5-[1-hydroxy-1-(1-methyl-1H-imidazol-4-yl)propyl]-1-(2-methoxyethoxy)-3-oxo-2,3-dihydro-1H-isoindol-2-yl]methyl}pyridine-3-carbonitrile |
| 430 | 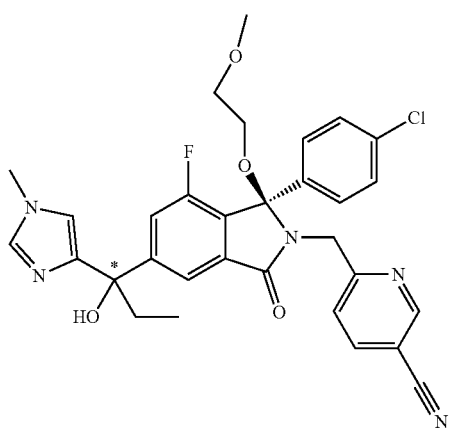 (*isolated as a single isomer at the position shown | 6-{[(1R)-1-(4-chlorophenyl)-7-fluoro-5-[1-hydroxy-1-(1-methyl-1H-imidazol-4-yl)propyl]-1-(2-methoxyethoxy)-3-oxo-2,3-dihydro-1H-isoindol-2-yl]methyl}pyridine-3-carbonitrile |
| 431 | 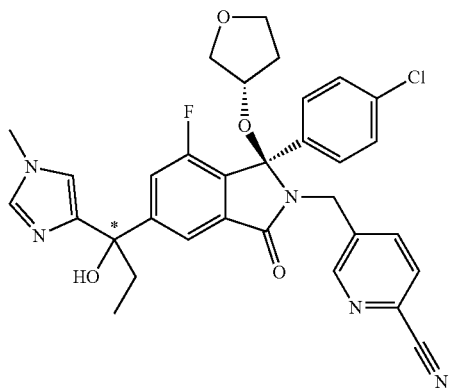 (*isolated as a single isomer at the position shown | 5-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyridine-2-carbonitrile |

| Ex. | Structure | Name |
|---|---|---|
| 432 | 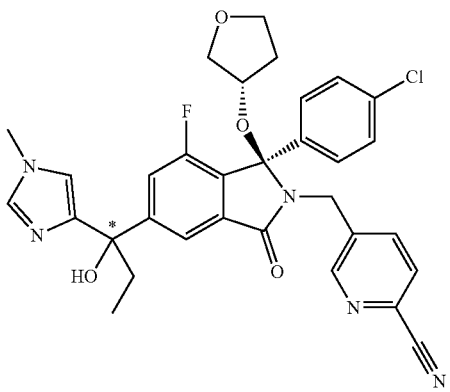<br>(*isolated as a single isomer at the position shown) | 5-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyridine-2-carbonitrile |
| 433 | 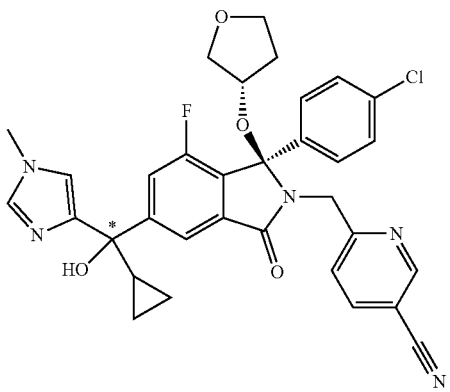<br>(*isolated as a single isomer at the position shown) | 6-{[(1R)-1-(4-chlorophenyl)-5-[cyclopropyl(hydroxy)(1-methyl-1H-imidazol-4-yl)methyl]-7-fluoro-3-oxo-1-[(3S)-oxolan-3-yloxy]-2,3-dihydro-1H-isoindol-2-yl]methyl}pyridine-3-carbonitrile |
| 434 | 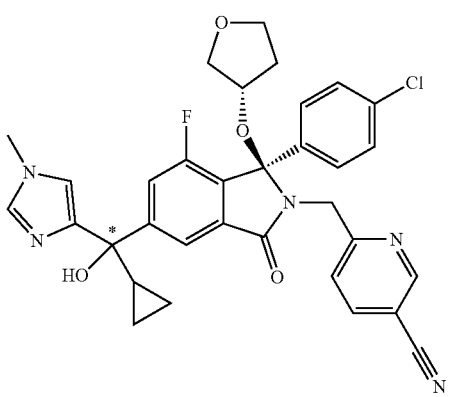<br>(*isolated as a single isomer at the position shown) | 6-{[(1R)-1-(4-chlorophenyl)-5-[cyclopropyl(hydroxy)(1-methyl-1H-imidazol-4-yl)methyl]-7-fluoro-3-oxo-1-[(3S)-oxolan-3-yloxy]-2,3-dihydro-1H-isoindol-2-yl]methyl}pyridine-3-carbonitrile |

| Ex. | Structure | Name |
|---|---|---|
| 435 | 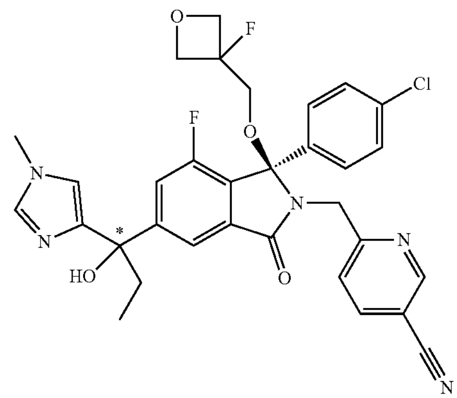 | 6-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl]methyl}pyridine-3-carbonitrile |
| | (*isolated as a single isomer at the position shown) | |
| 436 | 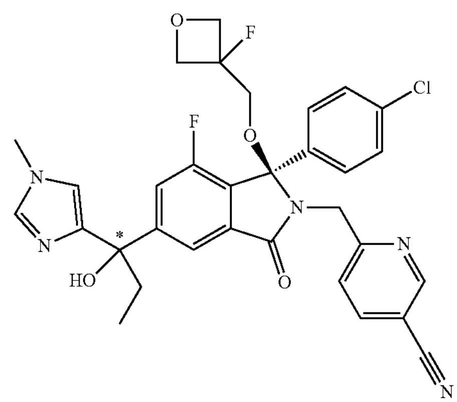 | 6-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl]methyl}pyridine-3-carbonitrile |
| | (*isolated as a single isomer at the position shown) | |
| 437 | 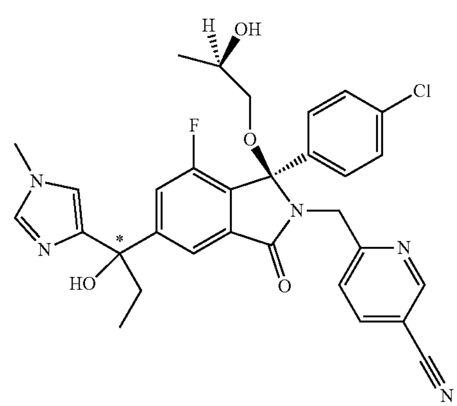 | 6-{[(1R)-1-(4-chlorophenyl)-7-fluoro-5-[1-hydroxy-1-(1-methyl-1H-imidazol-4-yl)propyl]-1-[(2R)-2-hydroxypropoxy]-3-oxo-2,3-dihydro-1H-isoindol-2-yl]methyl}pyridine-3-carbonitrile |
| | (*isolated as a single isomer at the position shown) | |

| Ex. | Structure | Name |
|---|---|---|
| 438 | 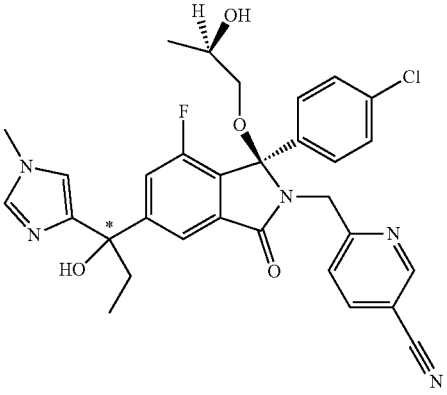 (*isolated as a single isomer at the position shown) | 6-{[(1R)-1-(4-chlorophenyl)-7-fluoro-5-[1-hydroxy-1-(1-methyl-1H-imidazol-4-yl)propyl]-1-[(2R)-2-hydroxypropoxy]-3-oxo-2,3-dihydro-1H-isoindol-2-yl]methyl}pyridine-3-carbonitrile |
| 439 | 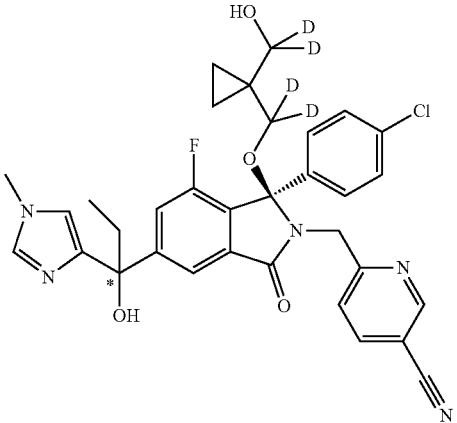 (*isolated as a single isomer at the position shown) | 6-{[(1R)-1-(4-chlorophenyl)-7-fluoro-1-({1-[hydroxy($^2$H$_2$)methyl]cyclopropyl}($^2$H$_2$)methoxy)-5-[1-hydroxy-1-(1-methyl-1H-imidazol-4-yl)propyl]-3-oxo-2,3-dihydro-1H-isoindol-2-yl]methyl}pyridine-3-carbonitrile |
| 440 | 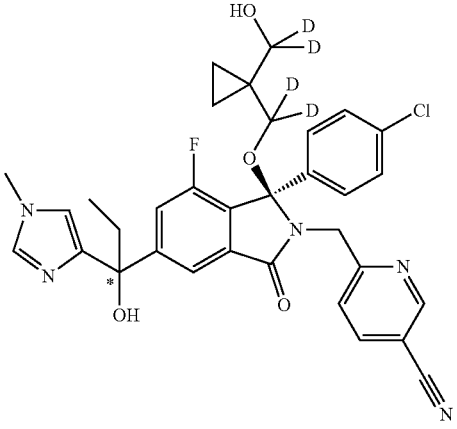 (*isolated as a single isomer at the position shown) | 6-{[(1R)-1-(4-chlorophenyl)-7-fluoro-1-({1-[hydroxy($^2$H$_2$)methyl]cyclopropyl}($^2$H$_2$)methoxy)-5-[1-hydroxy-1-(1-methyl-1H-imidazol-4-yl)propyl]-3-oxo-2,3-dihydro-1H-isoindol-2-yl]methyl}pyridine-3-carbonitrile |

| Ex. | Structure | Name |
|---|---|---|
| 441 and 442 | 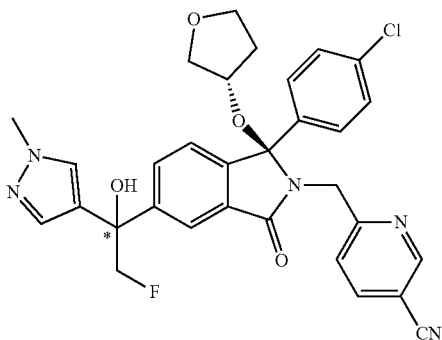 (*both isomers separated and isolated) | 6-{[(1R)-1-(4-Chlorophenyl)-7-fluoro-5-[2-fluoro-1-hydroxy-1-(1-methyl-1H-pyrazol-4-yl)ethyl]-3-oxo-1-[(3S)-oxolan-3-yloxy]-2,3-dihydro-1H-isoindol-2-yl]methyl}pyridine-3-carbonitrile |
| 443 and 444 | 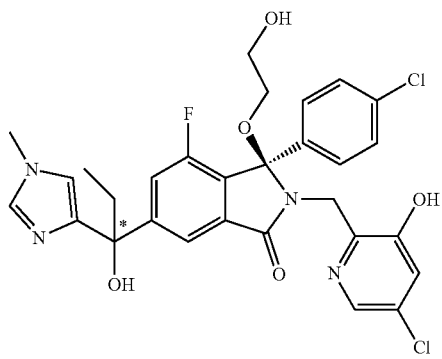 (*both isomers separated and isolated) | (3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one |
| 445 | 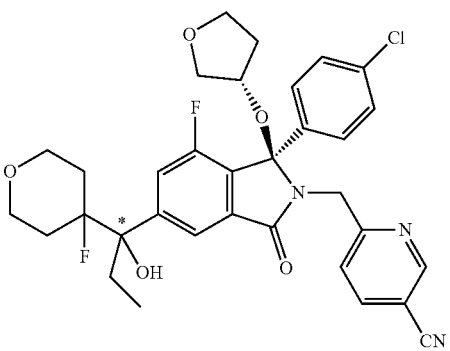 (*isolated as a single isomer at the position shown) | 6-{[(1R)-1-(4-chlorophenyl)-7-fluoro-5-[1-(4-fluorooxan-4-yl)-1-hydroxypropyl]-3-oxo-1-[(3S)-oxolan-3-yloxy]-2,3-dihydro-1H-isoindol-2-yl]methyl}pyridine-3-carbonitrile |

| Ex. | Structure | Name |
|---|---|---|
| 446 | 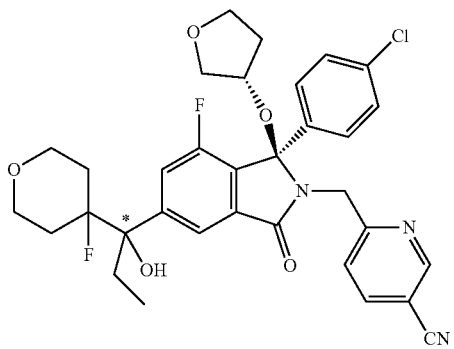 (*isolated as a single isomer at the position shown) | 6-{[(1R)-1-(4-chlorophenyl)-7-fluoro-5-[1-(4-fluorooxan-4-yl)-1-hydroxypropyl]-3-oxo-1-[(3S)-oxolan-3-yloxy]-2,3-dihydro-1H-isoindol-2-yl]methyl}pyridine-3-carbonitrile |
| 447 | 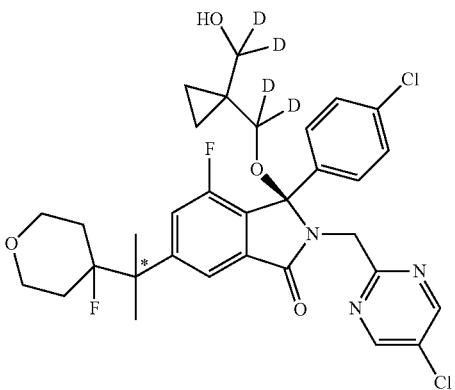 (*isolated as a single isomer at the position shown) | (3R)-3-(4-Chlorophenyl)-2-[(5-chloropyrimidin-2-yl)methyl]-4-fluoro-6-[1-(4-fluorooxan-4-yl)-1-hydroxyethyl]-3-({1-[hydroxy($^2H_2$)methyl]cyclopropyl}($^2H_2$)methoxy)-2,3-dihydro-1H-isoindol-1-one |
| 448 | 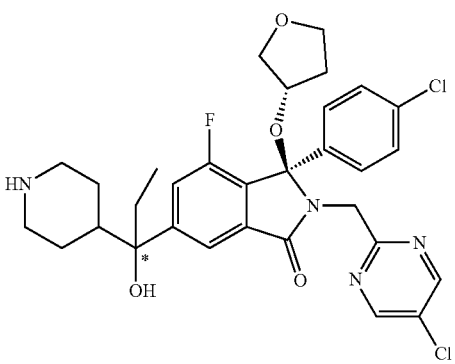 (*single isomer at position shown) | (3R)-3-(4-Chlorophenyl)-2-[(5-chloropyrimidin-2-yl)methyl]-4-fluoro-6-[1-hydroxy-1-(piperidin-4-yl)propyl]-3-[(3S)-oxolan-3-yloxy]-2,3-dihydro-1H-isoindol-1-one |

-continued

| Ex. | Structure | Name |
|---|---|---|
| 449 | (*single isomer at position shown) | (3R)-3-(4-chlorophenyl)-2-[(5-chloropyrimidin-2-yl)methyl]-4-fluoro-6-[1-hydroxy-1-(1-methylpiperidin-4-yl)propyl]-3-[(3S)-oxolan-3-yloxy]-2,3-dihydro-1H-isoindol-1-one |
| 450 | (*single isomer at position shown) | (3R)-3-(4-chlorophenyl)-2-[(5-chloropyrimidin-2-yl)methyl]-4-fluoro-6-[1-hydroxy-1-(piperidin-4-yl)propyl]-3-methoxy-2,3-dihydro-1H-isoindol-1-one |
| 451 and 452 | (*both isomers separated and isolated) | 2-[(1R)-1-(4-chlorophenyl)-2-[(5-chloropyridin-2-yl)methyl]-1-methoxy-3-oxo-2,3-dihydro-1H-isoindol-5-yl]-2-hydroxy-N-(1-methylpiperidin-4-yl)propanamide<br>Ex. 451 is the faster eluting isomer<br>Ex. 452 is the slower eluting isomer |
| 453 and 454 | (*both isomers separated and isolated) | 2-[(1R)-1-(4-Chlorophenyl)-2-[(5-chloropyridin-2-yl)methyl]-1-methoxy-3-oxo-2,3-dihydro-1H-isoindol-5-yl]-2-hydroxy-N-(1-methyl-1H-pyrazol-4-yl)propanamide<br>Ex. 453 is the faster eluting isomer<br>Ex. 454 is the slower eluting isomer |

| Ex. | Structure | Name |
|---|---|---|
| 455 and 456 | 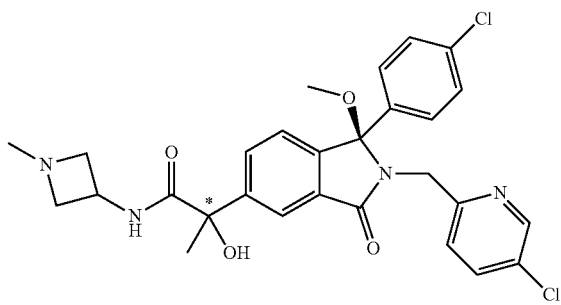<br>(*both isomers separated and isolated) | 2-[(1R)-1-(4-Chlorophenyl)-2-[(5-chloropyridin-2-yl)methyl]-1-methoxy-3-oxo-2,3-dihydro-1H-isoindol-5-yl]-2-hydroxy-N-(1-methylazetidin-3-yl)propanamide<br>Ex. 455 is the faster eluting isomer<br>Ex. 456 is the slower eluting isomer |
| 457 and 458 | 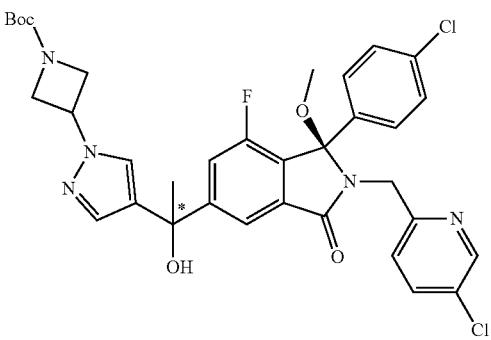<br>(*both isomers separated and isolated) | tert-Butyl 3-(4-{1-[(1R)-1-(4-chlorophenyl)-2-[(5-chloropyridin-2-yl)methyl]-7-fluoro-1-methoxy-3-oxo-2,3-dihydro-1H-isoindol-5-yl]-1-hydroxyethyl}-1H-pyrazol-1-yl)azetidine-1-carboxylate |
| 459 | 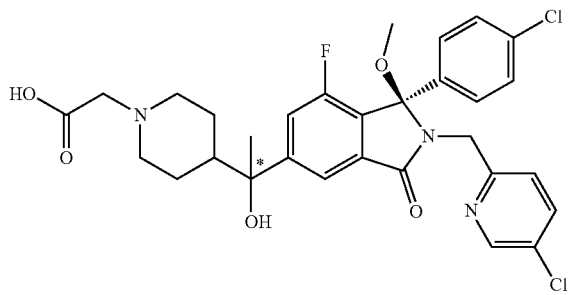<br>(*single isomer at position shown) | 2-(4-{1-[(1R)-1-(4-chlorophenyl)-2-[(5-chloropyridin-2-yl)methyl]-7-fluoro-1-methoxy-3-oxo-2,3-dihydro-1H-isoindol-5-yl]-1-hydroxyethyl}piperidin-1-yl)acetic acid<br>Ex. 459 is the slower eluting isomer |
| 460 | 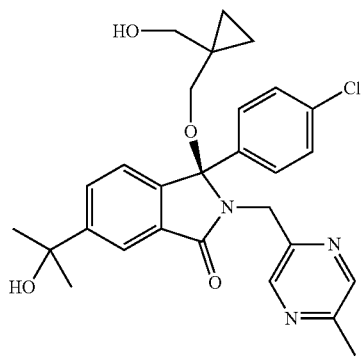 [SMILES: Cc1cnc(CN2C(=O)c3cc(C(C)(C)O)ccc3[C@]2(OCC2(CO)CC2)c2ccc(Cl)cc2)cn1] | (3R)-3-(4-Chlorophenyl)-3-{[1-(hydroxymethyl)cyclopropyl]methoxy}-6-(2-hydroxypropan-2-yl)-2-[(5-methylpyrazin-2-yl)methyl]-2,3-dihydro-1H-isoindol-1-one |

| Ex. | Structure | Name |
|---|---|---|
| 461 | (example prepared and isolated as a single isomer at the positions shown*) | 2-{[(1R)-1-(4-chlorophenyl)-7-fluoro-5-[1-hydroxy-1-(1-methyl-1H-imidazol-4-yl)propyl]-1-[(trans-3-hydroxycyclopentyl)oxy]-3-oxo-2,3-dihydro-1H-isoindol-2-yl]methyl}pyrimidine-5-carbonitrile |
| 462 | (*single isomer at position shown) | 2-{[(1R)-1-(4-chlorophenyl)-1-[(1-cyanocyclopropyl)methoxy]-7-fluoro-5-[1-hydroxy-1-(1-methyl-1H-imidazol-4-yl)propyl]-3-oxo-2,3-dihydro-1H-isoindol-2-yl]methyl}pyrimidine-5-carbonitrile |
| 463 | (*single isomer at position shown) | 2-{[(1R)-1-(4-chlorophenyl)-1-[(1-cyanocyclopropyl)methoxy]-7-fluoro-5-[1-hydroxy-1-(1-methyl-1H-imidazol-4-yl)propyl]-3-oxo-2,3-dihydro-1H-isoindol-2-yl]methyl}pyrimidine-5-carbonitrile |

-continued

| Ex. | Structure | Name |
|---|---|---|
| 464 | (*single isomer at position shown) | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-[cis-3-hydroxycyclobutoxy]-2,3-dihydro-1H-isoindol-1-one |
| 465 | (*single isomer at position shown) | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-[cis-3-hydroxycyclobutoxy]-2,3-dihydro-1H-isoindol-1-one |
| 466 | (*single isomer at position shown) | 6-{[(1R)-1-(4-chlorophenyl)-7-fluoro-5-[1-hydroxy-1-(1-methyl-1H-imidazol-4-yl)propyl]-1-(3-hydroxy-2-methylidenepropoxy)-3-oxo-2,3-dihydro-1H-isoindol-2-yl]methyl}pyridine-3-carbonitrile |

| Ex. | Structure | Name |
|---|---|---|
| 467 | 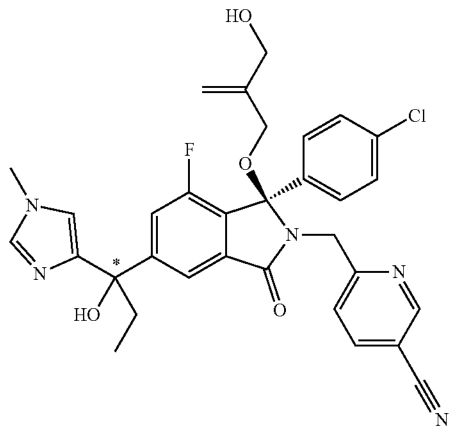 | 6-{[(1R)-1-(4-chlorophenyl)-7-fluoro-5-[1-hydroxy-1-(1-methyl-1H-imidazol-4-yl)propyl]-1-(3-hydroxy-2-methylidenepropoxy)-3-oxo-2,3-dihydro-1H-isoindol-2-yl]methyl}pyridine-3-carbonitrile |
| | (*single isomer at position shown) | |
| 468 | 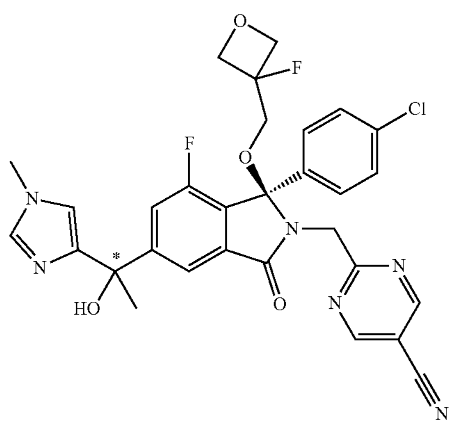 | 2-{[(1R)-1-(4-chlorophenyl)-7-fluoro-1-[(3-fluorooxetan-3-yl)methoxy]-5-[1-hydroxy-1-(1-methyl-1H-imidazol-4-yl)ethyl]-3-oxo-2,3-dihydro-1H-isoindol-2-yl]methyl}pyrimidine-5-carbonitrile |
| | (*single isomer at position shown) | |
| 469 | 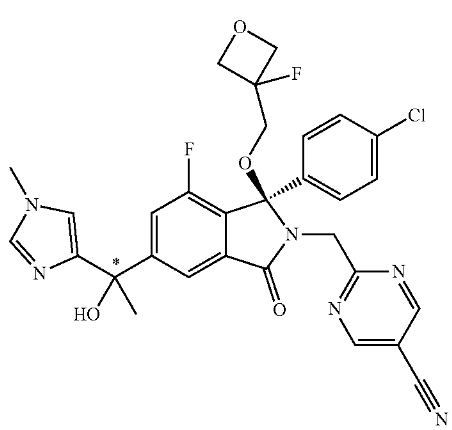 | 2-{[(1R)-1-(4-chlorophenyl)-7-fluoro-1-[(3-fluorooxetan-3-yl)methoxy]-5-[1-hydroxy-1-(1-methyl-1H-imidazol-4-yl)ethyl]-3-oxo-2,3-dihydro-1H-isoindol-2-yl]methyl}pyrimidine-5-carbonitrile |
| | (*single isomer at position shown) | |

| Ex. | Structure | Name |
|---|---|---|
| 470 | 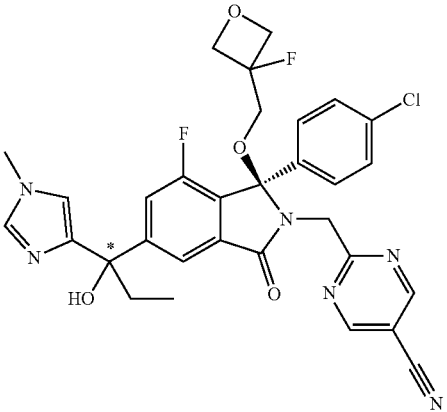 (*single isomer at position shown) | 2-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl]methyl}pyrimidine-5-carbonitrile |
| 471 | 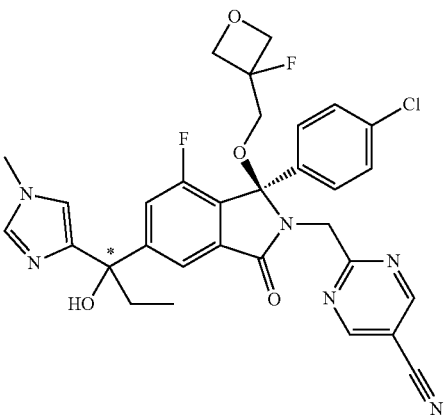 (*single isomer at position shown) | 2-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl]methyl}pyrimidine-5-carbonitrile |
| 472 | 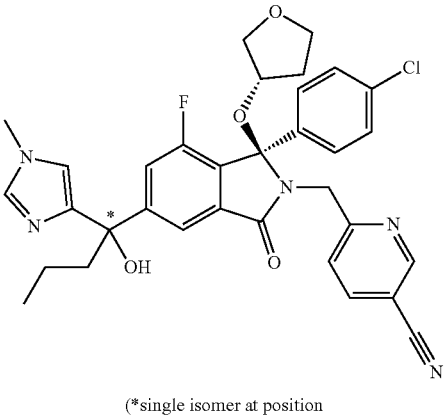 (*single isomer at position shown) | 6-{[(1R)-1-(4-chlorophenyl)-7-fluoro-5-[1-hydroxy-1-(1-methyl-1H-imidazol-4-yl)butyl]-3-oxo-1-[(3S)-oxolan-3-yloxy]-2,3-dihydro-1H-isoindol-2-yl]methyl}pyridine-3-carbonitrile |

| Ex. | Structure | Name |
|---|---|---|
| 473 | 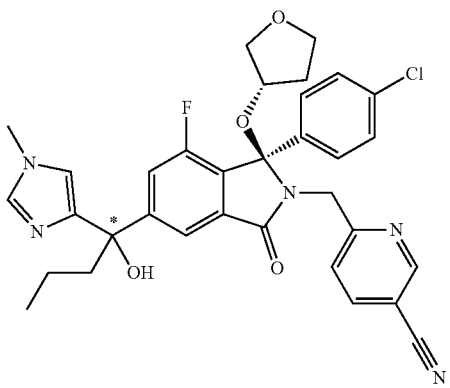<br>(*single isomer at position shown) | 6-{[(1R)-1-(4-chlorophenyl)-7-fluoro-5-[1-hydroxy-1-(1-methyl-1H-imidazol-4-yl)butyl]-3-oxo-1-[(3S)-oxolan-3-yloxy]-2,3-dihydro-1H-isoindol-2-yl]methyl}pyridine-3-carbonitrile |
| 474 | 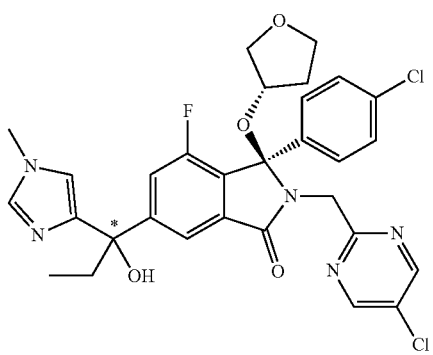<br>(*single isomer at position shown) | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-[(3S)-oxolan-3-yloxy]-2,3-dihydro-1H-isoindol-1-one |
| 475 | 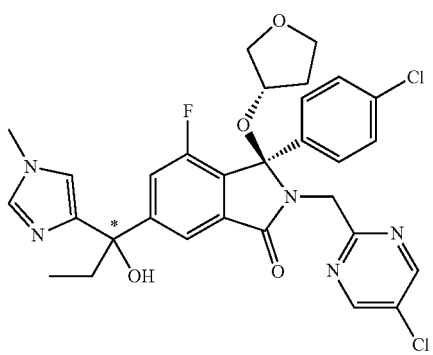<br>(*single isomer at position shown) | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-[(3S)-oxolan-3-yloxy]-2,3-dihydro-1H-isoindol-1-one |

| Ex. | Structure | Name |
|---|---|---|
| 476 | 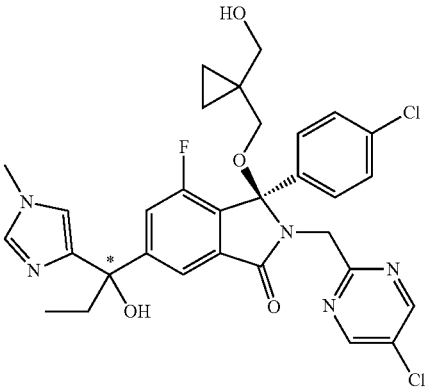 (*single isomer at position shown) | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-{[1-(hydroxymethyl)cyclopropyl]methoxy}-2,3-dihydro-1H-isoindol-1-one |
| 477 | 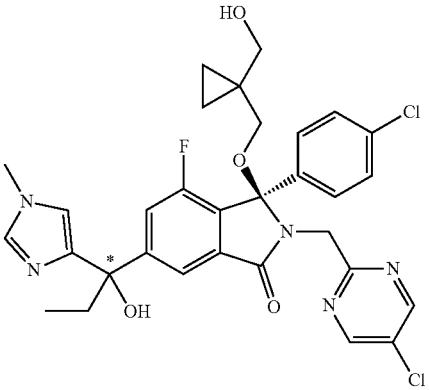 (*single isomer at position shown) | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-{[1-(hydroxymethyl)cyclopropyl]methoxy}-2,3-dihydro-1H-isoindol-1-one |
| 478 | 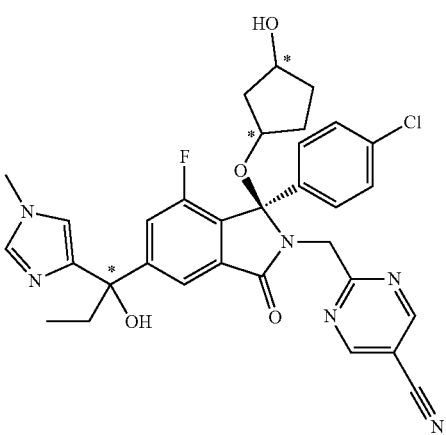 (*single isomer at position shown) | 2-{[(1R)-1-(4-chlorophenyl)-7-fluoro-5-[1-hydroxy-1-(1-methyl-1H-imidazol-4-yl)propyl]-1-[(trans-3-hydroxycyclopentyl)oxy]-3-oxo-2,3-dihydro-1H-isoindol-2-yl]methyl}pyrimidine-5-carbonitrile Ex. 478 is the faster eluting isomer |

| Ex. | Structure | Name |
|---|---|---|
| 479 | 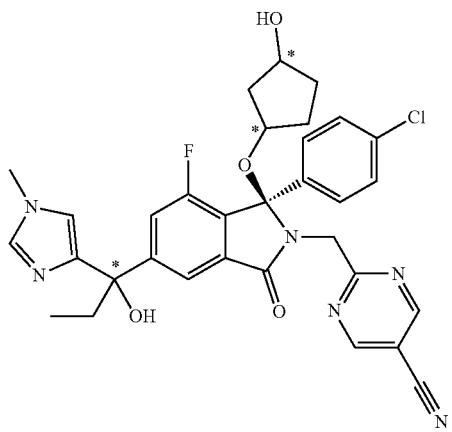<br>(*single isomer at position shown) | 2-{[(1R)-1-(4-chlorophenyl)-7-fluoro-5-[1-hydroxy-1-(1-methyl-1H-imidazol-4-yl)propyl]-1-[(trans-3-hydroxycyclopentyl)oxy]-3-oxo-2,3-dihydro-1H-isoindol-2-yl]methyl}pyrimidine-5-carbonitrile<br>Ex. 479 is the slower eluting isomer |
| 480 | 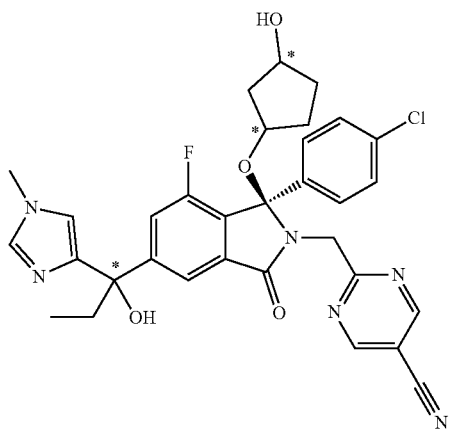<br>(*single isomer at position shown) | 2-{[(1R)-1-(4-chlorophenyl)-7-fluoro-5-[1-hydroxy-1-(1-methyl-1H-imidazol-4-yl)propyl]-1-[(trans-3-hydroxycyclopentyl)oxy]-3-oxo-2,3-dihydro-1H-isoindol-2-yl]methyl}pyrimidine-5-carbonitrile<br>Ex. 480 is the faster eluting isomer |
| 481 | 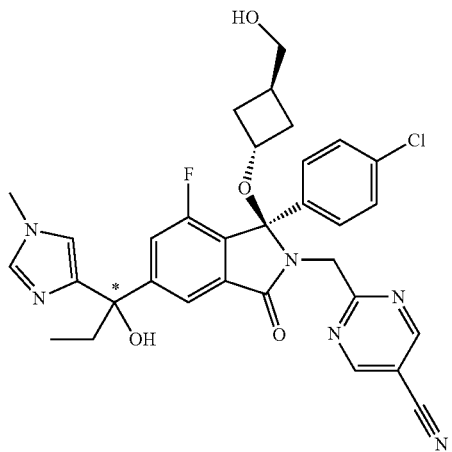<br>(*single isomer at position shown) | 2-{[(1R)-1-(4-chlorophenyl)-7-fluoro-5-[1-hydroxy-1-(1-methyl-1H-imidazol-4-yl)propyl]-3-oxo-1-[trans-3-(hydroxymethyl)cyclobutoxy]-2,3-dihydro-1H-isoindol-2-yl]methyl}pyrimidine-5-carbonitrile |

| Ex. | Structure | Name |
|---|---|---|
| 482 | (*single isomer at position shown) | 2-{[(1R)-1-(4-chlorophenyl)-7-fluoro-5-[1-hydroxy-1-(1-methyl-1H-imidazol-4-yl)propyl]-3-oxo-1-[trans-3-(hydroxymethyl)cyclobutoxy]-2,3-dihydro-1H-isoindol-2-yl]methyl}pyrimidine-5-carbonitrile |
| 483 | (*single isomer at position shown) | 2-{[(1R)-1-(4-chlorophenyl)-7-fluoro-5-[1-hydroxy-1-(1-methyl-1H-imidazol-4-yl)propyl]-3-oxo-1-{[trans-3-hydroxycyclobutyl]methoxy}-2,3-dihydro-1H-isoindol-2-yl]methyl}pyrimidine-5-carbonitrile |
| 484 | (*single isomer at position shown) | 2-{[(1R)-1-(4-chlorophenyl)-7-fluoro-5-[1-hydroxy-1-(1-methyl-1H-imidazol-4-yl)propyl]-3-oxo-1-{[trans-3-hydroxycyclobutyl]methoxy}-2,3-dihydro-1H-isoindol-2-yl]methyl}pyrimidine-5-carbonitrile |

| Ex. | Structure | Name |
|---|---|---|
| 485 | (*single isomer at position shown) | 1-({[(1R)-1-(4-chlorophenyl)-2-[(5-chloropyrimidin-2-yl)methyl]-7-fluoro-5-[1-hydroxy-1-(1-methyl-1H-imidazol-4-yl)propyl]-3-oxo-2,3-dihydro-1H-isoindol-1-yl]oxy}methyl)cyclopropane-1-carboxamide |
| 486 | (*single isomer at position shown) | 1-({[(1R)-1-(4-chlorophenyl)-2-[(5-chloropyrimidin-2-yl)methyl]-7-fluoro-5-[1-hydroxy-1-(1-methyl-1H-imidazol-4-yl)propyl]-3-oxo-2,3-dihydro-1H-isoindol-1-yl]oxy}methyl)cyclopropane-1-carboxamide |
| 487 | (*single isomer at position shown) | (3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-[cis-3-hydroxycyclobutoxy]-2,3-dihydro-1H-isoindol-1-one |

-continued

| Ex. | Structure | Name |
|---|---|---|
| 488 | 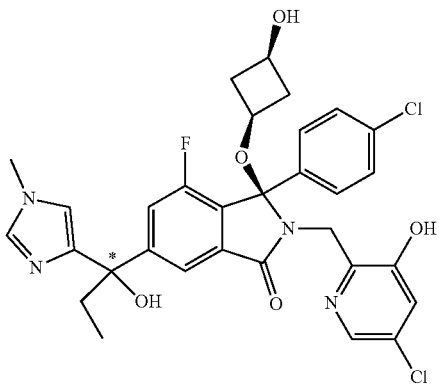 (*single isomer at position shown) | (3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-[cis-3-hydroxycyclobutoxy]-2,3-dihydro-1H-isoindol-1-one |
| 489 | 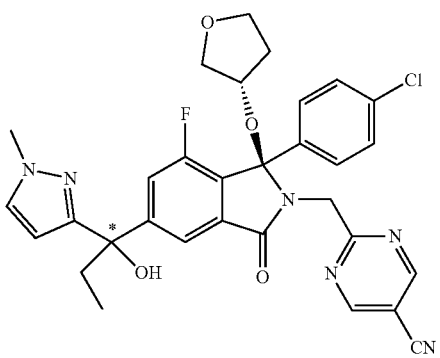 (*single isomer at position shown) | 2-{[(1R)-1-(4-chlorophenyl)-7-fluoro-5-[1-hydroxy-1-(1-methyl-1H-pyrazol-3-yl)propyl]-3-oxo-1-[(3S)-oxolan-3-yloxy]-2,3-dihydro-1H-isoindol-2-yl]methyl}pyrimidine-5-carbonitrile |
| 490 | 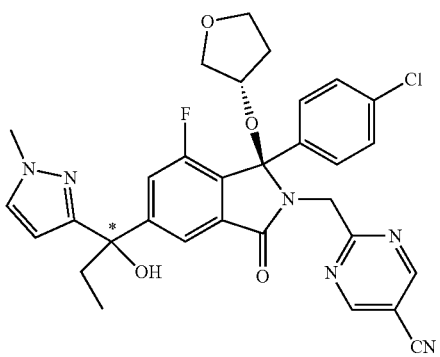 (*single isomer at position shown) | 2-{[(1R)-1-(4-chlorophenyl)-7-fluoro-5-[1-hydroxy-1-(1-methyl-1H-pyrazol-3-yl)propyl]-3-oxo-1-[(3S)-oxolan-3-yloxy]-2,3-dihydro-1H-isoindol-2-yl]methyl}pyrimidine-5-carbonitrile |

| Ex. | Structure | Name |
|---|---|---|
| 491 | 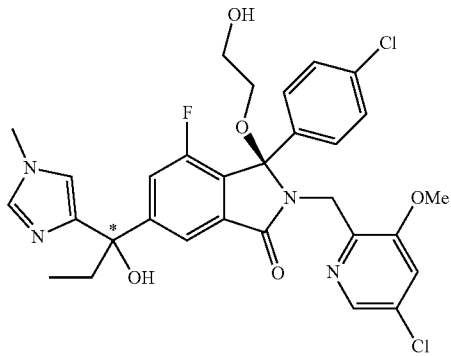<br>(*single isomer at position shown) | (3R)-2-[(5-chloro-3-methoxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one |
| 492 | 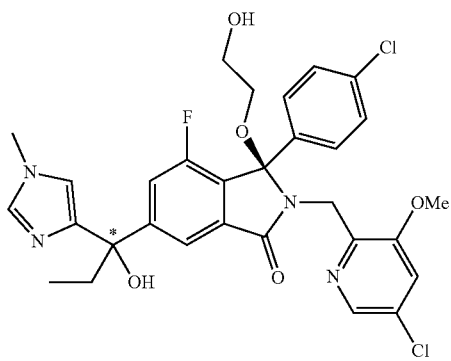<br>(*single isomer at position shown) | (3R)-2-[(5-chloro-3-methoxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one |
| 493 | 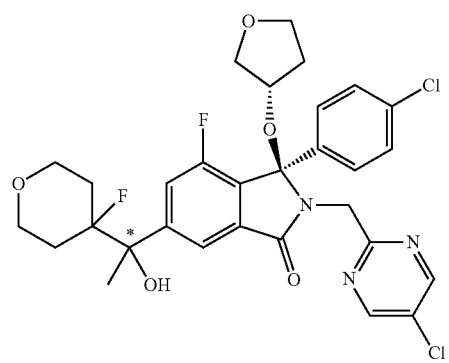<br>(*single isomer at position shown) | (3R)-3-(4-chlorophenyl)-2-[(5-chloropyrimidin-2-yl)methyl]-4-fluoro-6-[1-(4-fluorooxan-4-yl)-1-hydroxyethyl]-3-[(3S)-oxolan-3-yloxy]-2,3-dihydro-1H-isoindol-1-one |

| Ex. | Structure | Name |
|---|---|---|
| 494 | 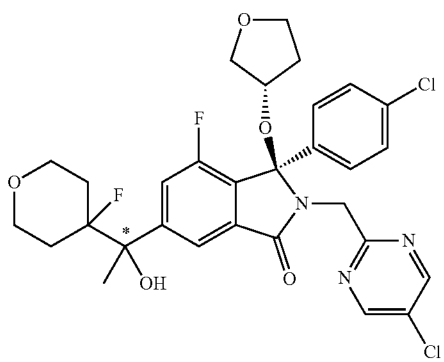 | (3R)-3-(4-chlorophenyl)-2-[(5-chloropyrimidin-2-yl)methyl]-4-fluoro-6-[1-(4-fluorooxan-4-yl)-1-hydroxyethyl]-3-[(3S)-oxolan-3-yloxy]-2,3-dihydro-1H-isoindol-1-one |
| 495 | 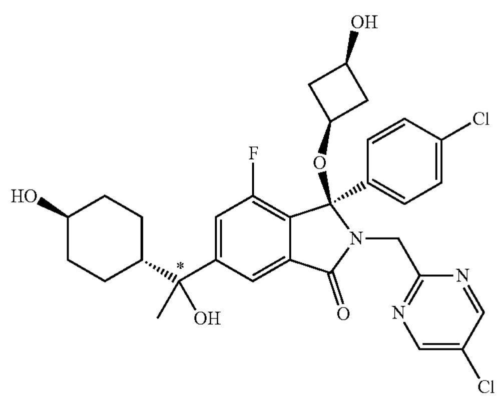 | (3R)-3-(4-chlorophenyl)-2-[(5-chloropyrimidin-2-yl)methyl]-4-fluoro-6-{1-hydroxy-1-[trans-4-hydroxycyclohexyl]}-3-[cis-3-hydroxycyclobutoxy]-2,3-dihydro-1H-isoindol-1-one<br>*slow eluting isomer |
| 496 | 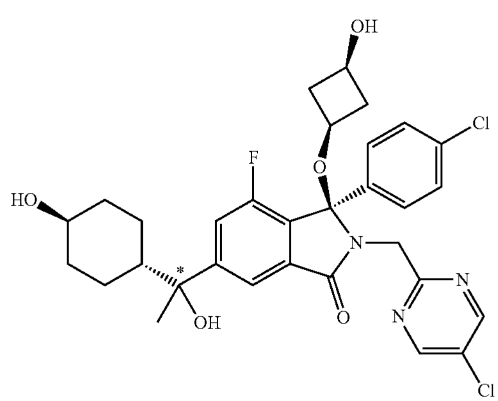 | (3R)-3-(4-chlorophenyl)-2-[(5-chloropyrimidin-2-yl)methyl]-4-fluoro-6-{1-hydroxy-1-[trans-4-hydroxycyclohexyl]}-3-[cis-3-hydroxycyclobutoxy]-2,3-dihydro-1H-isoindol-1-one: *fast eluting isomer |

| Ex. | Structure | Name |
|---|---|---|
| 497 | 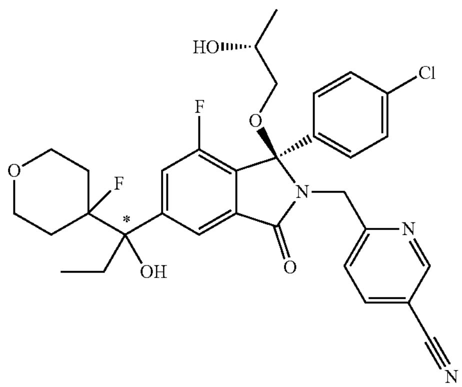 | 6-{[(1R)-1-(4-chlorophenyl)-7-fluoro-5-[1-(4-fluorooxan-4-yl)-1-hydroxypropyl]-1-[(2R)-2-hydroxypropoxy]-3-oxo-2,3-dihydro-1H-isoindol-2-yl]methyl}pyridine-3-carbonitrile |
| 498 | 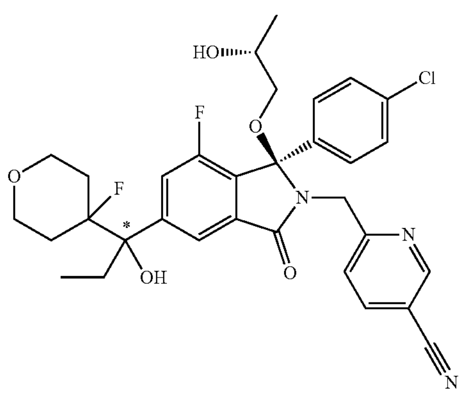 | 6-{[(1R)-1-(4-chlorophenyl)-7-fluoro-5-[1-(4-fluorooxan-4-yl)-1-hydroxypropyl]-1-[(2R)-2-hydroxypropoxy]-3-oxo-2,3-dihydro-1H-isoindol-2-yl]methyl}pyridine-3-carbonitrile |
| 499 | 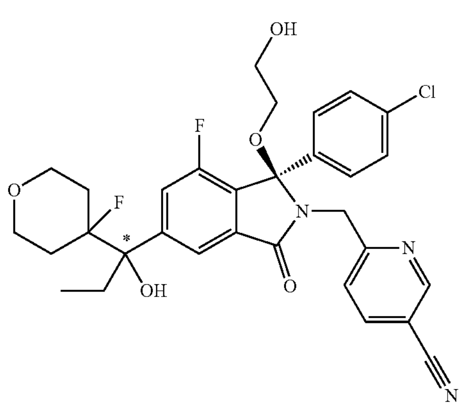 | 6-{[(1R)-1-(4-chlorophenyl)-7-fluoro-5-[1-(4-fluorooxan-4-yl)-1-hydroxypropyl]-1-(2-hydroxyethoxy)-3-oxo-2,3-dihydro-1H-isoindol-2-yl]methyl}pyridine-3-carbonitrile |

(*single isomer at position shown)

| Ex. | Structure | Name |
|---|---|---|
| 500 | 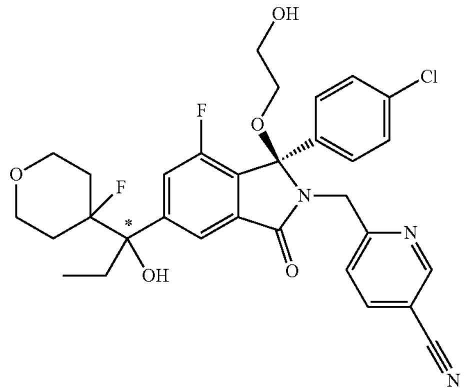 | 6-{[(1R)-1-(4-chlorophenyl)-7-fluoro-5-[1-(4-fluorooxan-4-yl)-1-hydroxypropyl]-1-(2-hydroxyethoxy)-3-oxo-2,3-dihydro-1H-isoindol-2-yl]methyl}pyridine-3-carbonitrile |
| | (*single isomer at position shown) | |
| 501 | 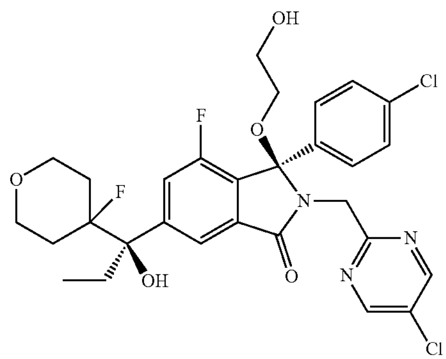 [SMILES: CC[C@@](O)(c1cc(F)c2c(c1)C(=O)N(Cc1ncc(Cl)cn1)[C@@]2(OCCO)c1ccc(Cl)cc1)C1(F)CCOCC1] | (3R)-3-(4-chlorophenyl)-2-[(5-chloropyrimidin-2-yl)methyl]-4-fluoro-6-[(1R)-1-(4-fluorooxan-4-yl)-1-hydroxypropyl]-3-(2-hydroxyethoxy)-2,3-dihydro-1H-isoindol-1-one |
| 502 | 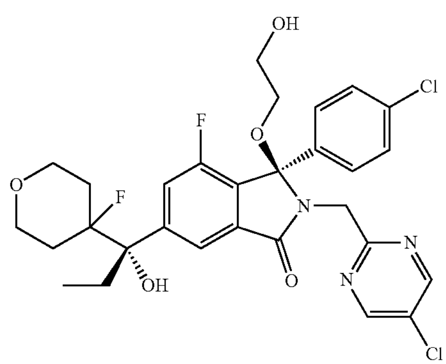 [SMILES: CC[C@](O)(c1cc(F)c2c(c1)C(=O)N(Cc1ncc(Cl)cn1)[C@@]2(OCCO)c1ccc(Cl)cc1)C1(F)CCOCC1] | (3R)-3-(4-chlorophenyl)-2-[(5-chloropyrimidin-2-yl)methyl]-4-fluoro-6-[(1S)-1-(4-fluorooxan-4-yl)-1-hydroxypropyl]-3-(2-hydroxyethoxy)-2,3-dihydro-1H-isoindol-1-one |
| 503 | 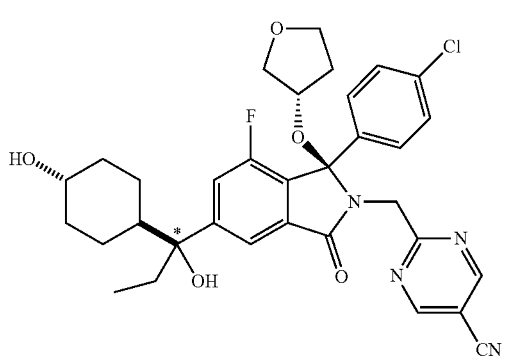 | 2-{[(1R)-1-(4-chlorophenyl)-7-fluoro-5-{1-hydroxy-1-[trans-4-hydroxycyclohexyl]propyl}-3-oxo-1-[(3S)-oxolan-3-yloxy]-2,3-dihydro-1H-isoindol-2-yl]methyl}pyrimidine-5-carbonitrile |
| | (*single isomer at position shown) | |

| Ex. | Structure | Name |
|---|---|---|
| 504 | 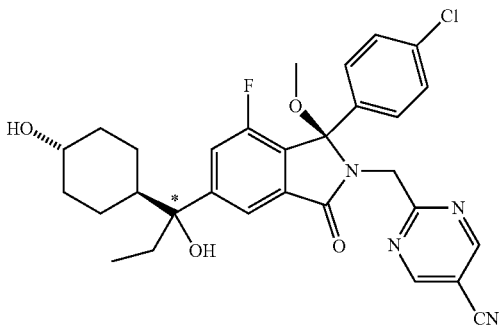<br>(*single isomer at position shown) | 2-{[(1R)-1-(4-chlorophenyl)-7-fluoro-5-{1-hydroxy-1-[trans-4-hydroxycyclohexyl]propyl}-1-methoxy-3-oxo-2,3-dihydro-1H-isoindol-2-yl]methyl}pyrimidine-5-carbonitrile |
| 505 | 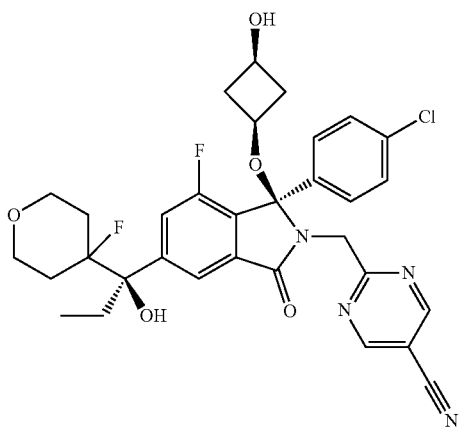 [SMILES: CC[C@@](O)(c1cc(F)c2c(c1)C(=O)N(Cc1ncc(C#N)cn1)[C@@]2(O[C@H]1C[C@@H](O)C1)c1ccc(Cl)cc1)C1(F)CCOCC1] | 2-{[(1R)-1-(4-chlorophenyl)-7-fluoro-5-[(1R)-1-(4-fluorooxan-4-yl)-1-hydroxypropyl]-3-oxo-1-[cis-3-hydroxycyclobutoxy]-2,3-dihydro-1H-isoindol-2-yl]methyl}pyrimidine-5-carbonitrile |
| 506 | 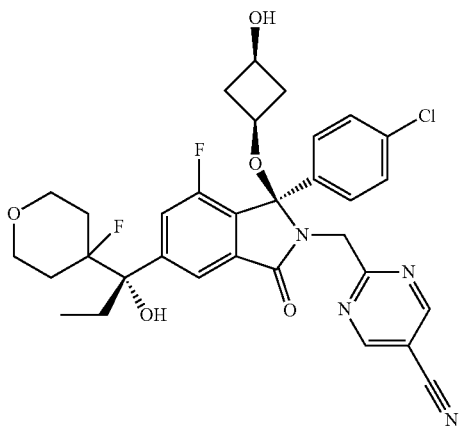 [SMILES: CC[C@](O)(c1cc(F)c2c(c1)C(=O)N(Cc1ncc(C#N)cn1)[C@@]2(O[C@H]1C[C@@H](O)C1)c1ccc(Cl)cc1)C1(F)CCOCC1] | 2-{[(1R)-1-(4-chlorophenyl)-7-fluoro-5-[(1S)-1-(4-fluorooxan-4-yl)-1-hydroxypropyl]-3-oxo-1-[cis-3-hydroxycyclobutoxy]-2,3-dihydro-1H-isoindol-2-yl]methyl}pyrimidine-5-carbonitrile |

-continued

| Ex. | Structure | Name |
|---|---|---|
| 507 | 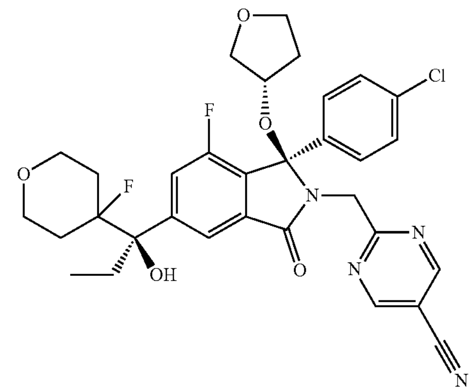 [SMILES: CC[C@@](O)(c1cc(F)c2c(c1)C(=O)N(Cc1ncc(C#N)cn1)[C@@]2(O[C@H]1CCOC1)c1ccc(Cl)cc1)C1(F)CCOCC1] | 2-{[(1R)-1-(4-chlorophenyl)-7-fluoro-5-[(1R)-1-(4-fluorooxan-4-yl)-1-hydroxypropyl]-3-oxo-1-[(3S)-oxolan-3-yloxy]-2,3-dihydro-1H-isoindol-2-yl]methyl}pyrimidine-5-carbonitrile |
| 508 | 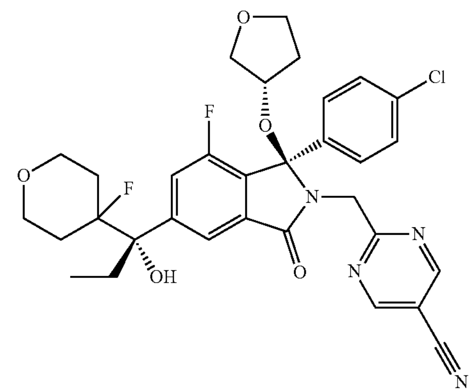 [SMILES: CC[C@](O)(c1cc(F)c2c(c1)C(=O)N(Cc1ncc(C#N)cn1)[C@@]2(O[C@H]1CCOC1)c1ccc(Cl)cc1)C1(F)CCOCC1] | 2-{[(1R)-1-(4-chlorophenyl)-7-fluoro-5-[(1S)-1-(4-fluorooxan-4-yl)-1-hydroxypropyl]-3-oxo-1-[(3S)-oxolan-3-yloxy]-2,3-dihydro-1H-isoindol-2-yl]methyl}pyrimidine-5-carbonitrile |
| 509 | 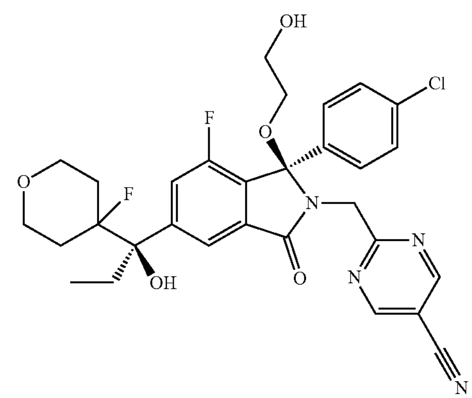 [SMILES: CC[C@@](O)(c1cc(F)c2c(c1)C(=O)N(Cc1ncc(C#N)cn1)[C@@]2(OCCO)c1ccc(Cl)cc1)C1(F)CCOCC1] | 2-{[(1R)-1-(4-chlorophenyl)-7-fluoro-5-[(1R)-1-(4-fluorooxan-4-yl)-1-hydroxypropyl]-1-(2-hydroxyethoxy)-3-oxo-2,3-dihydro-1H-isoindol-2-yl]methyl}pyrimidine-5-carbonitrile |
| 510 | (*single isomer at position shown) | 2-{[(1R)-1-(4-chlorophenyl)-7-fluoro-5-{1-hydroxy-1-[trans-4-hydroxycyclohexyl]propyl}-1-(2-hydroxyethoxy)-3-oxo-2,3-dihydro-1H-isoindol-2-yl]methyl}pyrimidine-5-carbonitrile |

-continued

| Ex. | Structure | Name |
|---|---|---|
| 511 | 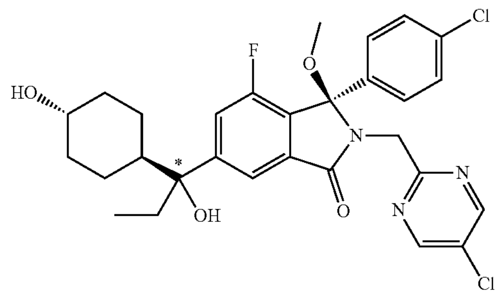 | (3R)-3-(4-chlorophenyl)-2-[(5-chloropyrimidin-2-yl)methyl]-4-fluoro-6-{1-hydroxy-1-[trans-4-hydroxycyclohexyl]propyl}-3-methoxy-2,3-dihydro-1H-isoindol-1-one |
| 512 | 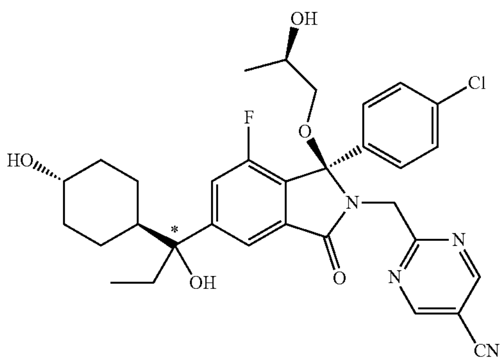 | 2-{[(1R)-1-(4-chlorophenyl)-7-fluoro-5-{1-hydroxy-1-[trans-4-hydroxycyclohexyl]propyl}-1-[(2R)-2-hydroxypropoxy]-3-oxo-2,3-dihydro-1H-isoindol-2-yl]methyl}pyrimidine-5-carbonitrile |
| 513 | 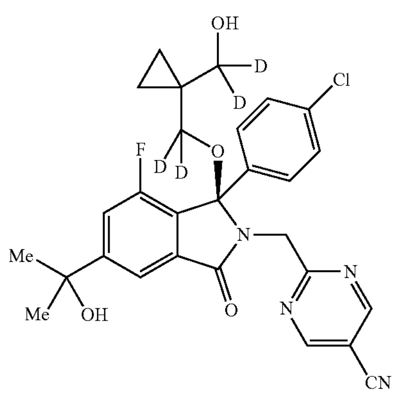 [SMILES: [2H]C([2H])(O)C1(C([2H])([2H])O[C@]2(c3ccc(Cl)cc3)c3c(F)cc(C(C)(C)O)cc3C(=O)N2Cc2ncc(C#N)cn2)CC1] | 2-{[(1R)-1-(4-chlorophenyl)-7-fluoro-1-({1-[hydroxydideuteromethyl]cyclopropyl}dideuteromethoxy)-5-(2-hydroxypropan-2-yl)-3-oxo-2,3-dihydro-1H-isoindol-2-yl]methyl}pyrimidine-5-carbonitrile |
| 514 | 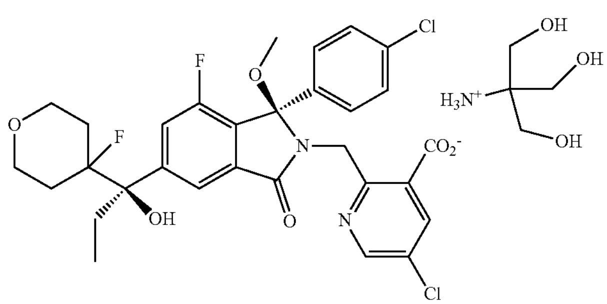 | 5-chloro-2-{[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}pyridine-3-carboxylic acid (tris(hydroxymethyl)aminomethane salt) |

| Ex. | Structure | Name |
|---|---|---|
| 515 | 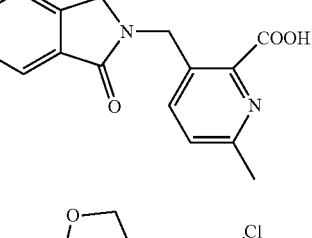 | 3-{[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}-6-methylpyridine-2-carboxylic acid |
| 516 | 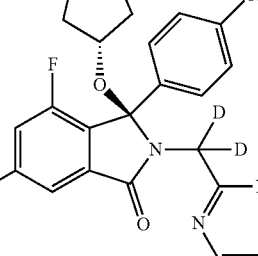<br>(isolated as a single isomer at the position shown*) | (3R)-3-(4-chlorophenyl)-2-[(5-chloropyrimidin-2-yl)dideuteromethyl]-4-fluoro-6-[1-(4-fluorooxan-4-yl)-1-hydroxyethyl]-3-[(3S)-oxolan-3-yloxy]-2,3-dihydro-1H-isoindol-1-one |
| 517 | 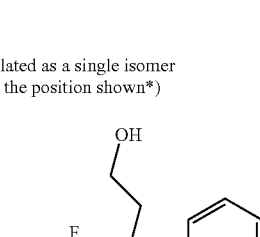<br>(isolated as a single isomer at the position shown*) | (3R)-3-(4-chlorophenyl)-2-[(5-chloropyrimidin-2-yl)methyl]-4-fluoro-6-{1-hydroxy-1-[trans-4-hydroxycyclohexyl]propyl}-3-(2-hydroxyethoxy)-2,3-dihydro-1H-isoindol-1-one |
| 518 | 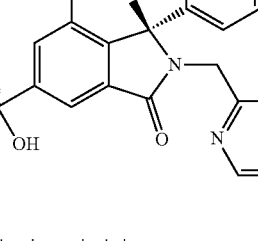<br>(*single isomer at position shown) | 6-{[(1R)-1-(4-chlorophenyl)-7-fluoro-5-{1-hydroxy-1-[trans-4-hydroxycyclohexyl]propyl}-3-oxo-1-[cis-3-hydroxycyclobutoxy]-2,3-dihydro-1H-isoindol-2-yl]methyl}pyridine-3-carbonitrile |

-continued

| Ex. | Structure | Name |
|---|---|---|
| 519 | (*single isomer at position shown) | (3R)-3-(4-chlorophenyl)-2-[(5-chloropyrimidin-2-yl)methyl]-4-fluoro-6-{1-hydroxy-[trans-4-hydroxycyclohexyl]propyl}-3-(2-hydroxyethoxy)-2,3-dihydro-1H-isoindol-1-one |
| 520 | (*single isomer at position shown) | 6-{[(1R)-1-(4-chlorophenyl)-7-fluoro-5-{1-hydroxy-1-[trans-4-hydroxycyclohexyl]propyl}-3-oxo-1-[cis-3-hydroxycyclobutoxy]-2,3-dihydro-1H-isoindol-2-yl]methyl}pyridine-3-carbonitrile |
| 521 | (*single isomer at position shown) | 6-{[(1R)-1-(4-chlorophenyl)-7-fluoro-5-{1-hydroxy-[trans-4-hydroxycyclohexyl]propyl}-1-methoxy-3-oxo-2,3-dihydro-1H-isoindol-2-yl]methyl}pyridine-3-carbonitrile |

| Ex. | Structure | Name |
|---|---|---|
| 522 and 523 | 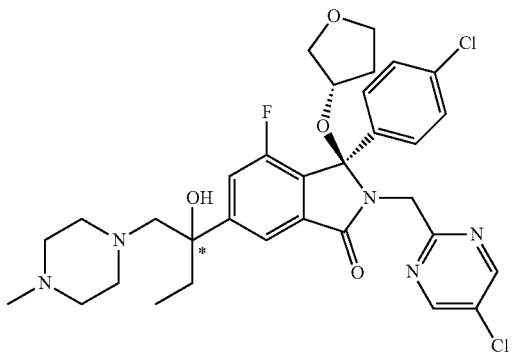 (*both isomers separated and isolated) | (3R)-3-(4-chlorophenyl)-2-[(5-chloropyrimidin-2-yl)methyl]-4-fluoro-6-[2-hydroxy-1-(4-methylpiperazin-1-yl)butan-2-yl]-3-[(3S)-oxolan-3-yloxy]-2,3-dihydro-1H-isoindol-1-one<br>Ex. 522 is the faster eluting isomer<br>Ex. 523 is the slower eluting isomer |
| 524 | 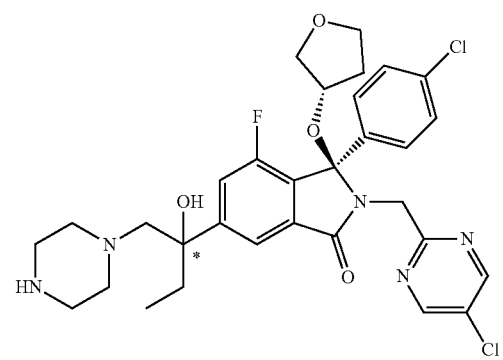 (*single isomer at position shown) | (3R)-3-(4-chlorophenyl)-2-[(5-chloropyrimidin-2-yl)methyl]-4-fluoro-6-[2-hydroxy-1-(piperazin-1-yl)butan-2-yl]-3-[(3S)-oxolan-3-yloxy]-2,3-dihydro-1H-isoindol-1-one<br>Ex. 524 is the faster eluting isomer |
| 525 | 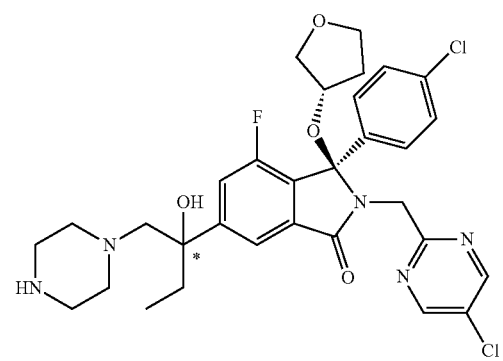 (*single isomer at position shown) | (3R)-3-(4-chlorophenyl)-2-[(5-chloropyrimidin-2-yl)methyl]-4-fluoro-6-[2-hydroxy-1-(piperazin-1-yl)butan-2-yl]-3-[(3S)-oxolan-3-yloxy]-2,3-dihydro-1H-isoindol-1-one<br>Ex. 525 is the slower eluting isomer |

| Ex. | Structure | Name |
|---|---|---|
| 526 | 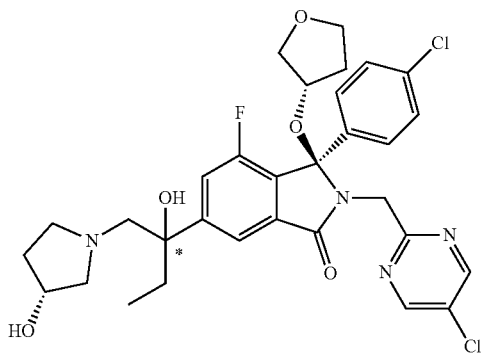 (*single isomer at position shown) | (3R)-3-(4-chlorophenyl)-2-[(5-chloropyrimidin-2-yl)methyl]-4-fluoro-6-{2-hydroxy-1-[(3R)-3-hydroxypyrrolidin-1-yl]butan-2-yl}-3-[(3S)-oxolan-3-yloxy]-2,3-dihydro-1H-isoindol-1-one<br>Ex. 526 is the faster eluting isomer |
| 527 | 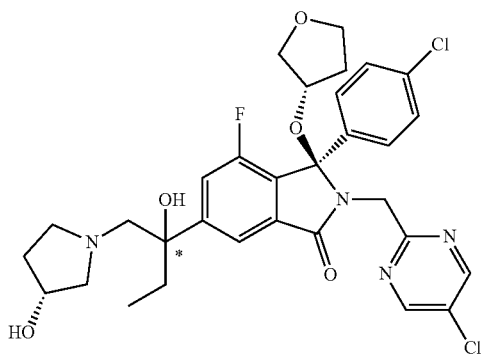 (*single isomer at position shown) | (3R)-3-(4-chlorophenyl)-2-[(5-chloropyrimidin-2-yl)methyl]-4-fluoro-6-{2-hydroxy-1-[(3R)-3-hydroxypyrrolidin-1-yl]butan-2-yl}-3-[(3S)-oxolan-3-yloxy]-2,3-dihydro-1H-isoindol-1-one<br>Ex. 527 is the slower eluting isomer |
| 528 | 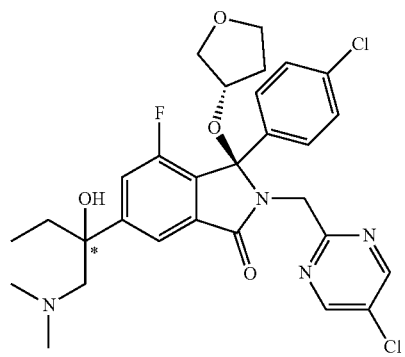 (*single isomer at position shown) | (3R)-3-(4-chlorophenyl)-2-[(5-chloropyrimidin-2-yl)methyl]-6-[1-(dimethylamino)-2-hydroxybutan-2-yl]-4-fluoro-3-[(3S)-oxolan-3-yloxy]-2,3-dihydro-1H-isoindol-1-one |

| Ex. | Structure | Name |
|---|---|---|
| 529 | 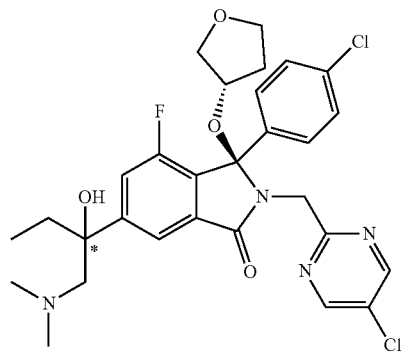 (*single isomer at position shown) | (3R)-3-(4-chlorophenyl)-2-[(5-chloropyrimidin-2-yl)methyl]-6-[1-(dimethylamino)-2-hydroxybutan-2-yl]-4-fluoro-3-[(3S)-oxolan-3-yloxy]-2,3-dihydro-1H-isoindol-1-one |
| 530 | 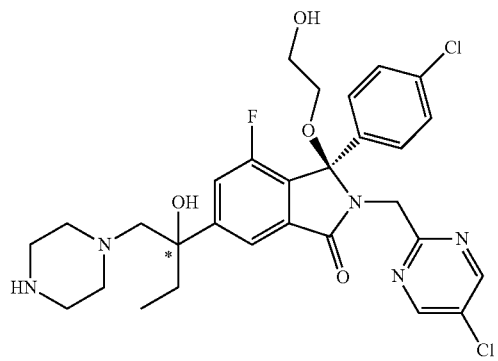 (*single isomer at position shown) | (3R)-3-(4-chlorophenyl)-2-[(5-chloropyrimidin-2-yl)methyl]-4-fluoro-6-[2-hydroxy-1-(piperazin-1-yl)butan-2-yl]-3-(2-hydroxyethoxy)-2,3-dihydro-1H-isoindol-1-one<br>Ex. 530 is the faster eluting isomer |
| 531 | 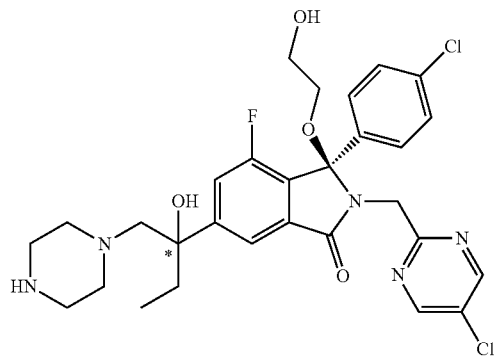 (*single isomer at position shown) | (3R)-3-(4-chlorophenyl)-2-[(5-chloropyrimidin-2-yl)methyl]-4-fluoro-6-[2-hydroxy-1-(piperazin-1-yl)butan-2-yl]-3-(2-hydroxyethoxy)-2,3-dihydro-1H-isoindol-1-one<br>Ex. 531 is the slower eluting isomer |

-continued

| Ex. | Structure | Name |
|---|---|---|
| 532 | (*single isomer at position shown) | (3R)-3-(4-chlorophenyl)-2-[(5-chloropyrimidin-2-yl)methyl]-4-fluoro-6-[2-hydroxy-1-(4-methylpiperazin-1-yl)butan-2-yl]-3-(2-hydroxyethoxy)-2,3-dihydro-1H-isoindol-1-one<br>Ex. 532 is the faster eluting isomer |
| 533 | (*single isomer at position shown) | (3R)-3-(4-chlorophenyl)-2-[(5-chloropyrimidin-2-yl)methyl]-4-fluoro-6-[2-hydroxy-1-(4-methylpiperazin-1-yl)butan-2-yl]-3-(2-hydroxyethoxy)-2,3-dihydro-1H-isoindol-1-one<br>Ex. 533 is the slower eluting isomer |
| 534 | (*single isomer at position shown) | 1-({[(1R)-1-(4-chlorophenyl)-2-[(5-chloropyrimidin-2-yl)methyl]-7-fluoro-5-[2-hydroxy-1-(4-methylpiperazin-1-yl)butan-2-yl]-3-oxo-2,3-dihydro-1H-isoindol-1-yl]oxy}methyl)cyclopropane-1-carbonitrile<br>Ex. 534 is the faster eluting isomer |

| Ex. | Structure | Name |
|---|---|---|
| 535 | 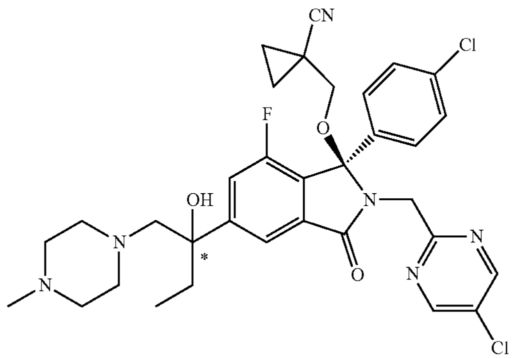 | 1-({[(1R)-1-(4-chlorophenyl)-2-[(5-chloropyrimidin-2-yl)methyl]-7-fluoro-5-[2-hydroxy-1-(4-methylpiperazin-1-yl)butan-2-yl]-3-oxo-2,3-dihydro-1H-isoindol-1-yl]oxy}methyl)cyclopropane-1-carbonitrile<br>Ex. 535 is the slower eluting isomer |
| 536 | 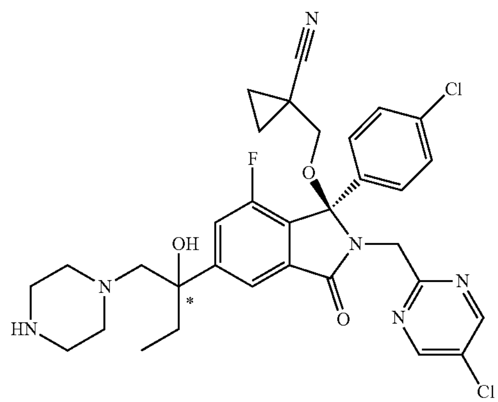 | 1-({[(1R)-1-(4-chlorophenyl)-2-[(5-chloropyrimidin-2-yl)methyl]-7-fluoro-5-[2-hydroxy-1-(piperazin-1-yl)butan-2-yl]-3-oxo-2,3-dihydro-1H-isoindol-1-yl]oxy}methyl)cyclopropane-1-carbonitrile<br>Ex. 536 is the faster eluting isomer |
| 537 | 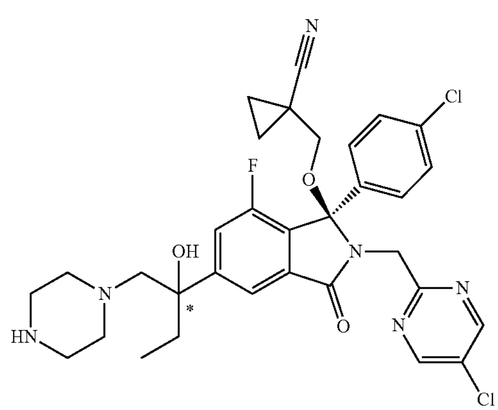 | 1-({[(1R)-1-(4-chlorophenyl)-2-[(5-chloropyrimidin-2-yl)methyl]-7-fluoro-5-[2-hydroxy-1-(piperazin-1-yl)butan-2-yl]-3-oxo-2,3-dihydro-1H-isoindol-1-yl]oxy}methyl)cyclopropane-1-carbonitrile<br>Ex. 537 is the slower eluting isomer |

| Ex. | Structure | Name |
|---|---|---|
| 538 | 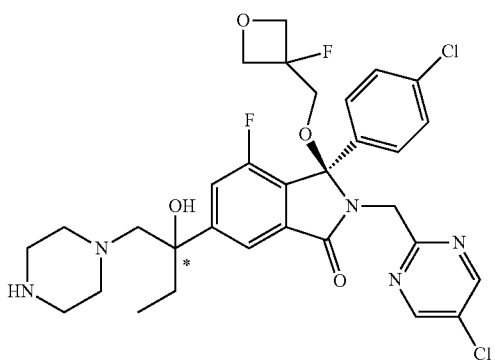 (*single isomer at position shown) | (3R)-3-(4-chlorophenyl)-2-[(5-chloropyrimidin-2-yl)methyl]-4-fluoro-3-[(3-fluorooxetan-3-yl)methoxy]-6-[2-hydroxy-1-(piperazin-1-yl)butan-2-yl]-2,3-dihydro-1H-isoindol-1-one<br>Ex. 538 is the faster eluting isomer |
| 539 | 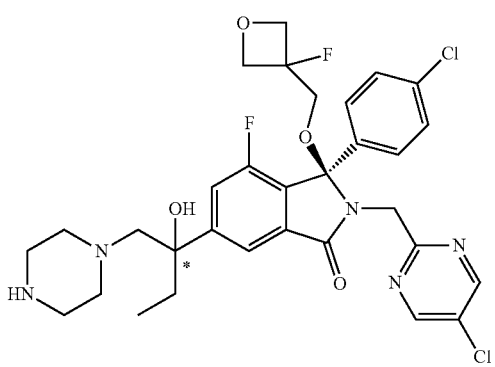 (*single isomer at position shown) | (3R)-3-(4-chlorophenyl)-2-[(5-chloropyrimidin-2-yl)methyl]-4-fluoro-3-[(3-fluorooxetan-3-yl)methoxy]-6-[2-hydroxy-1-(piperazin-1-yl)butan-2-yl]-2,3-dihydro-1H-isoindol-1-one<br>Ex. 539 is the slower eluting isomer |
| 540 | 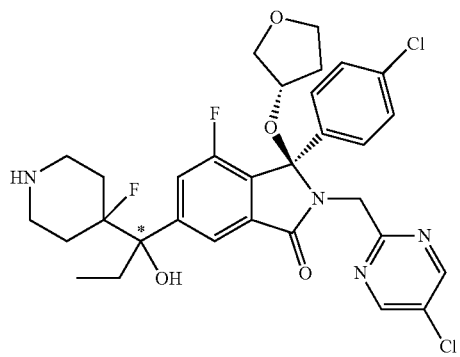 (*single isomer at position shown) | (3R)-3-(4-chlorophenyl)-2-[(5-chloropyrimidin-2-yl)methyl]-4-fluoro-6-[1-(4-fluoropiperidin-4-yl)-1-hydroxypropyl]-3-[(3S)-oxolan-3-yloxy]-2,3-dihydro-1H-isoindol-1-one |

| Ex. | Structure | Name |
|---|---|---|
| 541 | 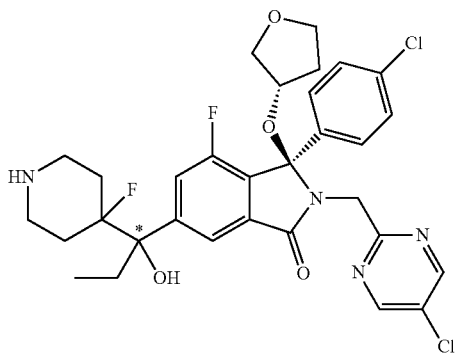<br>(*single isomer at position shown) | (3R)-3-(4-chlorophenyl)-2-[(5-chloropyrimidin-2-yl)methyl]-4-fluoro-6-[1-(4-fluoropiperidin-4-yl)-1-hydroxypropyl]-3-[(3S)-oxolan-3-yloxy]-2,3-dihydro-1H-isoindol-1-one |
| 541 a | 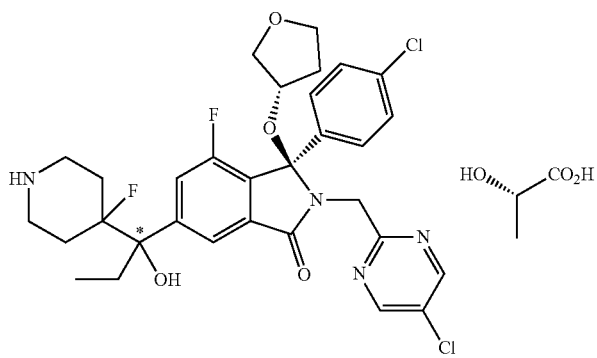<br>(*single isomer at position shown) | (3R)-3-(4-chlorophenyl)-2-[(5-chloropyrimidin-2-yl)methyl]-4-fluoro-6-[1-(4-fluoropiperidin-4-yl)-1-hydroxypropyl]-3-[(3S)-oxolan-3-yloxy]-2,3-dihydro-1H-isoindol-1-one-L-(+)-lactic acid salt |
| 542 | 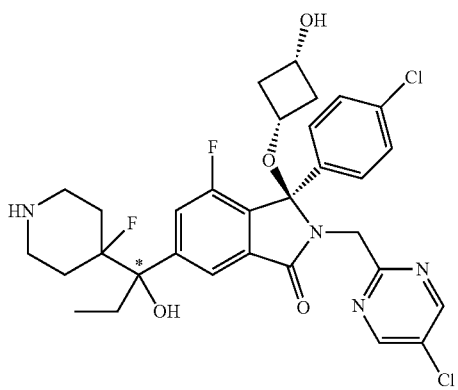<br>(*single isomer at position shown) | (3R)-3-(4-chlorophenyl)-2-[(5-chloropyrimidin-2-yl)methyl]-4-fluoro-6-[1-(4-fluoropiperidin-4-yl)-1-hydroxypropyl]-3-[cis-3-hydroxycyclobutoxy]-2,3-dihydro-1H-isoindol-1-one |

| Ex. | Structure | Name |
|---|---|---|
| 543 | 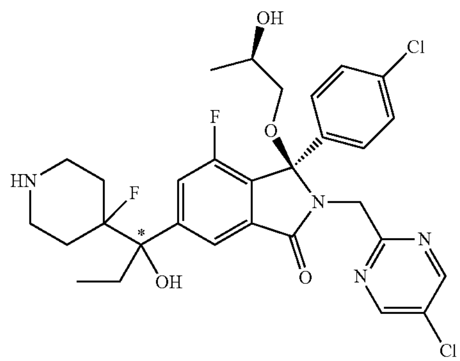 | (3R)-3-(4-chlorophenyl)-2-[(5-chloropyrimidin-2-yl)methyl]-4-fluoro-6-[1-(4-fluoropiperidin-4-yl)-1-hydroxypropyl]-3-[(2R)-2-hydroxypropoxy]-2,3-dihydro-1H-isoindol-1-one |
|  | (*single isomer at position shown) | |
| 544 | 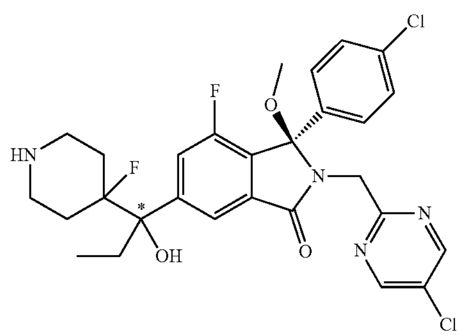 | (3R)-3-(4-chlorophenyl)-2-[(5-chloropyrimidin-2-yl)methyl]-4-fluoro-6-[1-(4-fluoropiperidin-4-yl)-1-hydroxypropyl]-3-methoxy-2,3-dihydro-1H-isoindol-1-one |
|  | (*single isomer at position shown) | |
| 545 | 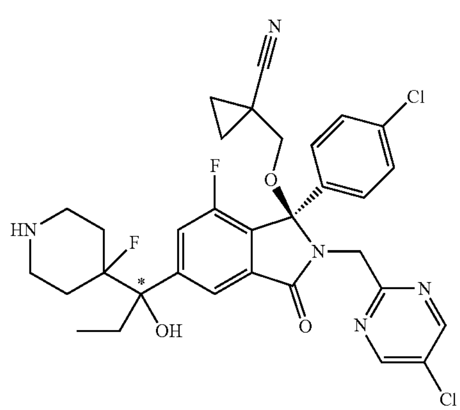 | 1-({[(1R)-1-(4-chlorophenyl)-2-[(5-chloropyrimidin-2-yl)methyl]-7-fluoro-5-[1-(4-fluoropiperidin-4-yl)-1-hydroxypropyl]-3-oxo-2,3-dihydro-1H-isoindol-1-yl]oxy}methyl)cyclopropane-1-carbonitrile |
|  | (*single isomer at position shown) | |

| Ex. | Structure | Name |
|---|---|---|
| 546 | 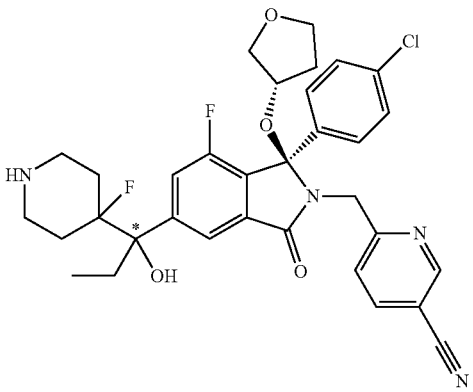 (*single isomer at position shown) | 6-{[(1R)-1-(4-chlorophenyl)-7-fluoro-5-[1-(4-fluoropiperidin-4-yl)-1-hydroxypropyl]-3-oxo-1-[(3S)-oxolan-3-yloxy]-2,3-dihydro-1H-isoindol-2-yl]methyl}pyridine-3-carbonitrile |
| 547 | 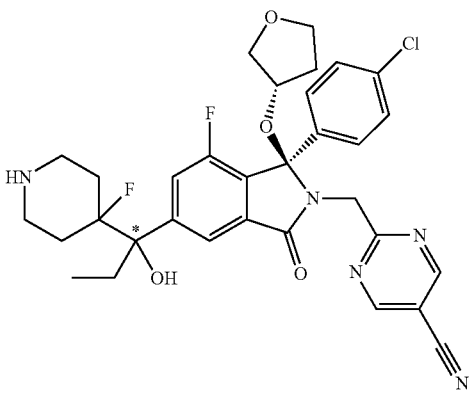 (*single isomer at position shown) | 2-{[(1R)-1-(4-chlorophenyl)-7-fluoro-5-[1-(4-fluoropiperidin-4-yl)-1-hydroxypropyl]-3-oxo-1-[(3S)-oxolan-3-yloxy]-2,3-dihydro-1H-isoindol-2-yl]methyl}pyrimidine-5-carbonitrile |
| 548 | 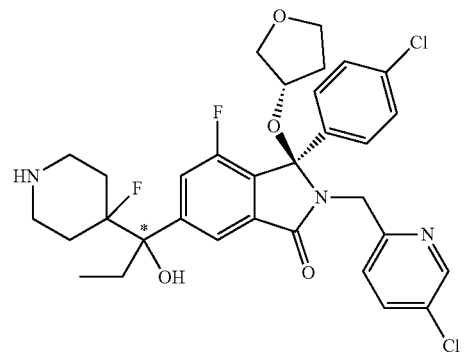 (*single isomer at position shown) | (3R)-3-(4-chlorophenyl)-2-[(5-chloropyridin-2-yl)methyl]-4-fluoro-6-[1-(4-fluoropiperidin-4-yl)-1-hydroxypropyl]-3-[(3S)-oxolan-3-yloxy]-2,3-dihydro-1H-isoindol-1-one |

| Ex. | Structure | Name |
|---|---|---|
| 549 | 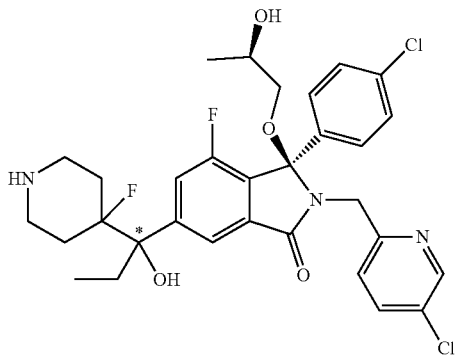 (*single isomer at position shown) | (3R)-3-(4-chlorophenyl)-2-[(5-chloropyridin-2-yl)methyl]-4-fluoro-6-[1-(4-fluoropiperidin-4-yl)-1-hydroxypropyl]-3-[(2R)-2-hydroxypropoxy]-2,3-dihydro-1H-isoindol-1-one |
| 550 | 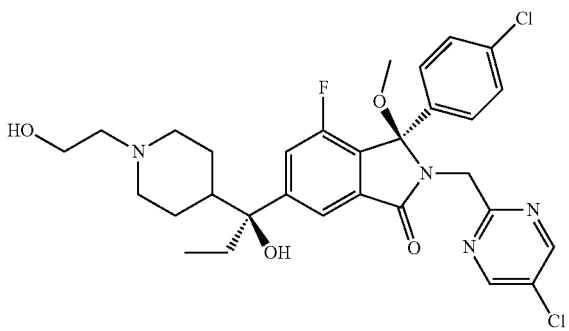 [SMILES: CC[C@@](O)(c1cc(F)c2c(c1)C(=O)N(Cc1ncc(Cl)cn1)[C@@]2(OC)c1ccc(Cl)cc1)C1CCN(CCO)CC1] | (3R)-3-(4-chlorophenyl)-2-[(5-chloropyrimidin-2-yl)methyl]-4-fluoro-6-[(1S)-1-hydroxy-1-[1-(2-hydroxyethyl)piperidin-4-yl]propyl]-3-methoxy-2,3-dihydro-1H-isoindol-1-one<br>Ex. 550 is the faster eluting isomer |
| 551 | 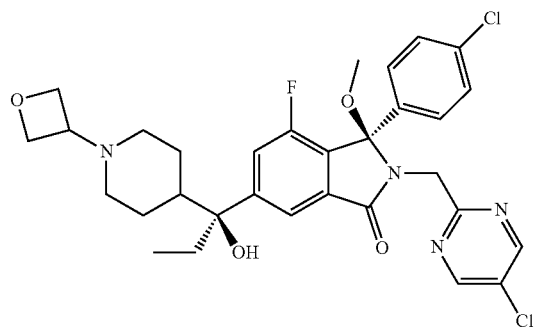 [SMILES: CC[C@@](O)(c1cc(F)c2c(c1)C(=O)N(Cc1ncc(Cl)cn1)[C@@]2(OC)c1ccc(Cl)cc1)C1CCN(C2COC2)CC1] | (3R)-3-(4-chlorophenyl)-2-[(5-chloropyrimidin-2-yl)methyl]-4-fluoro-6-[(1S)-1-hydroxy-1-[1-(oxetan-3-yl)piperidin-4-yl]propyl]-3-methoxy-2,3-dihydro-1H-isoindol-1-one |
| 552 | 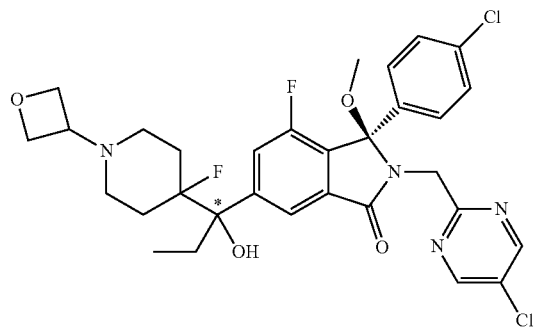 (*prepared and isolated as a single isomer) | (3R)-3-(4-chlorophenyl)-2-[(5-chloropyrimidin-2-yl)methyl]-4-fluoro-6-[1-[4-fluoro-1-(oxetan-3-yl)piperidin-4-yl]-1-hydroxypropyl]-3-methoxy-2,3-dihydro-1H-isoindol-1-one |

-continued

| Ex. | Structure | Name |
|---|---|---|
| 553 | 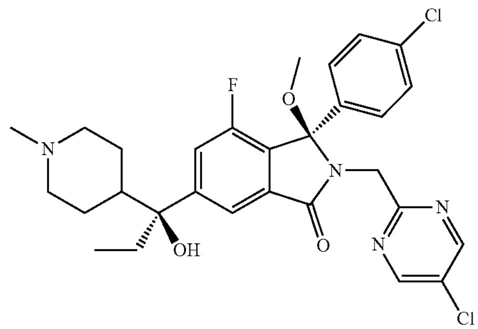 [SMILES: CC[C@@](O)(c1cc(F)c2c(c1)C(=O)N(Cc1ncc(Cl)cn1)[C@@]2(OC)c1ccc(Cl)cc1)C1CCN(C)CC1] | (3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-methoxy-2,3-dihydro-1H-isoindol-1-one |
| 554 | (*single isomer at position shown) | (3R)-3-(4-chlorophenyl)-2-[(5-chloropyrimidin-2-yl)methyl]-4-fluoro-6-[1-hydroxy-1-(1-methylpiperidin-4-yl)ethyl]-3-{[1-(hydroxymethyl)cyclopropyl]methoxy}-2,3-dihydro-1H-isoindol-1-one |
| 555 | (*single isomer at position shown) | (3R)-3-(4-chlorophenyl)-2-[(5-chloropyridin-2-yl)methyl]-4-fluoro-6-[1-hydroxy-1-(1-methylpiperidin-4-yl)ethyl]-3-{[1-(hydroxymethyl)cyclopropyl]methoxy}-2,3-dihydro-1H-isoindol-1-one |
| 556 | 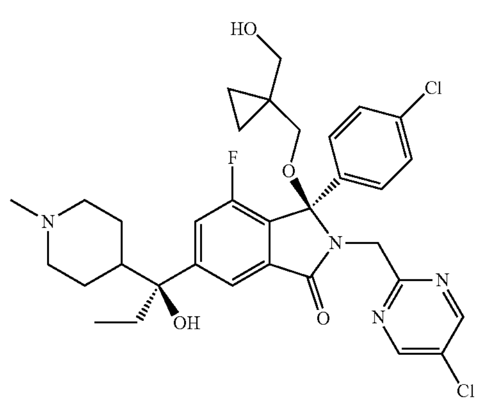 [SMILES: CC[C@@](O)(c1cc(F)c2c(c1)C(=O)N(Cc1ncc(Cl)cn1)[C@@]2(OCC1(CO)CC1)c1ccc(Cl)cc1)C1CCN(C)CC1] | (3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-{[1-(hydroxymethyl)cyclopropyl]methoxy}-2,3-dihydro-1H-isoindol-1-one |

| Ex. | Structure | Name |
|---|---|---|
| 557 | 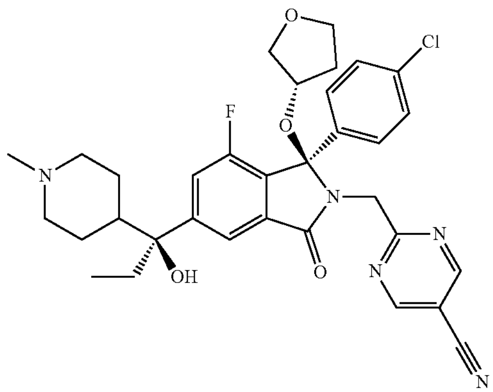 [SMILES: CC[C@@](O)(c1cc(F)c2c(c1)C(=O)N(Cc1ncc(C#N)cn1)[C@@]2(O[C@H]1CCOC1)c1ccc(Cl)cc1)C1CCN(C)CC1] | 2-{[(1R)-1-(4-chlorophenyl)-7-fluoro-5-[(1S)-1-hydroxy-1-(1-methylpiperidin-4-yl)propyl]-3-oxo-1-[(3S)-oxolan-3-yloxy]-2,3-dihydro-1H-isoindol-2-yl]methyl}pyrimidine-5-carbonitrile |
| 558 | (*single isomer at position shown) | (3R)-3-(4-chlorophenyl)-2-[(5-chloropyrimidin-2-yl)methyl]-4-fluoro-3-[(3-fluorooxetan-3-yl)methoxy]-6-[1-hydroxy-1-(1-methylpiperidin-4-yl)ethyl]-2,3-dihydro-1H-isoindol-1-one |
| 559 | 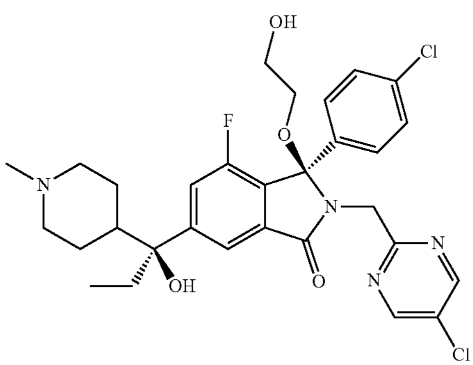 [SMILES: CC[C@@](O)(c1cc(F)c2c(c1)C(=O)N(Cc1ncc(Cl)cn1)[C@@]2(OCCO)c1ccc(Cl)cc1)C1CCN(C)CC1] | (3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-(2-hydroxyethoxy)-2,3-dihydro-1H-isoindol-1-one |
| 560 | 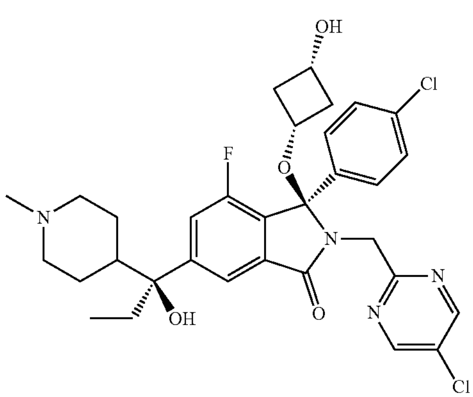 [SMILES: CC[C@@](O)(c1cc(F)c2c(c1)C(=O)N(Cc1ncc(Cl)cn1)[C@@]2(O[C@H]1C[C@@H](O)C1)c1ccc(Cl)cc1)C1CCN(C)CC1] | (3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-[cis-3-hydroxycyclobutoxy]-2,3-dihydro-1H-isoindol-1-one |

-continued

| Ex. | Structure | Name |
|---|---|---|
| 561 | (*single isomer at position shown) | 2-{[(1R)-1-(4-chlorophenyl)-7-fluoro-5-[1-(4-fluoro-1-methylpiperidin-4-yl)-1-hydroxypropyl]-3-oxo-1-[(3S)-oxolan-3-yloxy]-2,3-dihydro-1H-isoindol-2-yl]methyl}pyrimidine-5-carbonitrile |
| 562 | 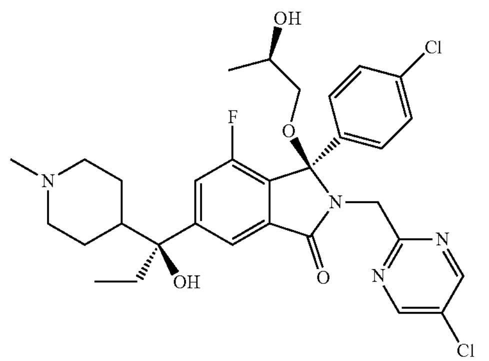 [SMILES: CC[C@@](O)(c1cc(F)c2c(c1)C(=O)N(Cc1ncc(Cl)cn1)[C@@]2(OC[C@@H](C)O)c1ccc(Cl)cc1)C1CCN(C)CC1] | (3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-[(2R)-2-hydroxypropoxy]-2,3-dihydro-1H-isoindol-1-one |
| 563 | (*single isomer at position shown) | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one |
| 563 a | (*single isomer at position shown) | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one-L-(+)-lactic acid salt |

| Ex. | Structure | Name |
|---|---|---|
| 563 b | 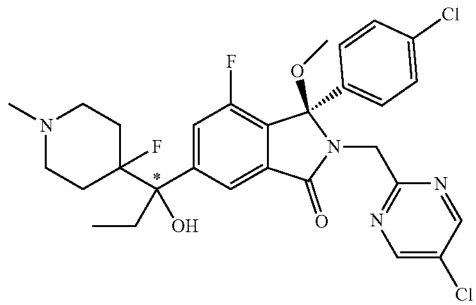 | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one-hydrochloride salt |
| 564 | 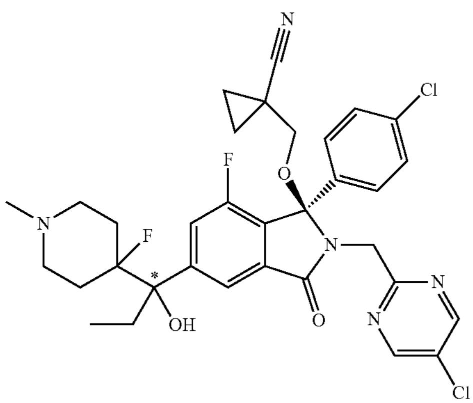 | 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile |
| 564 a | 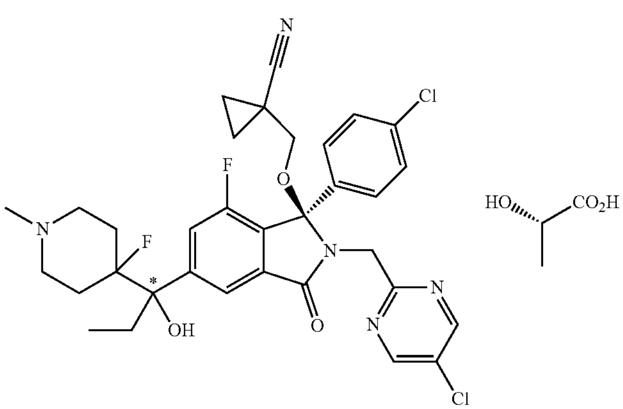 | 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile-L-(+)-lactic acid salt |

| Ex. | Structure | Name |
|---|---|---|
| 564 b | 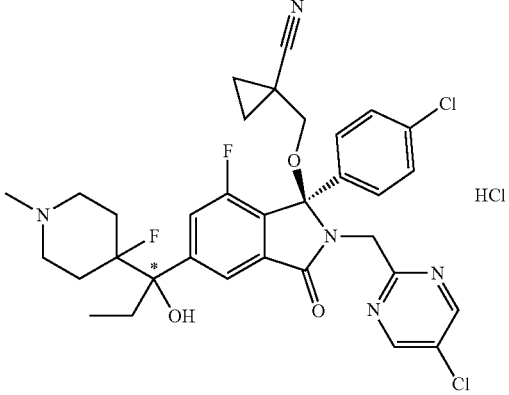 (*single isomer at position shown) | 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile-hydrochloride salt |
| 565 | 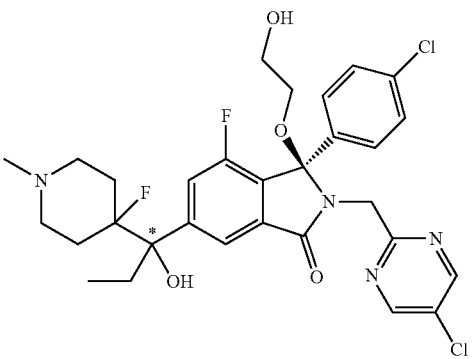 (*single isomer at position shown) | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-(2-hydroxyethoxy)-2,3-dihydro-1H-isoindol-1-one |
| 566 | 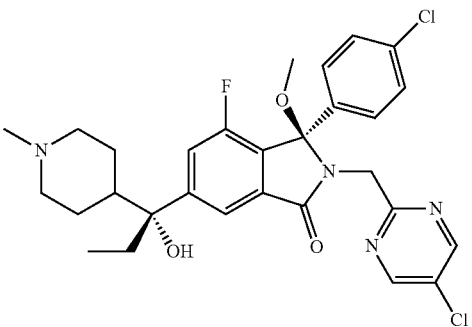 [SMILES: CC[C@](O)(c1cc(F)c2c(c1)C(=O)N(Cc1ncc(Cl)cn1)[C@@]2(OC)c1ccc(Cl)cc1)C1CCN(C)CC1] | (3R)-3-(4-chlorophenyl)-2-[(5-chloropyrimidin-2-yl)methyl]-4-fluoro-6-[(1R)-1-hydroxy-1-(1-methylpiperidin-4-yl)propyl]-3-methoxy-2,3-dihydro-1H-isoindol-1-one |
| 567 | 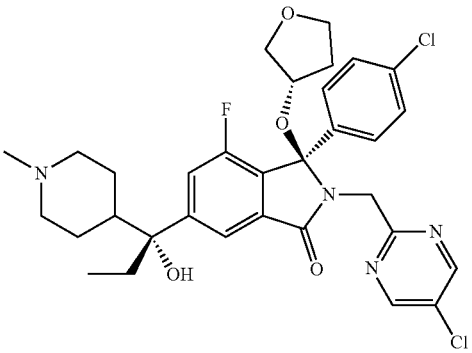 [SMILES: CC[C@](O)(c1cc(F)c2c(c1)C(=O)N(Cc1ncc(Cl)cn1)[C@@]2(O[C@H]1CCOC1)c1ccc(Cl)cc1)C1CCN(C)CC1] | (3R)-3-(4-chlorophenyl)-2-[(5-chloropyrimidin-2-yl)methyl]-4-fluoro-6-[(1R)-1-hydroxy-1-(1-methylpiperidin-4-yl)propyl]-3-[(3S)-oxolan-3-yloxy]-2,3-dihydro-1H-isoindol-1-one |

-continued

| Ex. | Structure | Name |
| --- | --- | --- |
| 568 | 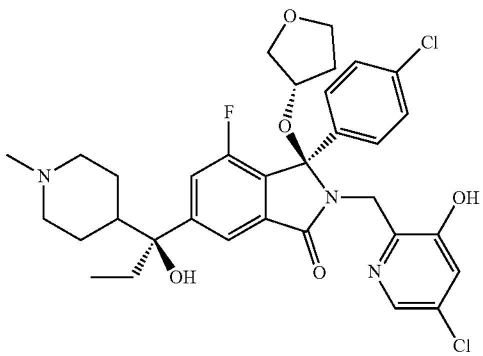 [SMILES: CC[C@@](O)(c1cc(F)c2c(c1)C(=O)N(Cc1ncc(Cl)cc1O)[C@@]2(O[C@H]1CCOC1)c1ccc(Cl)cc1)C1CCN(C)CC1] | 2-[(5-chloro-3-hydroxypyridin-2-yl)methyl]-3-(4-chlorophenyl)-4-fluoro-6-[(1S)-1-hydroxy-1-(1-methylpiperidin-4-yl)propyl]-3-[(3S)-oxolan-3-yloxy]-2,3-dihydro-1H-isoindol-1-one |
| 570 | (*single isomer at position shown) | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[cis-3-hydroxycyclobutoxy]-2,3-dihydro-1H-isoindol-1-one |
| 571 | (*single isomer at position shown) | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[(3S)-oxolan-3-yloxy]-2,3-dihydro-1H-isoindol-1-one |

-continued

| Ex. | Structure | Name |
|---|---|---|
| 572 | 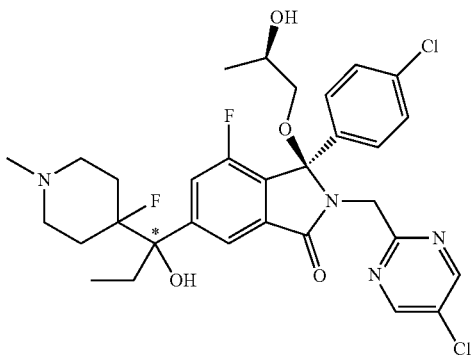<br>(*single isomer at position shown) | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[(2R)-2-hydroxypropoxy]-2,3-dihydro-1H-isoindol-1-one |
| 574 | 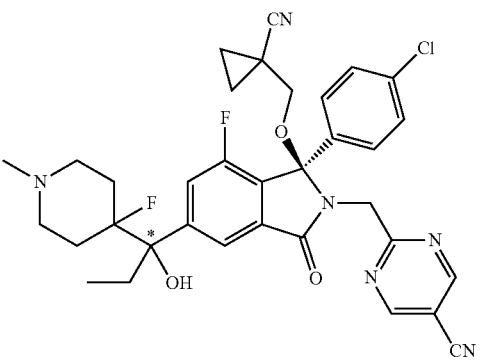<br>(*single isomer at position shown) | 2-{[(1R)-1-(4-chlorophenyl)-1-[(1-cyanocyclopropyl)methoxy]-7-fluoro-5-[1-(4-fluoro-1-methylpiperidin-4-yl)-1-hydroxypropyl]-3-oxo-2,3-dihydro-1H-isoindol-2-yl]methyl}pyrimidine-5-carbonitrile |
| 575 | 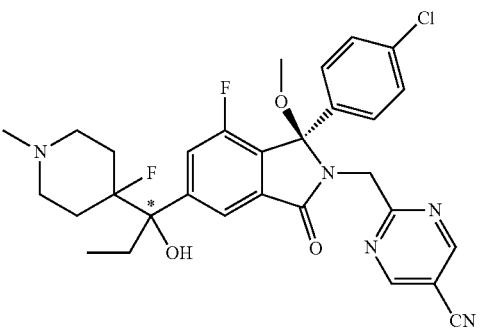<br>(*single isomer at position shown) | 2-{[(1R)-1-(4-chlorophenyl)-7-fluoro-5-[1-(4-fluoro-1-methylpiperidin-4-yl)-1-hydroxypropyl]-1-methoxy-3-oxo-2,3-dihydro-1H-isoindol-2-yl]methyl}pyrimidine-5-carbonitrile |

-continued

| Ex. | Structure | Name |
|---|---|---|
| 576 | (*single isomer separated and isolated) | 2-{[(1R)-1-(4-chlorophenyl)-7-fluoro-1-({1-[hydroxydideuteromethyl]cyclopropyl}dideuteromethoxy)-5-(2-hydroxybutan-2-yl)-3-oxo-2,3-dihydro-1H-isoindol-2-yl]methyl}pyrimidine-5-carbonitrile<br>Ex. 576 is the faster eluting isomer |
| 577 | (*single isomer separated and isolated) | 2-{[(1R)-1-(4-chlorophenyl)-7-fluoro-1-({1-[hydroxydideuteromethyl]cyclopropyl}dideuteromethoxy)-5-(2-hydroxybutan-2-yl)-3-oxo-2,3-dihydro-1H-isoindol-2-yl]methyl}pyrimidine-5-carbonitrile<br>Ex. 577 is the faster eluting isomer |
| 578 | (*single isomer at position shown) | (3R)-3-(4-chlorophenyl)-2-[(5-chloropyrimidin-2-yl)methyl]-4-fluoro-6-[1-(4-fluorooxan-4-yl)-1-hydroxyethyl]-3-(2-hydroxyethoxy)-2,3-dihydro-1H-isoindol-1-one |

| Ex. | Structure | Name |
|---|---|---|
| 579 | 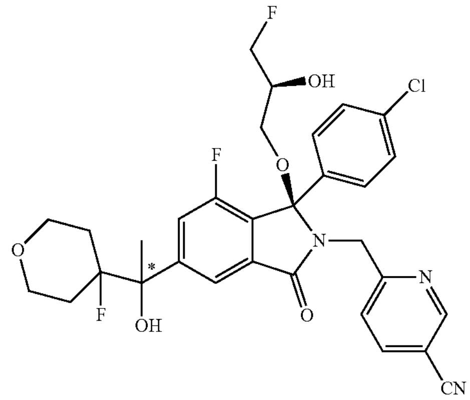 | 6-{[(1R)-1-(4-chlorophenyl)-7-fluoro-1-[(2S)-3-fluoro-2-hydroxypropoxy]-5-[1-(4-fluorooxan-4-yl)-1-hydroxyethyl]-3-oxo-2,3-dihydro-1H-isoindol-2-yl]methyl}pyridine-3-carbonitrile |
| | (*single isomer at position shown) | |
| 580 | 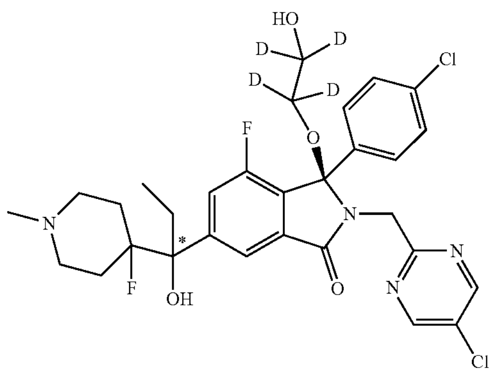 | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[2-hydroxy(1,1,2,2-tetradeutero)ethoxy]-2,3-dihydro-1H-isoindol-1-one |
| | (*single isomer at position shown) | |

Preparation of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic Acid

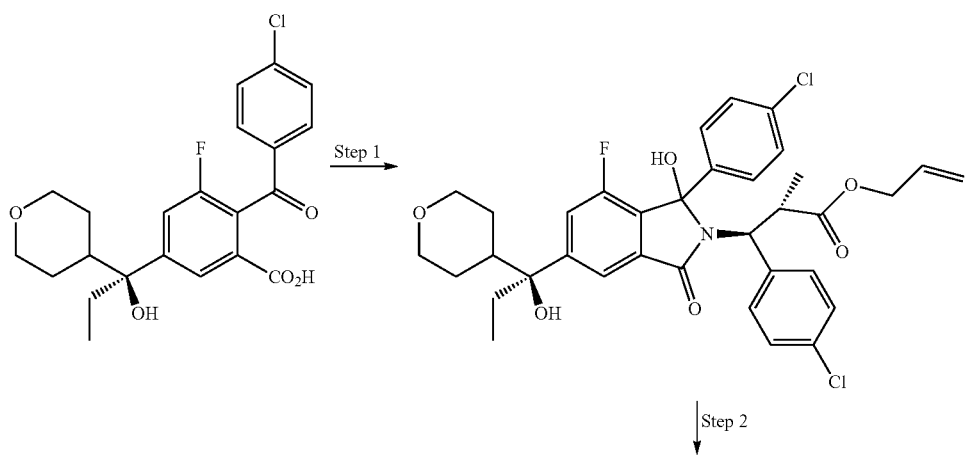

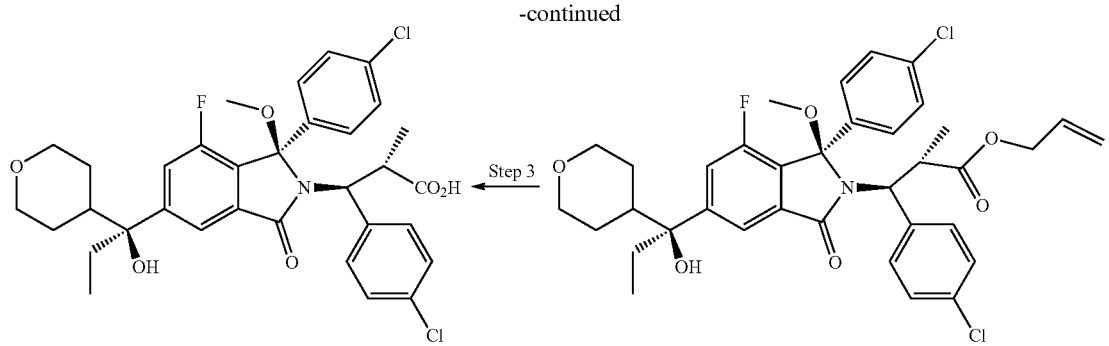

Step 1: Prop-2-en-1-yl (2S,3S)-3-(4-chlorophenyl)-3-[1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate To a solution of (S)-2-(4-chlorobenzoyl)-3-fluoro-5-(1-hydroxy-1-(tetrahydro-2H-pyran-4-yl)propyl)benzoic acid (Preparation 52) (0.686 g, 1.6 mmol), prop-2-en-1-yl (2S,3S)-3-amino-3-(4-chlorophenyl)-2-methylpropanoate (Preparation 62) (0.54 g, 2.12 mmol) and diisopropylethylamine (0.83 mL, 4.8 mmol) in DMF (15 mL) was added HATU (0.91 g, 2.4 mmol) and the reaction mixture was stirred for 2 hrs. Water was added and extracted with ethyl acetate. The organic phase was washed with saturated NaHCO$_3$, brine, dried and the solvent evaporated. The crude product was purified by chromatography to afford the title compound (0.75 g, 72%). MS: [M−H]$^-$=654.

Step 2: Prop-2-en-1-yl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate The title compound was prepared from ethyl (2S,3S)-3-(4-chlorophenyl)-3-[1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate and methanol in a similar manner as described in Preparation 10, but using MeOH instead of 1,1-bis(hydroxymethyl)cyclopropane. The diastereoisomers were separated by chiral SFC, the title compound was the faster eluting isomer. MS: [M+H]$^+$=670.

Step 3: (2S,3S)-3-(4-Chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid The title compound was prepared from prop-2-en-1-yl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate in an analogous fashion as described in Example 90, step 4. 1H NMR (400 MHz, DMSO-d6): 12.56-12.00 (1H, m), 7.71 (1H, s), 7.42 (1H, d), 7.02 (4H, d), 6.88 (3H, d), 4.91 (1H, s), 4.23 (1H, d), 3.99-3.85 (2H, m), 3.75 (1H, dd), 3.25-3.10 (5H, m), 2.02-1.90 (1H, m), 1.90-1.78 (2H, m), 1.67 (1H, d), 1.43-1.17 (6H, m), 0.95 (1H, d), 0.58 (3H, t). MS: [M+H]$^+$=630.

(2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic Acid (tris(hydroxymethyl)aminomethane Salt)

Compound above was dissolved in EtOH and 1 mol. eq. of tris(hydroxymethyl)aminomethane was added. The solvent was removed in vacuo to give a colourless solid. $^1$H NMR (500 MHz, DMSO-d6) δ 7.69 (s, 1H), 7.39 (d, J=10.7 Hz, 1H), 7.01 (broad s, 4H), 6.96-6.88 (m, 4H), 4.92 (broad s, 1H), 4.34-4.22 (m, 1H), 3.88 (dd, J=10.9, 4.2 Hz, 1H), 3.74 (dd, J=11.1, 4.2 Hz, 1H), 3.71-3.61 (m, 1H), 3.29 (s, 6H), 3.33-3.22 (m, 1H), 3.21-3.14 (m, 1H), 3.13 (s, 3H), 1.94 (tt, J=12.2, 3.6 Hz, 1H), 1.89-1.78 (m, 2H), 1.66 (d, J=12.8 Hz, 1H), 1.41-1.24 (m, 2H), 1.19 (d, J=6.8 Hz, 3H), 0.93 (d, J=13.2 Hz, 1H), 0.57 (t, J=7.3 Hz, 3H). MS: [M+H]$^+$=630.

Preparation of the Sodium Salt of SGI-110

The sodium salt of the compound of formula (1) was prepared as described in U.S. Pat. No. 7,700,567 (the content of which is hereby incorporated by reference).

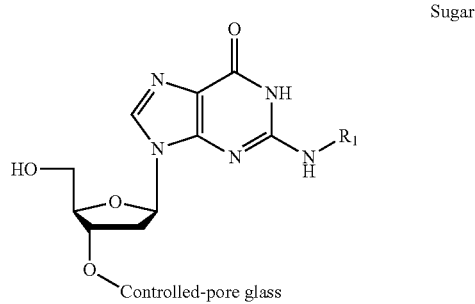

Phosphoramidite building block

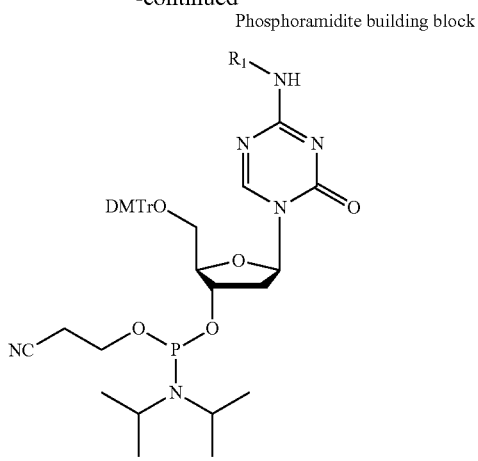

A protected 2'-deoxyguanosine-linked CPG solid support (where R₁=tert-butyl phenoxyacetyl) was coupled with 2-2.5 equivalents of phenoxyacetyl decitabine phosphoramidite (where R₁=phenoxyacetyl) in the presence of 60% of 0.3 M benzylthiotetrazole activator (in acetonitrile) for 10 minutes. The CPG solid support containing protected DpG dinucleotide was treated with 20 mL of 50 mM K₂CO₃ in methanol for 1 hour and 20 minutes. The coupled product was oxidized, the protective group was removed, and the resultant compound was washed, filtered, and purified by the ÄKTA Explorer 100 HPLC with a Gemini C18 preparative column (Phenomenex), 250×21.2 mm, 10 μm with guard column (Phenomenex), 50×21.2 mm, 10 μm, with 50 mM triethylammonium acetate (pH 7) in MilliQ water (Mobile Phase A) and 80% acetonitrile in MilliQ water (Mobile Phase B), with 2% to 20/25% Mobile Phase B in column volumes.

The ESI-MS (-ve) of the following DpG dinucleotide (SGI-110):

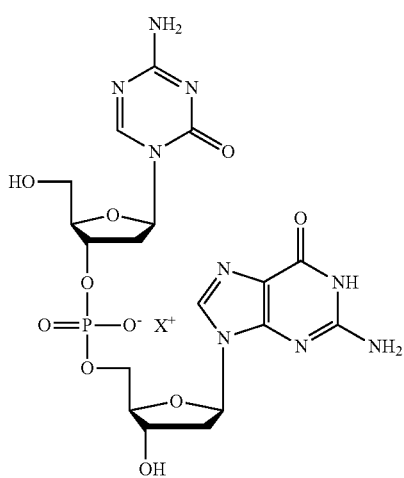

where X+=triethylammonium (calculated exact mass for the neutral compound $C_{18}H_{24}N_9P_{10}P$ is 557.14), exhibited m/z 556.1 [M−H]⁻ and 1113.1 for [2M−H]⁻ (see mass spectrum in FIG. 31 of U.S. Pat. No. 7,700,567).

The sodium salt of SGI-110, where X+=sodium, was obtained by re-dissolving the triethylammonium salt in 4 mL water, 0.2 mL 2M NaClO₄ solution. When 36 mL acetone was added, the dinucleotide precipitated. The solution was kept at −20° C. for several hours and centrifuged at 4000 rpm for 20 minutes. The supernatant was discarded and the solid was washed with 30 mL acetone followed by an additional centrifugation at 4000 rpm for 20 minutes. The precipitate, which was dissolved in water and freeze dried, exhibited m/z 556.0 [M−H]⁻ (see mass spectrum in FIG. 36 of U.S. Pat. No. 7,700,567).

Biological Assays
Compounds of Formula (I°)
MDM2-053 Interaction Using a 96-Well Plate Binding Assay (ELISA)

The ELISA assay was performed in streptavidin coated plates which were preincubated with 200 μl per well of 1 μg ml⁻¹ biotinylated IP3 peptide. The plates were ready to use for MDM2 binding after washing the plate with PBS.

Compounds and control solutions in DMSO aliquoted in 96-well plates were pre-incubated in a final 2.5-5% (v/v) DMSO concentration at room temperature (for example 20° C.) for 20 min with 190 μl aliquots of optimized concentrations of in vitro translated MDM2, before transfer of the MDM2-compound mixture to the b-IP3 streptavidin plates, and incubation at 4° C. for 90 min. After washing three times with PBS to remove unbound MDM2, each well was incubated at 20° C. for 1 hour with a TBS-Tween (50 mM Tris pH7.5; 150 mM NaCl; 0.05% Tween 20 nonionic detergent) buffered solution of primary mouse monoclonal anti-MDM2 antibody (Ab-5, Calbiochem, used at a 1/10000 or 1/200 dilution depending on the antibody stock solution used), then washed three times with TBS-Tween before incubation for 45 mins at 20° C. with a TBS-Tween buffered solution of a goat-anti-mouse horseradish peroxidase (HRP) conjugated secondary antibody (used at 1/20000 or 1/2000 depending on the antibody stock solution). The unbound secondary antibody was removed by washing three times with TBS-Tween. The bound HRP activity was measured by enhanced chemiluminesence (ECL™, Amersham Biosciences) using the oxidation of the diacylhydrazide substrate, luminol, to generate a quantifiable light signal. The percentage of MDM2 inhibition at a given concentration is calculated as the [1−(RLU detected in the compound treated sample−RLU negative DMSO control)÷(RLU of DMSO positive and negative controls)]×100 or as the (RLU detected in the compound treated sample÷RLU of DMSO controls)×100. The IC₅₀ was calculated using a plot of % MDM2 inhibition vs concentration and is the average of two or three independent experiments.

Western Blot Analysis

SJSA cells were treated for 6 hours with 5, 10 and 20 μM of compounds in 0.5% DMSO. The cells together with 0.5% DMSO only controls were washed with ice-cold phosphate buffered saline (PBS) and protein extracts prepared by lysing the cells in SDS buffer (62.5 mM Tris pH 6.8; 2% sodium dodecyl sulphate (SDS); 10% glycerol) with sonication for 2×5 seconds (Soniprep 150ME) to break down high molecular weight DNA and reduce the viscosity of the samples. The protein concentration of the samples was estimated using the Pierce BCA assay system (Pierce, Rockford, Ill.) and 50 μg aliquots of protein analysed using standard SDS-polyacrylamide gel electrophoresis (SDS-PAGE) and Western immunoblotting procedures. β-mercaptoethanol (5%) and bromophenol blue (0.05%) were added and the samples, which were then boiled for 5 minutes, followed by brief centrifugation, before loading onto a pre-cast 4-20% gradient Tris-Glycine buffered SDS-polyacrylamide gel (Invitrogen). Molecular weight standards (SeeBlue™, Invitrogen) were included on every gel and electrophoresis was carried out in a Novex XL tank (Invitrogen) at 180 volts for 90 minutes. The separated proteins were transferred electrophoretically overnight from the gel onto a Hybond C nitrocellulose membrane (Amersham) using a BioRad electrophoresis tank and 25 mM Tris, 190 mM glycine and 20% methanol transfer buffer at 30 volts or two hours at 70 volts. Primary antibodies used for immunodetection of the transferred proteins were: mouse monoclonal NCL-p53DO-7 (Novocastra) at 1:1000; MDM2(Ab-1, clone IF2) (Oncogene) at 1:500; WAF1 (Ab-1, clone 4D10) (Oncogene) at 1:100; Actin (AC40) (Sigma) at 1:1000. The secondary antibody used was peroxidase conjugated, affinity purified, goat anti-mouse (Dako) at 1:1000. Protein detection and visualisation was performed by enhanced chemiluminescence (ECL™ Amersham) with light detection by exposure to blue-sensitive autoradiography film (Super RX, Fuji).

Protocol A: SJSA-1 and SN40R2 Assays

The MDM2 amplified cell lines tested were an isogenic matched pair of p53 wild-type and mutated osteosarcoma (SJSA-1 and SN40R2, respectively). All cell cultures were grown in RPMI 1640 medium (Gibco, Paisley, UK) supplemented with 10% fetal calf serum and routinely tested and confirmed negative for *mycoplasma* infection. The growth of cells and its inhibition was measured using the sulphorhodamine B (SRB) method as previously outlined. 100 µl of $3\times10^4$/ml and $2\times10^4$/ml SJSA-1 and SN40R2 cells, respectively, were seeded into 96-well tissue culture plates and incubated at 37° C. in a 5% $CO_2$ humidified incubator for 24 hrs, after which the medium was replaced with 100 µl of test medium containing a range of MDM2-p53 antagonist concentrations and incubated for a further 72 hrs to allow cell growth before adding 25 µL of 50% trichloroacetic acid (TCA) to fix the cells for 1 h at 4° C. The TCA was washed off with distilled water and 100 µL of SRB dye (0.4% w/v in 1% acetic acid) (Sigma-Aldrich, Poole, Dorset) added to each well of the plate. Following incubation with the SRB dye at room temperature for 30 min, the plates were washed with 1% acetic acid and left to dry. The SRB stained protein, which is a measure of the number of cells in a well, was then resuspended in 100 µL of 10 mM Tris-HCl (pH 10.5) and the absorbance at λ=570 nm measured in each well using a FluoStar Omega Plate reader. The $GI_{50}$ was calculated by non-linear regression analysis of the data using Prism v4.0 statistical software.

Protocol B: SJSA-1 and SN40R2 Assays

The CellTiter-Glo® Luminescent Cell Viability Assay is a homogeneous method to determine the number of viable cells in culture based on quantitation of the ATP present, which signals the presence of metabolically active cells. Both SJSA-1 and SN40R2 were grown in RPMI 1640 (Life Technologies #61870) supplemented with 10% FBS (PAA #A15-204) and 10 U/ml penicillin/streptomycin. 2000 cells in 75 µl were seeded in each well of a 96 well plate and left at 37° C. in a 5% $CO_2$ humidified incubator for 24 hrs. A range of MDM2-p53 antagonist concentrations in DMSO was then added to the cells to a final DMSO concentration of 0.3%, and incubated for a further 72 hrs to allow cell growth. 100 µl of CTG reagent (Promega #G7573) was added to all wells and luminescence was measured on the topcount. The $EC_{50}$ values were determined from a sigmoidal 4 parameter curve fit using XLfit in conjunction with Activity Base (IDBS; Guildford, Surrey, UK).

Anti-Proliferative Activity

Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds (in 0.1% DMSO v/v) fora further 72 hours. At the end of the incubation period 10% (v/v) Alamar Blue is added and incubated for a further 6 hours prior to determination of fluorescent product at 535 nM ex/590 nM em. The anti-proliferative activities of compounds of the invention can be determined by measuring the ability of the compounds to inhibit growth in cancer cell lines for example as available from DSMZ, ECACC or ATCC.

Results: First Set of Examples Wherein Cyc is Phenyl

TABLE 1 biological data obtained from assays as described herein

| Patent Example | MDM2 IC50 (µM) | SJSA-1 IC50 (µM) (Protocol A) | SJSA1 IC50 (µM) (Protocol B) | SN40R2 IC50 (µM) (Protocol A) | SN40R2 IC50 (µM) (Protocol B) |
|---|---|---|---|---|---|
| 1 | 0.012 | 0.49 | 0.55 | 18 | 10% at 10 |
| 2 | 0.0046 | 0.33 | 0.46 | 17 | 22% at 10 |
| 3 | 0.093 | | | | |
| 4 | 0.043 | | | | |
| 5 | 0.14 | | | | |
| 6 | 0.12 | | | | |
| 7 | 0.0066 | | | | |
| 8 | 0.0047 | 0.33 | | 18 | |
| 9 | 0.011 | | | | |
| 10 | 0.0037 | 0.14 | | 7.5 | |
| 11 | 0.033 | | | | |
| 12 | 0.0058 | 0.51 | 0.69 | 5.9 | |
| 13 | 0.12 | 4.6 | | 5.9 | |
| 14 | 0.0050 | 0.83 | 0.49 | 10% at 30 | 9% at 10 |
| 15 | 0.019 | | | | |
| 16 | 0.14 | 2.1 | | 13 | |
| 17 | 0.063 | 0.95 | | 8.1 | |
| 18 | 0.045 | 0.80 | | 18 | |
| 19 | 0.022 | 0.62 | 2.0 | 13 | 13 |
| 20 | 0.011 | 0.33 | | 11 | |
| 21 | 0.0078 | 0.23 | 0.39 | 15 | 51% at 10 |
| 22 | 0.0052 | 0.21 | | 18 | |
| 24 | 0.0075 | 0.37 | 0.63 | 21 | 19% at 10 |
| 25 | 0.0072 | 0.71 | 1.1 | 25 | 14% at 10 |
| 26 | 0.032 | 1.7 | | 17 | |
| 27 | 0.065 | 2.1 | | 29% at 30 | |
| 28 | 0.026 | 0.93 | | 26% at 30 | |
| 29 | 0.11 | 1.4 | | 17 | |
| 30 | 0.086 | 2.4 | | 27 | |
| 31 | 0.038 | 1.2 | | 18 | |
| 32 | | 0.87 | | 15 | |
| 33 | 0.0019 | 9.1 | | 7% at 30 | |
| 34 | 0.0046 | 0.093 | | 9.9 | |
| 35 | 0.0018 | 0.16 | 0.69 | 23 | 13 |
| 36 | 0.0019 | 0.078 | | 17 | |
| 37 | 0.041 | 1.2 | | 13 | |
| 38 | 0.026 | 0.67 | | 17 | |
| 39 | 0.068 | 2.0 | | 18 | |
| 40 | 0.063 | 1.5 | | 17 | |
| 41 | 0.0016 | 0.14 | | 13 | |
| 42 | 34%@0.00030 | 0.011 | 0.03 | 12 | 10 |
| 43 | 47%@0.0010 | 0.57 | | 12 | |
| 44 | 0.0058 | 0.83 | | 6.8 | |
| 45 | 0.23 | | | | |
| 46 | 10.78 | | | | |
| 47 | 0.43 | | | | |
| 48 | 0.0073 | 0.46 | 0.97 | 17 | 24% at 10 |
| 49 | 0.082 | 1.6 | | 18 | |
| 50 | 0.00080 | 0.079 | 0.032 | 17 | 22% at 10 |
| 51 | 0.13 | | | | |
| 52 | 0.15 | 1.8 | | | |
| 53 | 0.12 | 1.9 | | | |
| 54 | 0.15 | | | | |
| 55 | | 1.7 | | 11 | |

TABLE 1-continued biological data obtained from assays as described herein

| Patent Example | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
|---|---|---|---|---|---|
| 56 | 0.12 | | | | |
| 57 | 0.061 | 1.4 | | 16 | |
| 58 | 0.018 | 0.59 | | 15 | |
| 59 | 0.0041 | 0.25 | | 19 | |
| 60 | 0.014 | | | | |
| 61 | 0.016 | 0.69 | | 44% at 30 | |
| 62 | 0.0023 | 0.055 | | 55% at 30 | |
| 63 | 71%@0.0010 | | 0.096 | | 19% at 10 |
| 64 | 0.0021 | | | | |
| 65 | 0.0018 | | 0.26 | | |
| 66 | 0.0030 | | | | |
| 67 | 60%@0.0010 | | 0.53 | | 9.4 |
| 68 | 0.0070 | | 1.8 | | 13 |
| 69 | 0.00070 | 0.081 | 0.16 | 15 | 6.6 |
| 70 | 0.0057 | | 0.68 | | 4.9 |
| 71 | 0.0020 | 0.66 | 0.7 | 44 | 3% at 10 |
| 72 | 0.0015 | 0.14 | 0.17 | 16 | 45% at 10 |
| 73 | 0.012 | | 3.6 | | 39% at 30 |
| 74 | 0.00050 | 0.28 | 1.0 | 28 | 13 |
| 75 | 73%@0.0010 | 0.12 | 0.35 | 22 | 12 |
| 76 | 0.0095 | | 1.0 | | 13 |
| 77 | 61%@0.00030 | | 0.46 | | 3.7 |
| 78 | 0.0046 | 0.41 | 1.4 | 5.9 | 4.2 |
| 79 | 0.0022 | | 8.1 | | 10% at 30 |
| 80 | 73%@0.0010 | | 0.83 | | 13 |
| 81 | 0.0026 | | | | |
| 82 | 0.0025 | 0.21 | | 51% at 30 | |
| 83 | 0.0010 | | 0.53 | | 11 |
| 84 | 39%@0.00030 | 0.065 | | 18 | |
| 85 | 0.00049 | | 0.049 | | 13 |
| 86 | 56%@0.10 | | | | |
| 87 | 82%@0.0030 | | 37% at 10 | | 1% at 10 |
| 88 | 0.00079 | 0.15 | 0.23 | 39 | 11% at 10 |
| 89 | 0.012 | | 3.6 | | 3% at 10 |
| 90 | 39%@0.030 | | 97% at 10 | | 6% at 10 |
| 91 | 78%@0.0010 | 0.080 | 0.059 | 26 | 13% at 10 |
| 92 | 76%@0.0010 | 0.080 | 0.084 | 36 | 12% at 10 |
| 93 | 49%@0.030 | | 3.3 | | 12% at 10 |
| 94 | 64%@0.10 | | | | |
| 95 | 87%@0.0010 | 0.036 | 0.022 | 16 | 21% at 10 |
| 96 | 0.00064 | 0.071 | 0.075 | 19 | 17% at 10 |
| 97 | 45%@0.10 | | | | |
| 98 | 0.0008 | 0.081 | 0.13 | 33 | 11% at 10 |
| 99 | 0.012 | | 3.2 | | 4% at 10 |
| 100 | 0.0063 | | 1.7 | | 7% at 10 |
| 101 | 55%@0.00030 | 0.026 | 0.026 | 18 | 11% at 3 |
| 102 | 0.017 | | 1.4 | | 26% at 10 |
| 103 | 55%@0.030 | | 0.8 | | 18% at 10 |
| 104 | 70%@0.10 | | 42% at 10 | | 5% at 10 |
| 105 | 92%@0.0010 | 0.022 | 0.05 | 33 | 20% at 10 |
| 106 | 57%@0.030 | | 3.2 | | 8% at 10 |
| 107 | 78%@0.0010 | 0.021 | 0.038 | 24 | 18% at 10 |
| 108 | 0.0061 | | 27% at 10 | | 29% at 10 |
| 109 | 92%@0.0010 | 0.012 | 0.02 | 26 | 75% at 10 |
| 110 | 76%@0.0010 | 0.026 | 0.013 | 17 | 30% at 10 |
| 111 | 61%@0.0010 | 0.024 | 0.037 | 9 | 51% at 10 |
| 113 | 57%@0.0010 | | 0.02 | | 10% at 10 |
| 114 | 81%@0.0010 | 0.029 | 0.063 | 20 | 15% at 10 |
| 115 | 73%@0.0010 | | 0.22 | | 2% at 10 |
| 116 | 88%@0.0010 | 0.08 | 0.14 | 44 | 12% at 10 |
| 117 | 45% at 0.03 | | 30% at 10 | | 19% at 10 |
| 118 | 87%@0.0010 | | 0.36 | | 8% at 10 |
| 119 | 54%@0.0010 | 0.06 | 0.2 | 39 | 7% at 10 |
| 120 | 76%@0.0010 | 0.063 | 0.095 | 40% at 50 | 4% at 10 |
| 121 | 93%@0.0010 | 0.015 | 0.015 | 26 | 18% at 10 |
| 122 | 88%@0.0010 | | 0.024 | | 20% at 10 |
| 123 | 42%@0.030 | | 107% at 10 | | 16% at 10 |
| 124 | 80%@0.0010 | 0.023 | 0.027 | 23 | 55% at 10 |
| 125 | 18%@0.10 | | | | |
| 126 | 0.0019 | 0.6 | 0.61 | 30 | 7% at 10 |
| 127 | 0.0045 | | 1.4 | | 14% at 10 |
| 128 | 39%@0.10 | | | | |
| 129 | 90%@0.0010 | 0.047 | 0.048 | 6 | 112% at 10 |
| 130 | 98%@0.0010 | | 0.23 | | 87% at 10 |
| 131 | 89%@0.0010 | 0.044 | 0.093 | 22 | −3% at 10 |
| 132 | 43%@0.030 | | 0.75 | | 34% at 10 |
| 133 | 6%@0.10 | | 37% at 10 | | 89% at 10 |
| 134 | 0.0011 | | 0.78 | | 2% at 10 |
| 135 | 40%@0.10 | | 20% at 10 | | 7% at 10 |
| 136 | 0.0013 | | 0.056 | | 86% at 10 |
| 137 | 0.00057 | | 0.15 | | 12% at 10 |

Where more than one data point has been obtained, the table above shows an average (e.g. geometric or arithmetic mean) of these data points.

It is of course to be understood that the invention is not intended to be restricted to the details of the above embodiments which are described by way of example only.

Results: Second Set of Examples Wherein cyc is Het

Results

TABLE 2 biological data obtained from assays as described herein

| E.g. | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
|---|---|---|---|---|---|
| 7 | 0.0036 | 0.11 | 0.34 | 26 | 8% at 10 |
| 8 | 0.053 | 2.0 | 3.8 | 34% at 30 | 11% at 10 |
| 6 | 0.023 | 1.7 | 2.5 | 13% at 30 | 4% at 10 |
| 9 | 0.015 | 0.82 | | 32% at 30 | |
| 93 | 0.030 | 1.0 | | 40% at 30 | |
| 31 | 0.017 | 0.55 | 0.76 | 20% at 30 | 0% at 10 |
| 1 | 0.0020 | 0.088 | 0.2 | 24 | 14% at 10 |
| 94 | 0.10 | 2.4 | | 15% at 30 | |
| 2 | 0.026 | 1.7 | 3.4 | 38% at 30 | 10% at 10 |
| 47 | 0.12 | 1.6 | | 24 | |
| 46 | 0.016 | 0.59 | 0.76 | 42% at 30 | 13% at 10 |
| 10 | 0.016 | 0.32 | | 6% at 30 | |
| 44 | 0.015 | 0.28 | | 24 | |
| 61 | 0.11 | 0.86 | | 26% at 30 | |
| 62 | 0.041 | 0.75 | | 29% at 30 | |
| 5 | 0.0038 | 0.20 | 0.28 | 20% at 30 | 7% at 10 |
| 38 | 0.0094 | 0.64 | | 15% at 30 | |
| 39 | 0.0044 | 0.17 | | 3% at 30 | |
| 45 | 0.0084 | 0.23 | | 27 | |
| 63 | 0.032 | 0.57 | | 27 | |
| 11 | 0.0087 | 0.23 | 0.46 | 15% at 30 | |
| 32 | 0.0012 | 0.089 | 0.14 | 27 | 9% at 10 |
| 12 | 0.046 | 1.5 | | 0% at 30 | |
| 33 | 0.010 | 0.61 | | 31% at 30 | |
| 13 | 0.0077 | 0.52 | 0.73 | 24 | 21% at 10 |
| 48 | 0.018 | 0.60 | 0.56 | 4% at 30 | −3% at 10 |
| 64 | 0.040 | 0.75 | | 3% at 30 | |
| 95 | 0.060 | 2.0 | | 19 | |
| 34 | 0.085 | 0.97 | 2.2 | 14% at 30 | 20% at 30 |
| 16 | 0.030 | 0.27 | | 24% at 30 | |
| 17 | 0.0038 | 0.10 | 0.21 | 29% at 30 | |
| 3 | 0.12 | 0.96 | | 7% at 30 | 9% at 30 |
| 14 | 0.029 | 0.55 | | 13% at 30 | |
| 15 | 0.0068 | 0.21 | | 22% at 30 | |
| 54 | 0.10 | 2.2 | | 25 | |
| 59 | 0.034 | 0.70 | | 34% at 30 | |
| 4 | 0.010 | 0.23 | 0.24 | 24% at 30 | 9% at 10 |
| 49 | 0.040 | 0.38 | | 18% at 30 | |
| 60 | 0.020 | 0.55 | | 27 | |
| 18 | 0.020 | 0.51 | | 20% at 30 | |

TABLE 2-continued biological data obtained from assays as described herein

| E.g. | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
|---|---|---|---|---|---|
| 19 | 0.0027 | 0.069 | | 20% at 30 | |
| 65 | 0.021 | 0.41 | | 24 | |
| 35 | 0.010 | 0.45 | 0.8 | 8% at 30 | 6% at 10 |
| 42 | 0.010 | 0.45 | 0.60 | 29% at 30 | 14% at 10 |
| 43 | 0.026 | 0.49 | 0.48 | 16% at 30 | 13% at 10 |
| 40 | 0.046 | 0.81 | 1.0 | 2% at 30 | 9% at 10 |
| 41 | 0.013 | 0.32 | 0.47 | 15% at 30 | 8% at 10 |
| 37 | 0.035 | 0.26 | | 25 | 12 |
| 50 | 0.0088 | 0.23 | | 24 | |
| 96 | 0.14 | | | | |
| 51 | 0.69 | | | | |
| 22 | 0.0018 | 0.16 | 0.059 | 19 | 13 |
| 23 | 0.0074 | 0.55 | | 17 | |
| 36 | 0.0051 | 0.21 | 0.18 | 13% at 30 | |
| 74 | 0.015 | 0.31 | | 24 | |
| 28 | 0.014 | 0.19 | | 44% at 30 | |
| 55 | 0.49 | | | | |
| 56 | 0.021 | 0.33 | | 24 | |
| 30 | 0.017 | 0.30 | | 0% at 30 | |
| 24 | 0.0077 | 0.24 | | 42% at 30 | |
| 25 | 0.0018 | 0.054 | 0.090 | 26 | 13% at 10 |
| 26 | 0.027 | 0.58 | | 28 | |
| 27 | 42%@0.0030 | 0.24 | 0.71 | 23 | 11% at 10 |
| 52 | 0.031 | 0.25 | | 15% at 30 | |
| 87 | 0.031 | 0.71 | | 19 | |
| 77 | 0.076 | 2.2 | | 48% at 30 | |
| 78 | 0.026 | 0.77 | | 26 | |
| 53 | 0.12 | | | | |
| 29 | 0.012 | 0.39 | 0.52 | 16% at 30 | 25% at 30 |
| 20 | 0.026 | 1.6 | | 4% at 30 | |
| 21 | 0.0052 | 0.27 | | 10% at 30 | |
| 119 | 0.018 | 0.53 | | 47% at 30 | |
| 118 | 0.034 | 0.67 | | 39% at 30 | |
| 79 | 0.0046 | 0.12 | 0.38 | 25 | 2% at 10 |
| 97 | 0.013 | 0.37 | | 24 | |
| 98 | 0.018 | 0.43 | | 23 | |
| 73 | 0.082 | 1.8 | | 0% at 30 | |
| 75 | 0.0045 | 0.14 | 0.47 | 29 | 15% at 10 |
| 70 | 0.0032 | 0.21 | | 48% at 30 | |
| 76 | 0.0065 | 0.54 | | 20 | |
| 71 | 0.082 | 5.3 | | 33% at 30 | |
| 124 | 0.093 | 1.9 | | 2% at 30 | |
| 122 | 0.033 | 0.68 | | 9.9 | |
| 123 | 0.0098 | 0.23 | | 21 | |
| 120 | 0.085 | 1.9 | | 39% at 30 | |
| 121 | 0.023 | 0.55 | | 28% at 30 | |
| 104 | 52%@1.0 | | | | |
| 105 | 0.015 | 0.40 | | 9.8 | |
| 67 | 0.029 | 0.71 | | 36% at 30 | |
| 85 | 0.0017 | 0.10 | | 34% at 30 | |
| 86 | 0.15 | | | | |
| 110 | 55%@1.0 | | | | |
| 111 | 0.059 | 2.0 | | 29 | |
| 106 | 0.52 | 5.2 | | 24 | |
| 107 | 0.016 | 0.38 | | 29 | |
| 108 | 0.79 | 8.2 | | 16 | |
| 109 | 0.11 | 1.7 | 3.5 | 18 | 24% at 10 |
| 114 | 0.12 | 2.0 | | 10% at 30 | |
| 115 | 81%@0.10 | 5.2 | | 13% at 30 | |
| 82 | 0.027 | 0.62 | | 32% at 30 | |
| 83 | 41%@0.0010 | 0.038 | | 36% at 30 | |
| 66 | 0.0099 | 0.51 | 0.73 | 18 | 13 |
| 89 | 0.011 | 0.45 | | 23% at 30 | |
| 90 | 0.00064 | 0.046 | | 24% at 30 | |
| 112 | 0.18 | 5.4 | | 15% at 30 | |
| 113 | 0.0069 | 0.50 | | 13% at 30 | |
| 84 | 0.022 | 1.3 | | 23% at 30 | |
| 99 | 35%@1.0 | | | | |
| 100 | 0.016 | 0.47 | | 38% at 20 | |
| 101 | 0.013 | 0.28 | | 25% at 30 | |
| 72 | 0.0086 | 0.36 | | 35% at 30 | |
| 81 | 0.11 | | | | |
| 91 | 41%@0.15 | | | | |
| 92 | 0.0059 | 0.24 | | 21 | |
| 102 | 37%@0.30 | | | | |
| 103 | 0.022 | 0.43 | | 9.5 | |
| 68 | 0.0016 | 3.2 | | 19% at 30 | |
| 69 | 0.0081 | 7.6 | | 32% at 30 | |
| 57 | 44%@0.30 | | | | |
| 58 | 0.0053 | 0.23 | | 24 | |
| 88 | 0.028 | 1.5 | | 12% at 30 | |
| 125 | 0.10 | | | | |
| 126 | 0.015 | | | | |
| 116 | 48%@0.10 | | | | |
| 117 | 0.0078 | 0.26 | | 26 | |
| 419 | 0.018 | 0.70 | | 21% at 30 | |
| 318 | 11%@0.025 | | | | |
| 319 | 0.0076 | 0.16 | | 14 | |
| 327 | 42%@0.30 | 9.3 | | 9% at 30 | |
| 328 | 42%@0.10 | 2.3 | | 25 | |
| 329 | 61%@0.30 | 3.0 | | 8% at 30 | |
| 330 | 36%@0.30 | 7.1 | | 18% at 30 | |
| 381 | 33%@0.30 | 46% at 10 | | 17 | |
| 382 | 0.036 | 0.82 | | 18 | |
| 383 | 31%@0.30 | 6.6 | | 18 | |
| 384 | 39%@0.030 | 0.36 | | 16 | |
| 157 | 39%@0.30 | 6.4 | | 30% at 30 | |
| 158 | 57%@0.10 | 1.2 | | 30% at 30 | |
| 242 | 35%@0.30 | 6.3 | | 6.2 | |
| 243 | 0.018 | 0.63 | | 5.8 | |
| 245 | 51%@0.30 | 7.4 | | 16 | |
| 241 | 0.012 | 0.58 | | 8.9 | |
| 239 | 0.015 | | | | |
| 248 | 37%@0.30 | | | | |
| 247 | 0.022 | 0.76 | | 18 | |
| 238 | 41%@0.30 | 52% at 10 | | 19 | |
| 246 | 37%@0.30 | 7.6 | | 18 | |
| 237 | 0.013 | 0.55 | | 16 | |
| 244 | 36%@0.30 | 40% at 10 | | 18 | |
| 240 | 0.032 | 0.91 | | 17 | |
| 159 | 0.031 | 1.2 | | 24 | |
| 160 | 43%@0.30 | | | | |
| 167 | 0.011 | 0.64 | | 19% at 30 | |
| 253 | 53%@1.0 | | | | |
| 253a | 0.035 | 0.85 | | 29 | |
| 252 | 41%@0.30 | | | | |
| 249 | 0.013 | 0.51 | | 34% at 30 | |
| 251 | 61%@1.0 | | | | |
| 250 | 0.0072 | 1.6 | | 18 | |
| 320 | 0.0060 | 2.7 | | 24 | |
| 321 | 0.0027 | 1.4 | | 22 | |
| 258 | 50%@1.0 | | | | |
| 257 | 0.12 | 1.9 | | 29% at 30 | |
| 256 | 59%@1.0 | | | | |
| 255 | 0.0032 | 0.51 | | 16 | 7.1 |
| 254 | 45%@0.30 | | | | |
| 259 | 0.0097 | 0.96 | | 5.5 | |
| 127 | 45%@0.0033 | 0.38 | | 20% at 30 | |
| 134 | 47%@0.30 | | | | |
| 135 | 0.049 | 1.6 | | 38% at 30 | |
| 323 | 46%@0.64 | | | | |
| 324 | 0.028 | 0.57 | | 23 | |
| 260 | 39%@1.0 | | | | |
| 261 | 0.048 | 0.65 | | 19 | |
| 169 | 0.0046 | 0.26 | | 43 | |
| 170 | 4%@0.10 | | | | |
| 275 | 43%@0.30 | | | | |
| 262 | 0.033 | 0.47 | | 22 | |
| 233 | 37%@1.0 | | | | |
| 234 | 0.015 | 0.38 | | 21 | |
| 128 | 0.11 | 2.4 | | 23 | |
| 129 | 0.0047 | 0.24 | | 21 | |
| 263 | 45%@1.0 | | | | |
| 264 | 0.043 | 0.67 | | 8.0 | |

TABLE 2-continued biological data obtained from assays as described herein

| E.g. | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
|---|---|---|---|---|---|
| 235 | 40%@1.0 | | | | |
| 236 | 0.041 | 0.72 | | 28 | |
| 316 | 0.0072 | 0.86 | | 17% at 30 | |
| 317 | 0.0016 | 0.19 | | 36% at 50 | |
| 377 | 0.11 | | | | |
| 378 | 52%@0.30 | | | | |
| 376 | 0.0040 | | 0.32 | | 18% at 10 |
| 302 | 63%@0.10 | 5.3 | | 9% at 30 | |
| 303 | 0.0016 | 0.55 | | 13% at 30 | |
| 268 | 45%@1.0 | | | | |
| 266 | 0.015 | | | | |
| 267 | 42%@1.0 | | | | |
| 265 | 0.044 | | | | |
| 289 | 0.012 | | | | |
| 291 | 45%@0.0010 | | | | |
| 292 | 0.021 | | | | |
| 172 | 0.13 | | | | |
| 171 | 0.14 | | | | |
| 270 | 33%@1.0 | | | | |
| 269 | 0.16 | | | | |
| 290 | 0.0025 | | | | |
| 168 | 0.039 | | | | |
| 175 | 0.0061 | | | | |
| 176 | 0.0010 | | | | |
| 379 | 52%@1.0 | | | | |
| 271 | 0.014 | | | | |
| 380 | 59%@1.0 | | | | |
| 274 | 0.0097 | | | | |
| 309 | 0.0023 | | | | |
| 273 | 47%@1.0 | | | | |
| 272 | 0.0088 | | | | |
| 177 | 47%@0.030 | | | | |
| 178 | 0.00079 | 0.16 | 0.10 | 43% at 50 | 18% at 30 |
| 145 | 0.21 | | | | |
| 147 | 44%@0.10 | | | | |
| 310 | 53%@0.0010 | | | | |
| 173 | 0.025 | | | | |
| 146 | 0.081 | | | | |
| 148 | 0.035 | | | | |
| 153 | 0.015 | | | | |
| 154 | 0.014 | | | | |
| 287 | 0.0031 | | | | |
| 151 | 32%@0.30 | | | | |
| 152 | 0.30 | | | | |
| 149 | 53%@1.0 | | | | |
| 150 | 49%@0.10 | | | | |
| 345 | 0.0037 | | | | |
| 346 | 46%@0.00030 | 0.031 | 0.012 | 20 | 12 |
| 288 | 0.046 | | | | |
| 281 | 58%@0.10 | | | | |
| 280 | 0.0063 | | | | |
| 131 | 0.092 | | | | |
| 130 | 0.0057 | | 0.17 | | 8% at 10 |
| 285 | 41%@0.10 | | | | |
| 284 | 0.0025 | | 0.017 | | 12% at 30 |
| 132 | 51%@0.30 | | | | |
| 133 | 33%@1.0 | | | | |
| 305 | 0.0015 | | 1.9 | | 32% at 30 |
| 282 | 0.0021 | | 0.061 | | 5% at 30 |
| 283 | 57%@0.10 | | | | |
| 304 | 0.0022 | | 0.36 | | 9.0 |
| 161 | 0.016 | | 4.3 | | 28% at 30 |
| 162 | 0.0022 | | 0.22 | | 13 |
| 308 | 0.044 | | | | |
| 136 | 0.037 | | 1.4 | | 13 |
| 137 | 0.0016 | 0.20 | 0.27 | 21 | 11 |
| 306 | 55%@0.030 | | 6.6 | | 13 |
| 199 | 49%@0.030 | | 0.83 | | 16% at 30 |
| 200 | 0.00071 | 0.066 | 0.099 | 40 | 21% at 30 |
| 189 | 0.013 | | 1.0 | | 47% at 30 |
| 190 | 0.037 | | 5.0 | | 19% at 30 |
| 205 | 0.0012 | 0.18 | 0.22 | 34 | 12 |
| 206 | 0.0015 | | 0.45 | | 13 |
| 207 | 56%@0.10 | | 2.2 | | 13 |
| 307 | 62%@0.030 | | 1.9 | | 11 |
| 315 | 0.46 | | 12 | | 13 |
| 163 | 0.042 | | 3.1 | | 13 |
| 164 | 0.034 | | 2.2 | | 28% at 30 |
| 165 | 0.017 | | 1.4 | | 13 |
| 166 | 48%@0.010 | | 3.8 | | 33% at 30 |
| 208 | 0.027 | | 2.3 | | 24% at 30 |
| 298 | 0.00066 | 0.22 | 0.55 | 7.6 | 8.9 |
| 299 | 0.0096 | | 2.0 | | 8.0 |
| 191 | 0.048 | | 2.5 | | 11 |
| 192 | 0.0021 | | 1.4 | | 11 |
| 420 | 68%@0.0010 | 0.49 | 0.87 | 17 | 4.4 |
| 301 | 75%@0.0010 | 0.070 | 0.036 | 28 | 12 |
| 286 | 0.0041 | | 0.68 | | 12 |
| 293 | 0.0011 | 0.11 | 0.37 | 35 | 45% at 30 |
| 209 | 0.0041 | 0.59 | 0.45 | 22% at 50 | 17% at 30 |
| 210 | 46%@0.030 | | | | 17% at 30 |
| 187 | 0.0055 | | 0.89 | | 5% at 10 |
| 188 | 49%@0.10 | | | | |
| 294 | 0.00093 | | 0.077 | | 23% at 10 |
| 197 | 0.00062 | | 0.21 | | 2% at 10 |
| 198 | 0.0050 | | | | |
| 211 | 0.0010 | 0.28 | 0.36 | 41% at 50 | 5% at 10 |
| 212 | 54%@0.030 | | | | |
| 202 | 72%@0.0010 | 0.064 | 0.11 | 24 | 13% at 10 |
| 201 | 0.0029 | | 0.76 | | 9% at 10 |
| 194 | 0.0033 | | | | |
| 193 | 0.00077 | 0.13 | 0.14 | 34 | 11% at 10 |
| 144 | 0.0021 | | 2.9 | | 3% at 10 |
| 300 | 60%@0.0010 | | | | |
| 179 | 48%@0.030 | | | | |
| 180 | 0.00095 | | 0.16 | | 14% at 10 |
| 295 | 0.00093 | | | | |
| 138 | 0.0044 | | 0.56 | | 18% at 10 |
| 139 | 42%@0.030 | | | | |
| 156 | 0.0011 | | 0.25 | | 9% at 10 |
| 213 | 0.0021 | 0.26 | 0.25 | 42% at 50 | 3% at 10 |
| 343 | 49%@0.10 | | | | |
| 203 | 0.0012 | 0.10 | 0.080 | 19% at 50 | 7% at 10 |
| 204 | 0.012 | | 0.94 | | −1% at 10 |
| 214 | 0.0014 | 0.26 | 0.22 | 12% at 50 | 0% at 10 |
| 215 | 51%@0.030 | | | | |
| 311 | 0.0026 | | 0.25 | | 11% at 10 |
| 312 | 57%@0.030 | | | | |
| 216 | 0.0032 | | 0.28 | | 1% at 10 |
| 217 | 52%@0.10 | | | | |
| 181 | 42%@0.010 | | | | |
| 182 | 0.0013 | | 0.88 | | 6% at 10 |
| 140 | 0.00070 | | 0.23 | | |
| 141 | 0.017 | | 1.8 | | |
| 142 | 0.00073 | | 0.23 | | |
| 143 | 0.0043 | | 0.86 | | |
| 277 | 0.0012 | | 1.2 | | 5% at 10 |
| 276 | 0.0036 | | 2.5 | | 33% at 10 |
| 279 | 0.00097 | | 0.57 | | 17% at 10 |
| 278 | 0.0034 | | 2.6 | | 18% at 10 |
| 196 | 0.0013 | 0.11 | 0.15 | 27% at 50 | 7% at 10 |
| 218 | 0.00086 | 0.22 | 0.43 | 31% at 50 | 4% at 10 |
| 219 | 0.00095 | 0.087 | 0.11 | 33 | 8% at 10 |
| 220 | 0.0081 | | 0.60 | | 14% at 10 |
| 296 | 62%@0.0010 | 0.11 | 0.16 | 32 | 12% at 10 |
| 195 | 0.0055 | | 0.61 | | 4% at 10 |
| 221 | 0.033 | | 2.2 | | 3% at 10 |
| 222 | 80%@0.0010 | 0.064 | 0.099 | 36 | 14% at 10 |
| 223 | 0.0026 | | 0.52 | | 8% at 10 |
| 324 | 0.0048 | | 2.2 | | 2% at 10 |
| 224 | 0.00070 | 0.078 | 0.12 | 47 | 6% at 10 |
| 226 | 0.0095 | | 0.57 | | 3% at 10 |
| 225 | 48%@0.030 | | 1.8 | | 9% at 10 |
| 347 | 63%@0.10 | | 1.7 | | |

TABLE 2-continued biological data obtained from assays as described herein

| E.g. | MDM2 IC50 (µM) | SJSA-1 IC50 (µM) (Protocol A) | SJSA1 IC50 (µM) (Protocol B) | SN40R2 IC50 (µM) (Protocol A) | SN40R2 IC50 (µM) (Protocol B) |
|---|---|---|---|---|---|
| 325 | 0.0013 | | 0.24 | | |
| 227 | 0.0048 | | 0.29 | | 8% at 10 |
| 228 | 61%@0.010 | | 0.21 | | |
| 174 | 0.0038 | | | | |
| 183 | 0.0042 | | 0.43 | | 4% at 10 |
| 184 | 0.00092 | | 0.14 | | 8% at 10 |
| 372 | 52%@0.10 | | 2.6 | | |
| 373 | 0.0023 | | 0.26 | | 12% at 10 |
| 297 | 0.0026 | | 0.76 | | 5% at 10 |
| 229 | 51%@0.10 | | 1.4 | | |
| 230 | 0.0055 | | 0.22 | | 0% at 10 |
| 344 | 0.010 | | 1.9 | | 0% at 10 |
| 231 | 0.0028 | | 0.33 | | 5% at 10 |
| 232 | 50%@0.10 | | 2.3 | | 5% at 10 |
| 185 | 47%@0.010 | | 2.2 | | 8% at 10 |
| 186 | 0.0089 | | 0.42 | | 2% at 10 |
| 313 | 0.0028 | | 0.95 | | 2% at 10 |
| 314 | 52%@0.010 | | 66% at 10 | | 9% at 10 |
| 155 | 0.0094 | | 0.31 | | |
| 353 | 69%@0.0010 | 0.19 | 0.27 | 44% at 50 | 6% at 10 |
| 352 | 0.0055 | | 1.1 | | 13% at 10 |
| 385 | 0.0061 | | 0.45 | | 5% at 10 |
| 354 | 0.0013 | 0.16 | 0.34 | 36 | 8% at 10 |
| 421 | 0.00084 | | 0.59 | | 5% at 10 |
| 357 | 0.0015 | | 0.30 | | 10% at 10 |
| 360 | 0.0032 | | 0.74 | | 9% at 10 |
| 358 | 74%@0.0010 | | 0.039 | | 9% at 10 |
| 359 | 50%@0.10 | | 3.9 | | 6% at 10 |
| 389 | 41%@0.10 | | 4.2 | | 9% at 10 |
| 390 | 0.0035 | | 0.63 | | 11% at 10 |
| 391 | 0.0066 | | 0.66 | | 2% at 10 |
| 350 | 54%@0.030 | | 0.51 | | 2% at 10 |
| 351 | 25%@0.10 | | 4.3 | | 5% at 10 |
| 405 | 0.010 | | 0.63 | | 6% at 10 |
| 406 | 54%@0.10 | | 3.9 | | 11% at 10 |
| 418 | 0.00081 | 0.12 | 0.28 | 25 | 8% at 10 |
| 326 | 50%@0.030 | | 2.0 | | 16% at 10 |
| 407 | 62%@0.0010 | | 0.58 | | −9% at 10 |
| 408 | 0.0011 | | 0.75 | | 5% at 10 |
| 409 | 0.0019 | 0.28 | 0.41 | 12% at 50 | 5% at 10 |
| 395 | 44%@0.030 | | | | |
| 396 | 0.0044 | | 0.28 | | 9% at 10 |
| 392 | 45%@0.10 | | | | |
| 340 | 56%@0.10 | | 2.0 | | |
| 348 | 0.0026 | | 0.27 | | 5% at 10 |
| 349 | 79%@0.0010 | 0.042 | 0.028 | 44 | 6% at 10 |
| 341 | 0.0023 | 0.53 | 0.50 | 15% at 30 | −0% at 10 |
| 386 | 0.00065 | 0.034 | 0.019 | 45 | 6% at 10 |
| 331 | 49%@0.030 | | | | |
| 403 | 52%@0.030 | | 1.2 | | 2% at 10 |
| 397 | 49%@0.030 | | 2.5 | | 7% at 10 |
| 422 | 0.0032 | | 1.1 | | |
| 404 | 0.0018 | 0.16 | 0.095 | 25 | 12% at 10 |
| 355 | 16%@0.10 | | 4.7 | | |
| 356 | 0.0059 | 1.1 | 0.96 | 17% at 50 | 5% at 10 |
| 410 | 0.0022 | | 0.19 | | 4% at 10 |
| 411 | 0.00093 | 0.11 | 0.077 | 40 | 6% at 10 |
| 412 | 0.0023 | | 0.27 | | 8% at 10 |
| 413 | 0.0020 | 0.22 | 0.24 | 41 | 12% at 10 |
| 398 | 0.0023 | 0.58 | 0.58 | 16% at 50 | 4% at 10 |
| 423 | 0.0020 | 0.24 | 0.25 | 34 | |
| 416 | 0.0011 | 0.17 | 0.15 | 19 | 25% at 10 |
| 417 | 0.0052 | | 0.41 | | 16% at 10 |
| 332 | 60%@0.030 | | 2.6 | | 5% at 10 |
| 414 | 60%@0.0030 | | 0.11 | | |
| 415 | 0.00084 | | 0.24 | | |
| 393 | 0.0065 | | 0.79 | | |
| 394 | 18%@0.10 | | | | |
| 424 | 45%@0.0030 | | 0.69 | | |
| 338 | 50%@0.030 | | 1.5 | | 6% at 10 |
| 337 | 48%@0.00010 | 0.051 | 0.058 | 46 | 7% at 10 |
| 361 | 0.0039 | | 0.78 | | 8% at 10 |
| 362 | 52%@0.10 | | | | |
| 425 | 0.0019 | | 0.74 | | 7% at 10 |
| 399 | 50%@0.00030 | | 11% at 10 | | 2% at 10 |
| 400 | 0.0031 | | 1.1 | | 4% at 10 |
| 363 | 48%@0.10 | | | | |
| 364 | 0.0055 | | 0.47 | | 9% at 10 |
| 333 | 0.0044 | | 0.22 | | 5% at 10 |
| 334 | 42%@0.10 | | 73% at 10 | | 4% at 10 |
| 365 | 0.0011 | 0.067 | 0.10 | 33% at 50 | −0% at 10 |
| 366 | 0.19 | | 2.7 | | 2% at 10 |
| 335 | 51%@0.10 | | 2.8 | | 7% at 10 |
| 336 | 56%@0.0010 | 0.10 | 0.16 | 42 | 4% at 10 |
| 401 | 37%@0.00030 | 0.0089 | 0.0098 | 36 | 6% at 10 |
| 402 | 0.0043 | | 0.21 | | 5% at 10 |
| 367 | 0.0026 | 0.22 | 0.11 | 46 | 1% at 10 |
| 368 | 27%@0.10 | | 52% at 10 | | 6% at 10 |
| 371 | 43%@0.030 | | 2.3 | | 3% at 10 |
| 374 | 0.00090 | 0.64 | 0.85 | 26% at 50 | 2% at 10 |
| 375 | 37%@0.10 | | | | |
| 387 | 42%@0.10 | | | | |
| 388 | 0.0021 | 0.066 | 0.23 | 39 | 4% at 10 |
| 369 | 0.00061 | 0.058 | 0.062 | 18% at 50 | 5% at 10 |
| 370 | 51%@0.10 | | 3.5 | | 0% at 10 |
| 339 | 0.00051 | | 0.21 | | 3% at 10 |
| 342 | 25%@0.10 | | 21% at 10 | | 4% at 10 |
| 428 | 65%@0.0010 | 0.11 | 0.19 | 22 | 12% at 10 |
| 429 | 65%@0.10 | | | | |
| 430 | 59%@0.0010 | 0.11 | 0.18 | 33% at 50 | 4% at 10 |
| 431 | 48%@0.0010 | 0.11 | 0.16 | 39% at 50 | 5% at 10 |
| 432 | 45%@0.030 | | 6.2 | | 8% at 10 |
| 443 | 58%@0.0010 | 0.11 | 0.093 | 38 | 3% at 10 |
| 444 | 63%@0.10 | | | | |
| 433 | 0.011 | | 1.5 | | 20% at 30 |
| 434 | 0.0013 | | 0.47 | | 7% at 10 |
| 448 | 84%@0.0010 | | 0.86 | | 48% at 30 |
| 445 | 43%@0.0010 | | 3.3 | | 16% at 10 |
| | 56%@0.10 | | | | |
| 446 | 76%@0.0010 | 0.018 | 0.023 | 29 | 13% at 10 |
| 447 | 74%@0.0010 | | 0.011 | | 10% at 10 |
| 435 | 66%@0.0010 | | 0.015 | | 0% at 10 |
| 436 | 53%@0.10 | | | | |
| 426 | 0.00072 | 0.22 | 0.32 | 29% at 50 | 4% at 10 |
| 427 | 41%@0.10 | | | | |
| 437 | 51%@0.030 | | 2.5 | | −4% at 10 |
| 438 | 0.0016 | | 0.34 | | 2% at 10 |
| 439 | 85%@0.0010 | 0.045 | 0.030 | 46% at 50 | 3% at 10 |
| 440 | 0.012 | | 1.9 | | 7% at 10 |
| 449 | 78%@0.0010 | 0.041 | 0.012 | 18 | 19% at 10 |
| 450 | 76%@0.0010 | | 0.38 | | 15% at 10 |
| 441 | 0.012 | | 1.5 | | 1% at 10 |
| 442 | 0.0034 | 0.42 | 0.50 | 26% at 50 | 6% at 10 |
| 451 | 0.078 | | | | |
| 452 | 0.15 | | | | |
| 453 | 0.094 | | | | |
| 454 | 0.035 | | | | |
| 455 | 58%@1.0 | | | | |
| 456 | 0.21 | | | | |
| 457 | 53%@0.30 | | | | |
| 458 | 44%@0.010 | | | | 12 |
| 459 | 0.0020 | | 6.4 | | 7% at 10 |
| 460 | 0.48 | | | | |
| 461 | 0.00053 | 0.075 | 0.091 | 19% at 50 | 6% at 10 |
| 462 | 80%@0.0010 | 0.073 | 0.047 | 37% at 50 | 4% at 10 |
| 463 | 73%@0.10 | | | | |
| 464 | 0.0019 | | 0.18 | | 46% at 10 |
| 465 | 29%@0.10 | | | | |
| 466 | 0.00086 | 0.21 | 0.14 | 41% at 50 | 4% at 10 |
| 467 | 36%@0.10 | | | | |
| 468 | 0.0035 | | 0.48 | | 2% at 10 |
| 469 | 52%@0.030 | | | | |
| 470 | 0.001 | | 0.1 | | 3% at 10 |
| 471 | 38%@0.10 | | 3.5 | | 2% at 10 |

TABLE 2-continued biological data obtained from assays as described herein

| E.g. | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
|---|---|---|---|---|---|
| 472 | 48%@0.0030 |  | 0.39 |  | 10% at 10 |
| 473 | 44%@0.10 |  | 104% at 10 |  | 11% at 10 |
| 474 | 38%@0.030 |  | 1.3 |  | 12% at 10 |
| 475 | 71%@0.0010 | 0.028 | 0.022 | 46% at 50 | 7% at 10 |
| 476 | 51%@0.030 |  | 0.6 |  | 4% at 10 |
| 477 | 86%@0.0010 | 0.013 | 0.0091 |  | 5% at 10 |
| 478 | 58%@0.10 |  | 81% at 10 |  | -0% at 10 |
| 479 | 0.0006 |  | 0.079 |  | 2% at 10 |
| 480 | 67%@0.10 |  | 3.7 |  | 2% at 10 |
| 481 | 0.0014 |  | 0.33 |  | 8% at 10 |
| 483 | 58%@0.0010 |  | 0.2 |  | 9% at 10 |
| 485 | 58%@0.10 |  | 4.2 |  | 3% at 10 |
| 486 | 59%@0.0010 | 0.075 | 0.051 | 10% at 50 | 7% at 10 |
| 493 | 0.00054 | 0.038 | 0.02 | 25 | 11% at 10 |
| 494 | 0.013 |  |  |  |  |
| 495 | 0.0011 | 0.068 | 0.054 | 34% at 50 | 7% at 10 |
| 496 | 56%@0.10 |  | 1.8 |  | -0% at 10 |
| 500 | 21%@0.10 |  | 16% at 10 |  | 6% at 10 |
| 501 | 0.0031 | 0.015 | 0.022 | 6.4 | 8% at 3.0 |
| 502 | 18%@0.10 |  | 4.9 |  | 11% at 10 |
| 503 | 87%@0.0010 |  | 0.011 |  | 13% at 10 |
| 505 | 60%@0.0010 |  | 0.027 |  | 5% at 10 |
| 506 | 36%@0.030 |  | 3.4 |  | 2% at 10 |
| 507 | 65%@0.0030 |  | 0.02 |  | 5% at 3 |
| 508 | 17%@0.10 |  | 11% at 10 |  | 9% at 10 |
| 509 | 0.00094 |  | 0.042 |  | 6% at 10 |
| 510 | 79%@0.0010 | 0.084 | 0.073 | 5% at 50 | 9% at 10 |
| 511 | 72%@0.0010 |  | 0.018 |  | 10% at 10 |
| 512 | 0.00048 | 0.053 | 0.025 | 27% at 50 | 5% at 10 |
| 514 |  |  | 0.64 |  | 3% at 10 |
| 516 | 0.0012 |  | 0.038 |  | 4% at 10 |
| 517 | 82%@0.0010 | 0.019 | 0.01 | 26% at 50 | 5% at 10 |
| 518 | 79%@0.0010 | 0.058 | 0.065 | 46% at 50 | 10% at 10 |
| 519 | 35%@0.030 |  | 1.9 |  | 12% at 10 |
| 520 | 32%@0.030 |  | 3.9 |  | 5% at 10 |
| 521 | 77%@0.0010 | 0.035 | 0.033 | 37 | 11% at 10 |
| 524 | 0.021 |  | 1.1 |  | 35% at 10 |
| 525 | 50%@0.0010 | 0.17 | 0.078 | 17 | 40% at 10 |
| 526 | 0.0013 | 0.11 | 0.11 |  | 9% at 10 |
| 527 | 0.017 |  | 1.4 |  | 14% at 10 |
| 528 | 0.0029 |  | 0.32 |  | 10% at 10 |
| 530 | 0.0031 |  | 0.39 |  | 2% at 10 |
| 531 | 42%@0.10 |  | 4.3 |  | 8% at 10 |
| 532 | 0.0031 |  | 0.14 |  | 7% at 10 |
| 533 | 44%@0.10 |  | 4 |  | 20% at 10 |
| 534 | 0.0088 |  | 0.7 |  | 44% at 10 |
| 535 | 65%@0.0010 | 0.05 | 0.058 | 18 | 45% at 10 |
| 536 | 64%@0.0010 |  | 0.13 |  | 46% at 10 |
| 522 | 0.0007 | 0.053 | 0.048 | 19 | 24% at 10 |
| 523 | 50%@0.030 |  | 1.5 |  | 29% at 10 |
| 537 |  |  | 0.76 |  | 45% at 10 |
| 538 | 44%@0.030 |  | 2.2 |  | 43% at 10 |
| 539 | 41%@0.0010 |  | 0.092 |  | 38% at 10 |
| 540 | 33%@0.030 |  | 1.8 |  | 62% at 10 |
| 541 | 64%@0.00030 | 0.19 | 0.014 | 13 | 10 |
| 542 | 57%@0.010 |  | 3.1 |  | -1% at 10 |
| 543 | 68%@0.0010 |  | 0.69 |  | -6% at 10 |
| 544 | 86%@0.0010 | 0.032 | 0.041 | 7.4 | 109% at 10 |
| 545 | 94%@0.0010 |  | 0.094 |  | 4% at 3 |
| 546 | 86%@0.0010 |  | 0.7 |  | 17% at 10 |
| 547 | 82%@0.0010 |  | 0.96 |  | 4% at 10 |
| 548 | 82%@0.0010 | 0.14 | 0.17 | 6.3 | 111% at 10 |
| 549 | 85%@0.0010 |  | 0.27 |  | 33% at 10 |
| 553 | 0.0006 |  | 0.065 |  | 24% at 10 |
| 554 | 74%@0.0010 | 0.21 | 0.07 | 46% at 50 | 11% at 10 |
| 555 | 55%@0.0010 |  | 0.079 |  | 58% at 10 |
| 556 | 91%@0.0010 | 0.056 | 0.0064 | 27 | 14% at 10 |
| 557 | 81%@0.0010 | 0.25 | 0.037 | 37% at 50 | 6% at 10 |
| 558 | 53%@0.0030 | 0.22 | 0.082 | 35 | 6% at 10 |
| 559 | 0.00062 | 0.46 | 0.052 | 22% at 50 | 1% at 10 |
| 560 | 30%@0.0010 |  | 0.13 |  | 3% at 10 |
| 561 | 47%@0.0010 | 0.021 | 0.065 | 26 | 12% at 10 |
| 562 | 0.0013 |  | 0.25 |  | 1% at 10 |
| 563 | 76%@0.0010 | 0.025 | 0.027 | 15 | 72% at 10 |
| 564 | 86%@0.0010 | 0.018 | 0.00038 | 16 | 10% at 3 |
| 565 | 65%@0.0010 | 0.045 | 0.035 | 33 | 11% at 10 |
| 566 | 47%@0.030 |  | 1.9 |  | 46% at 10 |
| 567 | 57%@0.10 |  |  |  |  |
| 568 | 76%@0.0010 |  | 0.094 |  | 36% at 10 |
| 570 | 83%@0.0010 | 0.034 | 0.046 |  | 26% at 10 |
| 571 | 77%@0.0010 | 0.023 | 0.0085 | 17 | 38% at 10 |
| 572 | 53%@0.00075 | 0.019 | 0.022 | 18 | 23% at 10 |
| 550 | 0.00098 | 0.077 | 0.056 | 17 | 33% at 10 |
| 551 | 70%@0.0010 | 0.031 | 0.026 | 36 | 13% at 10 |
| 552 | 79%@0.0010 | 0.028 | 0.02 | 21 | 7% at 10 |
| 513 | 0.0031 | 0.26 | 0.38 | 19% at 50 | 4% at 10 |
| 576 | 42%@0.0030 |  | 0.14 |  | 5% at 10 |
| 577 | 0.00093 |  | 0.079 |  | 7% at 10 |
| 491 | 0.0089 |  | 0.81 |  | 5% at 10 |
| 578 | 0.002 |  | 0.12 |  | 4% at 10 |
| 499 | 68%@0.0010 |  | 0.053 |  | 2% at 10 |
| 498 | 32%@0.10 |  | 96% at 10 |  | 4% at 10 |
| 497 | 83%@0.0010 | 0.039 | 0.046 | 45 | 10% at 10 |
| 487 | 59%@0.0010 | 0.12 | 0.025 | 27 | 12% at 10 |
| 488 | 56%@0.10 |  |  |  |  |
| 529 | 0.028 |  | 2.2 |  | 17% at 10 |
| 482 | 58%@0.10 |  | 5 |  | 3% at 10 |
| 484 |  |  | 4.9 |  | 2% at 10 |
| 574 | 45%@0.0010 | 0.021 | 0.016 | 17 | 27% at 10 |
| 575 | 38%@0.0010 | 0.028 | 0.066 | 21 | 14% at 10 |
| 504 | 71%@0.0010 | 0.039 | 0.034 | 48 | 0% at 10 |
| 492 | 31%@0.10 |  | 25% at 10 |  | 19% at 10 |
| 579 | 41%@0.030 |  | 19% at 10 |  | 4% at 10 |
| 515 | 0.0014 |  | 1.0 |  | 8% at 10 |
| 489 |  |  | 3.3 |  | -9% at 10 |
| 490 | 0.0023 |  | 0.27 |  | -0% at 10 |
| 580 |  |  | 0.014 |  | 13% at 10 |

Where more than one data point has been obtained, the table above shows an average (e.g. geometric or arithmetic mean) of these data points.

It is of course to be understood that the invention is not intended to be restricted to the details of the above embodiments which are described by way of example only.

SGI-110

A glycol/glycerin/ethanol (65:25:10) formulation, containing 100 mg/mL free base equivalent of the sodium salt of SGI-110 was administered to live animals. An analogous decitabine formulation was used for comparison (50 mg lyophilized decitabine powder vial reconstituted to 10 mg/mL with water for injection and administered as infusions by diluting in infusion bags).

Administration of a single dose of the formulations to monkeys (10 mg/kg) produced higher physiological concentrations of compound 1-1 (Cmax 1,130 ng/mL; AUC of 1,469 ng·hr/mL) than of decitabine (Cmax 160 ng/mL; AUC of 340 ng·hr/mL).

In a repeat dose study, monkeys were dosed 3x weekly subcutaneously (3 mg/kg). At day 15, the systemic exposure to compound 1-1 (Cmax 181 ng/mL; AUC of 592 ng·hr/mL) was greater than that of decitabine (Cmax 28 ng/mL; AUC of 99 ng·hr/mL). The pharmacokinetic parameters of the compounds did not vary significantly over the 22-day observation period, and minimal accumulation was detected. (see FIGS. 1 and 2 of WO 2013/033176) Pharmacodynamic properties (not shown) were monitored and were acceptable. Blood samples were drawn periodically to assay LINE-1 DNA methylation.

Decreases in LINE-1 DNA methylation, the indicator of biological activity, were observed, and the decrease continued until termination of the study on day 22. The observed LINE-1 methylation was significantly different (p<0.05) from the methylation level observed prior to initial dosing (see FIG. 3 of WO 2013/033176).

The formulation was well-tolerated in the species tested. Three regimens were evaluated: a) once daily subcutaneous dose in rats and rabbits for 5 days; b) once weekly subcutaneous dose in rabbits and cynomolgus monkeys for 28 days as tolerated; and c) twice weekly subcutaneous dose in rats for 28 days as tolerated. Rabbits tolerated the 5-day regimen well, up to a dose of 1.5 mg/kg/day, which is equivalent to 18 mg/kg/day in humans, and the weekly regimen up to a dose of 1.5 mg/kg/week for 3 weeks.

Cynomolgus monkeys tolerated the weekly regimen well, up to a dose of 3.0 mg/kg/week for 3 weeks, which is equivalent to 36 mg/kg/week. Rats tolerated much higher doses: 30 mg/kg/day over 5 days; and 20 mg/kg twice weekly for 4 weeks.

The main toxicity in all experiments was myelosuppression. However, the subcutaneous formulation tested exhibited less myelosuppression and faster recovery.

Combinations
Combination Protocol for Cell Proliferation

The effect of a compound of formula (I°) (Compound 1) in combination with an anticancer agent (Compound II) can be assessed using the following technique. Cells from human cells lines (e.g. SJSA-1) were seeded onto 96-well tissue culture plates at a concentration of $2.5 \times 10^3$, $6.0 \times 10^3$, or $4.0 \times 10^3$ cells/well respectively. Cells were allowed to recover for 24-48 hours prior to addition of compound(s) or vehicle control (0.35-0.5% DMSO) as follows:

Compounds were added concurrent for 72-96 hours. Following a total of 72-96 hours compound incubation, cells were fixed with ice-cold 10% (w/v) trichloroacetic acid for 1 hour on ice and then washed four times with $dH_2O$ using a plate washer (Labsystems Wellwash Ascent) and air-dried. Cells were then stained with 0.4% (w/v) Sulforhodamine B (Sigma) in 1% acetic acid for 20 min at room temperature and then washed four times with 1% (v/v) acetic acid and air-dried before the addition of 10 mM Tris buffer to solubilise the dye. Colourmetric product was quantified by reading at Abs490 nm or Abs570 nm on a Wallac Victor$^2$ plate reader (1420 multilabel counter, Perkin Elmer Life Sciences). The $IC_{50}$ for Compound II in the presence of varying doses of Compound I was determined. Synergy was determined when the $IC_{50}$ shifted down in the presence of sub-effective doses of Compound I. Additivity was determined when the response to Compound II and Compound I together resulted in an effect equivalent to the sum of the two compounds individually. Antagonistic effects were defined as those causing the $IC_{50}$ to shift upwards, i.e. those where the response to the two compounds was less than the sum of the effect of the two compounds individually.

Combination Protocol for Measuring Apoptosis

AML cell lines were plated out in wells of 6-well plates at $2.5 \times 10^5$ cells/ml and treated with 0.1% DMSO vehicle control, SGI-110 alone, (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid alone, or with a combination of SGI-110 and (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid. SGI-110 was added daily for three days. For the combination treatment of SGI-110 and (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, (2S,3S)-3-(4-chlorophenyl)-3-[(1R)-1-(4-chlorophenyl)-7-fluoro-5-[(1S)-1-hydroxy-1-(oxan-4-yppropyl]-1-methoxy-3-oxo-2,3-dihydro-1H-isoindol-2-yl]-2-methylpropanoic acid was added concurrently with SGI-110 on the third day and incubated for further 24 hrs in a $CO_2$ incubator at 37° C. At the end of compound treatments, cells were washed once with PBS and stained with 1 μM CellEvent Caspase-3/7 Green Detection Dye (ThermoFisher Scientific) in the dark for 30 minutes at 37° C. Percentage apoptosis was measured as percentage fluorescent cells with cleaved caspase-3 in a Guava easyCyte HT cytometer (Millipore). Cleaved caspase-3 staining was recorded in the FL1 channel, with unstained and DMSO control wells being used to set the gated stained and unstained cell populations.

Table 1 summarises the % apoptosis seen in Molm-13, MV-4-11, or ML-2 with the indicated compound treatments.

TABLE 1

Percentage cells apoptotic after incubation with the indicated compounds

| Cell lines | Compounds | % Apoptosis |
|---|---|---|
| Molm-13 | Vehicle control | 8.72 |
| | 10 nM SGI-110 | 36.08 |
| | 20 nM (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid | 32.48 |
| | 10 nM SGI-110 and 20 nM (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid | 89.14 |
| MV-4-11 | Vehicle control | 13.69 |
| | 10 nM SGI-110 | 26.12 |
| | 20 nM (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid | 30.83 |
| | 10 nM SGI-110 and 20 nM (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid | 52.41 |
| ML-2 | Vehicle control | 3.32 |
| | 10 nM SGI-110 | 3.93 |
| | 100 nM (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid | 15.15 |
| | 10 nM SGI-110 and 100 nM (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid | 32.7 |

Combination Protocol for Proliferation in Dose Matrix

AML cell lines were seeded onto 96-well tissue culture plates in triplicates at a concentration of $1 \times 10^4$ cells/well. Cells were allowed to recover for 16-24 hours prior to adding SGI-110 at a range of concentrations (0.003-3 μM). Following 24 hr incubation with SGI-110, (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid was added at a range of concentrations (0.001-10 μM) and incubated for additional 48 hrs. At the end of compound treatment, 20 μl Alamar blue was added. After further 5-6 hr incubation at 37° C. the plates were read on a Spectramax Gemini reader (Molecular Devices; excitation 535 nm, emission 590 nm). Viability was calculated as percentage of DMSO vehicle control and synergy between various dose combinations of SGI-110 and (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid was identified based on the HAS Synergy Model.

FIG. 1 shows percentage viability relative to the DMSO control at various dose combinations of SGI-110 and (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid.

FIG. 1: Percentage Viability Relative to DMSO Control Following SGI-110 and (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic Acid Combination Treatment Molm-13:
(2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (µM)

| SGI-110 (µM) | 0 | 0.001 | 0.003 | 0.01 | 0.03 | 0.1 | 0.3 | 1 | 3 | 10 |
|---|---|---|---|---|---|---|---|---|---|---|
| 0 | 100 | 98 | 99 | 84 | 52 | 37 | 27 | 24 | 22 | 15 |
| 0.003 | 96 | 96 | 89 | 68 | 33 | 25 | 18 | 16 | 16 | 14 |
| 0.01 | 84 | 76 | 68 | 41 | 27 | 18 | 14 | 12 | 12 | 10 |
| 0.03 | 72 | 66 | 55 | 35 | 23 | 17 | 13 | 12 | 12 | 10 |
| 0.1 | 53 | 41 | 35 | 27 | 18 | 13 | 11 | 10 | 11 | 9 |
| 0.3 | 39 | 31 | 29 | 23 | 16 | 13 | 10 | 10 | 10 | 9 |
| 1 | 31 | 25 | 24 | 19 | 14 | 11 | 10 | 9 | 10 | 8 |
| 3 | 22 | 23 | 22 | 18 | 13 | 11 | 10 | 10 | 9 | 8 |

MV-4-11:
(2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (µM)

| SGI-110 (µM) | 0 | 0.001 | 0.003 | 0.01 | 0.03 | 0.1 | 0.3 | 1 | 3 | 10 |
|---|---|---|---|---|---|---|---|---|---|---|
| 0 | 100 | 92 | 82 | 70 | 54 | 29 | 16 | 13 | 13 | 12 |
| 0.003 | 92 | 80 | 71 | 56 | 43 | 27 | 16 | 13 | 13 | 13 |
| 0.01 | 89 | 68 | 62 | 50 | 37 | 23 | 15 | 13 | 13 | 13 |
| 0.03 | 89 | 64 | 58 | 47 | 35 | 22 | 14 | 13 | 13 | 12 |
| 0.1 | 83 | 65 | 58 | 47 | 37 | 22 | 14 | 13 | 13 | 12 |
| 0.3 | 76 | 57 | 53 | 45 | 36 | 22 | 14 | 13 | 13 | 12 |
| 1 | 60 | 51 | 47 | 41 | 33 | 21 | 14 | 13 | 13 | 12 |
| 3 | 50 | 49 | 46 | 38 | 32 | 22 | 14 | 12 | 12 | 12 |

ML-2:
(2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (µM)

| SGI-110 (µM) | 0 | 0.001 | 0.003 | 0.01 | 0.03 | 0.1 | 0.3 | 1 | 3 | 10 |
|---|---|---|---|---|---|---|---|---|---|---|
| 0 | 100 | 100 | 94 | 78 | 59 | 47 | 30 | 16 | 15 | 9 |
| 0.003 | 94 | 96 | 85 | 69 | 52 | 38 | 23 | 14 | 13 | 10 |
| 0.01 | 92 | 91 | 77 | 59 | 47 | 31 | 19 | 13 | 12 | 9 |
| 0.03 | 87 | 82 | 68 | 53 | 45 | 30 | 19 | 13 | 12 | 9 |
| 0.1 | 78 | 78 | 65 | 51 | 43 | 29 | 20 | 14 | 13 | 8 |
| 0.3 | 74 | 72 | 62 | 51 | 43 | 29 | 19 | 14 | 13 | 8 |
| 1 | 61 | 58 | 55 | 48 | 44 | 29 | 21 | 15 | 14 | 8 |
| 3 | 45 | 45 | 45 | 41 | 36 | 26 | 19 | 15 | 14 | 8 |

Pharmaceutical Formulations Examples (i) Tablet Formulation

A tablet composition containing a compound of the invention is prepared by mixing an appropriate amount of the compound (for example 50-250 mg) with an appropriate diluent, disintegrant, compression agent and/or glidant. One possible tablet comprises 50 mg of the compound with 197 mg of lactose (BP) as diluent, and 3 mg magnesium stearate as a lubricant and compressing to form a tablet in known manner. The compressed tablet may be optionally film coated.

(ii) Capsule Formulation

A capsule formulation is prepared by mixing 100-250 mg of a compound of the invention with an equivalent amount of lactose and filling the resulting mixture into standard hard gelatin capsules. An appropriate disintegrant and/or glidant can be included in appropriate amounts as required.

(iii) Injectable Formulation I

A parenteral composition for administration by injection can be prepared by dissolving a compound of the invention (e.g. in a salt form) in water containing 10% propylene glycol to give a concentration of active compound of 1.5% by weight. The solution is then made isotonic, sterilised by filtration or by terminal sterilisation, filled into an ampoule or vial or pre-filled syringe, and sealed.

(iv) Injectable Formulation II

A parenteral composition for injection is prepared by dissolving in water a compound of the invention (e.g. in salt form) (2 mg/ml) and mannitol (50 mg/ml), sterile filtering the solution or by terminal sterilisation, and filling into sealable 1 ml vials or ampoules or pre-filled syringe.

(v) Injectable formulation III

A formulation for i.v. delivery by injection or infusion can be prepared by dissolving the compound of the invention (e.g. in a salt form) in water at 20 mg/ml and then adjusted for isotonicity. The vial is then sealed and sterilised by autoclaving or filled into an ampoule or vial or pre-filled syringe, sterilised by filtration and sealed.

(vi) Injectable formulation IV

A formulation for i.v. delivery by injection or infusion can be prepared by dissolving the compound of the invention (e.g. in a salt form) in water containing a buffer (e.g. 0.2 M acetate pH 4.6) at 20 mg/ml. The vial, ampoule or pre-filled syringe is then sealed and sterilised by autoclaving or sterilized by filtration and sealed.

(vii) Subcutaneous or Intramuscular Injection Formulation

A composition for sub-cutaneous or intramuscular administration is prepared by mixing a compound of the invention with pharmaceutical grade corn oil to give a concentration of 5-50 mg/ml. The composition is sterilised and filled into a suitable container.

(viii) Lyophilised formulation I

Aliquots of formulated compound of the invention are put into 50 ml vials and lyophilized. During lyophilisation, the compositions are frozen using a one-step freezing protocol at (−45° C.). The temperature is raised to 10° C. for annealing, then lowered to freezing at 45° C., followed by primary drying at +25° C. for approximately 3400 minutes, followed by a secondary drying with increased steps if temperature to 50° C. The pressure during primary and secondary drying is set at 80 millitorr.

(ix) Lyophilised formulation II

Aliquots of formulated compound of the invention or a salt thereof as defined herein are put into 50 mL vials and lyophilized. During lyophilisation, the compositions are frozen using a one-step freezing protocol at (−45° C.). The temperature is raised to 10° C. for annealing, then lowered to freezing at 45° C., followed by primary drying at +25° C. for approximately 3400 minutes, followed by a secondary drying with increased steps if temperature to 50° C. The pressure during primary and secondary drying is set at 80 millitorr.

(x) Lyophilised Formulation for use in i.v. administration III

An aqueous buffered solution is prepared by dissolving a compound of the invention in a buffer. The buffered solution is filled, with filtration to remove particulate matter, into a container (such as a Type 1 glass vial) which is then partially sealed (e.g. by means of a Fluorotec stopper). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. The solution is freeze dried using a suitable cycle. On completion of the freeze drying cycle the vials are back filled with nitrogen to atmospheric pressure, stoppered and secured (e.g. with an aluminium crimp). For intravenous administration, the freeze dried solid can be reconstituted with a pharmaceutically acceptable diluent, such as 0.9% saline or 5% dextrose. The solution can be dosed as is, or can be diluted further into an infusion bag (containing a pharmaceutically acceptable diluent, such as 0.9% saline or 5% dextrose), before administration.

(xii) Powder in a Bottle

A composition for oral administration is prepared by filling a bottle or vial with a compound of the invention. The composition is then reconstituted with a suitable diluent for example water, fruit juice, or commercially available vehicle such as OraSweet or Syrspend. The reconstituted solution may be dispensed into dosing cups or oral syringes for administration.

SGI-110: Preparation of a Kit

First Vessel: SGI-110 for Injection, 100 mg

The sodium salt of the compound of the formula:

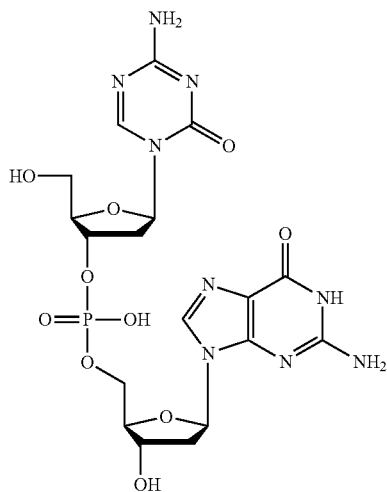

I-1

(also referred to herein as "SGI-110") was prepared as described in U.S. Pat. No. 7,700,567 (the content of which is hereby incorporated by reference—see in particular column 41, final two paragraphs) by coupling Is (where $R_1$=carbamate protective group) with phosphoramidite building block 1d:

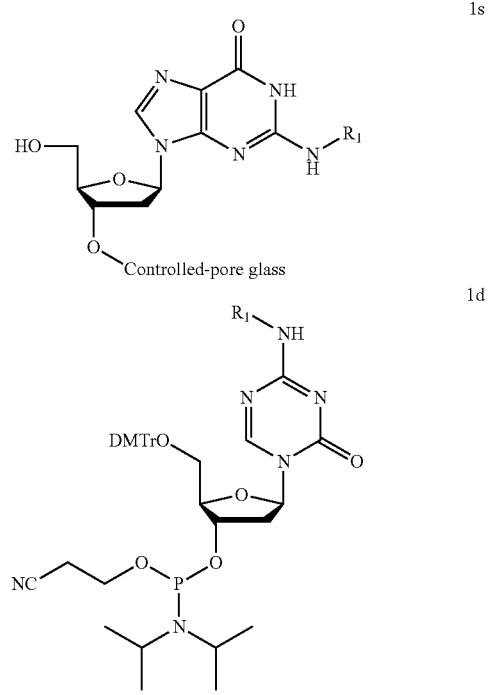

A protected 2'-deoxyguanosine-linked CPG solid support Is (where $R_1$=tert-butyl phenoxyacetyl) is coupled with 2-2.5 equivalents of phenoxyacetyl decitabine phosphoramidite (1d, where $R_1$=phenoxyacetyl) in the presence of 60% of 0.3 M benzylthiotetrazole activator (in acetonitrile) for 10 minutes. The CPG solid support containing protected DpG dinucleotide is treated with 20 mL of 50 mM $K_2CO_3$ in methanol for 1 hour and 20 minutes. The coupled product is oxidized, protective group removed, washed, filtered, and purified by the ÄKTA Explorer 100 HPLC with a Gemini C18 preparative column (Phenomenex), 250×21.2 mm, 10 μm with guard column (Phenomenex), 50×21.2 mm, 10 μm, with 50 mM triethylammonium acetate (pH 7) in MilliQ water (Mobile Phase A) and 80% acetonitrile in MilliQ water (Mobile Phase B), with 2% to 20/25% Mobile Phase B in column volumes.

The ESI-MS (-ve) of DpG dinucleotide 2b:

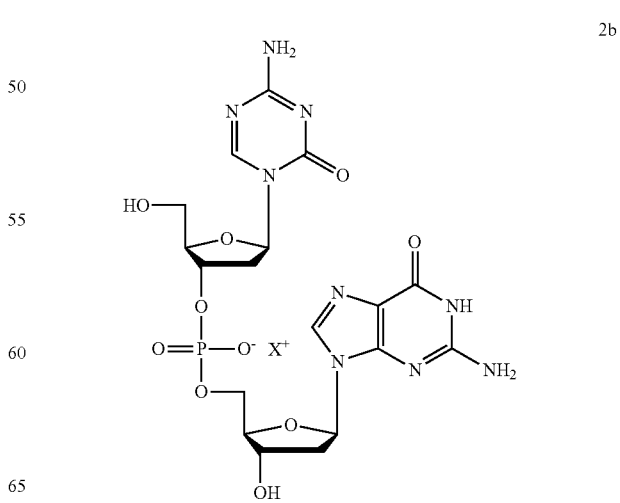

where $X^+$=triethylammonium (calculated exact mass for the neutral compound $C_{18}H_{24}N_9O_{10}P$ is 557.14), exhibited m/z 556.1 $[M-H]^-$ and 1113.1 for $[2M-H]^-$ (see mass spectrum in FIG. 31 of U.S. Pat. No. 7,700,567).

The sodium salt of the compound of formula I-1 (i.e. DpG dinucleotide 2b, where $X^+$=sodium; SGI-110) is obtained by re-dissolving the triethylammonium salt in 4 ml water, 0.2 ml 2M $NaClO_4$ solution. When 36 mL acetone is added, the dinucleotide precipitates. The solution is kept at −20° C. for several hours and centrifugated at 4000 rpm for 20 minutes. The supernatant is discarded and the solid is washed with 30 mL acetone followed by an additional centrifugation at 4000 rpm for 20 minutes. The precipitate is dissolved in water and freeze dried, which exhibited m/z 556.0 $[M-H]^-$ (see mass spectrum in FIG. 36 of U.S. Pat. No. 7,700,567).

Compounding and Filling of Bulk Formulation

Based on the assay value of SGI-110 lot, needed quantities of SGI-110 and DMSO are calculated and weighed appropriately for the intended batch scale.

2. SGI-110 is dissolved in DMSO utilizing an overhead mixer in an appropriately sized stainless steel (SS) vessel.

3. Upon complete solubilization of the drug in DMSO, samples of the bulk solution are tested using a UV or HPLC in-process method to determine that the amount of SGI-110 is within 95-105% of the target concentration.

4. Bulk solution is filtered through a series of two pre-sterilized 0.2 micron sterilizing filters that are DMSO compatible, and collected into a 2 L SS surge vessel.

Filtration rate is continuously adjusted by visual monitoring of quantity available for filling in the surge vessel.

One gram of the filtered bulk solution is filled into each of the 5 cc depyrogenated, clear glass vials and the operation is continued with until all of the filtered bulk solution is filled.

Each vial is automatically and partially stoppered on the fill line with a fluoropolymer coated, chlorobutyl rubber lyo stopper that is pre-sterilized.

Product vials are transferred to lyophilizer under aseptic transfer conditions for initiation of lyophilization cycle.

Lyophilization and Capping of Vials

Vials are lyophilized using the cycle parameters as below.

| Freezing | Primary/Secondary Drying | | | | | Final Set point (stoppering conditions) |
|---|---|---|---|---|---|---|
| Temperature | −40° C. | −5° C. | 10° C. | 30° C. | 60° C. | 25° C. |
| Ramp time (min) | 133 | 117 | 50 | 67 | 100 | — |
| Time (min.) | 360 | 1440 | 1440 | 1440 | 1440 | hold |
| Vacuum (mTorr) | (note: 100 mT for evacuation at −50° C.) | 100 | 100 | 50 | 50 | 50 mT before back fill |

2. Upon completion of the lyo cycle, lyophilizer is back filled with nitrogen, and the vials are completely and automatically stoppered.

3. Vials are aseptically transferred to an isolator where each of the vials is automatically capped with a blue aluminum flip-off cap.

4. Vials are visually inspected before proceeding with sampling for release testing, and the labeling and packaging operation. Vials are kept at 2-8° C. until ready.

Labeling and Packaging

Each vial is labeled per approved content, and packaged individually into heat-sealed aluminum foil pouch with a desiccant under vacuum. The foil pouch is labeled outside with the same label as was used for the product vial. Labeled and packaged vials are stored at 2-8° C. until further distribution.

Residual DMSO

Four batches of the same scale of 3000 vials/batch were prepared using the same process as described above. DMSO was consistently removed to the following residual levels to yield a solid white powder, demonstrating that lyophilization of SGI-110 out of DMSO as described above yields a safe and chemically stable SGI-110 powder:

| # | DMSO in mg/vial |
|---|---|
| Batch 1 | 25 |
| Batch 2 | 28 |
| Batch 3 | 27 |
| Batch 4 | 29 |

Second Vessel: SGI-110 Diluent for Reconstitution, 3 mL

Compounding and Filling of Bulk Formulation

Calculated quantities (see table below) of propylene glycol, ethanol, and glycerin in the aforementioned order are added into an appropriately sized stainless steel vessel equipped with an overhead mixer.

| | % of each ingredient | Grade | Function |
|---|---|---|---|
| Propylene glycol | 65 | NF, PhEur | Solvent |
| Glycerin | 25 | NF, PhEur | solvent |
| Alcohol/Ethanol | 10 | USP, PhEur | Thinning agent |

2. Intermittent mixing during addition of components is followed by at least 30 minutes of mixing to yield a well-mixed solution.

3. Bulk solution is filtered through a series of two pre-sterilized 0.2 micron compatible sterilizing filters, and collected into a 2 L SS surge vessel.

4. Filtration rate is adjusted by visual monitoring of quantity available for filling in the surge vessel.

At least 3.15 g, equivalent to 3.0 mL, of the filtered bulk solution is filled into each of the 5 cc depyrogenated, clear glass vials followed by automatic stoppering using fluoropolymer coated chlorobutyl rubber closures.

Stoppered vials are capped with sterilized white aluminum flip-off caps. Vials are visually inspected prior to sampling for the release testing and labeling operation and are stored at 2-30° C. until ready.

Labeling and Packaging

Each diluent vial is labeled per approved content. Labeled vials are stored at 2-30° C. until further distribution.

SGI-110: Preparation of Lyophilised Formulation

The sodium salt of SGI-110 was dissolved in DMSO at a defined concentration using an overhead mixer in an appropriately sized stainless steel (SS) vessel. Upon complete solubilization of the drug in DMSO, samples of the bulk solution were tested using a UV or HPLC in-process method to determine that the amount of the sodium salt of the compound of formula I was within 95-105% of the target concentration. The bulk solution was filtered through a series of two pre-sterilized 0.2 micron sterilizing filters that were DMSO-compatible, and collected into a 2 L SS surge vessel. The filtration rate was continuously adjusted by visual monitoring of quantity available for filling in the surge vessel. One gram aliquots of the filtered bulk solution were then filled into 5 cc depyrogenated, clear glass vials. Each vial was automatically and partially stopped on the fill line with a fluoropolymer coated, chlorobutyl rubber lyo stopper that was pre-sterilized. The product vials were transferred to a lyophilizer under aseptic transfer conditions for initiation of a lyophilization cycle. The lyophilizer used was a pilot scale lyophilizer, Lyobeta 35, IMA-Telstar, which has 1.02 m$^2$ of chamber space, an ice capacity of 35 kg, 22 kg/24 hr for condenser capacity.

Vials containing the solution were lyophilized using the cycle parameters set out below:

TABLE

Lyophilization cycle operating parameters

| Stage | Event | T (° C.) | P | Time (h) |
|---|---|---|---|---|
| | Load | 5 | Atm | 0.0 |
| First freezing stage | Ramp temperature | −45 | Atm | 1.0 |
| First freezing stage | Hold temperature | −45 | Atm | 1.5 |
| First warming stage | Ramp temperature | 0 | Atm | 1.3 |
| First warming stage | Hold temperature | 0 | Atm | 2.0 |
| Second freezing stage | Ramp temperature | −45 | Atm | 2.0 |
| Second freezing stage | Hold temperature | −45 | Atm | 2.0 |
| Primary drying stage | Decrease and hold pressure | −45 | 6 μbar | 4.0 |
| Primary drying stage | Ramp temperature | −20 | 6 μbar | 3.0 |
| Primary drying stage | Hold temperature | −20 | 6 μbar | 12.0 |
| Primary drying stage | Ramp temperature | −5 | 6 μbar | 3.0 |
| Primary drying stage | Hold temperature | −5 | 6 μbar | 24.0 |
| Secondary drying stage | Ramp temperature | 65 | 6 μbar | 6.0 |
| Secondary drying stage | Hold temperature | 65 | 6 μbar | 15.0 |

Upon completion of the lyophilization cycle, the lyophilizer was back-filled with nitrogen, and the vials were completely and automatically stoppered. Vials were aseptically transferred to an isolator where each of the vials was automatically capped with a blue aluminum flip-off cap. Vials were visually inspected before proceeding with sampling for release testing, and the labeling and packaging operation. Vials were kept at 2-8° C. until ready. Each vial was labeled for its content.

The invention claimed is:
1. A combination comprising:
(i) a compound of formula (I°):

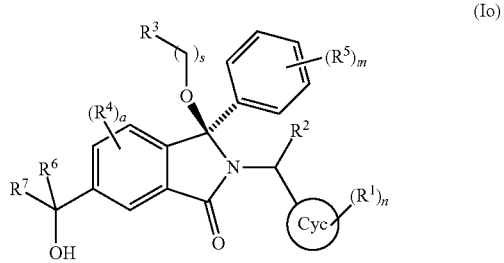

(Io)

or a tautomer or a solvate or a pharmaceutically acceptable salt thereof, wherein:

wherein cyc is phenyl or a heterocyclic group Het which is pyridinyl, pyrimidinyl, pyrazinyl or pyridazinyl, or an N-oxide thereof;

$R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, —$O_{0-1}$—$(CR^xR^y)_v$—$CO_2H$, —$(CR^xR^y)_v$—$CO_2C_{1-4}$alkyl, —$(CRxR^{31})_v$—$CON(C_{1-4}$alkyl$)_2$, —$P(=O)(R^x)_2$, —$S(O)_d$—$R^x$, —$S(O)_d$-heterocyclic group with 3 to 6 ring members and —$S(O)_d$—$N(R^8)_2$, wherein when cyc is Het then $R^1$ is attached to a carbon atom;

$R^2$ is selected from hydrogen, $C_{1-4}$alkyl, $C_{2-6}$alkenyl, hydroxy$C_{1-4}$alkyl, —$(CRxR^{31})_u$—$CO_2H$, —$(CR^xR^y)_u$—$CO_2C_{1-4}$alkyl, and —$(CR^xR^y)_u$—$CONR^xR^y$;

s is selected from 0 and 1;

$R^3$ is hydrogen or -(A)$_t$-(CR$^x$R$^y$)$_q$—X;

t is selected from 0 and 1;

q is selected from 0, 1 and 2;

wherein when $R^3$ is -(A)$_t$-(CR$^x$R$^y$)$_q$—X then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more heteroatoms selected from N, O, S and oxidised forms thereof;

X is selected from hydrogen, halogen, —CN, —$OR^9$, —$(CH_2)_v$—$CO_2H$, —$(CH_2)_v$—$CO_2C_{1-4}$alkyl, —$S(O)_d$—$R^x$, —$C(=O)$—$C_{1-4}$alkyl, —$S(O)_d$—$N(H)_e(C_{1-4}$alkyl$)_{2-e}$, —$NR^xR^y$, —$NHSO_2R^x$, —$NR^xCOR^y$, and —$C(=O)NR^xR^y$;

$R^4$ and $R^5$ are independently selected from halogen, nitrile, $C_{1-4}$alkyl, halo$C_{1-4}$alkyl, $C_{1-4}$alkoxy and halo$C_{1-4}$alkoxy;

$R^6$ and $R^1$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —$COOC_{1-6}$alkyl, —$(CH_2)_j$—$O$—$C_{1-6}$alkyl, —$(CH_2)_j$—$O$-(hydroxy$C_{1-6}$alkyl), —$C_{1-6}$alkyl-$NR^xR^y$, —$(CR^xR^y)_p$—$CONR^xR^y$, —$(CR^xR^y)_p$—$NR^xCOR^y$, —$(CR^xR^y)_p$—$O$—$CH_2$—$CONR^xR^y$, heterocyclic group with 3 to 7 ring members, —$CH_2$-heterocyclic group with 3 to 7 ring members, —$CH_2$—$O$-heterocyclic group with 3 to 7 ring members, —$CH_2$—$NH$-heterocyclic group with 3 to 7 ring members, —$CH_2$—$N(C_{1-6}$alkyl)-heterocyclic group with 3 to 7 ring members, —$C(=O)NH$-heterocyclic group with 3 to 7 ring members, $C_{3-8}$cycloalkyl, —$CH_2$—$C_{3-8}$cycloalkyl, —$CH_2$—$O$—$C_{3-8}$cycloalkyl, and $C_{3-8}$cycloalkenyl, wherein said cycloalkyl, cycloalkenyl or heterocyclic groups may be optionally substituted by one or more $R_z$ groups, and wherein in each instance the heterocyclic group comprises one or more heteroatoms selected from N, O, S and oxidised forms thereof;

or the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more heteroatoms selected from N, O, S and oxidised forms thereof, and wherein said $C_{3-6}$cycloalkyl and heterocyclyl groups may be optionally substituted by one or more $R^z$ groups;

$R^8$ and $R^9$ are independently selected from hydrogen, $C_{1-6}$alkyl, halo$C_{1-6}$alkyl, hydroxy$C_{1-6}$alkyl, —$(CH_2)_k$—O—$C_{1-6}$alkyl, —$(CH_2)_k$—O-(hydroxy$C_{1-6}$alkyl), hydroxy$C_{1-6}$alkoxy, —$(CH_2)_k$—$CO_2C_{1-6}$alkyl, —$(CH_2)_k$—$CO_2H$, —$C_{1-6}$ alkyl-N(H)$_e$($C_{1-4}$alkyl)$_{2-e}$, —$(CH_2)_j$—$C_{3-8}$cycloalkyl and —$(CH_2)_j$—$C_{3-8}$cycloalkenyl;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —$COOC_{1-6}$alkyl, —N(H)$_e$($C_{1-4}$alkyl)$_{2-e}$, —$C_{1-6}$alkyl-N(H)$_e$($C_{1-4}$alkyl)$_{2-e}$, —$(CH_2)_k$—C(=O)N(H)$_e$($C_{1-4}$alkyl)$_{2-e}$, $C_{3-8}$cycloalkyl and $C_{3-8}$cycloalkenyl;

or the RX and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =$CH_2$ group; $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_r$—$CO_2C_{1-6}$alkyl, —$(CH_2)_r$—$CO_2H$, —N(H)$_e$ ($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl, wherein if $R^7$ is pyridine then $R^z$ is other than —$NH_2$;

a, j, d, e, n, r and p are independently selected from 0, 1 and 2;

k and m are independently selected from 1 and 2;

u is selected from 0, 1, 2 and 3; and v is selected from 0 and 1; and (ii) a compound which is SGI-110

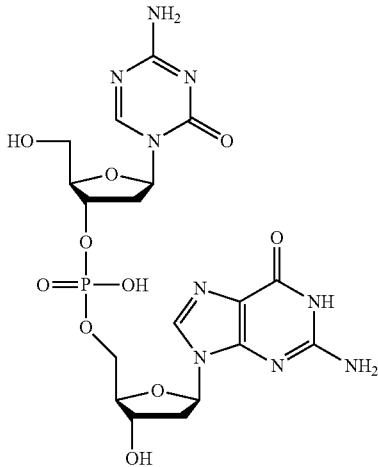

(SGI-110)

or a tautomer or a solvate or a pharmaceutically acceptable salt thereof.

2. A combination according to claim 1, wherein in the compound of formula (I°) cyc is phenyl and:
   $R^1$ is halogen, hydroxy, nitrile, $C_{1-4}$alkyl, $C_{2-4}$alkynyl, or $C_{1-4}$alkoxy; and/or
   n is 1 and $R^1$ is chloro or nitrile; and/or
   $R^2$ is selected from hydrogen, $C_{1-4}$alkyl, $C_{2-6}$alkenyl, and hydroxy$C_{1-4}$alkyl; and/or
   $R^2$ is hydrogen or —$(CR^xR^y)_u$—$CO_2H$.

3. A combination according to claim 1, wherein in the compound of formula (I°) cyc is phenyl and $R^3$ is -(A)$_t$-(CR$^x$R$^y$)$_q$—X and A is a $C_{3-6}$cycloalkyl group.

4. A combination according to claim 1, wherein in the compound of formula (I°) cyc is phenyl and $R^3$ is -(A)$_t$-(CR$^x$R$^y$)$_q$—X and A is a heterocyclic group with 3 to 5 ring members.

5. A combination according to claim 1, wherein in the compound of formula (I°) cyc is phenyl and:
   s is 1; and/or
   X is hydrogen, halogen, —CN, —OR$^9$, and —C(=O)NR$^x$R$^y$.

6. A combination according to claim 1, wherein the compound of formula (I°) is a compound of the formula

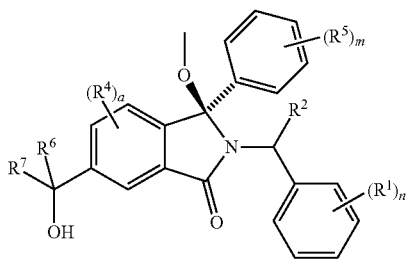

or a tautomer or a solvate or a pharmaceutically acceptable salt thereof.

7. A combination according to claim 6, wherein in the compound of formula (I°) cyc is phenyl and:
   a is 1, optionally wherein $R^4$ is F and at the 4-position of the isoindolinone ring; and/or
   m is 1 and the substituent $R^5$ is at the para-position of the phenyl group, optionally wherein $R^5$ is chloro; and/or $R^7$ is selected from a heterocyclic group with 3 to 7 ring members and a —$CH_2$-heterocyclic group with 3 to 7 ring members, wherein said heterocyclic groups may be optionally substituted by one or more $R^z$ groups, and wherein in each instance the heterocyclic group comprises one or more heteroatoms selected from N, O, S and oxidised forms thereof; and/or $R^6$ is methyl or ethyl.

8. A combination comprising:

(i) a compound selected from:
- (3R)-3-(4-chlorophenyl)-2-[(4-chlorophenyl)methyl]-3-{[1-(hydroxymethyl)cyclopropyl]methoxy}-6-(2-hydroxypropan-2-yl)-2,3-dihydro-1H-isoindol-1-one;
- (3R)-3-(4-chlorophenyl)-2-[(4-chlorophenyl)methyl]-4-fluoro-3-{[1-(hydroxymethyl)cyclopropyl]methoxy}-6-(2-hydroxypropan-2-yl)-2,3-dihydro-1H-isoindol-1-one;
- (3R)-3-(4-chlorophenyl)-2-[(4-chlorophenyl)methyl]-3-(2-hydroxyethoxy)-6-(2-hydroxypropan-2-yl)-2,3-dihydro-1H-isoindol-1-one;
- (3R)-3-(4-chlorophenyl)-2-[(4-chlorophenyl)methyl]-3-{[3-(hydroxymethyl)oxetan-3-yl]methoxy}-6-(2-hydroxypropan-2-yl)-2,3-dihydro-1H-isoindol-1-one;
- 1-({[(1R)-1-(4-chlorophenyl)-2-[(4-chlorophenyl)methyl]-5-(2-hydroxypropan-2-yl)-3-oxo-2,3-dihydro-1H-isoindol-1-yl]oxy}methyl)cyclopropane-1-carboxylic acid;
- (3R)-3-(4-chlorophenyl)-2-[(1S)-1-(4-chlorophenyl)ethyl]-3-(2,3-dihydroxy-2-methylpropoxy)-6-(2-hydroxypropan-2-yl)-2,3-dihydro-1H-isoindol-1-one;
- (3R)-3-(4-chlorophenyl)-2-[(1S)-1-(4-chlorophenyl)ethyl]-3-{[1-(hydroxymethyl)cyclopropyl]methoxy}-6-(2-hydroxypropan-2-yl)-2,3-dihydro-1H-isoindol-1-one;
- (3R)-3-(4-chlorophenyl)-2-[(4-chlorophenyl)methyl]-6-(1,2-dihydroxypropan-2-yl)-3-{[1-(hydroxymethyl)cyclopropyl]methoxy}-2,3-dihydro-1H-isoindol-1-one;
- (3R)-3-(4-chlorophenyl)-2-[(1S)-1-(4-chlorophenyl)ethyl]-6-(2-hydroxy-1-methoxypropan-2-yl)-3-{[1-(hydroxymethyl)cyclopropyl]methoxy}-2,3-dihydro-1H-isoindol-1-one;
- (3R)-3-(4-chlorophenyl)-2-[(4-chlorophenyl)methyl]-6-[1-(dimethylamino)-2-hydroxypropan-2-yl]-3-{[1-(hydroxymethyl)cyclopropyl]methoxy}-2,3-dihydro-1H-isoindol-1-one;
- (3S)-3-(4-chlorophenyl)-3-[(1R)-1-(4-chlorophenyl)-1-{[1-(hydroxymethyl)cyclopropyl]methoxy}-5-(2-hydroxypropan-2-yl)-3-oxo-2,3-dihydro-1H-isoindol-2-yl]propanoic acid;
- (3R)-3-(4-chlorophenyl)-2-[(1S)-1-(4-chlorophenyl)ethyl]-6-(1,2-dihydroxypropan-2-yl)-3-{[1-(hydroxymethyl)cyclopropyl]methoxy}-2,3-dihydro-1H-isoindol-1-one;
- (3R)-3-(4-chlorophenyl)-2-[(4-chlorophenyl)methyl]-3-(3-hydroxy-3-methylbutoxy)-6-(2-hydroxypropan-2-yl)-2,3-dihydro-1H-isoindol-1-one;
- (3R)-3-(4-chlorophenyl)-2-[(4-chlorophenyl)methyl]-6-(2-hydroxypropan-2-yl)-3-[(1H-pyrazol-4-yl)methoxy]-2,3-dihydro-1H-isoindol-1-one;
- 1-({[(1R)-1-(4-chlorophenyl)-2-[(4-chlorophenyl)methyl]-5-(2-hydroxypropan-2-yl)-3-oxo-2,3-dihydro-1H-isoindol-1-yl]oxy}methyl)cyclopropane-1-carbonitrile;
- N-{[1-({[(1R)-1-(4-chlorophenyl)-2-[(4-chlorophenyl)methyl]-5-(2-hydroxypropan-2-yl)-3-oxo-2,3-dihydro-1H-isoindol-1-yl]oxy}methyl)cyclopropyl]methyl}methanesulfonamide;
- (3R)-3-(4-chlorophenyl)-2-[(4-ethynylphenyl)methyl]-3-{[1-(hydroxymethyl)cyclopropyl]methoxy}-6-(2-hydroxypropan-2-yl)-2,3-dihydro-1H-isoindol-1-one;
- (3R)-3-(4-chlorophenyl)-2-[(4-ethynylphenyl)methyl]-4-fluoro-3-{[1-(hydroxymethyl)cyclopropyl]methoxy}-6-(2-hydroxypropan-2-yl)-2,3-dihydro-1H-isoindol-1-one;
- (3R)-3-(4-chlorophenyl)-6-(1,2-dihydroxypropan-2-yl)-2-[(4-ethynylphenyl)methyl]-4-fluoro-3-{[1-(hydroxymethyl)cyclopropyl]methoxy}-2,3-dihydro-1H-isoindol-1-one;
- 4-{[(1R)-1-(4-chlorophenyl)-7-fluoro-1-({1-[hydroxy($^2H_2$)methyl]cyclopropyl}($^2H_2$)methoxy)-5-(2-hydroxypropan-2-yl)-3-oxo-2,3-dihydro-1H-isoindol-2-yl]methyl}benzonitrile;
- 4-{[(1R)-1-(4-chlorophenyl)-1-{[1-(hydroxymethyl)cyclopropyl]methoxy}-5-(2-hydroxypropan-2-yl)-3-oxo-2,3-dihydro-1H-isoindol-2-yl]methyl}benzonitrile;
- (3R)-3-(4-chlorophenyl)-2-[(4-chlorophenyl)methyl]-6-(2-hydroxypropan-2-yl)-3-[(3-methyl oxetan-3-yl)methoxy]-2,3-dihydro-1H-isoindol-1-one;
- 4-{[(1R)-1-(4-chlorophenyl)-5-(1,2-dihydroxypropan-2-yl)-1-{[1-(hydroxymethyl)cyclopropyl]methoxy}-3-oxo-2,3-dihydro-1H-isoindol-2-yl]methyl}benzonitrile;
- (3R)-3-(4-chlorophenyl)-2-[(4-chlorophenyl)methyl]-3-[(1-hydroxycyclopropyl)methoxy]-6-(2-hydroxypropan-2-yl)-2,3-dihydro-1H-isoindol-1-one;
- 2-{[(1R)-1-(4-chlorophenyl)-2-[(4-chlorophenyl)methyl]-5-(2-hydroxypropan-2-yl)-3-oxo-2,3-dihydro-1H-isoindol-1-yl]oxy}-N,N-dimethylacetamide;
- (3R)-3-(4-chlorophenyl)-2-[(4-chlorophenyl)methyl]-6-(2-hydroxypropan-2-yl)-3-{[1-(methoxymethyl)cyclopropyl]methoxy}-2,3-dihydro-1H-isoindol-1-one;
- (3R)-3-(4-Chlorophenyl)-2-[(4-chlorophenyl)methyl]-3-{[1-(hydroxymethyl)cyclobutyl]methoxy}-6-(2-hydroxypropan-2-yl)-2,3-dihydro-1H-isoindol-1-one;
- 5-chloro-2-{[(1R)-1-(4-chlorophenyl)-1-{[1-(hydroxymethyl)cyclopropyl]methoxy}-5-(2-hydroxypropan-2-yl)-3-oxo-2,3-dihydro-1H-isoindol-2-yl]methyl}benzoic acid;
- (3R)-2-{[4-chloro-2-(morpholine-4-sulfonyl)phenyl]methyl}-3-(4-chlorophenyl)-3-{[1-(hydroxymethyl)cyclopropyl]methoxy}-6-(2-hydroxypropan-2-yl)-2,3-dihydro-1H-isoindol-1-one;
- 1-({[(1R)-2-[(4-chloro-2-methanesulfonyl phenyl)methyl]-1-(4-chlorophenyl)-7-fluoro-5-(2-hydroxypropan-2-yl)-3-oxo-2,3-dihydro-1H-isoindol-1-yl]oxy}methyl)cyclopropane-1-carboxamide;
- (3R)-2-[(4-chloro-2-methanesulfonylphenyl)methyl]-3-(4-chlorophenyl)-3-({1-[hydroxy($^2H_2$)methyl]cyclopropyl}($^2H_2$)methoxy)-6-(2-hydroxypropan-2-yl)-2,3-dihydro-1H-isoindol-1-one;
- (3R)-3-(4-chlorophenyl)-2-[(4-chlorophenyl)methyl]-6-(2-hydroxypropan-2-yl)-3-(oxolan-3-yloxy)-2,3-dihydro-1H-isoindol-1-one;

(3R)-3-(4-chlorophenyl)-2-[(4-chlorophenyl)methyl]-6-(2-hydroxypropan-2-yl)-3-[(oxolan-3-yl)methoxy]-2,3-dihydro-1H-isoindol-1-one;

(3R)-2-[(4-chloro-2-methanesulfonylphenyl)methyl]-3-(4-chlorophenyl)-4-fluoro-6-[1-hydroxy-1-(oxan-4-yl)ethyl]-3-{[1-(hydroxymethyl)cyclopropyl]methoxy}-2,3-dihydro-1H-isoindol-1-one;

(3R)-2-[(4-chloro-2-methanesulfonylphenyl)methyl]-3-(4-chlorophenyl)-4-fluoro-6-[2-hydroxy-1-(piperazin-1-yl)propan-2-yl]-3-{[1-(hydroxymethyl)cyclopropyl]methoxy}-2,3-dihydro-1H-isoindol-1-one;

(3R)-3-(4-chlorophenyl)-2-[(1S)-1-(4-chlorophenyl)ethyl]-3-{[(3S,4R)-4-hydroxyoxolan-3-yl]oxy}-6-(2-hydroxypropan-2-yl)-2,3-dihydro-1H-isoindol-1-one;

(3R)-3-(4-chlorophenyl)-2-[(1S)-1-(4-chlorophenyl)ethyl]-3-{[(3R,4S)-4-hydroxyoxolan-3-yl]oxy}-6-(2-hydroxypropan-2-yl)-2,3-dihydro-1H-isoindol-1-one;

(3R)-3-(4-chlorophenyl)-2-[(4-chlorophenyl)methyl]-6-(2-hydroxypropan-2-yl)-3-methoxy-2,3-dihydro-1H-isoindol-1-one;

(3R)-3-(4-chlorophenyl)-2-[(4-chlorophenyl)methyl]-3-({1-[hydroxy($^2$H$_2$)methyl]cyclopropyl}($^2$H$_2$)methoxy)-6-(2-hydroxypropan-2-yl)-2,3-dihydro-1H-isoindol-1-one;

(3R)-3-(4-chlorophenyl)-2-[(4-chlorophenyl)methyl]-6-(2-hydroxypropan-2-yl)-3-(3-hydroxypropoxy)-2,3-dihydro-1H-isoindol-1-one;

(3R)-2-[(4-chloro-2-methanesulfonylphenyl)methyl]-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one;

(3R)-3-(4-chlorophenyl)-2-[(4-chlorophenyl)methyl]-3-(2,2-difluoro-3-hydroxypropoxy)-6-(2-hydroxypropan-2-yl)-2,3-dihydro-1H-isoindol-1-one;

(3R)-3-(4-chlorophenyl)-2-[(4-chlorophenyl)methyl]-3-{[2-(hydroxymethyl)cyclobutyl]methoxy}-6-(2-hydroxypropan-2-yl)-2,3-dihydro-1H-isoindol-1-one;

(3R)-3-(4-chlorophenyl)-2-[(4-chlorophenyl)methyl]-6-[2-hydroxy-1-oxo-1-(pyrrolidin-1-yl)propan-2-yl]-3-{[1-(hydroxymethyl)cyclopropyl]methoxy}-2,3-dihydro-1H-isoindol-1-one;

2-[(1R)-1-(4-chlorophenyl)-2-[(4-chlorophenyl)methyl]-1-{[1-(hydroxymethyl)cyclopropyl]methoxy}-3-oxo-2,3-dihydro-1H-isoindol-5-yl]-2-hydroxy-N,N-dimethylpropanamide;

2-[(1R)-1-(4-chlorophenyl)-2-[(4-chlorophenyl)methyl]-1-{[1-(hydroxymethyl)cyclopropyl]methoxy}-3-oxo-2,3-dihydro-1H-isoindol-5-yl]-2-hydroxy-N-methylpropanamide;

(3R)-2-{[4-chloro-2-(methylsulfanyl)phenyl]methyl}-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one;

(3R)-2-[(4-chloro-2-methanesulfinylphenyl)methyl]-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one;

(3R)-2-[(4-chloro-2-methanesulfonylphenyl)methyl]-3-(4-chlorophenyl)-4-fluoro-6-(2-hydroxy-1-methoxypropan-2-yl)-3-{[1-(hydroxymethyl)cyclopropyl]methoxy}-2,3-dihydro-1H-isoindol-1-one;

(3R)-2-[(4-chloro-2-methanesulfonylphenyl)methyl]-3-(4-chlorophenyl)-6-(1,2-dihydroxypropan-2-yl)-4-fluoro-3-{[1-(hydroxymethyl)cyclopropyl]methoxy}-2,3-dihydro-1H-isoindol-1-one;

(3R)-2-[(4-chloro-2-methanesulfonylphenyl)methyl]-3-(4-chlorophenyl)-4-fluoro-6-[2-hydroxy-1-(4-methylpiperazin-1-yl)propan-2-yl]-3-[(3R)-oxolan-3-yl oxy]-2,3-dihydro-1H-isoindol-1-one;

(3R)-2-[(4-chloro-2-methanesulfonylphenyl)methyl]-3-(4-chlorophenyl)-4-fluoro-6-[2-hydroxy-1-(4-methylpiperazin-1-yl)propan-2-yl]-3-[(3S)-oxolan-3-yloxy]-2,3-dihydro-1H-isoindol-1-one;

(3S)-3-(4-chlorophenyl)-3-[(1R)-1-(4-chlorophenyl)-7-fluoro-5-(2-hydroxypropan-2-yl)-3-oxo-1-[(3S)-oxolan-3-yloxy]-2,3-dihydro-1H-isoindol-2-yl]propanoic acid;

1-({[(1R)-2-{[4-chloro-2-(hydroxymethyl)phenyl]methyl}-1-(4-chlorophenyl)-7-fluoro-5-(2-hydroxypropan-2-yl)-3-oxo-2,3-dihydro-1H-isoindol-1-yl]oxy}methyl)cyclopropane-1-carbonitrile;

1-({[(1R)-2-[(4-chloro-2-methanesulfonylphenyl)methyl]-1-(4-chlorophenyl)-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide;

(3R)-2-[(4-chloro-2-methanesulfonylphenyl)methyl]-3-(4-chlorophenyl)-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one;

(3R)-2-[(4-chloro-2-methanesulfonylphenyl)methyl]-3-(4-chlorophenyl)-4-fluoro-6-[2-hydroxy-1-(4-methylpiperazin-1-yl)propan-2-yl]-3-{[1-(hydroxymethyl)cyclopropyl]methoxy}-2,3-dihydro-1H-isoindol-1-one;

5-chloro-2-{[(1R)-1-(4-chlorophenyl)-1-[(1-cyanocyclopropyl)methoxy]-7-fluoro-5-(2-hydroxypropan-2-yl)-3-oxo-2,3-dihydro-1H-isoindol-2-yl]methyl}benzoic acid;

(3R)-2-[(4-chloro-2-methanesulfonylphenyl)methyl]-3-(4-chlorophenyl)-4-fluoro-6-[1-hydroxy-1-(1-methylpiperidin-4-yl)ethyl]-3-{[1-(hydroxymethyl)cyclopropyl]methoxy}-2,3-dihydro-1H-isoindol-1-one;

(3R)-2-{[4-chloro-2-(dimethylphosphoryl)phenyl]methyl}-3-(4-chlorophenyl)-4-fluoro-3-{[1-(hydroxymethyl)cyclopropyl]methoxy}-6-(2-hydroxypropan-2-yl)-2,3-dihydro-1H-isoindol-1-one;

(3R)-2-[(4-chloro-2-methanesulfonylphenyl)methyl]-3-(4-chlorophenyl)-4-fluoro-6-[hydroxy(oxan-4-yl)methyl]-3-{[1-(hydroxymethyl)cyclopropyl]methoxy}-2,3-dihydro-1H-isoindol-1-one;

1-({[(1R)-2-[(4-chloro-2-methanesulfonyl phenyl)methyl]-1-(4-chlorophenyl)-7-fluoro-5-[1-hydroxy-1-(oxan-4-yl)ethyl]-3-oxo-2,3-dihydro-1H-isoindol-1-yl]oxy}methyl)cyclopropane-1-carboxamide;

5-chloro-2-{[(1R)-1-(4-chlorophenyl)-7-fluoro-5-[1-hydroxy-1-(1-methylpiperidin-4-yl)ethyl]-1-methoxy-3-oxo-2,3-dihydro-1H-isoindol-2-yl]methyl}benzoic acid;

(3S)-3-(4-chlorophenyl)-3-[(1R)-1-(4-chlorophenyl)-7-fluoro-5-[1-hydroxy-1-(oxan-4-yl)ethyl]-1-methoxy-3-oxo-2,3-dihydro-1H-isoindol-2-yl]propanoic acid;

4-[(1R)-1-[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]-2-hydroxyethyl]benzonitrile;

4-{[(1R)-1-(4-chlorophenyl)-7-fluoro-5-[1-hydroxy-1-(1-methyl-1H-imidazol-4-yl)propyl]-3-oxo-1-[(3S)- oxolan-3-yloxy]-2,3-dihydro-1H-isoindol-2-yl]methyl}-3-(hydroxymethyl)benzonitrile;

4-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}benzonitrile;

4-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}benzonitrile;

(3S)-3-(4-chlorophenyl)-3-[(1R)-1-(4-chlorophenyl)-7-fluoro-5-[1-(4-fluorooxan-4-yl)-1-hydroxyethyl]-1-methoxy-3-oxo-2,3-dihydro-1H-isoindol-2-yl]propanoic acid;

(4S)-4-(4-chlorophenyl)-4-[(1R)-1-(4-chlorophenyl)-7-fluoro-5-[1-hydroxy-1-(1-methyl-1H-pyrazol-3-yl)propyl]-1-methoxy-3-oxo-2,3-dihydro-1H-isoindol-2-yl]butanoic acid;

(3S)-3-(4-chlorophenyl)-3-[(1R)-1-(4-chlorophenyl)-7-fluoro-5-[1-(4-fluorooxan-4-yl)-1-hydroxypropyl]-1-methoxy-3-oxo-2,3-dihydro-1H-isoindol-2-yl]propanoic acid;

(3S)-3-(4-chlorophenyl)-3-[(1R)-1-(4-chlorophenyl)-5-(1-cyclobutyl-1-hydroxyethyl)-7-fluoro-1-methoxy-3-oxo-2,3-dihydro-1H-isoindol-2-yl]propanoic acid;

(3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]propanoic acid;

(3S)-3-(4-chlorophenyl)-3-[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]propanoic acid;

(4S)-4-(4-chlorophenyl)-4-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]butanoic acid;

(4S)-4-(4-chlorophenyl)-4-[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]butanoic acid;

(4S)-4-(4-Chlorophenyl)-4-[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]butanoic acid;

(3S)-3-(4-chlorophenyl)-3-[(1R)-1-(4-chlorophenyl)-7-fluoro-5-[(1R)-1-(4-fluorooxan-4-yl)-1-hydroxypropyl]-1-trideuteromethoxy-3-oxo-2,3-dihydro-1H-isoindol-2-yl]propanoic acid;

(3S)-3-(4-chlorophenyl)-3-[(1R)-1-(4-chlorophenyl)-1-ethoxy-7-fluoro-5-[(1R)-1-(4-fluorooxan-4-yl)-1-hydroxypropyl]-3-oxo-2,3-dihydro-1H-isoindol-2-yl]propanoic acid;

(4S)-4-[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]-4-(4-methoxyphenyl)butanoic acid;

(4S)-4-(4-chlorophenyl)-4-[(1R)-1-(4-chlorophenyl)-7-fluoro-5-{1-hydroxy-1-[trans-4-hydroxycyclohexyl]propyl}-1-methoxy-3-oxo-2,3-dihydro-1H-isoindol-2-yl]butanoic acid;

2-(5-chloro-2-{[1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}phenoxy)acetic acid;

5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}benzoic acid;

5-chloro-2-{[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]methyl}benzoic acid;

5-chloro-2-{[(1R)-1-(4-chlorophenyl)-1-ethoxy-7-fluoro-5-[(1S)-1-hydroxy-1-(oxan-4-yl)propyl]-3-oxo-2,3-dihydro-1H-isoindol-2-yl]methyl}benzoic acid;

2-{[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}-5-methylbenzoic acid;

2-{[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}-5-methoxybenzoic acid;

2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl)-2-methylpropanoic acid;

2-(5-chloro-2-{[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]methyl}phenyl)acetic acid;

2-(5-chloro-2-{[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]methyl}phenyl)acetic acid;

(2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid;

(3S)-3-(4-chlorophenyl)-3-[(1R)-1-(4-chlorophenyl)-7-fluoro-1-[(3-fluorooxetan-3-yl)methoxy]-5-(2-hydroxybutan-2-yl)-3-oxo-2,3-dihydro-1H-isoindol-2-yl]propanoic acid;

(3S)-3-(4-chlorophenyl)-3-[(1R)-1-(4-chlorophenyl)-7-fluoro-5-[1-hydroxy-1-(pyridin-2-yl)propyl]-1-methoxy-3-oxo-2,3-dihydro-1H-isoindol-2-yl]propanoic acid;

(3R)-2-[(4-chloro-2-methanesulfonylphenyl)methyl]-3-(4-chlorophenyl)-4-fluoro-6-[1-(4-fluoropiperidin-4-yl)-1-hydroxypropyl]-3-methoxy-2,3-dihydro-1H-isoindol-1-one;

4-{[(1R)-1-(4-chlorophenyl)-7-fluoro-5-[(1S)-1-hydroxy-1-(1-methylpiperidin-4-yl)propyl]-3-oxo-1-[cis-3-hydroxycyclobutoxy]-2,3-dihydro-1H-isoindol-2-yl]methyl}benzonitrile;

(3S)-3-(4-chlorophenyl)-3-[(1R)-1-(4-chlorophenyl)-7-fluoro-5-[1-(4-fluoro-1-methylpiperidin-4-yl)-1-hydroxypropyl]-1-methoxy-3-oxo-2,3-dihydro-1H-isoindol-2-yl]propanoic acid;

tert-butyl 2-{4-[(1S)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetate;

tert-butyl 2-{4-[(1R)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetate;

2-{4-[(1S)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetic acid;

2-{4-[(1R)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}acetic acid;

methyl 3-{4-[(1S)-1-[(1R)-1-(4-chlorophenyl)-2-[(4-chlorophenyl)methyl]-7-fluoro-1-methoxy-3-oxo-2, 3-dihydro-1H-isoindol-5-yl]-1-hydroxypropyl]piperidin-1-yl}propanoate; and 3-{4-[(1S)-1-[(1R)-1-(4-chlorophenyl)-2-[(4-chlorophenyl)methyl]-7-fluoro-1-methoxy-3-oxo-2,3-dihydro-1H-isoindol-5-yl]-1-hydroxypropyl]piperidin-1-yl}propanoic acid;

or a tautomer, N-oxide, pharmaceutically acceptable salt or solvate thereof; and (ii) a compound which is SGI-110

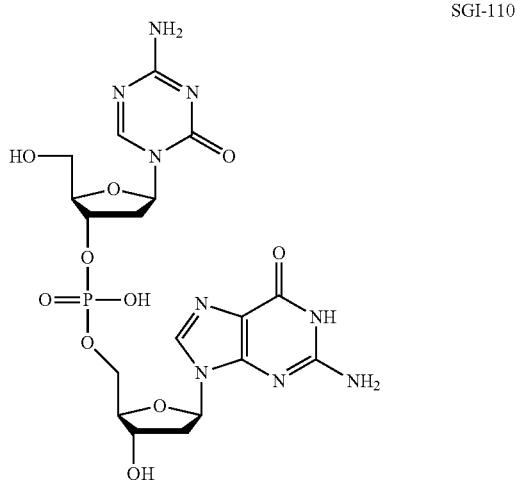

SGI-110 or a tautomer or a solvate or a pharmaceutically acceptable salt thereof.

9. A combination according to claim 1, wherein the compound of formula (I°) is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, or a tautomer, N-oxide, pharmaceutically acceptable salt or solvate thereof.

10. A combination comprising a combination as defined in claim 1 and one or more other therapeutic agents.

11. A combination according to claim 1 wherein:
the compound of formula (I°) and SGI-110 are physically associated; or
the compound of formula (I°) and SGI-110 are non-physically associated, optionally wherein the combination is in the form of a pharmaceutical kit or patient pack.

12. A pharmaceutical composition comprising a combination as defined in claim 1.

13. A method for the treatment of cancer comprising:
administering to a patient a combination according to claim 1; or
administering to a patient a pharmaceutical composition comprising a combination as defined in claim 1; or
administering to a patient in need thereof (i) SGI-110, or a tautomer, pharmaceutically acceptable salt or solvate thereof and (ii) a compound of formula (I°) as defined in claim 1, or a tautomer, N-oxide, pharmaceutically acceptable salt or solvate thereof,
wherein the cancer is selected from colon cancer, colorectal cancer, lung cancer, mesothelioma, breast cancer, osteosarcoma, fibrosarcoma, melanoma, liver cancer, leukemia, lymphoma, prostate cancer, liposarcoma, pancreatic cancer, ovarian cancer, gastric cancer, bladder cancer, epithelial cancer, multiple myeloma, soft tissue sarcoma, neuroblastoma, glioblastoma, a myeloproliferative disorder, a hematological malignancy, salivary gland cancer, and myelodysplastic syndrome.

14. A method according to claim 13, comprising administering a combination of (i) (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, or a tautomer, N-oxide, pharmaceutically acceptable salt or solvate thereof; and (ii) SGI-110, or a tautomer, pharmaceutically acceptable salt or solvate thereof.

15. A method for:
a. treating a disease or condition comprising or arising from abnormal cell growth in a mammal, wherein the disease or condition is selected from colon cancer, colorectal cancer, lung cancer, mesothelioma, breast cancer, osteosarcoma, fibrosarcoma, melanoma, liver cancer, leukemia, lymphoma, prostate cancer, liposarcoma, pancreatic cancer, ovarian cancer, gastric cancer, bladder cancer, epithelial cancer, multiple myeloma, soft tissue sarcoma, neuroblastoma, glioblastoma, a myeloproliferative disorder, a hematological malignancy, salivary gland cancer, and myelodysplastic syndrome; or
b. alleviating or reducing the incidence of a disease or condition comprising or arising from abnormal cell growth in a mammal, wherein the disease or condition is selected from colon cancer, colorectal cancer, lung cancer, mesothelioma, breast cancer, osteosarcoma, fibrosarcoma, melanoma, liver cancer, leukemia, lymphoma, prostate cancer, liposarcoma, pancreatic cancer, ovarian cancer, gastric cancer, bladder cancer, epithelial cancer, multiple myeloma, soft tissue sarcoma, neuroblastoma, glioblastoma, a myeloproliferative disorder, a hematological malignancy, salivary gland cancer, and myelodysplastic syndrome;
wherein the mammal is undergoing treatment with SGI-110, or a tautomer, pharmaceutically acceptable salt or solvate thereof,
the method comprising administering to the mammal a compound of formula (I°) as defined in claim 1, or a tautomer, N-oxide, pharmaceutically acceptable salt or solvate thereof.

16. A product containing as a first active ingredient a compound of formula (I°) as defined in claim 1, or a tautomer, N-oxide, pharmaceutically acceptable salt or solvate thereof, and as a further active ingredient SGI-110, or a tautomer, pharmaceutically acceptable salt or solvate thereof, as a combined preparation, wherein the product is for simultaneous, separate or sequential use in the treatment of patients suffering from colon cancer, colorectal cancer, lung cancer, mesothelioma, breast cancer, osteosarcoma, fibrosarcoma, melanoma, liver cancer, leukemia, lymphoma, prostate cancer, liposarcoma, pancreatic cancer, ovarian cancer, gastric cancer, bladder cancer, epithelial cancer, multiple myeloma, soft tissue sarcoma, neuroblastoma, glioblastoma, a myeloproliferative disorder, a hematological malignancy, salivary gland cancer, or myelodysplastic syndrome.

17. A method for inhibiting the interaction of p53 with MDM2 in a subject, comprising:
administering to the subject a combination according to claim 1; or
administering to the subject a pharmaceutical composition comprising a combination as defined in claim 1; or
administering to the subject (i) SGI-110, or a tautomer, pharmaceutically acceptable salt or solvate thereof and (ii) a compound of formula (I°) as defined in claim 1, or a tautomer, N-oxide, pharmaceutically acceptable salt or solvate thereof.

18. A method according to claim 17, wherein the subject is suffering from or at risk of suffering from a disease state or condition that is:

mediated by MDM2-p53; and/or cancer;

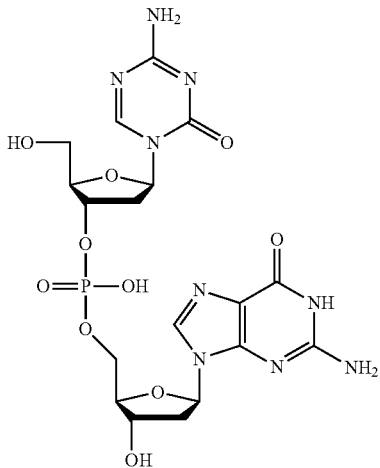

SGI-110 or a tautomer or a solvate or a pharmaceutically acceptable salt thereof.

19. A method according to claim 13 for the treatment of leukemia, wherein said leukemia is selected from acute myeloid leukemia, acute lymphocytic leukemia, chronic lymphocytic leukemia, and chronic myeloid leukemia.

20. A method according to claim 13 for the treatment of a myeloproliferative disorder selected from polycythemia vera, essential thrombocythemia and primary myelofibrosis.

21. A method according to claim 13 for the treatment of: lung cancer, wherein said lung cancer is non-small cell lung cancer; or lymphoma selected from diffuse large B-cell lymphoma, follicular lymphoma, and T-cell lymphoma.

* * * * *

UNITED STATES PATENT AND TRADEMARK OFFICE
CERTIFICATE OF CORRECTION

PATENT NO. : 11,236,047 B2
APPLICATION NO. : 16/497135
DATED : February 1, 2022
INVENTOR(S) : Chessari et al.

It is certified that error appears in the above-identified patent and that said Letters Patent is hereby corrected as shown below:

In the Claims

Column 556, Line 27: Claim 1, Delete "-$(CR^xR^{31})_v$-" and insert -- -$(CR^xR^y)_v$- --

Column 556, Line 32: Claim 1, Delete "-$(CR^xR^{31})_u$-" and insert -- -$(CR^xR^y)_u$- --

Column 557, Line 34: Claim 1, Delete "RX" and insert -- $R^x$ --

Column 562, Line 6: Claim 8, Delete "3-yl oxy]" and insert -- 3-yloxy] --

Column 564, Line 46: Claim 8, Delete "[ci s-3-hydroxycyclobutoxy]" and insert -- [cis-3-hydroxycyclobutoxy] --

Signed and Sealed this
Third Day of May, 2022

Katherine Kelly Vidal
*Director of the United States Patent and Trademark Office*